United States Patent
Langermann et al.

(10) Patent No.: US 9,957,312 B2
(45) Date of Patent: *May 1, 2018

(54) B7-H4 FUSION PROTEINS AND METHODS OF USE THEREOF

(71) Applicant: MedImmune, LLC, Gaithersburg, MD (US)

(72) Inventors: Solomon Langermann, Baltimore, MD (US); Linda Liu, Clarksville, MD (US); Joseph R. Podojil, Downers Grove, IL (US); Stephen D. Miller, Oak Park, IL (US); Shannon Marshall, Baltimore, MD (US)

(73) Assignee: MedImmune, LLC, Gaithersburg, MD (US)

(*) Notice: Subject to any disclaimer, the term of this patent is extended or adjusted under 35 U.S.C. 154(b) by 310 days.

This patent is subject to a terminal disclaimer.

(21) Appl. No.: 14/679,497

(22) Filed: Apr. 6, 2015

(65) Prior Publication Data
US 2016/0039905 A1 Feb. 11, 2016

Related U.S. Application Data

(63) Continuation of application No. 13/392,811, filed as application No. PCT/US2010/047366 on Aug. 31, 2010, now Pat. No. 9,011,853.

(60) Provisional application No. 61/238,605, filed on Aug. 31, 2009, provisional application No. 61/254,930, filed on Oct. 26, 2009, provisional application No. 61/266,854, filed on Dec. 4, 2009, provisional application No. 61/286,537, filed on Dec. 15, 2009, provisional application No. 61/378,361, filed on Aug. 30, 2010.

(51) Int. Cl.
| | |
|---|---|
| *C07K 14/705* | (2006.01) |
| *A61K 38/17* | (2006.01) |
| *C07K 16/28* | (2006.01) |
| *G01N 33/68* | (2006.01) |
| *A61K 9/00* | (2006.01) |
| *A61K 39/44* | (2006.01) |
| *A61K 38/00* | (2006.01) |

(52) U.S. Cl.
CPC ...... *C07K 14/70532* (2013.01); *A61K 9/0019* (2013.01); *A61K 38/1709* (2013.01); *A61K 39/44* (2013.01); *C07K 16/2827* (2013.01); *G01N 33/6863* (2013.01); *G01N 33/6866* (2013.01); *G01N 33/6869* (2013.01); *A61K 38/00* (2013.01); *C07K 2317/50* (2013.01); *C07K 2317/56* (2013.01); *C07K 2317/72* (2013.01); *C07K 2319/30* (2013.01); *C07K 2319/32* (2013.01); *G01N 2800/52* (2013.01)

(58) Field of Classification Search
None
See application file for complete search history.

(56) References Cited

U.S. PATENT DOCUMENTS

| | | | |
|---|---|---|---|
| 3,687,808 A | 8/1972 | Morgan | |
| 3,840,513 A | 10/1974 | Umezawa | |
| 4,034,074 A | 7/1977 | Miles | |
| 4,098,876 A | 7/1978 | Piasio | |
| 4,233,402 A | 11/1980 | Maggio | |
| 4,272,398 A | 6/1981 | Jaffe | |
| 4,376,110 A | 3/1983 | David | |
| 4,469,863 A | 9/1984 | Tso | |
| 4,634,664 A | 1/1987 | Oestberg | |
| 4,634,666 A | 1/1987 | Engleman | |
| 4,650,764 A | 3/1987 | Temin | |
| 4,704,692 A | 11/1987 | Ladner | |
| 4,769,330 A | 9/1988 | Paoletti | |
| 4,816,567 A | 3/1989 | Cabilly | |
| 4,853,871 A | 8/1989 | Pantoliano | |

(Continued)

FOREIGN PATENT DOCUMENTS

| | | |
|---|---|---|
| WO | 9007861 | 7/1990 |
| WO | 9110741 | 7/1991 |

(Continued)

OTHER PUBLICATIONS

Abbas et al., Cellular and Molecular Immunology, 2nd Ed., pp. 386, 407-and 40 (1994).
Benson, et al., "Mechanisms of autoimmunity in human diseases: a critical review of current dogma", Curr Opin Rheumatol., 26(2):197-203 (2014).
Blute, et at.,"Use of Gleason Score, Prostate Specific Antigen, Seminal Vesicle and Martin Status to Predict Biochemical Failure After Radical Prostatectomy," J. Urol, 2001. 165; 119-125 (2001).
Castriconi, et at., "Identification of 4lg-B7-H3 as a neuroblastoma-associated molecule that exerts a protective role from an NK cell-mediated lysis," FNAS, Aug. 24, 2004, 101 (34):12640-12645.
Chapoval, et al., "Immunoglobulin fusion proteins as a tool for evaluation of t-cell costimulatory molecules", Mol Biotechnol., 21:259-64 (2002).

(Continued)

*Primary Examiner* — Ilia Ouspenski
(74) *Attorney, Agent, or Firm* — Melissa Hunter-Ensor; Leslie Serunian; Greenberg Traurig, LLP

(57) ABSTRACT

Fusion proteins containing B7-H4 polypeptides are disclosed. The B7-H4 fusion proteins can include full-length B7-H4 polypeptides, or can contain a fragment of a full-length B7-H4 polypeptide, including some or all of the extracellular domain of the B7-H4 polypeptide. Methods for using the fusion proteins to downregulate T cell activation and for the treatment of inflammatory and autoimmune diseases and disorders are also disclosed. The B7-H4 fusion proteins are useful for treating inflammation by inhibiting or reducing differentiation, proliferation, activity, and/or cytokine production and/or secretion by ThI, ThI 7, Th22, and/or other cells that secrete, or cause other cells to secrete, inflammatory molecules, including, but not limited to, IL-1β, TNF-α, TGF-beta, IFN-γ, IL-17, IL-6, IL-23, IL-22, IL-21, and MMPs; or enhancing IL-IO secretion by Tregs, increasing the differentiation of Tregs, increasing the number of Tregs, or combinations thereof.

54 Claims, 36 Drawing Sheets

(56) References Cited

U.S. PATENT DOCUMENTS

| | | |
|---|---|---|
| 4,861,627 A | 8/1989 | Mathiowitz |
| 4,861,719 A | 8/1989 | Miller |
| 4,925,673 A | 5/1990 | Steiner |
| 4,946,778 A | 8/1990 | Ladner |
| 4,980,289 A | 12/1990 | Temin |
| 5,013,556 A | 5/1991 | Woodle |
| 5,120,727 A | 6/1992 | Kao |
| 5,124,263 A | 6/1992 | Temin |
| 5,155,020 A | 10/1992 | Paoletti |
| 5,162,333 A | 11/1992 | Failli |
| 5,175,099 A | 12/1992 | Wills |
| 5,202,332 A | 4/1993 | Hughes |
| 5,204,243 A | 4/1993 | Paoletti |
| 5,214,136 A | 5/1993 | Lin |
| 5,218,105 A | 6/1993 | Cook |
| 5,225,336 A | 7/1993 | Paoletti |
| 5,225,539 A | 7/1993 | Winter |
| 5,235,033 A | 8/1993 | Summertown |
| 5,240,846 A | 8/1993 | Collins |
| 5,260,203 A | 11/1993 | Ladner |
| 5,278,056 A | 1/1994 | Bank |
| 5,283,173 A | 2/1994 | Fields |
| 5,284,656 A | 2/1994 | Platz |
| 5,296,347 A | 3/1994 | LaMotteIII |
| 5,304,489 A | 4/1994 | Rosen |
| 5,385,908 A | 1/1995 | Nelson |
| 5,451,569 A | 9/1995 | Wong |
| 5,482,856 A | 1/1996 | Fell, Jr. |
| 5,484,790 A | 1/1996 | Failli |
| 5,530,006 A | 6/1996 | Waranis |
| 5,530,101 A | 6/1996 | Queen |
| 5,545,806 A | 8/1996 | Lonberg |
| 5,559,112 A | 9/1996 | Skotnicki |
| 5,565,332 A | 10/1996 | Hoogenboom |
| 5,567,709 A | 10/1996 | Skotnicki |
| 5,569,825 A | 10/1996 | Lonberg |
| 5,585,089 A | 12/1996 | Queen |
| 5,596,086 A | 1/1997 | Matteucci |
| 5,625,126 A | 4/1997 | Lonberg |
| 5,633,425 A | 5/1997 | Lonberg |
| 5,661,016 A | 8/1997 | Lonberg |
| 5,693,761 A | 12/1997 | Queen |
| 5,693,762 A | 12/1997 | Queen |
| 5,733,743 A | 3/1998 | Johnson |
| 5,736,142 A | 4/1998 | Sette |
| 5,741,957 A | 4/1998 | Deboer |
| 5,750,666 A | 5/1998 | Caruthers |
| 5,770,429 A | 6/1998 | Lonberg |
| 5,780,462 A | 7/1998 | Lee |
| 5,789,650 A | 8/1998 | Lonberg |
| 5,814,318 A | 9/1998 | Lonberg |
| 5,821,333 A | 10/1998 | Carter |
| 5,837,242 A | 11/1998 | Holliger |
| 5,849,992 A | 12/1998 | Meade |
| 5,858,657 A | 1/1999 | Winter |
| 5,871,907 A | 2/1999 | Winter |
| 5,874,299 A | 2/1999 | Lonberg |
| 5,877,218 A | 3/1999 | Herzig |
| 5,877,397 A | 3/1999 | Lonberg |
| 5,932,448 A | 8/1999 | Tso |
| 5,989,591 A | 11/1999 | Nagi |
| 6,015,809 A | 1/2000 | Zhu |
| 6,054,297 A | 4/2000 | Carter |
| 6,468,546 B1 | 10/2002 | Mitcham |
| 6,537,968 B1 | 3/2003 | Lezdey |
| 6,562,576 B2 | 5/2003 | Manfredi |
| 6,790,624 B2 | 9/2004 | Mayer |
| 6,808,901 B1 | 10/2004 | Neuberger |
| 6,891,030 B2 | 5/2005 | Chen |
| 6,933,146 B2 | 8/2005 | Helliwell |
| 6,962,980 B2 | 11/2005 | Mitcham |
| 6,982,323 B1 | 1/2006 | Wang |
| 7,132,511 B2 | 11/2006 | Carr |
| 7,189,563 B2 | 3/2007 | Eaton |
| 7,202,334 B1 | 4/2007 | Mitcham |
| 7,304,149 B2 | 12/2007 | Murphy |
| 7,449,300 B2 | 11/2008 | Chen |
| 7,622,565 B2 | 11/2009 | Chen |
| 7,732,131 B2 | 6/2010 | Moretta |
| 7,847,081 B2 | 12/2010 | Chen |
| 7,875,702 B2 | 1/2011 | Chen |
| 7,931,896 B2 | 4/2011 | Chen |
| 7,989,173 B2 | 8/2011 | Chen |
| 8,129,347 B2 | 3/2012 | Chen |
| 8,236,767 B2 | 8/2012 | Chen |
| 8,703,916 B2 | 4/2014 | Chen |
| 9,005,616 B2* | 4/2015 | Langermann ...... A61K 38/1709 424/134.1 |
| 9,011,853 B2* | 4/2015 | Langermann ...... A61K 38/1709 424/134.1 |
| 2002/0165347 A1 | 11/2002 | Fox |
| 2002/0168762 A1 | 11/2002 | Chen |
| 2004/0152105 A1 | 8/2004 | Vogt |
| 2004/0175380 A1 | 9/2004 | Allison |
| 2004/0180047 A1 | 9/2004 | Chen |
| 2004/0229795 A1 | 11/2004 | Roemisch |
| 2005/0163772 A1 | 7/2005 | Dong |
| 2005/0202536 A1 | 9/2005 | Chen |
| 2008/0159998 A1 | 7/2008 | Ichim |
| 2008/0160036 A1 | 7/2008 | Chen |
| 2008/0177039 A1 | 7/2008 | Chen |
| 2008/0206235 A1 | 8/2008 | Chen |
| 2009/0011444 A1 | 1/2009 | Chen |
| 2009/0018315 A1 | 1/2009 | Chen |
| 2009/0022747 A1 | 1/2009 | Chen |
| 2009/0087416 A1 | 4/2009 | Chen |
| 2009/0124573 A1 | 5/2009 | Mazmanian |
| 2009/0142342 A1 | 6/2009 | Chen |
| 2010/0203035 A1 | 8/2010 | Kwon |
| 2011/0171207 A1 | 7/2011 | Chen |
| 2011/0195073 A1 | 8/2011 | Chen |
| 2012/0039883 A1 | 2/2012 | Chen |
| 2012/0122021 A1 | 5/2012 | Hiramoto |
| 2012/0141504 A1 | 6/2012 | Chen |
| 2012/0177645 A1 | 7/2012 | Langermann |
| 2016/0039906 A1* | 2/2016 | Langermann ...... A61K 38/1709 424/85.2 |
| 2016/0146806 A1* | 5/2016 | Langermann ........ G01N 33/564 424/134.1 |

FOREIGN PATENT DOCUMENTS

| | | |
|---|---|---|
| WO | 9117271 | 11/1991 |
| WO | 9201047 | 1/1992 |
| WO | 9220791 | 11/1992 |
| WO | 9301222 | 1/1993 |
| WO | 9504738 | 2/1995 |
| WO | 9507707 | 3/1995 |
| WO | 9516691 | 6/1995 |
| WO | 9522972 | 8/1995 |
| WO | 9717613 | 5/1997 |
| WO | 9717614 | 5/1997 |
| WO | 9823635 | 6/1998 |
| WO | 9963068 | 12/1999 |
| WO | 0001385 | 1/2000 |
| WO | 0012758 | 3/2000 |
| WO | 0036107 | 6/2000 |
| WO | 0100814 | 1/2001 |
| WO | 0202587 | 1/2002 |
| WO | 0202624 | 1/2002 |
| WO | 0210187 | 2/2002 |
| WO | 2004022594 | 3/2004 |
| WO | 2004000221 | 12/2004 |
| WO | 2004113500 | 12/2004 |
| WO | 2006101487 | 9/2006 |
| WO | 2006124667 | 11/2006 |
| WO | 2006133396 | 12/2006 |
| WO | 2007039150 | 4/2007 |
| WO | 2007067681 | 8/2007 |
| WO | 08083239 | 7/2008 |
| WO | 2008083228 | 7/2008 |
| WO | 2008138017 | 11/2008 |

(56) References Cited

FOREIGN PATENT DOCUMENTS

| WO | 2009089036 | 7/2009 |
|---|---|---|
| WO | 2011026122 | 3/2011 |
| WO | 2011026132 | 3/2011 |

OTHER PUBLICATIONS

Cogent, et al., "Transgene silencing of the al-I gene in vegelative cells of Neurospora is mediated by a cytoplasmic effector and docs not depend on DNA-DNA interactions or DNA methylation," EMJ3O J., 1996, 15:3153-3163.

Cogent and Masinti, "Gene silencing in Ncurospora crassa requires a protein homologous to RNA-dependent RNA polymerase," Nature, 399:166-9 (1999).

Cole, et al., "The EBV-Hybridoma Technique and its Applicaqtion to Htiman Lung Cancer," Monoclonal Antibodies and Cancer TherapY. , Alan R. Lizs, Inc., pp. 77-96 (1985).

Cote, et al.,"Generation of human monoclonal antibodies reactive with cellular antigens," PNAS, 80:2026-30 (1983).

Crispen, et al., "Tumor cell and tumor vasculature expression of B7-H3 predict survival in clear cell renal cell carcinoma," Clin Cancer Res., 14(I 6): 5150-7 (2008).

Cristiano and Roth, "Molecular conjugates: a targeted gene delivery vector for molecular medicine," J. Mol. Med., 73:479-86 (1995).

Dimarco, et al., "Multivariate models to predict clinically important outcomes at prostateclomy for patients with organ-confined disease and needle biopsy Gleason scores of 6 or less," Urologic Oricol., 21 :439-46 (2003).

Figlin, et al, "Treatment of metastatic renal cell carcinoma with nephrectomy, interieul:in-2 and cytokine-primed or CD8(+) selected tumor infiltrating lymphocytes from primary tumor," J. Urol., 158:740-50 (1997).

Fire, et al., "Potent and specific genetic interference by double-stranded RNA in Caenorhabditis elegans" , Nature, 1998, 391:806-11 (1998).

Fyfe et al., "Results of treatment of 255 patients with metastatic renal cell carcinoma who received high-dose recombinant interleukin-2 therapy," J. Clin. Oncol , 13:688-96 (1995).

GcnBank Accession No. NM_025240, "*Homo sapiens* CD276 molecule (CD276), transcript variant 2, mRNA," dated Aug. 29, 2010, 3 pages.

Jennal, et al., "Cancer Statistics," CA Cancer J Clin , 55: 10-30 (2005).

Kennerdell and Carthew, "Use of dsRNA-mediated genetic interference to demonstrate that frizzled and frizzled 2 act in the wingless pathway" , Cell, 95:1017-26 (1998).

Kozbor and Roder, "The production of monoclonal antibodies from human lymphocyt es," Immunology Today, 4:72 (1983).

Leibovich, et al., "Prediction of progression after radical nephrectomy for patients with clear cell renal cell carcinoma: A stratification tool for prospective clinical trials," Cancer, 97:1663-71 (2003).

Loke and Allison, "Emerging mechanisms of immune regulation: the extended B7 family and regulatory T cells," Arthritis Research & Therapy, 6(5):208-14 (2004).

Loos, et al., "Expression of the costimulatory molecule B7-H3 is associated with prolonged survival in human pancreatic cancer." BMC Cancer, 9:463-73 (2009).

Luo, et al., "B7-H3 enhances tumor immunity in Vivo by Costimulating Rapid Clonal Expansion of Atnigen-Specific CD8\Cytolytic T Cells," J Immun., 173:5445-50 (2004).

Miller, et al., "Experminental autoimmune encephalomyelitis in the mouse" , Curr Protoc Immunol,, Unit-15.1:1-26 (2010).

Mischinger, et al., "Prognostic relevance of B7H I and B7H3 protein expressions in metastatic clear cc11 renal cell carcinoma," J. Clinical Oncolopgy, 2010 ASCO Annual Meeting Abstracts, vol. 28, No. 15 supp (May 20 Supplement): e15074, 3 pages, Jun. 14, 2010.

Misquitta and Paterson, "Targeted disruption of gene function in *Drosophila* by RNA interference (RNA-i): A role for nautilus in embryonic somatic muscle formation," PNAS, 96:1451-6 (1999).

Motzer, et al., "Renal-cell carcinoma," NEJM, 1996, 335:865-75 (1996).

Naef, et al., "Itraconazole comedication increases systemic levels of inhaled fluticasone in lung transplant recipients" , Respiration, 74:418-22 (2007).

Nepom, et al., "Challenges in the pursuit of immune tolerance" , Immunol. Rev., 241(1):49-62 (2011).

Pantuck, et al. "The changing natural history of renal cell carcinoma," J. Urol., 166: 1611-23 (2001).

Rieckmann, "Concepts of induction and escalation therapy in multiple sclerosis", J Neurological Sci., 277:S42-45 (2014).

Romano and Masino, "Quelling: transient inactivation of gene expression in Neurospora Cassa by transformation with homologous sequences," Mol. Microbiol., 5:3343-53 (1992).

Roth, et al., "B7-H3 ligand expression by prostate cancer: a novel marker of prognosis and potential target for therapy," Cancer Res, 97:7893-7900 (2007).

Sandborn, "Optimizing anti-tumor necrosis factor strategies in inflammatory bowel disease" , Curr Gastroenterol Rep., 5(6):501-5 (2003).

Sebo, et al, "Predicting prostate carcinoma volume and stage at radical prostatectomy by assessing needle biopsy specimens for percent surface area and cores positive for carcinoma, perineural invasion, Gleason score, DNA ploidy and proliferation, and preoperative serum prostate specific antigen: a report of 454 cases," Cancer, 91:2196-2204 (2001).

Sebo, et al., "Perineural invasion and MIB-1 positivity in addition fo Gleason score are significant preoperative predictors of progression after radical retropubic prostatectomy for prostate cancer," Am. J. Surg. Pathol., 26:431-9 (2002).

Shi, et ai., "Molecular regulation of Treg/Th17 balance" , Curr. Immunol., 28(6):510-13 (2008).

Singh, et al., "Biologics for rheumatoid arthritis: an overview of Cochrane reviews" , The Cochrane collaboration, John Wiley & Sons, pp. 1-55 (2009).

Suh, et al., "The immune regulatory protein B7-H3 premieres osteolblast differentiation and bone mineralization," PNAS, 101(35):12969-73 (2004).

Tandon, et al., "Intravenous dexamethasone vs methylprednisolone pulse therapy in the treatment of acute endothelial graft rejection" , Eye, 23:635-9 (2009).

UniProtKB/Swiss-Prot. Accession No. Q5ZPR3, "RecName: Full=CD276 antigen; AltName; Full-41g-B7-H3; AltName: Full-B7 hemolog 3; Short-B7-H3; AltName; Full=Costimolatory molecule; AltName: CD antigen-CD276; Flags: Precursor [*Homo sapiens*]," dated Sep. 7, 2010, 6 pages.

Wang, et al., "Early treatment of NOD mice with B7-H4 reduces the incidence of autoimmune diabetes" , Diabetes, 60:3246-55 (2011).

Wang, et al., "Local expression of B7-H4 by recombinant adenovirus transduction in mouse islets prolongs allograft survival" , Transplantation, 87(4):482-9 (2009).

Watanabe, et al., "BTLA is a lymphocyte inhibitory receptor with similarities to CTLA-4 anti PD-1". Naturc Immunol, 4(7):670-9 (2003).

Wu, et al., "Relationship between co-stimulatory molecule B7-H3 expression and gastric carcinoma histology and prognosis," World J Gastroenterol., 12(3):457-9 (2006).

Yi and Chen, "Fine tuning the immune response through B7-H3 and B7-H4" , Immunol. Rev., 229(1):145-51 (2009).

Zang, et al., "B7-H3 anal B7x are highly expressed in human prostate cancer and associated with disease spread and poor outcome," PNAS, 104:19458-63 (2007).

Zang, et al., "Turner associated endothelial expression of B7-H3 predicts survival in ovarian carcinomas," Mod Pathol., 23(8): 1104-12 (2010).

Adachi, "Tumoricidal effect of human macrophage-colony-stimulating factor against human-ovarian-carcinoma-bearing-athymic mice and its therapeutic effect when combined with cisplatin", Cancer Immunol. Immunother, 37(1):1-6, (1993).

(56) References Cited

OTHER PUBLICATIONS

Afzali, et al., "The role of T helper 17 (Th17) and regulatory T cells (Treg) in human organ transplantation and autoimmune disease", Clin Exp Immunol, 148(1):32-46 (2007).
Aldovini, "Humoral and cell-mediated immune responses to live recombinant BCG-HIV vaccines", Nature, 351:479-482 (1991).
Alegre, et al., "Mechanisms of CTLA-4-lg in tolerance induction", Curr Pharm Des, 12:149-60 (2006).
Alexander, et al., "Develpoment of high potency universal DR-restricted helper epitopes by modification of high affinity DR-blocking peptides", Immunity, 1(9):751-761 (1994).
Amoura, et al., "Nucleoaoma-restricted antibodies are detected before anti-dsDNA and/or antistone antibodies in serum of MRL-Mb Ipn/Igr and +/+mice, and are present in kidney eluates of lupus mice with proteinuria", Arthritis Rheum., 37(11):1684-8 (1984).
Angal, et al., "A single amino acid substitution abolishes the heterogeneity of chimeric mouse/human (igG4) antibody", Mol. Immunol, 30(1):105-8 (1993).
Arakawa, et al., "Formation of heterodimers from three neurotrophins, nerve growth factor, neurotrophin-3, and brain-derived neurotrophic factor", J. Biol. Chem., 269(45): 27833-39 (1994).
Attwood, "The Babel of Bioinformatics", Science Compass, 290:471-73 (2000).
Bird, "Single-chain antigen-binding proteins", Science, 242:423-426 (1988).
Blazar, et al., Infusion of anti B7.1 (CD60) and anti-B7.2 (CD66) monocolonal antibodies inhibits murine graft-versus-host disease lethality in part via direct effects on CD4+ and CD8+ T cells, J. Immunology, 157: 3250-3259 (1996).
Bona, et al., "Immnune Response : idiotype anti-idiotype network", CRC Crit. Rev. Immunol., 1:33-81 (1981).
Bonder, et al., "Essential role for neutropil recruitment to the liver in concanavalin A-induced hepatitis", J. Immunol., 172(1):45-53 (2004).
Bordignon, et al., "Gene therapy in peripheral blood lymphocytes and bone marrow for ADA-immunodeficient patients", Science, 270:470-475 (1995).
Brown, et al., "Treatment of mice with the neutrophil-depleting antibody RB6-BC5 results in early development of experimental lyme arthritis via the recruitment of Fr-l-polymorphonuclear leukecyte-like cells", Infect. Immun., 72(9):4956-65 (2004).
Cassatella, "The production of cytokines by polymorphonuclear neutrophils", Immunol. Today, 16(1):21-6 (1995).
Chambers and Allison, "Co-stimulation in T cell responses", Curr. Opin. Immunol., 9:396-404 (1997).
Chapman, "A phase I trial of intraperitoneal recombinant interleukin 2 in patients with ovarian carcinoma", Investigational New Drugs, 6(3):179-188. (1988).
Chapoval, et al., B7-H3: a costimulatory molecule for T cell activation and IFN-gamma production, Nat. Immunol., 2(3):269-74 (2001).
Chapoval, et al., "Immunoglobulin fusion proteins as a tool for evaluation of t-cell costimulatory molecules", Methods Mol. Med., 45:47-255(2000).
Chen, et al., "Impaired glucose homeostasis, neutrophil trafficking and function in mice lacking the glucose-6-phosphate transporter", Hum. Mol. Genet., 12:2547-2558 (2003).
Chen, "Co-inhibitory molecules of the B7-CD28 family in the control of T-cell Immunity", Nat. Rev. Immunol., 4(5):33647 (2004).
Chen, "Soluble TNF-alpha receptors are constitutively shed and downregulate adhesion molecule expression in malignant gliomas", J. Neuropathol. Exp. Neurol., 56(5), 541-550 (1997).
Chicz, et al., "Specifically and promiscuity among naturally processed peptides bound to HLA-DR alleles", J. Exp. Med., 178(1):27-47 (1993).
Choi, et al., "Genomic organization and expression analysis of B7-H4, an immune inhibitory molecule of the B7 family"., J. Immunol, 171:4650-4 (2003).

Co, et al., "Chimeric and humanized antibodies with specificially for the CD33 antigen", J. Immunol. 148(4):1149-1154 (1992).
Coyle, et al., "The CD28-related molecule ICOS is required for effective T cell-dependent immune responses", Immunity, 13(1):95-105 (2000).
Coyle, et al., "The expanding B7 superfamily: increasing complexity in costimulatory signals regulating T cell function", Nat. Immunol., 2(3):203-9 (2001).
Crystal, "Gene therapy strategies for pulmonary disease", Am. J. Med., 92(6A):44S-52S (1992).
Dau, et al., The fundamental basis for therapeutic plasmapheresis in autoimmune disease, Transfusion Sci., 17(2):235-44 (1996).
De Oca, et al., "Polymorphonuclear neutrophils are necessary for the recruitment of CD8(+) T cells in the liver in a pregnant mouse model of Chiamydophila abortus (Chlamydia paltttsci serotype I) infection", Infect. Immun., 68(3):1746-51 (2000).
Dong, et al., "B7-H1, a third member of the B7 family, co-stimulates T-cell proliferation and interleukin-10 secretion", Nat. Med., 5:1365-69 (1999).
Dong, et al., "B7-H1 determines accumulation and deletion of intrahepetic CD8 (+) T lymphocytes", Immunity, 20:327-336 (2004).
Dong, et al., "Costimulating aberrant T cell responses by B7-H1 autoantibodies in rheumatoid arthritis", J. Clin. Invest., 111(3):363-70 (2003).
Dong, et al., "Immune regulation by novel costimulatory molecules", Immunol. Res., 28:39-48 (2003).
Dong, et al., "Tumor-associated B7-H1 promotes T-cell apoptosis: a potential mechanism of immune evasion", Nature Med., 8:793-800 (2002).
Edwards, et al., "Comparison of toxicity and survival following intraperitoneal recombinant interleukin-2 for persistent ovarian cancer after platinum: twenty-fours-hour versus 7-day infusion", J. Clin. Oncol., 15(11):3399-3407 (1997).
Edwards, "The formation of a structure with the features of synovial lining by subcutaneous injection of air: an in vivo tissue culture system", J. Pathol., 134:147-156 (1981).
Emamaullee, et al., "Costimulatory blockade with belatacept in clinical and experimental transplantation—a review", Expert Opin. Biol. Ther. 9(6):789-96 (2009).
Eyles, et al., "Granulocyte colony-stimulating factor and neutrophils-forgotten mediators of inflammatory disease", Nat. Clin. Pract. Rheumatol., 2(9):500-1 0 (2006).
Faas, et al., "Primary structure and functional characterization of a soluble, alternatively spliced form of B7-1", J. Immunol., 164(12):6340-8 (2000).vbTab.
Falk, et al., "Pool sequencing of natural HLA-DR, DQ, and DP ligands reveals detailed peptide motifs, constraints of processing, and general rules", Immunogenetics, 39(4):230-242 (1994).
Fava, et al., "Critical role of peripheral blood phagocytes and the involvement of complement in tumour necrosis factor enhancement of passive collegen-arthritis", Clin. Exp. Immuno., 94(2): 261-8 (1993).
Feldmann, "Rheumatoid arthritis", Cell, 85(3):307-10 (1996).
Fink, "Monoclonal antibodies as diagnostics reagents for the identification and characterization of human tumor antigens", Prog. Clin. Pathol., 9:121-133 (1984).
Flies, et al., "Cutting edge: A monoclonal antibody specific for the programmed death-1 homolog prevents graft-versus-host disease in mouise models", J Immunol., 187:1537-41 (2011).
Freedman, et al., "Intraperitoneal adoptive immunotherapy of ovarian carcinoma with tumor-infiltrating lymphocytes and low-dose recombinant interleukin-2: a pilot trial", J. of Immunotherapy Emphasis Tumor Immunol., 16(3):196-210 (1994).
Freeman, et al., "Engagement of the PD-1 immunoinhibitory receptor by a novel B7 family member leads to negative regulation of lymphocyte activation", J. Exp. Med., 192(7):1027-34 (2000).
Gandhi, et al., "Costimulation targeting therapies in organ transplantation", Curr Opin Organ Transplant, 13:622-26 (2008).
Genbank Accession No. AY280972.1 "*Homo sapiens* immune costimulatory protein B7-H4 mRNA, complete cds", 2 pages, submitted Apr. 22, 2003, first published Jun. 1, 2003, accessed Feb. 18, 2009.

(56) References Cited

OTHER PUBLICATIONS

Genbank Accession No. NM_178594, "Mus musculus V-set domain containing T cell activation inhibitor 1 (Vtcn1), mRNA", 4 pages, submitted Oct. 1, 2009, updated Mar. 26, 2012, accessed May 15, 2012.
Guatelli, "Isothermal, in vitro amplification of nucleic acids by a multienzyme reaction modeled after retroviral replication", Proc. Natl. Acad. Sci. USA, 87(6):1874-1878 (1990).
Guo, et al., "All-trans retinol, vitamin D and other hydrophobic compounds bind in the axial pore of the five-stranded coiled-coil domain of cartilage oligomeric matrix protein", EMBO J., 17:5265-72 (1998).
Halloran, et al., "The role of an epithelial neutrophil-activating peptide-78-like protein in rat adjuvant-induced arthritis", J. Immunol., 162(12):7492-500 (1999).
Hammer, et al., "Promiscuous and allete-specific anchors in HLA-DR-binding peptides", Cell, 74(1):197-203 (1993).
Healy, et al., "Neutrophil transendothelial migration potential predicts rejection severity in human cardiac transplantation", Eur J Cardiothorac Surg. 29:760-6 (2006).
Henikoff, "Amino acid substitution matrics from protein blocks", Proc. Natl. Acad. Sci. U.S.A., 89:10915-10919 (1992).
Hickman, "Gene expression following direct injection of DNA into liver", Hum. Gene Ther., 5:1477-1483 (1994).
Hill, et al., "A field guide to foldamers", Chem Rev., 101(12):3893-1042 (2001).
Hochman, "An Active antibody fragment (Fv) composed of the variable portions of heavy and light chains",Biochemistry, 12:1130-1135 (1973).
Hoiseth and Stocker, "Aromatic-dependent *Salmonella* typhimurium are non-virulent and effective as live vaccines", Nature, 291, 238-239 (1981).
Hu, et al., "WD-40 repeat region regulates Apaf-1 self-association and procaspase-9 activation", J Biol Chem., 273:33489-94 (1998).
Huang, "Structural chemistry and therapeutic intervention of protein-protein interactions in immune response, human immunodeficiency virus entry, and apoptosis," Pharmacology and Therapeutics, 86:201-15 (2000).
Hubbard, et al., "Anti-neutrophil-elastase defenses of the lower respiratory tract in alpha 1-antitrypsin deficiency directly augmented with an aerosol of alpha 1-antitrypsin", Ann. Intern. Med., 111(3):206-12 (1989).
Huse, "Generation of a large combinatorial library of the immunoglobulin repertoire in phage lambda", Science, 246(4935):1275-1281 (1989).
Huston, "Protein engineering of antibody binding sites: recovery of specific activity in an anti-digoxin single-chain Fv analogue produced in *Escherichia coli*", Proc. Natl. Acad. Sci. USA, 85:5879-5883 (1988).
Hyrup, et al., "Peptide nucleic acids (PNA): synthesis, properties and potential applications", Bioorgan. Med. Chem. 4:5-23 (1996).
Ikonomidis, "Delivery of a viral antigen to the class I processing and presentation pathway by Listeria monocytogenes", J. Exp. Med., 180:2209-2218 (1994).
Jablonska and Peitruska, "Release of soluble tumor necrosis factor receptors from polymorphonuclear cells of breast cancer patients", Arch. Immunol. Ther. Exp. (Warsz), 45(5-6), 449-453 (1997).
Jeannin, et al., "Soluble CD86 is a costimulatory molecule for human T lymphocytes", Immunity, 13(3):303-12 (2000).
Jerne, "Towards a network theory of the immune system" Ann. Immunol., 125C:373-389 (1974).
Jost, "Mammalian expression and secretion of functional single-chain Fv molecules", J Biol Chem., 269:26267-26273 (1994).
Kakimoto, et al., "Suppressive effect of a neutrophil elastase inhibitor on the development of collagen-induced arthritis", Cell Immunol., 165(1):26-32 (1995).
Kamata, et al., "src homology 2 domain-containing tyrosine phosohatase SHP-1 controls the development of allergic airway inflammation", J. Clin. Invest., 111:109-119 (2003).
Katahira, et al., "Complex formation between Tap and p15 affects binding to FG-repeat nucleoparins and nucleocytoplasmic shuttling", J. Biol. Chem., 277:9242-6 (2002).
Keir and Sharpe, "The B7/CD28 costimulatory family in autoimmunity", Immunol. Rev., 204:128-43 (2005).
Keliey and Roths, "Interaction of mutant Ipr gene with background strain influences renal disease", Clin. Immuno. Immunopathol., 37(2):220-9 (1985).
Kikuchi, "Effects of granulocyte-colony-stimulating factor and interleukin-2 on escites formation and the survival time of nude mice bearing human ovarian cancer cells", Cancer Immunol., Immunother., 43(5): 257-261 (1998).
Kim, et al., "Clustering of Shaker-type K+ channels by interaction with a family of membrane-asociated guanylate kinases", Nature, 378: 85-8 (1995).
Kinoshita, et al., "Costimulation by B7-1 and B7-2 is required for autoimmune disease in MRL-Faslpr mice", J. Immunol., 164(11):6046-56 (2000).
Knapp and Liu, "Hydrodynamic delivery of DNA", Methods Mol. Bio., 245-245-50 (2004).
Kohler and Milstein, "Continuous cultures of fused cells secreting antibody of predefined specificity", Nature, 256:495-497 (1975).
Komau, et al., "Domain interaction between NMDA receptor subunits and the postsynaptic density protein PSD-95", Sci., 369:1737-40 (1995).
Kotzin, "Systemic pupus erthematosus", Cell, 85(3), 303-6 (1996).
Krambeck, et al., "B7-H4 expression in renal cell carcinoma and tumor vasculature: associations with cancer progression and survival", Proc. Natl. Acad. Sci. USA, 103 (27):10391-10396 (2006).
Krummel and Allison, "CTLA-4 engagement inhibits IL-2 accumulation and cell cycle progression upon activation of resting T cells", J. Exp. Med., 183:2533-40 (1996).
Kryczek, et al., "B7-H4 expression identifies a novel suppressive macrophage population in human ovarian carcinoma", J Exp. Med., 203:871-881 (2006).
Kryczek, et al., "Cutting edge: Induction of B7-H4 on APCs through IL-10: Novel suppressive mode for regulatory T cells", J. Immunol., 177(1):40-44 (2006).
Latchman, et al., "PD-L2 is a second ligand for PD-1 and inhibits T cell activation", Nature Immunol., 2:261-8 (2001).
Lenshow, et al., "CD28/B7 system of T cell costimulation", Annu. Rev. Immunol., 14:233-58 (1996).
Lewis, "PCRs Competitors are Alive and Well and Moving Raidly Towards Commercialization", Genetic Engineering News 12:1-3 (1992).
Li, et al., "Biochemical analysis of the regulatory T cell protein lymphocyte activation gene-3 (LAG-3 CD223)", J. Immunol., 173(11):6806-1 2 (2004).
Liang, et al., "Autoantibody responses and pathology regulated by B7-1 and B7-2 costimulation in MRL/Ipr lupus", J. Immunol., 165(6):3436-43 (2000).
Lissoni, "Intracavitary administration of interleukin-2 as palliative therapy for neoplastic effusions", Tumarl, 78(2):118-120 (1992).
Liu, "Cationic transfection lipids", Curr. Med. Chem., 10:1307-1315 (2003).
Lowenstein, "Simultaneous detection of amplicon and HSV-1 helper encoded proteins reveals that neurons and astrocytoms cells do express amplicon-borne transgenes in the absence of synthesis of virus immediate early proteins", Brain Res. Molec. Brain Res, 30:169-175 (1995).
Malashkevich, et al., "The crystal structure of a five-stranded coiled coil in COMP: a prototype ion channel", Science, 274: 761-5 (1996).
Malchesky, et al., "Are selective macromolecule removal plamapheresis systems useful for autoimmune diseasees or hyperlipidemia?", ASAIO J., 39(4):868-72 (1993).
Mathiowitz, "Novel microcapsules for delivery systems", Reactive Polymers, 6:275-283 (1987).
Mathiowitz, "Polyanhydride micropheres as drug carriers. II. microencapsulation by solvent removal", J. Appl. Polymer Sci., 35:755-774 (1988).

(56) References Cited

OTHER PUBLICATIONS

Mathiowitz and Langer, "Polyanhydride microspheres as drug carriers. I. Hot-melt microencapsulation", J. Controlled Release, 5:13-22 (1987).
Matta, et al., "IL-27 production and STAT3-dependent upregulation of B7-H1 mediate immune regulatory functions of liver plasmacytoid dendritic cells", J Immunol., 188:5227-37 (2012).
McColl, et al., "Treatment with anti-granulocyte antibodies inhibits the effector phase of experimental autoimmune encephalomyelitis", J. Immunol., 161(11), 6421-6 (1998).
McGrath and Nader, "The role of coinhibitory signaling pathways in transplantation and tolerance", Frontiers in Immunol., 3(47):1-17 (2012).
Medina, et al., "Therapeutic effect of phenantroline in two rat models of inflammatory bowel disease", Scand J Gastroenterol., 36(12):1314-9 (2001).
Metzler, et al., "Solution structure of human CTLA-4 and delineation of a CD80/CD86 binding site conserved in CD28", Nat. Struct. Biol., 4(7):527-31 (1997).
Michael, et al., "The hematologic aspects of disseminated (systemic) lupus erthematosus", Blood, 6(11):1059-72 (1951).
Moreland, et al., "Treatment of rheumatoid arthritis with a recombinant human tumor necrosis factor receptor (p75)-Fc fusion protein", N. Engl. J. Med., 337:141-7 (1997).
Moss, "Poxvirus expression vectors", Curr. Top. Microbiol. Immunol., 158:25-38 (1992).
Moss, "Poxvirus vectors: cytoplasmic expression of transferred genes", Curr. Opin. Genet. Dev. 3:86-90 (1993).
Moss, "Use of vaccinia virus as an infectious molecular cloning and expression vector", Gene Amplif Anal 3:201-213 (1983).
Moss, "Vaccinia virus: a tool for research and vaccine development", Science, 252:1662-1667 (1991).
Moss, "Vaccinia virus vectors", Biotechnology, 20: 345-362 (1992).
Mueller, et al., "Humanized porcine VCAM-specific monoclonal antibodies with chimeric IgG2/G4 constant regions block human leukocyte binding to porcine endothelial cells", Molecular Immonology, 34(6): 441-52 (1997).
Murphy, "Long-term correction of obesity and diabetes in genetically obese mice by a single inframuscular injection of recombinant adeno-associated virus encoding mouse leptin", Proc Natl Acad Sci., 94:13921-13926 (1997).
Nandakumar, et al., "Collagen type II-specific monoclonal antibody-induced arthritis in mice: description of the disease and the influence of age, sex, and genes", Am. J. Pathol., 163(5), 1827-37 (2003).
Nathan, "Neutrophils and immunity: challenges and opportunities", Nature Rev. Immunol., 6:173-182 (2006).
Needleman and Wunsch, "A general method applicable to the search for similarities in the amino acid sequence of two proteins", J. Mol. Biol., 48:443-453 (1970).
Newmark, et al., "Preparation and properties of adducts of streptokinase and streptokinase-plasmin complex with polyethylene glycol and pluronic Polyol F38", J. Appl. Biochem., 4:185-189 (1982).
Ostberg et al., "Human X (mouse X human) hybridomas stably producing human antibodies", Hybridoma, 2:361-367 (1983).
Ottow, et al., "Immunotherapy of intraperitioneal cancer with interleukin 2 and lymphokine-activated killer cells reduces tumor load and prolongs survival in murine models" Cellular immumology, 104:366-376 (1987).
Ou, et al., "B7-H4.Ig inhibits human beta-cell destruction mediated by beta cell-specific cytotoxic T cells derived from patients with type 1 diabetes", 54(Suppl. 1):A311 (2005).
O\Brien, "An improved method of preparing microcarriers for biolistic transfection", Brain Res. Brain Res. Protco., 10:12-15 (2002).
Parra and Bond, "Inverse agonism: from curiosity to accepted dogma, but is it clinically relevant?", Curr. Opin. Pharmacol., 7(2):146-50 (2007).

Paterson, et al., "The programmed deth-1 ligand 1:B7-1 pathway restrains diabetogenic effector T cells in vivo", J Immunol., 187(3):1097-1105 (2011).
Peplinski, "Vaccinia virus for human gene therapy", Surgical Oncology Clinics of North America, 7: 575-588 (1998).
Piccini and Paoletti, "Vaccinia: virus, vector, vaccine", Adv. Virus Res., 34:43-64 (1988).vbTab.
Pillai, et al., "Overview of immunosuppression in liver transplantation", World J Gastroenterol, 15(34): 4225-33 (2009).
Pillinger and Abramson, "The neutrophil in rheumatoid arthritis", Rheum. Dis. Clin. North. Am., 21(3):691-714 (1995).
Pluckthun, "Expression of functional antibody Fv and Fab fragments in *Escherichia coli*", Methods Enzymol., 178: 497-515 (1989).
Poirier, "Protective immunity evoked by oral administration of attenuated aroA *Salmonella* typhimurium expressing cloned streptococcal M protein", J. Exp. Med., 168:25-32 (1988).
Prasad, et al., "B7S1, a novel B7 family member that negatively regulates T cell activation", Immunity, 18(6):863-873 (2003).
Queen, et al., "A humanized antibody that binds to the interleukin 2 receptor", Proc. Natl. Acad. Sci. USA, 86(24):10029-10033 (1989).
Queen, et al., "Cell-type specific regulation of a kappa immunoglobulin gene by promoter and enhancer elements", Immunol. Rev., 89:49 (1986).
Quismorio, "Hemotalogica and lymphoid abnormalities in systemic lupus etythematosus"in Dublo\s Lupus Erthematosus, (eds. Wallace and Han), Lippincott & Williams:Phillidelphia, PA, pp. 793-819 (2002).
Radsak, et al., "The heat shock protein Gp96 binds to human neutrophils and monocytes and stimulates effector functions", Blood, 101:2810-2815 (2003).
Radsak, et al., "Triggering receptor expressed on myeloid cells-1 in neutrophil inflammatory responses: differential regulation of activation and survival", J. Immunol., 172:4956-4963 (2004).
Radziejewski, et al., "Heterodimers of the neurotrophic factors: formation, isolation, and differential stability", Biochem., 32(48): 13350-6 (1993).
Rajewsky, "Genetics, expression, and function of idiotypes", Ann. Rev. Immunol., 1:569-607 (1983).
Rathmell and Thompson, "The central effectors of cell death in the immune system", Annu. Rev. Immunol., 17:781-828 (1999).
Reynolds, "Chimeric viral vectors—the best of both worlds", Molecular Medicine Today, 5:25-31 (1999).
Rousseaux, "Optimal conditions for the preparation of proteolytic fragments from monoclonal IgG of different rat IgG subclasses", Meth. Enzymol., 121:663-69 (1986).
Sadoff, "Oral Salmonella typhimurium vaccine expressing circumsporozoite protein protects against malaria", Science, 240:336-338 (1988).
Salceda, et al. "The immunomodulatory protein B7-H4 is overexpressed in breast and ovarian cancers and promotes epithelial cell transformation", Exp. Cell Res., 306(1):128-41 (2005).
Samulski, "Targeted intergration of adeno-associated virus (AAV) into human chromosome 19", EMBO J., 10:3941-3950 (1991).
Santos, et al., "Anti-neutrophil monoclonal antibody therapy inhibits the development of adjuvant arthritis", Clin. Exp. Immunol., 107(2):24-53 (1997).
Scapini, et al., "The neutrophil as a cellular source of chemokines", Immunol. Rev., I77: 195-203 (2000).
Schafer, et al., "Induction of a cellular immune response to a foreign antigen by a recombinant Listeria monocytogenes vaccine", J. Immunol., 149:53-59 (1992).
Schimmer, et al., "Streptococcal cell wall-induced arthritis. Requirements for neutrophils, P-selectin, intercellular adhesion molecule-I, and macrophage-inflammatory protein-2", J. Immunol., 159(8):4103-8 (1997).
Sharon, et al., "Preparation of Fv fragment from the mouse myeloma XRPC-25 immunoglobulin possessing anti-dinitrophenyl activity", Biochemistry, 16:1591-1594 (1976).
Sica, et al., "B7-H4, a molecule of the B7 family, negatively regulates T cell immunity", Immunity, 18:849-861 (2003).

(56) References Cited

OTHER PUBLICATIONS

Simon, et al., "B7-H4 is a novel membrane-bound protein and a candidate serum and tissue biomarker for ovarian cancer", Cancer Res., 66(3):1570-1575 (2006).
Sinigaglia, et al., "A malaria T-cell epitope recognized in association with most mouse and human MHC class II molecules", Nature, 336(6201):778-780 (1988).
Skerra, "Assembly of a functional immunoglobulin Fv fragment in *Escherichia coli* ", Science, 240: 1038-1041 (1988).
Skolnick et al., "From genes to protein structure and function: novel applications of computational approaches in the genomic era", Trends Biotechnol., 18(1):34-9 (2000).
Son, "Cisplatin-based interferon gamma gene therapy of murine ovarian carcinoma", Cancer Gene Therapy, 4(6):391-396 (1997).
Soriano, "Targeted and nontargeted liposomes for in vivo transfer to rat liver cells of a plasmid containing the preproinsulin I gene", Proc. Natl. Acad. Sci. USA, 80:7128-7131 (1963).
Southwood, et al., "Several common HLA-DR types share largely overlapping peptide binding repertoires", J. Immunology, 160(7):3363-3373 (1998).
Sparano, et al., "Phase II trials of high-dose interleukin-2 and lymphokine-activated killer cells in advanced breast carcinoma and carcinoma of the lung, ovary, and pancreas and other tumors", J. of Immunotherapy Emphasis Tumor Immunol., 15(3):216-223 (1994).
Stavenhagen, et al., "Fc optimization of therapeutic antibodies enhances their ability to kill tumor cells in vitro and controls tumor expansion in vivo via low-affinity activating Fcgamma receptors", Cancer Res., 57(18):8862-90 (2007).
Stone, "Viral vectors for gene delivery and gene therapy within the endocrine system", J. Endocrinology, 164:103-118 (2000).
Stover, "New use of BCG for recombinant vaccines", Nature, 351:456-460 (1991).
Sudol, "Structure and function of the WW domain", Prog. Biophys. Mol. Bio., 65:113-32 (1996).
Sugaya, "Inhibition of tumor growth by direct intratumoral gene transfer of herpes simplex virus thymidine kinase gene with DNA-liposome complexes", Hum. Gene Ther., 7(2):223-230 (1996).
Suh, et al., "Generation and characterization of B7-H4/B7S1/B7x-deficient mice", Mol. Cell. Biol., 26:6403-6411 (2006).
Summerton and Weller, "Morpholino antisense oligomers: design, preparation, and properties", Antisense Nucleic Acid Drug Dev. 7:187-95 (1997).
Sun, et al., "B7-H3 and B7-H4 expression in non-small-cell lung cancer", Lung Cancer, 53 (2):143-151 (2006).
Sun, et al., "Costimulatory molecule-targeted antibody therapy of a spontaneous autoimmune disease", Nat. Med. 8(12):1405-13 (2002).
Swallow, et al., "B7h, a novel costimulatory homolog of B7.1 and B7.2, is induced by TNFalpha", Immunity, 11:423-432 (1999).
Szala, "The use of cationic liposomes DC-CHOL/DOPE and DDAB/DOPE for direct transfer of *Escherichia coli*cytosine deaminase gene into growing melanoma tumors", Gene Therapy, 3(11): 1026-1031 (1996).
Tada, et al., "CD28-deficient mice are highly resistant to collagen-induced arthritis", J. Immunol., 162(1):203-8 (1999).
Tamada, et al., "Cutting egde: selective impairment of CD8+ T cell function in mice lacking the TNF superfamily member LIGHT", J Immunol., 168:4832-4835 (2002).
Tamada, et al., "Modulation of T-cell-mediated immunity in tumor and graft-versus-host disease models through the LIGHT co-stimulatory pathway", Nature Med., 6:283-289 (2000).
Tamura, et al., "B7-H1 costimulation preferentially enhances CD28-independent T-helper cell function", Blood, 97:1809-1816 (2001).
Titomirov, "In vivo electroporation and stable transformation of skin cells of newborn mice by plasmid DNA", Biochim. Biophys. Acta., 1088:131-134 (1991).
Tringler, et al., "B7-H4 is highly expressed in ductal and lobular breast cancer", Clin. Cancer Res., 11(5):1842-1848 (2005).
Tringler, et al., "B7-H4 overexpression in ovarian tumors", Gynecol. Oncol., 100(1):44-52 (2006).
Tseng, et al., "B7-DC, a new dendritic cell molecule with potent costimulatory properties for T cells", J. Exp. Med., 193:839-846 (2001).
Tsushima, et al., "Preferential contribution of B7-H1 to programmed death-1-mediated regulation of hapten-specific allergic inflammatory responses", Eur. J. Immunol. 33:2773-2782 (2003).
Urbain, "Idiotypes, recurrent idiotypes and internal images", Ann. Immunol. 133D(2):179-189 (1982).
Vidal, et al., "Design of peptoid analogue dimers and measure of their affinity for Grb2 SH3 domains", Biochemistry, 43, 7336-44 ((2004).
Vincennti, et al., "Costimulation blockade in autoimmunity and transplantation", J Allergy Clin Immunol, 121(2):299-306 (2008).
Wahl., "Improved radioimaging and tumor localization with monoclonal F(ab')2", J. Nuc. Med. 24:316-325 (1983).
Walunas, et al., "CTLA-4 ligation blocks CD28-dependent T cell activation", J. Exp. Med., 183:2541-50 (1996).
Wan, et al., "Aberrant regulation of synovial T cell activation by soluble costimulatory molecules in rheumatoid arthritis", J.Immunol., 177(12):8844-50 (2006).
Wang, et al., "B7-H4 pathway in islet transplantation and $^2$-cell replacement therapies", J Transplant., Article ID 418902:1-8 (2011).
Wang, et al., "Costimulation of T cells by B7-H2, a B7-like molecule that binds ICOS", Blood, 96:2808-13 (2000).
Wang and Huang, "pH-sensitive immunoliposomes mediate target-cell-specific delivery and controlled expression of a foreign gene in mouse", Proc. Natl. Acad. Sci. USA, 84:7851 (1987).
Watanabe, et al., "BTLA is a lymphocyte inhibitory receptor with similarities to CTLA-4 and PD-1", Nature Immunol., 4(7):670-679 (2006).
Weiss, "Hot prospect for new gene amplifier", Science 254:1292-1293 (1991).
Weiss and Taylor, "Retrovirus receptors", Cell, 82:531-533 (1995).
Wilcox, et al., "Ligation of CD137 receptor prevents and reverses established anergy of CD8+ cytolytic T lymphocytes in vivo", Blood, 103:177-184 (2004).
Williams, et al., "Synergy between anti-CD4 and anti-tumor necrosis factor in the amelioration of established collagen-induced arthritis", Proc. Natl. Acad. Sci. U.S.A., 91:2762-6 (1994).
Wilson, "Hepatocyte-directed gene transfer in vivo leads to transient improvement of hypercholesterolemia in low density Ilpoprotein receptor-deficient rabbits", J. Biol. Chem., 267:963-967 (1992).
Winter, "Man-made antibodies", Nature, 349:293-299 (1991).
Wipke and Allen, "Essential role of neutrophils in the initiation and progression of a murine model of rheumatoid arthritis", J. Immunol., 167(3):1601-8 (2001).
Wolff, "Direct gene transfer into mouse muscle in vivo", Science, 247:1465-1468 (1990).
Wong, "Human GM-CSF: molecular Cloning of the complementary DNA and purification of the natural and recombinant proteins", Science, 228(4701):810-815 (1985).
Wu, "Receptor-mediated gene delivery and expression in vivo", J. Biol. Chem., 263:14621-14624 (1988).
Wu, "Targeting genes: delivery and persistent expression of a foreign gene driven by mammalian regulatory elements in vivo", J. Biol. Chem., 264:16985-16987 (1989).
Yang, et al., "The novel costimulatory programmed death ligand 1/B7.1 pathway is functional in inhibiting alloimmune responses in vivo", J Immunol., 187:1113-19 (2011).
Yoshinaga, et al., "T-cell co-stimulation through B7RP-1 and ICOS", Nature, 402:827-32 (1999).
Yu, "Liposome-mediated in vivo E1A gene transfer suppressed dissemination of ovariam cancer cells that overexpress HER-2/neu", Oncogene, 11(7):1383-1388 (1995).
Yuan, et al., "B7-H4 transfection prolongs beta-cell graft survival", Transplant Immun., 21(3):143-9 (2009).
Zakaria, et al., "Plasmapheresis in severe autoimmune hepatitis", Hepatology, 34(4):A529 (2001).

(56) References Cited

OTHER PUBLICATIONS

Zang, et al., "B7x: A widely expressed B7 family member that Inhibits T cell activation", Proc. Natl. Acad. Sci. USA, 100(18):10388-10392 (2003).

Zhou, et al., "Structure and ligand recognition of the phosphotyrosine binding domain of Shc", Nature, 378:584-92 (1995).

* cited by examiner

♦ Day 0: 50 ug of PLP$_{139-151}$ emulsified in CFA
♦ Injection of B7-H4-Ig (5 or 25 mg/kg) 3x/wk

B7-H4 FUSION PROTEINS AND METHODS OF USE THEREOF

CROSS-REFERENCE TO RELATED APPLICATIONS

This application is a continuation of U.S. application Ser. No. 13/392,811, now U.S. Pat. No. 9,011,853, filed Feb. 27, 2012, which is a 371 of International Application No. PCT/US2010/047366 filed under the Patent Cooperation Treaty on Aug. 31, 2010, which claims benefit of and priority to U.S. Provisional Patent Application No. 61/238, 605 filed on Aug. 31, 2009, U.S. Provisional Patent Application No. 61/266,854, filed on Dec. 4, 2009, U.S. Provisional Patent Application No. 61/254,930 filed on Oct. 26, 2009, U.S. Provisional Patent Application No. 61/286,537 filed on Dec. 15, 2009, and U.S. Provisional Patent Application No. 61/378,361 filed Aug. 30, 2010.

FIELD OF THE INVENTION

This invention relates to B7-H4 fusion proteins and methods for modulating immune responses in a subject using B7-H4 fusion proteins.

REFERENCE TO SEQUENCE LISTING

The Sequence Listing submitted as a text file named "AMP_110.NP2 CON_ST25.txt," created on May 13, 2015, and having a size of 327,182 bytes is hereby incorporated by reference.

BACKGROUND OF THE INVENTION

An antigen specific T cell response is mediated by two signals: first, engagement of the TCR with antigenic peptide presented in the context of MHC (signal 1), and second, a second antigen-independent signal delivered by contact between different receptor/ligand pairs (signal 2). This "second signal" is critical in determining the type of T cell response (activation versus tolerance) as well as the strength and duration of that response, and is regulated by both positive and negative signals from costimulatory molecules, such as the B7 family of proteins. The most extensively characterized T cell costimulatory pathway is B7-CD28, in which B7-1 (CD80) and B7-2 (CD86) each can engage the stimulatory CD28 receptor and the inhibitory CTLA-4 (CD152) receptor. In conjunction with signaling through the T cell receptor, CD28 ligation increases antigen-specific proliferation of T cells, enhances production of cytokines, stimulates differentiation and effector function, and promotes survival of T cells (Lenshow, et al., *Annu. Rev. Immunol.*, 14:233-258 (1996); Chambers and Allison, *Curr. Opin. Immunol.*, 9:396-404 (1997); and Rathmell and Thompson, *Annu. Rev. Immunol.*, 17:781-828 (1999)). In contrast, signaling through CTLA-4 is thought to deliver a negative signal that inhibits T cell proliferation, IL-2 production, and cell cycle progression (Krummel and Allison, *J. Exp. Med.*, 183:2533-2540 (1996); and Walunas, et al., *J. Exp. Med.*, 183:2541-2550 (1996)). Other members of the B7 family include B7-H1 (Dong, et al., *Nature Med.*, 5:1365-1369 (1999); and Freeman, et al., *J. Exp. Med.*, 192:1-9 (2000)), B7-DC (Tseng, et al., *J. Exp. Med.*, 193: 839-846 (2001); and Latchman, et al., *Nature Immunol.*, 2:261-268 (2001)), B7-H2 (Wang, et al., *Blood*, 96:2808-2813 (2000); Swallow, et al., *Immunity*, 11:423-432 (1999); and Yoshinaga, et al., *Nature*, 402:827-832 (1999)), B7-H3 (Chapoval, et al., *Nature Immunol.*, 2:269-274 (2001)) and B7-H4 (Choi, et al., *J. Immunol.*, 171:4650-4654 (2003); Sica, et al., *Immunity*, 18:849-861 (2003); Prasad, et al., *Immunity*, 18:863-873 (2003); and Zang, et al., *Proc. Natl. Acad. Sci. U.S.A.*, 100:10388-10392 (2003)). B7-H1 and B7-DC are ligands for PD-1, B7-H2 is a ligand for ICOS, and B7-H3 remains at this time an orphan ligand (Dong, et al., *Immunol. Res.*, 28:39-48 (2003)).

B7-H4 is member of the B7 family that is a negative regulator of T cell responses. Human and mouse B7-H4 share 87% amino acid identity, suggesting an important evolutionarily conserved function. Human and mouse B7-H4 mRNAs are expressed broadly in both lymphoid (spleen and thymus) and nonlymphoid organs (including lung, liver, testis, ovary, placenta, skeletal muscle, pancreas, and small intestine). Limited studies of B7-H4 protein expression indicate that B7-H4 is not expressed on freshly isolated human T cells, B cells, DC, and monocytes, but it can be induced on these cell types after in vitro stimulation. Immunohistochemical staining shows that B7-H4 is highly expressed in breast, renal, lung and ovarian tumors, and reverse transcriptase polymerase chain reaction (RT-PCR) analyses indicate that mouse B7-H4 also is highly expressed in a number of tumor cell lines, including prostate, lung, and colon carcinomas. B7-H4 is highly expressed by tumor associated macrophages (TAMs) and is present in tumor vasculature. Regulatory T cells (Tregs) induce upregulation of B7-H4 on TAMs via IL-6 and IL-10; this is thought to be one of the mechanisms by which Tregs contribute to immune suppression. (Kryczek, J. I., *J. Immunol.*, 177(1): 40-44 (2006)). B7-H4 expression has also been observed in tubule epithelial cells of diseased kidneys (Chen, Y., *Kidney Int.*, 70(12):2092-9 (2006) Epub 2006 Oct. 18).

The receptor for B7-H4 has not been cloned. B7-H4 has been shown not to bind to known CD28 family members such as CD28, CTLA-4, ICOS, and PD-1 (Sica, et al., *Immunity*, 18:849-861 (2003)), and these are therefore not potential receptors for B7-H4. Functional studies using B7-H4 transfectants and B7-H4-Ig fusion proteins demonstrate that B7-H4 delivers a signal that inhibits TCR-mediated $CD4^+$ and $CD8^+$ T cell proliferation, cell-cycle progression and IL-2 production. B7-1 costimulation cannot overcome B7-H4-Ig-induced inhibition. In agreement with the in vitro activity, B7-H4 knock-out mice develop autoimmunity. The broad and inducible expression of B7-H4, together with functional studies, suggests that B7-H4 serves to downregulate immune responses in peripheral tissues.

More recent results demonstrate that B7-H4 also acts as a negative regulator of neutrophil response. Neutrophils are a key component of the innate immune system and are a first line of host defense against pathogens. However, neutrophils can also contribute to chronic inflammation and autoimmune disease. B7-H4 knockout mice display increased Th1 responses and are more resistant to infection by *Listeria monocytogenes* due to an augmented immune response that is neutrophil dependent (Suh. W. K., et al., *Mol Cell Biol.*, 26(17):6403-11 (2006) and Zhu, G., et al., *Blood*, 113(8): 1759-67 (2009) Epub 2008 Dec. 24). Mice hydrodynamically transfected with monomeric B7-H4 IgV domain or extracellular domain (ECD) increased neutrophil response to lipopolysaccharide (LPS) and *Listeria* infection, while dimeric B7-H4-Ig reduces proliferation of bone marrow derived neutrophil precursors (Zhu, G., et al., *Blood*, 113 (8):1759-67 (2009) Epub 2008 Dec. 24).

Certain immune cells and immune cell signal transduction pathways are promising targets for new agents for treating immune disorders. For example Th1, Th17, Th22, and regulatory T cells (Tregs) play important roles in mediating autoimmunity and inflammation. Mounting evidence from numerous studies shows the importance of these immune cells in disorders such as rheumatoid arthritis, inflammatory bowel disease, multiple sclerosis, psoriasis, lupus erythematosus and uveitis. Most existing therapies target only one pathway at a time. Thus, there is a need for therapies that target multiple cells and pathways involved in autoimmunity and inflammation, such as Th1, Th17, Th22, Tregs, or other cells that secrete, or cause other cells to secrete, inflammatory molecules such as cytokines, metalloproteases, chemokines and other molecules, including, but not limited to, IL-1β, TNF-α, TGF-beta, IFN-γ, IL-17, IL-6, IL-23, IL-22, IL-21, IL-10 and MMPs.

Therefore it is an object of the invention to provide compositions and methods for modulating Th1, Th17, Th22, or other cells that secrete, or cause other cells to secrete, inflammatory molecules, including, but not limited to, IL-1β, TNF-α, TGF-beta, IFN-γ, IL-17, IL-6, IL-23, IL-22, IL-21, and MMPs.

It is another object of the invention to provide compositions and methods for modulation of at least two immune pathways that result in the secretion of one or more inflammatory molecules, including, but not limited to, IL-1β, TNF-α, TGF-beta, IFN-γ, IL-17, IL-6, IL-23, IL-22, IL-21, and MMPs, preferably by Th1, Th17 or Th22 cells.

It is another object of the invention to provide compositions and methods for modulation of the Treg cells and pathways, such as IL-10 and TGF-beta secretion.

It is another object of the invention to provide compositions and methods for modulating the proinflammatory activity of Th1, Th17 or Th22 T cells while simultaneously increasing or promoting the activity of Tregs.

It is an object of the invention to provide compositions containing B7-H4 polypeptides that function to decrease or inhibit antigen-specific proliferation of T cells, decrease or inhibit production of pro-inflammatory molecules by T cells, decrease or inhibit differentiation and effector function of Th1, Th17 or Th22 cells, and decrease or inhibit survival of Th1, Th17 or Th22 cells.

It is another object of the invention to provide compositions containing B7-H4 polypeptides that function to increase or promote the activity of Tregs, increase the production of inflammatory molecules such as IL-10 from Tregs, increase the differentiation of naïve T cells into Tregs, increase the number of Tregs, or increase the survival of Tregs.

It is another object of the invention to provide compositions containing B7-H4 polypeptides that function to inhibit or decrease the proinflammatory activity of Th1, Th17 or Th22 T cells while simultaneously increasing or promoting the activity of Tregs.

It is another object of the invention to provide isolated nucleic acid molecules encoding B7-H4 compositions.

It is another object of the invention to provide cells containing vectors that express nucleic acid molecules encoding B7-H4 compositions.

It is still a further object of the invention to provide methods for decreasing or inhibiting pro-inflammatory T cell activation by contacting them with B7-H4 compositions.

It is still a further object of the invention to provide methods for the treatment of inflammatory and autoimmune diseases and disorders.

It is still a further object of the invention to provide methods for administering B7-H4 compositions, nucleic acids encoding the same, or cells transfected or transduced with nucleic acids encoding B7-H4 compositions to a mammal in need thereof.

It is another object to provide compositions and methods for increasing Treg biological activity.

It is yet another object to provide compositions and methods for inhibiting or reducing eptitope spreading.

It is another object to provide compositions and methods for inhibiting differentiation of naïve T cells into Th1, Th17, Th22, or other cells that secrete, or cause other cells to secrete, pro-inflammatory molecules, including, but not limited to, IL-1β, TNF-α, TGF-beta, IFN-γ, IL-17, IL-6, IL-23, IL-22, IL-21, and MMPs.

It is another object to provide compositions and methods for inhibiting the differentiation and maturation of immature antigen-presenting cells.

It is another object of the invention to monitor patients who would benefit from treatment with the compositions and methods disclosed by measuring the levels of biomarkers such as inflammatory chemokines, cytokines or other molecules, or gene expression of biomarkers in the patient.

It is another object of the invention to identify patients who would benefit from treatment with the compositions and methods disclosed by measuring the levels of biomarkers such as inflammatory chemokines, cytokines or other molecules in the patient.

It is another object of the invention to identify patients who would benefit from treatment with the compositions and methods disclosed by identifying patients with polymorphisms in genes encoding biomarkers such as inflammatory chemokines, cytokines or other molecules.

It is another object of the invention to provide combination therapies for treating patients with inflammatory and autoimmune diseases and disorders.

It is another object of the invention to provide compositions for treating patients who do not respond to TNF blockers.

It is another object of the invention to provide compositions for treating chronic and persistent inflammation.

SUMMARY OF THE INVENTION

Fusion proteins containing B7-H4 polypeptides are disclosed. B7-H4 fusion polypeptides have a first fusion partner comprising all or a part of a B7-H4 protein fused to a second polypeptide directly or indirectly via a linker peptide sequence that is fused to the second polypeptide. The B7-H4 polypeptide may be of any species of origin. In preferred embodiments, the B7-H4 polypeptide is of murine, non-human primate or human origin. In one embodiment the B7-H4 fusion protein inhibits the inflammatory activity of Th1, Th17, Th22, or other cells that secrete, or cause other cells to secrete, inflammatory molecules, including, but not limited to, IL-1β, TNF-α, TGF-beta, IFN-γ, IL-17, IL-6, IL-23, IL-22, IL-21, and MMPs. The B7-H4 fusion protein can also increase the suppressive capacity of Tregs by increasing the production of molecules such as the cytokine IL-10.

The B7-H4 fusion proteins can include full-length B7-H4 polypeptides, or a fragment thereof. In one embodiment, the B7-H4 polypeptide is a soluble fragment of full-length B7-H4. Fragments include those that retain the ability to bind to their natural receptors and incorporate some, or all, of the extracellular domain of the B7-H4 polypeptide, and lack some or all of the intracellular and/or transmembrane domains. In one embodiment, B7-H4 polypeptide fragments include the entire extracellular domain of the B7-H4 polypeptide. In other embodiments, the soluble fragments of B7-H4 polypeptides include fragments of the extracellular domain that retain B7-H4 biological activity. B7-H4 polypeptide extracellular domains can include 1, 2, 3, 4, 5 or more contiguous amino acids from the transmembrane domain, and/or 1, 2, 3, 4, 5 or more contiguous amino acids from the signal sequence. Alternatively, the extracellular domain can have 1, 2, 3, 4, 5, or more contiguous amino acids removed from the C-terminus, N-terminus, or both. Variants of B7-H4 polypeptides and fragments thereof may also be used.

In one embodiment, the B7-H4 polypeptide may be fused to one or more domains of an Ig heavy chain constant region, preferably having an amino acid sequence corresponding to the hinge, $C_H2$ and $C_H3$ regions of a human immunoglobulin Cγ1 chain or to the hinge, $C_H2$ and $C_H3$ regions of a murine immunoglobulin Cγ2a chain.

The fusion proteins can be dimerized or multimerized to form homodimers, heterodimers, homomultimers or heteromultimers. Dimerization/multimerization partners can be arranged either in parallel or antiparallel orientations.

Isolated nucleic acids molecules encoding the fusion proteins, vectors and host cells incorporating the nucleic acids, and pharmaceutical and immunogenic compositions containing the fusion proteins are also provided. Immunogenic compositions contain antigens, a source of fusion protein and, optionally, adjuvant.

Methods for using the fusion proteins to decrease or inhibit pro-inflammatory T cell activation are disclosed. Therapeutic uses for the disclosed compositions include the treatment or alleviation of one or more symptoms of inflammatory and autoimmune diseases and disorders. The B7-H4 fusion proteins are useful for treating inflammation by any or all of the following: inhibiting or reducing differentiation of Th1, Th17, Th22, and/or other cells that secrete, or cause other cells to secrete, inflammatory molecules; inhibiting or reducing activity of Th1, Th17, Th22, and/or other cells that secrete, or cause other cells to secrete, inflammatory molecules; inhibiting or reducing the Th1 and/or Th17 pathways; inhibiting or reducing inflammatory molecule production and/or secretion by Th1, Th17, Th22, and/or other cells that secrete, or cause other cells to secrete, inflammatory molecules; inhibiting or reducing proliferation of Th1, Th17, Th22, and/or other cells that secrete, or cause other cells to secrete, inflammatory molecules; interacting with Tregs; enhancing Treg activity; enhancing IL-10 secretion by Tregs; increasing the number of Tregs; increasing the suppressive capacity of Tregs; or combinations thereof.

In one embodiment, B7-H4 polypeptides or fusion proteins enhance the suppressive activity of Tregs on the immune system. Tregs can suppress differentiation, proliferation, activity, and/or cytokine production and/or secretion by Th1, Th17, Th22, and/or other cells that secrete, or cause other cells to secrete, inflammatory molecules. In a preferred embodiment the B7-H4 polypeptides or fusion proteins enhance the suppressive activity of Tregs on naïve T cells to inhibit or reduce naïve T cells from differentiating into Th1, Th17 or Th22 cells and thereby reduce the number of Th1 or Th17, Th22, and/or other cells that secrete, or cause other cells to secrete, inflammatory molecules, including, but not limited to, IL-1β, TNF-α, TGF-beta, IFN-γ, IL-17, IL-6, IL-23, IL-22, IL-21, and MMPs in a subject.

One embodiment provides a method to inhibit or reduce epitope spreading in a subject by administering to the subject an effective amount of B7-H4 polypeptide or fusion proteins thereof. A preferred embodiment provides a method of administering an effective amount of B7-H4 polypeptide or fusion protein thereof to inhibit or reduce epitope spreading in patients with Multiple Sclerosis (MS) of systemic lupus erythematosus (SLE).

B7-H4 polypeptides, fragments or fusions thereof can be administered in combination with one or more additional therapeutic agents, including, but not limited to, antibodies against other lymphocyte surface markers (e.g., CD40, alpha-4 integrin) or against cytokines, other fusion proteins, e.g., CTLA4-Ig (Orencia®, belatacept), TNFR-Ig (Enbrel®), TNF-α blockers such as Remicade, Cimzia and Humira, CD73-Ig, cyclophosphamide (CTX) (i.e. Endoxan®, Cytoxan®, Neosar®, Procytox®, Revimmune™), methotrexate (MTX) (i.e. Rheumatrex®, Trexall®), belimumab (i.e. Benlysta®), Tysabri or other immunosuppressive drugs, anti-proliferatives, cytotoxic agents, or other compounds that may assist in immunosuppression.

In one embodiment, the additional therapeutic agent targets a different pathway involved in immune activation. In a preferred embodiment, the additional therapeutic agent is a CTLA-4 fusion protein, such as CTLA-4 Ig (abatacept). In a preferred embodiment, the additional therapeutic agent is a CTLA4-Ig fusion protein known as belatacept that contains two amino acid substitutions (L104E and A29Y) that markedly increase its avidity to CD86 in vivo.

In another embodiment, the second therapeutic agent is cyclophosphamide (CTX). In a preferred embodiment, B7-H4-Ig and CTX are coadministered in an effective amount to treat a chronic autoimmune disease or disorder such as Systemic lupus erythematosus (SLE).

In another embodiment, the second therapeutic agent increases the amount of adenosine in the serum. In a preferred embodiment, the second therapeutic is CD73-Ig, recombinant CD73, or another agent (e.g. a cytokine or monoclonal antibody or small molecule) that increases the expression of CD73. In another embodiment the second therapeutic agent is Interferon-beta.

In another embodiment, the second therapeutic is Tysabri or another therapeutic for MS. In a preferred embodiment, B7-H4-Ig is cycled with Tysabri or used during a drug holiday in order to allow less frequent dosing with the second therapeutic and reduce the risk of side effects such as PML and to prevent resistance to the second therapeutic.

In another embodiment, the second therapeutic agent is a small molecule that inhibits or reduces differentiation, proliferation, activity, and/or cytokine production and/or secretion by Th1, Th17, Th22, and/or other cells that secrete, or cause other cells to secrete, inflammatory molecules. In another embodiment, the second therapeutic agent is a small molecule that interacts with Tregs, enhances Treg activity, promotes or enhances IL-10 secretion by Tregs, increases the number of Tregs, increases the suppressive capacity of Tregs, or combinations thereof. In one embodiment, the small molecule is retinoic acid or a derivative thereof.

In another embodiment, the B7-H4 polypeptides, fusion proteins, or fragments thereof can be used to treat patients who do not respond to TNF blockers.

BRIEF DESCRIPTION OF THE DRAWINGS

In FIG. 1A, B7-H4-Ig targets T cells. In FIG. 1B, B7-H4-Ig blocks maturation of dendritic cells (DC).

DETAILED DESCRIPTION OF THE INVENTION

I. Definitions

Figure 1A:
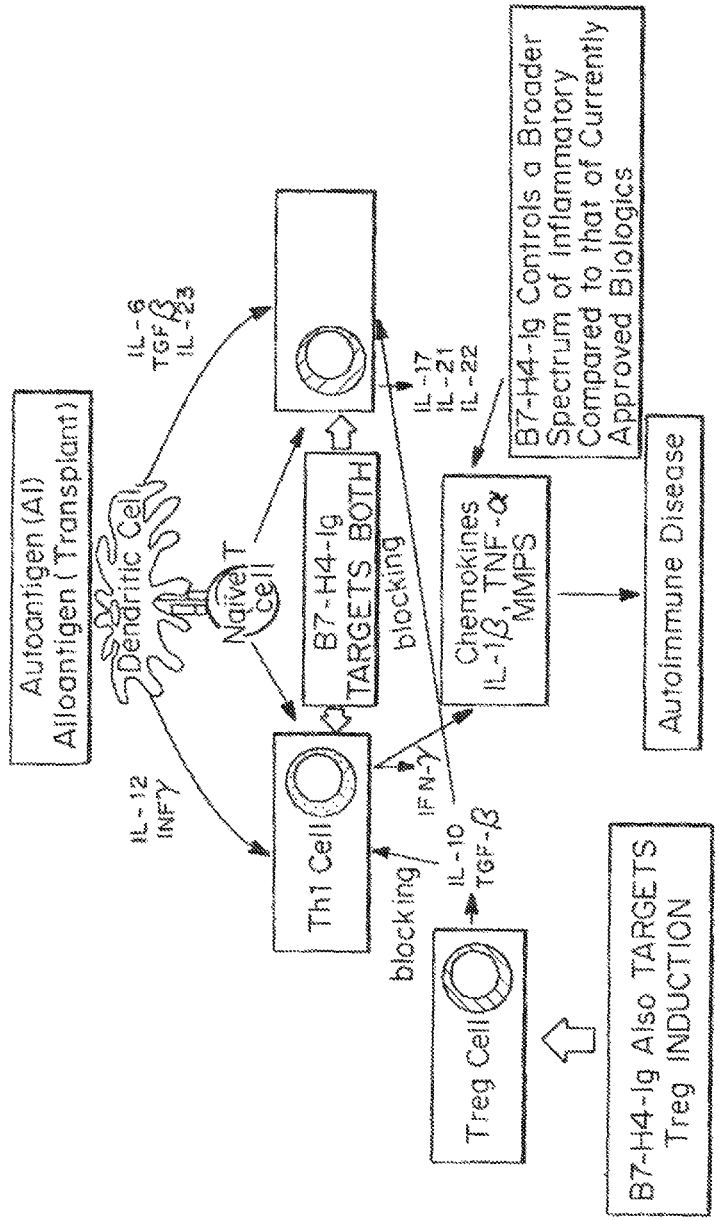
FIGS. 1A and 1B are diagrams illustrating modes of action for inhibiting inflammation using B7-H4-Ig.

As used herein the term "isolated" refers to a compound of interest (e.g., either a polynucleotide or a polypeptide) that is in an environment different from that in which the compound naturally occurs e.g. separated from its natural milieu such as by concentrating a peptide to a concentration at which it is not found in nature. "Isolated" includes compounds that are within samples that are substantially enriched for the compound of interest and/or in which the compound of interest is partially or substantially purified.

An "immune cell" refers to any cell from the hemopoietic origin including but not limited to T cells, B cells, monocytes, dendritic cells, and macrophages.

As used herein, the term "polypeptide" refers to a chain of amino acids of any length, regardless of modification (e.g., phosphorylation or glycosylation).

As used herein, a "costimulatory polypeptide" or "costimulatory molecule" is a polypeptide that, upon interaction with a cell-surface molecule on T cells, modulates T cell responses.

As used herein, a "costimulatory signaling" is the signaling activity resulting from the interaction between costimulatory polypeptides on antigen presenting cells and their receptors on T cells during antigen-specific T cell responses. Antigen-specific T cell response mediated by two signals: 1) engagement of the T cell Receptor (TCR) with antigenic peptide presented in the context of MHC (signal 1), and 2) a second antigen-independent signal delivered by contact between different costimulatory receptor/ligand pairs (signal 2). This "second signal" is critical in determining the type of T cell response (activation vs inhibition) as well as the strength and duration of that response, and is regulated by both positive and negative signals from costimulatory molecules, such as the B7 family of proteins.

As used herein, the term "B7 polypeptide" means a member of the B7 family of proteins that costimulate T cells including, but not limited to, B7-1, B7-2, B7-DC, B7-H5, B7-H1, B7-H2, B7-H3, B7-H4 and biologically active fragments and/or variants thereof. Representative biologically active fragments include the extracellular domain or fragments of the extracellular domain that costimulate T cells.

As used herein "soluble B7-H4" or "sH4" refers to fragments of B7-H4 that may be shed, secreted or otherwise extracted from cells that express B7-H4. Soluble fragments of B7-H4 include some or all of the extracellular domain of the B7-H4 polypeptide, and lack some or all of the intracellular and/or transmembrane domains. In one embodiment, soluble B7-H4 polypeptide fragments include the entire extracellular domain of the B7-H4 polypeptide. In other embodiments, the soluble fragments of B7-H4 polypeptides include fragments of the extracellular domain. Extracellular domains of B7-H4 polypeptides can be readily determined by those of skill in the art using standard methodologies such as hydropathy plotting.

As used herein, "inflammatory molecules" refers to molecules that results inflammatory responses including, but not limited to, cytokines and metalloproteases such as including, but not limited to, IL-1β, TNF-α, TGF-beta, IFN-γ, IL-17, IL-6, IL-23, IL-22, IL-21, and MMPs.

As used herein, a "vector" is a replicon, such as a plasmid, phage, or cosmid, into which another DNA segment may be inserted so as to bring about the replication of the inserted segment. The vectors described herein can be expression vectors.

As used herein, an "expression vector" is a vector that includes one or more expression control sequences As used herein, an "expression control sequence" is a DNA sequence that controls and regulates the transcription and/or translation of another DNA sequence.

"Operably linked" refers to an arrangement of elements wherein the components so described are configured so as to perform their usual or intended function. Thus, two different polypeptides operably linked together retain their respective biological functions while physically linked together.

As used herein, "valency" refers to the number of binding sites available per molecule.

As used herein, a "variant" polypeptide contains at least one amino acid sequence alteration as compared to the amino acid sequence of the corresponding wild-type polypeptide.

As used herein, "conservative" amino acid substitutions are substitutions wherein the substituted amino acid has similar structural or chemical properties.

As used herein, the term "host cell" refers to prokaryotic and eukaryotic cells into which a recombinant vector can be introduced.

As used herein, "transformed" and "transfected" encompass the introduction of a nucleic acid (e.g. a vector) into a cell by a number of techniques known in the art.

As used herein, the phrase that a molecule "specifically binds" or "displays specific binding" to a target refers to a binding reaction which is determinative of the presence of the molecule in the presence of a heterogeneous population of other biologics. Under designated immunoassay conditions, a specified molecule binds preferentially to a particular target and does not bind in a significant amount to other biologics present in the sample. Specific binding of an antibody to a target under such conditions requires the antibody be selected for its specificity to the target. A variety of immunoassay formats may be used to select antibodies specifically immunoreactive with a particular protein. For example, solid-phase ELISA immunoassays are routinely used to select monoclonal antibodies specifically immunoreactive with a protein. See, e.g., Harlow and Lane (1988) Antibodies, A Laboratory Manual, Cold Spring Harbor Publications, New York, for a description of immunoassay formats and conditions that can be used to determine specific immunoreactivity.

As used herein, the terms "immunologic", "immunological" or "immune" response is the development of a beneficial humoral (antibody mediated) and/or a cellular (mediated by antigen-specific T cells or their secretion products) response directed against a peptide in a recipient patient. Such a response can be an active response induced by administration of immunogen or a passive response induced by administration of antibody or primed T-cells. A cellular immune response is elicited by the presentation of polypeptide epitopes in association with Class I or Class II MHC molecules to activate antigen-specific CD4$^+$ T helper cells and/or CD8$^+$ cytotoxic T cells. The response may also involve activation of monocytes, macrophages, NK cells, basophils, dendritic cells, astrocytes, microglia cells, eosinophils, activation or recruitment of neutrophils or other components of innate immunity. The presence of a cell-mediated immunological response can be determined by proliferation assays (CD4$^+$ T cells) or CTL (cytotoxic T lymphocyte) assays. The relative contributions of humoral and cellular responses to the protective or therapeutic effect of an immunogen can be distinguished by separately isolating antibodies and T-cells from an immunized syngeneic animal and measuring protective or therapeutic effect in a second subject.

An "immunogenic agent" or "immunogen" is capable of inducing an immunological response against itself on administration to a mammal, optionally in conjunction with an adjuvant.

The terms "individual", "host", "subject", and "patient" are used interchangeably herein, and refer to a mammal, including, but not limited to, humans, rodents, such as mice and rats, and other laboratory animals.

II. Fusion Proteins

B7-H4 fusion polypeptides have a first fusion partner comprising all or a part of a B7-H4 protein fused to a second polypeptide directly or via a linker peptide sequence that is fused to the second polypeptide. The fusion proteins optionally contain a domain that functions to dimerize or multimerize two or more fusion proteins. The peptide/polypeptide linker domain can either be a separate domain, or alternatively can be contained within one of the other domains (B7-H4 polypeptide or second polypeptide) of the fusion protein. Similarly, the domain that functions to dimerize or multimerize the fusion proteins can either be a separate domain, or alternatively can be contained within one of the other domains (B7-H4 polypeptide, second polypeptide or peptide/polypeptide linker domain) of the fusion protein. In one embodiment, the dimerization/multimerization domain and the peptide/polypeptide linker domain are the same.

Fusion proteins disclosed herein are of formula I:

$$N—R_1—R_2—R_3—C$$

wherein "N" represents the N-terminus of the fusion protein, "C" represents the C-terminus of the fusion protein. In the preferred embodiment, "$R_1$" is a B7-H4 polypeptide, "$R_2$" is an optional peptide/polypeptide linker domain, and "$R_3$" is a second polypeptide. Alternatively, $R_3$ may be a B7-H4 polypeptide and $R_1$ may be a second polypeptide.

Dimerization or multimerization can occur between or among two or more fusion proteins through dimerization or multimerization domains. Alternatively, dimerization or multimerization of fusion proteins can occur by chemical crosslinking. The dimers or multimers that are formed can be homodimeric/homomultimeric or heterodimeric/heteromultimeric.

A. B7-H4 Polypeptides

In a preferred embodiment the B7-H4 polypeptide is from a mammalian species. In the most preferred embodiment, the B7-H4 polypeptide is of murine, non-human primate (*Pan troglodytes, Macaca mulatta* or *Macaca fascicularis*), or human origin. Useful murine B7-H4 polypeptides have at least about 80, 85, 90, 95 or 100% sequence identity to the B7-H4 polypeptide encoded by the nucleic acid having GenBank Accession Number NM_178594 or AY280973. Useful murine B7-H4 polypeptides have at least about 80, 85, 90, 95 or 100% sequence identity to the B7-H4 polypeptide according to GenBank Accession Number AAH32925.1 or NP_848709.2. Useful human B7-H4 polypeptides have at least about 80, 85, 90, 95 or 100% sequence identity to the B7-H4 polypeptide encoded by the nucleic acid having GenBank Accession Number AK026071. Useful human B7-H4 polypeptides have at least about 80, 85, 90, 95 or 100% sequence identity to the B7-H4 polypeptide according to GenBank Accession Number NP_078902.2 or BAB 15349.1.

Murine B7-H4 polypeptides can be encoded by a nucleotide sequence having at least 80%, 85%, 90%, 95%, 99%, or 100% sequence identity to:

```
                                                         (SEQ ID NO: 1)
atggcttcct tggggcagat catcttttgg agtattatta acatcatcat catcctggct    60
ggggccatcg cactcatcat tggctttggc atttcaggca agcacttcat cacggtcacg   120
accttcacct cagctggaaa cattggagag gacgggaccc tgagctgcac ttttgaacct   180
gacatcaaac tcaacggcat cgtcatccag tggctgaaag aaggcatcaa aggtttggtc   240
cacgagttca agaaggcaa agacgacctc tcacagcagc atgagatgtt cagaggccgc    300
acagcagtgt ttgctgatca ggtggtagtt ggcaatgctt ccctgagact gaaaaacgtg   360
cagctcacgg atgctggcac ctacacatgt tacatccgca cctcaaaagg caagggaat    420 gcaaaccttg agtataagac cggagccttc agtatgccag agataaatgt ggactataat   480
gccagttcag agagtttacg ctgcgaggct cctcggtggt tccccagcc cacagtggcc    540 tgggcatctc aagtcgacca aggagccaat ttctcagaag tctccaacac cagctttgag   600
ttgaactctg agaatgtgac catgaaggtc gtatctgtgc tctacaatgt cacaatcaac   660
aacacatact cctgtatgat tgaaaacgac attgccaaag ccaccgggga catcaaagtg   720
acagattcag aggtcaaaag gcgaagtcag ctgcagttgc tgaactctgg gccttccccg   780 tgtgttttttt cttctgcctt tgtggctggc tgggcactcc tatctctctc ctgttgcctg   840
atgctaagat ga.                                                       852
```

Murine B7-H4 polypeptides can have at least 80%, 85%, 90%, 95%, 99%, or 100% sequence identity to:

```
                                                         (SEQ ID NO: 2)
MASLGQIIFW SIINIIIILA GAIALIIGFG ISGKHFITVT TFTSAGNIGE DGTLSCTFEP    60

DIKLNGIVIQ WLKEGIKGLV HEFKEGKDDL SQQHEMFRGR TAVFADQVVV GNASLRLKNV   120

QLTDAGTYTC YIRSSKGKGN ANLEYKTGAF SMPEINVDYN ASSESLRCEA PRWFPQPTVA   180

WASQVDQGAN FSEVSNTSFE LNSENVTMKV VSVLYNVTIN NTYSCMIEND IAKATGDIKV   240

TDSEVKRRSQ LQLLNSGPSP CVSSSAFVAG WALLSLSCCL MLR,                    283

(SEQ ID NO: 3)
MEWSWVFLFF LSVTTGVHSG FGISGKHFIT VTTFTSAGNI GEDGTLSCTF EPDIKLNGIV    60

IQWLKEGIKG LVHEFKEGKD DLSQQHEMFR GRTAVFADQV VVGNASLRLK NVQLTDAGTY   120

TCYIRSSKGK GNANLEYKTG AFSMPEINVD YNASSESLRC EAPRWFPQPT VAWASQVDQG   180

ANFSEVSNTS FELNSENVTM KVVSVLYNVT INNTYSCMIE NDIAKATGDI KVTDSEVKRR   240

SQLQLLNSGP SPCVSSSAFV AGWALLSLSC CLMLR,                             275

(SEQ ID NO: 4)
GFGISGKHFI TVTTFTSAGN IGEDGTLSCT FEPDIKLNGI VIQWLKEGIK GLVHEFKEGK    60

DDLSQQHEMF RGRTAVFADQ VVVGNASLRL KNVQLTDAGT YTCYIRSSKG KGNANLEYKT   120

GAFSMPEINV DYNASSESLR CEAPRWFPQP TVAWASQVDQ GANFSEVSNT SFELNSENVT   180

MKVVSVLYNV TINNTYSCMI ENDIAKATGD IKVTDSEVKR RSQLQLLNSG PSPCVSSSAF   240

VAGWALLSLS CCLMLR,                                                  256

(SEQ ID NO: 5)
MASLGQIIFW SIINIIIILA GAIALIIGFG ISGKHFITVT TFTSAGNIGE DGTLSCTFEP    60

DIKLNGIVIQ WLKEGIKGLV HEFKEGKDDL SQQHEMFRGR TAVFADQVVV GNASLRLKNV   120

QLTDAGTYTC YIRTSKGKGN ANLEYKTGAF SMPEINVDYN ASSESLRCEA PRWFPQPTVA   180

WASQVDQGAN FSEVSNTSFE LNSENVTMKV VSVLYNVTIN NTYSCMIEND IAKATGDIKV   240

TDSEVKRRSQ LQLLNSGPSP CVFSSAFVAG WALLSLSCCL MLR,                    283
```

-continued (SEQ ID NO: 6)
MEWSWVFLFF LSVTTGVHSG FGISGKHFIT VTTFTSAGNI GEDGTLSCTF EPDIKLNGIV   60

IQWLKEGIKG LVHEFKEGKD DLSQQHEMFR GRTAVFADQV VVGNASLRLK NVQLTDAGTY  120

TCYIRTSKGK GNANLEYKTG AFSMPEINVD YNASSESLRC EAPRWFPQPT VAWASQVDQG  180

ANFSEVSNTS FELNSENVTM KVVSVLYNVT INNTYSCMIE NDIAKATGDI KVTDSEVKRR  240

SQLQLLNSGP SPCVFSSAFV AGWALLSLSC CLMLR,                           275
or (SEQ ID NO: 7)
GFGISGKHFI TVTTFTSAGN IGEDGTLSCT FEPDIKLNGI VIQWLKEGIK GLVHEFKEGK   60

DDLSQQHEMF RGRTAVFADQ VVVGNASLRL KNVQLTDAGT YTCYIRTSKG KGNANLEYKT  120

GAFSMPEINV DYNASSESLR CEAPRWFPQP TVAWASQVDQ GANFSEVSNT SFELNSENVT  180

MKVVSVLYNV TINNTYSCMI ENDIAKATGD IKVTDSEVKR RSQLQLLNSG PSPCVFSSAF  240

VAGWALLSLS CCLMLR                                                 256

Human B7-H4 polypeptides can be encoded by a nucleotide sequence having at least 80%, 85%, 90%, 95%, 99%, or 100% sequence identity to:

(SEQ ID NO: 8)
atggcttccc tggggcagat cctcttctgg agcataatta gcatcatcat tattctggct   60
ggagcaattg cactcatcat tggctttggt atttcaggga cactccat cacagtcact  120 actgtcgcct cagctgggaa cattggggag gatggaatcc tgagctgcac ttttgaacct  180
gacatcaaac tttctgatat cgtgatacaa tggctgaagg aaggtgtttt aggcttggtc  240
catgagttca agaaggcaa agatgagctg tcggagcagg atgaaatgtt cagaggccgg  300
acagcagtgt ttgctgatca agtgatagtt ggcaatgcct ctttgcggct gaaaaacgtg  360
caactcacag atgctggcac ctacaaatgt tatatcatca cttctaaagg caaggggaat  420
gctaaccttg agtataaaac tggagccttc agcatgccgg aagtgaatgt ggactataat  480
gccagctcag agaccttgcg tgtgaggct ccccgatggt tcccccagcc cacagtggtc  540
tgggcatccc aagttgacca gggagccaac ttctcggaag tctccaatac cagctttgag  600
ctgaactctg agaatgtgac catgaaggtt gtgtctgtgc tctacaatgt tacgatcaac  660
aacacatact cctgtatgat tgaaaatgac attgccaaag caacagggga tatcaaagtg  720
acagaatcgg agatcaaaag gcggagtcac ctacagctgc taaactcaaa ggcttctctg  780
tgtgtctctt ctttctttgc catcagctgg gcacttctgc ctctcagccc ttacctgatg  840 ctaaaataa.                                                        849

Human B7-H4 polypeptides can have at least 80%, 85%, 90%, 95%, 99%, or 100% sequence identity to:

(SEQ ID NO: 9)
MASLGQILFW SIISIIIILA GAIALIIGFG ISGRHSITVT TVASAGNIGE DGILSCTFEP   60

DIKLSDIVIQ WLKEGVLGLV HEFKEGKDEL SEQDEMFRGR TAVFADQVIV GNASLRLKNV  120

QLTDAGTYKC YIITSKGKGN ANLEYKTGAF SMPEVNVDYN ASSETLRCEA PRWFPQPTVV  180

WASQVDQGAN FSEVSNTSFE LNSENVTMKV VSVLYNVTIN NTYSCMIEND IAKATGDIKV  240

TESEIKRRSH LQLLNSKASL CVSSFFAISW ALLPLSPYLM LK,                   282

(SEQ ID NO: 10)
MEWSWVFLFF LSVTTGVHSG FGISGRHSIT VTTVASAGNI GEDGILSCTF EPDIKLSDIV   60

IQWLKEGVLG LVHEFKEGKD ELSEQDEMFR GRTAVFADQV IVGNASLRLK NVQLTDAGTY  120

```
KCYIITSKGK GNANLEYKTG AFSMPEVNVD YNASSETLRC EAPRWFPQPT VVWASQVDQG  180

ANFSEVSNTS FELNSENVTM KVVSVLYNVT INNTYSCMIE NDIAKATGDI KVTESEIKRR  240

SHLQLLNSKA SLCVSSFFAI SWALLPLSPY LMLK,                             274

(SEQ ID NO: 11)
GFGISGRHSI TVTTVASAGN IGEDGILSCT FEPDIKLSDI VIQWLKEGVL GLVHEFKEGK   60

DELSEQDEMF RGRTAVFADQ VIVGNASLRL KNVQLTDAGT YKCYIITSKG KGNANLEYKT  120

GAFSMPEVNV DYNASSETLR CEAPRWFPQP TVVWASQVDQ GANFSEVSNT SFELNSENVT  180

MKVVSVLYNV TINNTYSCMI ENDIAKATGD IKVTESEIKR RSHLQLLNSK ASLCVSSFFA  240

ISWALLPLSP YLMLK,                                                  255

(SEQ ID NO: 12)
MASLGQILFW SIISIIIILA GAIALIIGFG ISGRHSITVT TVASAGNIGE DGIQSCTFEP   60

DIKLSDIVIQ WLKEGVLGLV HEFKEGKDEL SEQDEMFRGR TAVFADQVIV GNASLRLKNV  120

QLTDAGTYKC YIITSKGKGN ANLEYKTGAF SMPEVNVDYN ASSETLRCEA PRWFPQPTVV  180

WASQVDQGAN FSEVSNTSFE LNSENVTMKV VSVLYNVTIN NTYSCMIEND IAKATGDIKV  240

TESEIKRRSH LQLLNSKASL CVSSFFAISW ALLPLSPYLM LK,                    282

(SEQ ID NO: 13)
MEWSWVFLFF LSVTTGVHSG FGISGRHSIT VTTVASAGNI GEDGIQSCTF EPDIKLSDIV   60

IQWLKEGVLG LVHEFKEGKD ELSEQDEMFR GRTAVFADQV IVGNASLRLK NVQLTDAGTY  120

KCYIITSKGK GNANLEYKTG AFSMPEVNVD YNASSETLRC EAPRWFPQPT VVWASQVDQG  180

ANFSEVSNTS FELNSENVTM KVVSVLYNVT INNTYSCMIE NDIAKATGDI KVTESEIKRR  240

SHLQLLNSKA SLCVSSFFAI SWALLPLSPY LMLK,                             274
or
                                                        (SEQ ID NO: 14)
GFGISGRHSI TVTTVASAGN IGEDGIQSCT FEPDIKLSDI VIQWLKEGVL GLVHEFKEGK   60

DELSEQDEMF RGRTAVFADQ VIVGNASLRL KNVQLTDAGT YKCYIITSKG KGNANLEYKT  120

GAFSMPEVNV DYNASSETLR CEAPRWFPQP TVVWASQVDQ GANFSEVSNT SFELNSENVT  180

MKVVSVLYNV TINNTYSCMI ENDIAKATGD IKVTESEIKR RSHLQLLNSK ASLCVSSFFA  240

ISWALLPLSP YLMLK.                                                  255
```

Non-human primate B7-H4 polypeptides can have at least 80%, 85%, 90%, 95%, 99%, or 100% sequence identity to:

```
                                                        (SEQ ID NO: 15)
MKPLTSRIIS IIIILAGAIA LIIGFGISGR HSITVTTVAS AGNIGEDGIL SCTFEPDIKL   60

SDIVIQWLKE GVLGLVHEFK EGKDELSEQD EMFRGRTAVF ADQVIVGNAS LRLKNVQLTD  120

AGTYKCYIIT SKGKGNANLE YKTGAFSMPE VNVDYNASSE TLRCEAPRWF PQPTVVWASQ  180

IDQGANFSEV SNTSFELNSE NVTMKVVSVL YNATINNTYS CMIENDIAKA TGDIKVTESE  240

IKRRSHLQLL NSKASLCVSS FFAISWALLP LSPYLMLK,                         278
or
                                                        (SEQ ID NO: 16)
GFGISGRHSI TVTTVASAGN IGEDGILSCT FEPDIKLSDI VIQWLKEGVL GLVHEFKEGK   60

DELSEQDEMF RGRTAVFADQ VIVGNASLRL KNVQLTDAGT YKCYIITSKG KGNANLEYKT  120

GAFSMPEVNV DYNASSETLR CEAPRWFPQP TVVWASQIDQ GANFSEVSNT SFELNSENVT  180

MKVVSVLYNA TINNTYSCMI ENDIAKATGD IKVTESEIKR RSHLQLLNSK ASLCVSSFFA  240

ISWALLPLSP YLMLK,                                                  255
or
```

-continued (SEQ ID NO: 17)
```
MASLGQILFW SIISIIFILA GAIALIIGFG ISGRHSITVT TVASAGNIGE DGILSCTFEP  60

DIKLSDIVIQ WLKEGVIGLV HEFKEGKDEL SEQDEMFRGR TAVFADQVIV GNASLRLKNV 120

QLTDAGTYKC YIITSKGKGN ANLEYKTGAF SMPEVNVDYN ASSETLRCEA PRWFPQPTVV 180

WASQVDQGAN FSEVSNTSFE LNSENVTMKV VSVLYNVTIN NTYSCMIEND IAKATGDIKV 240

TESEIKRRSH LQLLNSKASL CVSSFLAISW ALLPLAPYLM LK,                 282
```
or (SEQ ID NO: 18)
```
GFGISGRHSI TVTTVASAGN IGEDGILSCT FEPDIKLSDI VIQWLKEGVI GLVHEFKEGK  60

DELSEQDEMF RGRTAVFADQ VIVGNASLRL KNVQLTDAGT YKCYIITSKG KGNANLEYKT 120

GAFSMPEVNV DYNASSETLR CEAPRWFPQP TVVWASQVDQ GANFSEVSNT SFELNSENVT 180

MKVVSVLYNV TINNTYSCMI ENDIAKATGD IKVTESEIKR RSHLQLLNSK ASLCVSSFLA 240

ISWALLPLAP YLMLK,                                               255
```
or (SEQ ID NO: 19)
```
MASLGQILFW SIISIIFILA GAIALIIGFG ISGRHSITVT TVASAGNIGE DGILSCTFEP  60

DIKLSDIVIQ WLKEGVIGLV HEFKEGKDEL SEQDEMFRGR TAVFADQVIV GNASLRLKNV 120

QLTDAGTYKC YIITSKGKGN ANLEYKTGAF SMPEVNVDYN ASSETLRCEA PRWFPQPTVV 180

WASQVDQGAN FSEVSNTSFE LNSENVTMKV VSVLYNVTIN NTYSCMIEND IAKATGDIKV 240

TESEIKRRSH LQLLNSKASL CVSSFLAISW ALPPLAPYLM LK,                 282
```
or (SEQ ID NO: 20)
```
GFGISGRHSI TVTTVASAGN IGEDGILSCT FEPDIKLSDI VIQWLKEGVI GLVHEFKEGK  60

DELSEQDEMF RGRTAVFADQ VIVGNASLRL KNVQLTDAGT YKCYIITSKG KGNANLEYKT 120

GAFSMPEVNV DYNASSETLR CEAPRWFPQP TVVWASQVDQ GANFSEVSNT SFELNSENVT 180

MKVVSVLYNV TINNTYSCMI ENDIAKATGD IKVTESEIKR RSHLQLLNSK ASLCVSSFLA 240

ISWALPPLAP YLMLK,                                               255
``` where SEQ ID NOs:15 and 16 are chimapanzee (*Pan troglodytes*) polypeptide sequences, SEQ ID NOs:17 and 18 are rhesus monkey (*Macaca mulatta*) polypeptide sequences, and SEQ ID NOs:19 and 20 are cynomolgus monkey (*Macaca fascicularis*) polypeptide sequences.

Nucleic acids encoding B7-H4 polypeptides may be optimized for expression in the expression host of choice. Codons may be substituted with alternative codons encoding the same amino acid to account for differences in codon usage between the mammal from which the B7-H4 nucleic acid sequence is derived and the expression host. In this manner, the nucleic acids may be synthesized using expression host-preferred codons.

1. Fragments of B7-H4 Polypeptides

The B7-H4 proteins contain two immunoglobulin domains within the extracellular, the IgV domain (or V domain) and the IgC domain (or C domain), which are related to the variable and constant domains of antibodies. The domains can be identified by anyone skilled in the art by searching against family and domain databases. The IgV domain is believed to be responsible for receptor binding, based on functional data from the isolated IgV domain as well as by analogy to the other B7 family members. Each Ig domain of extracellular domain includes one disulfide bond formed between intradomain cystein residues, as is typical for this fold and may be important for structure-function. In SEQ ID NOS: 2, 5, 9 and 12 these cysteines are located at residues 56 and 130 for the IgV domain, and 168 and 225 for the IgC domain. In addition, there is one predicted N-linked glycosylation site in the IgV domain and six glycosylation sites in the IgC domain, which are conserved between mouse and human B7-H4 sequences.

In one embodiment, the first fusion partner is a fragment of B7-H4. As used herein, a fragment of B7-H4 refers to any subset of the polypeptide that is at least one amino acid shorter than full length protein. Useful fragments are those that retain the ability to bind to their natural receptor or receptors. A B7-H4 polypeptide that is a fragment of full-length B7-H4 typically has at least 20 percent, 30 percent, 40 percent, 50 percent, 60 percent, 70 percent, 80 percent, 90 percent, 95 percent, 98 percent, 99 percent, 100 percent, or even more than 100 percent of the ability to bind its natural receptor(s) as compared to full-length B7-H4.

Fragments of B7-H4 polypeptides include soluble fragments. Soluble B7-H4 polypeptide fragments are fragments of B7-H4 polypeptides that may be shed, secreted or otherwise extracted from the producing cells. Soluble fragments of B7-H4 polypeptides include some or all of the extracellular domain of the receptor polypeptide, and lack some or all of the intracellular and/or transmembrane domains. In one embodiment, B7-H4 polypeptide fragments include the entire extracellular domain of the B7-H4 polypeptide. In other embodiments, the soluble fragments of B7-H4 polypeptides include fragments of the extracellular domain that retain B7-H4 biological activity. The extracellular domain can include 1, 2, 3, 4, or 5 contiguous amino acids from the transmembrane domain, and/or 1, 2, 3, 4, or 5 contiguous amino acids from the signal sequence. Alternatively, the extracellular domain can have 1, 2, 3, 4, 5 or more amino acids removed from the C-terminus, N-terminus, or both. In some embodiments the extracellular domain is only the IgV domain, or the region between the conserved cysteines of the IgV domain located at residues 56 and 130 of the full-length protein.

Generally, the B7-H4 polypeptides or fragments thereof are expressed from nucleic acids that include sequences that encode a signal sequence. The signal sequence is generally cleaved from the immature polypeptide to produce the mature polypeptide lacking the signal sequence. SEQ ID NOs: 4, 7, 11, 14, 16, 18 and 20 each lack a signal peptide. The signal sequence of B7-H4 can be replaced by the signal sequence of another polypeptide using standard molecule biology techniques to affect the expression levels, secretion, solubility, or other property of the polypeptide. The signal sequence that is used to replace the B7-H4 signal sequence can be any known in the art. SEQ ID NOs: 2, 3, 5, 6, 9, 10, 12, 13, 15, 17 and 19 each contain a signal peptide.

In a preferred embodiment, the fusion protein includes the extracellular domain of B7-H4, or a fragment thereof fused to an Ig Fc region. Recombinant B7-H4-Ig fusion proteins can be prepared by fusing the coding region of the extracellular domain of B7-H4 or a fragment thereof to the Fc region of human IgG1 or mouse IgG2a, as described previously (Chapoval, et al., *Methods Mol. Med.*, 45:247-255 (2000)).

a. Murine B7-DC Extracellular Domain Fusion Partners

In one embodiment, the first fusion partner of the fusion protein includes the extracellular domain of murine B7-H4 or a fragment thereof. The first fusion partner can be encoded by a nucleotide sequence having at least 80%, 85%, 90%, 95%, 99%, or 100% sequence identity to:

```
                                                            (SEQ ID NO: 21)
atggcttcct tggggcagat catcttttgg agtattatta acatcatcat catcctggct    60
ggggccatcg cactcatcat tggctttggc atttcaggca agcacttcat cacggtcacg   120
accttcacct cagctggaaa cattggagag gacgggaccc tgagctgcac ttttgaacct   180
gacatcaaac tcaacggcat cgtcatccag tggctgaaag aaggcatcaa aggtttggtc   240
cacgagttca agaaggcaa agacgacctc tcacagcagc atgagatgtt cagaggccgc   300
acagcagtgt ttgctgatca ggtggtagtt ggcaatgctt ccctgagact gaaaaacgtg   360
cagctcacgg atgctggcac ctacacatgt tacatccgca cctcaaaagg caaagggaat   420
gcaaaccttg agtataagac cggagccttc agtatgccag agataaatgt ggactataat   480
gccagttcag agagtttacg ctgcgaggct cctcggtggt tcccccagcc cacagtggcc   540
tgggcatctc aagtcgacca aggagccaat ttctcagaag tctccaacac cagctttgag   600
ttgaactctg agaatgtgac catgaaggtc gtatctgtgc tctacaatgt cacaatcaac   660
aacacatact cctgtatgat tgaaaacgac attgccaaag ccaccgggga catcaaagtg   720
acagattcag aggtcaaaag gcgaagtcag ctgcagttgc tgaactctgg g,            771

(SEQ ID NO: 22)
atggagtggt catgggtttt tctgttcttt cttagcgtga ctacaggcgt ccattcagga    60
ttcggcataa gcggcaagca cttcatcaca gttacaacgt ttacaagtgc ggggaacatt   120
ggggaagatg gaacattgtc atgtacattt gagccagata tcaaactcaa tggaatagta   180
attcagtggc ttaaggaggg catcaagggc ctggtccacg aatttaagga ggggaaagac   240
gatctgtctc agcagcacga gatgttcagg ggcagaaccg ccgtcttcgc agaccaggtt   300
gtggtaggca acgccagttt gcggctgaaa aacgtgcagc tgactgacgc cggcacctac   360
acatgctata tccggtcctc taagggcaag gggaacgcta atctcgagta caaaacaggc   420
gccttttcta tgccagagat caacgtggac tataacgcaa gctctgaaag tctgagatgc   480
gaggcgccaa ggtggttccc tcagcccacc gtcgcgtggg cttcccaggt ggatcaaggc   540
gccaactttt ctgaggtttc taacaccagc ttcgaactga acagcgaaaa tgtgacaatg   600
aaggtagtca gcgttctgta taacgtgacc atcaacaata cttactcctg tatgatagaa   660
aatgatatag ccaaggctac aggagatatt aaagtgacgg attcagaagt gaaaaggagg   720
agtcaactgc aactcttgaa tagcggc,                                     747
or
```

```
                                                        (SEQ ID NO: 23)
atggagtggt catgggtttt tctgttcttt cttagcgtga ctacaggcgt ccattcagga    60
ttcggcataa gcggcaagca cttcatcaca gttacaacgt ttacaagtgc ggggaacatt   120
ggggaagatg gaacattgtc atgtacattt gagccagata tcaaactcaa tggaatagta   180
attcagtggc ttaaggaggg catcaagggc ctggtccacg aatttaagga ggggaaagac   240
gatctgtctc agcagcacga gatgttcagg ggcagaaccg ccgtcttcgc agaccaggtt   300
gtggtaggca acgccagttt gcggctgaaa aacgtgcagc tgactgacgc cggcacctac   360
acatgctata tccggaccct taagggcaag gggaacgcta atctcgagta caaaacaggc   420 gcctttctcta tgccagagat caacgtggac tataacgcaa gctctgaaag tctgagatgc   480
gaggcgccaa ggtggttccc tcagcccacc gtcgcgtggg cttcccaggt ggatcaaggc   540
gccaactttt ctgaggtttc taacaccagc ttcgaactga acagcgaaaa tgtgacaatg   600
aaggtagtca gcgttctgta taacgtgacc atcaacaata cttactcctg tatgatagaa   660
aatgatatag ccaaggctac aggagatatt aaagtgacgg attcagaagt gaaaaggagg   720
agtcaactgc aactcttgaa tagcggc.                                      747
```

In another embodiment, the first fusion partner can have at least 80%, 85%, 90%, 95%, 99%, or 100% sequence identity to the murine amino acid sequence:

```
                                                        (SEQ ID NO: 24)
MEWSWVFLFF LSVTTGVHSG FGISGKHFIT VTTFTSAGNI GEDGTLSCTF EPDIKLNGIV    60

IQWLKEGIKG LVHEFKEGKD DLSQQHEMFR GRTAVFADQV VVGNASLRLK NVQLTDAGTY   120

TCYIRSSKGK GNANLEYKTG AFSMPEINVD YNASSESLRC EAPRWFPQPT VAWASQVDQG   180

ANFSEVSNTS FELNSENVTM KVVSVLYNVT INNTYSCMIE NDIAKATGDI KVTDSEVKRR   240

SQLQLLNSG,                                                          249

(SEQ ID NO: 25)
MEWSWVFLFF LSVTTGVHSG FGISGKHFIT VTTFTSAGNI GEDGTLSCTF EPDIKLNGIV    60

IQWLKEGIKG LVHEFKEGKD DLSQQHEMFR GRTAVFADQV VVGNASLRLK NVQLTDAGTY   120

TCYIRTSKGK GNANLEYKTG AFSMPEINVD YNASSESLRC EAPRWFPQPT VAWASQVDQG   180

ANFSEVSNTS FELNSENVTM KVVSVLYNVT INNTYSCMIE NDIAKATGDI KVTDSEVKRR   240

SQLQLLNSG,                                                          249

(SEQ ID NO: 26)
MASLGQIIFW SIINIIIILA GAIALIIGFG ISGKHFITVT TFTSAGNIGE DGTLSCTFEP    60

DIKLNGIVIQ WLKEGIKGLV HEFKEGKDDL SQQHEMFRGR TAVFADQVVV GNASLRLKNV   120

QLTDAGTYTC YIRSSKGKGN ANLEYKTGAF SMPEINVDYN ASSESLRCEA PRWFPQPTVA   180

WASQVDQGAN FSEVSNTSFE LNSENVTMKV VSVLYNVTIN NTYSCMIEND IAKATGDIKV   240

TDSEVKRRSQ LQLLNSG,                                                 257
or (SEQ ID NO: 27)
MASLGQIIFW SIINIIIILA GAIALIIGFG ISGKHFITVT TFTSAGNIGE DGTLSCTFEP    60

DIKLNGIVIQ WLKEGIKGLV HEFKEGKDDL SQQHEMFRGR TAVFADQVVV GNASLRLKNV   120

QLTDAGTYTC YIRTSKGKGN ANLEYKTGAF SMPEINVDYN ASSESLRCEA PRWFPQPTVA   180

WASQVDQGAN FSEVSNTSFE LNSENVTMKV VSVLYNVTIN NTYSCMIEND IAKATGDIKV   240

TDSEVKRRSQ LQLLNSG.                                                 257
```

The signal sequence is removed in the mature protein. Additionally, signal peptides from other polypeptides or organisms can be used to enhance the secretion of the fusion protein from a host during manufacture. SEQ ID NO:28 provides the murine amino acid sequence of SEQ ID NO:24 and SEQ ID NO:26 without the signal sequence:

```
                                                   (SEQ ID NO: 28)
GFGISGKHFI TVTTFTSAGN IGEDGTLSCT FEPDIKLNGI VIQWLKEGIK GLVHEFKEGK   60

DDLSQQHEMF RGRTAVFADQ VVVGNASLRL KNVQLTDAGT YTCYIRSSKG KGNANLEYKT  120

GAFSMPEINV DYNASSESLR CEAPRWFPQP TVAWASQVDQ GANFSEVSNT SFELNSENVT  180

MKVVSVLYNV TINNTYSCMI ENDIAKATGD IKVTDSEVKR RSQLQLLNSG.            230
```

SEQ ID NO:29 provides the murine amino acid sequence of SEQ ID NO:25 and SEQ ID NO:27 without the signal sequence:

```
                                                   (SEQ ID NO: 29)
GFGISGKHFI TVTTFTSAGN IGEDGTLSCT FEPDIKLNGI VIQWLKEGIK GLVHEFKEGK   60

DDLSQQHEMF RGRTAVFADQ VVVGNASLRL KNVQLTDAGT YTCYIRTSKG KGNANLEYKT  120

GAFSMPEINV DYNASSESLR CEAPRWFPQP TVAWASQVDQ GANFSEVSNT SFELNSENVT  180

MKVVSVLYNV TINNTYSCMI ENDIAKATGD IKVTDSEVKR RSQLQLLNSG             230
```

In another embodiment, the first fusion partner of the fusion protein includes the IgV domain of murine B7-H4. In one embodiment, the IgV domain includes at least from the cysteine at position 56 of SEQ ID NO:2 or SEQ ID NO:5 to the cysteine at position 130 of SEQ ID NO:2 or SEQ ID NO:5. In another embodiment, the IgV domain contains a fragment of at least 25 or 50 amino acids of the polypeptide defined by this amino acid range.

The first fusion partner can be encoded by a nucleotide sequence having at least 80%, 85%, 90%, 95%, 99%, or 100% sequence identity to the following nucleotide sequence encoding an exemplary IgV domain:

```
                                                   (SEQ ID NO: 30)
ggattcggca taagcggcaa gcacttcatc acagttacaa cgtttacaag tgcggggaac   60
attggggaag atggaacatt gtcatgtaca tttgagccag atatcaaact caatggaata  120
gtaattcagt ggcttaagga gggcatcaag ggcctggtcc acgaatttaa ggagggaaa   180 gacgatctgt ctcagcagca cgagatgttc aggggcagaa ccgccgtctt cgcagaccag  240
gttgtggtag gcaacgccag tttgcggctg aaaaacgtgc agctgactga cgccggcacc  300
tacacatgct atatccggtc ctctaagggc aaggggaacg ctaatctcga gtacaaaaca  360
ggcgcctttt ctatgccaga gatcaac                                      387
or
                                                   (SEQ ID NO: 31)
ggattcggca taagcggcaa gcacttcatc acagttacaa cgtttacaag tgcggggaac   60
attggggaag atggaacatt gtcatgtaca tttgagccag atatcaaact caatggaata  120
gtaattcagt ggcttaagga gggcatcaag ggcctggtcc acgaatttaa ggagggaaa   180 gacgatctgt ctcagcagca cgagatgttc aggggcagaa ccgccgtctt cgcagaccag  240
gttgtggtag gcaacgccag tttgcggctg aaaaacgtgc agctgactga cgccggcacc  300
tacacatgct atatccggac ctctaagggc aaggggaacg ctaatctcga gtacaaaaca  360
ggcgcctttt ctatgccaga gatcaac.                                     387
```

The first fusion partner can have at least 80%, 85%, 90%, 95%, 99%, or 100% sequence identity to the murine amino acid sequence:

```
                                                     (SEQ ID NO: 32)
GFGISGKHFI TVTTFTSAGN IGEDGTLSCT FEPDIKLNGI VIQWLKEGIK GLVHEFKEGK    60

DDLSQQHEMF RGRTAVFADQ VVVGNASLRL KNVQLTDAGT YTCYIRSSKG KGNANLEYKT   120

GAFSMPEIN,                                                         129
```
or
```
                                                     (SEQ ID NO: 33)
GFGISGKHFI TVTTFTSAGN IGEDGTLSCT FEPDIKLNGI VIQWLKEGIK GLVHEFKEGK    60

DDLSQQHEMF RGRTAVFADQ VVVGNASLRL KNVQLTDAGT YTCYIRTSKG KGNANLEYKT   120

GAFSMPEIN.                                                         129
``` b. Human Extracellular Domain Fusion Partners

In another embodiment, the first fusion partner of the fusion protein includes the extracellular domain of human B7-H4 or a fragment thereof. The first fusion partner can be encoded by a nucleotide sequence having at least 80%, 85%, 90%, 95%, 99%, or 100% sequence identity to:

```
                                                              (SEQ ID NO: 34)
         atggcttccc tggggcagat cctcttctgg agcataatta gcatcatcat tattctggct    60
ggagcaattg cactcatcat tggctttggt atttcaggga gacactccat cacagtcact   120
actgtcgcct cagctgggaa cattggggag gatgaaatcc tgagctgcac ttttgaacct   180
gacatcaaac tttctgatat cgtgatacaa tggctgaagg aaggtgtttt aggcttggtc   240
catgagttca agaaggcaa agatgagctg tcggagcagg atgaaatgtt cagaggccgg    300
acagcagtgt ttgctgatca agtgatagtt ggcaatgcct ctttgcggct gaaaaacgtg   360
caactcacag atgctggcac ctacaaatgt tatatcatca cttctaaagg caaggggaat   420
gctaaccttg agtataaaac tggagccttc agcatgccgg aagtgaatgt ggactataat   480
gccagctcag agaccttgcg gtgtgaggct ccccgatggt tcccccagcc cacagtggtc   540
tgggcatccc aagttgacca gggagccaac ttctcggaag tctccaatac cagctttgag   600
ctgaactctg agaatgtgac catgaaggtt gtgtctgtgc tctacaatgt tacgatcaac   660
aacacatact cctgtatgat tgaaaatgac attgccaaag caacagggga tatcaaagtg   720
acagaatcgg agatcaaaag gcggagt,                                      747

(SEQ ID NO: 35)
         atggcttccc tggggcagat cctcttctgg agcataatta gcatcatcat tattctggct    60
ggagcaattg cactcatcat tggctttggt atttcaggga gacactccat cacagtcact   120
actgtcgcct cagctgggaa cattggggag gatggaatcc tgagctgcac ttttgaacct   180
gacatcaaac tttctgatat cgtgatacaa tggctgaagg aaggtgtttt aggcttggtc   240
catgagttca agaaggcaa agatgagctg tcggagcagg atgaaatgtt cagaggccgg    300
acagcagtgt ttgctgatca agtgatagtt ggcaatgcct ctttgcggct gaaaaacgtg   360
caactcacag atgctggcac ctacaaatgt tatatcatca cttctaaagg caaggggaat   420
gctaaccttg agtataaaac tggagccttc agcatgccgg aagtgaatgt ggactataat   480
gccagctcag agaccttgcg gtgtgaggct ccccgatggt tcccccagcc cacagtggtc   540
tgggcatccc aagttgacca gggagccaac ttctcggaag tctccaatac cagctttgag   600
ctgaactctg agaatgtgac catgaaggtt gtgtctgtgc tctacaatgt tacgatcaac   660
aacacatact cctgtatgat tgaaaatgac attgccaaag caacagggga tatcaaagtg   720
acagaatcgg agatc,                                                   735
```

-continued (SEQ ID NO: 36)
```
atggcttccc tggggcagat cctcttctgg agcataatta gcatcatcat tattctggct    60
ggagcaattg cactcatcat tggctttggt atttcaggga gacactccat cacagtcact   120
actgtcgcct cagctgggaa cattggggag gatggaatcc tgagctgcac ttttgaacct   180
gacatcaaac tttctgatat cgtgatacaa tggctgaagg aaggtgtttt aggcttggtc   240
catgagttca agaaggcaa agatgagctg tcggagcagg atgaaatgtt cagaggccgg    300
acagcagtgt ttgctgatca agtgatagtt ggcaatgcct ctttgcggct gaaaaacgtg   360
caactcacag atgctggcac ctacaaatgt tatatcatca cttctaaagg caagggaat    420
gctaaccttg agtataaaac tggagccttc agcatgccgg aagtgaatgt ggactataat   480
gccagctcag agaccttgcg tgtgaggct ccccgatggt tcccccagcc cacagtggtc    540
tgggcatccc aagttgacca gggagccaac ttctcggaag tctccaatac cagctttgag   600
ctgaactctg agaatgtgac catgaaggtt gtgtctgtgc tctacaatgt tacgatcaac   660
aacacatact cctgtatgat tgaaaatgac attgccaaag caacagggga tatcaaagtg   720
acagaatcgg agatcaaaag gcggagtcac ctacagctgc taaactcaaa ggcttct,    777
```
(SEQ ID NO: 37)
```
atggaatgga gctgggtatt tctgtttttc ctgtcagtaa cgactggcgt ccattcaggc    60
ttcggcatca gtggacggca cagtatcaca gtgaccaccg tcgcctccgc tggcaatata   120
ggtgaggatg gcatccagtc ctgtacctt gagccggaca tcaaactgtc tgacatagtg    180
atacaatggc tgaaggaggg ggtgctcggt ctggtacatg agtttaagga agggaaggat   240
gaactgtccg agcaggatga gatgttccgg gggaggaccg ctgtgttcgc cgatcaggta   300
atcgtcggaa atgcaagtct cagattgaaa aatgtgcaac tgactgatgc tggcacgtat   360
aaatgctaca ttatcacaag taagggcaaa ggaaatgcta accttgagta taaaacaggc   420
gcattctcaa tgcccgaggt caatgtcgac tataatgcca gcagtgaaac attgcgctgt   480
gaagctcccc gctggttccc ccagccaacc gtggtctggg cctctcaggt tgatcagggg   540
gctaactttt ccgaggtgag caacaccagc ttcgaactca actctgagaa tgtgaccatg   600
aaagttgtgt ctgtcctgta taatgtaaca atcaacaaca cttattcatg catgattgaa   660
aacgacatcg ccaaggcaac aggtgatatt aaggtaactg aatccgagat caaacggcgg   720
tct,                                                               723
```
(SEQ ID NO: 38)
```
atggaatgga gctgggtatt tctgtttttc ctgtcagtaa cgactggcgt ccattcaggc    60
ttcggcatca gtggacggca cagtatcaca gtgaccaccg tcgcctccgc tggcaatata   120
ggtgaggatg gcatccagtc ctgtacctt gagccggaca tcaaactgtc tgacatagtg    180
atacaatggc tgaaggaggg ggtgctcggt ctggtacatg agtttaagga agggaaggat   240
gaactgtccg agcaggatga gatgttccgg gggaggaccg ctgtgttcgc cgatcaggta   300
atcgtcggaa atgcaagtct cagattgaaa aatgtgcaac tgactgatgc tggcacgtat   360
aaatgctaca ttatcacaag taagggcaaa ggaaatgcta accttgagta taaaacaggc   420
gcattctcaa tgcccgaggt caatgtcgac tataatgcca gcagtgaaac attgcgctgt   480
gaagctcccc gctggttccc ccagccaacc gtggtctggg cctctcaggt tgatcagggg   540
gctaactttt ccgaggtgag caacaccagc ttcgaactca actctgagaa tgtgaccatg   600
aaagttgtgt ctgtcctgta taatgtaaca atcaacaaca cttattcatg catgattgaa   660
aacgacatcg ccaaggcaac aggtgatatt aaggtaactg aatccgagat c,            711
```

-continued (SEQ ID NO: 39)
```
atggaatgga gctgggtatt tctgtttttc ctgtcagtaa cgactggcgt ccattcaggc    60
ttcggcatca gtggacggca cagtatcaca gtgaccaccg tcgcctccgc tggcaatata   120
ggtgaggatg gcatccagtc ctgtaccttt gagccggaca tcaaactgtc tgacatagtg   180
atacaatggc tgaaggaggg ggtgctcggt ctggtacatg agtttaagga agggaaggat   240
gaactgtccg agcaggatga gatgttccgg gggaggaccg ctgtgttcgc cgatcaggta   300
atcgtcggaa atgcaagtct cagattgaaa aatgtgcaac tgactgatgc tggcacgtat   360
aaatgctaca ttatcacaag taagggcaaa ggaaatgcta accttgagta taaaacaggc   420
gcattctcaa tgcccgaggt caatgtcgac tataatgcca gcagtgaaac attgcgctgt   480
gaagctcccc gctggttccc ccagccaacc gtggtctggg cctctcaggt tgatcagggg   540
gctaactttt ccgaggtgag caacaccagc ttcgaactca actctgagaa tgtgaccatg   600
aaagttgtgt ctgtcctgta taatgtaaca atcaacaaca cttattcatg catgattgaa   660
aacgacatcg ccaaggcaac aggtgatatt aaggtaactg aatccgagat caaacggcgg   720
tctcacctac agctgctaaa ctcaaaggct tct,                                753
```

(SEQ ID NO: 40)
```
atggaatgga gctgggtatt tctgtttttc ctgtcagtaa cgactggcgt ccattcaggc    60
ttcggcatca gtggacggca cagtatcaca gtgaccaccg tcgcctccgc tggcaatata   120
ggtgaggatg gcatcctgtc ctgtaccttt gagccggaca tcaaactgtc tgacatagtg   180
atacaatggc tgaaggaggg ggtgctcggt ctggtacatg agtttaagga agggaaggat   240
gaactgtccg agcaggatga gatgttccgg gggaggaccg ctgtgttcgc cgatcaggta   300
atcgtcggaa atgcaagtct cagattgaaa aatgtgcaac tgactgatgc tggcacgtat   360
aaatgctaca ttatcacaag taagggcaaa ggaaatgcta accttgagta taaaacaggc   420
gcattctcaa tgcccgaggt caatgtcgac tataatgcca gcagtgaaac attgcgctgt   480
gaagctcccc gctggttccc ccagccaacc gtggtctggg cctctcaggt tgatcagggg   540
gctaactttt ccgaggtgag caacaccagc ttcgaactca actctgagaa tgtgaccatg   600
aaagttgtgt ctgtcctgta taatgtaaca atcaacaaca cttattcatg catgattgaa   660
aacgacatcg ccaaggcaac aggtgatatt aaggtaactg aatccgagat caaacggcgg   720
tct,                                                                 723
```

(SEQ ID NO: 41)
```
atggaatgga gctgggtatt tctgtttttc ctgtcagtaa cgactggcgt ccattcaggc    60
ttcggcatca gtggacggca cagtatcaca gtgaccaccg tcgcctccgc tggcaatata   120
ggtgaggatg gcatcctgtc ctgtaccttt gagccggaca tcaaactgtc tgacatagtg   180
atacaatggc tgaaggaggg ggtgctcggt ctggtacatg agtttaagga agggaaggat   240
gaactgtccg agcaggatga gatgttccgg gggaggaccg ctgtgttcgc cgatcaggta   300
atcgtcggaa atgcaagtct cagattgaaa aatgtgcaac tgactgatgc tggcacgtat   360
aaatgctaca ttatcacaag taagggcaaa ggaaatgcta accttgagta taaaacaggc   420
gcattctcaa tgcccgaggt caatgtcgac tataatgcca gcagtgaaac attgcgctgt   480
gaagctcccc gctggttccc ccagccaacc gtggtctggg cctctcaggt tgatcagggg   540
gctaactttt ccgaggtgag caacaccagc ttcgaactca actctgagaa tgtgaccatg   600
aaagttgtgt ctgtcctgta taatgtaaca atcaacaaca cttattcatg catgattgaa   660
aacgacatcg ccaaggcaac aggtgatatt aaggtaactg aatccgagat c,            711
or
```

-continued

```
                                                        (SEQ ID NO: 42)
atggaatgga gctgggtatt tctgtttttc ctgtcagtaa cgactggcgt ccattcaggc    60
ttcggcatca gtggacggca cagtatcaca gtgaccaccg tcgcctccgc tggcaatata   120
ggtgaggatg gcatcctgtc ctgtaccttt gagccggaca tcaaactgtc tgacatagtg   180
atacaatggc tgaaggaggg ggtgctcggt ctggtacatg agtttaagga agggaaggat   240
gaactgtccg agcaggatga gatgttccgg gggaggaccg ctgtgttcgc cgatcaggta   300
atcgtcggaa atgcaagtct cagattgaaa aatgtgcaac tgactgatgc tggcacgtat   360
aaatgctaca ttatcacaag taagggcaaa ggaaatgcta accttgagta taaaacaggc   420
gcattctcaa tgcccgaggt caatgtcgac tataatgcca gcagtgaaac attgcgctgt   480
gaagctcccc gctggttccc ccagccaacc gtggtctggg cctctcaggt tgatcagggg   540 gctaacttt ccgaggtgag caacaccagc ttcgaactca actctgagaa tgtgaccatg   600
aaagttgtgt ctgtcctgta taatgtaaca atcaacaaca cttattcatg catgattgaa   660
aacgacatcg ccaaggcaac aggtgatatt aaggtaactg aatccgagat caaacggcgg   720
tctcacctac agctgctaaa ctcaaaggct tct.                              753
```

In another embodiment, the first fusion partner can have at least 80%, 85%, 90%, 95%, 99%, or 100% sequence identity to the human amino acid sequence:

```
                                                        (SEQ ID NO: 43)
MEWSWVFLFF LSVTTGVHSG FGISGRHSIT VTTVASAGNI GEDGIQSCTF EPDIKLSDIV    60

IQWLKEGVLG LVHEFKEGKD ELSEQDEMFR GRTAVFADQV IVGNASLRLK NVQLTDAGTY   120

KCYIITSKGK GNANLEYKTG AFSMPEVNVD YNASSETLRC EAPRWFPQPT VVWASQVDQG   180

ANFSEVSNTS FELNSENVTM KVVSVLYNVT INNTYSCMIE NDIAKATGDI KVTESEIKRR   240

S                                                                  241

(SEQ ID NO: 44)
MEWSWVFLFF LSVTTGVHSG FGISGRHSIT VTTVASAGNI GEDGIQSCTF EPDIKLSDIV    60

IQWLKEGVLG LVHEFKEGKD ELSEQDEMFR GRTAVFADQV IVGNASLRLK NVQLTDAGTY   120

KCYIITSKGK GNANLEYKTG AFSMPEVNVD YNASSETLRC EAPRWFPQPT VVWASQVDQG   180

ANFSEVSNTS FELNSENVTM KVVSVLYNVT INNTYSCMIE NDIAKATGDI KVTESEI,    237

(SEQ ID NO: 45)
MEWSWVFLFF LSVTTGVHSG FGISGRHSIT VTTVASAGNI GEDGIQSCTF EPDIKLSDIV    60

IQWLKEGVLG LVHEFKEGKD ELSEQDEMFR GRTAVFADQV IVGNASLRLK NVQLTDAGTY   120

KCYIITSKGK GNANLEYKTG AFSMPEVNVD YNASSETLRC EAPRWFPQPT VVWASQVDQG   180

ANFSEVSNTS FELNSENVTM KVVSVLYNVT INNTYSCMIE NDIAKATGDI KVTESEIKRR   240

SHLQLLNSKA S,                                                      251

(SEQ ID NO: 46)
MEWSWVFLFF LSVTTGVHSG FGISGRHSIT VTTVASAGNI GEDGILSCTF EPDIKLSDIV    60

IQWLKEGVLG LVHEFKEGKD ELSEQDEMFR GRTAVFADQV IVGNASLRLK NVQLTDAGTY   120

KCYIITSKGK GNANLEYKTG AFSMPEVNVD YNASSETLRC EAPRWFPQPT VVWASQVDQG   180

ANFSEVSNTS FELNSENVTM KVVSVLYNVT INNTYSCMIE NDIAKATGDI KVTESEIKRR   240

S,                                                                 241

(SEQ ID NO: 47)
MEWSWVFLFF LSVTTGVHSG FGISGRHSIT VTTVASAGNI GEDGILSCTF EPDIKLSDIV    60

IQWLKEGVLG LVHEFKEGKD ELSEQDEMFR GRTAVFADQV IVGNASLRLK NVQLTDAGTY   120
```

-continued

```
KCYIITSKGK GNANLEYKTG AFSMPEVNVD YNASSETLRC EAPRWFPQPT VVWASQVDQG   180

ANFSEVSNTS FELNSENVTM KVVSVLYNVT INNTYSCMIE NDIAKATGDI KVTESEI,    237

(SEQ ID NO: 48)
MEWSWVFLFF LSVTTGVHSG FGISGRHSIT VTTVASAGNI GEDGILSCTF EPDIKLSDIV   60

IQWLKEGVLG LVHEFKEGKD ELSEQDEMFR GRTAVFADQV IVGNASLRLK NVQLTDAGTY   120

KCYIITSKGK GNANLEYKTG AFSMPEVNVD YNASSETLRC EAPRWFPQPT VVWASQVDQG   180

ANFSEVSNTS FELNSENVTM KVVSVLYNVT INNTYSCMIE NDIAKATGDI KVTESEIKRR   240

SHLQLLNSKA S,                                                      251

(SEQ ID NO: 49)
MASLGQILFW SIISIIIILA GAIALIIGFG ISGRHSITVT TVASAGNIGE DGIQSCTFEP   60

DIKLSDIVIQ WLKEGVLGLV HEFKEGKDEL SEQDEMFRGR TAVFADQVIV GNASLRLKNV   120

QLTDAGTYKC YIITSKGKGN ANLEYKTGAF SMPEVNVDYN ASSETLRCEA PRWFPQPTVV   180

WASQVDQGAN FSEVSNTSFE LNSENVTMKV VSVLYNVTIN NTYSCMIEND IAKATGDIKV   240

TESEIKRRS,                                                         249

(SEQ ID NO: 50)
MASLGQILFW SIISIIIILA GAIALIIGFG ISGRHSITVT TVASAGNIGE DGIQSCTFEP   60

DIKLSDIVIQ WLKEGVLGLV HEFKEGKDEL SEQDEMFRGR TAVFADQVIV GNASLRLKNV   120

QLTDAGTYKC YIITSKGKGN ANLEYKTGAF SMPEVNVDYN ASSETLRCEA PRWFPQPTVV   180

WASQVDQGAN FSEVSNTSFE LNSENVTMKV VSVLYNVTIN NTYSCMIEND IAKATGDIKV   240

TESEI,                                                             245

(SEQ ID NO: 51)
MASLGQILFW SIISIIIILA GAIALIIGFG ISGRHSITVT TVASAGNIGE DGIQSCTFEP   60

DIKLSDIVIQ WLKEGVLGLV HEFKEGKDEL SEQDEMFRGR TAVFADQVIV GNASLRLKNV   120

QLTDAGTYKC YIITSKGKGN ANLEYKTGAF SMPEVNVDYN ASSETLRCEA PRWFPQPTVV   180

WASQVDQGAN FSEVSNTSFE LNSENVTMKV VSVLYNVTIN NTYSCMIEND IAKATGDIKV   240

TESEIKRRSH LQLLNSKAS,                                              259

(SEQ ID NO: 52)
MASLGQILFW SIISIIIILA GAIALIIGFG ISGRHSITVT TVASAGNIGE DGILSCTFEP   60

DIKLSDIVIQ WLKEGVLGLV HEFKEGKDEL SEQDEMFRGR TAVFADQVIV GNASLRLKNV   120

QLTDAGTYKC YIITSKGKGN ANLEYKTGAF SMPEVNVDYN ASSETLRCEA PRWFPQPTVV   180

WASQVDQGAN FSEVSNTSFE LNSENVTMKV VSVLYNVTIN NTYSCMIEND IAKATGDIKV   240

TESEIKRRS,                                                         249

(SEQ ID NO: 53)
MASLGQILFW SIISIIIILA GAIALIIGFG ISGRHSITVT TVASAGNIGE DGILSCTFEP   60

DIKLSDIVIQ WLKEGVLGLV HEFKEGKDEL SEQDEMFRGR TAVFADQVIV GNASLRLKNV   120

QLTDAGTYKC YIITSKGKGN ANLEYKTGAF SMPEVNVDYN ASSETLRCEA PRWFPQPTVV   180

WASQVDQGAN FSEVSNTSFE LNSENVTMKV VSVLYNVTIN NTYSCMIEND IAKATGDIKV   240

TESEI,                                                             245
or
                                                       (SEQ ID NO: 54)
MASLGQILFW SIISIIIILA GAIALIIGFG ISGRHSITVT TVASAGNIGE DGILSCTFEP   60

DIKLSDIVIQ WLKEGVLGLV HEFKEGKDEL SEQDEMFRGR TAVFADQVIV GNASLRLKNV   120

QLTDAGTYKC YIITSKGKGN ANLEYKTGAF SMPEVNVDYN ASSETLRCEA PRWFPQPTVV   180

WASQVDQGAN FSEVSNTSFE LNSENVTMKV VSVLYNVTIN NTYSCMIEND IAKATGDIKV   240

TESEIKRRSH LQLLNSKAS.                                              259
```

The signal sequence will be removed in the mature protein. Additionally, signal peptides from other polypeptides or organisms can be used to enhance the secretion of the fusion protein from a host during manufacture. SEQ ID NO:55 provides the human amino acid sequence of SEQ ID NO:43 and SEQ ID NO:49 without the signal sequence:

```
                                                    (SEQ ID NO: 55)
GFGISGRHSI TVTTVASAGN IGEDGIQSCT FEPDIKLSDI VIQWLKEGVL GLVHEFKEGK    60

DELSEQDEMF RGRTAVFADQ VIVGNASLRL KNVQLTDAGT YKCYIITSKG KGNANLEYKT   120

GAFSMPEVNV DYNASSETLR CEAPRWFPQP TVVWASQVDQ GANFSEVSNT SFELNSENVT   180

MKVVSVLYNV TINNTYSCMI ENDIAKATGD IKVTESEIKR RS.                    222
```

SEQ ID NO:56 provides the human amino acid sequence of SEQ ID NO:46 and SEQ ID NO:52 without the signal sequence:

```
                                                    (SEQ ID NO: 56)
GFGISGRHSI TVTTVASAGN IGEDGILSCT FEPDIKLSDI VIQWLKEGVL GLVHEFKEGK    60

DELSEQDEMF RGRTAVFADQ VIVGNASLRL KNVQLTDAGT YKCYIITSKG KGNANLEYKT   120

GAFSMPEVNV DYNASSETLR CEAPRWFPQP TVVWASQVDQ GANFSEVSNT SFELNSENVT   180

MKVVSVLYNV TINNTYSCMI ENDIAKATGD IKVTESEIKR RS.                    222
```

SEQ ID NO:57 provides the human amino acid sequence of SEQ ID NO:44 and SEQ ID NO:50 without the signal sequence:

```
                                                    (SEQ ID NO: 57)
GFGISGRHSI TVTTVASAGN IGEDGIQSCT FEPDIKLSDI VIQWLKEGVL GLVHEFKEGK    60

DELSEQDEMF RGRTAVFADQ VIVGNASLRL KNVQLTDAGT YKCYIITSKG KGNANLEYKT   120

GAFSMPEVNV DYNASSETLR CEAPRWFPQP TVVWASQVDQ GANFSEVSNT SFELNSENVT   180

MKVVSVLYNV TINNTYSCMI ENDIAKATGD IKVTESEI.                         218
```

SEQ ID NO:58 provides the human amino acid sequence of SEQ ID NO:47 and SEQ ID NO:53 without the signal sequence:

```
                                                    (SEQ ID NO: 58)
GFGISGRHSI TVTTVASAGN IGEDGILSCT FEPDIKLSDI VIQWLKEGVL GLVHEFKEGK    60

DELSEQDEMF RGRTAVFADQ VIVGNASLRL KNVQLTDAGT YKCYIITSKG KGNANLEYKT   120

GAFSMPEVNV DYNASSETLR CEAPRWFPQP TVVWASQVDQ GANFSEVSNT SFELNSENVT   180

MKVVSVLYNV TINNTYSCMI ENDIAKATGD IKVTESEI.                         218
```

SEQ ID NO:59 provides the human amino acid sequence of SEQ ID NO:45 and SEQ ID NO:51 without the signal sequence:

```
                                                    (SEQ ID NO: 59)
GFGISGRHSI TVTTVASAGN IGEDGIQSCT FEPDIKLSDI VIQWLKEGVL GLVHEFKEGK    60

DELSEQDEMF RGRTAVFADQ VIVGNASLRL KNVQLTDAGT YKCYIITSKG KGNANLEYKT   120

GAFSMPEVNV DYNASSETLR CEAPRWFPQP TVVWASQVDQ GANFSEVSNT SFELNSENVT   180

MKVVSVLYNV TINNTYSCMI ENDIAKATGD IKVTESEIKR RSHLQLLNSK AS.         232
```

SEQ ID NO:60 provides the human amino acid sequence of SEQ ID NO:48 and SEQ ID NO:54 without the signal sequence:

```
                                                          (SEQ ID NO: 60)
GFGISGRHSI TVTTVASAGN IGEDGILSCT FEPDIKLSDI VIQWLKEGVL GLVHEFKEGK     60

DELSEQDEMF RGRTAVFADQ VIVGNASLRL KNVQLTDAGT YKCYIITSKG KGNANLEYKT    120

GAFSMPEVNV DYNASSETLR CEAPRWFPQP TVVWASQVDQ GANFSEVSNT SFELNSENVT    180

MKVVSVLYNV TINNTYSCMI ENDIAKATGD IKVTESEIKR RSHLQLLNSK AS.           232
```

In other embodiments the final alanine and serine residues are removed from SEQ ID NOS: 45, 48, 51, 54, 59, and 60.

In another embodiment, the first fusion partner of the fusion protein includes the IgV domain of human B7-H4. In one embodiment, the IgV domain includes at least from the cysteine at position 56 of SEQ ID NO:9 or SEQ ID NO:12 to the cysteine at position 130 of SEQ ID NO:9 or SEQ ID NO:12. In another embodiment, the IgV domain contains a fragment of at least 25 or 50 amino acids of the polypeptide defined by this amino acid range.

The first fusion partner can be encoded by a nucleotide sequence having at least 80%, 85%, 90%, 95%, 99%, or 100% sequence identity to the following nucleotide sequence encoding an exemplary IgV domain:

```
                                                          (SEQ ID NO: 61)
ggcttcggca tcagtggacg gcacagtatc acagtgacca ccgtcgcctc cgctggcaat     60
ataggtgagg atggcatcca gtcctgtacc tttgagccgg acatcaaact gtctgacata    120
gtgatacaat ggctgaagga gggggtgctc ggtctggtac atgagtttaa ggaagggaag    180
gatgaactgt ccgagcagga tgagatgttc cgggggagga ccgctgtgtt cgccgatcag    240
gtaatcgtcg gaaatgcaag tctcagattg aaaaatgtgc aactgactga tgctggcacg    300
tataaatgct acattatcac aagtaagggc aaaggaaatg ctaaccttga gtataaaaca    360
ggcgcattct caatgcccga ggtcaat                                        387
or
                                                          (SEQ ID NO: 62)
ggcttcggca tcagtggacg gcacagtatc acagtgacca ccgtcgcctc cgctggcaat     60
ataggtgagg atggcatcct gtcctgtacc tttgagccgg acatcaaact gtctgacata    120
gtgatacaat ggctgaagga gggggtgctc ggtctggtac atgagtttaa ggaagggaag    180
gatgaactgt ccgagcagga tgagatgttc cgggggagga ccgctgtgtt cgccgatcag    240
gtaatcgtcg gaaatgcaag tctcagattg aaaaatgtgc aactgactga tgctggcacg    300
tataaatgct acattatcac aagtaagggc aaaggaaatg ctaaccttga gtataaaaca    360
ggcgcattct caatgcccga ggtcaat.                                       387
```

The first fusion partner can have at least 80%, 85%, 90%, 95%, 99%, or 100% sequence identity to the human amino acid sequence:

```
                                                          (SEQ ID NO: 63)
GFGISGRHSI TVTTVASAGN IGEDGIQSCT FEPDIKLSDI VIQWLKEGVL GLVHEFKEGK     60

DELSEQDEMF RGRTAVFADQ VIVGNASLRL KNVQLTDAGT YKCYIITSKG KGNANLEYKT    120

GAFSMPEVN,                                                           129
or
                                                          (SEQ ID NO: 64)
GFGISGRHSI TVTTVASAGN IGEDGILSCT FEPDIKLSDI VIQWLKEGVL GLVHEFKEGK     60

DELSEQDEMF RGRTAVFADQ VIVGNASLRL KNVQLTDAGT YKCYIITSKG KGNANLEYKT    120

GAFSMPEVN.                                                           129
``` c. Non-Human Primate Extracellular Domain Fusion Partners

In another embodiment, the first fusion partner of the fusion protein includes the extracellular domain of non-human primate B7-H4 or a fragment thereof. Exemplary non-human primates include, but are not limited to, chimapanzee (*Pan troglodytes*), rhesus monkey (*Macaca mulatta*) and cynomolgus monkey (*Macaca fascicularis*).

The first fusion partner can have at least 80%, 85%, 90%, 95%, 99%, or 100% sequence identity to the chimapanzee (*Pan troglodytes*) amino acid sequence:

```
                                                       (SEQ ID NO: 65)
MKPLTSRIIS IIIILAGAIA LIIGFGISGR HSITVTTVAS AGNIGEDGIL SCTFEPDIKL    60

SDIVIQWLKE GVLGLVHEFK EGKDELSEQD EMFRGRTAVF ADQVIVGNAS LRLKNVQLTD   120

AGTYKCYIIT SKGKGNANLE YKTGAFSMPE VNVDYNASSE TLRCEAPRWF PQPTVVWASQ   180

IDQGANFSEV SNTSFELNSE NVTMKVVSVL YNATINNTYS CMIENDIAKA TGDIKVTESE   240

IKRRS,                                                              245

(SEQ ID NO: 66)
MKPLTSRIIS IIIILAGAIA LIIGFGISGR HSITVTTVAS AGNIGEDGIL SCTFEPDIKL    60

SDIVIQWLKE GVLGLVHEFK EGKDELSEQD EMFRGRTAVF ADQVIVGNAS LRLKNVQLTD   120

AGTYKCYIIT SKGKGNANLE YKTGAFSMPE VNVDYNASSE TLRCEAPRWF PQPTVVWASQ   180

IDQGANFSEV SNTSFELNSE NVTMKVVSVL YNATINNTYS CMIENDIAKA TGDIKVTESE   240

I,                                                                  241
or
                                                       (SEQ ID NO: 67)
MKPLTSRIIS IIIILAGAIA LIIGFGISGR HSITVTTVAS AGNIGEDGIL SCTFEPDIKL    60

SDIVIQWLKE GVLGLVHEFK EGKDELSEQD EMFRGRTAVF ADQVIVGNAS LRLKNVQLTD   120

AGTYKCYIIT SKGKGNANLE YKTGAFSMPE VNVDYNASSE TLRCEAPRWF PQPTVVWASQ   180

IDQGANFSEV SNTSFELNSE NVTMKVVSVL YNATINNTYS CMIENDIAKA TGDIKVTESE   240

IKRRSHLQLL NSKAS.                                                   255
```

The signal sequence will be removed in the mature protein. Additionally, signal peptides from other polypeptides or organisms can be used to enhance the secretion of the fusion protein from a host during manufacture.

SEQ ID NO:68 provides the chimapanzee amino acid sequence of SEQ ID NO:65 without the signal sequence:

```
                                                       (SEQ ID NO: 68)
GFGISGRHSI TVTTVASAGN IGEDGILSCT FEPDIKLSDI VIQWLKEGVL GLVHEFKEGK    60

DELSEQDEMF RGRTAVFADQ VIVGNASLRL KNVQLTDAGT YKCYIITSKG KGNANLEYKT   120

GAFSMPEVNV DYNASSETLR CEAPRWFPQP TVVWASQIDQ GANFSEVSNT SFELNSENVT   180

MKVVSVLYNA TINNTYSCMI ENDIAKATGD IKVTESEIKR RS.                     222
```

SEQ ID NO:69 provides the chimapanzee amino acid sequence of SEQ ID NO:66 without the signal sequence:

```
                                                       (SEQ ID NO: 69)
GFGISGRHSI TVTTVASAGN IGEDGILSCT FEPDIKLSDI VIQWLKEGVL GLVHEFKEGK    60

DELSEQDEMF RGRTAVFADQ VIVGNASLRL KNVQLTDAGT YKCYIITSKG KGNANLEYKT   120

GAFSMPEVNV DYNASSETLR CEAPRWFPQP TVVWASQIDQ GANFSEVSNT SFELNSENVT   180

MKVVSVLYNA TINNTYSCMI ENDIAKATGD IKVTESEI.                          218
```

SEQ ID NO:70 provides the chimapanzee amino acid sequence of SEQ ID NO:67 without the signal sequence:

```
                                                      (SEQ ID NO: 70)
GFGISGRHSI TVTTVASAGN IGEDGILSCT FEPDIKLSDI VIQWLKEGVL GLVHEFKEGK    60

DELSEQDEMF RGRTAVFADQ VIVGNASLRL KNVQLTDAGT YKCYIITSKG KGNANLEYKT   120

GAFSMPEVNV DYNASSETLR CEAPRWFPQP TVVWASQIDQ GANFSEVSNT SFELNSENVT   180

MKVVSVLYNA TINNTYSCMI ENDIAKATGD IKVTESEIKR RSHLQLLNSK AS.          232
```

The first fusion partner can have at least 80%, 85%, 90%, 95%, 99%, or 100% sequence identity to the rhesus monkey (*Macaca mulatta*) amino acid sequence:

```
                                                      (SEQ ID NO: 71)
MASLGQILFW SIISIIFILA GAIALIIGFG ISGRHSITVT TVASAGNIGE DGILSCTFEP    60

DIKLSDIVIQ WLKEGVIGLV HEFKEGKDEL SEQDEMFRGR TAVFADQVIV GNASLRLKNV   120

QLTDAGTYKC YIITSKGKGN ANLEYKTGAF SMPEVNVDYN ASSETLRCEA PRWFPQPTVV   180

WASQVDQGAN FSEVSNTSFE LNSENVTMKV VSVLYNVTIN NTYSCMIEND IAKATGDIKV   240

TESEIKRRS,                                                         249
```

```
                                                      (SEQ ID NO: 72)
MASLGQILFW SIISIIFILA GAIALIIGFG ISGRHSITVT TVASAGNIGE DGILSCTFEP    60

DIKLSDIVIQ WLKEGVIGLV HEFKEGKDEL SEQDEMFRGR TAVFADQVIV GNASLRLKNV   120

QLTDAGTYKC YIITSKGKGN ANLEYKTGAF SMPEVNVDYN ASSETLRCEA PRWFPQPTVV   180

WASQVDQGAN FSEVSNTSFE LNSENVTMKV VSVLYNVTIN NTYSCMIEND IAKATGDIKV   240

TESEI,                                                             245
```
or
```
                                                      (SEQ ID NO: 73)
MASLGQILFW SIISIIFILA GAIALIIGFG ISGRHSITVT TVASAGNIGE DGILSCTFEP    60

DIKLSDIVIQ WLKEGVIGLV HEFKEGKDEL SEQDEMFRGR TAVFADQVIV GNASLRLKNV   120

QLTDAGTYKC YIITSKGKGN ANLEYKTGAF SMPEVNVDYN ASSETLRCEA PRWFPQPTVV   180

WASQVDQGAN FSEVSNTSFE LNSENVTMKV VSVLYNVTIN NTYSCMIEND IAKATGDIKV   240

TESEIKRRSH LQLLNSKAS.                                               259
```

The signal sequence will be removed in the mature protein. Additionally, signal peptides from other polypeptides or organisms can be used to enhance the secretion of the fusion protein from a host during manufacture.

SEQ ID NO:74 provides the rhesus monkey amino acid sequence of SEQ ID NO:71 without the signal sequence:

```
                                                      (SEQ ID NO: 74)
GFGISGRHSI TVTTVASAGN IGEDGILSCT FEPDIKLSDI VIQWLKEGVI GLVHEFKEGK    60

DELSEQDEMF RGRTAVFADQ VIVGNASLRL KNVQLTDAGT YKCYIITSKG KGNANLEYKT   120

GAFSMPEVNV DYNASSETLR CEAPRWFPQP TVVWASQVDQ GANFSEVSNT SFELNSENVT   180

MKVVSVLYNV TINNTYSCMI ENDIAKATGD IKVTESEIKR RS.                     222
```

SEQ ID NO:75 provides the rhesus monkey amino acid sequence of SEQ ID NO:72 without the signal sequence:

```
                                                      (SEQ ID NO: 75)
GFGISGRHSI TVTTVASAGN IGEDGILSCT FEPDIKLSDI VIQWLKEGVI GLVHEFKEGK    60

DELSEQDEMF RGRTAVFADQ VIVGNASLRL KNVQLTDAGT YKCYIITSKG KGNANLEYKT   120
```

```
GAFSMPEVNV DYNASSETLR CEAPRWFPQP TVVWASQVDQ GANFSEVSNT SFELNSENVT    180

MKVVSVLYNV TINNTYSCMI ENDIAKATGD IKVTESEI.                           218
```

SEQ ID NO:76 provides the rhesus monkey amino acid sequence of SEQ ID NO:73 without the signal sequence:

```
                                                          (SEQ ID NO: 76)
GFGISGRHSI TVTTVASAGN IGEDGILSCT FEPDIKLSDI VIQWLKEGVI GLVHEFKEGK     60

DELSEQDEMF RGRTAVFADQ VIVGNASLRL KNVQLTDAGT YKCYIITSKG KGNANLEYKT    120

GAFSMPEVNV DYNASSETLR CEAPRWFPQP TVVWASQVDQ GANFSEVSNT SFELNSENVT    180

MKVVSVLYNV TINNTYSCMI ENDIAKATGD IKVTESEIKR RSHLQLLNSK AS.           232
```

The first fusion partner can have at least 80%, 85%, 90%, 95%, 99%, or 100% sequence identity to the cynomolgus monkey (*Macaca fascicularis*) amino acid sequence:

```
                                                          (SEQ ID NO: 77)
MASLGQILFW SIISIIFILA GAIALIIGFG ISGRHSITVT TVASAGNIGE DGILSCTFEP     60

DIKLSDIVIQ WLKEGVIGLV HEFKEGKDEL SEQDEMFRGR TAVFADQVIV GNASLRLKNV    120

QLTDAGTYKC YIITSKGKGN ANLEYKTGAF SMPEVNVDYN ASSETLRCEA PRWFPQPTVV    180

WASQVDQGAN FSEVSNTSFE LNSENVTMKV VSVLYNVTIN NTYSCMIEND IAKATGDIKV    240

TESEIKRRS,                                                          249

(SEQ ID NO: 78)
MASLGQILFW SIISIIFILA GAIALIIGFG ISGRHSITVT TVASAGNIGE DGILSCTFEP     60

DIKLSDIVIQ WLKEGVIGLV HEFKEGKDEL SEQDEMFRGR TAVFADQVIV GNASLRLKNV    120

QLTDAGTYKC YIITSKGKGN ANLEYKTGAF SMPEVNVDYN ASSETLRCEA PRWFPQPTVV    180

WASQVDQGAN FSEVSNTSFE LNSENVTMKV VSVLYNVTIN NTYSCMIEND IAKATGDIKV    240

TESEI,                                                              245
or
                                                          (SEQ ID NO: 79)
MASLGQILFW SIISIIFILA GAIALIIGFG ISGRHSITVT TVASAGNIGE DGILSCTFEP     60

DIKLSDIVIQ WLKEGVIGLV HEFKEGKDEL SEQDEMFRGR TAVFADQVIV GNASLRLKNV    120

QLTDAGTYKC YIITSKGKGN ANLEYKTGAF SMPEVNVDYN ASSETLRCEA PRWFPQPTVV    180

WASQVDQGAN FSEVSNTSFE LNSENVTMKV VSVLYNVTIN NTYSCMIEND IAKATGDIKV    240

TESEIKRRSH LQLLNSKAS.                                               259
```

The signal sequence will be removed in the mature protein. Additionally, signal peptides from other polypeptides or organisms can be used to enhance the secretion of the fusion protein from a host during manufacture.

SEQ ID NO:80 provides the cynomolgus monkey amino acid sequence of SEQ ID NO:77 without the signal sequence:

```
                                                          (SEQ ID NO: 80)
GFGISGRHSI TVTTVASAGN IGEDGILSCT FEPDIKLSDI VIQWLKEGVI GLVHEFKEGK     60

DELSEQDEMF RGRTAVFADQ VIVGNASLRL KNVQLTDAGT YKCYIITSKG KGNANLEYKT    120

GAFSMPEVNV DYNASSETLR CEAPRWFPQP TVVWASQVDQ GANFSEVSNT SFELNSENVT    180

MKVVSVLYNV TINNTYSCMI ENDIAKATGD IKVTESEIKR RS.                     222
```

SEQ ID NO:81 provides the cynomolgus monkey amino acid sequence of SEQ ID NO:78 without the signal sequence:

```
                                                      (SEQ ID NO: 81)
GFGISGRHSI TVTTVASAGN IGEDGILSCT FEPDIKLSDI VIQWLKEGVI GLVHEFKEGK   60

DELSEQDEMF RGRTAVFADQ VIVGNASLRL KNVQLTDAGT YKCYIITSKG KGNANLEYKT  120

GAFSMPEVNV DYNASSETLR CEAPRWFPQP TVVWASQVDQ GANFSEVSNT SFELNSENVT  180

MKVVSVLYNV TINNTYSCMI ENDIAKATGD IKVTESEI.                        218
```

SEQ ID NO:82 provides the cynomolgus monkey amino acid sequence of SEQ ID NO:79 without the signal sequence:

```
                                                      (SEQ ID NO: 82)
GFGISGRHSI TVTTVASAGN IGEDGILSCT FEPDIKLSDI VIQWLKEGVI GLVHEFKEGK   60

DELSEQDEMF RGRTAVFADQ VIVGNASLRL KNVQLTDAGT YKCYIITSKG KGNANLEYKT  120

GAFSMPEVNV DYNASSETLR CEAPRWFPQP TVVWASQVDQ GANFSEVSNT SFELNSENVT  180

MKVVSVLYNV TINNTYSCMI ENDIAKATGD IKVTESEIKR RSHLQLLNSK AS.         232
```

In other embodiments the final alanine and serine residues are removed from SEQ ID NOS:67, 70, 73, 76, 79, and 82.

In another embodiment, the first fusion partner of the fusion protein includes the IgV domain of chimpanzee B7-H4. In another embodiment, the IgV domain includes at least from the cysteine at position 52 of SEQ ID NO:15 to the cysteine at position 126 of SEQ ID NO:15. In another embodiment, the IgV domain contains a fragment of at least 25 or 50 amino acids of the polypeptide defined by this amino acid range.

The first fusion partner can have at least 80%, 85%, 90%, 95%, 99%, or 100% sequence identity to the following chimpanzee amino acid sequence of the following exemplary IgV domain:

```
                                                      (SEQ ID NO: 83)
GFGISGRHSI TVTTVASAGN IGEDGILSCT FEPDIKLSDI VIQWLKEGVL GLVHEFKEGK   60

DELSEQDEMF RGRTAVFADQ VIVGNASLRL KNVQLTDAGT YKCYIITSKG KGNANLEYKT  120

GAFSMPEVN.                                                        129
```

In another embodiment, the first fusion partner of the fusion protein includes the IgV domain of rhesus monkey B7-H4. In one embodiment, the IgV domain includes at least from the cysteine at position 56 of SEQ ID NO:17 to the cysteine at position 130 of SEQ ID NO:17. In another embodiment, the IgV domain contains a fragment of at least 25 or 50 amino acids of the polypeptide defined by this amino acid range.

The first fusion protein can have at least 80%, 85%, 90%, 95%, 99%, or 100% sequence identity to the rhesus monkey amino acid sequence of the following exemplary IgV domain:

In another embodiment, the first fusion partner of the fusion protein includes the IgV domain of cynomolgus monkey B7-H4. In one embodiment, the IgV domain includes at least from the cysteine at position 56 of SEQ ID NO:19 to the cysteine at position 130 of SEQ ID NO:19. In another embodiment, the IgV domain contains a fragment of at least 25 or 50 amino acids of the polypeptide defined by this amino acid range.

The first fusion protein can have at least 80%, 85%, 90%, 95%, 99%, or 100% sequence identity to the cynomolgus monkey amino acid sequence of the following exemplary IgV domain:

```
                                                      (SEQ ID NO: 84)
GFGISGRHSI TVTTVASAGN IGEDGILSCT FEPDIKLSDI VIQWLKEGVI GLVHEFKEGK   60

DELSEQDEMF RGRTAVFADQ VIVGNASLRL KNVQLTDAGT YKCYIITSKG KGNANLEYKT  120

GAFSMPEVN.                                                        129
```

```
                                                          (SEQ ID NO: 85)
GFGISGRHSI TVTTVASAGN IGEDGILSCT FEPDIKLSDI VIQWLKEGVI GLVHEFKEGK   60

DELSEQDEMF RGRTAVFADQ VIVGNASLRL KNVQLTDAGT YKCYIITSKG KGNANLEYKT  120

GAFSMPEVN.                                                        129
``` d. B7-H4 Extracellular Domain Fragments

The B7-H4 extracellular domain can contain one or more amino acids from the signal peptide or the putative transmembrane domain of B7-H4. During secretion, the number of amino acids of the signal peptide that are cleaved can vary depending on the expression system and the host. Additionally, fragments of B7-H4 extracellular domain missing one or more amino acids from the C-terminus or the N-terminus that retain the ability to bind to the B7-H4 receptor can be used as a fusion partner for the disclosed fusion proteins.

For example, suitable fragments of murine B7-H4 that can be used as a first fusion partner include, but are not limited to, the following:
32-257, 32-256, 32-255, 32-254, 32-253, 32-252, 32-251, 32-250, 32-249, 31-257, 31-256, 31-255, 31-254, 31-253, 31-252, 31-251, 31-250, 31-249, 30-257, 30-256, 30-255, 30-254, 30-253, 30-252, 30-251, 30-250, 30-249, 29-257, 29-256, 29-255, 29-254, 29-253, 29-252, 29-251, 29-250, 29-249, 28-257, 28-256, 28-255, 28-254, 28-253, 28-252, 28-251, 28-250, 28-249, 27-257, 27-256, 27-255, 27-254, 27-253, 27-252, 27-251, 27-250, 27-249, 26-257, 26-256, 26-255, 26-254, 26-253, 26-252, 26-251, 26-250, 26-249, 25-257, 25-256, 25-255, 25-254, 25-253, 25-252, 25-251, 25-250, 25-249, 24-257, 24-256, 24-255, 24-254, 24-253, 24-252, 24-251, 24-250, 24-249, of SEQ ID NO:26 or SEQ ID NO:27, or 24-249, 24-248, 24-247, 24-246, 24-245, 24-244, 24-243, 24-242, 24-241, 23-249, 23-248, 23-247, 23-246, 23-245, 23-244, 23-243, 23-242, 23-241, 22-249, 22-248, 22-247, 22-246, 22-245, 22-244, 22-243, 22-242, 22-241, 21-249, 21-248, 21-247, 21-246, 21-245, 21-244, 21-243, 21-242, 21-241, 20-249, 20-248, 20-247, 20-246, 20-245, 20-244, 20-243, 20-242, 20-241, 19-249, 19-248, 19-247, 19-246, 19-245, 19-244, 19-243, 19-242, 19-241, 18-249, 18-248, 18-247, 18-246, 18-245, 18-244, 18-243, 18-242, 18-241, 17-249, 17-248, 17-247, 17-246, 17-245, 17-244, 17-243, 17-242, 17-241, 16-249, 16-248, 16-247, 16-246, 16-245, 16-244, 16-243, 16-242, 16-241, of SEQ ID NO:24 or SEQ ID NO:25.

Additional suitable fragments of murine B7-H4 include, but are not limited to, the following:
  28-257, 28-258, 28-259, 28-260, 28-261, 28-262, 28-263, 29-257, 29-258, 29-259, 29-260, 29-261, 29-262, 29-263, 30-257, 30-258, 30-259, 30-260, 30-261, 30-262, 30-263, 31-257, 31-258, 31-259, 31-260, 31-261, 31-262, 31-263, 32-257, 32-258, 32-259, 32-260, 32-261, 32-262, 32-263,
of SEQ ID NO:2 or SEQ ID NO:5, optionally with one to five amino acids of a signal peptide attached to the N-terminal end. The signal peptide may be any disclosed herein, including those contained within SEQ ID NOs:2, 3, 5, 6, 9, 10, 12, 13, 15, 17 and 19, or may be any signal peptide known in the art.

Additional suitable fragments of murine B7-H4 include, but are not limited to, fragments containing at least 25, 20, 75, 100 or 125 amino acids of the IgV domain as set forth in SEQ ID NO:32 or SEQ ID NO:33. Exemplary fragments include, but are not limited to:

16-144, 16-145, 16-146, 16-147, 16-148, 16-149, 16-150, 16-151, 16-152, 17-144, 17-145, 17-146, 17-147, 17-148, 17-149, 17-150, 17-151, 17-152, 18-144, 18-145, 18-146, 18-147, 18-148, 18-149, 18-150, 18-151, 18-152, 19-144, 19-145, 19-146, 19-147, 19-148, 19-149, 19-150, 19-151, 19-152, 20-144, 20-145, 20-146, 20-147, 20-148, 20-149, 20-150, 20-151, 20-152, 21-144, 21-145, 21-146, 21-147, 21-148, 21-149, 21-150, 21-151, 21-152, 22-144, 22-145, 22-146, 22-147, 22-148, 22-149, 22-150, 22-151, 22-152, 23-144, 23-145, 23-146, 23-147, 23-148, 23-149, 23-150, 23-151, 23-152, 24-144, 24-145, 24-146, 24-147, 24-148, 24-149, 24-150, 24-151, 24-152, of SEQ ID NO:24 or SEQ ID NO:25, or 24-152, 24-153, 24-154, 24-155, 24-156, 24-157, 24-158, 24-159, 24-160, 25-152, 25-153, 25-154, 25-155, 25-156, 25-157, 25-158, 25-159, 25-160, 26-152, 26-153, 26-154, 26-155, 26-156, 26-157, 26-158, 26-159, 26-160, 27-152, 27-153, 27-154, 27-155, 27-156, 27-157, 27-158, 27-159, 27-160, 28-152, 28-153, 28-154, 28-155, 28-156, 28-157, 28-158, 28-159, 28-160, 29-152, 29-153, 29-154, 29-155, 29-156, 29-157, 29-158, 29-159, 29-160, 30-152, 30-153, 30-154, 30-155, 30-156, 30-157, 30-158, 30-159, 30-160, 31-152, 31-153, 31-154, 31-155, 31-156, 31-157, 31-158, 31-159, 31-160, 32-152, 32-153, 32-154, 32-155, 32-156, 32-157, 32-158, 32-159, 32-160, of SEQ ID NO:26 or SEQ ID NO:27, optionally with one to five amino acids of a signal peptide attached to the N-terminal end. The signal peptide may be any disclosed herein, including those contained within SEQ ID NOs:2, 3, 5, 6, 9, 10, 12, 13, 15, 17 and 19, or may be any signal peptide known in the art.

Exemplary suitable fragments of human B7-H4 that can be used as a first fusion partner include, but are not limited to, the following:
32-249, 32-248, 32-247, 32-246, 32-245, 32-244, 32-243, 32-242, 32-241, 31-249, 31-248, 31-247, 31-246, 31-245, 31-244, 31-243, 31-242, 31-241, 30-249, 30-248, 30-247, 30-246, 30-245, 30-244, 30-243, 30-242, 30-241, 29-249, 29-248, 29-247, 29-246, 29-245, 29-244, 29-243, 29-242, 29-241, 28-249, 28-248, 28-247, 28-246, 28-245, 28-244, 28-243, 28-242, 28-241, 27-249, 27-248, 27-247, 27-246, 27-245, 27-244, 27-243, 27-242, 27-241, 26-249, 26-248, 26-247, 26-246, 26-245, 26-244, 26-243, 26-242, 26-241, 25-249, 25-248, 25-247, 25-246, 25-245, 25-244, 25-243, 25-242, 25-241, 24-249, 24-248, 24-247, 24-246, 24-245, 24-244, 24-243, 24-242, 24-241, of SEQ ID NO:49, or SEQ ID NO:52, or 32-245, 32-244, 32-243, 32-242, 32-241, 32-240, 32-239, 32-238, 32-237, 31-245, 31-244, 31-243, 31-242, 31-241, 31-240, 31-239, 31-238, 31-237, 30-245, 30-244, 30-243, 30-242, 30-241, 30-240, 30-239, 30-238, 30-237, 29-245, 29-244, 29-243, 29-242, 29-241, 29-240, 29-239, 29-238, 29-237, 28-245, 28-244, 28-243, 28-242, 28-241, 28-240, 28-239, 28-238, 28-237, 27-245, 27-244, 27-243, 27-242, 27-241, 27-240, 27-239, 27-238, 27-237, 26-245, 26-244, 26-243, 26-242, 26-241, 26-240, 26-239, 26-238, 26-237, 25-245, 25-244, 25-243, 25-242, 25-241, 25-240, 25-239, 25-238, 25-237, 24-245, 24-244, 24-243, 24-242, 24-241, 24-240, 24-239, 24-238, 24-237, of SEQ ID NO:50 or SEQ ID NO:53, or 32-259, 32-258, 32-257, 32-256, 32-255, 32-254, 32-253, 32-252, 32-251, 31-259, 31-258, 31-257, 31-256, 31-255, 31-254, 31-253, 31-252, 31-251, 30-259, 30-258, 30-257, 30-256, 30-255, 30-254, 30-253, 30-252, 30-251, 29-259, 29-258, 29-257, 29-256, 29-255, 29-254, 29-253, 29-252, 29-251, 28-259, 28-258, 28-257, 28-256, 28-255, 28-254, 28-253, 28-252, 28-251, 27-259, 27-258, 27-257, 27-256, 27-255, 27-254, 27-253, 27-252, 27-251, 26-259, 26-258, 26-257, 26-256, 26-255, 26-254, 26-253, 26-252, 26-251, 25-259, 25-258, 25-257, 25-256, 25-255, 25-254, 25-253, 25-252, 25-251, 24-259, 24-258, 24-257, 24-256, 24-255, 24-254, 24-253, 24-252, 24-251, of SEQ ID NO:51 or SEQ ID NO:54, or 24-241, 24-240, 24-239, 24-238, 24-237, 24-236, 24-235, 24-234, 24-233, 23-241, 23-240, 23-239, 23-238, 23-237, 23-236, 23-235, 23-234, 23-233, 22-241, 22-240, 22-239, 22-238, 22-237, 22-236, 22-235, 22-234, 22-233, 21-241, 21-240, 21-239, 21-238, 21-237, 21-236, 21-235, 21-234, 21-233, 20-241, 20-240, 20-239, 20-238, 20-237, 20-236, 20-235, 20-234, 20-233, 19-241, 19-240, 19-239, 19-238, 19-237, 19-236, 19-235, 19-234, 19-233, 18-241, 18-240, 18-239, 18-238, 18-237, 18-236, 18-235, 18-234, 18-233, 17-241, 17-240, 17-239, 17-238, 17-237, 17-236, 17-235, 17-234, 17-233, 16-241, 16-240, 16-239, 16-238, 16-237, 16-236, 16-235, 16-234, 16-233, of SEQ ID NO:43 or SEQ ID NO:46, or 24-237, 24-236, 24-235, 24-234, 24-233, 24-232, 24-231, 24-230, 24-229, 23-237, 23-236, 23-235, 23-234, 23-233, 23-232, 23-231, 23-230, 23-229, 22-237, 22-236, 22-235, 22-234, 22-233, 22-232, 22-231, 22-230, 22-229, 21-237, 21-236, 21-235, 21-234, 21-233, 21-232, 21-231, 21-230, 21-229, 20-237, 20-236, 20-235, 20-234, 20-233, 20-232, 20-231, 20-230, 20-229, 19-237, 19-236, 19-235, 19-234, 19-233, 19-232, 19-231, 19-230, 19-229, 18-237, 18-236, 18-235, 18-234, 18-233, 18-232, 18-231, 18-230, 18-229, 17-237, 17-236, 17-235, 17-234, 17-233, 17-232, 17-231, 17-230, 17-229, 16-237, 16-236, 16-235, 16-234, 16-233, 16-232, 16-231, 16-230, 16-229, of SEQ ID NO:44 or SEQ ID NO:47, or 24-251, 24-250, 24-249, 24-248, 24-247, 24-246, 24-245, 24-244, 24-243, 23-251, 23-250, 23-249, 23-248, 23-247, 23-246, 23-245, 23-244, 23-243, 22-251, 22-250, 22-249, 22-248, 22-247, 22-246, 22-245, 22-244, 22-243, 21-251, 21-250, 21-249, 21-248, 21-247, 21-246, 21-245, 21-244, 21-243, 20-251, 20-250, 20-249, 20-248, 20-247, 20-246, 20-245, 20-244, 20-243, 19-251, 19-250, 19-249, 19-248, 19-247, 19-246, 19-245, 19-244, 19-243, 18-251, 18-250, 18-249, 18-248, 18-247, 18-246, 18-245, 18-244, 18-243, 17-251, 17-250, 17-249, 17-248, 17-247, 17-246, 17-245, 17-244, 17-243, 16-251, 16-250, 16-249, 16-248, 16-247, 16-246, 16-245, 16-244, 16-243, of SEQ ID NO:45 or SEQ ID NO:48.

Additional suitable fragments of human B7-H4 include, but are not limited to, the following:

27-249, 27-250, 27-251, 27-252, 27-253, 27-254, 27-255, 27-256, 27-257, 27-259, 27-260, 28-249, 28-250, 28-251, 28-252, 28-253, 28-254, 28-255, 28-256, 28-257, 28-259, 28-260, 29-249, 29-250, 29-251, 29-252, 29-253, 29-254, 29-255, 29-256, 29-257, 29-259, 29-260, 30-249, 30-250, 30-251, 30-252, 30-253, 30-254, 30-255, 30-256, 30-257, 30-259, 30-260, 31-249, 31-250, 31-251, 31-252, 31-253, 31-254, 31-255, 31-256, 31-257, 31-259, 31-260, 32-249, 32-250, 32-251, 32-252, 32-253, 32-254, 32-255, 32-256, 32-257, 32-259, 32-260 of SEQ ID NO:9 or SEQ ID NO:12, optionally with one to five amino acids of a signal peptide attached to the N-terminal end. The signal peptide may be any disclosed herein, including those contained within SEQ ID NOs:2, 3, 5, 6, 9, 10, 12, 13, 15, 17 and 19, or may be any signal peptide known in the art.

Additional suitable fragments of human B7-H4 include, but are not limited to, fragments containing at least 25, 20, 75, 100 or 125 amino acids of the IgV domain as set forth in SEQ ID NO:63 or SEQ ID NO:64. Exemplary fragments include, but are not limited to:

16-144, 16-145, 16-146, 16-147, 16-148, 16-149, 16-150, 16-151, 16-152, 17-144, 17-145, 17-146, 17-147, 17-148, 17-149, 17-150, 17-151, 17-152, 18-144, 18-145, 18-146, 18-147, 18-148, 18-149, 18-150, 18-151, 18-152, 19-144, 19-145, 19-146, 19-147, 19-148, 19-149, 19-150, 19-151, 19-152, 20-144, 20-145, 20-146, 20-147, 20-148, 20-149, 20-150, 20-151, 20-152, 21-144, 21-145, 21-146, 21-147, 21-148, 21-149, 21-150, 21-151, 21-152, 22-144, 22-145, 22-146, 22-147, 22-148, 22-149, 22-150, 22-151, 22-152, 23-144, 23-145, 23-146, 23-147, 23-148, 23-149, 23-150, 23-151, 23-152, 24-144, 24-145, 24-146, 24-147, 24-148, 24-149, 24-150, 24-151, 24-152, of any of SEQ ID NO:43, SEQ ID NO:44, SEQ ID NO:45, SEQ ID NO:46, SEQ ID NO:47, or SEQ ID NO:48, or 24-152, 24-153, 24-154, 24-155, 24-156, 24-157, 24-158, 24-159, 24-160, 25-152, 25-153, 25-154, 25-155, 25-156, 25-157, 25-158, 25-159, 25-160, 26-152, 26-153, 26-154, 26-155, 26-156, 26-157, 26-158, 26-159, 26-160, 27-152, 27-153, 27-154, 27-155, 27-156, 27-157, 27-158, 27-159, 27-160, 28-152, 28-153, 28-154, 28-155, 28-156, 28-157, 28-158, 28-159, 28-160, 29-152, 29-153, 29-154, 29-155, 29-156, 29-157, 29-158, 29-159, 29-160, 30-152, 30-153, 30-154, 30-155, 30-156, 30-157, 30-158, 30-159, 30-160, 31-152, 31-153, 31-154, 31-155, 31-156, 31-157, 31-158, 31-159, 31-160, 32-152, 32-153, 32-154, 32-155, 32-156, 32-157, 32-158, 32-159, 32-160, of any of SEQ ID NO:49, SEQ ID NO:50, SEQ ID NO:51, SEQ ID NO:52, SEQ ID NO:53, or SEQ ID NO:54, optionally with one to five amino acids of a signal peptide attached to the N-terminal end. The signal peptide may be any disclosed herein, including those contained within SEQ ID NOs:2, 3, 5, 6, 9, 10, 12, 13, 15, 17 and 19, or may be any signal peptide known in the art.

Exemplary suitable fragments of non-human primate B7-H4 that can be used as a first fusion partner include, but are not limited to, the following: 32-249, 32-248, 32-247, 32-246, 32-245, 32-244, 32-243, 32-242, 32-241, 31-249, 31-248, 31-247, 31-246, 31-245, 31-244, 31-243, 31-242, 31-241, 30-249, 30-248, 30-247, 30-246, 30-245, 30-244, 30-243, 30-242, 30-241, 29-249, 29-248, 29-247, 29-246, 29-245, 29-244, 29-243, 29-242, 29-241, 28-249, 28-248, 28-247, 28-246, 28-245, 28-244, 28-243, 28-242, 28-241, 27-249, 27-248, 27-247, 27-246, 27-245, 27-244, 27-243, 27-242, 27-241, 26-249, 26-248, 26-247, 26-246, 26-245, 26-244, 26-243, 26-242, 26-241, 25-249, 25-248, 25-247, 25-246, 25-245, 25-244, 25-243, 25-242, 25-241, 24-249, 24-248, 24-247, 24-246, 24-245, 24-244, 24-243, 24-242, 24-241, of SEQ ID NO:71, or SEQ ID NO:77, or 32-245, 32-244, 32-243, 32-242, 32-241, 32-240, 32-239, 32-238, 32-237, 31-245, 31-244, 31-243, 31-242, 31-241, 31-240, 31-239, 31-238, 31-237, 30-245, 30-244, 30-243, 30-242, 30-241, 30-240, 30-239, 30-238, 30-237, 29-245, 29-244, 29-243, 29-242, 29-241, 29-240, 29-239, 29-238, 29-237, 28-245, 28-244, 28-243, 28-242, 28-241, 28-240, 28-239, 28-238, 28-237, 27-245, 27-244, 27-243, 27-242, 27-241, 27-240, 27-239, 27-238, 27-237, 26-245, 26-244, 26-243, 26-242, 26-241, 26-240, 26-239, 26-238, 26-237, 25-245, 25-244, 25-243, 25-242, 25-241, 25-240, 25-239, 25-238, 25-237, 24-245, 24-244, 24-243, 24-242, 24-241, 24-240, 24-239, 24-238, 24-237, of SEQ ID NO:72 or SEQ ID NO:78, or 32-259, 32-258, 32-257, 32-256, 32-255, 32-254, 32-253, 32-252, 32-251, 31-259, 31-258, 31-257, 31-256, 31-255, 31-254, 31-253, 31-252, 31-251, 30-259, 30-258, 30-257, 30-256, 30-255, 30-254, 30-253, 30-252, 30-251, 29-259, 29-258, 29-257, 29-256, 29-255, 29-254, 29-253, 29-252, 29-251, 28-259, 28-258, 28-257, 28-256, 28-255, 28-254, 28-253, 28-252, 28-251, 27-259, 27-258, 27-257, 27-256, 27-255, 27-254, 27-253, 27-252, 27-251, 26-259, 26-258, 26-257, 26-256, 26-255, 26-254, 26-253, 26-252, 26-251, 25-259, 25-258, 25-257, 25-256, 25-255, 25-254, 25-253, 25-252, 25-251, 24-259, 24-258, 24-257, 24-256, 24-255, 24-254, 24-253, 24-252, 24-251, of SEQ ID NO:73 or SEQ ID NO:79, or 28-245, 28-244, 28-243, 28-242, 28-241, 28-240, 28-239, 28-238, 28-237, 27-245, 27-244, 27-243, 27-242, 27-241, 27-240, 27-239, 27-238, 27-237, 26-245, 26-244, 26-243, 26-242, 26-241, 26-240, 26-239, 26-238, 26-237, 25-245, 25-244, 25-243, 25-242, 25-241, 25-240, 25-239, 25-238, 25-237, 24-245, 24-244, 24-243, 24-242, 24-241, 24-240, 24-239, 24-238, 24-237, 23-245, 23-244, 23-243, 23-242, 23-241, 23-240, 23-239, 23-238, 23-237, 22-245, 22-244, 22-243, 22-242, 22-241, 22-240, 22-239, 22-238, 22-237, 21-245, 21-244, 21-243, 21-242, 21-241, 21-240, 21-239, 21-238, 21-237, 20-245, 20-244, 20-243, 20-242, 20-241, 20-240, 20-239, 20-238, 20-237, of SEQ ID NO:65, or 28-241, 28-240, 28-239, 28-238, 28-237, 28-236, 28-235, 28-234, 28-233, 27-241, 27-240, 27-239, 27-238, 27-237, 27-236, 27-235, 27-234, 27-233, 26-241, 26-240, 26-239, 26-238, 26-237, 26-236, 26-235, 26-234, 26-233, 25-241, 25-240, 25-239, 25-238, 25-237, 25-236, 25-235, 25-234, 25-233, 24-241, 24-240, 24-239, 24-238, 24-237, 24-236, 24-235, 24-234, 24-233, 23-241, 23-240, 23-239, 23-238, 23-237, 23-236, 23-235, 23-234, 23-233, 22-241, 22-240, 22-239, 22-238, 22-237, 22-236, 22-235, 22-234, 22-233, 21-241, 21-240, 21-239, 21-238, 21-237, 21-236, 21-235, 21-234, 21-233, 20-241, 20-240, 20-239, 20-238, 20-237, 20-236, 20-235, 20-234, 20-233, of SEQ ID NO:66, or 28-255, 28-254, 28-253, 28-252, 28-251, 28-250, 28-249, 28-248, 28-247, 27-255, 27-254, 27-253, 27-252, 27-251, 27-250, 27-249, 27-248, 27-247, 26-255, 26-254, 26-253, 26-252, 26-251, 26-250, 26-249, 26-248, 26-247, 25-255, 25-254, 25-253, 25-252, 25-251, 25-250, 25-249, 25-248, 25-247, 24-255, 24-254, 24-253, 24-252, 24-251, 24-250, 24-249, 24-248, 24-247, 23-255, 23-254, 23-253, 23-252, 23-251, 23-250, 23-249, 23-248, 23-247, 22-255, 22-254, 22-253, 22-252, 22-251, 22-250, 22-249, 22-248, 22-247, 21-255, 21-254, 21-253, 21-252, 21-251, 21-250, 21-249, 21-248, 21-247, 20-255, 20-254, 20-253, 20-252, 20-251, 20-250, 20-249, 20-248, 20-247, of SEQ ID NO:67.

Additional suitable fragments of non-human primate B7-H4 include, but are not limited to, the following:
27-249, 27-250, 27-251, 27-252, 27-253, 27-254, 27-255, 27-256, 27-257, 27-259, 27-260,
28-249, 28-250, 28-251, 28-252, 28-253, 28-254, 28-255, 28-256, 28-257, 28-259, 28-260,
29-249, 29-250, 29-251, 29-252, 29-253, 29-254, 29-255, 29-256, 29-257, 29-259, 29-260,
30-249, 30-250, 30-251, 30-252, 30-253, 30-254, 30-255, 30-256, 30-257, 30-259, 30-260,
31-249, 31-250, 31-251, 31-252, 31-253, 31-254, 31-255, 31-256, 31-257, 31-259, 31-260,
32-249, 32-250, 32-251, 32-252, 32-253, 32-254, 32-255, 32-256, 32-257, 32-259, 32-260 of SEQ ID NO:17 or SEQ ID NO:19, optionally with one to five amino acids of a signal peptide attached to the N-terminal end. The signal peptide may be any disclosed herein, including those contained within SEQ ID NOs:2, 3, 5, 6, 9, 10, 12, 13, 15, 17 and 19, or may be any signal peptide known in the art.

Additional suitable fragments of non-human primate B7-H4 include, but are not limited to, the following:
23-245, 23-246, 23-247, 23-248, 23-249, 23-250, 23-251, 23-252, 23-253, 23-254, 23-255,
24-245, 24-246, 24-247, 24-248, 24-249, 24-250, 24-251, 24-252, 24-253, 24-254, 24-255,
25-245, 25-246, 25-247, 25-248, 25-249, 25-250, 25-251, 25-252, 25-253, 25-254, 25-255,
26-245, 26-246, 26-247, 26-248, 26-249, 26-250, 26-251, 26-252, 26-253, 26-254, 26-255,
27-245, 27-246, 27-247, 27-248, 27-249, 27-250, 27-251, 27-252, 27-253, 27-254, 27-255,
28-245, 28-246, 28-247, 28-248, 28-249, 28-250, 28-251, 28-252, 28-253, 28-254, 28-255 of SEQ ID NO:15, optionally with one to five amino acids of a signal peptide attached to the N-terminal end. The signal peptide may be any disclosed herein, including those contained within SEQ ID NOs:2, 3, 5, 6, 9, 10, 12, 13, 15, 17 and 19, or may be any signal peptide known in the art.

Additional suitable fragments of non-human primate B7-H4 include, but are not limited to, fragments containing at least 25, 20, 75, 100 or 125 amino acids of the IgV domain as set forth in SEQ ID NO:83, SEQ ID NO:84 or SEQ ID NO:85. Exemplary fragments include, but are not limited to: 20-148, 20-149, 20-150, 20-151, 20-152, 20-153, 20-154, 20-155, 20-156, 21-148, 21-149, 21-150, 21-151, 21-152, 21-153, 21-154, 21-155, 21-156, 22-148, 22-149, 22-150, 22-151, 22-152, 22-153, 22-154, 22-155, 22-156, 23-148, 23-149, 23-150, 23-151, 23-152, 23-153, 23-154, 23-155, 23-156, 24-148, 24-149, 24-150, 24-151, 24-152, 24-153, 24-154, 24-155, 20-156, 25-148, 25-149, 25-150, 25-151, 25-152, 25-153, 25-154, 25-155, 25-156, 26-148, 26-149, 26-150, 26-151, 26-152, 26-153, 26-154, 26-155, 26-156, 27-148, 27-149, 27-150, 27-151, 27-152, 27-153, 27-154, 27-155, 27-156, 28-148, 28-149, 28-150, 28-151, 28-152, 28-153, 28-154, 28-155, 28-156, of any of SEQ ID NO:65, SEQ ID NO:66, or SEQ ID NO:67, or 24-152, 24-153, 24-154, 24-155, 24-156, 24-157, 24-158, 24-159, 24-160, 25-152, 25-153, 25-154, 25-155, 25-156, 25-157, 25-158, 25-159, 25-160, 26-152, 26-153, 26-154, 26-155, 26-156, 26-157, 26-158, 26-159, 26-160, 27-152, 27-153, 27-154, 27-155, 27-156, 27-157, 27-158, 27-159, 27-160, 28-152, 28-153, 28-154, 28-155, 28-156, 28-157, 28-158, 28-159, 28-160, 29-152, 29-153, 29-154, 29-155, 29-156, 29-157, 29-158, 29-159, 29-160, 30-152, 30-153, 30-154, 30-155, 30-156, 30-157, 30-158, 30-159, 30-160, 31-152, 31-153, 31-154, 31-155, 31-156, 31-157, 31-158, 31-159, 31-160, 32-152, 32-153, 32-154, 32-155, 32-156, 32-157, 32-158, 32-159, 32-160, of any of SEQ ID NO:71, SEQ ID NO:72, SEQ ID NO:73, SEQ ID NO:77, SEQ ID NO:78, or SEQ ID NO:79, optionally with one to five amino acids of a signal peptide attached to the N-terminal end. The signal peptide may be any disclosed herein, including those contained within SEQ ID NOs:2, 3, 5, 6, 9, 10, 12, 13, 15, 17 and 19, or may be any signal peptide known in the art.

2. Variants of B7-H4 Polypeptides

Useful variants include those that increase biological activity, as indicated by any of the assays described herein, or that increase half life or stability of the protein. The B7-H4 polypeptides and B7-H4 fragments, or fusions thereof having B7-H4 activity, can be engineered to increase biological activity. In a preferred embodiment, the B7-H4 polypeptide or fusion protein has been modified with at least one amino acid substitution, deletion, or insertion that increases the binding of the molecule to an immune cell, for example a T cell, and transmits an inhibitory signal into the T cell.

Other preferred variants are those B7-H4 polypetpides that are engineered to selectively bind to one type of T cell versus other immune cells. For example, the B7-H4 polypeptide can be engineered to bind preferentially to Tregs, Th0, Th1, Th17, or Th22 cells. Preferential binding refers to binding that is at least 10%, 20%, 30%, 40%, 50%, 60%, 70%, 80%, 90%, 95%, or greater for one type of cell over another type of cell.

Still other variants of B7-H4 can be engineered to have reduced binding to immune cells relative to wildtype B7-H4. These variants can be used in combination with variants having stronger binding properties to modulate the immune response with a moderate impact.

Finally, variant B7-H4 polypeptides can be engineered to have an increased half-life relative to wildtype. These variants typically are modified to resist enzymatic degradation. Exemplary modifications include modified amino acid residues and modified peptide bonds that resist enzymatic degradation. Various modifications to achieve this are known in the art. For example, the juxtamembrane region of B7-H4 includes a dibasic motif, KRRS, which could potentially be recognized and cleaved, for example by a member of the proprotein convertase family of proteases. This motif (KRRS) can be removed to increase half life. The variants can be modified to adjust for effects of affinity for the receptor on the half life of B7-H4 polypeptides, fragments, or fusions thereof at serum and endosomal pH.

B. Second Polypeptide

The B7-H4 polypeptide may be fused to a second polypeptide. The presence of the second polypeptide can alter the solubility, stability, affinity and/or valency of the B7-H4 fusion polypeptide. As used herein, "valency" refers to the number of binding sites available per molecule. In one embodiment the second polypeptide is a polypeptide from a different source or different protein.

In one embodiment, the second polypeptide contains one or more domains of an immunoglobulin heavy chain constant region, preferably having an amino acid sequence corresponding to the hinge, $C_H2$ and $C_H3$ regions of a human immunoglobulin Cγ1 chain or to the hinge, $C_H2$ and $C_H3$ regions of a murine immunoglobulin Cγ2a chain. SEQ ID NOS: 88 and 89 provide exemplary sequences for the hinge, $C_H2$ and $C_H3$ regions of a human immunoglobulin Cγ1.

In a preferred dimeric fusion protein, the dimer results from the covalent bonding of Cys residue in the hinge region of two of the Ig heavy chains that are the same Cys residues that are disulfide linked in dimerized normal Ig heavy chains. Such proteins are referred to as B7-H4-Ig.

In one embodiment, the immunoglobulin constant domain may contain one or more amino acid insertions, deletions or substitutions that enhance binding to specific cell types, increase the bioavailablity, or increase the stability of the B7-H4 polypeptides, fusion proteins, or fragments thereof. Suitable amino acid substitutions include conservative and non-conservative substitutions, as described above.

In another embodiment the second polypeptide may have a conjugation domain through which additional molecules can be bound to the B7-H4 fusion proteins. In one such embodiment, the conjugated molecule is capable of targeting the fusion protein to a particular organ or tissue. In another such embodiment the conjugated molecule is another immunomodulatory agent that can enhance or augment the effects of the B7-H4 fusion protein. In another embodiment the conjugated molecule is Polyethylene Glycol (PEG).

The Fc portion of the fusion protein may be varied by isotype or subclass, may be a chimeric or hybrid, and/or may be modified, for example to improve effector functions, control of half-life, tissue accessibility, augment biophysical characteristics such as stability, and improve efficiency of production (and less costly). Many modifications useful in construction of disclosed fusion proteins and methods for making them are known in the art, see for example Mueller, et al., *Mol. Immun.*, 34(6):441-452 (1997), Swann, et al., *Cur. Opin. Immun.*, 20:493-499 (2008), and Presta, *Cur. Opin. Immun.* 20:460-470 (2008). In some embodiments the Fc region is the native IgG1, IgG2, or IgG4 Fc region. In some embodiments the Fc region is a hybrid, for example a chimeric consisting of IgG2/IgG4 Fc constant regions. Modications to the Fc region include, but are not limited to, IgG4 modified to prevent binding to Fc gamma receptors and complement, IgG1 modified to improve binding to one or more Fc gamma receptors, IgG1 modified to minimize effector function (amino acid changes), IgG1 with altered/no glycan (typically by changing expression host), and IgG1 with altered pH-dependent binding to FcRn. The Fc region may include the entire hinge region, or less than the entire hinge region.

The therapeutic outcome in patients treated with rituximab (a chimeric mouse/human IgG1 monoclonal antibody against CD20) for non-Hodgkin's lymphoma or Waldenstrom's macroglobulinemia correlated with the individual's expression of allelic variants of Fcγ receptors with distinct intrinsic affinities for the Fc domain of human IgG1. In particular, patients with high affinity alleles of the low affinity activating Fc receptor CD16A (FcγRIIIA) showed higher response rates and, in the cases of non-Hodgkin's lymphoma, improved progression-free survival. In another embodiment, the Fc domain may contain one or more amino acid insertions, deletions or substitutions that reduce binding to the low affinity inhibitory Fc receptor CD32B (FcγRIIB) and retain wild-type levels of binding to or enhance binding to the low affinity activating Fc receptor CD16A (FcγRIIIA).

Another embodiment includes IgG2-4 hybrids and IgG4 mutants that have reduce binding to FcR which increase their half life. Representative IG2-4 hybrids and IgG4 mutants are described in Angal, S. et al., *Molecular Immunology*, 30(1):105-108 (1993); Mueller, J. et al., *Molecular Immnology*, 34(6): 441-452 (1997); and U.S. Pat. No. 6,982,323 to Wang et al. In some embodiments the IgG1 and/or IgG2 domain is deleted for example, Angal et al. describe IgG1 and IgG2 having serine 241 replaced with a proline.

In a preferred embodiment, the Fc domain contains amino acid insertions, deletions or substitutions that enhance binding to CD16A. A large number of substitutions in the Fc domain of human IgG1 that increase binding to CD16A and reduce binding to CD32B are known in the art and are described in Stavenhagen, et al., *Cancer Res.*, 57(18):8882-90 (2007). Exemplary variants of human IgG1 Fc domains with reduced binding to CD32B and/or increased binding to CD16A contain F243L, R929P, Y300L, V3051 or P296L substitutions. These amino acid substitutions may be present in a human IgG1 Fc domain in any combination. In one embodiment, the human IgG1 Fc domain variant contains a F243L, R929P and Y300L substitution. In another embodiment, the human IgG1 Fc domain variant contains a F243L, R929P, Y300L, V3051 and P296L substitution. In another embodiment, the human IgG1 Fc domain variant contains an N297Q substitution, as this mutation abolishes FcR binding.

C. Peptide or Polypeptide Linker Domain

The disclosed B7-H4 fusion proteins optionally contain a peptide or polypeptide linker domain that separates the B7-H4 polypeptide from the second polypeptide.

1. Hinge Region of Antibodies

In one embodiment, the linker domain contains the hinge region of an immunoglobulin. In a preferred embodiment, the hinge region is derived from a human immunoglobulin. Suitable human immunoglobulins that the hinge can be derived from include IgG, IgD and IgA. In a preferred embodiment, the hinge region is derived from human IgG. Amino acid sequences of immunoglobulin hinge regions and other domains are well known in the art.

In one embodiment, B7-H4 fusion polypeptides contain the hinge, $C_H2$ and $C_H3$ regions of a human immunoglobulin Cγ1 chain encoded by a nucleic acid having at least 80%, 85%, 90%, 95%, 99% or 100% sequence identity to:

```
                                                          (SEQ ID NO: 86)
gagcctaagt catgtgacaa gacccatacg tgcccaccct gtcccgctcc agaactgctg    60
gggggaccta gcgtttcttt gttcccccca aagcccaagg acaccctcat gatctcacgg   120
actcccgaag taacatgcgt agtagtcgac gtgagccacg aggatcctga agtgaagttt   180
aattggtacg tggacggagt cgaggtgcat aatgccaaaa ctaaacctcg ggaggagcag   240
tataacagta cctaccgcgt ggtatccgtc ttgacagtgc tccaccagga ctggctgaat   300
ggtaaggagt ataaatgcaa ggtcagcaac aaagctcttc ccgcccaat tgaaaagact    360 atcagcaagg ccaagggaca accccgcgag ccccaggttt acacccttcc accttcacga   420
gacgagctga ccaagaacca ggtgtctctg acttgtctgg tcaaaggttt ctatccttcc   480
gacatcgcag tggagtggga gtcaaacggg cagcctgaga ataactacaa gaccacaccc   540
ccagtgcttg atagcgatgg gagcttttttc ctctacagta agctgactgt ggacaaatcc   600
cgctggcagc agggaaacgt tttctcttgt agcgtcatgc atgaggccct ccacaaccat   660
tatactcaga aaagcctgag tctgagtccc ggcaaa,                           696
or
                                                          (SEQ ID NO: 87)
gacaagaccc atacgtgccc accctgtccc gctccagaac tgctgggggg acctagcgtt    60
ttcttgttcc ccccaaagcc caaggacacc ctcatgatct cacggactcc cgaagtaaca   120
tgcgtagtag tcgacgtgag ccacgaggat cctgaagtga agtttaattg gtacgtggac   180
ggagtcgagg tgcataatgc caaaactaaa cctcgggagg agcagtataa cagtacctac   240
cgcgtggtat ccgtcttgac agtgctccac caggactggc tgaatggtaa ggagtataaa   300
tgcaaggtca gcaacaaagc tcttcccgcc ccaattgaaa agactatcag caaggccaag   360
ggacaacccc gcgagcccca ggtttacacc cttccacctt cacgagacga gctgaccaag   420
aaccaggtgt ctctgacttg tctggtcaaa ggtttctatc cttccgacat cgcagtggag   480
tgggagtcaa acgggcagcc tgagaataac tacaagacca cccccagt gcttgatagc    540 gatgggagct ttttcctcta cagtaagctg actgtggaca aatcccgctg gcagcaggga   600 aacgtttttct cttgtagcgt catgcatgag gccctccaca accattatac tcagaaaagc   660
ctgagtctga gtcccggcaa a.                                          681
```

The hinge, $C_H2$ and $C_H3$ regions of a human immunoglobulin Cγ1 chain encoded by SEQ ID NO:86 has the following amino acid sequence:

```
                                                          (SEQ ID NO: 88)
EPKSCDKTHT CPPCPAPELL GGPSVFLFPP KPKDTLMISR TPEVTCVVVD VSHEDPEVKF    60

NWYVDGVEVH NAKTKPREEQ YNSTYRVVSV LTVLHQDWLN GKEYKCKVSN KALPAPIEKT   120
```

```
ISKAKGQPRE PQVYTLPPSR DELTKNQVSL TCLVKGFYPS DIAVEWESNG QPENNYKTTP  180

PVLDSDGSFF LYSKLTVDKS RWQQGNVFSC SVMHEALHNH YTQKSLSLSP GK.         232
```

The hinge, CH2 and CH3 regions of a human immunoglobulin Cγ1 chain encoded by SEQ ID NO:87 has the following amino acid sequence:

```
                                                     (SEQ ID NO: 89)
DKTHTCPPCP APELLGGPSV FLFPPKPKDT LMISRTPEVT CVVVDVSHED PEVKFNWYVD   60

GVEVHNAKTK PREEQYNSTY RVVSVLTVLH QDWLNGKEYK CKVSNKALPA PIEKTISKAK  120

GQPREPQVYT LPPSRDELTK NQVSLTCLVK GFYPSDIAVE WESNGQPENN YKTTPPVLDS  180

DGSFFLYSKL TVDKSRWQQG NVFSCSVMHE ALHNHYTQKS LSLSPGK.              227
```

The hinge can be further shortened to remove amino acids 1, 2, 3, 4, 5, or combinations thereof of SEQ ID NO:89. In one embodiment, amino acids 1 and 2 of SEQ ID NO:89 are deleted.

In another embodiment, the B7-H4 fusion polypeptides contain the hinge, $C_H2$ and $C_H3$ regions of a murine immunoglobulin Cγ2a chain encoded by a nucleic acid having at least 80%, 85%, 90%, 95%, 99% or 100% sequence identity to:

```
                                                     (SEQ ID NO: 90)
gagccaagag gtcctacgat caagccctgc ccgccttgta aatgcccagc tccaaatttg   60
ctgggtggac cgtcagtctt tatcttcccg ccaaagataa aggacgtctt gatgattagt  120
ctgagcccca tcgtgacatg cgttgtggtg gatgtttcag aggatgaccc cgacgtgcaa  180
atcagttggt tcgttaacaa cgtggaggtg cataccgctc aaacccagac ccacagagag  240
gattataaca gcaccctgcg ggtagtgtcc gccctgccga tccagcatca ggattggatg  300
agcgggaaag agttcaagtg taaggtaaac aacaaagatc tgccagcgcc gattgaacga  360
accattagca gccgaaagg gagcgtgcgc gcacctcagg tttacgtcct tcctccacca  420
gaagaggaga tgacgaaaaa gcaggtgacc ctgacatgca tggtaactga ctttatgcca  480
gaagatattt acgtggaatg gactaataac ggaaagacag agctcaatta caagaacact  540
gagcctgttc tggattctga tggcagctac tttatgtact ccaaattgag ggtcgagaag  600
aagaattggg tcgagagaaa cagttatagt tgctcagtgg tgcatgaggg cctccataat  660
catcacacca caaagtcctt cagccgaacg cccgggaaa                         699
```

The hinge, $C_H2$ and $C_H3$ regions of a murine immunoglobulin Cγ2a chain encoded by SEQ ID NO:90 has the following amino acid sequence:

```
                                                     (SEQ ID NO: 91)
EPRGPTIKPC PPCKCPAPNL LGGPSVFIFP PKIKDVLMIS LSPIVTCVVV DVSEDDPDVQ   60

ISWFVNNVEV HTAQTQTHRE DYNSTLRVVS ALPIQHQDWM SGKEFKCKVN NKDLPAPIER  120

TISKPKGSVR APQVYVLPPP EEEMTKKQVT LTCMVTDFMP EDIYVEWTNN GKTELNYKNT  180

EPVLDSDGSY FMYSKLRVEK KNWVERNSYS CSVVHEGLHN HHTTKSFSRT PGK         233
```

In another embodiment, the linker domain contains a hinge region of an immunoglobulin as described above, and further includes one or more additional immunoglobulin domains.

2. Other Peptide/Polypeptide Linker Domains

Other suitable peptide/polypeptide linker domains include naturally occurring or non-naturally occurring peptides or polypeptides. Peptide linker sequences are at least 2 amino acids in length. Preferably the peptide or polypeptide domains are flexible peptides or polypeptides. A "flexible linker" herein refers to a peptide or polypeptide containing two or more amino acid residues joined by peptide bond(s) that provides increased rotational freedom for two polypeptides linked thereby than the two linked polypeptides would have in the absence of the flexible linker. Such rotational freedom allows two or more antigen binding sites joined by the flexible linker to each access target antigen(s) more efficiently. Exemplary flexible peptides/polypeptides include, but are not limited to, the amino acid sequences Gly-Ser, Gly-Ser-Gly-Ser (SEQ ID NO:92), Ala-Ser, Gly-Gly-Gly-Ser (SEQ ID NO:93), $(Gly_4\text{-}Ser)_3$ (SEQ ID NO:94) and $(Gly_4\text{-}Ser)_4$ (SEQ ID NO:95). Additional flexible peptide/polypeptide sequences are well known in the art.

D. Dimerization, Multimerization and Targeting Domains

The fusion proteins disclosed herein optionally contain a dimerization or multimerization domain that functions to dimerize or multimerize two or more fusion proteins. The domain that functions to dimerize or multimerize the fusion proteins can either be a separate domain, or alternatively can be contained within one of the other domains (B7-H4 polypeptide, second polypeptide, or peptide/polypeptide linker domain) of the fusion protein.

1. Dimerization Domains

A "dimerization domain" is formed by the association of at least two amino acid residues or of at least two peptides or polypeptides (which may have the same, or different, amino acid sequences). The peptides or polypeptides may interact with each other through covalent and/or non-covalent association(s). Preferred dimerization domains contain at least one cysteine that is capable of forming an intermolecular disulfide bond with a cysteine on the partner fusion protein. The dimerization domain can contain one or more cysteine residues such that disulfide bond(s) can form between the partner fusion proteins. In one embodiment, dimerization domains contain one, two or three to about ten cysteine residues. In a preferred embodiment, the dimerization domain is the hinge region of an immunoglobulin.

Additional exemplary dimerization domain can be any known in the art and include, but not limited to, coiled coils, acid patches, zinc fingers, calcium hands, a $C_H1$-$C_L$ pair, an "interface" with an engineered "knob" and/or "protruberance" as described in U.S. Pat. No. 5,821,333, leucine zippers (e.g., from jun and/or fos) (U.S. Pat. No. 5,932,448), SH2 (src homology 2), SH3 (src Homology 3) (Vidal, et al., *Biochemistry*, 43, 7336-44 ((2004)), phosphotyrosine binding (PTB) (Zhou, et al., *Nature*, 378:584-592 (1995)), WW (Sudol, *Prog. Biochys. Mol. Bio.*, 65:113-132 (1996)), PDZ (Kim, et al., *Nature*, 378: 85-88 (1995); Komau, et al., *Science*, 269:1737-1740 (1995)) 14-3-3, WD40 (Hu, et al., *J Biol Chem.*, 273, 33489-33494 (1998)) EH, Lim, an isoleucine zipper, a receptor dimer pair (e.g., interleukin-8 receptor (IL-8R); and integrin heterodimers such as LFA-1 and GPIIIb/IIIa), or the dimerization region(s) thereof, dimeric ligand polypeptides (e.g. nerve growth factor (NGF), neurotrophin-3 (NT-3), interleukin-8 (IL-8), vascular endothelial growth factor (VEGF), VEGF-C, VEGF-D, PDGF members, and brain-derived neurotrophic factor (BDNF) (Arakawa, et al., *J. Biol. Chem.*, 269(45): 27833-27839 (1994) and Radziejewski, et al., *Biochem.*, 32(48): 1350 (1993)) and can also be variants of these domains in which the affinity is altered. The polypeptide pairs can be identified by methods known in the art, including yeast two hybrid screens. Yeast two hybrid screens are described in U.S. Pat. Nos. 5,283,173 and 6,562,576. Affinities between a pair of interacting domains can be determined using methods known in the art, including as described in Katahira, et al., *J. Biol. Chem.*, 277, 9242-9246 (2002)). Alternatively, a library of peptide sequences can be screened for heterodimerization, for example, using the methods described in WO 01/00814. Useful methods for protein-protein interactions are also described in U.S. Pat. No. 6,790,624.

2. Multimerization Domains

A "multimerization domain" is a domain that causes three or more peptides or polypeptides to interact with each other through covalent and/or non-covalent association(s). Suitable multimerization domains include, but are not limited to, coiled-coil domains. A coiled-coil is a peptide sequence with a contiguous pattern of mainly hydrophobic residues spaced 3 and 4 residues apart, usually in a sequence of seven amino acids (heptad repeat) or eleven amino acids (undecad repeat), which assembles (folds) to form a multimeric bundle of helices. Coiled-coils with sequences including some irregular distribution of the 3 and 4 residues spacing are also contemplated. Hydrophobic residues are in particular the hydrophobic amino acids Val, Ile, Leu, Met, Tyr, Phe and Trp. "Mainly hydrophobic" means that at least 50% of the residues must be selected from the mentioned hydrophobic amino acids.

The coiled coil domain may be derived from laminin. In the extracellular space, the heterotrimeric coiled coil protein laminin plays an important role in the formation of basement membranes. Apparently, the multifunctional oligomeric structure is required for laminin function. Coiled coil domains may also be derived from the thrombospondins in which three (TSP-1 and TSP-2) or five (TSP-3, TSP-4 and TSP-5) chains are connected, or from COMP (COMPcc) (Guo, et al., *EMBO J.*, 1998, 17: 5265-5272) which folds into a parallel five-stranded coiled coil (Malashkevich, et al., *Science*, 274: 761-765 (1996)).

Additional coiled-coil domains derived from other proteins, and other domains that mediate polypeptide multimerization are known in the art and are suitable for use in the disclosed fusion proteins.

In another embodiment, B7-H4 polypeptides, fusion proteins, or fragments thereof can be induced to form multimers by binding to a second multivalent polypeptide, such as an antibody. Antibodies suitable for use to multimerize B7-H4 polypeptides, fusion proteins, or fragments thereof include, but are not limited to, IgM antibodies and cross-linked, multivalent IgG, IgA, IgD, or IgE complexes.

3. Targeting Domains

The B7-H4 polypeptides and fusion proteins can contain a targeting domain to target the molecule to specific sites in the body. Preferred targeting domains target the molecule to areas of inflammation. Exemplary targeting domains are antibodies, or antigen binding fragments thereof that are specific for inflamed tissue or to a proinflammatory cytokine including but not limited to IL17, IL-4, IL-6, IL-12, IL-21, IL-22, and IL-23. In the case of neurological disorders such as Multiple Sclerosis, the targeting domain may target the molecule to the CNS or may bind to VCAM-1 on the vascular epithelium. Additional targeting domains can be peptide aptamers specific for a proinflammatory molecule. In other embodiments, the B7-H4 fusion protein can include a binding partner specific for a polypeptide displayed on the surface of an immune cell, for example a T cell. In still other embodiments, the targeting domain specifically targets activated immune cells. Preferred immune cells that are targeted include Th0, Th1, Th17 and Th22 T cells, other cells that secrete, or cause other cells to secrete inflammatory molecules including, but not limited to, IL-1β, TNF-α, TGF-beta, IFN-γ, IL-17, IL-6, IL-23, IL-22, IL-21, and MMPs, and Tregs. For example, a targeting domain for Tregs may bind specifically to CD25.

E. Exemplary Fusion Proteins

A representative murine B7-H4 fusion protein is encoded by a nucleic acid having at least 80%, 85%, 90%, 95%, 99% or 100% sequence identity to:

(SEQ ID NO: 96)
```
atggcttcct tggggcagat catcttttgg agtattatta acatcatcat catcctggct      60
ggggccatcg cactcatcat tggctttggc atttcaggca agcacttcat cacggtcacg     120
accttcacct cagctggaaa cattggagag gacgggaccc tgagctgcac ttttgaacct     180
gacatcaaac tcaacggcat cgtcatccag tggctgaaag aaggcatcaa aggtttggtc     240
cacgagttca agaaggcaa agacgacctc tcacagcagc atgagatgtt cagaggccgc      300
acagcagtgt ttgctgatca ggtggtagtt ggcaatgctt ccctgagact gaaaaacgtg     360
cagctcacgg atgctggcac ctacacatgt tacatccgca cctcaaaagg caagggaat      420
gcaaaccttg agtataagac cggagccttc agtatgccag agataaatgt ggactataat     480
gccagttcag agagtttacg ctgcgaggct cctcggtggt tcccccagcc cacagtggcc     540
tgggcatctc aagtcgacca aggagccaat ttctcagaag tctccaacac cagctttgag     600
ttgaactctg agaatgtgac catgaaggtc gtatctgtgc tctacaatgt cacaatcaac     660
aacacatact cctgtatgat tgaaaacgac attgccaaag ccaccgggga catcaaagtg     720
acagattcag aggtcaaaag gcgaagtcag ctgcagttgc tgaactctgg ggagccaaga     780
ggtcctacga tcaagccctg cccgccttgt aaatgcccag ctccaaattt gctgggtgga     840
ccgtcagtct ttatcttccc gccaaagata aggacgtct gatgattag tctgagcccc      900
atcgtgacat gcgttgtggt ggatgtttca gaggatgacc ccgacgtgca atcagttgg      960
ttcgttaaca acgtggaggt gcataccgct caaacccaga cccacagaga ggattataac    1020
agcaccctgc gggtagtgtc cgccctgccg atccagcatc aggattggat gagcgggaaa    1080
gagttcaagt gtaaggtaaa caacaaagat ctgccagcgc cgattgaacg aaccattagc    1140
aagccgaaag ggagcgtgcg cgcacctcag gtttacgtcc ttcctccacc agaagaggag    1200
atgacgaaaa agcaggtgac cctgacatgc atggtaactg actttatgcc agaagatatt    1260
tacgtggaat ggactaataa cggaaagaca gagctcaatt acaagaacac tgagcctgtt    1320
ctggattctg atggcagcta ctttatgtac tccaaattga gggtcgagaa gaagaattgg    1380
gtcgagagaa acagttatag ttgctcagtg gtgcatgagg gcctccataa tcatcacacc    1440
acaaagtcct tcagccgaac gcccgggaaa,                                    1470
```
(SEQ ID NO: 97)
```
atggagtggt catgggtttt tctgttcttt cttagcgtga ctacaggcgt ccattcagga      60
ttcggcataa gcggcaagca cttcatcaca gttacaacgt ttacaagtgc ggggaacatt     120
ggggaagatg gaacattgtc atgtacattt gagccagata tcaaactcaa tggaatagta     180
attcagtggc ttaaggaggg catcaagggc ctggtccacg aatttaagga ggggaaagac     240
gatctgtctc agcagcacga gatgttcagg ggcagaaccg ccgtcttcgc agaccaggtt     300
gtggtaggca acgccagttt gcggctgaaa aacgtgcagc tgactgacgc cggcacctac     360
acatgctata tccggtcctc taagggcaag gggaacgcta atctcgagta caaacaggc      420
gccttttcta tgccagagat caacgtggac tataacgcaa gctctgaaag tctgagatgc     480
gaggcgccaa ggtggttccc tcagcccacc gtcgcgtggg cttcccaggt ggatcaaggc     540
gccaactttt ctgaggtttc taacaccagc ttcgaactga cagcgaaaa tgtgacaatg     600
aaggtagtca gcgttctgta taacgtgacc atcaacaata cttactcctg tatgatagaa     660
aatgatatat ccaaggctac aggagatatt aaagtgacgg attcagaagt gaaaggagg    720
agtcaactgc aactcttgaa tagcggcgag ccaagaggtc ctacgatcaa gccctgcccg    780
ccttgtaaat gccagctcc aaatttgctg ggtggaccgt cagtctttat cttcccgcca     840
aagataaagg acgtcttgat gattagtctg agccccatcg tgacatgcgt tgtggtggat    900
```

```
gtttcagagg atgaccccga cgtgcaaatc agttggttcg ttaacaacgt ggaggtgcat    960
accgctcaaa cccagaccca cagagaggat tataacagca ccctgcgggt agtgtccgcc   1020
ctgccgatcc agcatcagga ttggatgagc gggaaagagt tcaagtgtaa ggtaaacaac   1080
aaagatctgc cagcgccgat tgaacgaacc attagcaagc cgaaagggag cgtgcgcgca   1140
cctcaggttt acgtccttcc tccaccagaa gaggagatga cgaaaaagca ggtgaccctg   1200
acatgcatgg taactgactt tatgccagaa gatatttacg tggaatggac taataacgga   1260
aagacagagc tcaattacaa gaacactgag cctgttctgg attctgatgg cagctacttt   1320
atgtactcca aattgagggt cgagaagaag aattgggtcg agagaaacag ttatagttgc   1380
tcagtggtgc atgagggcct ccataatcat cacaccacaa agtccttcag ccgaacgccc   1440
gggaaa                                                               1446
```
or
```
                                                                   (SEQ ID NO: 98)
atggagtggt catgggtttt tctgttcttt cttagcgtga ctacaggcgt ccattcagga     60
ttcggcataa gcggcaagca cttcatcaca gttacaacgt ttacaagtgc ggggaacatt    120
ggggaagatg gaacattgtc atgtacattt gagccagata tcaaactcaa tggaatagta    180
attcagtggc ttaaggaggg catcaagggc ctggtccacg aatttaagga ggggaaagac    240
gatctgtctc agcagcacga gatgttcagg ggcagaaccg ccgtcttcgc agaccaggtt    300
gtggtaggca acgccagttt gcggctgaaa aacgtgcagc tgactgacgc cggcacctac    360
acatgctata tccggacctc taagggcaag gggaacgcta atctcgagta caaaacaggc    420
gccttttcta tgccagagat caacgtggac tataacgcaa gctctgaaag tctgagatgc    480
gaggcgccaa ggtggttccc tcagcccacc gtcgcgtggg cttcccaggt ggatcaaggc    540
gccaactttt ctgaggtttc taacaccagc ttcgaactga acagcgaaaa tgtgacaatg    600
aaggtagtca gcgttctgta taacgtgacc atcaacaata cttactcctg tatgatagaa    660
aatgatatag ccaaggctac aggagatatt aaagtgacgg attcagaagt gaaaaggagg    720
agtcaactgc aactcttgaa tagcggcgag ccaagaggtc ctacgatcaa gccctgcccg    780
ccttgtaaat gcccagctcc aaatttgctg ggtggaccgt cagtctttat cttcccgcca    840
aagataaagg acgtcttgat gattagtctg agccccatcg tgacatgcgt tgtggtggat    900
gtttcagagg atgaccccga cgtgcaaatc agttggttcg ttaacaacgt ggaggtgcat    960
accgctcaaa cccagaccca cagagaggat tataacagca ccctgcgggt agtgtccgcc   1020
ctgccgatcc agcatcagga ttggatgagc gggaaagagt tcaagtgtaa ggtaaacaac   1080
aaagatctgc cagcgccgat tgaacgaacc attagcaagc cgaaagggag cgtgcgcgca   1140
cctcaggttt acgtccttcc tccaccagaa gaggagatga cgaaaaagca ggtgaccctg   1200
acatgcatgg taactgactt tatgccagaa gatatttacg tggaatggac taataacgga   1260
aagacagagc tcaattacaa gaacactgag cctgttctgg attctgatgg cagctacttt   1320
atgtactcca aattgagggt cgagaagaag aattgggtcg agagaaacag ttatagttgc   1380
tcagtggtgc atgagggcct ccataatcat cacaccacaa agtccttcag ccgaacgccc   1440
gggaaa                                                               1446
```

In another embodiment, a representative murine B7-H4 fusion protein has at least 80%, 85%, 90%, 95%, 99% or 100% sequence identity to:

```
                                                     (SEQ ID NO: 99)
MASLGQIIFW SIINIIIILA GAIALIIGFG ISGKHFITVT TFTSAGNIGE DGTLSCTFEP   60
DIKLNGIVIQ WLKEGIKGLV HEFKEGKDDL SQQHEMFRGR TAVFADQVVV GNASLRLKNV  120
QLTDAGTYTC YIRSSKGKGN ANLEYKTGAF SMPEINVDYN ASSESLRCEA PRWFPQPTVA  180
WASQVDQGAN FSEVSNTSFE LNSENVTMKV VSVLYNVTIN NTYSCMIEND IAKATGDIKV  240
TDSEVKRRSQ LQLLNSGEPR GPTIKPCPPC KCPAPNLLGG PSVFIFPPKI KDVLMISLSP  300
IVTCVVVDVS EDDPDVQISW FVNNVEVHTA QTQTHREDYN STLRVVSALP IQHQDWMSGK  360
EFKCKVNNKD LPAPIERTIS KPKGSVRAPQ VYVLPPPEEE MTKKQVTLTC MVTDFMPEDI  420
YVEWTNNGKT ELNYKNTEPV LDSDGSYFMY SKLRVEKKNW VERNSYSCSV VHEGLHNHHT  480
TKSFSRTPGK,                                                       490

(SEQ ID NO: 100)
MASLGQIIFW SIINIIIILA GAIALIIGFG ISGKHFITVT TFTSAGNIGE DGTLSCTFEP   60
DIKLNGIVIQ WLKEGIKGLV HEFKEGKDDL SQQHEMFRGR TAVFADQVVV GNASLRLKNV  120
QLTDAGTYTC YIRTSKGKGN ANLEYKTGAF SMPEINVDYN ASSESLRCEA PRWFPQPTVA  180
WASQVDQGAN FSEVSNTSFE LNSENVTMKV VSVLYNVTIN NTYSCMIEND IAKATGDIKV  240
TDSEVKRRSQ LQLLNSGEPR GPTIKPCPPC KCPAPNLLGG PSVFIFPPKI KDVLMISLSP  300
IVTCVVVDVS EDDPDVQISW FVNNVEVHTA QTQTHREDYN STLRVVSALP IQHQDWMSGK  360
EFKCKVNNKD LPAPIERTIS KPKGSVRAPQ VYVLPPPEEE MTKKQVTLTC MVTDFMPEDI  420
YVEWTNNGKT ELNYKNTEPV LDSDGSYFMY SKLRVEKKNW VERNSYSCSV VHEGLHNHHT  480
TKSFSRTPGK,                                                       490

(SEQ ID NO: 101)
MEWSWVFLFF LSVTTGVHSG FGISGKHFIT VTTFTSAGNI GEDGTLSCTF EPDIKLNGIV   60
IQWLKEGIKG LVHEFKEGKD DLSQQHEMFR GRTAVFADQV VVGNASLRLK NVQLTDAGTY  120
TCYIRSSKGK GNANLEYKTG AFSMPEINVD YNASSESLRC EAPRWFPQPT VAWASQVDQG  180
ANFSEVSNTS FELNSENVTM KVVSVLYNVT INNTYSCMIE NDIAKATGDI KVTDSEVKRR  240
SQLQLLNSGE PRGPTIKPCP PCKCPAPNLL GGPSVFIFPP KIKDVLMISL SPIVTCVVVD  300
VSEDDPDVQI SWFVNNVEVH TAQTQTHRED YNSTLRVVSA LPIQHQDWMS GKEFKCKVNN  360
KDLPAPIERT ISKPKGSVRA PQVYVLPPPE EEMTKKQVTL TCMVTDFMPE DIYVEWTNNG  420
KTELNYKNTE PVLDSDGSYF MYSKLRVEKK NWVERNSYSC SVVHEGLHNH HTTKSFSRTP  480
GK                                                                482
or
                                                     (SEQ ID NO: 102)
MEWSWVFLFF LSVTTGVHSG FGISGKHFIT VTTFTSAGNI GEDGTLSCTF EPDIKLNGIV   60
IQWLKEGIKG LVHEFKEGKD DLSQQHEMFR GRTAVFADQV VVGNASLRLK NVQLTDAGTY  120
TCYIRTSKGK GNANLEYKTG AFSMPEINVD YNASSESLRC EAPRWFPQPT VAWASQVDQG  180
ANFSEVSNTS FELNSENVTM KVVSVLYNVT INNTYSCMIE NDIAKATGDI KVTDSEVKRR  240
SQLQLLNSGE PRGPTIKPCP PCKCPAPNLL GGPSVFIFPP KIKDVLMISL SPIVTCVVVD  300
VSEDDPDVQI SWFVNNVEVH TAQTQTHRED YNSTLRVVSA LPIQHQDWMS GKEFKCKVNN  360
KDLPAPIERT ISKPKGSVRA PQVYVLPPPE EEMTKKQVTL TCMVTDFMPE DIYVEWTNNG  420
KTELNYKNTE PVLDSDGSYF MYSKLRVEKK NWVERNSYSC SVVHEGLHNH HTTKSFSRTP  480
GK.                                                               482
```

The amino acid sequence of the murine B7-H4 fusion protein of SEQ ID NO:99 and SEQ ID NO:101 without the signal sequence is:

```
                                                         (SEQ ID NO: 103)
GFGISGKHFI TVTTFTSAGN IGEDGTLSCT FEPDIKLNGI VIQWLKEGIK GLVHEFKEGK    60
DDLSQQHEMF RGRTAVFADQ VVVGNASLRL KNVQLTDAGT YTCYIRSSKG KGNANLEYKT   120
GAFSMPEINV DYNASSESLR CEAPRWFPQP TVAWASQVDQ GANFSEVSNT SFELNSENVT   180
MKVVSVLYNV TINNTYSCMI ENDIAKATGD IKVTDSEVKR RSQLQLLNSG EPRGPTIKPC   240
PPCKCPAPNL LGGPSVFIFP PKIKDVLMIS LSPIVTCVVV DVSEDDPDVQ ISWFVNNVEV   300
HTAQTQTHRE DYNSTLRVVS ALPIQHQDWM SGKEFKCKVN NKDLPAPIER TISKPKGSVR   360
APQVYVLPPP EEEMTKKQVT LTCMVTDFMP EDIYVEWTNN GKTELNYKNT EPVLDSDGSY   420
FMYSKLRVEK KNWVERNSYS CSVVHEGLHN HHTTKSFSRT PGK.                    463
```

The amino acid sequence of the murine B7-H4 fusion protein of SEQ ID NO:100 and SEQ ID NO:102 without the signal sequence is:

```
                                                         (SEQ ID NO: 104)
GFGISGKHFI TVTTFTSAGN IGEDGTLSCT FEPDIKLNGI VIQWLKEGIK GLVHEFKEGK    60
DDLSQQHEMF RGRTAVFADQ VVVGNASLRL KNVQLTDAGT YTCYIRTSKG KGNANLEYKT   120
GAFSMPEINV DYNASSESLR CEAPRWFPQP TVAWASQVDQ GANFSEVSNT SFELNSENVT   180
MKVVSVLYNV TINNTYSCMI ENDIAKATGD IKVTDSEVKR RSQLQLLNSG EPRGPTIKPC   240
PPCKCPAPNL LGGPSVFIFP PKIKDVLMIS LSPIVTCVVV DVSEDDPDVQ ISWFVNNVEV   300
HTAQTQTHRE DYNSTLRVVS ALPIQHQDWM SGKEFKCKVN NKDLPAPIER TISKPKGSVR   360
APQVYVLPPP EEEMTKKQVT LTCMVTDFMP EDIYVEWTNN GKTELNYKNT EPVLDSDGSY   420
FMYSKLRVEK KNWVERNSYS CSVVHEGLHN HHTTKSFSRT PGK.                    463
```

A representative human B7-H4 fusion protein is encoded by a nucleic acid having at least 80%, 85%, 90%, 95%, 99% or 100% sequence identity to:

```
                                                         (SEQ ID NO: 105)
atggcttccc tggggcagat cctcttctgg agcataatta gcatcatcat tattctggct    60
ggagcaattg cactcatcat tggctttggt atttcaggga gacactccat cacagtcact   120
actgtcgcct cagctgggaa cattggggag gatggaatcc tgagctgcac ttttgaacct   180
gacatcaaac tttctgatat cgtgatacaa tggctgaagg aaggtgtttt aggcttggtc   240
catgagttca agaaggcaa agatgagctg tcggagcagg atgaaatgtt cagaggccgg   300
acagcagtgt ttgctgatca agtgatagtt ggcaatgcct ctttgcggct gaaaaacgtg   360
caactcacag atgctggcac ctacaaatgt tatatcatca cttctaaagg caggggaat   420
gctaaccttg agtataaaac tggagccttc agcatgccgg aagtgaatgt ggactataat   480
gccagctcag agaccttgcg gtgtgaggct ccccgatggt tcccccagcc cacagtggtc   540
tgggcatccc aagttgacca gggagccaac ttctcggaag tctccaatac cagctttgag   600
ctgaactctg agaatgtgac catgaaggtt gtgtctgtgc tctacaatgt tacgatcaac   660
aacacatact cctgtatgat tgaaaatgac attgccaaag caacagggga tatcaaagtg   720
acagaatcgg agatcaaaag gcggagtgag cctaagtcat gtgacaagac ccatacgtgc   780
ccacccctgtc ccgctccaga actgctgggg ggacctagcg ttttcttgtt cccccaaag   840
```

-continued

```
cccaaggaca ccctcatgat ctcacggact cccgaagtaa catgcgtagt agtcgacgtg    900
agccacgagg atcctgaagt gaagtttaat tggtacgtgg acggagtcga ggtgcataat    960
gccaaaacta aacctcggga ggagcagtat aacagtacct accgcgtggt atccgtcttg   1020
acagtgctcc accaggactg gctgaatggt aaggagtata aatgcaaggt cagcaacaaa   1080
gctcttcccg ccccaattga aaagactatc agcaaggcca agggacaacc ccgcgagccc   1140
caggtttaca cccttccacc ttcacgagac gagctgacca agaaccaggt gtctctgact   1200
tgtctggtca aaggtttcta tccttccgac atcgcagtgg agtgggagtc aaacgggcag   1260
cctgagaata actacaagac cacacccccca gtgcttgata gcgatgggag ctttttcctc   1320
tacagtaagc tgactgtgga caaatcccgc tggcagcagg gaaacgtttt ctcttgtagc   1380
gtcatgcatg aggccctcca caaccattat actcagaaaa gcctgagtct gagtcccggc   1440 aaa,                                                                1443
                                                  (SEQ ID NO: 106)
atggaatgga gctgggtatt tctgttttc ctgtcagtaa cgactggcgt ccattcaggc     60
ttcggcatca gtggacggca cagtatcaca gtgaccaccg tcgcctccgc tggcaatata   120
ggtgaggatg gcatccagtc ctgtacctt gagccggaca tcaaactgtc tgacatagtg   180
atacaatggc tgaaggaggg ggtgctcggt ctggtacatg agtttaagga agggaaggat   240
gaactgtccg agcaggatga gatgttccgg gggaggaccg ctgtgttcgc cgatcaggta   300
atcgtcggaa atgcaagtct cagattgaaa aatgtgcaac tgactgatgc tggcacgtat   360
aaatgctaca ttatcacaag taagggcaaa ggaaatgcta accttgagta taaaacaggc   420
gcattctcaa tgcccgaggt caatgtcgac tataatgcca gcagtgaaac attgcgctgt   480
gaagctcccc gctggttccc ccagccaacc gtggtctggg cctctcaggt tgatcagggg   540
gctaactttt ccgaggtgag caacaccagc ttcgaactca actctgagaa tgtgaccatg   600
aaagttgtgt ctgtcctgta taatgtaaca atcaacaaca cttattcatg catgattgaa   660
aacgacatcg ccaaggcaac aggtgatatt aaggtaactg aatccgagat caaacggcgg   720
tctgagccta agtcatgtga caagacccat acgtgcccac cctgtcccgc tccagaactg   780 ctgggggac ctagcgtttt cttgttcccc ccaaagccca aggacaccct catgatctca   840
cggactcccg aagtaacatg cgtagtagtc gacgtgagcc acgaggatcc tgaagtgaag   900
tttaattggt acgtggacgg agtcgaggtg cataatgcca aaactaaacc tcgggaggag   960
cagtataaca gtacctaccg cgtggtatcc gtcttgacag tgctccacca ggactggctg   1020
aatggtaagg agtataaatg caaggtcagc aacaaagctc ttcccgcccc aattgaaaag   1080
actatcagca aggccaaggg acaaccccgc gagccccagg tttacacccct tccaccttca   1140 cgagacgagc tgaccaagaa ccaggtgtct ctgacttgtc tggtcaaagg tttctatcct   1200
tccgacatcg cagtggagtg ggagtcaaac gggcagcctg agaataacta caagaccaca   1260 ccccagtgc ttgatagcga tgggagcttt ttcctctaca gtaagctgac tgtggacaaa   1320
tcccgctggc agcagggaaa cgttttctct gtagcgtca tgcatgaggc cctccacaac   1380
cattatactc agaaaagcct gagtctgagt cccggcaaa,                         1419
                                                  (SEQ ID NO: 107)
atggaatgga gctgggtatt tctgttttc ctgtcagtaa cgactggcgt ccattcaggc     60
ttcggcatca gtggacggca cagtatcaca gtgaccaccg tcgcctccgc tggcaatata   120
ggtgaggatg gcatccagtc ctgtacctt gagccggaca tcaaactgtc tgacatagtg   180
atacaatggc tgaaggaggg ggtgctcggt ctggtacatg agtttaagga agggaaggat   240
gaactgtccg agcaggatga gatgttccgg gggaggaccg ctgtgttcgc cgatcaggta   300
```

```
atcgtcggaa atgcaagtct cagattgaaa aatgtgcaac tgactgatgc tggcacgtat    360
aaatgctaca ttatcacaag taagggcaaa ggaaatgcta accttgagta taaaacaggc    420
gcattctcaa tgcccgaggt caatgtcgac tataatgcca gcagtgaaac attgcgctgt    480
gaagctcccc gctggttccc ccagccaacc gtggtctggg cctctcaggt tgatcagggg    540
gctaactttt ccgaggtgag caacaccagc ttcgaactca actctgagaa tgtgaccatg    600
aaagttgtgt ctgtcctgta taatgtaaca atcaacaaca cttattcatg catgattgaa    660
aacgacatcg ccaaggcaac aggtgatatt aaggtaactg aatccgagat caaacggcgg    720
tctgacaaga cccatacgtg cccaccctgt cccgctccag aactgctggg gggacctagc    780
gttttcttgt tccccccaaa gcccaaggac accctcatga tctcacggac tcccgaagta    840
acatgcgtag tagtcgacgt gagccacgag gatcctgaag tgaagtttaa ttggtacgtg    900
gacggagtcg aggtgcataa tgccaaaact aaacctcggg aggagcagta taacagtacc    960
taccgcgtgg tatccgtctt gacagtgctc caccaggact ggctgaatgg taaggagtat    1020
aaatgcaagg tcagcaacaa agctcttccc gccccaattg aaaagactat cagcaaggcc    1080
aagggacaac cccgcgagcc ccaggtttac acccttccac cttcacgaga cgagctgacc    1140
aagaaccagg tgtctctgac ttgtctggtc aaaggtttct atccttccga catcgcagtg    1200
gagtgggagt caaacgggca gcctgagaat aactacaaga ccacaccccc agtgcttgat    1260
agcgatggga gcttttcct ctacagtaag ctgactgtgg acaaatcccg ctggcagcag    1320
ggaaacgttt tctcttgtag cgtcatgcat gaggccctcc acaaccatta tactcagaaa    1380
agcctgagtc tgagtcccgg caaa,                                          1404

(SEQ ID NO: 108)
atggaatgga gctgggtatt tctgtttttc ctgtcagtaa cgactggcgt ccattcaggc     60
ttcggcatca gtggacggca cagtatcaca gtgaccaccg tcgcctccgc tggcaatata    120
ggtgaggatg gcatccagtc ctgtacccttt gagccggaca tcaaactgtc tgacatagtg    180
atacaatggc tgaaggaggg ggtgctcggt ctggtacatg agtttaagga agggaaggat    240
gaactgtccg agcaggatga gatgttccgg gggaggaccg ctgtgttcgc cgatcaggta    300
atcgtcggaa atgcaagtct cagattgaaa aatgtgcaac tgactgatgc tggcacgtat    360
aaatgctaca ttatcacaag taagggcaaa ggaaatgcta accttgagta taaaacaggc    420
gcattctcaa tgcccgaggt caatgtcgac tataatgcca gcagtgaaac attgcgctgt    480
gaagctcccc gctggttccc ccagccaacc gtggtctggg cctctcaggt tgatcagggg    540
gctaactttt ccgaggtgag caacaccagc ttcgaactca actctgagaa tgtgaccatg    600
aaagttgtgt ctgtcctgta taatgtaaca atcaacaaca cttattcatg catgattgaa    660
aacgacatcg ccaaggcaac aggtgatatt aaggtaactg aatccgagat cgacaagacc    720
catacgtgcc cacccctgtcc cgctccagaa ctgctggggg gacctagcgt tttcttgttc    780
cccccaaagc ccaaggacac cctcatgatc tcacggactc ccgaagtaac atgcgtagta    840
gtcgacgtga gccacgagga tcctgaagtg aagtttaatt ggtacgtgga cggagtcgag    900
gtgcataatg ccaaaactaa acctcgggag gagcagtata acagtaccta ccgcgtggta    960
tccgtcttga cagtgctcca ccaggactgg ctgaatggta aggagtataa atgcaaggtc    1020
agcaacaaag ctcttcccgc cccaattgaa aagactatca gcaaggccaa gggacaaccc    1080
cgcgagcccc aggtttacac ccttccacct tcacgagacg agctgaccaa gaaccaggtg    1140
tctctgactt gtctggtcaa aggtttctat ccttccgaca tcgcagtgga gtgggagtca    1200
aacgggcagc ctgagaataa ctacaagacc acaccccag tgcttgatag cgatgggagc    1260
```

```
tttttcctct acagtaagct gactgtggac aaatcccgct ggcagcaggg aaacgttttc      1320
tcttgtagcg tcatgcatga ggccctccac aaccattata ctcagaaaag cctgagtctg      1380
agtcccggca aa,                                                         1392
                                                              (SEQ ID NO: 109)
atggaatgga gctgggtatt tctgttttc ctgtcagtaa cgactggcgt ccattcaggc         60
ttcggcatca gtggacggca cagtatcaca gtgaccaccg tcgcctccgc tggcaatata       120
ggtgaggatg gcatccagtc ctgtacctt gagccggaca tcaaactgtc tgacatagtg       180
atacaatggc tgaaggaggg ggtgctcggt ctggtacatg agtttaagga agggaaggat       240
gaactgtccg agcaggatga gatgttccgg gggaggaccg ctgtgttcgc cgatcaggta       300
atcgtcggaa atgcaagtct cagattgaaa aatgtgcaac tgactgatgc tggcacgtat       360
aaatgctaca ttatcacaag taagggcaaa ggaaatgcta accttgagta taaaacaggc       420
gcattctcaa tgcccgaggt caatgtcgac tataatgcca gcagtgaaac attgcgctgt       480
gaagctcccc gctggttccc ccagccaacc gtggtctggg cctctcaggt tgatcagggg       540
gctaactttt ccgaggtgag caacaccagc ttcgaactca actctgagaa tgtgaccatg       600
aaagttgtgt ctgtcctgta taatgtaaca atcaacaaca cttattcatg catgattgaa       660
aacgacatcg ccaaggcaac aggtgatatt aaggtaactg aatccgagat caaacggcgg       720
tctcacctgc agctgctgaa ctccaaggac aagacccata cgtgcccacc ctgtcccgct       780
ccagaactgc tgggggggacc tagcgttttc ttgttccccc caaagcccaa ggacaccctc       840
atgatctcac ggactcccga gtaacatgc gtagtagtcg acgtgagcca cgaggatcct       900
gaagtgaagt ttaattggta cgtggacgga gtcgaggtgc ataatgccaa aactaaacct       960
cgggaggagc agtataacag tacctaccgc gtggtatccg tcttgacagt gctccaccag      1020
gactggctga atggtaagga gtataaatgc aaggtcagca caaagctct cccgcccca      1080 attgaaaaga ctatcagcaa ggccaaggga caaccccgcg agcccaggt ttacacctt      1140 ccaccttcac gagacgagct gaccaagaac caggtgtctc tgacttgtct ggtcaaaggt      1200
ttctatcctt ccgacatcgc agtggagtgg gagtcaaacg ggcagcctga gaataactac      1260
aagaccacac ccccagtgct tgatagcgat gggagctttt tcctctacag taagctgact      1320
gtggacaaat cccgctggca gcagggaaac gttttctctt gtagcgtcat gcatgaggcc      1380
ctccacaacc attatactca gaaaagcctg agtctgagtc ccggcaaa,                  1428
                                                              (SEQ ID NO: 110)
atggaatgga gctgggtatt tctgttttc ctgtcagtaa cgactggcgt ccattcaggc         60
ttcggcatca gtggacggca cagtatcaca gtgaccaccg tcgcctccgc tggcaatata       120
ggtgaggatg gcatcctgtc ctgtacctt gagccggaca tcaaactgtc tgacatagtg       180
atacaatggc tgaaggaggg ggtgctcggt ctggtacatg agtttaagga agggaaggat       240
gaactgtccg agcaggatga gatgttccgg gggaggaccg ctgtgttcgc cgatcaggta       300
atcgtcggaa atgcaagtct cagattgaaa aatgtgcaac tgactgatgc tggcacgtat       360
aaatgctaca ttatcacaag taagggcaaa ggaaatgcta accttgagta taaaacaggc       420
gcattctcaa tgcccgaggt caatgtcgac tataatgcca gcagtgaaac attgcgctgt       480
gaagctcccc gctggttccc ccagccaacc gtggtctggg cctctcaggt tgatcagggg       540
gctaactttt ccgaggtgag caacaccagc ttcgaactca actctgagaa tgtgaccatg       600
aaagttgtgt ctgtcctgta taatgtaaca atcaacaaca cttattcatg catgattgaa       660
aacgacatcg ccaaggcaac aggtgatatt aaggtaactg aatccgagat caaacggcgg       720
```

-continued

```
tctgagccta agtcatgtga caagacccat acgtgcccac cctgtcccgc tccagaactg    780
ctgggggac ctagcgtttt cttgttcccc ccaaagccca aggacaccct catgatctca     840
cggactcccg aagtaacatg cgtagtagtc gacgtgagcc acgaggatcc tgaagtgaag    900
tttaattggt acgtggacgg agtcgaggtg cataatgcca aaactaaacc tcgggaggag    960
cagtataaca gtacctaccg cgtggtatcc gtcttgacag tgctccacca ggactggctg   1020
aatggtaagg agtataaatg caaggtcagc aacaaagctc ttcccgcccc aattgaaaag   1080
actatcagca aggccaaggg acaacccgc gagcccagg tttacaccct tccaccttca     1140
cgagacgagc tgaccaagaa ccaggtgtct ctgacttgtc tggtcaaagg tttctatcct   1200
tccgacatcg cagtggagtg ggagtcaaac gggcagcctg agaataacta caagaccaca   1260
cccccagtgc ttgatagcga tgggagcttt ttcctctaca gtaagctgac tgtggacaaa   1320
tcccgctggc agcagggaaa cgttttctct tgtagcgtca tgcatgaggc cctccacaac   1380
cattatactc agaaaagcct gagtctgagt cccggcaaa,                         1419
                                               (SEQ ID NO: 111)
atggaatgga gctgggtatt tctgtttttc ctgtcagtaa cgactggcgt ccattcaggc     60
ttcggcatca gtggacggca cagtatcaca gtgaccaccg tcgcctccgc tggcaatata    120
ggtgaggatg gcatcctgtc ctgtacctt gagccggaca tcaaactgtc tgacatagtg    180
atacaatggc tgaaggaggg ggtgctcggt ctggtacatg agtttaagga agggaaggat   240
gaactgtccg agcaggatga gatgttccgg gggaggaccg ctgtgttcgc cgatcaggta   300
atcgtcggaa atgcaagtct cagattgaaa aatgtgcaac tgactgatgc tggcacgtat   360
aaatgctaca ttatcacaag taagggcaaa ggaaatgcta accttgagta taaaacaggc   420
gcattctcaa tgcccgaggt caatgtcgac tataatgcca gcagtgaaaac attgcgctgt   480
gaagctcccc gctggttccc ccagccaacc gtggtctggg cctctcaggt tgatcagggg    540
gctaacttt ccgaggtgag caacaccagc ttcgaactca actctgagaa tgtgaccatg   600
aaagttgtgt ctgtcctgta taatgtaaca atcaacaaca cttattcatg catgattgaa   660
aacgacatcg ccaaggcaac aggtgatatt aaggtaactg aatccgagat caaacggcgg   720
tctgacaaga cccatacgtg cccacccgt cccgctccag aactgctggg gggacctagc   780
gttttcttgt tcccccaaa gcccaaggac accctcatga tctcacggac tcccgaagta   840
acatgcgtag tagtcgacgt gagccacgag gatcctgaag tgaagtttaa ttggtacgtg   900
gacggagtcg aggtgcataa tgccaaaact aaacctcggg aggagcagta taacagtacc   960
taccgcgtgg tatccgtctt gacagtgctc caccaggact ggctgaatgg taaggagtat  1020
aaatgcaagg tcagcaacaa agctcttccc gccccaattg aaaagactat cagcaaggcc  1080
aagggacaac ccgcgagcc ccaggtttac acccttccac cttcacgaga cgagctgacc  1140
aagaaccagg tgtctctgac ttgtctggtc aaaggtttct atccttccga catcgcagtg  1200
gagtgggagt caaacgggca gcctgagaat aactacaaga ccacaccccc agtgcttgat  1260
agcgatggga gcttttcct ctacagtaag ctgactgtgg acaaatcccg ctggcagcag  1320
ggaaacgttt tctcttgtag cgtcatgcat gaggccctcc acaaccatta tactcagaaa  1380
agcctgagtc tgagtcccgg caaa,                                       1404
                                               (SEQ ID NO: 112)
atggaatgga gctgggtatt tctgtttttc ctgtcagtaa cgactggcgt ccattcaggc     60
ttcggcatca gtggacggca cagtatcaca gtgaccaccg tcgcctccgc tggcaatata    120
ggtgaggatg gcatcctgtc ctgtacctt gagccggaca tcaaactgtc tgacatagtg    180
atacaatggc tgaaggaggg ggtgctcggt ctggtacatg agtttaagga agggaaggat   240
```

-continued

```
gaactgtccg agcaggatga gatgttccgg gggaggaccg ctgtgttcgc cgatcaggta    300
atcgtcggaa atgcaagtct cagattgaaa aatgtgcaac tgactgatgc tggcacgtat    360
aaatgctaca ttatcacaag taagggcaaa ggaaatgcta accttgagta taaaacaggc    420
gcattctcaa tgcccgaggt caatgtcgac tataatgcca gcagtgaaac attgcgctgt    480
gaagctcccc gctggttccc ccagccaacc gtggtctggg cctctcaggt tgatcagggg    540
gctaactttt ccgaggtgag caacaccagc ttcgaactca actctgagaa tgtgaccatg    600
aaagttgtgt ctgtcctgta taatgtaaca atcaacaaca cttattcatg catgattgaa    660
aacgacatcg ccaaggcaac aggtgatatt aaggtaactg aatccgagat cgacaagacc    720
catacgtgcc caccctgtcc cgctccagaa ctgctggggg gacctagcgt tttcttgttc    780
cccccaaagc ccaaggacac cctcatgatc tcacggactc ccgaagtaac atgcgtagta    840
gtcgacgtga gccacgagga tcctgaagtg aagtttaatt ggtacgtgga cggagtcgag    900
gtgcataatg ccaaaactaa acctcgggag gagcagtata acagtaccta ccgcgtggta    960
tccgtcttga cagtgctcca ccaggactgg ctgaatggta aggagtataa atgcaaggtc   1020
agcaacaaag ctcttcccgc cccaattgaa aagactatca gcaaggccaa gggacaaccc   1080
cgcgagcccc aggtttacac ccttccacct tcacgagacg agctgaccaa gaaccaggtg   1140
tctctgactt gtctggtcaa aggtttctat ccttccgaca tcgcagtgga gtgggagtca   1200
aacgggcagc ctgagaataa ctacaagacc acaccccag tgcttgatag cgatgggagc   1260 ttttcctct acagtaagct gactgtggac aaatcccgct ggcagcaggg aaacgttttc   1320
tcttgtagcg tcatgcatga ggccctccac aaccattata ctcagaaaag cctgagtctg   1380
agtcccggca aa,                                                      1392 or                                                      (SEQ ID NO: 113)
atggaatgga gctgggtatt tctgttttc ctgtcagtaa cgactggcgt ccattcaggc     60
ttcggcatca gtgacggca cagtatcaca gtgaccaccg tcgcctccgc tggcaatata    120
ggtgaggatg gcatcctgtc ctgtaccttt gagccggaca tcaaactgtc tgacatagtg    180
atacaatggc tgaaggaggg ggtgctcggt ctggtacatg agtttaagga agggaaggat    240
gaactgtccg agcaggatga gatgttccgg gggaggaccg ctgtgttcgc cgatcaggta    300
atcgtcggaa atgcaagtct cagattgaaa aatgtgcaac tgactgatgc tggcacgtat    360
aaatgctaca ttatcacaag taagggcaaa ggaaatgcta accttgagta taaaacaggc    420
gcattctcaa tgcccgaggt caatgtcgac tataatgcca gcagtgaaac attgcgctgt    480
gaagctcccc gctggttccc ccagccaacc gtggtctggg cctctcaggt tgatcagggg    540
gctaactttt ccgaggtgag caacaccagc ttcgaactca actctgagaa tgtgaccatg    600
aaagttgtgt ctgtcctgta taatgtaaca atcaacaaca cttattcatg catgattgaa    660
aacgacatcg ccaaggcaac aggtgatatt aaggtaactg aatccgagat caaacgcgg    720 tctcacctgc agctgctgaa ctccaaggac aagacccata cgtgcccacc ctgtcccgct    780
ccagaactgc tggggggacc tagcgttttc ttgttccccc caaagcccaa ggacaccctc    840
atgatctcac ggactcccga gtaacatgc gtagtagtcg acgtgagcca cgaggatcct    900
gaagtgaagt ttaattggta cgtggacgga tcgaggtgc ataatgccaa aactaaacct    960
cgggaggagc agtataacag tacctaccgc gtggtatccg tcttgacagt gctccaccag   1020
gactggctga atggtaagga gtataaatgc aaggtcagca acaaagctct tcccgcccca   1080
attgaaaaga ctatcagcaa ggccaaggga caaccccgcg agccccaggt ttacaccctt   1140
```

```
ccaccttcac gagacgagct gaccaagaac caggtgtctc tgacttgtct ggtcaaaggt    1200
ttctatcctt ccgacatcgc agtggagtgg gagtcaaacg ggcagcctga gaataactac    1260
aagaccacac ccccagtgct tgatagcgat gggagctttt tcctctacag taagctgact    1320
gtggacaaat cccgctggca gcagggaaac gttttctctt gtagcgtcat gcatgaggcc    1380
ctccacaacc attatactca gaaaagcctg agtctgagtc ccggcaaa.                1428
```

In another embodiment, a representative human B7-H4 fusion protein has at least 80%, 85%, 90%, 95%, 99% or 100% sequence identity to:

```
                                                        (SEQ ID NO: 114)
MASLGQILFW SIISIIIILA GAIALIIGFG ISGRHSITVT TVASAGNIGE DGIQSCTFEP    60

DIKLSDIVIQ WLKEGVLGLV HEFKEGKDEL SEQDEMFRGR TAVFADQVIV GNASLRLKNV   120

QLTDAGTYKC YIITSKGKGN ANLEYKTGAF SMPEVNVDYN ASSETLRCEA PRWFPQPTVV   180

WASQVDQGAN FSEVSNTSFE LNSENVTMKV VSVLYNVTIN NTYSCMIEND IAKATGDIKV   240

TESEIKRRSE PKSCDKTHTC PPCPAPELLG GPSVFLFPPK PKDTLMISRT PEVTCVVVDV   300

SHEDPEVKFN WYVDGVEVHN AKTKPREEQY NSTYRVVSVL TVLHQDWLNG KEYKCKVSNK   360

ALPAPIEKTI SKAKGQPREP QVYTLPPSRD ELTKNQVSLT CLVKGFYPSD IAVEWESNGQ   420

PENNYKTTPP VLDSDGSFFL YSKLTVDKSR WQQGNVFSCS VMHEALHNHY TQKSLSLSPG   480

K.                                                                  481
```

In another embodiment, a representative human B7-H4 fusion protein has at least 80%, 85%, 90%, 95%, 99% or 100% sequence identity to:

```
                                                        (SEQ ID NO: 115)
MASLGQILFW SIISIIIILA GAIALIIGFG ISGRHSITVT TVASAGNIGE DGIQSCTFEP    60

DIKLSDIVIQ WLKEGVLGLV HEFKEGKDEL SEQDEMFRGR TAVFADQVIV GNASLRLKNV   120

QLTDAGTYKC YIITSKGKGN ANLEYKTGAF SMPEVNVDYN ASSETLRCEA PRWFPQPTVV   180

WASQVDQGAN FSEVSNTSFE LNSENVTMKV VSVLYNVTIN NTYSCMIEND IAKATGDIKV   240

TESEIKRRSD KTHTCPPCPA PELLGGPSVF LFPPKPKDTL MISRTPEVTC VVVDVSHEDP   300

EVKFNWYVDG VEVHNAKTKP REEQYNSTYR VVSVLTVLHQ DWLNGKEYKC KVSNKALPAP   360

IEKTISKAKG QPREPQVYTL PPSRDELTKN QVSLTCLVKG FYPSDIAVEW ESNGQPENNY   420

KTTPPVLDSD GSFFLYSKLT VDKSRWQQGN VFSCSVMHEA LHNHYTQKSL SLSPGK,      476

(SEQ ID NO: 116)
MASLGQILFW SIISIIIILA GAIALIIGFG ISGRHSITVT TVASAGNIGE DGIQSCTFEP    60

DIKLSDIVIQ WLKEGVLGLV HEFKEGKDEL SEQDEMFRGR TAVFADQVIV GNASLRLKNV   120

QLTDAGTYKC YIITSKGKGN ANLEYKTGAF SMPEVNVDYN ASSETLRCEA PRWFPQPTVV   180

WASQVDQGAN FSEVSNTSFE LNSENVTMKV VSVLYNVTIN NTYSCMIEND IAKATGDIKV   240

TESEIDKTHT CPPCPAPELL GGPSVFLFPP KPKDTLMISR TPEVTCVVVD VSHEDPEVKF   300

NWYVDGVEVH NAKTKPREEQ YNSTYRVVSV LTVLHQDWLN GKEYKCKVSN KALPAPIEKT   360

ISKAKGQPRE PQVYTLPPSR DELTKNQVSL TCLVKGFYPS DIAVEWESNG QPENNYKTTP   420

PVLDSDGSFF LYSKLTVDKS RWQQGNVFSC SVMHEALHNH YTQKSLSLSP GK,          472

(SEQ ID NO: 117)
MASLGQILFW SIISIIIILA GAIALIIGFG ISGRHSITVT TVASAGNIGE DGIQSCTFEP    60

DIKLSDIVIQ WLKEGVLGLV HEFKEGKDEL SEQDEMFRGR TAVFADQVIV GNASLRLKNV   120
```

-continued

```
QLTDAGTYKC YIITSKGKGN ANLEYKTGAF SMPEVNVDYN ASSETLRCEA PRWFPQPTVV    180

WASQVDQGAN FSEVSNTSFE LNSENVTMKV VSVLYNVTIN NTYSCMIEND IAKATGDIKV    240

TESEIKRRSH LQLLNSKDKT HTCPPCPAPE LLGGPSVFLF PPKPKDTLMI SRTPEVTCVV    300

VDVSHEDPEV KFNWYVDGVE VHNAKTKPRE EQYNSTYRVV SVLTVLHQDW LNGKEYKCKV    360

SNKALPAPIE KTISKAKGQP REPQVYTLPP SRDELTKNQV SLTCLVKGFY PSDIAVEWES    420

NGQPENNYKT TPPVLDSDGS FFLYSKLTVD KSRWQQGNVF SCSVMHEALH NHYTQKSLSL    480

SPGK,                                                                484

(SEQ ID NO: 118)
MASLGQILFW SIISIIIILA GAIALIIGFG ISGRHSITVT TVASAGNIGE DGILSCTFEP     60

DIKLSDIVIQ WLKEGVLGLV HEFKEGKDEL SEQDEMFRGR TAVFADQVIV GNASLRLKNV    120

QLTDAGTYKC YIITSKGKGN ANLEYKTGAF SMPEVNVDYN ASSETLRCEA PRWFPQPTVV    180

WASQVDQGAN FSEVSNTSFE LNSENVTMKV VSVLYNVTIN NTYSCMIEND IAKATGDIKV    240

TESEIKRRSE PKSCDKTHTC PPCPAPELLG GPSVFLFPPK PKDTLMISRT PEVTCVVVDV    300

SHEDPEVKFN WYVDGVEVHN AKTKPREEQY NSTYRVVSVL TVLHQDWLNG KEYKCKVSNK    360

ALPAPIEKTI SKAKGQPREP QVYTLPPSRD ELTKNQVSLT CLVKGFYPSD IAVEWESNGQ    420

PENNYKTTPP VLDSDGSFFL YSKLTVDKSR WQQGNVFSCS VMHEALHNHY TQKSLSLSPG    480

K,                                                                   481

(SEQ ID NO: 119)
MASLGQILFW SIISIIIILA GAIALIIGFG ISGRHSITVT TVASAGNIGE DGILSCTFEP     60

DIKLSDIVIQ WLKEGVLGLV HEFKEGKDEL SEQDEMFRGR TAVFADQVIV GNASLRLKNV    120

QLTDAGTYKC YIITSKGKGN ANLEYKTGAF SMPEVNVDYN ASSETLRCEA PRWFPQPTVV    180

WASQVDQGAN FSEVSNTSFE LNSENVTMKV VSVLYNVTIN NTYSCMIEND IAKATGDIKV    240

TESEIKRRSD KTHTCPPCPA PELLGGPSVF LFPPKPKDTL MISRTPEVTC VVVDVSHEDP    300

EVKFNWYVDG VEVHNAKTKP REEQYNSTYR VVSVLTVLHQ DWLNGKEYKC KVSNKALPAP    360

IEKTISKAKG QPREPQVYTL PPSRDELTKN QVSLTCLVKG FYPSDIAVEW ESNGQPENNY    420

KTTPPVLDSD GSFFLYSKLT VDKSRWQQGN VFSCSVMHEA LHNHYTQKSL SLSPGK,       476

(SEQ ID NO: 120)
MASLGQILFW SIISIIIILA GAIALIIGFG ISGRHSITVT TVASAGNIGE DGILSCTFEP     60

DIKLSDIVIQ WLKEGVLGLV HEFKEGKDEL SEQDEMFRGR TAVFADQVIV GNASLRLKNV    120

QLTDAGTYKC YIITSKGKGN ANLEYKTGAF SMPEVNVDYN ASSETLRCEA PRWFPQPTVV    180

WASQVDQGAN FSEVSNTSFE LNSENVTMKV VSVLYNVTIN NTYSCMIEND IAKATGDIKV    240

TESEIDKTHT CPPCPAPELL GGPSVFLFPP KPKDTLMISR TPEVTCVVVD VSHEDPEVKF    300

NWYVDGVEVH NAKTKPREEQ YNSTYRVVSV LTVLHQDWLN GKEYKCKVSN KALPAPIEKT    360

ISKAKGQPRE PQVYTLPPSR DELTKNQVSL TCLVKGFYPS DIAVEWESNG QPENNYKTTP    420

PVLDSDGSFF LYSKLTVDKS RWQQGNVFSC SVMHEALHNH YTQKSLSLSP GK,            472

(SEQ ID NO: 121)
MASLGQILFW SIISIIIILA GAIALIIGFG ISGRHSITVT TVASAGNIGE DGILSCTFEP     60

DIKLSDIVIQ WLKEGVLGLV HEFKEGKDEL SEQDEMFRGR TAVFADQVIV GNASLRLKNV    120

QLTDAGTYKC YIITSKGKGN ANLEYKTGAF SMPEVNVDYN ASSETLRCEA PRWFPQPTVV    180

WASQVDQGAN FSEVSNTSFE LNSENVTMKV VSVLYNVTIN NTYSCMIEND IAKATGDIKV    240

TESEIKRRSH LQLLNSKDKT HTCPPCPAPE LLGGPSVFLF PPKPKDTLMI SRTPEVTCVV    300

VDVSHEDPEV KFNWYVDGVE VHNAKTKPRE EQYNSTYRVV SVLTVLHQDW LNGKEYKCKV    360

SNKALPAPIE KTISKAKGQP REPQVYTLPP SRDELTKNQV SLTCLVKGFY PSDIAVEWES    420
```

```
NGQPENNYKT TPPVLDSDGS FFLYSKLTVD KSRWQQGNVF SCSVMHEALH NHYTQKSLSL    480

SPGK,                                                                484

(SEQ ID NO: 122)
MEWSWVFLFF LSVTTGVHSG FGISGRHSIT VTTVASAGNI GEDGIQSCTF EPDIKLSDIV     60

IQWLKEGVLG LVHEFKEGKD ELSEQDEMFR GRTAVFADQV IVGNASLRLK NVQLTDAGTY    120

KCYIITSKGK GNANLEYKTG AFSMPEVNVD YNASSETLRC EAPRWFPQPT VVWASQVDQG    180

ANFSEVSNTS FELNSENVTM KVVSVLYNVT INNTYSCMIE NDIAKATGDI KVTESEIKRR    240

SEPKSCDKTH TCPPCPAPEL LGGPSVFLFP PKPKDTLMIS RTPEVTCVVV DVSHEDPEVK    300

FNWYVDGVEV HNAKTKPREE QYNSTYRVVS VLTVLHQDWL NGKEYKCKVS NKALPAPIEK    360

TISKAKGQPR EPQVYTLPPS RDELTKNQVS LTCLVKGFYP SDIAVEWESN GQPENNYKTT    420

PPVLDSDGSF FLYSKLTVDK SRWQQGNVFS CSVMHEALHN HYTQKSLSLS PGK,          473

(SEQ ID NO: 123)
MEWSWVFLFF LSVTTGVHSG FGISGRHSIT VTTVASAGNI GEDGIQSCTF EPDIKLSDIV     60

IQWLKEGVLG LVHEFKEGKD ELSEQDEMFR GRTAVFADQV IVGNASLRLK NVQLTDAGTY    120

KCYIITSKGK GNANLEYKTG AFSMPEVNVD YNASSETLRC EAPRWFPQPT VVWASQVDQG    180

ANFSEVSNTS FELNSENVTM KVVSVLYNVT INNTYSCMIE NDIAKATGDI KVTESEIKRR    240

SDKTHTCPPC PAPELLGGPS VFLFPPKPKD TLMISRTPEV TCVVVDVSHE DPEVKFNWYV    300

DGVEVHNAKT KPREEQYNST YRVVSVLTVL HQDWLNGKEY KCKVSNKALP APIEKTISKA    360

KGQPREPQVY TLPPSRDELT KNQVSLTCLV KGFYPSDIAV EWESNGQPEN NYKTTPPVLD    420

SDGSFFLYSK LTVDKSRWQQ GNVFSCSVMH EALHNHYTQK SLSLSPGK,                468

(SEQ ID NO: 124)
MEWSWVFLFF LSVTTGVHSG FGISGRHSIT VTTVASAGNI GEDGIQSCTF EPDIKLSDIV     60

IQWLKEGVLG LVHEFKEGKD ELSEQDEMFR GRTAVFADQV IVGNASLRLK NVQLTDAGTY    120

KCYIITSKGK GNANLEYKTG AFSMPEVNVD YNASSETLRC EAPRWFPQPT VVWASQVDQG    180

ANFSEVSNTS FELNSENVTM KVVSVLYNVT INNTYSCMIE NDIAKATGDI KVTESEIDKT    240

HTCPPCPAPE LLGGPSVFLF PPKPKDTLMI SRTPEVTCVV VDSHEDPEV KFNWYVDGVE     300

VHNAKTKPRE EQYNSTYRVV SVLTVLHQDW LNGKEYKCKV SNKALPAPIE KTISKAKGQP    360

REPQVYTLPP SRDELTKNQV SLTCLVKGFY PSDIAVEWES NGQPENNYKT TPPVLDSDGS    420

FFLYSKLTVD KSRWQQGNVF SCSVMHEALH NHYTQKSLSL SPGK,                    464

(SEQ ID NO: 125)
MEWSWVFLFF LSVTTGVHSG FGISGRHSIT VTTVASAGNI GEDGIQSCTF EPDIKLSDIV     60

IQWLKEGVLG LVHEFKEGKD ELSEQDEMFR GRTAVFADQV IVGNASLRLK NVQLTDAGTY    120

KCYIITSKGK GNANLEYKTG AFSMPEVNVD YNASSETLRC EAPRWFPQPT VVWASQVDQG    180

ANFSEVSNTS FELNSENVTM KVVSVLYNVT INNTYSCMIE NDIAKATGDI KVTESEIKRR    240

SHLQLLNSKD KTHTCPPCPA PELLGGPSVF LFPPKPKDTL MISRTPEVTC VVVDVSHEDP    300

EVKFNWYVDG VEVHNAKTKP REEQYNSTYR VVSVLTVLHQ DWLNGKEYKC KVSNKALPAP    360

IEKTISKAKG QPREPQVYTL PPSRDELTKN QVSLTCLVKG FYPSDIAVEW ESNGQPENNY    420

KTTPPVLDSD GSFFLYSKLT VDKSRWQQGN VFSCSVMHEA LHNHYTQKSL SLSPGK,       476

(SEQ ID NO: 126)
MEWSWVFLFF LSVTTGVHSG FGISGRHSIT VTTVASAGNI GEDGILSCTF EPDIKLSDIV     60

IQWLKEGVLG LVHEFKEGKD ELSEQDEMFR GRTAVFADQV IVGNASLRLK NVQLTDAGTY    120

KCYIITSKGK GNANLEYKTG AFSMPEVNVD YNASSETLRC EAPRWFPQPT VVWASQVDQG    180

ANFSEVSNTS FELNSENVTM KVVSVLYNVT INNTYSCMIE NDIAKATGDI KVTESEIKRR    240
```

```
SEPKSCDKTH TCPPCPAPEL LGGPSVFLFP PKPKDTLMIS RTPEVTCVVV DVSHEDPEVK   300

FNWYVDGVEV HNAKTKPREE QYNSTYRVVS VLTVLHQDWL NGKEYKCKVS NKALPAPIEK   360

TISKAKGQPR EPQVYTLPPS RDELTKNQVS LTCLVKGFYP SDIAVEWESN GQPENNYKTT   420

PPVLDSDGSF FLYSKLTVDK SRWQQGNVFS CSVMHEALHN HYTQKSLSLS PGK,         473

(SEQ ID NO: 127)
MEWSWVFLFF LSVTTGVHSG FGISGRHSIT VTTVASAGNI GEDGILSCTF EPDIKLSDIV    60

IQWLKEGVLG LVHEFKEGKD ELSEQDEMFR GRTAVFADQV IVGNASLRLK NVQLTDAGTY   120

KCYIITSKGK GNANLEYKTG AFSMPEVNVD YNASSETLRC EAPRWFPQPT VVWASQVDQG   180

ANFSEVSNTS FELNSENVTM KVVSVLYNVT INNTYSCMIE NDIAKATGDI KVTESEIKRR   240

SDKTHTCPPC PAPELLGGPS VFLFPPKPKD TLMISRTPEV TCVVVDVSHE DPEVKFNWYV   300

DGVEVHNAKT KPREEQYNST YRVVSVLTVL HQDWLNGKEY KCKVSNKALP APIEKTISKA   360

KGQPREPQVY TLPPSRDELT KNQVSLTCLV KGFYPSDIAV EWESNGQPEN NYKTTPPVLD   420

SDGSFFLYSK LTVDKSRWQQ GNVFSCSVMH EALHNHYTQK SLSLSPGK,              468

(SEQ ID NO: 128)
MEWSWVFLFF LSVTTGVHSG FGISGRHSIT VTTVASAGNI GEDGILSCTF EPDIKLSDIV    60

IQWLKEGVLG LVHEFKEGKD ELSEQDEMFR GRTAVFADQV IVGNASLRLK NVQLTDAGTY   120

KCYIITSKGK GNANLEYKTG AFSMPEVNVD YNASSETLRC EAPRWFPQPT VVWASQVDQG   180

ANFSEVSNTS FELNSENVTM KVVSVLYNVT INNTYSCMIE NDIAKATGDI KVTESEIDKT   240

HTCPPCPAPE LLGGPSVFLF PPKPKDTLMI SRTPEVTCVV VDVSHEDPEV KFNWYVDGVE   300

VHNAKTKPRE EQYNSTYRVV SVLTVLHQDW LNGKEYKCKV SNKALPAPIE KTISKAKGQP   360

REPQVYTLPP SRDELTKNQV SLTCLVKGFY PSDIAVEWES NGQPENNYKT TPPVLDSDGS   420

FFLYSKLTVD KSRWQQGNVF SCSVMHEALH NHYTQKSLSL SPGK,                  464
or
                                                    (SEQ ID NO: 129)
MEWSWVFLFF LSVTTGVHSG FGISGRHSIT VTTVASAGNI GEDGILSCTF EPDIKLSDIV    60

IQWLKEGVLG LVHEFKEGKD ELSEQDEMFR GRTAVFADQV IVGNASLRLK NVQLTDAGTY   120

KCYIITSKGK GNANLEYKTG AFSMPEVNVD YNASSETLRC EAPRWFPQPT VVWASQVDQG   180

ANFSEVSNTS FELNSENVTM KVVSVLYNVT INNTYSCMIE NDIAKATGDI KVTESEIKRR   240

SHLQLLNSKD KTHTCPPCPA PELLGGPSVF LFPPKPKDTL MISRTPEVTC VVVDVSHEDP   300

EVKFNWYVDG VEVHNAKTKP REEQYNSTYR VVSVLTVLHQ DWLNGKEYKC KVSNKALPAP   360

IEKTISKAKG QPREPQVYTL PPSRDELTKN QVSLTCLVKG FYPSDIAVEW ESNGQPENNY   420

KTTPPVLDSD GSFFLYSKLT VDKSRWQQGN VFSCSVMHEA LHNHYTQKSL SLSPGK.     476
```

The amino acid sequence of the human B7-H4 fusion protein of SEQ ID NO:114 and SEQ ID NO:122 without the signal sequence is:

```
                                                    (SEQ ID NO: 130)
GFGISGRHSI TVTTVASAGN IGEDGIQSCT FEPDIKLSDI VIQWLKEGVL GLVHEFKEGK    60

DELSEQDEMF RGRTAVFADQ VIVGNASLRL KNVQLTDAGT YKCYIITSKG KGNANLEYKT   120

GAFSMPEVNV DYNASSETLR CEAPRWFPQP TVVWASQVDQ GANFSEVSNT SFELNSENVT   180

MKVVSVLYNV TINNTYSCMI ENDIAKATGD IKVTESEIKR RSEPKSCDKT HTCPPCPAPE   240

LLGGPSVFLF PPKPKDTLMI SRTPEVTCVV VDVSHEDPEV KFNWYVDGVE VHNAKTKPRE   300

EQYNSTYRVV SVLTVLHQDW LNGKEYKCKV SNKALPAPIE KTISKAKGQP REPQVYTLPP   360
```

-continued

```
SRDELTKNQV SLTCLVKGFY PSDIAVEWES NGQPENNYKT TPPVLDSDGS FFLYSKLTVD    420

KSRWQQGNVF SCSVMHEALH NHYTQKSLSL SPGK.                               454
```

The amino acid sequence of the human B7-H4 fusion protein of SEQ ID NO:115 and SEQ ID NO:123 without the signal sequence is:

```
                                                          (SEQ ID NO: 131)
GFGISGRHSI TVTTVASAGN IGEDGIQSCT FEPDIKLSDI VIQWLKEGVL GLVHEFKEGK    60

DELSEQDEMF RGRTAVFADQ VIVGNASLRL KNVQLTDAGT YKCYIITSKG KGNANLEYKT    120

GAFSMPEVNV DYNASSETLR CEAPRWFPQP TVVWASQVDQ GANFSEVSNT SFELNSENVT    180

MKVVSVLYNV TINNTYSCMI ENDIAKATGD IKVTESEIKR RSDKTHTCPP CPAPELLGGP    240

SVFLFPPKPK DTLMISRTPE VTCVVVDVSH EDPEVKFNWY VDGVEVHNAK TKPREEQYNS    300

TYRVVSVLTV LHQDWLNGKE YKCKVSNKAL PAPIEKTISK AKGQPREPQV YTLPPSRDEL    360

TKNQVSLTCL VKGFYPSDIA VEWESNGQPE NNYKTTPPVL DSDGSFFLYS KLTVDKSRWQ    420

QGNVFSCSVM HEALHNHYTQ KSLSLSPGK.                                    449
```

The amino acid sequence of the human B7-H4 fusion protein of SEQ ID NO:116 and SEQ ID NO:124 without the signal sequence is:

```
                                                          (SEQ ID NO: 132)
GFGISGRHSI TVTTVASAGN IGEDGIQSCT FEPDIKLSDI VIQWLKEGVL GLVHEFKEGK    60

DELSEQDEMF RGRTAVFADQ VIVGNASLRL KNVQLTDAGT YKCYIITSKG KGNANLEYKT    120

GAFSMPEVNV DYNASSETLR CEAPRWFPQP TVVWASQVDQ GANFSEVSNT SFELNSENVT    180

MKVVSVLYNV TINNTYSCMI ENDIAKATGD IKVTESEIDK THTCPPCPAP ELLGGPSVFL    240

FPPKPKDTLM ISRTPEVTCV VVDVSHEDPE VKFNWYVDGV EVHNAKTKPR EEQYNSTYRV    300

VSVLTVLHQD WLNGKEYKCK VSNKALPAPI EKTISKAKGQ PREPQVYTLP PSRDELTKNQ    360

VSLTCLVKGF YPSDIAVEWE SNGQPENNYK TTPPVLDSDG SFFLYSKLTV DKSRWQQGNV    420

FSCSVMHEAL HNHYTQKSLS LSPGK.                                        445
```

The amino acid sequence of the human B7-H4 fusion protein of SEQ ID NO:117 and SEQ ID NO:125 without the signal sequence is:

```
                                                          (SEQ ID NO: 133)
GFGISGRHSI TVTTVASAGN IGEDGIQSCT FEPDIKLSDI VIQWLKEGVL GLVHEFKEGK    60

DELSEQDEMF RGRTAVFADQ VIVGNASLRL KNVQLTDAGT YKCYIITSKG KGNANLEYKT    120

GAFSMPEVNV DYNASSETLR CEAPRWFPQP TVVWASQVDQ GANFSEVSNT SFELNSENVT    180

MKVVSVLYNV TINNTYSCMI ENDIAKATGD IKVTESEIKR RSHLQLLNSK DKTHTCPPCP    240

APELLGGPSV FLFPPKPKDT LMISRTPEVT CVVVDVSHED PEVKFNWYVD GVEVHNAKTK    300

PREEQYNSTY RVVSVLTVLH QDWLNGKEYK CKVSNKALPA PIEKTISKAK GQPREPQVYT    360

LPPSRDELTK NQVSLTCLVK GFYPSDIAVE WESNGQPENN YKTTPPVLDS DGSFFLYSKL    420

TVDKSRWQQG NVFSCSVMHE ALHNHYTQKS LSLSPGK.                           457
```

The amino acid sequence of the human B7-H4 fusion protein of SEQ ID NO:118 and SEQ ID NO:126 without the signal sequence is:

```
                                                              (SEQ ID NO: 134)
GFGISGRHSI TVTTVASAGN IGEDGILSCT FEPDIKLSDI VIQWLKEGVL GLVHEFKEGK   60

DELSEQDEMF RGRTAVFADQ VIVGNASLRL KNVQLTDAGT YKCYIITSKG KGNANLEYKT  120

GAFSMPEVNV DYNASSETLR CEAPRWFPQP TVVWASQVDQ GANFSEVSNT SFELNSENVT  180

MKVVSVLYNV TINNTYSCMI ENDIAKATGD IKVTESEIKR RSEPKSCDKT HTCPPCPAPE  240

LLGGPSVFLF PPKPKDTLMI SRTPEVTCVV VDVSHEDPEV KFNWYVDGVE VHNAKTKPRE  300

EQYNSTYRVV SVLTVLHQDW LNGKEYKCKV SNKALPAPIE KTISKAKGQP REPQVYTLPP  360

SRDELTKNQV SLTCLVKGFY PSDIAVEWES NGQPENNYKT TPPVLDSDGS FFLYSKLTVD  420

KSRWQQGNVF SCSVMHEALH NHYTQKSLSL SPGK.                             454
```

The amino acid sequence of the human B7-H4 fusion protein of SEQ ID NO:119 and SEQ ID NO:127 without the signal sequence is:

```
                                                              (SEQ ID NO: 135)
GFGISGRHSI TVTTVASAGN IGEDGILSCT FEPDIKLSDI VIQWLKEGVL GLVHEFKEGK   60

DELSEQDEMF RGRTAVFADQ VIVGNASLRL KNVQLTDAGT YKCYIITSKG KGNANLEYKT  120

GAFSMPEVNV DYNASSETLR CEAPRWFPQP TVVWASQVDQ GANFSEVSNT SFELNSENVT  180

MKVVSVLYNV TINNTYSCMI ENDIAKATGD IKVTESEIKR RSDKTHTCPP CPAPELLGGP  240

SVFLFPPKPK DTLMISRTPE VTCVVVDVSH EDPEVKFNWY VDGVEVHNAK TKPREEQYNS  300

TYRVVSVLTV LHQDWLNGKE YKCKVSNKAL PAPIEKTISK AKGQPREPQV YTLPPSRDEL  360

TKNQVSLTCL VKGFYPSDIA VEWESNGQPE NNYKTTPPVL DSDGSFFLYS KLTVDKSRWQ  420

QGNVFSCSVM HEALHNHYTQ KSLSLSPGK.                                   449
```

The amino acid sequence of the human B7-H4 fusion protein of SEQ ID NO:120 and SEQ ID NO:128 without the signal sequence is:

```
                                                              (SEQ ID NO: 136)
GFGISGRHSI TVTTVASAGN IGEDGILSCT FEPDIKLSDI VIQWLKEGVL GLVHEFKEGK   60

DELSEQDEMF RGRTAVFADQ VIVGNASLRL KNVQLTDAGT YKCYIITSKG KGNANLEYKT  120

GAFSMPEVNV DYNASSETLR CEAPRWFPQP TVVWASQVDQ GANFSEVSNT SFELNSENVT  180

MKVVSVLYNV TINNTYSCMI ENDIAKATGD IKVTESEIDK THTCPPCPAP ELLGGPSVFL  240

FPPKPKDTLM ISRTPEVTCV VVDVSHEDPE VKFNWYVDGV EVHNAKTKPR EEQYNSTYRV  300

VSVLTVLHQD WLNGKEYKCK VSNKALPAPI EKTISKAKGQ PREPQVYTLP PSRDELTKNQ  360

VSLTCLVKGF YPSDIAVEWE SNGQPENNYK TTPPVLDSDG SFFLYSKLTV DKSRWQQGNV  420

FSCSVMHEAL HNHYTQKSLS LSPGK.                                       445
```

The amino acid sequence of the human B7-H4 fusion protein of SEQ ID NO:121 and SEQ ID NO:129 without the signal sequence is:

```
                                                              (SEQ ID NO: 137)
GFGISGRHSI TVTTVASAGN IGEDGILSCT FEPDIKLSDI VIQWLKEGVL GLVHEFKEGK   60

DELSEQDEMF RGRTAVFADQ VIVGNASLRL KNVQLTDAGT YKCYIITSKG KGNANLEYKT  120

GAFSMPEVNV DYNASSETLR CEAPRWFPQP TVVWASQVDQ GANFSEVSNT SFELNSENVT  180
```

```
MKVVSVLYNV TINNTYSCMI ENDIAKATGD IKVTESEIKR RSHLQLLNSK DKTHTCPPCP  240

APELLGGPSV FLFPPKPKDT LMISRTPEVT CVVVDVSHED PEVKFNWYVD GVEVHNAKTK  300

PREEQYNSTY RVVSVLTVLH QDWLNGKEYK CKVSNKALPA PIEKTISKAK GQPREPQVYT  360

LPPSRDELTK NQVSLTCLVK GFYPSDIAVE WESNGQPENN YKTTPPVLDS DGSFFLYSKL  420

TVDKSRWQQG NVFSCSVMHE ALHNHYTQKS LSLSPGK.                         457
```

The aforementioned exemplary fusion proteins can incorporate any combination of the variants described herein. In another embodiment the terminal lysine of the aforementioned exemplary fusion proteins is deleted.

The disclosed fusion proteins can be isolated using standard molecular biology techniques. For example, an expression vector containing a DNA sequence encoding a B7-H4-Ig fusion protein is transfected into 293 cells by calcium phosphate precipitation and cultured in serum-free DMEM. The supernatant is collected at 72 h and the fusion protein is purified by Protein G, or preferably Protein A SEPHAROSE® columns (Pharmacia, Uppsala, Sweden).

F. Fusion Protein Dimers and Multimers

B7-H4 fusion polypeptides can be dimerized or multimerized. Dimerization or multimerization can occur between or among two or more fusion proteins through dimerization or multimerization domains, including those described above. Alternatively, dimerization or multimerization of fusion proteins can occur by chemical crosslinking Fusion protein dimers can be homodimers or heterodimers. Fusion protein multimers can be homomultimers or heteromultimers.

Fusion protein dimers as disclosed herein are of formula II:

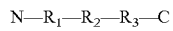

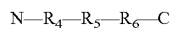

or, alternatively, are of formula III:

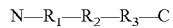

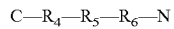

wherein the fusion proteins of the dimer provided by formula II are defined as being in a parallel orientation and the fusion proteins of the dimer provided by formula III are defined as being in an antiparallel orientation. Parallel and antiparallel dimers are also referred to as cis and trans dimers, respectively. "N" and "C" represent the N- and C-termini of the fusion protein, respectively. The fusion protein constituents "$R_1$", "$R_2$" and "$R_3$" are as defined above with respect to formula I. With respect to both formula II and formula III, "$R_4$" is a B7-H4 polypeptide or a second polypeptide, "$R_5$" is an optional peptide/polypeptide linker domain, and "$R_6$" is a B7-H4 polypeptide or a second polypeptide, wherein "$R_6$" is a B7-H4 polypeptide when "$R_4$" is a second polypeptide, and "$R_6$" is a second polypeptide when "$R_4$" is a B7-H4 polypeptide. In one embodiment, "$R_1$" is a B7-H4 polypeptide, "$R_4$" is also a B7-H4 polypeptide, and "$R_3$" and "$R_6$" are both second polypeptides.

Fusion protein dimers of formula II are defined as homodimers when "$R_1$"="$R_4$", "$R_2$"="$R_5$" and "$R_3$"="$R_6$". Similarly, fusion protein dimers of formula III are defined as homodimers when "$R_1$"="$R_6$", "$R_2$"="$R_5$" and "$R_3$"="$R_4$". Fusion protein dimers are defined as heterodimers when these conditions are not met for any reason. For example, heterodimers may contain domain orientations that meet these conditions (i.e., for a dimer according to formula II, "$R_1$" and "$R_4$" are both B7-H4 polypeptides, "$R_2$" and "$R_5$" are both peptide/polypeptide liker domains and "$R_3$" and "$R_6$" are both second polypeptides), however the species of one or more of these domains is not identical. For example, although "$R_3$" and "$R_6$" may both be B7-H4 polypeptides, one polypeptide may contain a wild-type B7-H4 amino acid sequence while the other polypeptide may be a variant B7-H4 polypeptide. An exemplary variant B7-H4 polypeptide is B7-H4 polypeptide that has been modified to have increased or decreased binding to a target cell, increased activity on immune cells, increased or decreased half life or stability. Dimers of fusion proteins that contain either a $C_H1$ or $C_L$ region of an immunoglobulin as part of the polypeptide linker domain preferably form heterodimers wherein one fusion protein of the dimer contains a $C_H1$ region and the other fusion protein of the dimer contains a $C_L$ region.

Fusion proteins can also be used to form multimers. As with dimers, multimers may be parallel multimers, in which all fusion proteins of the multimer are aligned in the same orientation with respect to their N- and C-termini. Multimers may be antiparallel multimers, in which the fusion proteins of the multimer are alternatively aligned in opposite orientations with respect to their N- and C-termini. Multimers (parallel or antiparallel) can be either homomultimers or heteromultimers.

G. Peptide and Polypeptide Modifications

The fusion proteins may be modified by chemical moieties that may be present in polypeptides in a normal cellular environment, for example, phosphorylation, methylation, amidation, sulfation, acylation, glycosylation, sumoylation and ubiquitylation. Fusion proteins may also be modified with a label capable of providing a detectable signal, either directly or indirectly, including, but not limited to, radioisotopes and fluorescent compounds.

The fusion proteins may also be modified by chemical moieties that are not normally added to polypeptides in a cellular environment. For example, the disclosed fusion proteins may also be modified by covalent attachment of polymer chains, including, but not limited to, polyethylene glycol polymer (PEG) chains (i.e. pegylation). Conjugation of macromolecules to PEG has emerged recently as an effective strategy to alter the pharmacokinetic (PK) profiles of a variety of drugs, and thereby to improve their therapeutic potential. PEG conjugation increases retention of drugs in the circulation by protecting against enzymatic digestion, slowing filtration by the kidneys and reducing the generation of neutralizing antibodies. In addition, PEG conjugates can be used to allow multimerization of the fusion proteins.

Modifications may be introduced into the molecule by reacting targeted amino acid residues of the polypeptide with an organic derivatizing agent that is capable of reacting with selected side chains or terminal residues. Another modification is cyclization of the protein.

Examples of chemical derivatives of the polypeptides include lysinyl and amino terminal residues derivatized with succinic or other carboxylic acid anhydrides. Derivatization with a cyclic carboxylic anhydride has the effect of reversing the charge of the lysinyl residues. Other suitable reagents for derivatizing amino-containing residues include imidoesters such as methyl picolinimidate; pyridoxal phosphate; pyridoxal; chloroborohydride; trinitrobenzenesulfonic acid; O-methylisourea; 2,4 pentanedione; and transaminase-catalyzed reaction with glyoxylate. Carboxyl side groups, aspartyl or glutamyl, may be selectively modified by reaction with carbodiimides (R—N=C=N—R') such as 1-cyclohexyl-3-(2-morpholinyl-(4-ethyl)carbodiimide or 1-ethyl-3-(4-azonia-4,4-dimethylpentyl) carbodiimide. Furthermore, aspartyl and glutamyl residues can be converted to asparaginyl and glutaminyl residues by reaction with ammonia. Fusion proteins may also include one or more D-amino acids that are substituted for one or more L-amino acids.

H. Modified Binding Properties

Binding properties of the B7-H4 polypeptides, fragments and fusions thereof (collectively referred to as B7-H4 polypeptides) are relevant to the dose and dose regimen to be administered. In one embodiment the disclosed B7-H4 polypeptides have binding properties to at least one receptor on a T cell that demonstrate a higher term, or higher percentage, of occupancy of receptor molecules on immune cells relative to other ligands of the receptor molecules. In other embodiments, the disclosed B7-H4 polypeptides have reduced binding affinity to a receptor on T cells relative to wildtype B7-H4, allowing the protein to dissociate in a period of less than three months, two months, one month, three weeks, two weeks, one week, or a few days after administration.

In some embodiments the B7-H4 polypeptides, or fragments, or fusions thereof have a relatively high affinity for its receptor, and may therefore have a relatively slow off rate. In other embodiments, the B7-H4 polypeptides are administered intermittently over a period of days, weeks or months to dampen immune responses which are allowed to recover prior to the next administration, which may serve to reduce the immune response without completely turning the immune response off and may avoid long term side effects.

III. Isolated Nucleic Acid Molecules

Isolated nucleic acid sequences encoding B7-H4 polypeptides, fragments and fusions thereof are disclosed herein. Useful murine B7-H4 nucleic acids have at least about 80, 85, 90, 95 or 100% sequence identity to the B7-H4 nucleic acid having GenBank Accession Number NM_178594 or AY280973. Useful human B7-H4 nucleic acids have at least about 80, 85, 90, 95 or 100% sequence identity to the B7-H4 nucleic acid having GenBank Accession Number AK026071. As used herein, "isolated nucleic acid" refers to a nucleic acid that is separated from other nucleic acid molecules that are present in a mammalian genome, including nucleic acids that normally flank one or both sides of the nucleic acid in a mammalian genome (e.g., nucleic acids that encode non-B7-H4 proteins). The term "isolated" as used herein with respect to nucleic acids also includes the combination with any non-naturally-occurring nucleic acid sequence, since such non-naturally-occurring sequences are not found in nature and do not have immediately contiguous sequences in a naturally-occurring genome.

An isolated nucleic acid can be, for example, a DNA molecule, provided one of the nucleic acid sequences normally found immediately flanking that DNA molecule in a naturally-occurring genome is removed or absent. Thus, an isolated nucleic acid includes, without limitation, a DNA molecule that exists as a separate molecule independent of other sequences (e.g., a chemically synthesized nucleic acid, or a cDNA or genomic DNA fragment produced by PCR or restriction endonuclease treatment), as well as recombinant DNA that is incorporated into a vector, an autonomously replicating plasmid, a virus (e.g., a retrovirus, lentivirus, adenovirus, or herpes virus), or into the genomic DNA of a prokaryote or eukaryote. In addition, an isolated nucleic acid can include an engineered nucleic acid such as a recombinant DNA molecule that is part of a hybrid or fusion nucleic acid. A nucleic acid existing among hundreds to millions of other nucleic acids within, for example, a cDNA library or a genomic library, or a gel slice containing a genomic DNA restriction digest, is not to be considered an isolated nucleic acid.

Nucleic acids encoding B7-H4 fusion polypeptides may be optimized for expression in the expression host of choice. Codons may be substituted with alternative codons encoding the same amino acid to account for differences in codon usage between the mammal from which the B7-H4 nucleic acid sequence is derived and the expression host. In this manner, the nucleic acids may be synthesized using expression host-preferred codons.

Nucleic acids can be in sense or antisense orientation, or can be complementary to a reference sequence encoding a B7-H4 polypeptide. Nucleic acids can be DNA, RNA, or nucleic acid analogs. Nucleic acid analogs can be modified at the base moiety, sugar moiety, or phosphate backbone. Such modification can improve, for example, stability, hybridization, or solubility of the nucleic acid. Modifications at the base moiety can include deoxyuridine for deoxythymidine, and 5-methyl-2'-deoxycytidine or 5-bromo-2'-deoxycytidine for deoxycytidine. Modifications of the sugar moiety can include modification of the 2' hydroxyl of the ribose sugar to form 2'-O-methyl or 2'-O-allyl sugars. The deoxyribose phosphate backbone can be modified to produce morpholino nucleic acids, in which each base moiety is linked to a six membered, morpholino ring, or peptide nucleic acids, in which the deoxyphosphate backbone is replaced by a pseudopeptide backbone and the four bases are retained. See, for example, Summerton and Weller (1997) *Antisense Nucleic Acid Drug Dev.* 7:187-195; and Hyrup et al. (1996) *Bioorgan. Med. Chem.* 4:5-23. In addition, the deoxyphosphate backbone can be replaced with, for example, a phosphorothioate or phosphorodithioate backbone, a phosphoroamidite, or an alkyl phosphotriester backbone.

Nucleic acids encoding polypeptides can be administered to subjects in need thereof. Nucleic delivery involves introduction of "foreign" nucleic acids into a cell and ultimately, into a live animal. Compositions and methods for delivering nucleic acids to a subject are known in the art (see Understanding Gene Therapy, Lemoine, N. R., ed., BIOS Scientific Publishers, Oxford, 2008).

IV. Vectors and Host Cells

Vectors encoding B7-H4 polypeptides, fragments and fusions thereof are also provided. Nucleic acids, such as those described above, can be inserted into vectors for expression in cells. As used herein, a "vector" is a replicon, such as a plasmid, phage, virus or cosmid, into which another DNA segment may be inserted so as to bring about the replication of the inserted segment. Vectors can be expression vectors. An "expression vector" is a vector that includes one or more expression control sequences, and an "expression control sequence" is a DNA sequence that controls and regulates the transcription and/or translation of another DNA sequence.

Nucleic acids in vectors can be operably linked to one or more expression control sequences. As used herein, "operably linked" means incorporated into a genetic construct so that expression control sequences effectively control expression of a coding sequence of interest. Examples of expression control sequences include promoters, enhancers, and transcription terminating regions. A promoter is an expression control sequence composed of a region of a DNA molecule, typically within 100 nucleotides upstream of the point at which transcription starts (generally near the initiation site for RNA polymerase II). To bring a coding sequence under the control of a promoter, it is necessary to position the translation initiation site of the translational reading frame of the polypeptide between one and about fifty nucleotides downstream of the promoter. Enhancers provide expression specificity in terms of time, location, and level. Unlike promoters, enhancers can function when located at various distances from the transcription site. An enhancer also can be located downstream from the transcription initiation site. A coding sequence is "operably linked" and "under the control" of expression control sequences in a cell when RNA polymerase is able to transcribe the coding sequence into mRNA, which then can be translated into the protein encoded by the coding sequence.

Suitable expression vectors include, without limitation, plasmids and viral vectors derived from, for example, bacteriophage, baculoviruses, tobacco mosaic virus, herpes viruses, cytomegalo virus, retroviruses, vaccinia viruses, adenoviruses, and adeno-associated viruses. Numerous vectors and expression systems are commercially available from such corporations as Novagen (Madison, Wis.), Clontech (Palo Alto, Calif.), Stratagene (La Jolla, Calif.), and Invitrogen Life Technologies (Carlsbad, Calif.).

An expression vector can include a tag sequence. Tag sequences, are typically expressed as a fusion with the encoded polypeptide. Such tags can be inserted anywhere within the polypeptide including at either the carboxyl or amino terminus. Examples of useful tags include, but are not limited to, green fluorescent protein (GFP), glutathione S-transferase (GST), polyhistidine, c-myc, hemagglutinin, Flag™ tag (Kodak, New Haven, Conn.), maltose E binding protein and protein A. In one embodiment, a nucleic acid molecule encoding a B7-H4 fusion polypeptide is present in a vector containing nucleic acids that encode one or more domains of an Ig heavy chain constant region, preferably having an amino acid sequence corresponding to the hinge, $C_H2$ and $C_H3$ regions of a human immunoglobulin $C\gamma1$ chain.

Vectors containing nucleic acids to be expressed can be transferred into host cells. The term "host cell" is intended to include prokaryotic and eukaryotic cells into which a recombinant expression vector can be introduced. As used herein, "transformed" and "transfected" encompass the introduction of a nucleic acid molecule (e.g., a vector) into a cell by one of a number of techniques. Although not limited to a particular technique, a number of these techniques are well established within the art. Prokaryotic cells can be transformed with nucleic acids by, for example, electroporation or calcium chloride mediated transformation. Nucleic acids can be transfected into mammalian cells by techniques including, for example, calcium phosphate co-precipitation, DEAE-dextran-mediated transfection, lipofection, electroporation, or microinjection. Host cells (e.g., a prokaryotic cell or a eukaryotic cell such as a CHO cell) can be used to, for example, produce the B7-H4 fusion polypeptides described herein.

The vectors described can be used to express B7-H4 in cells, for example, cells for transplantation such as islet cells. An exemplary vector includes, but is not limited to, an adenoviral vector. One approach includes nucleic acid transfer into primary cells in culture followed by autologous transplantation of the ex vivo transformed cells into the host, either systemically or into a particular organ or tissue. Ex vivo methods can include, for example, the steps of harvesting cells from a subject, culturing the cells, transducing them with an expression vector, and maintaining the cells under conditions suitable for expression of the encoded polypeptides. These methods are known in the art of molecular biology. The transduction step can be accomplished by any standard means used for ex vivo gene therapy, including, for example, calcium phosphate, lipofection, electroporation, viral infection, and biolistic gene transfer. Alternatively, liposomes or polymeric microparticles can be used. Cells that have been successfully transduced then can be selected, for example, for expression of the coding sequence or of a drug resistance gene. The cells then can be lethally irradiated (if desired) and injected or implanted into the subject. In one embodiment, expression vectors containing nucleic acids encoding fusion proteins are transfected into cells that are administered to a subject in need thereof.

In vivo nucleic acid therapy can be accomplished by direct transfer of a functionally active DNA into mammalian somatic tissue or organ in vivo. For example, nucleic acids encoding polypeptides disclosed herein can be administered directly to lymphoid tissues or tumors. Alternatively, lymphoid tissue specific targeting can be achieved using lymphoid tissue-specific transcriptional regulatory elements (TREs) such as a B lymphocyte-, T lymphocyte-, or dendritic cell-specific TRE. Lymphoid tissue specific TREs are known in the art.

Nucleic acids may also be administered in vivo by viral means. Nucleic acid molecules encoding fusion proteins may be packaged into retrovirus vectors using packaging cell lines that produce replication-defective retroviruses, as is well-known in the art. Other virus vectors may also be used, including recombinant adenoviruses and vaccinia virus, which can be rendered non-replicating. In addition to naked DNA or RNA, or viral vectors, engineered bacteria may be used as vectors.

Nucleic acids may also be delivered by other carriers, including liposomes, polymeric micro- and nanoparticles and polycations such as asialoglycoprotein/polylysine.

In addition to virus- and carrier-mediated gene transfer in vivo, physical means well-known in the art can be used for direct transfer of DNA, including administration of plasmid DNA and particle-bombardment mediated gene transfer.

V. Pharmaceutical Compositions

Pharmaceutical compositions including B7-H4 polypeptides, fragments, fusion polypeptides, nucleic acids, and vectors disclosed herein are provided. Pharmaceutical compositions containing peptides or polypeptides may be for administration by parenteral (intramuscular, intraperitoneal, intravenous (IV) or subcutaneous injection), transdermal (either passively or using iontophoresis or electroporation), or transmucosal (nasal, vaginal, rectal, or sublingual) routes of administration or using bioerodible inserts and can be formulated in dosage forms appropriate for each route of administration.

In some in vivo approaches, the compositions disclosed herein are administered to a subject in a therapeutically effective amount. As used herein the term "effective amount" or "therapeutically effective amount" means a dosage sufficient to treat, inhibit, or alleviate one or more symptoms of the disorder being treated or to otherwise provide a desired pharmacologic and/or physiologic effect. The precise dosage will vary according to a variety of factors such as subject-dependent variables (e.g., age, immune system health, etc.), the disease, and the treatment being effected.

For the polypeptide compositions disclosed herein and nucleic acids encoding the same, as further studies are conducted, information will emerge regarding appropriate dosage levels for treatment of various conditions in various patients, and the ordinary skilled worker, considering the therapeutic context, age, and general health of the recipient, will be able to ascertain proper dosing. The selected dosage depends upon the desired therapeutic effect, on the route of administration, and on the duration of the treatment desired. For polypeptide compositions, generally dosage levels of 0.001 to 20 mg/kg of body weight daily are administered to mammals. Generally, for intravenous injection or infusion, dosage may be lower.

In certain embodiments, the polypeptide compositions are administered locally, for example by injection directly into a site to be treated. Typically, the injection causes an increased localized concentration of the polypeptide compositions which is greater than that which can be achieved by systemic administration. For example, in the case of a neurological disorder like Multiple Sclerosis, the protein may be administered locally to a site near the CNS. The polypeptide compositions can be combined with a matrix as described above to assist in creating a increased localized concentration of the polypeptide compositions by reducing the passive diffusion of the polypeptides out of the site to be treated.

A. Formulations for Parenteral Administration

In a preferred embodiment, compositions disclosed herein, including those containing peptides and polypeptides, are administered in an aqueous solution, by parenteral injection. The formulation may also be in the form of a suspension or emulsion. In general, pharmaceutical compositions are provided including effective amounts of a peptide or polypeptide, and optionally include pharmaceutically acceptable diluents, preservatives, solubilizers, emulsifiers, adjuvants and/or carriers. Such compositions optionally include one or more for the following: diluents, sterile water, buffered saline of various buffer content (e.g., Tris-HCl, acetate, phosphate), pH and ionic strength; and additives such as detergents and solubilizing agents (e.g., TWEEN 20 (polysorbate-20), TWEEN 80 (polysorbate-80)), anti-oxidants (e.g., ascorbic acid, sodium metabisulfite), and preservatives (e.g., Thimersol, benzyl alcohol) and bulking substances (e.g., lactose, mannitol). Examples of non-aqueous solvents or vehicles are propylene glycol, polyethylene glycol, vegetable oils, such as olive oil and corn oil, gelatin, and injectable organic esters such as ethyl oleate. The formulations may be lyophilized and redissolved/resuspended immediately before use. The formulation may be sterilized by, for example, filtration through a bacteria retaining filter, by incorporating sterilizing agents into the compositions, by irradiating the compositions, or by heating the compositions.

B. Formulations for Topical Administration

Fusion proteins disclosed herein can be applied topically. Topical administration does not work well for most peptide formulations, although it can be effective especially if applied to the lungs, nasal, oral (sublingual, buccal), vaginal, or rectal mucosa.

Compositions can be delivered to the lungs while inhaling and traverse across the lung epithelial lining to the blood stream when delivered either as an aerosol or spray dried particles having an aerodynamic diameter of less than about 5 microns.

A wide range of mechanical devices designed for pulmonary delivery of therapeutic products can be used, including but not limited to nebulizers, metered dose inhalers, and powder inhalers, all of which are familiar to those skilled in the art. Some specific examples of commercially available devices are the Ultravent nebulizer (Mallinckrodt Inc., St. Louis, Mo.); the Acorn II nebulizer (Marquest Medical Products, Englewood, Colo.); the Ventolin metered dose inhaler (Glaxo Inc., Research Triangle Park, N.C.); and the Spinhaler powder inhaler (Fisons Corp., Bedford, Mass.). Nektar, Alkermes and Mannkind all have inhalable insulin powder preparations approved or in clinical trials where the technology could be applied to the formulations described herein.

Formulations for administration to the mucosa will typically be spray dried drug particles, which may be incorporated into a tablet, gel, capsule, suspension or emulsion. Standard pharmaceutical excipients are available from any formulator. Oral formulations may be in the form of chewing gum, gel strips, tablets or lozenges.

Transdermal formulations may also be prepared. These will typically be ointments, lotions, sprays, or patches, all of which can be prepared using standard technology. Transdermal formulations will require the inclusion of penetration enhancers.

C. Controlled Delivery Polymeric Matrices

Fusion proteins disclosed herein may also be administered in controlled release formulations. Controlled release polymeric devices can be made for long term release systemically following implantation of a polymeric device (rod, cylinder, film, disk) or injection (microparticles). The matrix can be in the form of microparticles such as microspheres, where peptides are dispersed within a solid polymeric matrix or microcapsules, where the core is of a different material than the polymeric shell, and the peptide is dispersed or suspended in the core, which may be liquid or solid in nature. Unless specifically defined herein, microparticles, microspheres, and microcapsules are used interchangeably. Alternatively, the polymer may be cast as a thin slab or film, ranging from nanometers to four centimeters, a powder produced by grinding or other standard techniques, or even a gel such as a hydrogel.

Either non-biodegradable or biodegradable matrices can be used for delivery of fusion polypeptides or nucleic acids encoding the fusion polypeptides, although biodegradable matrices are preferred. These may be natural or synthetic polymers, although synthetic polymers are preferred due to the better characterization of degradation and release profiles. The polymer is selected based on the period over which release is desired. In some cases linear release may be most useful, although in others a pulse release or "bulk release" may provide more effective results. The polymer may be in the form of a hydrogel (typically in absorbing up to about 90% by weight of water), and can optionally be crosslinked with multivalent ions or polymers.

The matrices can be formed by solvent evaporation, spray drying, solvent extraction and other methods known to those skilled in the art. Bioerodible microspheres can be prepared using any of the methods developed for making microspheres for drug delivery, for example, as described by Mathiowitz and Langer, *J. Controlled Release*, 5:13-22 (1987); Mathiowitz, et al., *Reactive Polymers*, 6:275-283 (1987); and Mathiowitz, et al., *J. Appl. Polymer Sci.*, 35:755-774 (1988).

The devices can be formulated for local release to treat the area of implantation or injection—which will typically deliver a dosage that is much less than the dosage for treatment of an entire body—or systemic delivery. These can be implanted or injected subcutaneously, into the muscle, fat, or swallowed.

VI. Methods of Manufacture

A. Methods for Producing Fusion Proteins

The disclosed fusion proteins can be manufactured using conventional techniques that are known in the art. Isolated fusion proteins can be obtained by, for example, chemical synthesis or by recombinant production in a host cell. To recombinantly produce a fusion protein, a nucleic acid containing a nucleotide sequence encoding the fusion protein can be used to transform, transduce, or transfect a bacterial or eukaryotic host cell (e.g., an insect, yeast, or mammalian cell). In general, nucleic acid constructs include a regulatory sequence operably linked to a nucleotide sequence encoding the fusion protein. Regulatory sequences (also referred to herein as expression control sequences) typically do not encode a gene product, but instead affect the expression of the nucleic acid sequences to which they are operably linked.

Useful prokaryotic and eukaryotic systems for expressing and producing polypeptides are well known in the art include, for example, *Escherichia coli* strains such as BL-21, and cultured mammalian cells such as CHO cells.

In eukaryotic host cells, a number of viral-based expression systems can be utilized to express fusion proteins. Viral based expression systems are well known in the art and include, but are not limited to, baculoviral, SV40, retroviral, or vaccinia based viral vectors.

Mammalian cell lines that stably express variant fusion proteins can be produced using expression vectors with appropriate control elements and a selectable marker. For example, the eukaryotic expression vectors pCR3.1 (Invitrogen Life Technologies) and p91023(B) (see Wong et al. (1985) *Science* 228:810-815) are suitable for expression of variant polypeptides in, for example, Chinese hamster ovary (CHO) cells, COS-1 cells, human embryonic kidney 293 cells, NIH3T3 cells, BHK21 cells, MDCK cells, and human vascular endothelial cells (HUVEC). Additional suitable expression systems include the GS Gene Expression System™ available through Lonza Group Ltd.

Following introduction of an expression vector by electroporation, lipofection, calcium phosphate, or calcium chloride co-precipitation, DEAE dextran, or other suitable transfection method, stable cell lines can be selected (e.g., by metabolic selection, or antibiotic resistance to G418, kanamycin, or hygromycin). The transfected cells can be cultured such that the polypeptide of interest is expressed, and the polypeptide can be recovered from, for example, the cell culture supernatant or from lysed cells. Alternatively, a fusion protein can be produced by (a) ligating amplified sequences into a mammalian expression vector such as pcDNA3 (Invitrogen Life Technologies), and (b) transcribing and translating in vitro using wheat germ extract or rabbit reticulocyte lysate.

Fusion proteins can be isolated using, for example, chromatographic methods such as affinity chromatography, ion exchange chromatography, hydrophobic interaction chromatography, DEAE ion exchange, gel filtration, and hydroxylapatite chromatography. In some embodiments, fusion proteins can be engineered to contain an additional domain containing amino acid sequence that allows the polypeptides to be captured onto an affinity matrix. For example, an Fc-fusion polypeptide in a cell culture supernatant or a cytoplasmic extract can be isolated using a protein A column. In addition, a tag such as c-myc, hemagglutinin, polyhistidine, or Flag™ (Kodak) can be used to aid polypeptide purification. Such tags can be inserted anywhere within the polypeptide, including at either the carboxyl or amino terminus. Other fusions that can be useful include enzymes that aid in the detection of the polypeptide, such as alkaline phosphatase. Immunoaffinity chromatography also can be used to purify polypeptides. Fusion proteins can additionally be engineered to contain a secretory signal (if there is not a secretory signal already present) that causes the fusion protein to be secreted by the cells in which it is produced. The secreted fusion proteins can then conveniently be isolated from the cell media.

B. Methods for Producing Isolated Nucleic Acid Molecules

Isolated nucleic acid molecules can be produced by standard techniques, including, without limitation, common molecular cloning and chemical nucleic acid synthesis techniques. For example, polymerase chain reaction (PCR) techniques can be used to obtain an isolated nucleic acid encoding a variant polypeptide. PCR is a technique in which target nucleic acids are enzymatically amplified. Typically, sequence information from the ends of the region of interest or beyond can be employed to design oligonucleotide primers that are identical in sequence to opposite strands of the template to be amplified. PCR can be used to amplify specific sequences from DNA as well as RNA, including sequences from total genomic DNA or total cellular RNA. Primers typically are 14 to 40 nucleotides in length, but can range from 10 nucleotides to hundreds of nucleotides in length. General PCR techniques are described, for example in *PCR Primer: A Laboratory Manual*, ed. by Dieffenbach and Dveksler, Cold Spring Harbor Laboratory Press, 1995. When using RNA as a source of template, reverse transcriptase can be used to synthesize a complementary DNA (cDNA) strand. Ligase chain reaction, strand displacement amplification, self-sustained sequence replication or nucleic acid sequence-based amplification also can be used to obtain isolated nucleic acids. See, for example, Lewis (1992) *Genetic Engineering News* 12:1; Guatelli et al. (1990) *Proc. Natl. Acad. Sci. USA* 87:1874-1878; and Weiss (1991) *Science* 254:1292-1293.

Isolated nucleic acids can be chemically synthesized, either as a single nucleic acid molecule or as a series of oligonucleotides (e.g., using phosphoramidite technology for automated DNA synthesis in the 3' to 5' direction). For example, one or more pairs of long oligonucleotides (e.g., >100 nucleotides) can be synthesized that contain the desired sequence, with each pair containing a short segment of complementarity (e.g., about 15 nucleotides) such that a duplex is formed when the oligonucleotide pair is annealed. DNA polymerase can be used to extend the oligonucleotides, resulting in a single, double-stranded nucleic acid molecule per oligonucleotide pair, which then can be ligated into a vector. Isolated nucleic acids can also obtained by mutagenesis. Fusion protein-encoding nucleic acids can be mutated using standard techniques, including oligonucleotide-directed mutagenesis and/or site-directed mutagenesis through PCR. See, *Short Protocols in Molecular Biology*. Chapter 8, Green Publishing Associates and John Wiley & Sons, edited by Ausubel et al, 1992. Examples of amino acid positions that can be modified include those described herein.

VII. Methods of Therapeutic Use

The B7-H4 polypeptides, or fragments, or fusions thereof disclosed herein are useful as therapeutic agents. Immune cells, preferably T cells, can be contacted in vivo or ex vivo with B7-H4 fusion polypeptides to decrease or inhibit immune responses including, but not limited to inflammation. The T cells contacted with B7-H4 fusion polypeptides can be any cell which express the T cell receptor, including α/β and γ/δ T cell receptors. T-cells include all cells which express CD3, including T-cell subsets which also express CD4 and CD8. T-cells include both naive and memory cells and effector cells such as CTL. T-cells also include regulatory cells such as Th1, Tc1, Th2, Tc2, Th3, Th17, Th22, Treg, and Tr1 cells. T-cells also include NKT-cells and similar unique classes of the T-cell lineage. For example the compositions can be used to modulate Th1, Th17, Th22, or other cells that secrete, or cause other cells to secrete, inflammatory molecules, including, but not limited to, IL-1β, TNF-α, TGF-beta, IFN-γ, IL-17, IL-6, IL-23, IL-22, IL-21, and MMPs. The compositions can also be used to increase or promote the activity of Tregs, increase the production of cytokines such as IL-10 from Tregs, increase the differentiation of Tregs, increase the number of Tregs, or increase the survival of Tregs.

In some embodiments, the disclosed B7-H4 polypeptides, or fragments, or fusions thereof are administered in combination with a second therapeutic. Combination therapies may be useful in immune modulation. In some embodiments, B7-H4 polypeptides, or fragments, or fusions can be used to attenuate or reverse the activity of a pro-inflammatory drug, and/or limit the adverse effects of such drugs.

Other immune cells that can be treated with the disclosed B7-H4 polypeptides, fragments, or fusion thereof include T cell precursors, antigen presenting cells such as dendritic cells and monocytes or their precursors, B cells or combinations thereof. The B7-H4 compositions can be used to modulate the production of antibodies by B cells by contacting the B cells with an effective amount of the B7-H4 composition to inhibit or reduce antibody production by the B cell relative to a control. The B7-H4 compositions can also modulate the production of cytokines by the B cells.

A. Methods of Treating Inflammatory Responses

A preferred embodiment provides methods for treating or alleviating one or more symptoms of inflammation. In a more preferred embodiment, the compositions and methods disclosed are useful for treating chronic and persistent inflammation. Inflammation in general can be treated using the disclosed B7-H4 polypeptides or fragment or fusions thereof.

An immune response including inflammation can be inhibited or reduced in a subject, preferably a human, by administering an effective amount of B7-H4 polypeptide or fragment, or fusion thereof to inhibit or reduce the biological activity of an immune cell or to reduce the amounts of proinflammatory molecules at a site of inflammation. Exemplary proinflammatory molecules include, but are not limited to, IL-1β, TNF-α, TGF-beta, IFN-γ, IL-17, IL-6, IL-23, IL-22, IL-21, and MMPs.

Th1 and Th17 are exemplary T cells that can be targeted for inhibition by B7-H4 polypeptides, fusion proteins or fragments thereof to inhibit or reduce inflammation. The B7-H4 fusion proteins are useful for treating inflammation by any or all of the following: inhibiting or reducing differentiation of Th1, Th17, Th22, and/or other cells that secrete, or cause other cells to secrete, inflammatory molecules, including, but not limited to, IL-1β, TNF-α, TGF-beta, IFN-γ, IL-17, IL-6, IL-23, IL-22, IL-21, and MMPs; inhibiting or reducing activity of Th1, Th17, Th22, and/or other cells that secrete, or cause other cells to secrete, inflammatory molecules, including, but not limited to, IL-1β, TNF-α, TGF-beta, IFN-γ, IL-17, IL-6, IL-23, IL-22, IL-21, and MMPs; inhibiting or reducing the Th1 and/or Th17 pathways; inhibiting or reducing cytokine production and/or secretion by Th1, Th17, Th22, and/or other cells that secrete, or cause other cells to secrete, inflammatory molecules, including, but not limited to, IL-1β, TNF-α, TGF-beta, IFN-γ, IL-17, IL-6, IL-23, IL-22, IL-21, and MMPs; inhibiting or reducing proliferation of Th1, Th17, Th22, and/or other cells that secrete, or cause other cells to secrete, inflammatory molecules, including, but not limited to, IL-1β, TNF-α, TGF-beta, IFN-γ, IL-17, IL-6, IL-23, IL-22, IL-21, and MMPs.

Additionally, B7-H4-Ig can cause Tregs to have an enhanced suppressive effect on an immune response. Tregs can suppress differentiation, proliferation, activity, and/or cytokine production and/or secretion by Th1, Th17, Th22, and/or other cells that secrete, or cause other cells to secrete, inflammatory molecules, including, but not limited to, IL-1β, TNF-α, TGF-beta, IFN-γ, IL-17, IL-6, IL-23, IL-22, IL-21, and MMPs. For example, B7-H4-Ig can cause Tregs to have an enhanced suppressive effect on Th1 and/or Th17 cells to reduce the level of IFN-γ and IL-17 produced, respectively. B7-H4-Ig can also act directly on Tregs to promote or enhance production of IL-10 to suppress the Th1 and Th17 pathway, or to increase the number of Tregs.

Figure 1B:
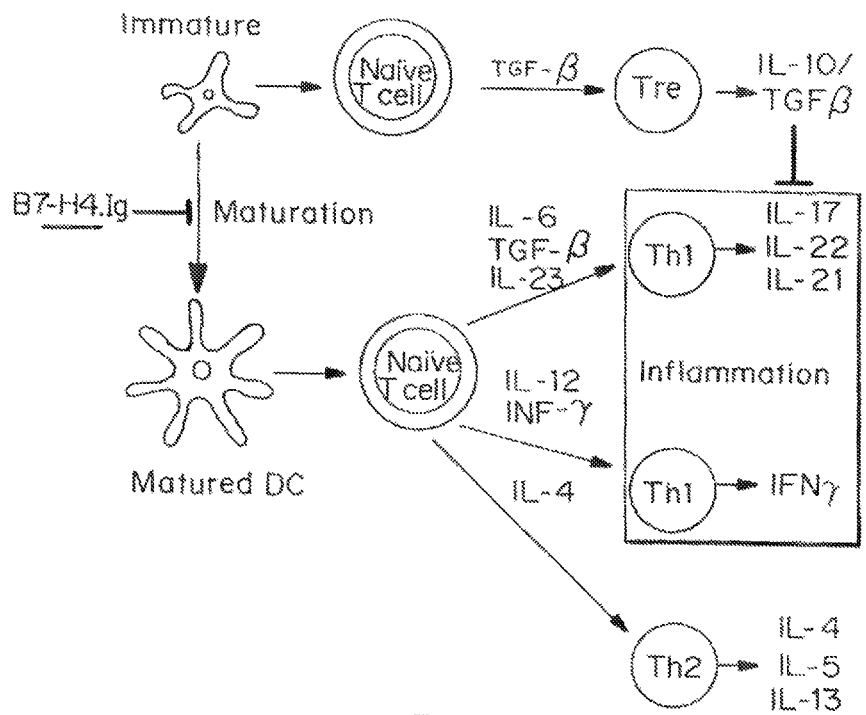

FIGS. 1A and 1B show two proposed modes of action of B7-H4 fusion proteins for inhibiting inflammation. FIG. 1A shows B7-H4-Ig acts at multiple points in multiple T cell pathways. For example, B7-H4-Ig can inhibit the differentiation of naïve T cells into either Th1 or Th17 cells. Alternatively, B7-H4-Ig can interact with Th1 cells or Th17 cells, or both to inhibit or reduce the production of proinflammatory molecules. Additionally, B7-H4-Ig can increase the differentiation of and/or cause Tregs to have an enhanced suppressive effect on the Th1 and Th17 pathways to reduce the level of INF-γ and/or IL-17 produced. B7-H4-Ig enhances the production of IL-10 from Tregs and this inhibits the activity of Th1 and Th17 cells.

FIG. 1B shows a second model in which B7-H4-Ig targets immature antigen presenting cells, such as dentritic cells (DCs), and inhibits cell maturation. Immature, antigen-capturing, dentritic cells have the capacity to mature into antigen-presenting, T cell-priming cells; converting antigens into immunogens and expressing molecules such as cytokines, chemokines, costimulatory molecules and proteases to initiate an immune response. The ability of DCs to regulate immunity is dependent on DC maturation. A variety of factors can induce maturation following antigen uptake and processing within DCs, including: whole bacteria or bacterial-derived antigens (e.g. lipopolysaccharide, LPS), inflammatory molecules, ligation of select cell surface receptors (e.g. CD40) and viral products (e.g. double-stranded RNA).

The maturation process involves a signal to the DC that leads to increased surface expression of MHC class I and II molecules and the production of costimulatory molecules.

In the model presented in FIG. 1B, B7-H4-Ig blocks DC maturation, which prevents the development of naïve T cells into either Th1 or Th17 cells, and reduces the production of proinflammatory molecules. Additionally, B7-H4-Ig can increase the pool of immature DC favoring the differentiation of and/or causing Tregs to have an enhanced suppressive effect on the Th1 and Th17 pathways to reduce the level of INF-γ and/or IL-17 produced. In this way, B7-H4-Ig enhances the production of IL-10 from Tregs and this inhibits the activity of Th1 and Th17 cells.

1. Inhibition of the Th1 Pathway a. Inhibition of Th1 Development

One method for inhibiting or reducing inflammation includes administering an effective amount of a B7-H4 polypeptide, fusion protein, variants thereof, or fragments thereof to inhibit Th1 development in a subject in need thereof. It has been discovered that inflammation can be inhibited or reduced by blocking naïve T cells from differentiating into Th1 cells by administering B7-H4 polypeptides, fusion proteins, fragments thereof or variants thereof. In one embodiment, the B7-H4 polypeptides or fusion protein thereof increases the suppressive ability of Tregs on naïve T cells to inhibit or reduce naïve T cells from differentiating into Th1 cells and thereby reduce the number of Th1 cells in a subject. Alternatively, the B7-H4 polypeptides or fusion protein thereof inhibits or reduces proliferation of TH1 cells. B7-H4 polypeptides, fragments or fusions proteins thereof may also reduce naïve T cells from differentiating into Th1 cells, by blocking antigen presenting cell maturation. By restricting the number of Th1 cells that can develop in the subject, the amount of proinflammatory molecules such as INF-γ can be reduced or contained. INF-γ stimulates the production or release of other proinflammatory molecules including IL-1β, TNF-α, and MMPs. Thus, by controlling the number of Th1 cells in a subject, the levels of these other proinflammatory molecules can be controlled, thereby reducing inflammatory responses.

b. Inhibition of Proinflammatory Molecules

Another embodiment provides a method of inhibiting or reducing inflammation in a subject by administering to the subject an effective amount of a B7-H4 polypeptide, fusion protein thereof, or fragment thereof to inhibit or reduce production of proinflammatory molecules by Th1 cells. Exemplary proinflammatory molecules produced by Th1 cells includes IFN-γ. In this embodiment the B7-H4 polypeptide, fusion protein thereof, or fragment thereof can interact directly with the Th1 cell and inhibit or reduce IFN-γ production by the Th1 cells. In this embodiment, the amount of proinflammatory molecules is regulated rather than the population of Th1 cells.

2. Inhibition of the Th17 Pathway a. Inhibition of Th17 Development

Inflammation can also be inhibited or reduced in a subject by administering an effective amount of a B7-H4 polypeptide, fragment or fusion thereof, to inhibit or block naïve T cells from developing into Th17 cells. In one embodiment, the B7-H4 polypeptide or fusion protein increases the suppressive activity of Tregs on the differentiation of naïve T cells into Th17 cells by an amount sufficient to reduce the number of Th17 cells in a subject. Alternatively, the B7-H4 polypeptide or fusion protein thereof inhibits or reduces proliferation of TH17 cells. B7-H4 polypeptides or fusions proteins thereof may also reduce naïve T cells from differentiating into Th17 cells, by blocking antigen presenting cell maturation. By reducing the population of Th17 cells in a subject, the amount of IL-17 can be reduced, as well as IL-22 and IL-21. IL-17 is a proinflammatory cytokine that causes increases in other proinflammatory molecules such as IL-1β, TNF-α, and MMPs. Thus, by reducing the amount of IL-17 these other proinflammatory molecules can be reduced, thereby reducing or inhibiting inflammation.

b. Inhibition of IL-17 Production

Still another embodiment provides a method for treating inflammation in a subject by administering an effective amount of B7-H4 polypeptide, fusion protein thereof, or fragments thereof, to inhibit production of IL-17 by Th17 cells, as well as IL-22 and IL-21. In this embodiment, the B7-H4 polypeptide or fusion protein can act directly on Th17 cells, for example by binding to Th17 cells resulting in inhibition of IL-17 (or IL-22 and IL-21) production by those Th17 cells. As noted above, inhibition or reduction of IL-17 (and IL-22 or IL-21) leads to the reduction of other proinflammatory molecules, thereby reducing or inhibiting inflammation.

3. Inhibiting Th1 and Th17 Pathways

The disclosed B7-H4 polypeptides, fusion proteins, and fragments thereof can be used to inhibit both the Th1 and Th17 pathways simultaneously. Using one anti-inflammatory agent to inhibit two separate pathways provides more robust inhibition or reduction of the immune response.

4. Tregs

Inflammation can also be treated by administering B7-H4 polypeptides, fusion proteins thereof, or fragments thereof to a subject in an amount effective to enhance the suppressive activity of IL-10 producing Tregs to enhance suppressive activity on the Th1 and/or Th17 pathways. In this embodiment the disclosed B7-H4 polypeptides and fusion proteins cause an increased suppressive effect on IFN-γ and/or IL-17 production relative to Tregs alone.

Another embodiment provides a method for treating inflammation by administering an effective amount of B7-H4 polypeptide, fusion proteins thereof, or fragments thereof to increase production of IL-10 by Tregs. Increased production of IL-10 results in the descreased production of IL-17 by Th17 cells and deceased production of IFN-α by Th1 cells. In this embodiment, the B7-H4 polypeptides, fusion proteins, and fragments thereof can interact directly with Tregs to increase IL-10 production by the Tregs.

Still another embodiment provides a method for treating inflammation by administering an effective amount of B7-H4 polypeptides, fusion proteins thereof, and fragments thereof to inhibit or interfere with the Th1 pathway, Th17 pathway and to enhance the suppressive effect on the Th1 and Th17 pathway by Tregs (see FIG. 1A). B7-H4 polypeptides or fusions proteins thereof may also increase the pool of Tregs by blocking antigen presenting cell maturation (see FIG. 1B).

The B7-H4 polypeptides, fusion proteins thereof and fragments thereof can also be administered to a subject in an amount effective to increase Treg cell populations or numbers.

IL-10 and TGF-β production by Tregs can be increased relative to a control by contacting the Tregs with an effective amount of B7-H4 polypeptides, B7-H4 fusion proteins, or fragments thereof having B7-H4 activity. The increase can occur in vitro or in vivo.

5. Soluble B7-H4

Soluble B7-H4 (sH4) acts as a decoy molecule that competes with the cell surface B7-H4 for binding to the B7-H4 receptor and does not result in an inhibitory signal to the T cell. B7-H4 inhibits cell cycle progression of T cells in the presence of antigen stimulation. B7-H4 can inhibit innate immunity by suppressing proliferation of neutrophil progenitors. It is believed that elevated levels of sH4 block the inhibitory effect of endogenous B7-H4.

Therefore, an inflammatory response can be treated by interfering with the biological activity of sH4 in vivo, for example, by administering to an individual in need thereof an effective amount of an agent that inhibits or decreases the ability of sH4 to bind to the B7-H4 receptor, or augments the activity of the endogenous inhibitory B7-H4 molecules. Interference of sH4 biological activity can be accomplished by administering B7-H4 fusion polypeptides disclosed herein.

Administration is not limited to the treatment of existing conditions, diseases or disorders (i.e. an existing inflammatory or autoimmune disease or disorder) but can also be used to prevent or lower the risk of developing such diseases in an individual, i.e., for prophylactic use. Potential candidates for prophylactic vaccination include individuals with a high risk of developing an inflammatory or autoimmune disease or disorder, i.e., with a personal or familial history of certain types of autoimmune disorders.

B. Inflammatory Disease to be Treated

Representative inflammatory or autoimmune diseases and disorders that may be treated using B7-H4 fusion polypeptides include, but are not limited to, rheumatoid arthritis, systemic lupus erythematosus, alopecia areata, ankylosing spondylitis, antiphospholipid syndrome, autoimmune Addison's disease, autoimmune hemolytic anemia, autoimmune hepatitis, autoimmune inner ear disease, autoimmune lymphoproliferative syndrome (alps), autoimmune thrombocytopenic purpura (ATP), Bechet's disease, bullous pemphigoid, cardiomyopathy, celiac sprue-dermatitis, chronic fatigue syndrome immune deficiency syndrome (CFIDS), chronic inflammatory demyelinating polyneuropathy, cicatrical pemphigoid, cold agglutinin disease, Crest syndrome, Crohn's disease, Degos disease, dermatomyositis, dermatomyositis-juvenile, discoid lupus, essential mixed cryoglobulinemia, fibromyalgia-fibromyositis, Grave's disease, Guillain-Barre syndrome, Hashimoto's thyroiditis, idiopathic pulmonary fibrosis, idiopathic thrombocytopenia purpura (ITP), IgA nephropathy, insulin dependent diabetes (Type I), juvenile arthritis, Meniere's disease, mixed connective tissue disease, multiple sclerosis, myasthenia gravis, pemphigus vulgaris, pernicious anemia, polyarteritis nodosa, polychondritis, polyglandular syndromes, polymyalgia rheumatica, polymyositis and dermatomyositis, primary agammaglobulinemia, primary biliary cirrhosis, psoriasis, Raynaud's phenomenon, Reiter's syndrome, rheumatic fever, sarcoidosis, scleroderma, Sjogren's syndrome, stiff-man syndrome, Takayasu arteritis, temporal arteritis/giant cell arteritis, ulcerative colitis, uveitis, vasculitis, vitiligo, and Wegener's granulomatosis.

B7-H4 acts at multiple points in the inflammatory pathway and at a higher level whereby it acts as a master regulator to control to influence the expression and/or activity of effectory cytokines such as TNF-α. Therefore, the B7-H4 compositions described herein are particularly useful for treating patients that do not respond to TNF-α blockers such as Enbrel, Remicade, Cimzia and Humira, or where TNF-α blockers are not safe or effective. In addition, because of its activity as a master regulator in the inflammatory pathway, the B7-H4 compositions disclosed are particularly useful for treating chronic and persistent inflammation. In a preferred embodiment, the B7-H4 compositions described herein are used to treat relapsing and/or remitting multiple sclerosis.

C. Inhibition of Epitope Spreading

Epitope spreading refers to the ability of B and T cell immune response to diversify both at the level of specificity, from a single determinant to many sites on an auto antigen, and at the level of V gene usage (Monneaux, F. et al., *Arthritis & Rheumatism,* 46(6): 1430-1438 (2002). Epitope spreading is not restricted to systemic autoimmune disease. It has been described in T cell dependent organ specific diseases such as IDDM and multiple sclerosis in humans and EAE induced experimental animals with a variety of myelin proteins.

Epitope spreading involves the acquired recognition of new epitopes in the same self molecule as well as epitopes residing in proteins that are associated in the same macromolecular complex. Epitope spreading can be assessed by measuring delayed-type hypersensitivity (DTH) responses, methods of which are known in the art.

One embodiment provides a method for inhibiting or reducing epitope spreading in a subject by administering to the subject an effective amount of B7-H4 polypeptide, fragment or fusion protein thereof. In a preferred embodiment the B7-H4 polypeptide, fragment or fusion protein thereof inhibits epitope spreading in individuals with multiple sclerosis. Preferably, the B7-H4 polypeptide or fusion thereof inhibits or blocks multiple points of the inflammation pathway.

Yet another embodiment provides a method for inhibiting or reducing epitope spreading in subjects with multiple sclerosis by administering to a subject an effective amount of B7-H4 polypeptide, fragment or fusion protein thereof to inhibit or reduce differentiation of, proliferation of, activity of, and/or cytokine production and/or secretion by Th1, Th17, Th22, and/or other cells that secrete, or cause other cells to secrete, inflammatory molecules, including, but not limited to, IL-1β, TNF-α, TGF-beta, IFN-γ, IL-17, IL-6, IL-23, IL-22, IL-21, and MMPs. Another embodiment provides a method for treating multiple sclerosis by administering to a subject an effective amount of B7-H4 polypeptide, fragment or fusion protein thereof to interact with Tregs, enhance Treg activity, promote or enhances IL-10 secretion by Tregs, increase the number of Tregs, increase the suppressive capacity of Tregs, or combinations thereof.

D. Combination Therapy

B7-H4 fusion polypeptides can be used alone or in combination with additional therapeutic agents. The additional therapeutic agents include, but are not limited to, immunosuppressive agents (e.g., antibodies against other lymphocyte surface markers (e.g., CD40, alpha-4 integrin) or against cytokines), other fusion proteins (e.g., CTLA-4-Ig (Orencia®), TNFR-Ig (Enbrel®)), TNF-α blockers such as Enbrel, Remicade, Cimzia and Humira, cyclophosphamide (CTX) (i.e. Endoxan®, Cytoxan®, Neosar®, Procytox®, Revimmune™), methotrexate (MTX) (i.e. Rheumatrex®, Trexall®), belimumab (i.e. Benlysta®), or other immunosuppressive drugs (e.g., cyclosporin A, FK506-like compounds, rapamycin compounds, or steroids), anti-proliferatives, cytotoxic agents, or other compounds that may assist in immunosuppression.

In a preferred embodiment, the additional therapeutic agent functions to inhibit or reduce T cell activation through a separate pathway. In one such embodiment, the additional therapeutic agent is a CTLA-4 fusion protein, such as CTLA-4-Ig (abatacept). CTLA-4-Ig fusion proteins compete with the costimulatory receptor, CD28, on T cells for binding to CD80/CD86 (B7-1/B7-2) on antigen presenting cells, and thus function to inhibit T cell activation. In another embodiment, the additional therapeutic agent is a CTLA-4-

Ig fusion protein known as belatacept. Belatacept contains two amino acid substitutions (L104E and A29Y) that markedly increase its avidity to CD86 in vivo. In another embodiment, the additional therapeutic agent is Maxy-4.

In another embodiment, the second therapeutic agent is cyclophosphamide (CTX). Cyclophosphamide (the generic name for Endoxan®, Cytoxan®, Neosar®, Procytox®, Revimmune™), also known as cytophosphane, is a nitrogen mustard alkylating agent from the oxazophorines group. It is used to treat various types of cancer and some autoimmune disorders. In a preferred embodiment, B7-H4-Ig and CTX are coadministered in effective amount to prevent or treat a chronic autoimmune disease or disorder such as Systemic lupus erythematosus (SLE). Cyclophosphamide (CTX) is the primary drug used for diffuse proliferative glomerulonephritis in patients with renal lupus. As described in detail in Example 18 below, it has been discovered that a combination treatment with a low dose of cyclophosphamide (50 mg/kg, once every 2 weeks), the current treatment modality in humans, plus B7-H4-Ig resulted in prevention of lupus disease progression in the MRL/lpr lupus model. In some embodiments the combination therapy is administered in an effective amount to reduce the blood or serum levels of anti-double stranded DNA (anti-ds DNA) auto antibodies and/or to reduce proteinuria in a patient in need thereof.

In another embodiment, the second therapeutic agent increases the amount of adenosine in the serum, see, for example, WO 08/147482. In a preferred embodiment, the second therapeutic is CD73-Ig, recombinant CD73, or another agent (e.g. a cytokine or monoclonal antibody or small molecule) that increases the expression of CD73, see for example WO 04/084933. In another embodiment the second therapeutic agent is Interferon-beta.

In another embodiment, the second therapeutic is Tysabri or another therapeutic for MS. In a preferred embodiment, B7-H4-Ig is cycled with Tysabri or used during a drug holiday in order to allow less frequent dosing with the second therapeutic and reduce the risk of side effects such as PML and to prevent resistance to the second therapeutic.

In another embodiment, the second therapeutic agent preferentially treats chronic inflammation, whereby the treatment regimen targets both acute and chronic inflammation. In a preferred embodiment the second therapeutic is a TNF-α blocker.

In another embodiment, the second therapeutic agent is a small molecule that inhibits or reduces differentiation, proliferation, activity, and/or cytokine production and/or secretion by Th1, Th17, Th22, and/or other cells that secrete, or cause other cells to secrete, inflammatory molecules, including, but not limited to, IL-1β, TNF-α, TGF-beta, IFN-γ, IL-17, IL-6, IL-23, IL-22, IL-21, and MMPs. In another embodiment, the second therapeutic agent is a small molecule that interacts with Tregs, enhances Treg activity, promotes or enhances IL-10 secretion by Tregs, increases the number of Tregs, increases the suppressive capacity of Tregs, or combinations thereof.

Typically useful small molecules are organic molecules, preferably small organic compounds having a molecular weight of more than 100 and less than about 2,500 daltons, more preferably between 100 and 2000, more preferably between about 100 and about 1250, more preferably between about 100 and about 1000, more preferably between about 100 and about 750, more preferably between about 200 and about 500 daltons. Small molecules comprise functional groups necessary for structural interaction with proteins, particularly hydrogen bonding, and typically include at least an amine, carbonyl, hydroxyl or carboxyl group, preferably at least two of the functional chemical groups. The small molecules often comprise cyclical carbon or heterocyclic structures and/or aromatic or polyaromatic structures substituted with one or more of the above functional groups. Small molecules also include biomolecules including peptides, saccharides, fatty acids, steroids, purines, pyrimidines, derivatives, structural analogs or combinations thereof. In one embodiment, the small molecule is retinoic acid or a derivative thereof. The examples below demonstrate that retinoic acid inhibits or reduces differentiation and/or activity of Th17 cells.

In a preferred embodiment, the compositions are used in combination or succession with compounds that increase Treg activity or production. Exemplary Treg enhancing agents include but are not limited to glucocorticoid fluticasone, salmeterol, antibodies to IL-12, IFN-γ, and IL-4; vitamin D3, and dexamethasone, and combinations thereof. Antibodies to other proinflammatory molecules can also be used in combination or alternation with the disclosed B7-H4 polypeptides, fusion proteins, or fragments thereof. Preferred antibodies bind to IL-6, IL-23, IL-22 or IL-21.

As used herein the term "rapamycin compound" includes the neutral tricyclic compound rapamycin, rapamycin derivatives, rapamycin analogs, and other macrolide compounds which are thought to have the same mechanism of action as rapamycin (e.g., inhibition of cytokine function). The language "rapamycin compounds" includes compounds with structural similarity to rapamycin, e.g., compounds with a similar macrocyclic structure, which have been modified to enhance their therapeutic effectiveness. Exemplary Rapamycin compounds are known in the art (See, e.g. WO95122972, WO 95116691, WO 95104738, U.S. Pat. Nos. 6,015,809; 5,989,591; U.S. Pat. Nos. 5,567,709; 5,559,112; 5,530,006; 5,484,790; 5,385,908; 5,202,332; 5,162,333; 5,780,462; 5,120,727).

The language "FK506-like compounds" includes FK506, and FK506 derivatives and analogs, e.g., compounds with structural similarity to FK506, e.g., compounds with a similar macrocyclic structure which have been modified to enhance their therapeutic effectiveness. Examples of FK506-like compounds include, for example, those described in WO 00101385. Preferably, the language "rapamycin compound" as used herein does not include FK506-like compounds.

Other suitable therapeutics include, but are not limited to, anti-inflammatory agents. The anti-inflammatory agent can be non-steroidal, steroidal, or a combination thereof. One embodiment provides oral compositions containing about 1% (w/w) to about 5% (w/w), typically about 2.5% (w/w) or an anti-inflammatory agent. Representative examples of non-steroidal anti-inflammatory agents include, without limitation, oxicams, such as piroxicam, isoxicam, tenoxicam, sudoxicam; salicylates, such as aspirin, disalcid, benorylate, trilisate, safapryn, solprin, diflunisal, and fendosal; acetic acid derivatives, such as diclofenac, fenclofenac, indomethacin, sulindac, tolmetin, isoxepac, furofenac, tiopinac, zidometacin, acematacin, fentiazac, zomepirac, clindanac, oxepinac, felbinac, and ketorolac; fenamates, such as mefenamic, meclofenamic, flufenamic, niflumic, and tolfenamic acids; propionic acid derivatives, such as ibuprofen, naproxen, benoxaprofen, flurbiprofen, ketoprofen, fenoprofen, fenbufen, indopropfen, pirprofen, carprofen, oxaprozin, pranoprofen, miroprofen, tioxaprofen, suprofen, alminoprofen, and tiaprofenic; pyrazoles, such as phenylbutazone, oxyphenbutazone, feprazone, azapropazone, and trimethazone. Mixtures of these non-steroidal anti-inflammatory agents may also be employed.

Representative examples of steroidal anti-inflammatory drugs include, without limitation, corticosteroids such as hydrocortisone, hydroxyl-triamcinolone, alpha-methyl dexamethasone, dexamethasone-phosphate, beclomethasone dipropionates, clobetasol valerate, desonide, desoxymethasone, desoxycorticosterone acetate, dexamethasone, dichlorisone, diflorasone diacetate, diflucortolone valerate, fluadrenolone, fluclorolone acetonide, fludrocortisone, flumethasone pivalate, fluosinolone acetonide, fluocinonide, flucortine butylesters, fluocortolone, fluprednidene (fluprednylidene) acetate, flurandrenolone, halcinonide, hydrocortisone acetate, hydrocortisone butyrate, methylprednisolone, triamcinolone acetonide, cortisone, cortodoxone, flucetonide, fludrocortisone, difluorosone diacetate, fluradrenolone, fludrocortisone, diflurosone diacetate, fluradrenolone acetonide, medrysone, amcinafel, amcinafide, betamethasone and the balance of its esters, chloroprednisone, chlorprednisone acetate, clocortelone, clescinolone, dichlorisone, diflurprednate, flucloronide, flunisolide, fluoromethalone, fluperolone, fluprednisolone, hydrocortisone valerate, hydrocortisone cyclopentylpropionate, hydrocortamate, meprednisone, paramethasone, prednisolone, prednisone, beclomethasone dipropionate, triamcinolone, and mixtures thereof.

In another embodiment, the additional therapeutic agents include compositions that inhibit or interfere with sH4 activity, to treat inflammatory disorders in subjects. In one embodiment, B7-H4 fusion polypeptides are administered to a subject for the treatment of an inflammatory disease wherein the subject has little or non-detectable amounts of sH4. In another embodiment, B7-H4 fusion polypeptides are administered to treat one or more symptoms of an inflammatory disease in subjects having elevated levels of sH4. Elevated levels of sH4 can be determined by comparing levels of sH4 is subjects known to have an inflammatory disorder with levels of sH4 in subjects that do not have an inflammatory disorder.

E. Pharmacodynamic Markers

The effectiveness of treatments using the B7-H4 polypeptides, fragments thereof, or fusion proteins thereof can be determined by assaying a sample obtained from a subject receiving treatment with B7-H4 polypeptides or fusion proteins thereof for changes in levels of biomarkers such as serum proteins, preferably pro-inflammatory cytokines, chemokines, acute phase markers, and/or antibodies, such as total IgG, or specific disease-related IgG, or other serum proteins for example sH4. For example, baseline levels of biomarkers in a serum sample obtained from a subject can be determined prior to treatment with B7-H4 polypeptides or fusion proteins. After or during treatment with B7-H4 polypeptides or fusion proteins thereof, biomarker levels in blood samples from the subject can be monitored. A change in biomarker level, for example a decline in cytokine levels, relative to baseline levels indicates that the treatment is effective in reducing one or more symptoms of an inflammatory disorder. Alternatively, the cytokine levels in blood samples from a subject undergoing treatment with B7-H4 polypeptides or fusion proteins thereof can be compared to predetermined levels of biomarkers determined from subjects without inflammatory disorders. In some embodiments the level of only one biomarker is monitored. In other embodiments, the levels of 2, 3, 4, 5 or more biomarkers are monitored.

The effectiveness of treatments using the B7-H4 polypeptides, fragments thereof, or fusion proteins can also be determined by assaying a sample obtained from a subject receiving treatment with B7-H4 polypeptides or fusion proteins thereof for changes in levels lymphocyte populations, such as increased numbers of Treg, or decreased numbers of activated Th1 or Th17 cells compared to a control.

In some embodiments, the effectiveness of treatments using the B7-H4 polypeptides, fragaments thereof, or fusion proteins are determined by monitoring disease specific markers or symptoms, using methods known in the art. For example imaging can be employed to assess effectiveness of treatment for Multiple Sclerosis, or delayed-type hypersensitive (DTH) can be monitored to assess effectiveness of treatment for lupus.

The effectiveness of treatments using the B7-H4 polypeptides, fragments thereof, or fusion proteins thereof can also be determined by assaying a sample obtained from a subject receiving treatment with B7-H4 polypeptides or fusion proteins thereof for changes in the expression levels of genes, including, but not limited to, those encoding serum proteins, preferably pro-inflammatory cytokines and/or chemokines, as well as secreted factors, cell surface receptors, and transcription factors that are characteristic of Th1, Th17, and Treg cells. Methods of measuring gene expression are well known in the art and include, but are not limited to, quantitative RT-PCR and microarray analysis.

Exemplary markers that can be monitored to determine the effectiveness of treatment with B7-H4 polypeptides, fragments and fusion proteins thereof, can be found throughout the examples below, particularly in Tables 8A-D, 9A-D, and 10A-B, FIGS. 57 and 58, and include, but are not limited to, one or more of IL-1β, TNF-α, TGF-beta, IFN-γ, IL-10, IL-17, IL-6, IL-23, IL-22, IL-21, and MMPs. Biomarkers particularly useful for monitoring arthritis are described in Example 3 and Tables 8A-D, 9A-D, and 10A-B below, and preferably include, but are not limited to, CRP, ET-1, IL-6, MCP-1, MCP-3, MIP-2 and TNF-α. Another marker useful for monitoring the effectiveness of treatment with B7-H4 polypeptides, fragments and fusions thereof, and combination therapies incorporating these proteins, is the level of CD73 in a tissue fluid of a patient, see for example WO 09/05352.

F. Patient Selection

The effectiveness of the B7-H4 polypeptides, fragments and fusion proteins thereof described herein can be predicted by pre-screening target patients for levels of biomarkers, or gene expression as described above, or polymorphisms within the genes encoding downstream effector genes.

In a non-limiting example, patients that have elevated levels of one or more inflammatory cytokines or chemokines relative to a subject that does not have an inflammatory disorder can be selected for treatment with a B7-H4 polypeptide, fragment or fusion protein. Alternatively, patients that have a polymorphism in or more inflammatory cytokine or chemokine genes can be selected for treatment with a B7-H4 polypeptide or fusion protein. For example, patients with particular polymorphisms within the IL-10 gene may be expected to respond more or less well to treatment with B7-H4 compositions, depending on the nature of the polymorphism. Exemplary molecules and their respective genes that can be screened to determine if B7-H4 composition treatment will be effective include, but are not limited to, one or more of IL-1β, TNF-α, TGF-beta, IFN-γ, IL-10, IL-17, IL-6, IL-23, IL-22, IL-21, and MMPs. Another marker useful for selecting patients for treatment with B7-H4 polypeptides, fragments and fusions thereof, and combination therapies incorporating these proteins, is the level of CD73 in a tissue fluid of a patient. Inflammatory molecule levels can be measured by known methods including, but not limited to, quantitative RT-PCR and ELISA. Methods of identifying gene polymorphisms are well known in the art and include, but are not limited to, DNA sequencing and DNA microarrays.

Patients can also be monitored for the efficacy of a treatment with a B7-H4 polypeptide or fusion protein for an inflammatory disorder by screening the patients for levels of one or more inflammatory molecules during the course of treatment and increasing the amount of B7-H4 administered to the subject if the levels of one or more cytokines is elevated in the subject compared to levels in a control subject that does not have an inflammatory disorder, or decreasing the amount of B7-H4 administered to the subject if the levels of one or more cytokines is reduced in the subject compared to levels in a control subject that does not have an inflammatory disorder.

EXAMPLES

Figure 2:
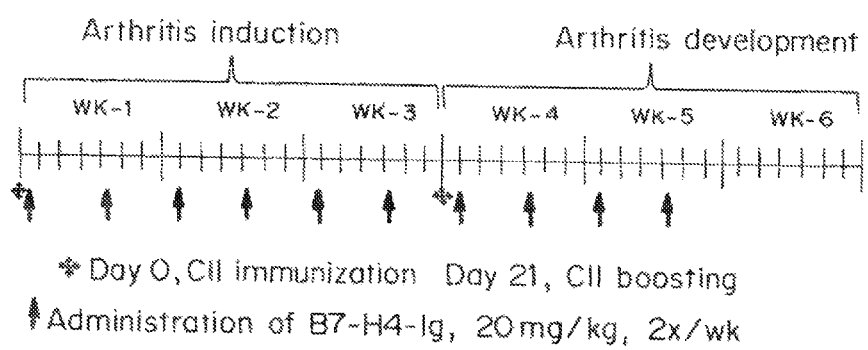
FIG. 2 is a diagram illustrating arthritis induction and treatment for the collagen induced arthritis (CIA) prophylactic model.

Example 1: B7-H4-Ig (Murine) in the Collagen-Induced Arthritis (CIA) Prophylactic Model Methods and Materials CIA is a well-characterized mouse model for human RA, in which injection of collagen II (CII) into DBA/1J mice induces swelling and progressive inflammation in joints resulting in arthritis. As shown in FIG. 2, DBA/1J mice (Jackson Labs) were administrated intraperitoneally (IP), 0.5 mg of B7-H4-Ig (20 mg/kg) on the same day as the CII immunization. B7-H4-Ig treatment continued 2 times each week, up to 6 weeks. On day 21, mice were rechallenged with CII emulsified in IFA. FIG. 2 outlines a brief experimental design. Day 40 was the last B7-H4-Ig treatment. Mouse paws/joints were monitored 2 times every week starting on day 26 using the arthritis scoring system displayed on Table 1.

TABLE 1

Scoring system for subjective evaluation of arthritis severity.

| Disease Score | Degree of Inflammation |
|---|---|
| 0 | No evidence of erythema and swelling |
| 1 | Erythema and mild swelling confined to the tarsals or ankle joint |
| 2 | Erythema and mild swelling extending from the ankle to the tarsals |
| 3 | Erythema and moderate swelling extending from the ankle to metatarsal joints |
| 4 | Erythema and severe swelling encompass the ankle, foot, and digits, or ankylosis. |

Results

Figure 3:
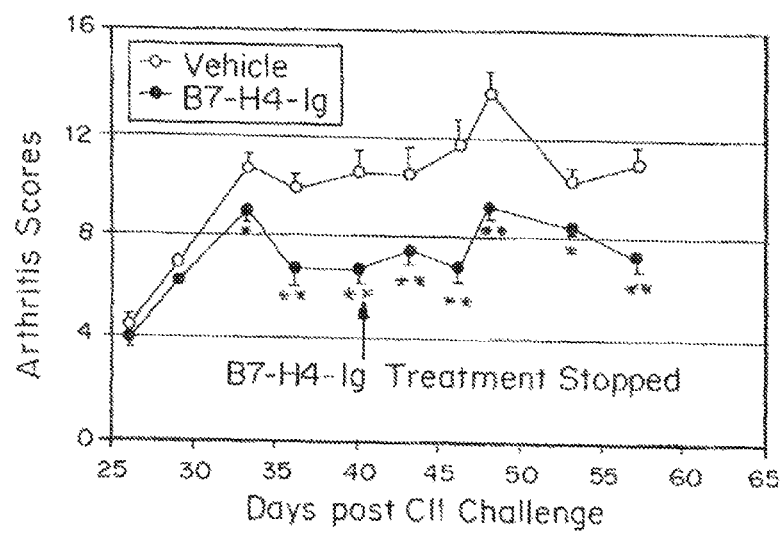
FIG. 3 is a line graph of arthritis scores versus post collagen II (CII) challenge in mice treated with B7-H4-Ig (filled circles) and mice treated with vehicle (open circles) in the prophylactic model.

The overall arthritis scores of the B7-H4-Ig treated CIA mice were significantly lower than the scores for vehicle-injected CIA mice on days 33 and beyond as shown in FIG. 3.

Example 2: Therapeutic CIA Model

Methods and Materials

Figure 4:
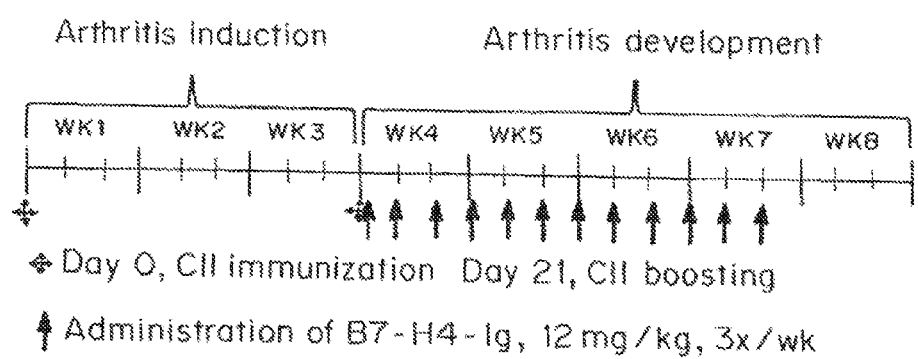
FIG. 4 is a diagram illustrating arthritis induction and treatment for the CIA therapeutic model.

FIG. 4 outlines a brief experimental design of the CIA therapeutic study. DBA/1J mice were first immunized with chicken CII emulsified in CFA. Twenty one days later, the mice were rechallenged with CII emulsified in IFA and randomized into 2 groups. Group 1 (n=10) were IP injected with 300 µg of B7-H4-Ig, 3 times a week for 4 weeks. Group 2 (n=10) were injected with vehicle. Mouse paws/joints were monitored and scored 3 times a week.

Results

Figure 5:
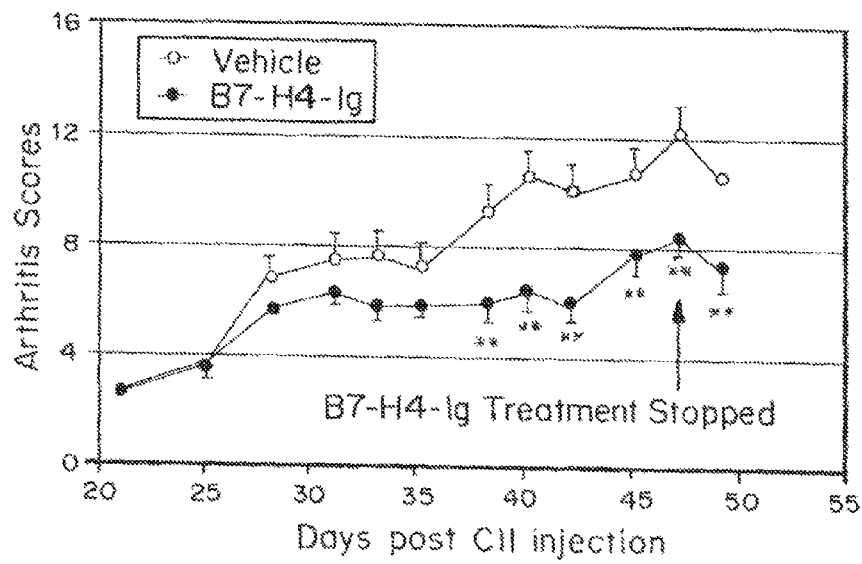
FIG. 5 is a line graph of arthritis scores versus post CII challenge in mice treated with B7-H4-Ig (filled circles) and mice treated with vehicle (open circles) in the therapeutic model.

As shown in FIG. 5, B7-H4-Ig could significantly suppress arthritis development. The overall arthritis scores of the B7-H4-Ig treated CIA mice were significantly lower than the ones of vehicle injected CIA mice on days 38 and beyond.

Example 3: Treatment of CIA Using Human B7-H4-Ig

Materials and Methods

Animals

DBA/1 mice (Taconic Farms, Inc. DBA1B0)
Ear tag (National Band 1005-1)
Electric clipper (Oster)

Induction of CIA

Hooke Kit™ Chicken Collagen/CFA Emulsion (Hooke Laboratories EK-0210)
Hooke Kit™ Chicken Collagen/IFA Emulsion (Hooke Laboratories EK-0211)

Treatment

B7-H4-Ig
RPA110010
Synagis® (palivizumab, MedImmune NDC#60574-4112-1); used as a human $IgG_1$ isotype control
Murine B7-H4-Ig
Murine $IgG_{2a}$ isotype control (BioXCell C1.18)
Syringe, 3 mL with Luer-Lok tip (BD 309585)
Needle, 27 gauge (BD 305109)
Amplimmune formulation buffer (10 mM sodium phosphate, pH 7.5, 8% w/w sucrose, 0.01% polysorbate-80)

Serum Collection

Lancet, (Medipoint Goldenrod 4 mm)
Microtainer® Serum Separator Tubes (BD 365956)

Induction of Arthritis

DBA/1 mice (10 per group) aged 7-9 weeks were used for the CIA model. Mice from several vendors (Jackson Laboratories, Harlan Laboratories, and Taconic Farms) were tested and it was determined that Taconic mice are most appropriate for the CIA studies. Taconic mice develop more consistent and severe disease symptoms and show continued disease progression, while mice from the other vendors often show stable, less severe disease, even in the absence of treatment. female (F) mice in AA#79 and male (M) mice in AA#80, were tested to determine which gender to use in future experiments.

On the day before the study is initiated, the hair on the right flank of each mouse was removed using an electric clipper. A metal identification tag was placed on the right ear of each mouse. On Day 0, mice were immunized with 100 µL of chicken collagen type II/Complete Freund's Adjuvant (CII/CFA) emulsion in the right flank. On Day 20, the hair on the left flank of each mouse was removed using an electric clipper, and on Day 21, mice were immunized with 100 µL of chicken collagen type II/Incomplete Freund's Adjuvant (CII/IFA) emulsion in the left flank. Pre-filled syringes of CII/CFA and CII/IFA emulsion purchased from Hooke Laboratories were used to ensure consistent dosing with and potency of the immunogen.

Disease Monitoring

Early arthritis symptoms, such as erythema and mild swelling, usually appear on Day 21, and on Day 28, more severe symptoms such as swelling in many digits and inflammation extending to the tarsal joint are typically present. Each limb is evaluated for severity of arthritis symptoms three times a week using a widely accepted arthritis severity score system, shown in Table 2. The scores from each of the 4 limbs are summed to yield the disease score of each mouse.

TABLE 2

Scoring system for evaluation of arthritis severity in each limb

| Disease Score | Degree of Inflammation |
|---|---|
| 0 | Normal paw with no evidence of erythema or swelling |
| 1 | Erythema of the paw |
| 2 | Erythema of the paw and mild swelling in one toe |
| 3 | Entire paw inflamed and swollen |
| 4 | Erythema and severe swelling encompass the ankle, foot, and digits, or ankylosis. If the paw is ankylosed, the mouse cannot grip the wire top of the cage |

Treatment

Figure 6:
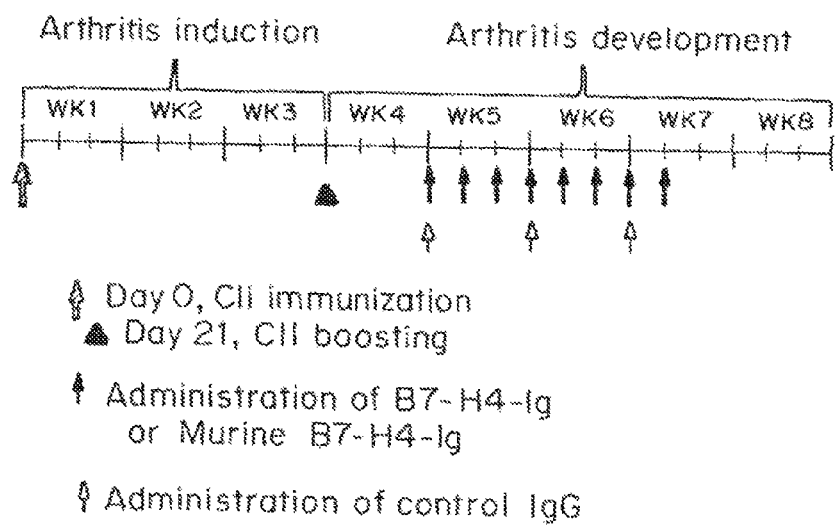
FIG. 6 is a diagram illustrating representative disease induction and dosing regimen for the therapeutic CIA model.

A representative timeline for induction of disease and treatment in a therapeutic murine CIA model is shown in FIG. 6. This treatment regimen is used for proof-of-concept studies. Regimens using fewer doses, less frequent administration, and/or lower dosages may also be effective. Treatment was initiated when the average disease score for the study animals was greater than four. This corresponded to Day 29 in AA#79 and Day 24 in AA#80. By waiting until animals are symptomatic, it was ensured that the model is performed in a therapeutic rather than prophylactic mode. Treatment groups are shown in Table 3.

TABLE 3

AA#79 and AA#80 treatment groups.

| Group | # Mice | Treatment | Dosing Regimen | Dosing Level |
|---|---|---|---|---|
| A | 10 | Vehicle | 3 × weekly, 8 doses | |
| B | 10 | Murine IgG2a control | 1 × weekly, 3 doses | 20 mg/kg |
| C | 10 | Murine B7-H4-Ig | 3 × weekly, 8 doses | 20 mg/kg |
| D | 10 | Synagis ® (human IgG1 control) | 1 × weekly, 3 doses | 20 mg/kg |
| E | 10 | B7-H4-Ig | 3 × weekly, 8 doses | 20 mg/kg |
| F | 10 | RPA110010 | 3 × weekly, 8 doses | 20 mg/kg |

B7-H4-Ig, RPA110010, and murine B7-H4-Ig proteins were administered by intraperitoneal (IP) injection 3 times a week for a total of 8 doses. RPA110010 is an extracellular domain variant of B7-H4-Ig, SEQ ID NO:126. Control murine and human IgG proteins were given once a week for a total of 3 doses. B7-H4-Ig is cleared from circulation more rapidly than control IgG, so different dosing schedules are used to compensate for this difference. All proteins were diluted to the desired concentration (500 µg in 500 µL, or 1 mg/mL) with sterile PBS immediately before injection. Vehicle control mice receive Amplimmune formulation buffer diluted 1:10 in PBS, with an injection volume of 500 pt.

Serum Biomarker Analysis

In AA#80, serum samples were collected on Day 27, Day 34, Day 41 and Day 55 via the submandibular vein. Approximately 200 µL of blood per mouse was collected in Microtainer® serum separator tubes. Serum was removed following centrifugation and stored at <−65° C. until analysis.

Selected serum samples were sent to Rules-Based Medicine (Austin, Tex.) for quantitative immunoassay multi-analyte profiling of serum samples, with the goal of identifying biomarkers that could be used to monitor disease progression and response to B7-H4-Ig treatment. Day 27, Day 34, and Day 41 sera from the three representative mice in the B7-H4-Ig group (tag #3332, 3334, and 3338) and three representative mice in the Synagis® group (tag #3324, 3329, and 3330) were analyzed for levels of 58 analytes using the RodentMAP v2.9 Testing Service.

Data from the Rules-Based Medicine analysis was analyzed using Microsoft Excel and GraphPad Prism software. T-tests were performed to compare the levels of each analyte in the B7-H4-Ig versus Synagis® treated samples. No correction was made for multiple comparisons. Additionally, correlation coefficients were calculated for each analyte versus disease score.

Results

Efficacy of B7-H4-Ig in the CIA Model

Figure 7:
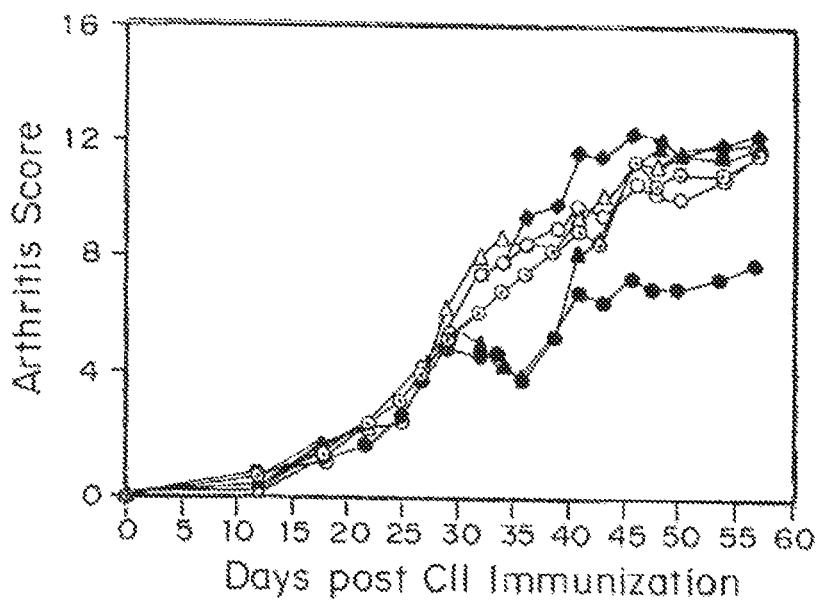
FIG. 7 is a line graph showing the Arthritis Score in female mice (AA#79) as a function of time post CII immunization (days). Vehicle, murine IgG, murine B7-H4-Ig, Synagis®, B7-H4-Ig, and RPA110010 treatments are shown.
Figure 8:
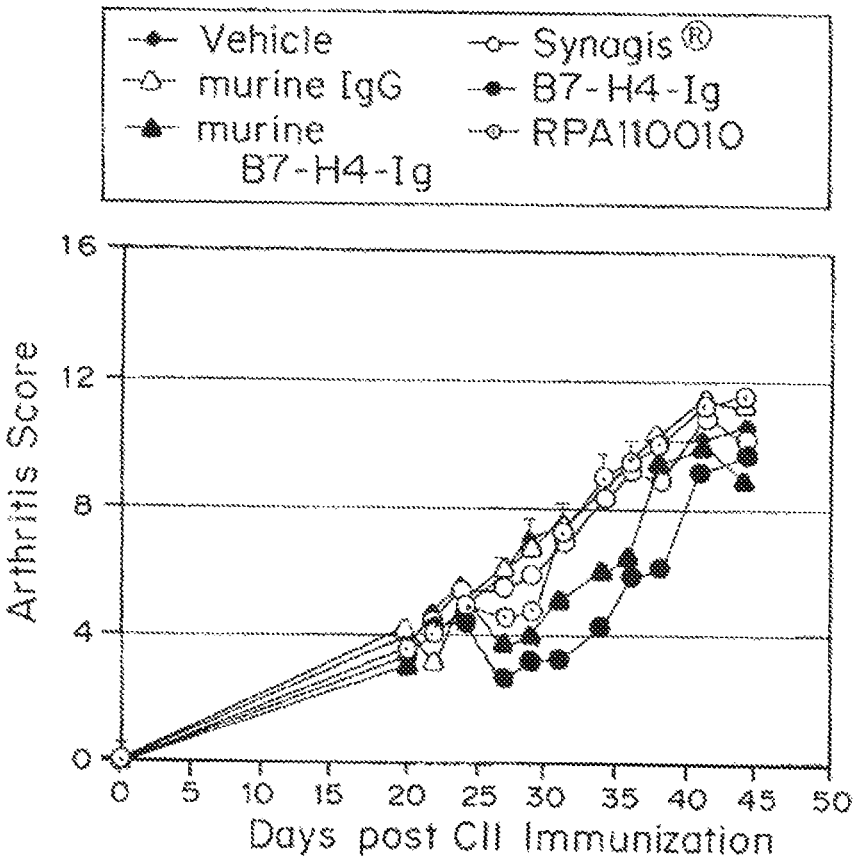
FIG. 8 is a line graph showing the Arthritis Score in male mice (AA#80) as a function of time post CII immunization (days). Vehicle, murine IgG, murine B7-H4-Ig, Synagis®, B7-H4-Ig, and RPA110010 treatments are shown.

As shown in FIGS. 7 and 8 and Tables 4A, 4B, 5A, 5B, 6, and 7, in both AA#79 and AA#80, mice treated with B7-H4-Ig and murine B7-H4-Ig had lower disease scores than mice in the control groups, consistent with the results of earlier studies. B7-H4-Ig shows superior efficacy in both studies, and in AA#79 disease stabilization in the B7-H4-Ig group is sustained after cessation of treatment. The RPA110010 variant was not effective in either study.

TABLE 4A

AA#79 CIA disease scores

| | Tag# | 12 | 18 | 22 | 25 | 27 | 29 | 32 | 34 | 36 | 39 | 41 | 43 | 46 | 48 | 50 | 54 | 57 |
|---|---|---|---|---|---|---|---|---|---|---|---|---|---|---|---|---|---|---|
| A: Vehicle | 3041 | 0 | 0 | 2 | 4 | 4 | 6 | 7 | 7 | 9 | 11 | 13 | 15 | 15 | 14 | 14 | 13 | 15 |
| | 3042 | 0 | 2 | 3 | 2 | 4 | 6 | 7 | 8 | 9 | 10 | 15 | 14 | 15 | 15 | 15 | 13 | 12 |
| | 3043 | 0 | 0 | 2 | 2 | 6 | 8 | 12 | 13 | 13 | 13 | 13 | 12 | 15 | 14 | 15 | 16 | 14 |
| | 3044 | 1 | 3 | 3 | 4 | 4 | 4 | 10 | 10 | 14 | 11 | 13 | 12 | 12 | 13 | 11 | 12 | 11 |
| | 3045 | 1 | 2 | 3 | 3 | 4 | 6 | 6 | 7 | 7 | 6 | 10 | 11 | 10 | 13 | 12 | 12 | 13 |
| | 3046 | 1 | 2 | 2 | 3 | 4 | 6 | 7 | 7 | 8 | 10 | 10 | 10 | 10 | 10 | 8 | 11 | 13 |
| | 3047 | 0 | 3 | 4 | 4 | 5 | 6 | 5 | 6 | 6 | 5 | 6 | 6 | 8 | 7 | 6 | 6 | 8 |
| | 3048 | 0 | 1 | 2 | 3 | 4 | 7 | 8 | 6 | 8 | 7 | 6 | 10 | 11 | 9 | 8 | 11 | 11 |
| | 3049 | 1 | 4 | 4 | 4 | 6 | 8 | 10 | 9 | 11 | 14 | 6 | 14 | 14 | 14 | 13 | 13 | 13 |
| | 3050 | 0 | 2 | 2 | 4 | 4 | 6 | 8 | 10 | 12 | 12 | 6 | 12 | 14 | 13 | 14 | 14 | 14 |

TABLE 4A-continued

AA#79 CIA disease scores

| | Tag# | \multicolumn{16}{c}{Study Day} |
| | | 12 | 18 | 22 | 25 | 27 | 29 | 32 | 34 | 36 | 39 | 41 | 43 | 46 | 48 | 50 | 54 | 57 |
|---|---|---|---|---|---|---|---|---|---|---|---|---|---|---|---|---|---|---|
| B: Murine IgG | 3051 | 0 | 2 | 2 | 4 | 4 | 6 | 7 | 7 | 7 | 8 | 6 | 9 | 10 | 9 | 10 | 11 | 11 |
| Control | 3052 | 0 | 2 | 3 | 4 | 4 | 7 | 6 | 6 | 6 | 5 | 6 | 6 | 8 | 8 | 6 | 6 | 9 |
| | 3053 | 0 | 2 | 2 | 3 | 7 | 9 | 10 | 12 | 11 | 11 | 6 | 12 | 14 | 15 | 14 | 14 | 13 |
| | 3054 | 0 | 1 | 2 | 4 | 4 | 6 | 12 | 12 | 11 | 12 | 6 | 13 | 12 | 12 | 13 | 15 | 13 |
| | 3055 | 1 | 0 | 3 | 4 | 6 | 7 | 8 | 7 | 7 | 8 | 6 | 7 | 9 | 9 | 8 | 10 | 11 |
| | 3056 | 0 | 2 | 3 | 4 | 3 | 7 | 8 | 8 | 8 | 7 | 6 | 12 | 12 | 11 | 13 | 13 | 12 |
| | 3057 | 1 | 1 | 2 | 4 | 4 | 6 | 7 | 9 | 8 | 8 | 6 | 9 | 9 | 10 | 9 | 9 | 10 |
| | 3058 | 0 | 0 | 2 | 3 | 5 | 7 | 10 | 10 | 10 | 11 | 6 | 14 | 15 | 15 | 15 | 14 | 13 |
| | 3059 | 0 | 2 | 3 | 3 | 4 | 5 | 7 | 6 | 7 | 6 | 6 | 8 | 10 | 12 | 15 | 12 | 13 |
| | 3060 | 0 | 2 | 3 | 4 | 6 | 7 | 9 | 12 | 12 | 10 | 6 | 13 | 14 | 12 | 16 | 16 | 15 |

TABLE 4B

AA#79 CIA disease scores

| | Tag# | \multicolumn{16}{c}{Study Day} |
| | | 12 | 18 | 22 | 25 | 27 | 29 | 32 | 34 | 36 | 39 | 41 | 43 | 46 | 48 | 50 | 54 | 57 |
|---|---|---|---|---|---|---|---|---|---|---|---|---|---|---|---|---|---|---|
| C: Murine | 3061 | 1 | 2 | 4 | 4 | 5 | 5 | 5 | 2 | 2 | 5 | 6 | 6 | 6 | 6 | 5 | 4 | 8 |
| B7-H4-Ig | 3062 | 0 | 2 | 2 | 3 | 4 | 5 | 5 | 3 | 6 | 7 | 6 | 9 | 12 | 13 | 12 | 11 | 13 |
| | 3063 | 2 | 3 | 3 | 4 | 6 | 7 | 3 | 2 | 3 | 7 | 6 | 11 | 14 | 13 | 14 | 14 | 12 |
| | 3064 | 0 | 2 | 2 | 3 | 4 | 7 | 8 | 8 | 7 | 8 | 6 | 13 | 15 | 14 | 12 | 14 | 13 |
| | 3065 | 1 | 2 | 2 | 3 | 4 | 5 | 3 | 2 | 2 | 2 | 6 | 9 | 9 | 10 | 9 | 9 | 10 |
| | 3066 | 0 | 2 | 4 | 3 | 4 | 7 | 9 | 10 | 9 | 9 | 6 | 11 | 15 | 14 | 14 | 14 | 14 |
| | 3067 | 0 | 1 | 2 | 4 | 4 | 6 | 6 | 3 | 2 | 1 | 6 | 4 | 6 | 10 | 11 | 10 | 10 |
| | 3068 | 1 | 0 | 2 | 4 | 3 | 6 | 5 | 3 | 1 | 4 | 6 | 8 | 12 | 12 | 14 | 15 | 15 |
| | 3069 | 0 | 3 | 2 | 3 | 5 | 6 | 3 | 4 | 2 | 6 | 6 | 10 | 12 | 13 | 12 | 10 | 10 |
| | 3070 | 1 | 2 | 3 | 4 | 4 | 5 | 8 | 8 | 8 | 8 | 6 | 9 | 12 | 14 | 15 | 15 | 13 |

TABLE 5A

AA#79 CIA disease scores

| | Tag# | \multicolumn{16}{c}{Study Day} |
| | | 12 | 18 | 22 | 25 | 27 | 29 | 32 | 34 | 36 | 39 | 41 | 43 | 46 | 48 | 50 | 54 | 57 |
|---|---|---|---|---|---|---|---|---|---|---|---|---|---|---|---|---|---|---|
| D: Syngis | 3071 | 1 | 0 | 3 | 2 | 4 | 5 | 6 | 6 | 7 | 9 | 10 | 8 | 9 | 9 | 7 | 8 | 8 |
| | 3072 | 0 | 0 | 3 | 2 | 3 | 5 | 7 | 7 | 9 | 9 | 9 | 9 | 8 | 9 | 11 | 11 | 13 |
| | 3073 | 2 | 1 | 2 | 2 | 4 | 6 | 6 | 7 | 8 | 12 | 11 | 11 | 15 | 14 | 14 | 14 | 15 |
| | 3074 | 0 | 1 | 2 | 3 | 5 | 5 | 5 | 5 | 5 | 6 | 7 | 6 | 9 | 5 | 4 | 6 | 6 |
| | 3075 | 0 | 2 | 4 | 2 | 5 | 6 | 10 | 10 | 11 | 11 | 12 | 12 | 14 | 13 | 11 | 13 | 13 |
| | 3076 | 1 | 2 | 2 | 5 | 7 | 6 | 9 | 9 | 9 | 8 | 10 | 11 | 11 | 11 | 11 | 12 | 14 |
| | 3077 | 2 | 1 | 2 | 2 | 4 | 5 | 9 | 10 | 10 | 11 | 13 | 11 | 12 | 13 | 12 | 12 | 13 |
| | 3078 | 1 | 1 | 2 | 2 | 4 | 4 | 7 | 6 | 8 | 6 | 6 | 6 | 6 | 5 | 9 | 8 | 7 |
| | 3079 | 1 | 2 | 2 | 3 | 5 | 6 | 8 | 9 | 9 | 9 | 10 | 10 | 10 | 12 | 12 | 13 | 12 |
| | 3080 | 0 | 2 | 3 | 2 | 6 | 10 | 10 | 11 | 11 | 12 | 11 | 12 | 14 | 13 | 12 | 12 | 15 |
| E: Human | 3081 | 1 | 2 | 2 | 2 | 3 | 6 | 5 | 4 | 4 | 5 | 5 | 3 | 4 | 5 | 6 | 3 | 5 |
| B7-H4-Ig | 3082 | 0 | 2 | 2 | 2 | 5 | 5 | 4 | 2 | 5 | 12 | 12 | 10 | 9 | 10 | 9 | 10 | 11 |
| | 3083 | 1 | 1 | 2 | 3 | 4 | 4 | 4 | 4 | 1 | 6 | 7 | 6 | 10 | 10 | 9 | 10 | 10 |
| | 3084 | 0 | 1 | 2 | 2 | 3 | 4 | 5 | 5 | 6 | 9 | 10 | 9 | 11 | 10 | 10 | 13 | 10 |
| | 3085 | 0 | 1 | 2 | 3 | 4 | 5 | 2 | 5 | 3 | 3 | 5 | 3 | 3 | 6 | 6 | 5 | 5 |
| | 3086 | 0 | 0 | 1 | 4 | 4 | 7 | 9 | 12 | 12 | 11 | 10 | 10 | 10 | 11 | 12 | 13 | 12 |
| | 3087 | 1 | 1 | 1 | 3 | 5 | 6 | 6 | 5 | 3 | 1 | 6 | 6 | 5 | 5 | 4 | 4 | 6 |
| | 3088 | 2 | 3 | 2 | 2 | 3 | 5 | 4 | 4 | 2 | 2 | 3 | 4 | 3 | 2 | 3 | 2 | 5 |
| | 3089 | 2 | 2 | 2 | 3 | 4 | 5 | 6 | 5 | 3 | 5 | 7 | 8 | 10 | 7 | 8 | 7 | 7 |
| | 3090 | 1 | 1 | 2 | 3 | 5 | 4 | 4 | 3 | 1 | 2 | 7 | 7 | 9 | 5 | 5 | 8 | 8 |

TABLE 5B

AA#79 CIA disease scores

| | Tag# | \_\_\_\_Study Day\_\_\_\_ |||||||||||||||||
|---|---|---|---|---|---|---|---|---|---|---|---|---|---|---|---|---|---|
| | | 12 | 18 | 22 | 25 | 27 | 29 | 32 | 34 | 36 | 39 | 41 | 43 | 46 | 48 | 50 | 54 | 57 |
| F: RPA110010 | 3091 | 0 | 2 | 2 | 4 | 4 | 6 | 6 | 5 | 6 | 7 | 6 | 7 | 10 | 8 | 10 | 7 | 9 |
| | 3092 | 1 | 1 | 3 | 4 | 5 | 5 | 6 | 6 | 5 | 6 | 9 | 11 | 12 | 10 | 12 | 10 | 12 |
| | 3093 | 0 | 2 | 2 | 3 | 4 | 5 | 6 | 6 | 5 | 9 | 8 | 7 | 12 | 8 | 9 | 11 | 10 |
| | 3094 | 1 | 1 | 3 | 3 | 5 | 8 | 10 | 11 | 10 | 11 | 11 | 10 | 14 | 12 | 12 | 13 | 12 |
| | 3095 | 1 | 1 | 2 | 4 | 4 | 7 | 9 | 11 | 12 | 13 | 13 | 14 | 14 | 14 | 14 | 13 | 16 |
| | 3096 | 0 | 2 | 4 | 3 | 4 | 5 | 4 | 6 | 7 | 7 | 7 | 4 | 11 | 13 | 13 | 12 | 12 |
| | 3097 | 0 | 2 | 2 | 2 | 4 | 5 | 4 | 3 | 6 | 4 | 4 | 3 | 9 | 5 | 3 | 5 | 6 |
| | 3098 | 2 | 3 | 3 | 3 | 5 | 4 | 5 | 5 | 7 | 6 | 8 | 5 | 8 | 10 | 11 | 12 | 13 |
| | 3099 | 1 | 1 | 3 | 3 | 5 | 5 | 5 | 6 | 7 | 6 | 8 | 9 | 9 | 10 | 11 | 11 | 12 |
| | 3100 | 1 | 1 | 2 | 4 | 4 | 5 | 9 | 12 | 12 | 15 | 16 | 16 | 16 | 16 | 16 | 16 | 14 |

TABLE 6

AA#80 CIA disease scores

| | Tag# | \_\_\_\_Study Day\_\_\_\_ ||||||||||
|---|---|---|---|---|---|---|---|---|---|---|---|
| | | 20 | 22 | 24 | 27 | 29 | 31 | 34 | 36 | 38 | 41 | 44 |
| A: Vehicle | 3291 | 4 | 3 | 5 | 5 | 7 | 10 | 12 | 14 | 14 | 14 | 13 |
| | 3292 | 2 | 2 | 4 | 3 | 5 | 4 | 9 | 10 | 9 | 10 | 11 |
| | 3293 | 7 | 5 | 7 | 6 | 8 | 6 | 8 | 10 | 10 | 10 | 10 |
| | 3294 | 3 | 3 | 4 | 5 | 5 | 6 | 6 | 6 | 6 | 5 | 6 |
| | 3295 | 5 | 4 | 5 | 6 | 7 | 8 | 11 | 11 | 11 | 14 | 12 |
| | 3296 | 4 | 5 | 7 | 6 | 7 | 9 | 9 | 10 | 12 | 12 | 13 |
| | 3297 | 6 | 5 | 7 | 9 | 12 | 11 | 12 | 11 | 13 | 12 | 11 |
| | 3298 | 3 | 4 | 5 | 6 | 7 | 8 | 7 | 7 | 9 | 8 | 9 |
| | 3299 | 3 | 3 | 3 | 6 | 6 | 7 | 8 | 7 | 10 | 9 | 12 |
| | 3300 | 1 | 3 | 2 | 5 | 6 | 6 | 7 | 7 | 7 | 9 | 9 |
| B: Murine IgG Control | 3301 | 5 | 5 | 6 | 5 | 8 | 11 | 13 | 15 | 15 | 16 | 16 |
| | 3302 | 5 | 2 | 5 | 5 | 5 | 5 | 6 | 8 | 10 | 10 | 11 |
| | 3303 | 6 | 4 | 5 | 6 | 9 | 10 | 9 | 10 | 10 | 10 | 10 |
| | 3304 | 7 | 4 | 6 | 7 | 7 | 7 | 10 | 10 | 10 | 9 | 10 |
| | 3305 | 3 | 3 | 6 | 6 | 6 | 7 | 9 | 11 | 12 | 12 | 12 |
| | 3306 | 1 | 4 | 5 | 6 | 5 | 7 | 6 | 7 | 8 | 9 | 9 |
| | 3307 | 4 | 2 | 5 | 7 | 11 | 12 | 13 | 15 | 16 | 16 | 15 |
| | 3308 | 2 | 1 | 6 | 6 | 6 | 5 | 6 | 7 | 9 | 13 | 13 |
| | 3309 | 4 | 3 | 3 | 7 | 4 | 6 | 5 | 7 | 6 | 9 | 8 |
| | 3310 | 5 | 4 | 5 | 5 | 6 | 6 | 8 | 7 | 7 | 10 | 8 |
| C: Murine B7-H4-Ig | 3311 | 3 | 4 | 5 | 3 | 3 | 9 | 12 | 11 | 12 | 12 | 11 |
| | 3312 | 3 | 6 | 4 | 3 | 3 | 1 | 3 | 3 | 8 | 9 | 9 |
| | 3313 | 3 | 5 | 6 | 4 | 5 | 5 | 6 | 6 | 9 | 8 | 4 |
| | 3314 | 8 | 8 | 10 | 7 | 7 | 8 | 10 | 11 | 13 | 11 | 12 |
| | 3315 | 2 | 3 | 3 | 2 | 1 | 3 | 2 | 6 | 8 | 6 | 8 |
| | 3316 | 3 | 5 | 8 | 3 | 4 | 7 | 6 | 8 | 8 | 9 | 7 |
| | 3317 | 4 | 6 | 6 | 7 | 7 | 7 | 11 | 12 | 12 | 13 | 12 |
| | 3318 | 1 | 3 | 5 | 3 | 4 | 4 | 1 | 1 | 7 | 12 | 11 |
| | 3319 | 0 | 2 | 2 | 2 | 2 | 1 | 1 | 0 | 9 | 10 | 7 |
| | 3320 | 3 | 5 | 6 | 4 | 4 | 7 | 8 | 7 | 9 | 9 | 8 |

TABLE 7

AA#80 CIA disease scores

| | Tag# | \_\_\_\_Study Day\_\_\_\_ ||||||||||
|---|---|---|---|---|---|---|---|---|---|---|---|
| | | 20 | 22 | 24 | 27 | 29 | 31 | 34 | 36 | 38 | 41 | 44 |
| D: Syngis | 3321 | 2 | 5 | 3 | 7 | 4 | 8 | 8 | 11 | 10 | 14 | 12 |
| | 3322 | 4 | 4 | 5 | 6 | 7 | 8 | 7 | 8 | 7 | 10 | 7 |
| | 3323 | 6 | 8 | 8 | 8 | 11 | 11 | 11 | 13 | 12 | 13 | 13 |
| | 3324 | 4 | 4 | 5 | 2 | 4 | 7 | 10 | 11 | 10 | 12 | 12 |
| | 3325 | 4 | 5 | 5 | 6 | 6 | 8 | 10 | 10 | 11 | 12 | 10 |
| | 3326 | 1 | 2 | 6 | 4 | 5 | 5 | 7 | 8 | 11 | 13 | 14 |
| | 3327 | 2 | 4 | 5 | 6 | 5 | 6 | 8 | 7 | 6 | 7 | 7 |
| | 3328 | 5 | 5 | 6 | 6 | 5 | 6 | 6 | 8 | 8 | 8 | 8 |
| | 3329 | 3 | 2 | 5 | 4 | 6 | 3 | 8 | 8 | 6 | 9 | 7 |
| | 3330 | 4 | 5 | 6 | 5 | 5 | 6 | 8 | 8 | 7 | 10 | 11 |

TABLE 7-continued

AA#80 CIA disease scores

| | Tag# | \_\_\_\_Study Day\_\_\_\_ ||||||||||
|---|---|---|---|---|---|---|---|---|---|---|---|
| | | 20 | 22 | 24 | 27 | 29 | 31 | 34 | 36 | 38 | 41 | 44 |
| E: Human B7-H4-Ig | 3331 | 4 | 4 | 4 | 3 | 2 | 2 | 2 | 3 | 3 | 4 | 3 |
| | 3332 | 2 | 4 | 5 | 2 | 2 | 3 | 5 | 7 | 7 | 9 | 11 |
| | 3333 | 2 | 4 | 2 | 2 | 3 | 2 | 1 | 4 | 9 | 9 | 11 |
| | 3334 | 3 | 4 | 5 | 3 | 2 | 2 | 4 | 5 | 5 | 6 | 8 |
| | 3335 | 3 | 3 | 4 | 2 | 1 | 1 | 2 | 6 | 3 | 9 | 9 |
| | 3336 | 4 | 5 | 5 | 3 | 5 | 4 | 5 | 7 | 6 | 10 | 12 |
| | 3337 | 5 | 5 | 4 | 4 | 5 | 4 | 6 | 7 | 10 | 13 | 14 |
| | 3338 | 5 | 5 | 5 | 2 | 2 | 5 | 4 | 4 | 3 | 9 | 4 |
| | 3339 | 2 | 5 | 5 | 2 | 2 | 2 | 5 | 4 | 3 | 9 | 11 |
| | 3340 | 3 | 2 | 6 | 3 | 7 | 7 | 8 | 11 | 12 | 13 | 13 |
| F: PRA110010 | 3341 | 6 | 5 | 5 | 6 | 5 | 7 | 9 | 12 | 10 | 12 | 12 |
| | 3342 | 6 | 6 | 7 | 7 | 6 | 11 | 13 | 12 | 12 | 12 | 12 |
| | 3343 | 3 | 4 | 5 | 4 | 5 | 10 | 13 | 12 | 13 | 13 | 13 |
| | 3344 | 4 | 4 | 5 | 5 | 7 | 12 | 16 | 16 | 16 | 16 | 16 |
| | 3345 | 4 | 3 | 5 | 3 | 2 | 4 | 6 | 4 | 4 | 7 | 9 |
| | 3346 | 1 | 3 | 5 | 3 | 2 | 2 | 3 | 5 | 9 | 11 | 12 |
| | 3347 | 4 | 5 | 5 | 5 | 4 | 7 | 5 | 7 | 11 | 13 | 12 |
| | 3348 | 3 | 3 | 5 | 5 | 5 | 6 | 5 | 7 | 6 | 9 | 7 |
| | 3349 | 3 | 4 | 4 | 2 | 2 | 4 | 11 | 11 | 11 | 11 | 14 |
| | 3350 | 1 | 3 | 5 | 5 | 9 | 9 | 8 | 9 | 7 | 8 | 8 |

By Day 21 following CII immunization, most animals had begun to develop inflammatory symptoms and the severity of disease continued to progress through Day 45. B7-H4-Ig treated mice show a prolonged period of stable disease scores, and in AA#79 this effect is maintained after treatment is stopped. Disease scores are transiently stabilized in the murine B7-H4-Ig treated animals during treatment (Day 29-Day 46 in AA#79 and Day 24-Day 41 in AA#80) but quickly rebound. Disease progression in the control treatment groups and RPA110010 all display a similar profile.

Serum Biomarker Analysis

Serum levels of several proteins were found to correlate with disease progression and/or differ between B7-H4-Ig and Synagis® treated mice, as shown in Tables 8A-D, 9A-D, and 10A-B, and described below. Tables 8A-D and 9A-D show the Rules Based Medicine complete data set. Tables 8A, 8B, 8C, and 8D show the first half of the complete data set following quantitative immunoassay multi-analyte profiling of serum samples from mice treated with B7-H4-Ig, or Synagis® to identify biomarkers that could be used to monitor disease progression and response to B7-H4-Ig treatment. Tables 9A, 9B, 9C, and 9D show the second half of the complete data set following quantitative immunoassay multi-analyte profiling analysis of serum samples from mice treated with B7-H4-Ig, or Synagis® to identify biomarkers that could be used to monitor disease progression and response to B7-H4-Ig treatment. Tables 10A and 10B show the quantitative immunoassay multi-analyte profiling Data Analysis Summary for the complete data set of Tables 8A-D and 9A-D. Analytes are marked with an asterisk (*) if there is a difference (p less than 0.05) between Synagis® and B7-H4-Ig treated groups at Day 27, Day 34, Day 41, or overall, or if the correlation coefficient between the analyte and the clinical score is less than 0.3. These markers may serve as objective measures of disease severity and/or biomarkers for response to B7-H4-Ig treatment.

TABLE 8A

| | | | Sample # | | | |
|---|---|---|---|---|---|---|
| | | | 1 | 2 | 3 | 7 |
| | | | \multicolumn{4}{c}{Group Human IgG1 Control Mouse #} |
| | | | #3324 | #3329 | #3330 | #3324 |
| | | | \multicolumn{4}{c}{Day} |
| Analytes | Units | LDD | 27 | 27 | 27 | 34 |
| clinical score | | | 2 | 4 | 5 | 10 |
| Apo A1 (Apoilpoprotem A1) | ug/ml | 10.4 | 37.6 | 53 | 44.4 | 48 |
| CD40 | pg/ml | 12 | 39.9 | 119 | 151 | 57.1 |
| CD40 Ligand | pg/ml | 92 | 1600 | 1120 | 1930 | 1730 |
| CRP (C Reactive Protein) | ug/ml | 0.83 | 10.8 | 10.9 | 9.26 | 13.1 |
| EGF (Epidermal Growth Factor) | pg/ml | 39.1 | 18.4 | 26.3 | 22.4 | 21.4 |
| Endothelin-1 | pg/ml | 66.95 | 20.2 | 22.2 | 42.6 | 22.2 |
| Eotaxin | pg/ml | 12.25 | 558 | 662 | 778 | 599 |
| Factor VII | ng/ml | 0.958 | 35.6 | 32.4 | 40.6 | 25 |
| FGF-9 (Fibroblast Growth Factor-9) | ng/ml | 0.9926 | <low> | <low> | <low> | <low> |
| FGF-basic (Fibroblast Growth Factor-basic) | ng/ml | 0.577 | 15.7 | 17.8 | 17.8 | 17.8 |
| Fibrinogen | ug/ml | 170 | <low> | <low> | <low> | <low> |
| GCP-2 (Granulocyte Chemotactic Potein-2) | ng/ml | 0.0245 | 15.3 | 17.2 | 19 | 14.1 |
| GM-CSF (Granulocyte Macrophage-Colony Stimulating Factor) | pg/ml | 8.746 | <low> | <low> | <low> | <low> |
| GST-alpha (Glutathione S-Transferase alpha) | ng/ml | 0.42 | <low> | <low> | 0.326 | <low> |
| Haptoglobin | ug/ml | 0.64 | 185 | 119 | 133 | 115 |
| IFN-gamma (Interferon-gamma) | pg/ml | 67.82 | 7.14 | 3.58 | 7.14 | 3.58 |
| IgA (Interferch-gamma) | ug/ml | 1.89 | 26.8 | 58.1 | 6.56 | 15.6 |
| IL-10 (Interleukin-10) | pg/ml | 109.26 | <low> | <low> | <low> | <low> |
| IL-11 (Interleukin-11) | pg/ml | 87.38 | <low> | 25.2 | 21.3 | <low> |
| IL-12p70-(interleukin-12p70) | ng/ml | 0.5712 | <low> | <low> | <low> | <low> |
| IL-17-(Interleukin-17) | ng/ml | 0.152 | <low> | 0.00572 | <low> | 0.80451 |
| IL-18 (Interleukin-18) | ng/ml | 0.674 | 30.9 | 13.3 | 13.3 | 11.9 |
| IL-1alpha (Interleukin-1alpha) | ng/ml | 44.92 | 385 | 310 | 676 | 398 |
| IL-1beta (Interleukin-1beta) | ng/ml | 0.447 | 3.58 | 4.35 | 5.87 | 4.36 |
| IL-2 (Interleukin-2) | pg/ml | 67 | <low> | <low> | <low> | <low> |
| IL-3 (Interleukin-3) | pg/ml | 21.274 | <low> | <low> | <low> | <low> |
| IL-4 (Interleukin-4) | pg/ml | 73.54 | <low> | 17.7 | <low> | 17.7 |

TABLE 8B

| | | | Sample # | | | | |
|---|---|---|---|---|---|---|---|
| | | | 8 | 9 | 13 | 14 | 15 |
| | | | \multicolumn{5}{c}{Group Human IgG1 Control Mouse #} |
| | | | #33329 | #3330 | #3324 | #3329 | #3330 |
| | | | \multicolumn{5}{c}{Day} |
| Analytes | Units | LDD | 34 | 34 | 41 | 41 | 41 |
| clinical score | | | 8 | 8 | 12 | 9 | 10 |
| Apo A1 (Apoilpoprotein A1) | ug/ml | 10.4 | 41.3 | 50.1 | 47.7 | 39 | 43.2 |
| CD40 | pg/ml | 12 | 99.2 | 135 | 39.9 | 96.7 | 95.4 |
| CD40 Ligand | pg/ml | 92 | 1120 | 1470 | 1850 | 2260 | 1270 |
| CRP (C Reactive Protein) | ug/ml | 0.83 | 16.6 | 12.7 | 17.2 | 13.9 | 21.3 |
| EGF (Epidermal Growth Factor) | pg/ml | 39.1 | 20.4 | 18.4 | 22.4 | 20.4 | 28.3 |
| Endothelin-1 | pg/ml | 66.95 | 25.9 | 32.5 | 25.9 | 21.2 | 28.5 |
| Eotaxin | pg/ml | 12.25 | 580 | 712 | 619 | 582 | 587 |
| factor VII | ng/ml | 0.958 | 34.3 | 37.5 | 27.7 | 29.7 | 36.9 |
| FGF-9 (Fibroblast Growth Factor-9) | ng/ml | 0.9926 | <low> | <low> | <low> | 0.196 | <low> |
| FGF-basic (Fibroblast Growth Factor-basic) | ng/ml | 0.577 | 16.8 | 17.8 | 18.8 | 17.8 | 17.8 |
| Fibrinogen | ug/ml | 170 | <low> | <low> | <low> | <low> | 207 |
| GCP-2 (Granulocyte Chemotactic Potein-2) | ng/ml | 0.0245 | 17.4 | 15.5 | 17.2 | 18.4 | 15.7 |

TABLE 8B-continued

|  |  |  | Sample # | | | | |
| --- | --- | --- | --- | --- | --- | --- | --- |
|  |  |  | 8 | 9 | 13 | 14 | 15 |
|  |  |  | | | Group | | |
|  |  |  | | | Human IgG1 Control | | |
|  |  |  | | | Mouse # | | |
|  |  |  | #33329 | #3330 | #3324 | #3329 | #3330 |
|  |  |  | | | Day | | |
| Analytes | Units | LDD | 34 | 34 | 41 | 41 | 41 |
| GM-CSF (Granulocyte Macrophage-Colony Stimulating Factor) | pg/ml | 8.746 | <low> | <low> | <low> | <low> | <low> |
| GST-alpha (Glutathione S-Transferase alpha) | ng/ml | 0.42 | <low> | <low> | <low> | 0.108 | <low> |
| Haptoglobin | ug/ml | 0.64 | 209 | 97.4 | 251 | 215 | 235 |
| IFN-gamma (Interferon-gamma) | pg/ml | 67.82 | 3.58 | 5.36 | 7.14 | 7.14 | 7.14 |
| IgA (Interferch-gamma) | ug/ml | 1.89 | 43.1 | 9.7 | 59.3 | 13.4 | 15.2 |
| IL-10 (Interleukin-10) | pg/ml | 109.26 | <low> | <low> | <low> | 65 | <low> |
| IL-11 (Interleukin-11) | pg/ml | 87.38 | <low> | <low> | 40.9 | 32.4 | 21.3 |
| IL-12p70-(interleukin-12p70) | ng/ml | 0.5712 | 0.0532 | 0.0532 | <low> | 0.0914 | 0.0532 |
| IL-17-(Interleukin-17) | ng/ml | 0.152 | <low> | <low> | 0.00572 | 0.00808 | <low> |
| IL-18 (Interleukin-18) | ng/ml | 0.674 | 11.3 | 11.1 | 14.1 | 13.1 | 12.3 |
| IL-1alpha (Interleukin-1alpha) | pg/ml | 44.92 | 297 | 470 | 447 | 529 | 2200 |
| IL-1beta (Interleukin-1beta) | ng/ml | 0.447 | 5.12 | 4.36 | 5.12 | 4.35 | 3.58 |
| IL-2 (Interleukin-2) | pg/ml | 67 | <low> | 8.57 | <low> | <low> | <low> |
| IL-3 (Interleukin-3) | pg/ml | 21.274 | <low> | <low> | <low> | <low> | <low> |
| IL-4 (Interleukin-4) | pg/ml | 73.54 | 17.7 | 17.7 | 35.7 | 35.7 | <low> |

TABLE 8C

|  |  |  | Sample # | | | |
| --- | --- | --- | --- | --- | --- | --- |
|  |  |  | 4 | 5 | 6 | 10 |
|  |  |  | | Group | | |
|  |  |  | | Human B7-H4-Ig | | |
|  |  |  | | Mouse # | | |
|  |  |  | #3332 | #3334 | #3338 | #3332 |
|  |  |  | | Day | | |
| Analytes | Units | LDD | 27 | 27 | 27 | 34 |
| clinical score |  |  | 2 | 3 | 2 | 5 |
| Apo A1 (Apoilpoprotein A1) | ug/ml | 10.4 | 57.3 | 53.7 | 42.7 | 37.8 |
| CD40 | pg/ml | 12 | 135 | 135 | 151 | 96.7 |
| CD40 Ligand | pg/ml | 92 | 1980 | 1550 | 1320 | 1370 |
| CRP (C Reactive Protein) | ug/ml | 0.83 | 13.4 | 8.16 | 7.98 | 17.2 |
| EGF (Epidermal Growth Factor) | pg/ml | 39.1 | 18.4 | 21.4 | 20.4 | 22.4 |
| Endothelin-1 | pg/ml | 66.95 | 20.2 | 20.2 | 17.1 | 22.2 |
| Eotaxin | pg/ml | 12.25 | 626 | 613 | 623 | 630 |
| Factor VII | ng/ml | 0.958 | 33 | 29.1 | 26.4 | 31.7 |
| FGF-9 (Fibroblast Growth Factor-9) | ng/ml | 0.9926 | <low> | <low> | <low> | <low> |
| FGF-basic (Fibroblast Growth Factor-basic) | ng/ml | 0.577 | 18.8 | 17.8 | 16.8 | 17.8 |
| Fibrinogen | ug/ml | 170 | <low> | <low> | <low> | 136 |
| GCP-2 (Granulocyte Chemotactic Potein-2) | ng/ml | 0.0245 | 18 | 18.5 | 16.6 | 17.1 |
| GM-CSF (Granulocyte Macrophage-Colony Stimulating Factor) | pg/ml | 8.746 | <low> | <low> | <low> | <low> |
| GST-alpha (Glutathione S-Transferase alpha) | ng/ml | 0.42 | <low> | <low> | <low> | <low> |
| Haptoglobin | ug/ml | 0.64 | 161 | 204 | 123 | 281 |
| IFN-gamma (Interferon-gamma) | pg/ml | 67.82 | <low> | <low> | 7.14 | 7.14 |
| IgA (Interferch-gamma) | ug/ml | 1.89 | 18.7 | 69.7 | 36.1 | 31 |
| IL-10 (Interleukin-10) | pg/ml | 109.26 | <low> | <low> | 94.2 | 94.2 |
| IL-11 (Interleukin-11) | pg/ml | 87.38 | <low> | <low> | 27 | 17.1 |
| IL-12p70-(interleukin-12p70) | ng/ml | 0.5712 | 0.0532 | <low> | 0.0532 | 0.0725 |
| IL-17-(Interleukin-17) | ng/ml | 0.152 | <low> | <low> | 0.00451 | 0.0152 |
| IL-18 (Interleukin-18) | ng/ml | 0.674 | 13.3 | 14.1 | 11.7 | 11.7 |
| IL-1alpha (Interleukin-1alpha) | pg/ml | 44.92 | 468 | 284 | 381 | 361 |
| IL-1beta (Interleukin-1beta) | ng/ml | 0.447 | 4.36 | 4.36 | 1.98 | 5.12 |
| IL-2 (Interleukin-2) | pg/ml | 67 | <low> | <low> | <low> | <low> |
| IL-3 (Interleukin-3) | pg/ml | 21.274 | <low> | <low> | <low> | <low> |
| IL-4 (Interleukin-4) | pg/ml | 73.54 | <low> | 27.9 | 17.7 | 17.7 |

TABLE 8D

| | | | Sample # | | | | |
|---|---|---|---|---|---|---|---|
| | | | 11 | 12 | 16 | 17 | 18 |
| | | | \multicolumn{5}{c}{Group Human B7-H4-Ig} |
| | | | \multicolumn{5}{c}{Mouse #} |
| | | | #3334 | #3338 | #3332 | #3334 | #3338 |
| | | | \multicolumn{5}{c}{Day} |
| Analytes | Units | LDD | 34 | 34 | 41 | 41 | 41 |
| clinical score | | | 4 | 4 | 9 | 6 | 9 |
| Apo A1 (Apoilpoprotein A1) | ug/ml | 10.4 | 48.5 | 54.1 | 46.8 | 49.5 | 46 |
| CD40 | pg/ml | 12 | 147 | 136 | 108 | 105 | 140 |
| CD40 Ligand | pg/ml | 92 | 2030 | 2180 | 1680 | 1630 | 1830 |
| CRP (C Reactive Protein) | ug/ml | 0.83 | 8.79 | 12.4 | 17.1 | 10.6 | 12.1 |
| EGF (Epidermal Growth Factor) | pg/ml | 39.1 | 14.3 | 20.4 | 28.4 | 16.3 | 18.4 |
| Endothelin-1 | pg/ml | 66.95 | 22.2 | 20.2 | 21.2 | 20.2 | 16 |
| Eotaxin | pg/ml | 12.25 | 602 | 700 | 629 | 493 | 694 |
| Factor VII | ng/ml | 0.958 | 33 | 29.1 | 36.9 | 30.4 | 27.7 |
| FGF-9 (Fibroblast Growth Factor-9) | ng/ml | 0.9926 | <low> | <low> | <low> | <low> | <low> |
| FGF-basic (Fibroblast Growth Factor-basic) | ng/ml | 0.577 | 17.8 | 17.8 | 19.9 | 17.8 | 18.8 |
| Fibrinogen | ug/ml | 170 | <low> | <low> | <low> | 118 | <low> |
| GCP-2 (Granulocyte Chemotactic Potein-2) | ng/ml | 0.0245 | 18.1 | 16.2 | 16.9 | 16.3 | 20.9 |
| GM-CSF (Granulocyte Macrophage-Colony Stimulating Factor) | pg/ml | 8.746 | <low> | <low> | <low> | <low> | <low> |
| GST-alpha (Glutathione S-Transferase alpha) | ng/ml | 0.42 | 4.16 | 2.96 | 1.01 | 0.477 | 1.64 |
| Haptoglobin | ug/ml | 0.64 | 162 | 140 | 267 | 270 | 193 |
| IFN-gamma (Interferon-gamma) | pg/ml | 67.82 | 7.14 | 3.58 | 3.58 | 3.58 | 7.14 |
| IgA (Interferch-gamma) | ug/ml | 1.89 | 12.1 | 45.4 | 12.3 | 59.9 | 14.1 |
| IL-10 (Interleukin-10) | pg/ml | 109.26 | <low> | <low> | <low> | <low> | <low> |
| IL-11 (Interleukin-11) | pg/ml | 87.38 | 17.1 | 17.1 | 17.1 | <low> | <low> |
| IL-12p70-(interleukin-12p70) | ng/ml | 0.5712 | <low> | <low> | <low> | <low> | 0.0914 |
| IL-17-(Interleukin-17) | ng/ml | 0.152 | 0.00808 | 0.00572 | 0.00572 | <low> | 0.00572 |
| IL-18 (Interleukin-18) | ng/ml | 0.674 | 10.9 | 13.1 | 13.3 | 11.7 | 11.5 |
| IL-1alpha (Interleukin-1alpha) | pg/ml | 44.92 | 447 | 587 | 488 | 284 | 1950 |
| IL-1beta (Interleukin-1beta) | ng/ml | 0.447 | 3.58 | 5.12 | 4.36 | 5.12 | 5.12 |
| IL-2 (Interleukin-2) | pg/ml | 67 | <low> | <low> | <low> | <low> | <low> |
| IL-3 (Interleukin-3) | pg/ml | 21.274 | <low> | <low> | <low> | <low> | <low> |
| IL-4 (Interleukin-4) | pg/ml | 73.54 | <low> | 17.7 | 35.7 | 17.7 | 17.7 |

TABLE 9A

| | | | Sample # | | |
|---|---|---|---|---|---|
| | | | 1 | 2 | 3 |
| | | | \multicolumn{3}{c}{Group Human LgG1 Control} |
| | | | \multicolumn{3}{c}{Mouse #} |
| | | | #3324 | #3329 | #3330 |
| | | | \multicolumn{3}{c}{Day} |
| Analytes | Units | LDD | 27 | 27 | 27 |
| IL-5 (Interleukin-5) | ng/ml | 0.194 | 0.438 | 0.403 | 0.264 |
| IL-6 (Interleukin-6) | pg/ml | 13.852 | 6.27 | 6.27 | <low> |
| IL-7 (Interleukin-7) | ng/ml | 0.309 | 0.0593 | <low> | <low> |
| IP-10 (Inducible Protein-10) | pg/ml | 40.28 | 45.3 | 52 | 55.5 |
| KC/GROalpha (Melanoma Growth Stimulatory Activity Protein) | ng/ml | 0.1739 | 0.0804 | 0.0795 | 0.0633 |
| LiF (leukemia infabitory Factor) | pg/ml | 43.6 | 1650 | 1390 | 1470 |
| Lymphotactin | pg/ml | 85.48 | 198 | 178 | 189 |
| MCP-1 (Monocyte Chemoattractant Protein-1) | pg/ml | 16.924 | 74.4 | 64.7 | 70.5 |
| MCP-3 (Monocyte Chemoattractant Protein-3) | pg/ml | 31.36 | 168 | 149 | 138 |
| MCP-5 (Monocyte Chemcattractant Protein-5) | pg/ml | 46.38 | 35.7 | 37.1 | 35.5 |
| M-CSF (Macrophage-Colony Stimulating Factor | ng/ml | 0.01795 | 6.19 | 6.6 | 6.59 |
| MDC (Macrophage-Derived Chemokine) | pg/ml | 21.85 | 1250 | 1310 | 1070 |
| MIP-1alpha (Macrophage Inflammatory Protein-1alpha) | ng/ml | 0.2255 | 3.03 | 3.32 | 3.03 |
| MIP-1beta (Macrophage Inflammatory Protein-1beta) | pg/ml | 77.65 | 173 | 173 | 150 |
| MIP-1gamma (Macrophage Inflammatory Protein-1gamma) | ng/ml | 0.0736 | 36.9 | 37.1 | 37.9 |
| MIP-2 (Macrophage Inflammatory Protein-2) | pg/ml | 7.174 | 16.1 | 22.2 | 23.4 |
| MIP-3beta (Macrophage Inflammatory Protein-3beta) | ng/ml | 0.465 | 2.89 | 3.05 | 2.6 |
| MMP-9 (Matrix Metalloproteinase-9) | ng/ml | 10 | 166 | 177 | 431 |
| MPO (Mycloperoxidase) | ng/ml | 0.95 | 216 | 191 | 265 |
| Myoglobin | ng/ml | 24 | 8.96 | 11.4 | 23.8 |
| OSM (Oncostatin M) | ng/ml | 0.13 | <low> | 0.0103 | <low> |

TABLE 9A-continued

| | | | Sample # | | |
|---|---|---|---|---|---|
| | | | 1 | 2 | 3 |
| | | | Group | | |
| | | | Human LgG1 Control | | |
| | | | Mouse # | | |
| | | | #3324 | #3329 | #3330 |
| | | | Day | | |
| Analytes | Units | LDD | 27 | 27 | 27 |
| RANTCS (Regulation Upon Activation Normal T-Cell Expressed and Secreted) | pg/ml | 0.5 | 0.0826 | <low> | <low> |
| SAP (Setrum Amtyloid P) | ug/ml | 5.4 | 40.5 | 34.2 | 42.9 |
| SCF (Stem Cell Factor) | pg/ml | 75.17 | 226 | 207 | 220 |
| SGOT (Serum Glutamic-Oxaloacetic Transaminase) | ug/ml | 1.86 | 84.6 | 79.7 | 75.4 |
| TEMP-1 (Tissue Inhibitor of Metalicproteinase Type-1) | ng/ml | 0.18 | 1.38 | 1.13 | 1.23 |
| Tissue Factor | ng/ml | 0.5175 | 9.17 | 10 | 9.17 |
| TNF-alpha (Tumor Necrosis Factor-alpha) | ng/ml | 0.137 | 0.0965 | <low> | <low> |
| TPO (Thromboprotetin) | ng/ml | 2.66 | 38.9 | 34.2 | 38.9 |
| VCAM-1 (Vescular Cell Adhesion Molecule-1) | ng/ml | 19 | 2260 | 2080 | 3160 |
| VEGF (Vescular Endotheial Cell Growth Factor) | pg/ml | 38.2 | 144 | 1.36 | 1.39 |
| VWF (Van Willebrand Factor) | ng/ml | 98.6 | 125 | 131 | 155 |

TABLE 9B

| | | | Sample # | | | | | |
|---|---|---|---|---|---|---|---|---|
| | | | 7 | 8 | 9 | 13 | 14 | 15 |
| | | | Group | | | | | |
| | | | Human LgG1 Control | | | | | |
| | | | Mouse # | | | | | |
| | | | #3324 | #3329 | #3330 | #3324 | #3329 | #3330 |
| | | | Day | | | | | |
| Analytes | Units | LDD | 34 | 34 | 34 | 41 | 41 | 41 |
| IL-5 (Interleukin-5) | ng/ml | 0.194 | 0.333 | 0.474 | 0.333 | 0.616 | 0.368 | 0.333 |
| IL-6 (Interleukin-6) | pg/ml | 13.852 | 13.2 | 98 | 34.1 | 74.2 | 67.5 | 93.7 |
| IL-7 (Interleukin-7) | ng/ml | 0.309 | 0.0593 | <low> | <low> | 0.0593 | 0.0593 | <low> |
| IP-10 (Inducible Protein-10) | pg/ml | 40.28 | 68.1 | 52 | 84.3 | 54.7 | 68.1 | 66.8 |
| KC/GROalpha (Melanoma Growth Stimulatory Activity Protein) | ng/ml | 0.1739 | 0.165 | 0.403 | 0.275 | 0.295 | 0.298 | 0.624 |
| LIF (Leukemia Infabitory Factor) | pg/ml | 43.6 | 1620 | 1620 | 1430 | 1650 | 1580 | 1470 |
| Lymphotactin | pg/ml | 85.48 | 219 | 151 | 205 | 178 | 183 | 194 |
| MCP-1 (Monocyte Chemoattractant Protein 1) | pg/ml | 16.924 | 99.8 | 78.3 | 117 | 90.2 | 129 | 105 |
| MCP-3 (Monocyte Chemoattractant Protein-3) | pg/ml | 31.36 | 188 | 180 | 193 | 235 | 236 | 242 |
| MCP-5 (Monocyte Chemoattractant Protein-5) | pg/ml | 46.38 | 37.5 | 46.2 | 41 | 45.6 | 47.4 | 52.8 |
| M-CSF (Macrophage-Colony Stimulating Factor) | ng/ml | 0.01795 | 6.46 | 6.3 | 6.09 | 6.38 | 5.22 | 6.37 |
| MDC (Macrophage-Derived Chemokine) | pg/ml | 21.85 | 1270 | 1320 | 1130 | 1410 | 1430 | 1150 |
| MIP-1alpha (Macrophage Inflammatory Protein-1alpha) | ng/ml | 0.2255 | 3.13 | 2.88 | 2.93 | 3.03 | 3.13 | 3.32 |
| MIP-1beta (Macrophage Inflammatory Protein-1beta) | pg/ml | 77.65 | 259 | 157 | 358 | 144 | 115 | 152 |
| MIP-1gamma (Macrophage Inflammatory Protein-1gamma) | ng/ml | 0.0736 | 42.2 | 41 | 40.9 | 45.4 | 44.8 | 44.8 |
| MIP-2 (Macrophage Inflammatory Protein-2) | pg/ml | 7.174 | 27.2 | 32.3 | 33.6 | 33.6 | 33.6 | 50.3 |
| MIP-3beta (Macrophage Inflammatory Protein-3beta) | ng/ml | 0.465 | 2.63 | 2.52 | 2.67 | 3.27 | 2.73 | 2.35 |
| MMP-9 (Matrix Metalloproteinase-9) | ng/ml | 10 | 207 | 259 | 283 | 272 | 250 | 1120 |
| MPO (Myeloperoxidase) | ng/ml | 0.95 | 253 | 253 | 254 | 259 | 263 | 240 |
| Myoglobin | ng/ml | 24 | 10 | 9.69 | 12.7 | 49.8 | 90.2 | 385 |
| OSM (Oncostatin M) | ng/ml | 0.13 | <low> | <low> | 0.00578 | <low> | 0.0103 | 0.0103 |
| RANTCS (Regulation Upon Activation Normal T-Cell Expressed and Secreted) | pg/ml | 0.5 | 0.0826 | <low> | <low> | <low> | 0.163 | <low> |
| SAP (Setrum Amtyloid P) | ug/ml | 5.4 | 38.4 | 48.6 | 38.3 | 49.2 | 46.2 | 48.8 |
| SCF (Stem Cell Factor) | pg/ml | 75.17 | 214 | 182 | 214 | 214 | 249 | 201 |
| SGOT (Serum Glutamic-Oxaloacetic Transaminase) | ug/ml | 1.86 | 75 | 140 | 81.9 | 84 | 93.9 | 78.4 |
| TEMP-1 (Tissue Inhibitor of Metalicproteinase Type-1) | ng/ml | 0.18 | 1.7 | 1.88 | 1.31 | 3.54 | 3.21 | 4.33 |
| Tissue Factor | ng/ml | 0.5175 | 10.8 | 10 | 12.5 | 10.8 | 9.17 | 11.7 |
| TNF-alpha (Tumor Necrosis Factor-alpha) | ng/ml | 0.137 | 0.0778 | <low> | 0.0326 | 0.122 | 0.027 | <low> |
| TPO (Thromboprotetin) | ng/ml | 2.66 | 36.1 | 34.2 | 39.8 | 38 | 39.8 | 32.4 |
| VCAM-1 (Vescular Cell Adhesion Molecule-1) | ng/ml | 19 | 2290 | 2120 | 2450 | 2130 | 1890 | 1900 |
| VEGF (Vescular Endotheial Cell Growth Factor) | pg/ml | 38.2 | 92.6 | 128 | 114 | 150 | 171 | 212 |
| VWF (Von Willebrand Factor) | ng/ml | 98.6 | 107 | 92.4 | 139 | 131 | 103 | 111 |

TABLE 9C

| | | | Sample # | | | | |
|---|---|---|---|---|---|---|---|
| | | | 4 | 5 | 6 | 10 | 11 |
| | | | \multicolumn{5}{c}{Group Human B7-H4 Ig} |
| | | | \multicolumn{5}{c}{Mouse #} |
| | | | #3332 | #3334 | #3338 | #3332 | #3334 |
| | | | \multicolumn{5}{c}{Day} |
| Analytes | Units | LDD | 27 | 27 | 27 | 34 | 34 |
| IL-5 (Interleukin-5) | ng/ml | 0.194 | 0.474 | 0.333 | 0.333 | 0.474 | 0.264 |
| IL-6 (Interleukin-6) | pg/ml | 13.852 | 9.38 | 5.23 | <low> | 105 | 5.57 |
| IL-7 (Interleukin-7) | ng/ml | 0.309 | <low> | <low> | 0.102 | 0.0823 | <low> |
| IP-10 (Inducible Protein-10) | pg/ml | 40.28 | 57.3 | 55.5 | 38.6 | 81 | 59 |
| KC/GROalpha (Melanoma Growth Stimulatory Activity Protein) | ng/ml | 0.1739 | 0.156 | 0.0626 | 0.049 | 0.376 | 0.0813 |
| LIF (Leukemia Infabitory Factor) | pg/ml | 43.6 | 1540 | 1500 | 1500 | 1430 | 1500 |
| Lymphotactin | pg/ml | 85.48 | 164 | 169 | 194 | 196 | 162 |
| MCP-1 (Monocyte Chemoattractant Protein-1) | pg/ml | 16.924 | 72.6 | 55.4 | 66.9 | 84.6 | 56 |
| MCP-3 (Monocyte Chemoattractant Protein-3) | pg/ml | 31.36 | 160 | 120 | 129 | 208 | 101 |
| MCP-5 (Monocyte Chemoattractant Protein-5) | pg/ml | 46.38 | 41.4 | 33.8 | 29.4 | 57.8 | 29.2 |
| M-CSF (Macrophage-Colony Stimulating Factor | ng/ml | 0.01795 | 6.88 | 6.51 | 6.21 | 5.79 | 6.35 |
| MDC (Macrophage-Derived Chemokine) | pg/ml | 21.85 | 1250 | 1110 | 1040 | 1390 | 1120 |
| MIP-1alpha (Macrophage Inflammatory Protein-1alpha) | ng/ml | 0.2255 | 2.83 | 3.13 | 3.03 | 3.03 | 2.88 |
| MIP-1beta (Macrophage Inflammatory Protein-1beta) | pg/ml | 77.65 | 110 | 115 | 173 | 181 | 127 |
| MIP-1gamma (Macrophage Inflammatory Protein-1gamma) | ng/ml | 0.0736 | 43.2 | 38.6 | 32.1 | 50.4 | 30.1 |
| MIP-2 (Macrophage Inflammatory Protein-2) | pg/ml | 7.174 | 20.9 | 16.3 | 21.6 | 36.8 | 26.6 |
| MIP-3beta (Macrophage Inflammatory Protein-3beta) | ng/ml | 0.465 | 2.6 | 2.79 | 2.52 | 2.79 | 2.49 |
| MMP-9 (Matrix Metalloproteinase-9) | ng/ml | 10 | 266 | 140 | 266 | 503 | 334 |
| MPO (Myeloperoxidase) | ng/ml | 0.95 | 245 | 227 | 191 | 247 | 254 |
| Myoglobin | ng/ml | 24 | 17.5 | 12.1 | 9.69 | 14.6 | 9.33 |
| OSM (Oncostatin M) | ng/ml | 0.13 | <low> | <low> | 0.00578 | 0.0103 | 0.0103 |
| RANTCS (Regulation Upon Activation Normal T-Cell Expressed and Secreted) | pg/ml | 0.5 | 0.0826 | <low> | 0.0826 | 0.105 | 0.105 |
| SAP (Setrurn Amtyioid P) | ug/ml | 5.4 | 41 | 39.5 | 30.7 | 51.8 | 31 |
| SCF (Stem Cell factor) | pg/ml | 75.17 | 204 | 194 | 275 | 182 | 220 |
| SGOT (Serum Glutamic-Oxaloacetic Transaminase) | ug/ml | 1.86 | 74.3 | 84.6 | 94.3 | 114 | 73.1 |
| TEMP-1 (Tissue Inhibitor of Metallcproteinase Type-1) | ng/ml | 0.18 | 1.38 | 1.31 | 1.14 | 4.85 | 1.22 |
| Tissue Factor | ng/ml | 0.5175 | 8.32 | 11.7 | 10 | 10.8 | 10.4 |
| TNF-alpha (Tumor Necrosis Factor-alpha) | ng/ml | 0.137 | <low> | <low> | <low> | <low> | <low> |
| TPO (Thrumsboprotetin) | ng/ml | 2.66 | 38 | 39.8 | 34.2 | 43.4 | 30.4 |
| VCAM-1 (Vescular Cell Adhesion Molecule-1) | ng/ml | 19 | 2250 | 2120 | 2130 | 1860 | 2190 |
| VEGF (Vescular Endotheial Cell Growth Factor) | pg/ml | 38.2 | 150 | 128 | 160 | 160 | 141 |
| VWF (Von Willebrand Factor) | ng/ml | 98.6 | 143 | 123 | 107 | 101 | 137 |

TABLE 9D

| | | | Sample # | | | |
|---|---|---|---|---|---|---|
| | | | 12 | 16 | 17 | 18 |
| | | | \multicolumn{4}{c}{Group Human B7-H4 Ig} |
| | | | \multicolumn{4}{c}{Mouse #} |
| | | | #3338 | #3332 | #3334 | #3338 |
| | | | \multicolumn{4}{c}{Day} |
| Analytes | Units | LDD | 34 | 41 | 41 | 41 |
| IL-5 (Interleukin-5) | ng/ml | 0.194 | 0.403 | 0.474 | 0.254 | 0.264 |
| IL-6 (Interleukin-6) | pg/ml | 13.852 | 14.5 | 49.5 | 56.2 | 14.5 |
| IL-7 (Interleukin-7) | ng/ml | 0.309 | <low> | <low> | <low> | <low> |
| IP-10 (Inducible Protein-10) | pg/ml | 40.28 | 54.2 | 69.3 | 47.6 | 59 |
| KC/GROalpha (Melanoma Growth Stimulatory Activity Protein) | ng/ml | 0.1739 | 0.148 | 0.264 | 0.221 | 0.0683 |
| LIF (Leukemia Infabrtory Factor) | pg/ml | 43.6 | 1480 | 1540 | 1540 | 1980 |
| Lymphotactin | pg/ml | 85.48 | 197 | 187 | 148 | 187 |
| MCP-1 (Monocyte Chemoattractant Protein-1) | pg/ml | 16.924 | 101 | 71.9 | 53.1 | 74.8 |
| MCP-3 (Monocyte Chemoattractant Protein-3) | pg/ml | 31.36 | 139 | 197 | 115 | 132 |
| MCP-5 (Monocyte Chemoattractant Protein-5) | pg/ml | 46.38 | 46.7 | 48.8 | 35.7 | 37.9 |
| M-CSF (Macrophage-Colony Stimulating factor | ng/ml | 0.01795 | 6.51 | 5.02 | 5.67 | 6.07 |
| MDC (Macrophage-Derived Chemokine) | pg/ml | 21.85 | 1360 | 1350 | 1110 | 1290 |
| MIP-1alpha (Macrophage Inflammatory Protein-1alpha) | ng/ml | 0.2255 | 3.08 | 3.13 | 2.93 | 3.03 |
| MIP-1beta (Macrophage Inflammatory Protein-1beta) | pg/ml | 77.65 | 277 | 148 | 70.7 | 115 |
| MIP-1gamma (Macrophage Inflammatory Protein-1gamma) | ng/ml | 0.0736 | 41 | 42.8 | 32.7 | 42.5 |
| MIP-2 (Macrophage Inflammatory Protein-2) | pg/ml | 7.174 | 22.2 | 25.9 | 23.4 | 19.7 |
| MIP-3beta (Macrophage Inflammatory Protein-3beta) | ng/ml | 0.465 | 3.11 | 3.05 | 3.03 | 2.87 |

TABLE 9D-continued

|  |  |  | Sample # | | | |
| --- | --- | --- | --- | --- | --- | --- |
|  |  |  | 12 | 16 | 17 | 18 |
|  |  |  | Group Human B7-H4 Ig Mouse # | | | |
|  |  |  | #3338 | #3332 | #3334 | #3338 |
|  |  |  | Day | | | |
| Analytes | Units | LDD | 34 | 41 | 41 | 41 |
| MMP-9 (Matrix Metalloproteinase-9) | ng/ml | 10 | 255 | 233 | 225 | 561 |
| MPO (Myeloperoxidase) | ng/ml | 0.95 | 242 | 208 | 228 | 285 |
| Myoglobin | ng/ml | 24 | 30.5 | 10 | 8.58 | 63.6 |
| OSM (Oncostatin M) | ng/ml | 0.13 | <low> | <low> | <low> | <low> |
| RANTCS (Regulation Upon Activation Normal T-Cell Expressed and Secreted) | pg/ml | 0.5 | <low> | 0.0826 | <low> | 0.105 |
| SAP (Setrum Amtyloid P) | ug/ml | 5.4 | 42.6 | 47.9 | 38.6 | 46 |
| SCF (Stem Cell Factor) | pg/ml | 75.17 | 217 | 175 | 198 | 210 |
| SGOT (Serum Glutamic-Oxaloacetic Transaminase) | ug/ml | 1.86 | 55.8 | 85.8 | 93.9 | 71.1 |
| TEMP-1 (Tissue Inhibitor of Metalicproteinase Type-1) | ng/ml | 0.18 | 1.49 | 4.78 | 1.74 | 2.16 |
| Tissue factor | ng/ml | 0.5175 | 13.3 | 10.8 | 9.17 | 9.37 |
| TNF-alpha (Tumor Necrosis Factor-alpha) | ng/ml | 0.137 | <low> | <low> | <low> | <low> |
| TPO (Thrombsoprotetin) | ng/ml | 2.66 | 36.1 | 33 | 32.4 | 36.1 |
| VCAM-1 (Vescular Cell Adhesion Molecule-1) | ng/ml | 19 | 2470 | 1840 | 1940 | 2390 |
| VEGF (Vescular Endotheial Cell Growth Factor) | pg/ml | 38.2 | 155 | 125 | 120 | 155 |
| VWF (von Willebrand Factor) | ng/ml | 98.6 | 135 | 113 | 111 | 133 |

TABLE 10A

|  |  | Human LgG1 control vs. human B7-H4 Ig | | | | R2 vs.clin. |
| --- | --- | --- | --- | --- | --- | --- |
| Analytes | Units | D27 | D34 | D41 | ALL | Score |
| clinical score* |  | 0.12 | 0.00* | 0.08 | 0.04* |  |
| Apo A1 (Apoliprotein A1) | ug/ml | 0.19 | 0.48 | 0.10 | 0.10 | 0.04 |
| CD40* | pg/ml | 0.17 | 0.17 | 0.07 | 0.01* | 0.19 |
| CD 40 Ligand | pg/ml | 0.42 | 0.12 | 0.40 | 0.21 | 0.00 |
| CRP (C Reactive Protein)* | ug/ml | 0.41 | 0.33 | 0.11 | 0.13 | 0.44* |
| EGF (Epidermal Growth Factor) | pg/ml | 0.20 | 0.36 | 0.25 | 0.11 | 0.04 |
| Endothein-1* | pg/ml | 0.14 | 0.08 | 0.04* | 0.01* | 0.05 |
| Eotaxin | pg/ml | 0.26 | 0.40 | 0.45 | 0.40 | 0.00 |
| Factor VII | ng/ml | 0.05 | 0.41 | 0.48 | 0.12 | 0.01 |
| FGF-9 (Fibroblast Growth Factor-9) | ng/ml |  |  |  |  |  |
| FGF-basic (Fibroblast Growth Factor-basic) | ng/ml | 0.24 | 0.19 | 0.18 | 0.09 | 0.19 |
| Fibrinogen | ug/ml |  |  |  |  |  |
| GCP-2 (Granulocyte Chemotactic Protein-2) | ng/ml | 0.34 | 0.13 | 0.30 | 0.10 | 0.00 |
| GM-CSF (Granulocyte Macrophage-Colony Stimulating Factor) | pg/ml |  |  |  |  |  |
| GST-alpha (Flutahione S-Transferase alpha)* | ng/ml |  |  |  | * |  |
| Haptoglobin | ug/ml | 0.31 | 0.19 | 0.37 | 0.17 | 0.11 |
| IFN-gamma (Interferon-gamma) | pg/ml |  | 0.13 | 0.06 | 0.44 | 0.08 |
| IgA (Immunoglobulin A) | ug/ml | 0.32 | 0.33 | 0.49 | 0.29 |  |
| IL-10 (Interleukin-10) | pg/ml |  |  |  |  |  |
| IL-11 (Interleukin-11) | pg/ml |  |  |  |  |  |
| IL-12p70 (Interleukin-12p70) | ng/ml |  |  |  |  |  |
| IL-17 (Interleukin-17) | ng/ml |  |  |  |  |  |
| IL-18 (Inteleukin-18) | ng/ml | 0.32 | 0.27 | 0.13 | 0.50 | 0.01 |
| IL-1alpha (Interleukin-1alpha) | pg/ml | 0.28 | 0.20 | 0.43 | 0.42 | 0.15 |
| IL-1beta (Interleukin-1beta) | ng/ml | 0.19 | 0.50 | 0.19 | 0.34 | 0.10 |
| IL-2 (Interleukin-2) | pg/ml |  |  |  |  |  |
| IL-3 (Interleukin-3) | pg/ml |  |  |  |  |  |
| IL-4 (Interleukin-4) | pg/mi |  |  |  |  |  |
| IL-5 (Interleukin-5) | ng/ml | 0.44 | 0.50 | 0.20 | 0.26 | 0.03 |
| IL-6 (Interleukin-6)* | pg/ml | 0.33 | 0.44 | 0.06 | 0.22 | 0.32* |

TABLE 10B

| Analytes | Units | Human LgG1 control vs. human B7-H4 Ig | | | | R2 vs.clin. |
| --- | --- | --- | --- | --- | --- | --- |
| | | D27 | D34 | D41 | ALL | Score |
| IL-7 (Interleukin-7) | ng/ml | | | | | |
| IP-10 (Inducible Protein-10) | pg/ml | 0.06 | 0.40 | 0.29 | 0.46 | 0.13 |
| KC/GROalpha (Melanoma Growth Stimulatory Activity Protein)* | ng/ml | 0.36 | 0.31 | 0.07 | 0.11 | 0.34* |
| LIF (Leukemia Inhibitory Factor) | pg/ml | 0.40 | 0.13 | 0.41 | 0.26 | 0.12 |
| Lymphotactin | pg/ml | 0.16 | 0.33 | 0.24 | 0.10 | 0.04 |
| MCP-1 (Monocyte Chemoattractant Protein-1)* | pg/ml | 0.23 | 0.18 | 0.02* | 0.02* | 0.29 |
| MCP-3 (Monocyte Chemoattractant Proten-3)* | pg/ml | 0.18 | 0.15 | 0.01* | 0.01* | 0.44* |
| MCP-5 (Monocyte Chemoattractant Protein-5) | pg/ml | 0.37 | 0.37 | 0.07 | 0.29 | 0.23 |
| M-CSF (Macrophage-Colony Stimulating Factor) | ng/ml | 0.39 | 0.40 | 0.50 | 0.50 | 0.12 |
| MDC (Macrophage-Derived Chemokine) | pg/ml | 0.23 | 0.33 | 0.26 | 0.28 | 0.16 |
| MIP 1alpha (Macrophage Inflammatory Protein-1alpha) | ng/ml | 0.19 | 0.44 | 0.14 | 0.11 | 0.05 |
| MIP-1beta (Macrophage Inflammatory Protein-1beta) | pg/ml | 0.10 | 0.22 | 0.18 | 0.11 | 0.01 |
| MIP-1gamma (Macrophage Inflammatory Protein-1gamma) | ng/ml | 0.42 | 0.44 | 0.08 | 0.22 | 0.27 |
| MIP-2 (Macrophage Inflammatory Protein-2)* | pg/ml | 0.37 | 0.31 | 0.03* | 0.05 | 0.39* |
| MIP-3beta (Macrophage Inflammatory Protein-3beta) | ng/ml | 0.12 | 0.16 | 0.25 | 0.30 | 0.01 |
| MMP-9 (Matrix Metalloproteinase-9)* | ng/ml | 0.37 | 0.03* | 0.27 | 0.39 | 0.10 |
| MPO (Myeloperoxidase) | ng/ml | 0.46 | 0.06 | 0.30 | 0.25 | 0.26 |
| Myoglobin | ng/ml | 0.38 | 0.16 | 0.12 | 0.13 | 0.16 |
| OSM (Oncostatin M) | ng/ml | | | | | |
| RANTES (Regulation Upon Activiation, Normal T-Cell Expressed and Secreted) | pg/ml | | | | | |
| SAP (Serum Amyloid P)* | ug/ml | 0.32 | 0.50 | 0.13 | 0.26 | 0.32* |
| SCF (Stem Cell Factor) | pg/ml | 0.41 | 0.43 | 0.07 | 0.19 | 0.03 |
| SGOT (Serum Glutamic-Oxaloacetic Transaminase | ug/ml | 0.26 | 0.27 | 0.43 | 0.29 | 0.01 |
| TIMP-1 (Tissue Inhibitor of Metalloproteinase Type-1) | ng/ml | 0.39 | 0.25 | 0.24 | 0.48 | 0.32 |
| Tissue Factor | ng/ml | 0.31 | 0.38 | 0.21 | 0.37 | 0.08 |
| TNF-alpha (Tumor Necrosis Factor-alpha)* | ng/ml | | | | | |
| TPO (Thrombopoietin) | ng/ml | 0.50 | 0.49 | 0.34 | 0.39 | 0.00 |
| VCAM-1 (Vascular Cell Adhesion Molecule-1) | ng/ml | 0.19 | 0.33 | 0.33 | 0.23 | 0.04 |
| VEGF (Vascular Endothellal Cell Growth Factor)* | pg/ml | 0.28 | 0.01* | 0.05 | 0.47 | 0.00 |
| vWF (von Willebrand Factor) | ng/ml | 0.19 | 0.28 | 0.37 | 0.49 | 0.07 |

C-Reactive Protein (CRP)

Figure 9:
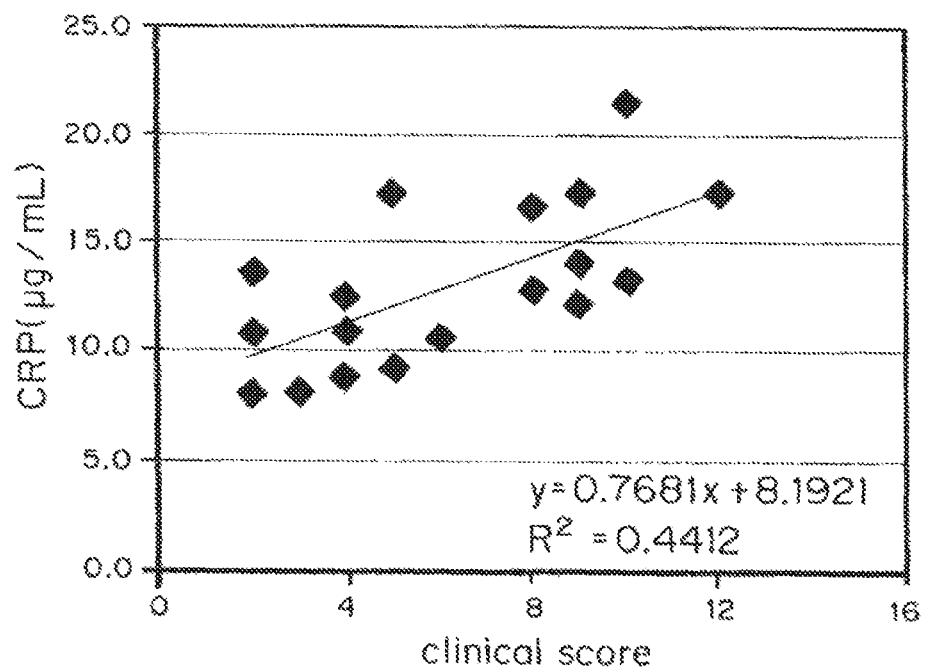
FIG. 9 is a line graph showing serum levels of C-Reactive Protein (CRP) (μg/ml) versus clinical score.

CRP protein levels correlate with clinical score, as shown in FIG. 9, however CRP levels are not significantly different between the two groups. CRP is a commonly used clinical biomarker for inflammation and is well accepted as a marker for RA disease activity. High concentrations of CRP predict joint erosion. CRP has been used as a biomarker in a rhesus CIA model, but is not commonly used as a biomarker in mouse. SAP, described below, rather than CRP is considered the dominant acute phase protein in mouse.

Endothelin 1 (ET-1)

Figure 10:
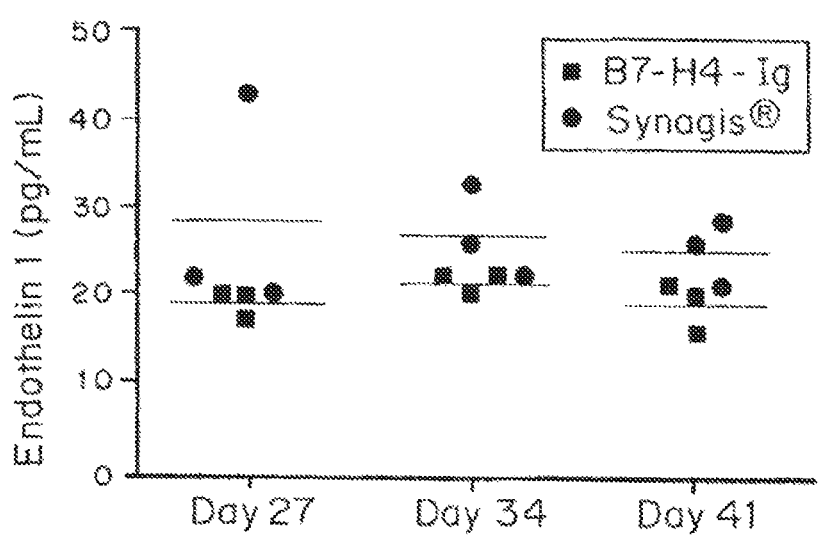
FIG. 10 is a plot showing the serum levels of Endothelin 1 (ET-1) (pg/ml) in mice treated with B7-H4-Ig (-■-) or Synagis® (-●-) at day 27, day 34, and day 41 post CII immunization.

ET-1 levels are significantly lower in B7-H4-Ig treated mice at Day 41 and overall, as shown in FIG. 10. Endothelins act as potent vasoconstrictors. Elevated plasma levels have been reported in RA patients. ET-1 may also play a role in recruiting neutrophils to the synovium.

Glutathione S-Transferase Alpha (GST-α)

GST-α levels are undetectable in 7/9 serum samples from Synagis®-treated mice, but detectable in 5/9 serum samples from B7-H4-Ig treated mice, including 2/3 Day 34 samples and 3/3 Day 41 samples. GST-α is involved in the detoxification of small molecules and elevated levels can indicate liver toxicity. In all cases the levels detected were only slightly above the limit of detection.

Interleukin-6 (IL-6)

Figure 11:
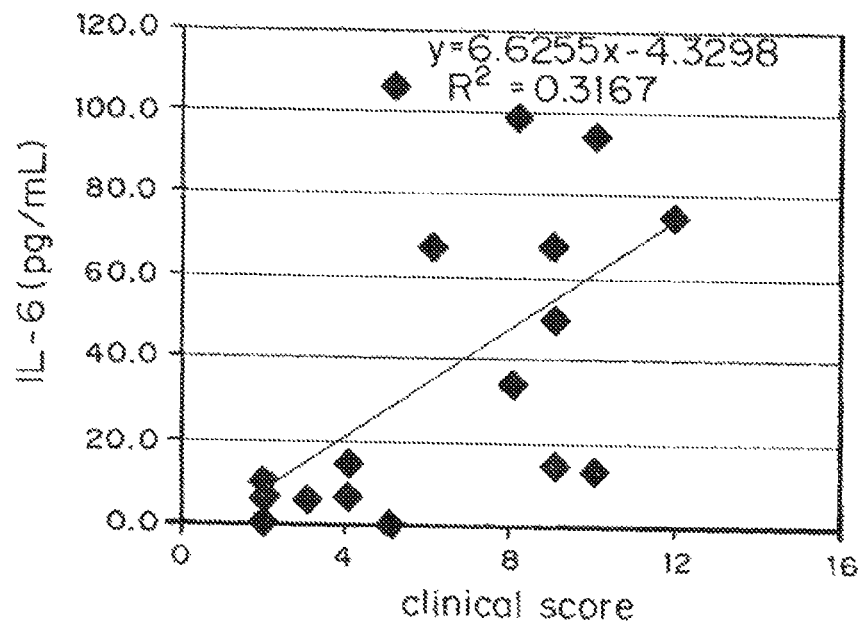
FIG. 11 is a line graph showing serum levels of IL-6 (pg/ml) versus clinical score.

IL-6 levels increase with disease score, as shown in FIG. 11. The highest levels are all in the Synagis® treated group, but the difference between Synagis® and B7-H4-Ig groups did not reach statistical significance in this study. An earlier study showed that treatment with murine B7-H4-Ig decreases IL-6 levels in the CIA model.

Growth-Related Alpha Protein (Gro-α)

Levels of Gro-α (also called chemokine (C—X—C motif) ligand 1, CXCL1) increase with disease score. The highest levels are all in the Synagis® treated group, but this does not reach statistical significance in this study. Gro-α is involved in neutrophil chemotaxis and activation.

Monocyte Chemotactic Protein-1 (MCP-1)

Figure 12:
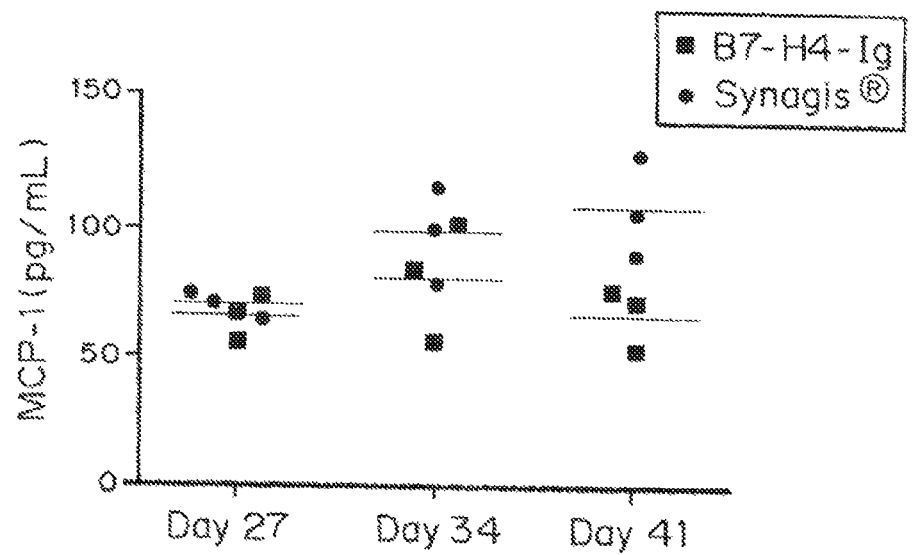
FIG. 12 is a plot showing the serum levels of Monocyte Chemotactic Protein-1 (MPC-1) (pg/ml) in mice treated with B7-H4-Ig (-■-) or Synagis® (-●-) at day 27, day 34, and day 41 post CII immunization.

Levels of MCP-1 (also called chemokine (C—C motif) ligand 2, CCL2) are significantly lower in B7-H4-Ig treated mice at Day 41 and overall, as shown in FIG. 12. MCP-1 recruits monocytes, memory T cells, and dendritic cells to sites of injury or inflammation. MCP-1 promotes macrophage recruitment to the joints in RA, perpetuating inflammation. An earlier study showed that murine B7-H4-Ig also decreases MCP-1 levels in the CIA model.

Monocyte Chemotactic Protein-3 (MCP-3)

Figure 13:
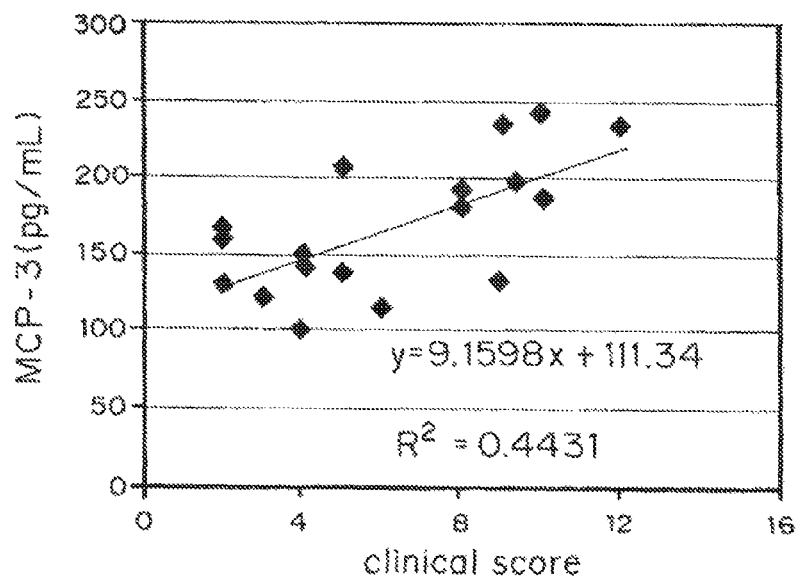
FIG. 13 is a line graph showing serum levels of Monocyte Chemotactic Protein-3 (MPC-3) (pg/ml) versus clinical score.
Figure 14:
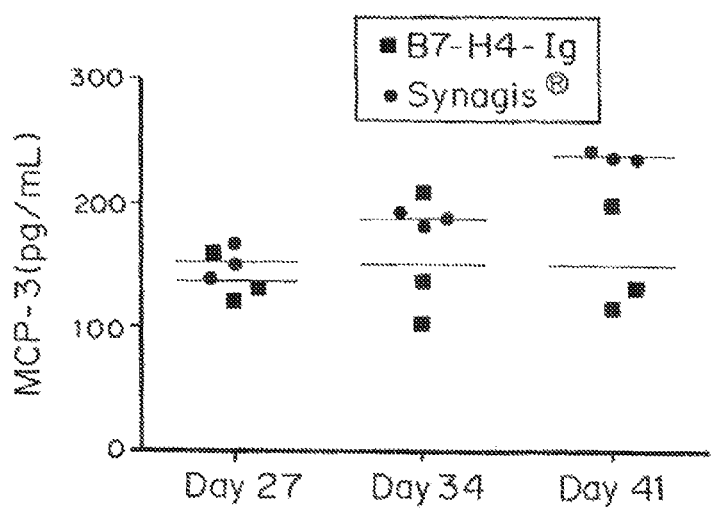
FIG. 14 is a plot showing the serum levels of Monocyte Chemotactic Protein-3 (MPC-3) (pg/ml) in mice treated with B7-H4-Ig (-■-) or Synagis® (-●-) at day 27, day 34, and day 41 post CII immunization.

Levels of MCP-3 (also called chemokine (C—C motif) ligand 7, CCL7) increase with disease score, and are significantly lower in B7-H4-Ig treated mice at Day 41 and overall, as shown in FIGS. 13 and 14. MCP-3 is 74% identical to MCP-1. MCP-3 is a monocyte and T cell chemoattractant.

Macrophage Inflammatory Protein-2 (MIP-2)

Figure 15:
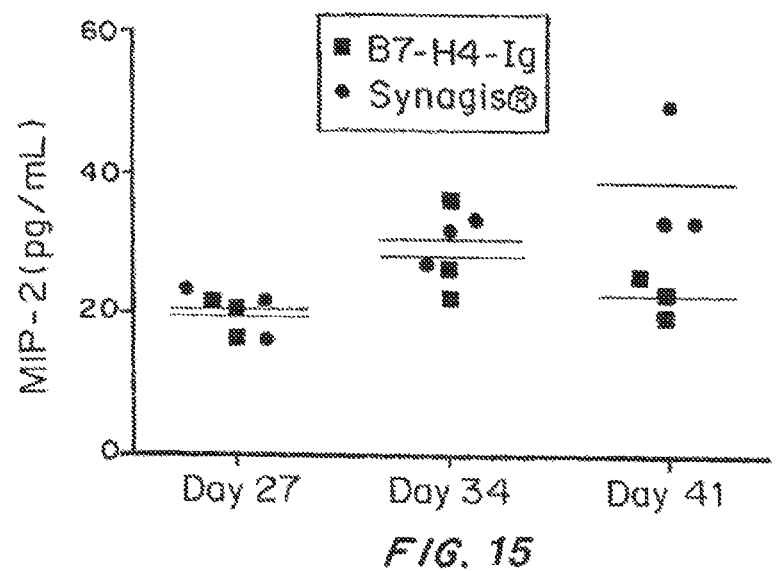
FIG. 15 is a plot showing the serum levels of Marcophage Inflammatory Protein-2 (MIP-2) (pg/ml) in mice treated with B7-H4-Ig (-■-) or Synagis® (-●-) at day 27, day 34, and day 41 post CII immunization.

MIP-2 (also called chemokine (C—X—C motif) ligand 14, CXCL14) levels increase with disease score. Levels are significantly lower in B7-H4-Ig treated mice than Synagis® treated mice at Day 41, as shown in FIG. 15. MIP-2 is potent chemoattractant for neutrophils.

Serum Amyloid Protein (SAP)

SAP levels increase with disease score, but not significantly different between B7-H4-Ig and Synagis treated groups. SAP is considered the major acute phase protein in mice and a general marker of inflammation.

Tumor Necrosis Factor Alpha (TNF-α)

Figure 16:
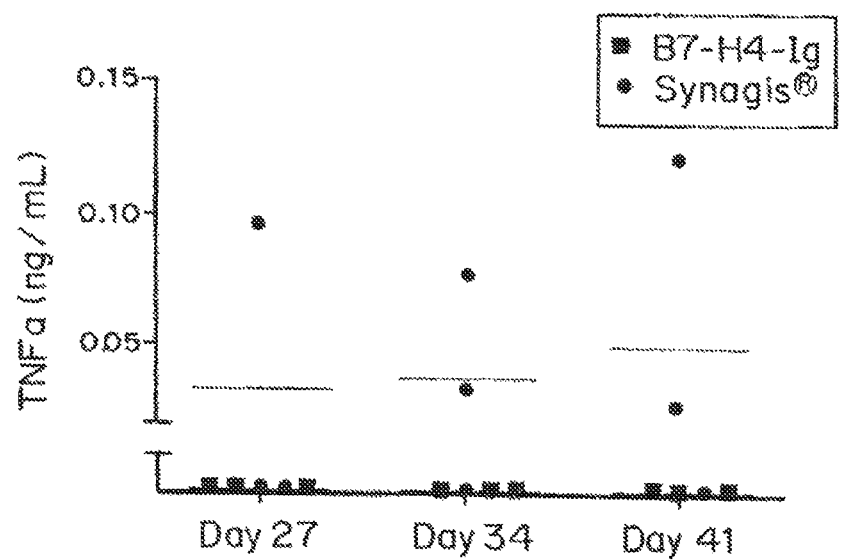
FIG. 16 is a plot showing the serum levels of TNFα (ng/ml) in mice treated with B7-H4-Ig (-■-) or Synagis® (-●-) at day 27, day 34, and day 41 post CII immunization.

Levels are above the limit of detection in 5/9 serum samples from Synagis® treated mice, but none of the sera from B7-H4-Ig treated mice, as shown in FIG. 16. TNF-α is a key mediator of RA disease activity. An earlier study showed that treatment with murine B7-H4-Ig decreases TNF-α levels in the CIA model.

In the data presented in Example 3, B7-H4-Ig shows strong efficacy in murine models of CIA, and is able to stabilize disease scores compared to vehicle and control IgG treated animals. B7-H4-Ig appears to be more potent than murine B7-H4-Ig in female and male DBA/1 mice, and induced a long term protective effect in the female mice. The course of disease is slightly different in the male and female mice. Human B7-H4-Ig is more potent than its murine analog in the CIA model, while RPA110010 was not active in AA#79 or AA#80. In the context of the murine $T_H17$ differentiation assay, B7-H4-Ig and RPA110010 have similar activity and murine B7-H4-Ig is more potent. It is possible that the pharmacokinetic properties of these three molecules differ. Further studies will be performed to assess the relative activity of these molecules in vitro and in vivo.

Serum protein analysis performed by Rules-Based Medicine confirmed earlier studies and provided new readouts for CIA model disease progression and response to B7-H4-Ig treatment. The most promising markers include CRP, ET-1, IL-6, MCP-1, MCP-3, MIP-2 and TNF-α.

The results of the serum biomarker study, as well as previously published results suggest that B7-H4-Ig may affect neutrophil maturation and migration into the synovium (Zhu, G. et al., *Blood* 113, 1759-1767 (2009), Azuma, T. et al., *PLoS. Med.* 6, e1000166 (2009)).

Example 4: B7-H4-Ig Reduces Proinflammatory Molecules

Methods and Materials

Plasma was collected on day 33 from mice treated as described in Example 3 and analyzed for proinflammatory molecules, e.g. TNFα, IL6, and chemokine (MCP-1) using the BD™ Cytometric Bead Array (CBA) Flex Sets.

Results

Figure 17A:
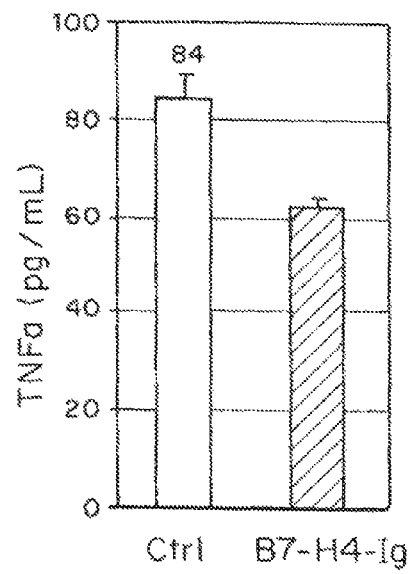
FIGS. 17A, 17B, and 17C are bar graphs showing plasma proinflammatory cytokine and chemokine levels of mice treated with B7-H4-Ig (solid bar) or vehicle control (open bar) for the indicated proinflammatory cytokine/chemokine TNFα (A), IL-6 (B), and MCP-1 (C).
Figure 17B:
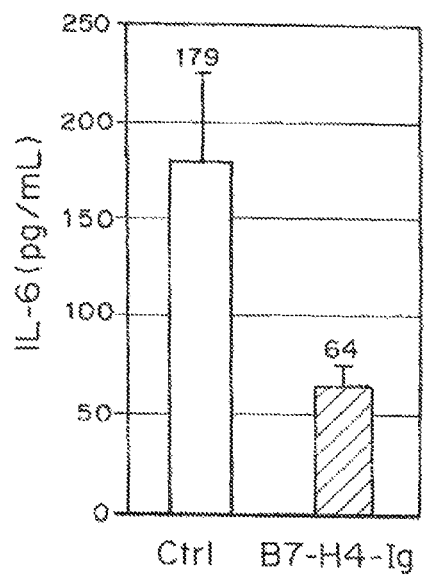
Figure 17C:
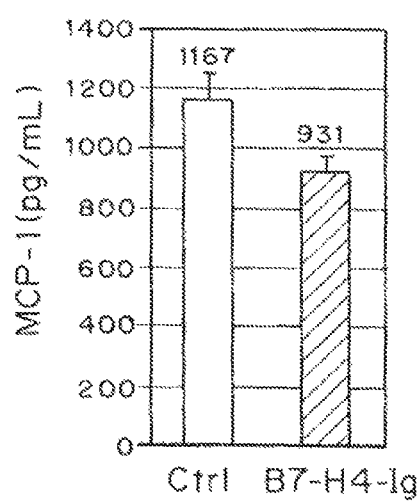

Data presented in FIGS. 17A, 17B, and 17C, respectively, demonstrate B7-H4-Ig significantly reduced TNFα, IL6 and MCP-1 production in the treated CIA mice.

Example 5: B7-H4-Ig Affects Cytokine Production and T Cell Differentiation

Materials and Methods

Mice

BALB/c mice, DO11.10, and C57BL/6 mice were purchased from Jackson Laboratory. SJL mice were purchased from Harlan. All mice were maintained according to NIH guidelines. Mice used in the study were between 6 and 9 weeks of age.

Other Reagents

Mouse Control IgG: Rockland, #010-0102; CD4+ T cell negative isolation kit: Miltenyi, #130-090-860; CD62L+ positive selection magnetic beads: Miltenyi, #130-049-701; CD25+ T cell depletion: anti-mCD25-PE: Miltenyi, #120-000-900, and anti-PE magnetic beads, Miltenyi: #120-000-294; Dynabeads® Mouse CD3/CD28 T Cell Expander beads: Invitrogen, #11452D; Mouse Cytokine Kit: Millipore, MPXMCYTO-70K; 96-well flat bottom: Costar, #3596; β-mercaptoethanol: Invitrogen, #21985-023; HL-1 media: Lonza #344017; OVA$_{323-339}$: ISQAVHAAHAEINEAGR (SEQ ID NO:138); PLP$_{130-151}$: HSLGKWLGHPDKF (SEQ ID NO: 139); PLP$_{130-151}$: NTWTTCQSIAFPSK (SEQ ID NO:140); MOG$_{35-55}$: MEVGWYRSPFSRVVHLYRNGK (SEQ ID NO:141); were synthesized; MILLIPLEXTMMAP: Millipore Cytokines and Antibodies Table 11 lists detail information on cytokines and antibodies used for in vitro T helper cell polarization.

TABLE 11

Cytokines and antibodies for in vitro T helper cell polarization

|  | Reagent | Vendor (Cat#) | Desired (per well) | 100x Stock |
|---|---|---|---|---|
| Th1 cells | rIL-2 (human) | NCI | 1.066 ng/mL (128 U/mL) | 106 ng/mL (12800 U/mL) |
|  | rIL-12 | eBioscience (14-8121) | 4 ng/mL | 400 ng/mL |
|  | anti-IL-4 (11B11) | eBioscience (16-7041) | 1 μg/mL | 100 μg/mL |
| Th17 cells | rTGF-β human TGF-β | R&D Systems (240-B-010) | 10 ng/mL | 1000 ng/mL |
|  | IL-6 | eBioscience (14-8061) | 50 ng/mL | 5000 ng/mL |
|  | IL-23 | eBioscience (14-8231) | 4 ng/mL | 400 ng/mL |
|  | anti-IL-4 (11B11) | eBioscience (16-7041) | 1 μg/mL | 100 μg/mL |
|  | anti-IFN-γ | eBioscience (16-7311) | 1 μg/mL | 100 μg/mL |
|  | anti-IL-2 | eBioscience (16-7021) | 1 μg/mL | 100 μg/mL |

Isolation of CD4+ CD62L+ Naïve T Cells

Mouse splenocytes were first removed isolated from DO11.10 mice, which express an MHC class II restricted T cell receptor specific for OVA$_{323-339}$. Mouse CD4+ T cells were purified using a Miltenyi CD4+ T cell negative isolation kit (Cat#130-090-860). Naïve CD4+ T cells were further purified using the Miltenyi anti-CD62L+ positive selection magnetic beads (cat#130-049-701).

In Vitro Th1 Polarization

CD4+CD62L+ naïve T cells with or without CD25+ T cells were cultured in serum free HL-1 media in the presence of rIL-2 (1 ng/mL), rIL-12 (4 ng/mL) and anti-IL-4 (1 μg/mL). Activity of murine B7-H4-Ig was tested in a number of formats (soluble and insoluble presentation of B7-H4-Ig). Murine B7-H4-Ig was also assessed for activity on T cells activated non-specifically or with antigen-specific stimulation. To provide murine B7-H4-Ig in an immobilized format, 96-well flat bottom plates were first coated with murine B7-H4-Ig, 100 μl per well at 1 μg/mL, and incubated at 37° C. for 2 hours. To provide murine B7-H4-Ig in soluble form, murine B7-H4-Ig was added to the tissue culture at 1 μg/mL or as indicated in the brief describes of the drawings and on the figures for dose dependent studies. For non-specific antigen activation, Mouse CD3/CD28 T Cell Expander beads (Dynabeads®; Invitrogen, Cat#11452D) were added into each well, at a 1:1 cell to bead ratio. For OVA specific activation, splenocytes were first isolated from Balb/C mice as antigen presenting cells (APC) followed by irradiation at 3000 rads for 45 minutes and then added into each well, at a 1:1, APC to responder cell, ratio. OVA$_{323-339}$ peptide was added into the culture at 20 μg/mL.

In Vitro Th17 Polarization

CD4+ CD62L+ naïve T cells with or without CD25+ T cells were cultured in serum free HL-1 media in the presence of rTGF-β (10 ng/mL), IL-6 (50 ng/mL), IL-23 (4 ng/mL), anti-IL-4 (1 μg/mL), anti-IFN-γ (1 μg/mL) and anti-IL-2 (1 μg/mL). To provide murine B7-H4-Ig in an immobilized format, 96-well flat bottom plates were first coated with murine B7-H4-Ig, 100 μl per well at 1 μg/mL, and incubated at 37° C. for 2 hours. To provide murine B7-H4-Ig in soluble form, murine B7-H4-Ig was added to the tissue culture at 1 μg/mL or as indicated in the brief description of the drawings and on the figures for dose dependent studies. For non-specific antigen activation, Mouse CD3/CD28 T Cell Expander beads (Dynabeads®; Invitrogen, Cat#11452D) was added into each well, at a 1:1 cell to bead ratio. For OVA specific activation, splenocytes were first isolated from Balb/C mice as antigen presenting cells (APC) followed by irradiation at 3000 rads for 45 minutes and then added into each well, at a 1:1, APC to responder cell, ratio. $OVA_{323-339}$ peptide was added into the culture at 20 μg/mL.

Proliferation Analysis

[$^3$H]-Thymidine (1 μCi/well) was added into each well 24 hr post co-incubation. Proliferation was determined by uptake of [$^3$H]-thymidine detected at 48 hr post [$^3$H]-thymidine addition using a Topcount Microplate Scintillation Counter (Packard Instruments, Meridan, Conn.). Results are expressed as the mean of triplicate cultures±SEM.

Cytokine Analysis

Supernatants were collected from plates without [$^3$H]-Thymidine at 72 hr for cytokine analysis. Cytokine measurements were performed using the Mouse Cytokine 10-Plex system (Millipore) and Luminex Liquidchip analyzer (Qiagen, Valencia, Calif.) or ELISA.

Results

To demonstrate murine B7-H4-Ig bioactivity in vitro, B7-H4-Ig was added in the T cell polarization culture. The ability of B7-H4-Ig to inhibit T cell proliferation was determined by [$^3$H]-thymidine incorporation and cytokine production via MILLIPLEXTMMAP. In addition, the interaction between B7-H4-Ig and Treg cells was evaluated by comparing the T cell polarization culture outcome in the presence or absence of $CD4^+CD25^+$ Treg cells.

Figure 18:
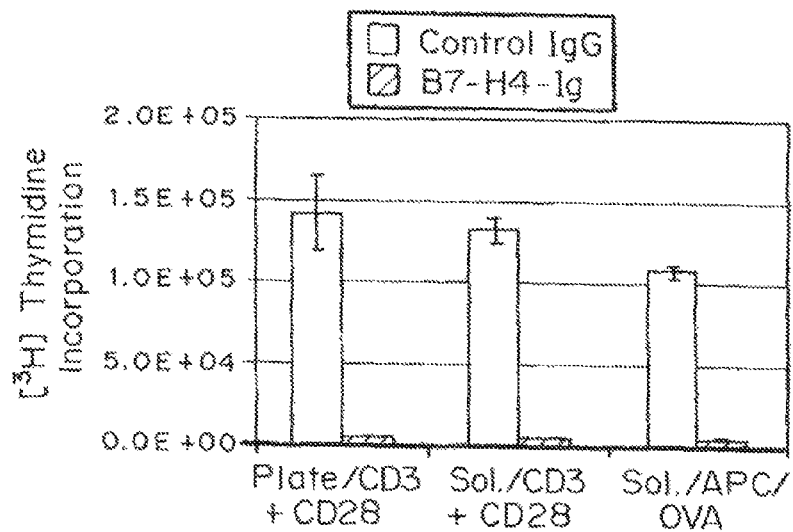
FIG. 18 is a bar graph of mouse T cell proliferation ([$^3$H] thymidine incorporation) of naïve T cells cultured under CD4$^+$ Th1 promoting conditions with control IgG (open bars) or B7-H4-Ig (hatched bars) bound to the culture plate, or in solution, and activated with either anti-CD3/CD28 bound to beads or with antigen presenting cells pulsed with ovalbumin peptide.
Figure 19:
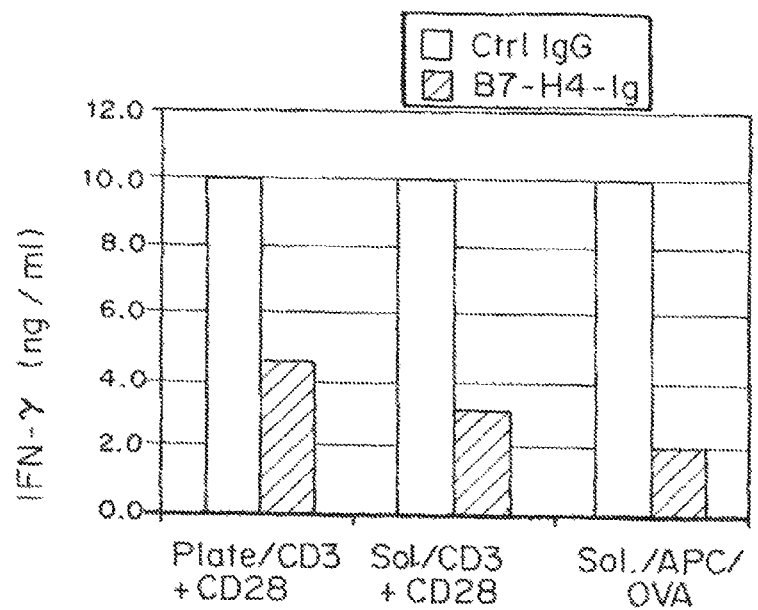
FIG. 19 is a bar graph of IFN-γ (ng/ml) produced by mouse naïve CD4$^+$ T cells cultured under Th1 promoting conditions with control IgG (open bars) or B7-H4-Ig (hatched bars) bound to the culture plate, or in solution, activated with either anti-CD3/CD28 bound to beads or with antigen presenting cells pulsed with ovalbumin peptide.

B7-H4-Ig treatment alters $CD4^+$ T cell activation and differentiation under both Th1 cell- and Th17 cell in vitro polarization culture conditions. Mouse $CD4^+CD62L^+$ T cells were first isolated from DO11.10 mice using Miltenyi kits. As shown in FIG. 18, naïve $CD4^+CD62L^+$ T cells activated in the presence of Th1 cell-promoting conditions in vitro (with IL2, IL-12 and anti-IL4) in the presence of murine B7-H4-Ig significantly inhibited mouse $CD4^+CD62L^+$ naïve T cell proliferation after stimulation with either Dynabeads® Mouse CD3/CD28 T Cell Expander beads (anti-CD3+anti-CD28) for non-specific stimulation, and also when naïve $CD4^+CD62L^+$ T cells were activated in the presence of $OVA_{323-339}$ pulsed APC (APC/OVA). Similar results were obtained when the $CD4^+$ T cells were activated under both bead and APC activating conditions. Additionally, FIG. 19 shows that murine B7-H4-Ig significantly decreased the level of IFN-γ produced from mouse $CD4^+CD62L^+$ naïve T cells under these same conditions. In all cases similar results were seen whether B7-H4-Ig was added in solution (Sol) or bound (Plate) to plates.

Figure 20:
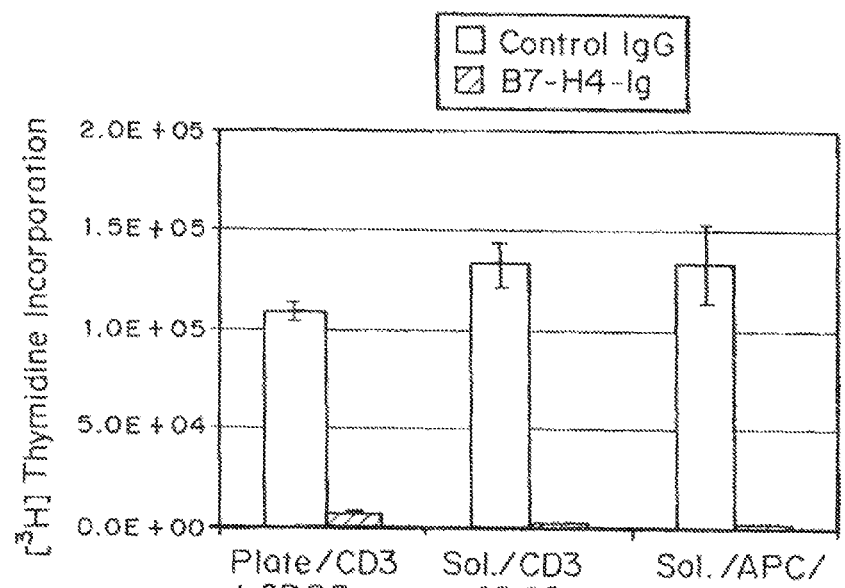
FIG. 20 is a bar graph mouse T cell proliferation ([$^3$H] thymidine incorporation) of naïve CD4$^+$ T cells cultured under Th17 promoting conditions with control IgG (open bars) or B7-H4-Ig (hatched bars) bound to the culture plate, or in solution, and activated with either anti-CD3/CD28 bound to beads or with antigen presenting cells pulsed with ovalbumin peptide.
Figure 21:
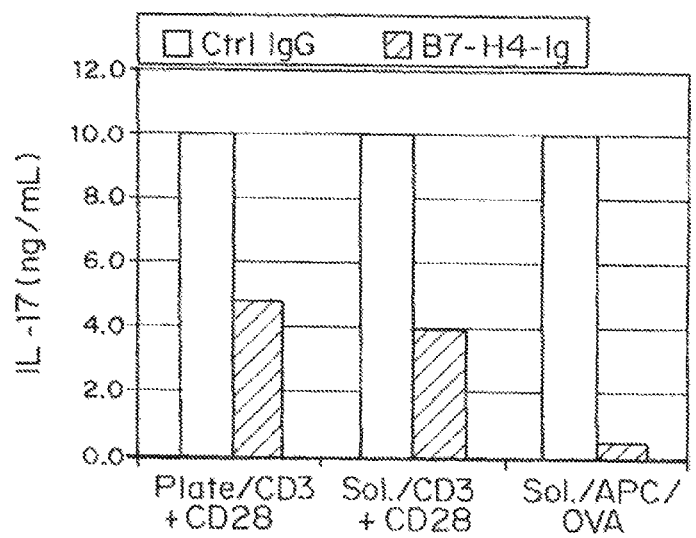
FIG. 21 is a bar graph of IL-17 (ng/ml) produced by mouse naïve T cells cultured under Th17 promoting conditions with control IgG (open bars) or B7-H4-Ig (hatched bars) bound to the culture plate, or in solution, and activated with either anti-CD3/CD28 bound to beads or with antigen presenting cells pulsed with ovalbumin peptide.
Figure 22:
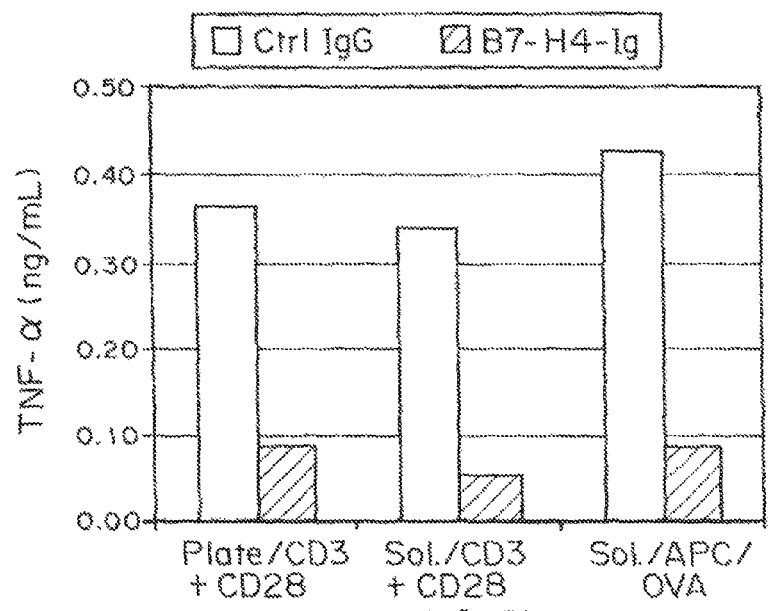
FIG. 22 is a bar graph of TNF-α (ng/ml) produced by mouse naïve T cells cultured under Th17 promoting conditions with control IgG (open bars) or B7-H4-Ig (hatched bars) bound to the culture plate or in solution, and activated with either anti-CD3/CD28 bound to beads or with antigen presenting cells pulsed with ovalbumin peptide.

It is believed that both MS and EAE are Th1 cell/Th17 cell-mediated, therefore, it was next determined if B7-H4-Ig was able to inhibit naïve $CD4^+CD62L^+$ T cell differentiation when activated in the presence of Th17 cell-promoting in vitro culture conditions. As shown in FIG. 20, naïve $CD4^+CD62L^+$ T cells were activated in the presence of Th17 cell-promoting conditions in vitro (with rTGF-β, IL-6, IL-23, anti-IL-4, anti-IFN-γ and anti-IL-2). Murine B7-H4-Ig significantly inhibited mouse $CD4^+CD62L^+$ naïve T cell proliferation after stimulation with either Dynabeads® Mouse CD3/CD28 T Cell Expander beads (anti-CD3+anti-CD28) for non-specific stimulation, or when naïve $CD4^+CD62L^+$ T cells were activated in the presence of $OVA_{323-339}$ pulsed APC (APC/OVA). Similar results were obtained when the $CD4^+$ T cells were activated under both bead and APC activating conditions. Additionally, FIGS. 21 and 22, respectively, show that murine B7-H4-Ig significantly decreased the level of IL-17 and TNF-α produced from mouse $CD4^+CD62L^+$ naïve T cells induced under these same conditions Similar results were seen when B7-H4-Ig was added in solution (Sol) or bound (Plate) to plates.

Figure 23:
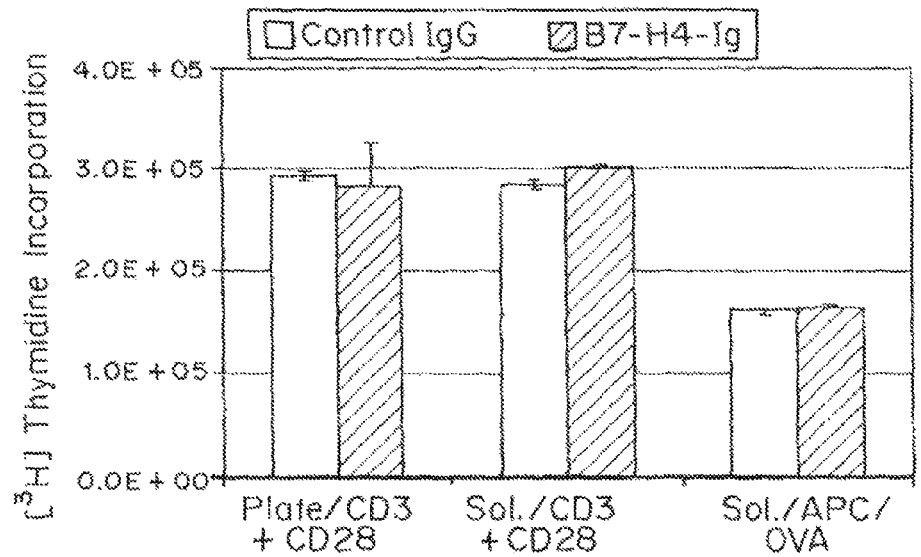
FIG. 23 is a bar graph of mouse T cell proliferation ([$^3$H] thymidine incorporation) of naïve CD4$^+$ T cells cultured under Th2 promoting conditions with control IgG (open bars) or B7-H4-Ig (hatched bars) bound to the culture plate, or in solution, and activated with either anti-CD3/CD28 bound to beads or with antigen presenting cells pulsed with ovalbumin peptide.

The above in vitro Th1/Th17 assay was repeated 3 times using B7-H4-Ig from the same batch, which consistently demonstrated that B7-H4-Ig inhibited Th1/Th17 cell proliferation and IFN-γ and IL17 production. B7-H4-Ig has no impact on Th2 cells using the same target, naïve $CD4^+CD62L^+$ T cells, under Th2 in vitro polarization conditions: IL-2, IL-4, anti-IL12 and anti-IFN-γ (FIG. 23).

Figure 24:
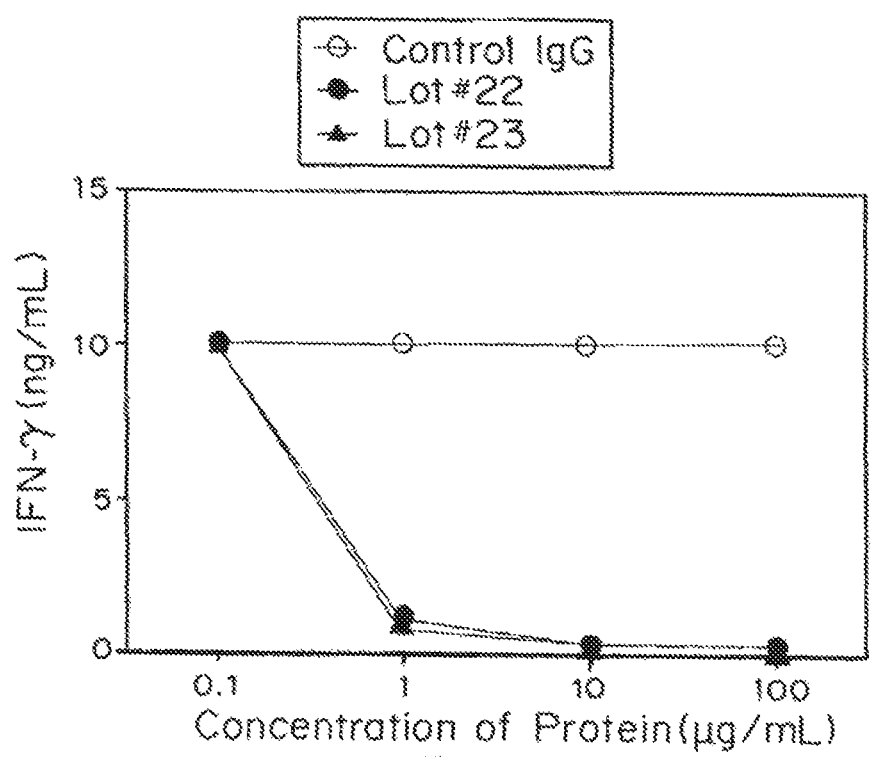
FIG. 24 is a line graph showing INF-γ (ng/ml) produced by mouse naïve T cells cultured under Th1 promoting conditions and stimulated with ovalbumin peptide, as a function of concentration (μg/ml) of control IgG (-○-) or B7-H4-Ig Lot #22 (-●-) or B7-H4-Ig Lot #23 (-▲-).
Figure 25:
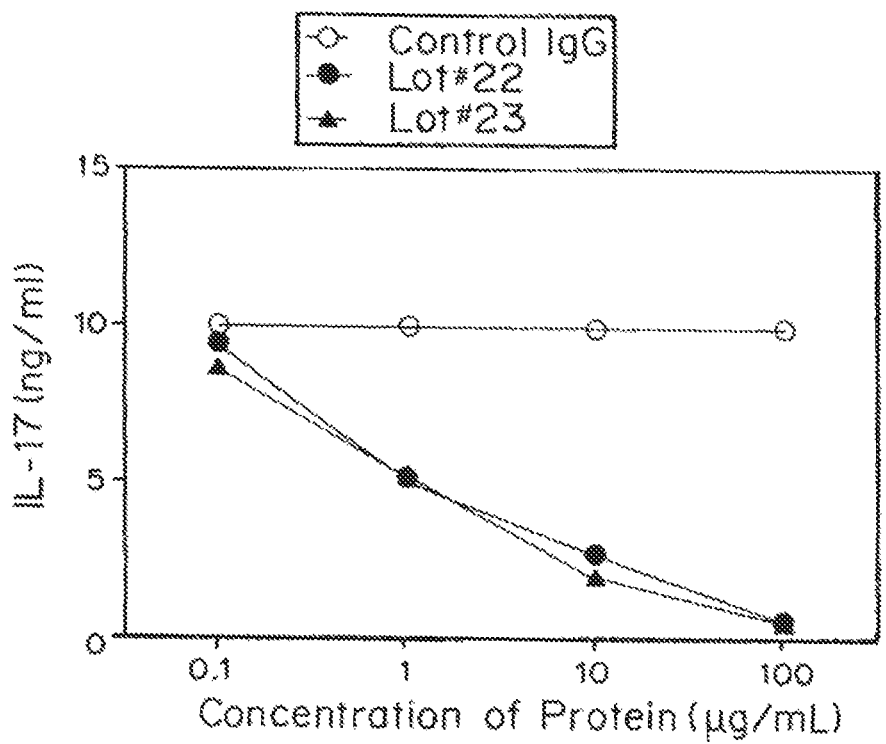
FIG. 25 is a line graph showing IL-17 (ng/ml) produced by mouse naïve T cells cultured under Th17 promoting conditions and stimulated with ovalbumin peptide, as a function of concentration (μg/ml) of control IgG (-○-) or B7-H4-Ig Lot #22 (-●-) or B7-H4-Ig Lot #23 (-▲-).

Identical in vitro bioactivity of murine B7-H4-Ig from different batches has been demonstrated. As shown in FIGS. 24 and 25, B7-H4-Ig from Lot#22 and Lot#23 resulted in similar inhibition of IFN-γ and IL-17 production in a dose dependent manner under the Th1 and Th17 in vitro polarization conditions, respectively. This data not only proves consistency of the Th1/Th17 assay but also consistency of the B7-H4-Ig production process.

Example 6: Human B7-H4-Ig Inhibits Mouse Th17 Cells

Materials and Methods

The human and mouse B7-H4 proteins are 95% homologous. Human B7-H4-Ig was tested for cross-reactivity with murine T cells. Naïve $CD4^+$ T cells were isolated as described above. Upon purification, murine naïve $CD4^+$ T cells were polarized in the presence of IL-2, IL-12 and anti-IL4 for Th1 cell-promoting conditions, or TGF-β, IL-6, IL-23, anti-IL4, anti-IFNγ and anti-IL-2 for Th17 cell-promoting conditions, as described in Example 5 for murine B7-H4-Ig in vitro bioactivity. Human B7-H4-Ig was directly added into the culture at 0, 0.1, 1 or 10 μg/mL. Human Control IgG1 (Synagis®) was added into the culture to bring the final protein concentration to 10 μg/mL.

Results

Figure 26:
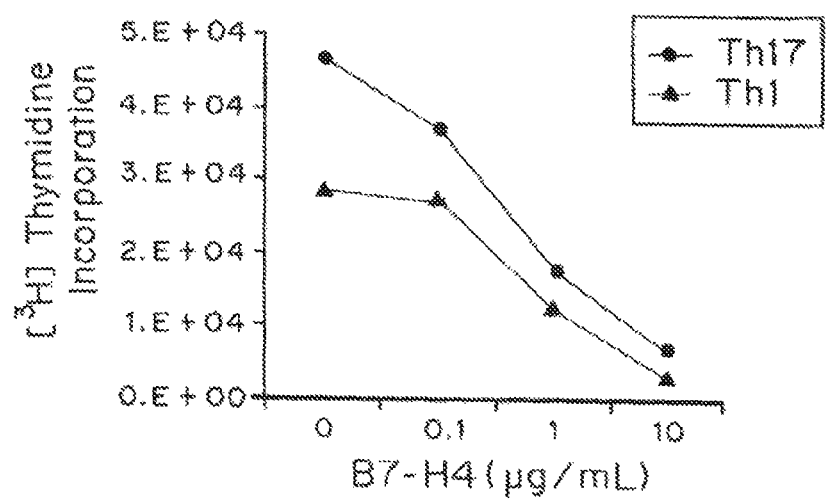
FIG. 26 is a line graph of mouse T cell proliferation ([$^3$H] thymidine incorporation) of naïve CD4$^+$ T cells cultured under Th1 (-●-) or Th17 (-▲-) promoting conditions, stimulated with anti-CD3/CD28 bound to beads, and treated with increasing concentrations of human B7-H4-Ig (μg/ml) added directly to the culture (solution).
Figure 27:
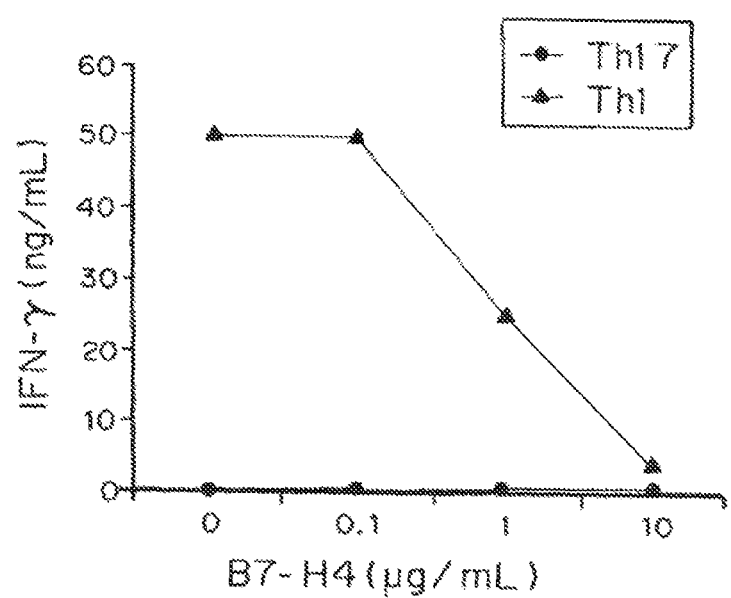
FIG. 27 is a line graph of IFN-γ (ng/ml) produced by mouse naïve CD4$^+$ T cells cultured under Th1 (-●-) or Th17 (-▲-) promoting conditions, stimulated with anti-CD3/CD28 bound to beads, and treated with increasing concentrations of human B7-H4-Ig (μg/ml) added directly to the culture (solution).
Figure 28:
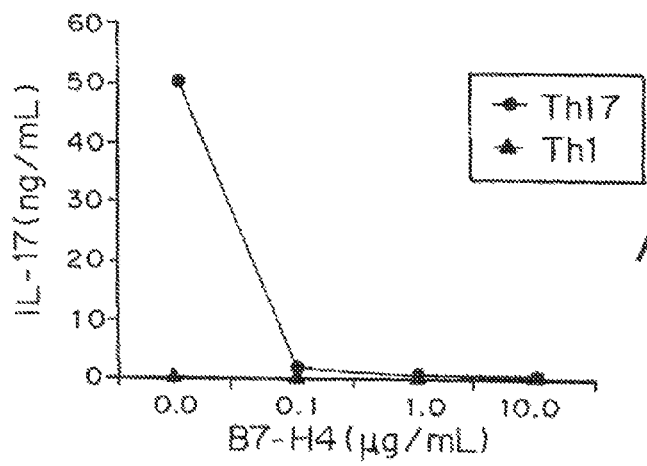
FIG. 28 is a line graph of IL17 (ng/ml) produced by mouse naïve CD4$^+$ T cells cultured under Th1 (-●-) or Th17 (-▲-) promoting conditions, stimulated with anti-CD3/CD28 bound to beads, and treated with increasing concentrations of human B7-H4-Ig (μg/ml) added directly to the culture (solution).

Data presented in FIGS. 26, 27, and 28 show human B7-H4-Ig cross reacted with mouse naïve $CD4^+$ T cells and blocked murine Th1/Th17 proliferation (FIG. 26) in a dose dependent manner, which correlated with reduced IFN-γ production in Th1 cells (FIG. 27) and IL-17 production in Th17 cells (FIG. 28). The same results were obtained when using human B7-H4-Ig from a different batch.

Example 7: B7-H4-Ig Affects Tregs

Methods and Materials

Depletion of $CD4^+CD25^+$ T Cells $CD4^+CD25^+$ Treg cells were depleted using anti-mCD25-PE (Miltenyi Cat#120-000-900) and anti-PE magnetic beads (Miltenyi Cat#120-000-294) prior to the $CD62L^+$ positive selection. After depletion of $CD4^+CD25^+$ T cells, $CD25^+/P3^+$ cells were decreased from approximately 5% to 1%.

Results $CD4^+CD25^+$ Treg cells were optionally depleted (−$CD25^+$ T cells) from DO11.10 mouse $CD4^+CD62L^+$ naïve T cell population prior to in vitro $Th_1$ polarization in the presence of $OVA_{323-339}$ peptide pulsed APC and B7-H4-Ig.

It was found that the extent to which B7-H4-Ig decreased the level of naïve $CD4^+CD62L^+$ T cell proliferation and cytokine production when activated in the presence of either Th1 cell- or Th17 cell-promoting conditions was correlated to the age of the mouse from which the naïve CD4$^+$CD62L$^+$ T cells were isolated. Initial selection for naïve CD4$^+$CD62L$^+$ T cells was based upon negative selection for CD4$^+$ T cells followed by positive selection for CD62L$^+$ cells via use of the AutoMax. Since the number of Treg cells present within a mouse increases with age and Treg cells are CD4$^+$CD62L$^+$CD25$^+$, it was next determined if depletion of CD25$^+$ cells, i.e., Treg and activated CD4$^+$ T cells, during the CD4$^+$ T cell negative selection would alter the ability of B7-H4-Ig to inhibit naïve CD4$^+$CD62L$^+$ T cell production of IFN-γ when activated in the presence of Th1 cell-promoting conditions.

Figure 29A:
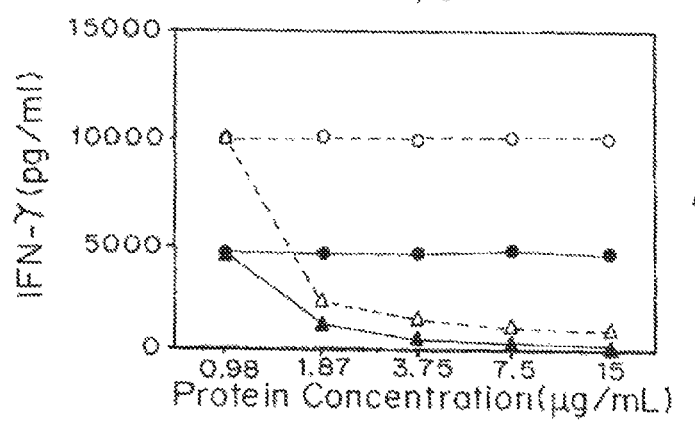
FIGS. 29A and 29B are line graphs of IFN-γ (ng/ml) in (A) and IL-10 (ng/ml) in (B) produced by CD4$^+$CD62$^+$ naïve mouse T cells in the presence or absence of CD25$^+$ T cells cultured under Th1 promoting conditions, stimulated with antigen presenting cells pulsed with ovalbumin peptide, and treated with different concentrations (μg/ml) of control IgG or B7-H4-Ig. T cells containing CD25$^+$ T cells treated with control IgG are shown as (●) or B7-H4-Ig are shown as (▲). T cells with CD25$^+$ T cells depleted and treated with IgG are shown as (○) or B7-H4-Ig are shown as (Δ).
Figure 29B:
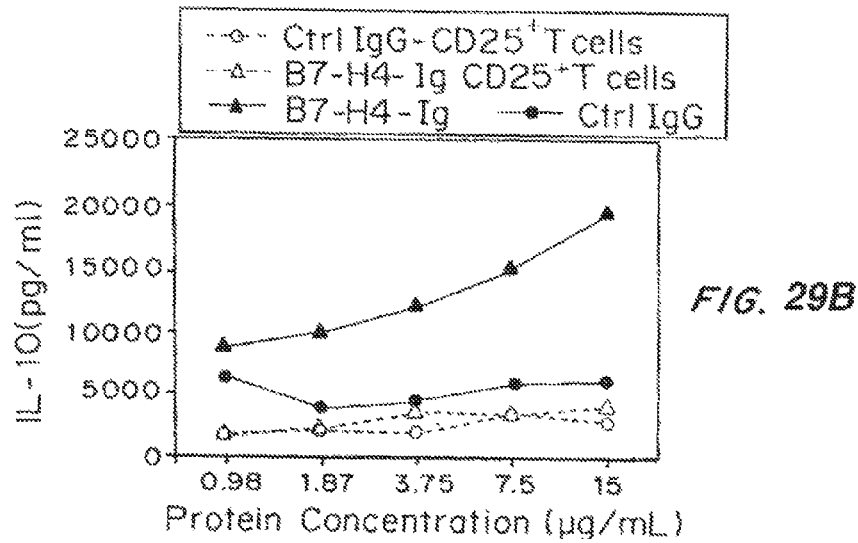

CD4$^+$CD62L$^+$ naïve T cells were first isolated from DO11.10 mice and polarized to Th1 cells in the presence of rIL-2 (1 ng/mL), rIL-12 (4 ng/mL) and anti-IL-4 (1 µg/mL), and stimulated with OVA$_{323-339}$ pulsed APC (APC/OVA). Murine B7-H4-Ig or Control IgG at various doses was added directly to the culture. As shown in FIG. 29A, depletion of Treg (open circle) resulted in higher IFN-γ production as compared to IFN-γ levels when Treg cells were present (solid circle). The B7-H4-Ig mediated decrease in IFN-γ production was dose dependent (open triangles), and the inhibition was more profound in the presence of CD4$^+$CD25$^+$ Treg cells (solid triangle). Conversely, B7-H4-Ig increased IL-10 production in a dose dependent manner (solid triangles—FIG. 29B).

Figure 30A:
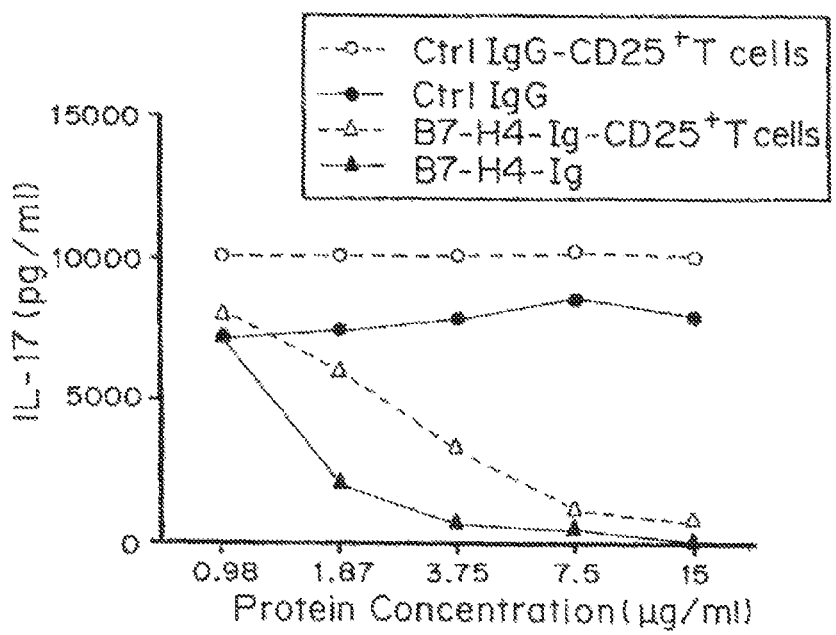
FIGS. 30A and 30B are a line graphs of IL-17A (ng/ml) in (A) and IL-10 (ng/ml) in (B) produced by CD4$^+$CD62$^+$ naïve mouse T cells in the presence or absence of CD25$^+$ T cells cultured under Th17 promoting conditions, stimulated with antigen presenting cells pulsed with ovalbumin peptide, and treated with different concentrations (μg/ml) of control IgG or B7-H4-Ig. T cells containing CD25+ T cells treated with control IgG are shown as (●) or B7-H4-Ig are shown as (▲). T cells with CD25+ T cells depleted and treated with IgG are shown as (○) or B7-H4-Ig are shown as (Δ).
Figure 30B:
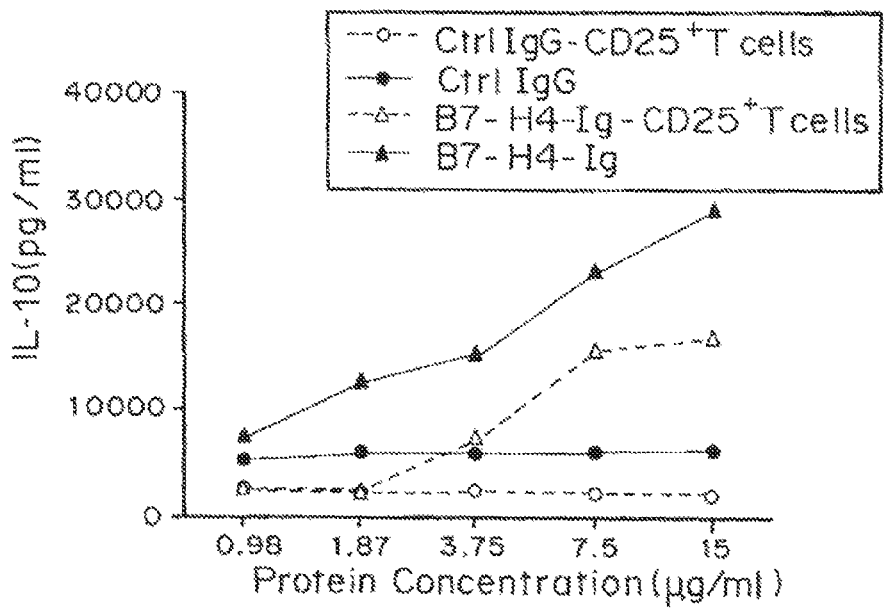

The effect of depletion of CD4$^+$CD25$^+$ Treg cells (−CD25$^+$ T cells) from DO11.10 mouse CD4$^+$CD62L$^+$ naïve T cells prior to in vitro Th17 polarization in the presence of OVA$_{323-339}$ peptide pulsed APC and various amounts of murine B7-H4-Ig was also tested. CD4$^+$CD62L$^+$ naïve T cells were first isolated from DO11.10 mice. CD4$^+$CD25 included or depleted cells (−CD25+ T cells) were polarized to Th17 cells in the presence of rTGF-β (10 ng/mL), IL-6 (50 ng/mL), IL-23 (4 ng/mL), anti-IL-4 (1 µg/mL), anti-IFN-γ (1 µg/mL) and anti-IL-2 (1 µg/mL), and stimulated with OVA$_{323-339}$ pulsed APC (APC/OVA). Murine B7-H4-Ig or Control IgG at various doses was added directly to the culture. As shown in FIG. 30A, the depletion of Treg (open circle) resulted in higher IL-17 production as compared to IL-17 levels when Treg cells were present (solid circle). The decrease in IL-17 production was found to be dose dependent (open triangles). The inhibition was consistently higher when CD4$^+$CD25$^+$ Treg cells were present (solid triangle). In contrast, FIG. 30B shows that murine B7-H4-Ig increased IL-10 production in a dose dependent manner (open triangles) and the increase in IL-10 was greater when CD4$^+$CD25$^+$ Treg cells were present (solid triangle).

In vitro B7-H4-Ig inhibits proliferation and differentiation of naïve OVA$_{323-339}$-specific transgenic CD4$^+$ T cells into either Th1 or Th17 cells when stimulated with either OVA$_{323-339}$-pulsed syngeneic APC or antigen non-specific anti CD3/CD28 coated beads. Furthermore, B7-H4-Ig reduces the level of IFN-γ and IL-17/TNFα produced by Th1 cells and Th17 cells, respectively. The reduction of IFN-γ and IL-17 production was less pronounced when CD4$^+$CD25$^+$ T regulatory cells are depleted from the purified CD4$^+$CD62L$^+$ naïve CD4$^+$ T cells. Most importantly, B7-H4-Ig dose dependently increases IL-10 production during Th1/Th17 polarization when CD4$^+$CD25$^+$ T regulatory cells are present. These data show that B7-H4-Ig may act in part upon Treg cells to upregulate IL-10 expression and inhibit Th1 and Th17 effector differentiation and function.

Example 8: B7-H4-Ig Promotes iTreg Induction

Materials and Methods
In Vitro Induction of iTreg Cells
CD4$^+$CD62L$^+$ naïve T cells were first labeled with CFSE (5 µM) for 10 min at room temperature. The dye was quenched by the addition of 0.5 volumes of ice-cold fetal calf serum. The cells were incubated on ice for 5 min followed by centrifugation to collect the cell pellet. The cells were washed 2 more times in HL-1 culture media. The cells were then cultured in the presence of TGF-β (10 ng/mL) and IL-2 (10, 50, 100 U/mL) for 3 days before intracellular staining with anti-FoxP3 APC. FACS analysis was conducted to detect the FoxP3$^+$, in vitro expanded iTreg cells.

Results
The above findings suggest that B7-H4-Ig induces naïve CD4$^+$CD62L$^+$ T cells to differentiate toward a Treg cell phenotype and/or directly enhances Treg cell function. Therefore, it was next examined if B7-H4-Ig treatment of naïve CD4$^+$CD62L$^+$ T cells in the presence of inducible Treg (iTreg) cell-promoting conditions would results in an increase in the numbers of CD4$^+$CD25$^+$FoxP3$^+$ iTreg cells. First the in vitro iTreg induction culture conditions were optimized to allow for experimental conditions to assess what additional effect, if any, B7-H4-Ig has on iTreg induction. CD4$^+$ T cells were isolated from female SJL mice. Purified mouse CD4$^+$CD62L$^+$ T cells were first labeled with CSFE and induced to iTreg cells in the presence of TGF-β (10 ng/mL) and IL-2 at concentrations of 0, 50 or 100 U/mL. FACS analysis was performed 3 days later to detect FoxP3 expression and CFSE content. A FoxP3 positive and CFSE diluted cell population was detected when using 100 U/mL of IL-2 for iTreg differentiation. The size of this cell population decreased when using less IL-2.

To assess the role of B7-H4-Ig in iTreg differentiation, the suboptimal iTreg conditions (10 ng/mL of TGF-β and 50 U/mL of IL-2), were used. This was done so that if B7-H4-Ig did in fact induce an increase in the percentage of CD4$^+$CD25$^+$FoxP3$^+$ cells, it would be clear that the B7-H4-Ig-induced increase was not masked by the TGF-β/IL-2 effect. FACS analysis of staned cells revealed naïve CD4$^+$CD62L$^+$ T cells were induced to express FoxP3 and CD25 in vitro, i.e., iTreg, when the naïve CD4$^+$CD62L$^+$ T cells were activated in the presence of suboptimal iTreg cell-promoting condition, 10 ng/mL of TGF-β and 50 U/mL of IL-2. Different amounts of murine B7-H4-Ig (0, 1, 5 or 10 µg/mL) were added. B7-H4-Ig increased the percentage of FoxP3$^+$CD25$^+$ iTregs in a dose-dependent manner with the highest percentage of FoxP3$^+$CD25$^+$ T cells induced when the naïve CD4$^+$CD62L$^+$ T cells were activated in the presence of 10 µg/ml of B7-H4-Ig. In contrast, when naïve CD4$^+$CD62L$^+$ T cells were activated in the presence of 10 µg/ml control IgG, no increase in FoxP3$^+$CD25$^+$ iTregs was seen.

Example 9: B7-H4-Ig Modulates CD4$^+$ T Cell Activation and nTreg Suppression Function Materials and Methods
In Vitro Suppression Assay
Spleens and lymph nodes were harvested from 10 FoxP3-GFP mice on a B6 background. Cells were made into a single cell suspension, and a total of 1.76×10$^9$ cells were collected. 1×10$^8$ cells were set aside to be irradiated for APCs in the assay. Naïve CD4$^+$ T cells were purified from the rest of the cells as described above. A total of 6.2×10$^8$ naïve CD4$^+$ T cells were collected. 5×10$^7$ cells were set aside to be effector T cells in the experiment. The remainder of the cells (5.7×10⁸) were stained with anti-CD4 PE-Cy7, and the PE-Cy7$^+$/GFP$^+$ cells were sorted via MoFlo. A total of 4×10⁶ nTreg (CD4$^+$/FoxP3$^+$) cells were collected from the MoFlo at 99% purity. The suppression assay cultures were set up with 1×10⁵ effector T cells+1×10⁵ irradiated APCs+αCD3 (1 µg/mL) at a final volume of 200 µl in a round bottom plate. The culture wells also received various ratios of nTreg cells: B7-H4-Ig.

Results

Figure 31:
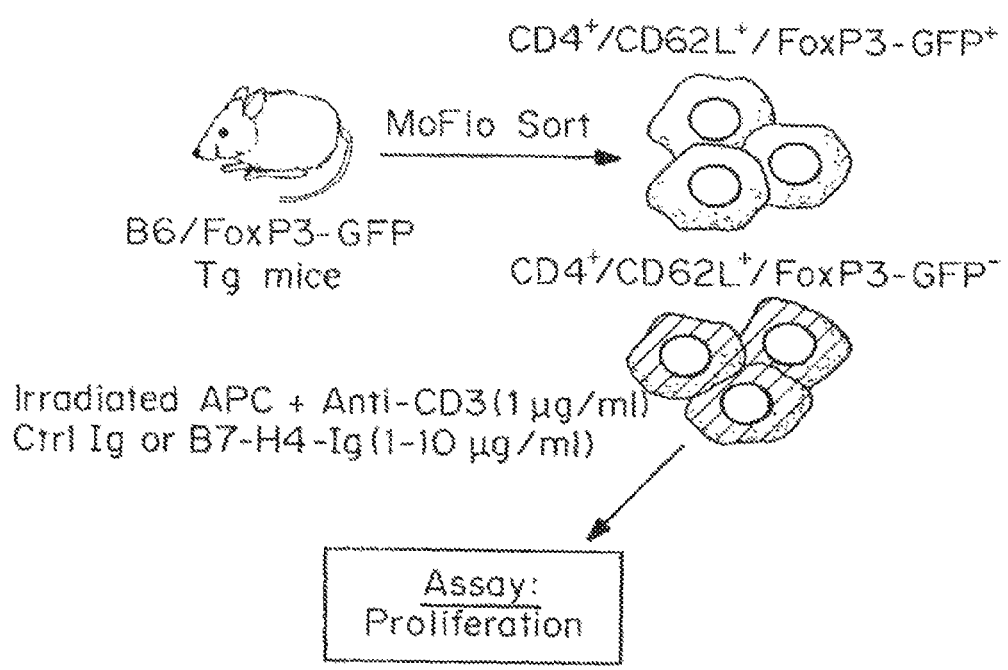
FIG. 31 is a flow chart illustrating the nTreg suppression assay.
Figure 32:
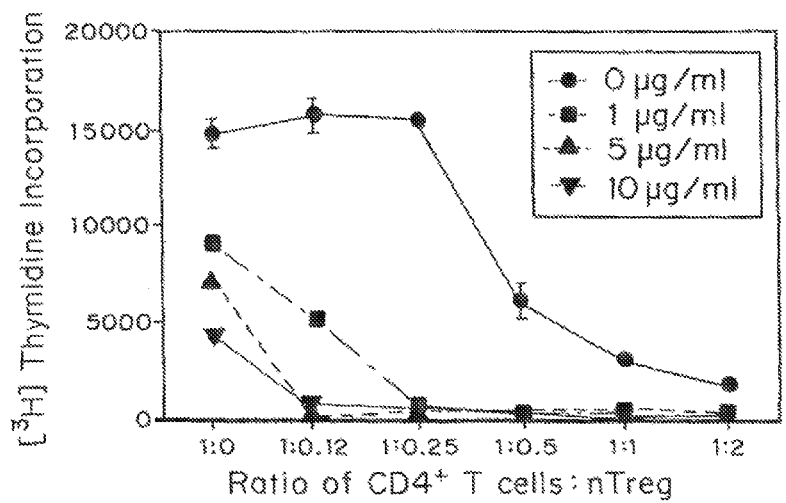
FIG. 32 is a line graph of T cell proliferation ([$^3$H] thymidine incorporation) for naïve CD4+/GFP− responder T cells and CD4+/GFP+ nTreg cells at ratios of 1:0, 1:0.12, 1:0.25, 1:0.5, 1:1 and 1:2, plus irradiated non purified splenocytes as antigen presenting cells (APC), anti-CD3 antibody, and varying amounts of murine B7-h4-Ig (0 (-●-), 1 (-■-), 5 (-▲-), or 10 (-▼-) μg/mL)).

To further determine the effect of B7-H4-Ig on Treg cell function, an in vitro Treg suppression assay using natural Treg (nTreg) cells purified from B6/FoxP3-GFP mouse spleens and lymph nodes was conducted. In this transgenic mouse, the GFP transgene is under the regulation of the FoxP3 specific promoter, allowing the detection of nTreg cells expressing the endogenous FoxP3 by green fluorescence.

nTreg cells (CD4$^+$/CD62L$^+$/FoxP3-GFP$^+$) were isolated from B6/FoxP3-GFP mice by MoFLo sorting. Naïve GFP$^-$ T cells CD4$^+$/CD62L$^+$/FoxP3-GFP$^-$) were used as responder cells. Increasing numbers of the nTreg cells were added to constant numbers of naïve CD4$^+$CD62L$^+$ T cells, irradiated splenocytic APCs, and anti-CD3 (FIG. 31). As shown in FIG. 32, various responder:nTreg ratios were employed using a fixed responder cell number (1×10⁵) with increasing Treg cells (0, 1.25×10⁴, 2.5×10⁴, 5×10⁴, 1×10⁵, 2×10⁵) resulting in ratios of 1:0, 1:0.12, 1:0.25, 1:0.5, 1:1 and 1:2 fixed responder/nTreg. Various amounts of B7-H4-Ig (0, 1, 5, or 10 mg/mL) were added to the suppression assays and responder cell proliferation was assessed by [³H]-thymidine 3 days later.

As shown in FIG. 32, in the absence of nTreg cells (ratio at 1:0) B7-H4-Ig suppressed CD4$^+$ T cell activation and proliferation in a dose dependent manner. In the absence of B7-H4-Ig (closed circles), nTreg prevented CD4$^+$ T cell activation, also in a dose dependent fashion. At the ratio 1:2 (1 responder:2 nTreg), nTreg cells almost abolished CD4$^+$ T cell activation. Significant suppression was observed when both nTreg and murine B7-H4-Ig were present. At the 1:0.12 and 1:0.25 ratios of T cell responder:nTreg no suppression was detected in the absence of murine B7-H4-Ig. However, 5 or 10 µg/mL of B7-H4-Ig completely blocked anti-CD3 induced T cell activation. In the absence of B7-H4-Ig, suppression increased only in the presence of more nTreg, ratios of 1:0.5, 1:0, 1:1 and 1:2 responder/nTreg.

Example 10: B7-H4-Ig Modulates the Induction and Progression of Disease in the PLP$_{139-151}$ Peptide Induced Relapsing-EAE (R-EAE)

Methods and Materials
PLP Induced R-EAE Model

For PLP$_{139-151}$-induced R-EAE, 6- to 7-wk-old female SJL mice were immunized s.c. with 100 µL of an emulsion containing 200 µg of M. tuberculosis H37Ra and 50 µg of PLP$_{130-151}$ (HSLGKWLGHPDKF) (SEQ ID NO:139) distributed over three spots on the flank. Individual animals were observed daily and clinical scores assessed in a blinded fashion on a 0-5 scale as shown in Table 11 (Miller, et al., Curr. Protocols Immulo., Chapter 12, Unit 15.1). Unless otherwise mentioned, all mice were age and sex-matched for all experiments.

Figure 33:
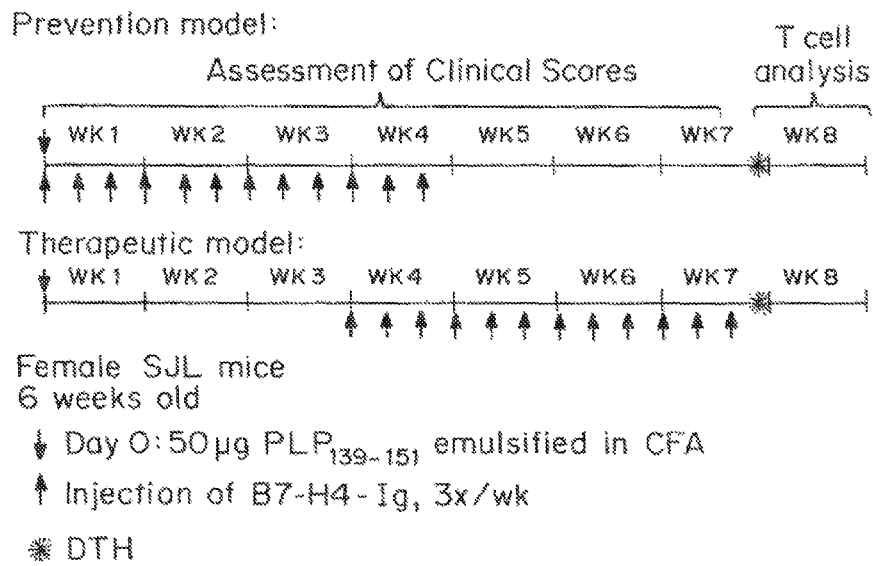
FIG. 33 is a schematic illustration of experimental auto-immune encephalomyelitis (EAE) induction and treatment regimen in an in vivo study utilizing an auto-immune R-EAE murine model for Multiple Sclerosis (MS).

FIG. 33 shows a typical B7-H4-Ig treatment regimen. Mice were randomly divided into four groups. For the disease prevention model, B7-H4-Ig or control IgG at 3 mg/kg was injected intraperitoneally (i.p.) on the same day as PLP$_{130-151}$ priming. For the therapeutic model, B7-H4-Ig or control IgG at 3 mg/kg was given i.p. beginning on approximately Day 21 post PLP$_{130-151}$ priming. In both cases, B7-H4-Ig was administrated, 3 times a week, for 2-4 weeks.

Delayed-Type Hypersensitivity (DTH) Responses

DTH responses were quantitated using a 24 hr ear swelling assay as previously described. Pre-challenge ear thickness was determined using a Mitutoyo model 7326 engineer's micrometer (Schlesinger's Tools, Brooklyn, N.Y.). Immediately thereafter, DTH responses were elicited by injecting 10 µg of peptide in 10 µL of PBS into the dorsal surface of the ear using a 100 µL Hamilton syringe fitted with a 30 gauge needle. The increase in ear thickness over pre-challenge measurements was determined 24 hr after ear challenge. Results are expressed in units of 10$^{-4}$ inches±SEM. Results are expressed as the change in ear thickness in units of 10$^{-4}$ inches±SEM. The measurements were carried out independently by 2 investigators who did not know the identity of the experimental groups. Significance of ear swelling in murine B7-H4-Ig treated mice over Control IgG injected mice was assessed by the Student's t test.

In Vitro Antigen-Specific Recall Responses

Draining lymph nodes (axillary, brachial, and inguinal) were harvested, and single cell suspensions were obtained by mashing through sterile 60-mesh wire screens. In 96-well microtiter plates, 5×10⁵ erythrocyte-free (Tris-NH$_4$Cl-treated) lymph node cells per well were incubated in supplemented culture medium with or without antigen at 37° C. in 7% CO$_2$ for 24 hr and then pulsed with 1 µCi/well of [³H]-Thymidine for the final 48 h of culture. Proliferation was determined by uptake of [³H]-Thymidine detected using a Topcount Microplate Scintillation Counter (Packard Instruments, Meridan, Conn.). Results are expressed as the mean of triplicate cultures from individual animal±SEM. Supernatants were collected at 72 hr for cytokine analysis. Cytokine measurements were performed using the Mouse Cytokine 10-Plex system and Luminex Liquidchip analyzer (Qiagen, Valencia, Calif.) or ELISA.

Results

T cells specific for the inducing epitope (PLP$_{139-151}$ peptide) in the PLP R-EAE animal model, cause acute CNS damage resulting in induction of T cell responses to endogenous encephalitogenic myelin epitopes, which are exposed to the immune system as a result of the initial acute damage. This progression of the relapsing-remitting disease course in R-EAE has been shown to be mediated by de novo activation of naïve T cells specific for PLP$_{178-191}$ peptides, a process known as epitope spreading. During the disease course of R-EAE mice develop an ascending paralytic demyelinating disease characterized by a relapsing-remitting clinical course, which is a validated model for MS (Miller, et al., Curr Protoc Immunol., Chapter 15:Unit 15.1 (2010)).

To determine the therapeutic benefit of B7-H4-Ig, murine B7-H4-Ig was tested in the PLP$_{139-151}$-induced R-EAE mouse model both for prevention of disease (treatment begun on the same day of disease induction) and therapeutic intervention (treatment begun during the disease remission) settings (FIG. 33). In both cases the disease course was followed for about 2 months to assess clinical disease following the grading system shown in Table 12.

TABLE 12

Grading System for Clinical Assessment of EAE

| Score | Clinical Signs |
|---|---|
| 0 | Normal mouse; no overt signs of disease |
| 1 | Limp tail[a] or hind limb weakness[b] but not both |
| 2 | Limp tail[a] or hind limb weakness[b] |
| 3 | Partial hind limb paralysis[c] |
| 4 | Complete hind limb paralysis[d] |
| 5 | Moribund state; death by EAE; sacrifice for humane reasons |

[a]Limp tail: complete flaccidity of the tail, and absence of curling at the tip of the tail when mouse is picked up.
[b]Hind limb weakness: observed as a waddling gait, the objective sign being that, in walking, mouse's hind limbs fall through the wire cage tops.
[c]Partial hind limb paralysis: mouse can no longer use hind limbs to maintain rump posture or walk but can still move one or both limbs to some extent.
[d]Complete hind limb paralysis: total loss of movement in hind limbs; mouse drags itself only on its forelimbs. Mice at this stage are given food on the cage floor, long sipper tubes, and daily subcutaneous saline injections to prevent death by dehydration.

This was done along with monitoring DTH responses and in vitro recall responses to spread epitopes by assaying for cytokine secretion following ex vivo stimulation of T cells with peptides.

B7-H4-Ig Prevents Relapsing Disease in the R-EAE Model

Female SJL mice were first immunized with PLP139-151 peptide emulsified in CFA and then randomized into 2 groups for either prevention or therapeutic treatment. For each treatment regimen there were 2 subgroups, with one subgroup receiving Control IgG and the other subgroup receiving murine B7-H4-Ig. Both Control IgG and murine B7-H4-Ig were given at 3 mg/kg, 3 times a week for 4 weeks. Prevention treatment (FIG. 34) means that murine B7-H4-Ig or Control IgG was administered starting on the day at PLP immunization (t=0). Therapeutic treatment (FIG. 35) means that murine B7-H4-Ig or Control IgG was administered beginning on Day 21 (t=21). The data is presented as the mean clinical score over the 55 day time course with 5 mice per group, and the clinical scores and injection were conducted double blinded.

Figure 34:
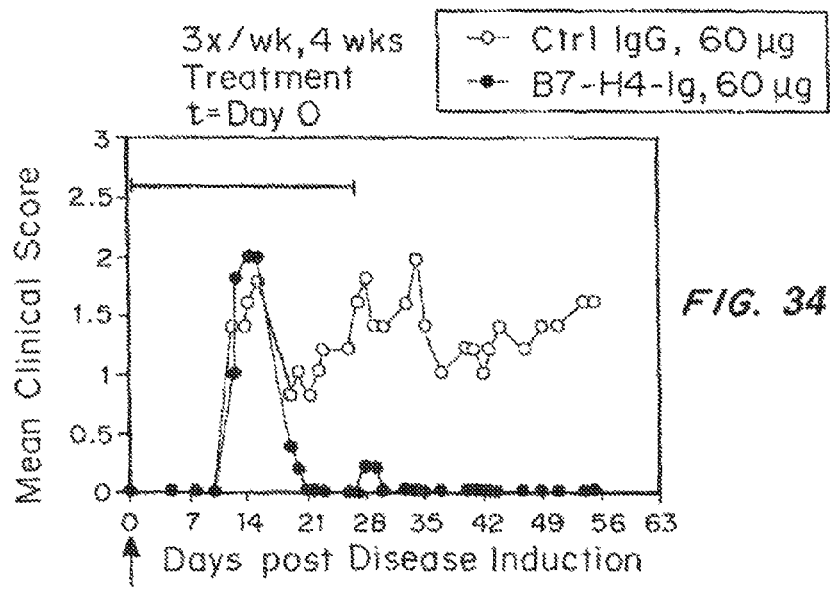
FIG. 34 is a line graph of mean clinical score versus days post disease induction in EAE induced SJL mice at treatment day=0 with 60 μg (3 mg/kg) control IgG (○); or 60 μg (3 mg/kg) B7-H4-Ig (●).
Figure 35:
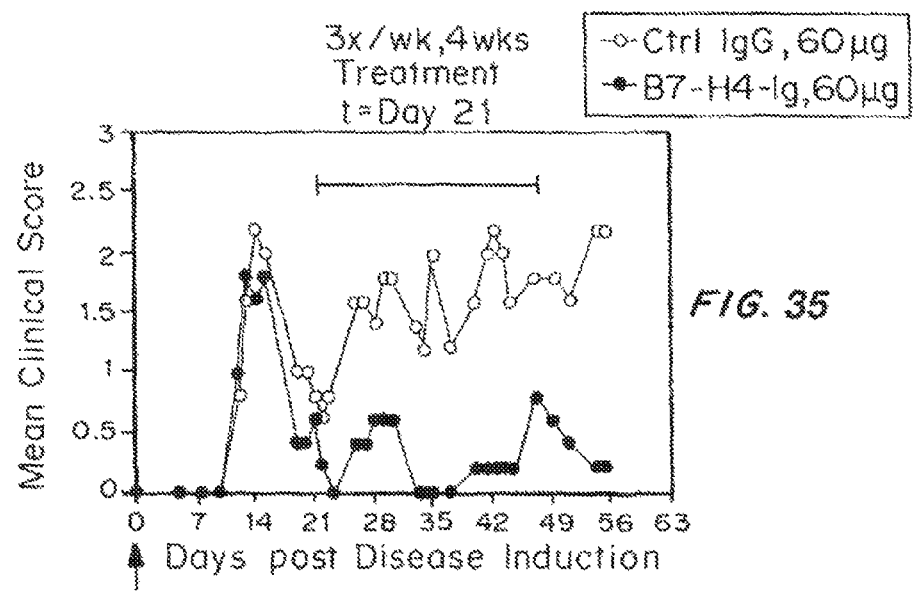
FIG. 35 is a line graph of mean clinical score versus days post disease induction in EAE induced SJL mice at treatment day=21 with 60 μg (3 mg/kg) control IgG (○); or 60 μg (3 mg/kg) B7-H4-Ig (●).

The data presented in FIGS. 34 and 35 show the clinical scores for murine B7-H4-Ig versus control IgG in both the preventative and therapeutic treatment regimens. The data shows that murine B7-H4-Ig decreased and/or prevented R-EAE disease relapse with both treatment regimens. The clinical scores on the control IgG injected R-EAE mice averaged 1.5 to 2.5, versus 0-0.5 for B7-H4-Ig treated animals. The difference between the murine B7-H4-Ig treated mice and Control IgG injected mice was significant.

B7-H4-Ig Prevents Epitope Spreading

Figure 36:
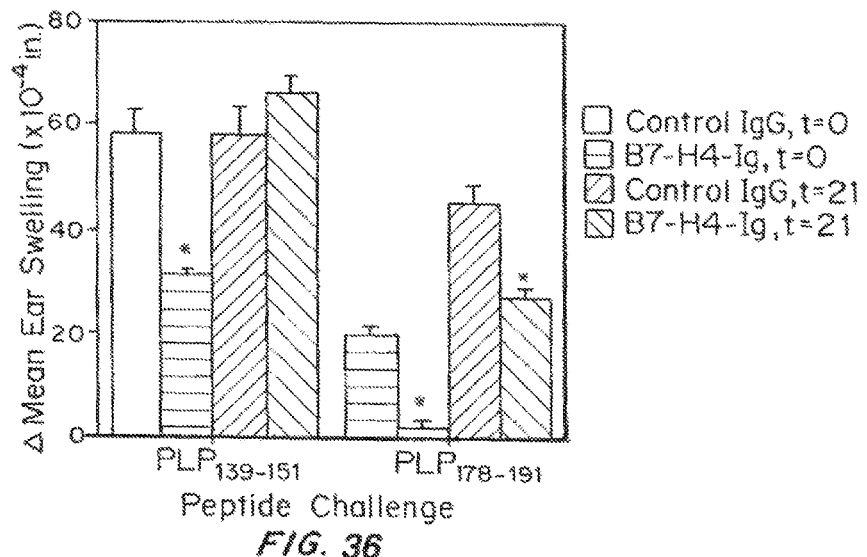
FIG. 36 is a bar graph of Delayed-Type Hypersensitivity (DTH) Responses at day 55 as measured by Mean Ear Swelling (×10$^{-4}$ inches) in EAE mice treated with control IgG or murine B7-H4-Ig at day 0 or day 21, following ear challenge with PLP$_{139-151}$ or PLP$_{178-191}$ on day 50. Open rectangle is control IgG administered at t=0, horizontal hatched rectangle is B7-H4-Ig administered at t=0, right hatched rectangle is Control IgG at t=21, and left hatched rectangle is B7-H4-Ig administered at t=21. *DTH response significantly less than Control IgG injected mice, p less than 0.01.

To determine the effect of B7-H4-Ig on blocking CD4+ T cell mediated activity specific for the primary myelin-derived epitope $PLP_{139-151}$ and epitope spreading, peptide-specific responses in vivo via DTH on all 4 treatment groups were analyzed. Mice were ear challenged with 10 μg of the indicated peptides on Day 50, and swelling was measured 24 h later. Ear swelling was evaluated and plotted in FIG. 36 (*DTH response significantly less than Control IgG injected mice, p less than 0.01). The present data show that murine B7-H4-Ig treatment significantly reduced the response to the dominant epitope $PLP_{139-151}$ with treatment starting on Day 0, and no inhibition of the $PLP_{139-151}$ response if murine B7-H4-Ig treatment was begun on Day 21. In contrast, the response to the spread epitope $PLP_{178-191}$-specific response was significantly reduced when murine B7-H4-Ig treatment was started on both Day 0 and Day 21.

B7-H4-Ig Reduced $PLP_{178-191}$ Specific T Cell Proliferation

Figure 37:
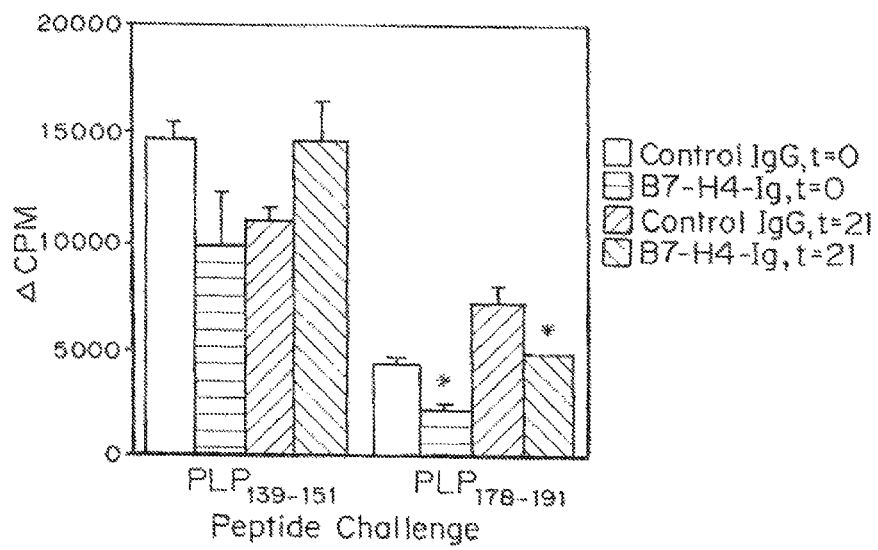
FIG. 37 is a bar graph of T cell proliferation (ΔCPU (counts per minute)) of T cells isolated from lymph nodes of EAE mice treated with B7-H4-Ig and Control IgG at day 0 or day 21, following treatment with PLP$_{139-151}$, the disease inducing dominant epitope, and PLP$_{178-191}$, the spread epitope-specific peptide, in vitro. Open rectangle is control IgG administered at t=0, horizontal hatched rectangle is B7-H4-Ig administered at t=0, right hatched rectangle is Control IgG at t=21, and left hatched rectangle is B7-H4-Ig administered at t=21. *[$^3$H]-thymidine incorporation significantly less than Control IgG injected mice, p less than 0.01.

Lymph nodes were isolated from the murine B7-H4-Ig and Control IgG injected EAE mice as described above. T cells were harvested and were elicited with $PLP_{139-151}$, the disease inducing dominant epitope, and $PLP_{178-191}$, the spread epitope-specific peptide, in vitro. [$^3$H]-thymidine was added to the in vitro stimulation assay to analyze T cell proliferation. In vitro peptide recall stimulation assays show that both murine B7-H4-Ig treatment regimens reduced $PLP_{178-191}$-specific (the spreading epitope) T cell proliferation in vitro (FIG. 37, *[$^3$H]-thymidine incorporation significantly less than Control IgG injected mice, p less than 0.01). There was no significant difference in $PLP_{139-151}$-specific (the primary peptide) T cell proliferation.

B7-H4-Ig Down Regulated $PLP_{139-151}$ and $PLP_{178-191}$ Specific T Cell Response Lymph nodes were isolated from Control IgG and murine B7-H4-Ig treated mice as described above. T cells were harvested and immune responses were elicited with $PLP_{139-151}$, the disease inducing dominant epitope, and $PLP_{178-191}$, the spread epitope peptide, in vitro. Supernatant was collected and analyzed for IFN-γ via commercially available ELISA kit.

Figure 38:
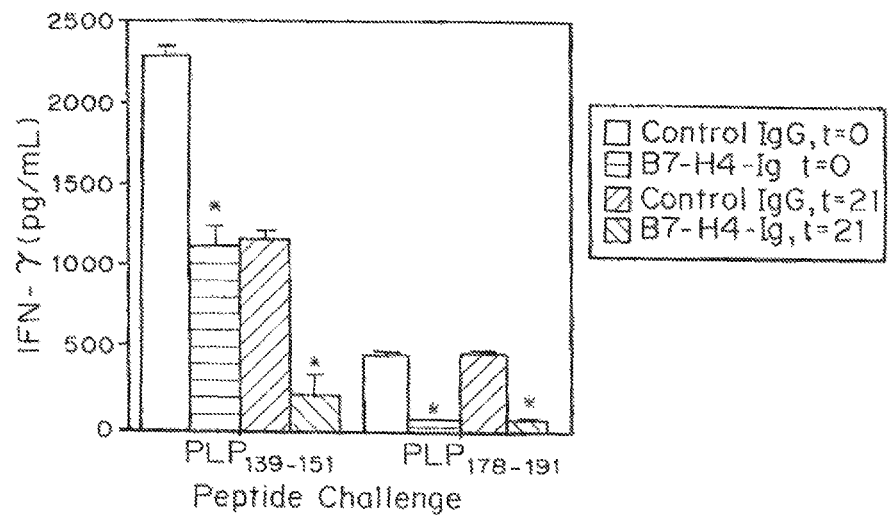
FIG. 38 is a bar graph of IFN-γ (pg/ml) produced by T cells isolated from lymph nodes of EAE mice treated with B7-H4-Ig and Control IgG at day 0 or day 21, following treatment with PLP$_{139-151}$, the disease inducing dominant epitope, and PLP$_{178-191}$, the spread epitope-specific peptide, in vitro. Open rectangle is control IgG administered at t=0, horizontal hatched rectangle is B7-H4-Ig administered at t=0, right hatched rectangle is Control IgG at t=21, and left hatched rectangle is B7-H4-Ig administered at t=21. *IFN-γ production significantly less than Control IgG injected mice, p less than 0.01.

The above experiments clearly show that B7-H4-Ig impacted the relapsing disease. DTH analysis (FIG. 36) and IFN-γ production as measured in ex vivo T cell recall studies using the $PLP_{139-151}$ peptide (FIG. 38, *IFN-γ production significantly less than Control IgG injected mice, p less than 0.01) demonstrate B7-H4-Ig specific inhibition of immune response to $PLP_{139-151}$ peptide when B7-H4-Ig was administered on Day 0, suggesting B7-H4-Ig may affect the acute disease phase.

B7-H4-Ig Prevents Epitope Spreading

Figure 39:
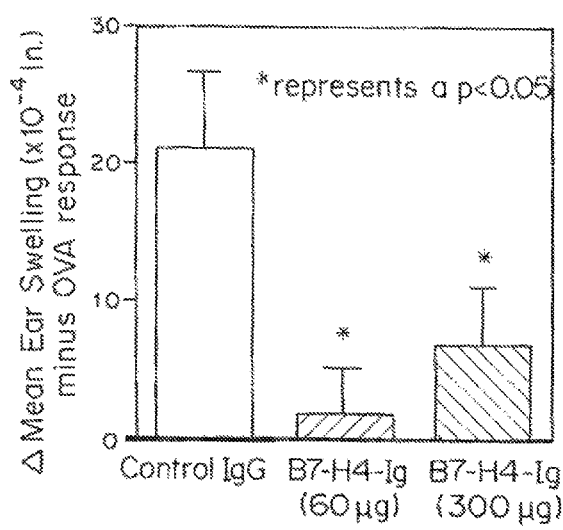
FIG. 39 is a bar graph of Δ Mean Ear Swelling (×10$^{-4}$ inches) minus OVA response in EAE mice treated with 5 injections of 60 μg B7-H4-Ig, 300 μg B7-H4-Ig, or Control IgG between day 0 and day 10 post disease induction, following ear challenge with PLP$_{139-151}$ or OVA$_{323-339}$ peptide (negative control) on day 10. *DTH response significantly less than Control IgG injected mice.

To clarify the effect of B7-H4-Ig on the EAE acute phase, a $2^{nd}$ in vivo experiment was conducted in the $PLP_{139-151}$ induced R-EAE model. DTH responses in murine B7-H4-Ig and Control IgG injected EAE mice were assayed as described above. Mice were ear challenged with 10 μg of $PLP_{139-151}$ on Day 10, and swelling was measured 24 h later. In this study, two different doses of B7-H4-Ig were given to SJL mice (n=10 per treatment group) on Day 0, at 60 μg (3 mg/kg) or 300 μg (15 mg/kg). After 5 injections of B7-H4-Ig, on Day 10 post disease induction, five mice were used for DTH analysis followed by ex vivo T cell antigen recall analysis. As shown in FIG. 39 (*DTH response significantly less than Control IgG injected mice), when B7-H4-Ig was given on Day 0, both 3 mg/kg (60 μg) and 15 mg/kg (300 μg) doses significantly inhibited the immune response to the inducing $PLP_{139-151}$ peptide as measured by the DTH response to $PLP_{139-151}$ peptide versus $OVA_{323-339}$ peptide (negative control).

Figure 40:
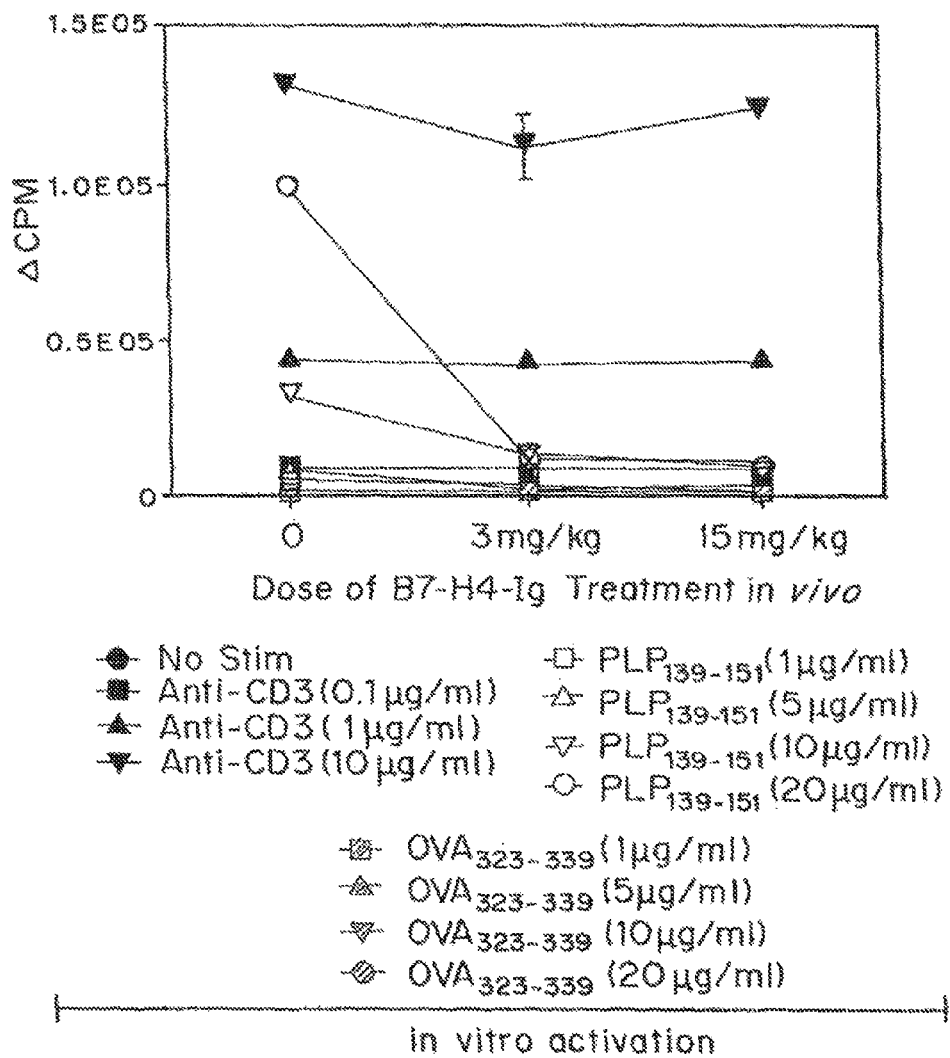
FIG. 40 is a line graph of proliferation (ΔCPU (counts per minute)) of T cells isolated from lymph nodes of EAE mice described in FIG. 42, reactivated in vitro in the presence of anti-CD3 (0.1-10 μg/mL), PLP$_{139-151}$ (1-20 μg/mL), or OVA$_{323-339}$ (1-20 μg/mL).

Draining lymph nodes were harvested from the animals, and single cell suspensions prepared as described above and reactivated in vitro in the presence of anti-CD3 (0.1-10 μg/mL), $PLP_{139-151}$ (1-20 μg/mL), or $OVA_{323-339}$ (1-20 μg/mL). T cell proliferation in vitro was analyzed by [$^3$H] thymidine incorporation. FIG. 40 (*[$^3$H]-thymidine incorporation significantly less than Control IgG injected mice, p less than 0.01) shows robust T cell proliferation with cells from both Control IgG and B7-H4-Ig injected mouse groups when stimulated with anti-CD3, while the negative control peptide, $OVA_{323-339}$, did not elicit any response. In contrast, T cells from B7-H4-Ig injected groups, at both 3 and 15 mg/kg doses, showed little to no response to $PLP_{139-151}$ peptide stimulation. Both the DTH response and the ex vivo T cell proliferation upon primary $PLP_{139-151}$ peptide recall demonstrate that B7-H4-Ig protects against the EAE acute phase in addition to its clear effect on relapsing disease.

Example 11: B7-H4-Ig Blocks Pathogenic $CD4^+$ T Cell Infiltration and Promotes Accumulation of Tregs Materials and Methods
Immunochemical Staining Mice were anesthetized with nembutal and perfused with phosphate-buffered saline (PBS). Brains and spinal cords from each mouse were frozen in OCT (Miles Laboratories; Elkhart, Ind.) in liquid nitrogen. Tissue from the lower lumbar region of the spinal cord was sectioned at 6 µm on a Reichert-Jung 1800 cryotome and mounted on Superfrost Plus electrostatically charged slides. Cross-sections (10 µm thick for brains and 6 µm for spinal cords) from longitudinal sections of brain and spinal cord were performed. Tissues were stained with biotin-conjugated antibody to mouse CD4, PLP and FoxP3. Positive staining of biotinylated antibodies was visualized by a Tyramide Signal Amplification (TSA) Direct kit (NEN, Boston, Mass.) according to manufacturer's instructions and fluoroscein anti-mouse IgG (Vector Laboratories). Sections were counterstained with 4,6-diamidino-2-phenylindole (DAPI; Sigma-Aldrich) and then coverslipped with Vectashieldmounting medium (Vector Laboratories). Slides were examined and images were acquired via epifluorescence using the SPOT RT camera (Diagnostic Instruments, Sterling Heights, Mich.). Sections from each group were analyzed at 40 or 100× magnification.

Results

The in vitro iTreg induction study with B7-H4-Ig provides evidence that B7-H4-Ig promotes iTreg differentiation (Example 8). Using purified nTreg cells from FoxP3-GFP transgenic mice in the in vitro suppression assay, a decrease in activation and proliferation of $CD4^+$ T effector cells by B7-H4-Ig was demonstrated (Example 9, FIG. 38). The addition of B7-H4-Ig to the suppression assay in the presence of low numbers of nTreg cells has a significant effect on blocking effector T cell activation and proliferation in vitro.

Figure 41:
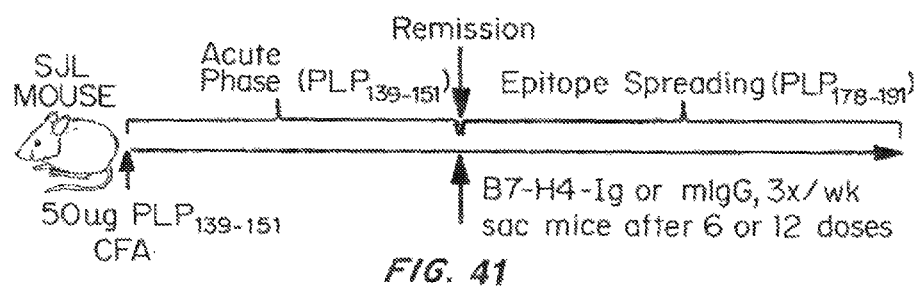
FIG. 41 is a schematic illustration of experimental auto-immune encephalomyelitis (EAE) induction and treatment regimen in an in vivo study utilizing an auto-immune R-EAE murine model for Multiple Sclerosis (MS).

The effect of B7-H4-Ig treatment on the number of Treg cells in vivo was analyzed in this study. The effect of B7-H4-Ig on the number and phenotype of $CD4^+$ T cells infiltrating into the CNS following B7-H4-Ig treatment, the relevant site for activity in vivo, was determined. As shown in FIG. 41, SLJ mice (10 mice per groups) were immunized with $PLP_{139-151}$ following the standard protocol to induce R-EAE disease. SJL mice were first immunized with $PLP_{139-151}$ peptide. B7-H4-Ig treatment started during remission (Day 23). Mice received mouse Control IgG, 100 µg, or B7-H4-Ig at either 60 or 300 µg, 3 times per week for 2 weeks or 4 weeks. Half of the animals (5 mice from each group) were euthanized on Day 35, after 6 doses of B7-H4-Ig. The rest of the animals (5 mice from each group) were euthanized on Day 50, after 12 doses of B7-H4-Ig. Mouse spleens, draining lymph nodes, spinal cords and brains were collected, tissues were made into a single cell suspension and counted via the use of a hemocytometer, and analyzed for the presence of effector/memory $CD4^+$ T cells ($CD4^+CD44^+$) and Treg cells ($CD4^+CD25^+FoxP3^+$). Whole cerebellar and lumbar spinal cord tissue samples were snap frozen and processed as described above to analyze the number of $CD4^+$ and $FoxP3^+$ cells present within the CNS by histology.

Figure 42A:
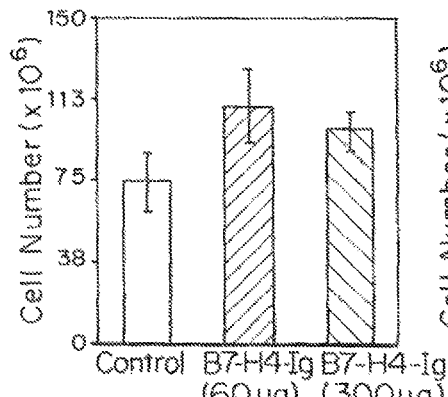
FIGS. 42A, 42B, and 42C are bar graphs showing the total lymphocyte cell number (×10$^6$) in the spleen (A), draining lymph nodes (B), and CNS (C) isolated on day 50 from SJL mice immunized with 50 μg of PLP peptide emulsified in CFA. Mice were treated with Control IgG or B7-H4-Ig during remission: 60 or 300 μg per dose, 3 doses/wk, for 2 weeks (6 doses).
Figure 42B:
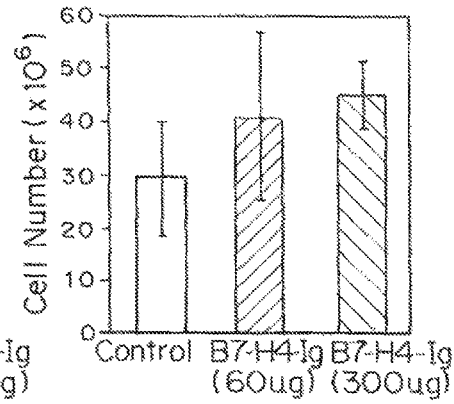
Figure 42C:
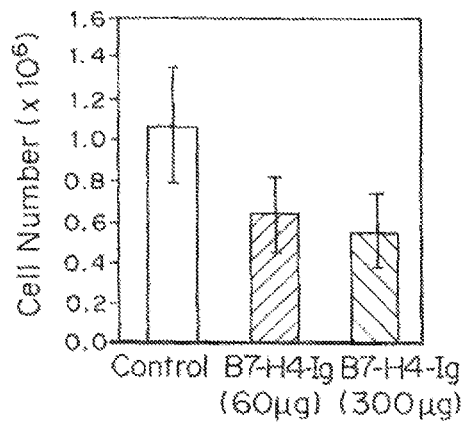

As demonstrated in FIGS. 42A, 42B, and 42C, treatment with murine B7-H4-Ig showed a trend toward increasing numbers of $CD4^+$ T cells in the spleens (42A) and the draining lymph nodes (42B), and in contrast a decrease in the total numbers of infiltrating $CD4^+$ T cells within the CNS (42B) after 6 treatments.

Figure 43A:
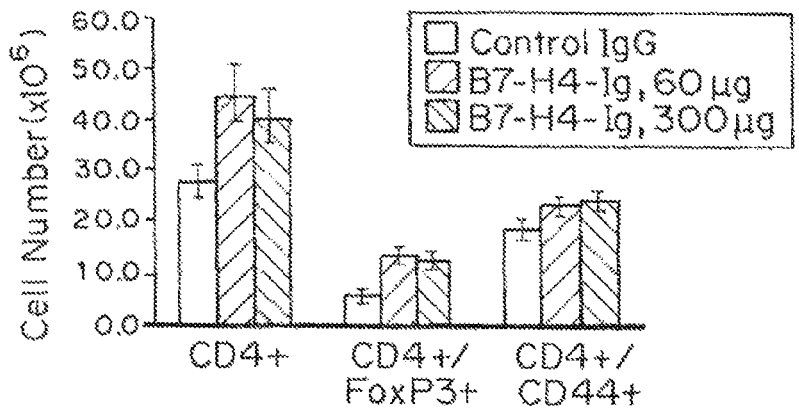
FIGS. 43A, 43B, and 43C are bar graphs showing T cell subset number (×10$^6$) isolated from the spleen (A), draining lymph node (B), or CNS (C) as described in FIGS. 42A, 42B, and 42C, respectively, which were CD4 (T cells), CD4+/FoxP3+ (Treg), and CD4+/CD44+ (effector/memory T cells). The data is presented as the mean number of cells for each phenotype from individual mouse.
Figure 43B:
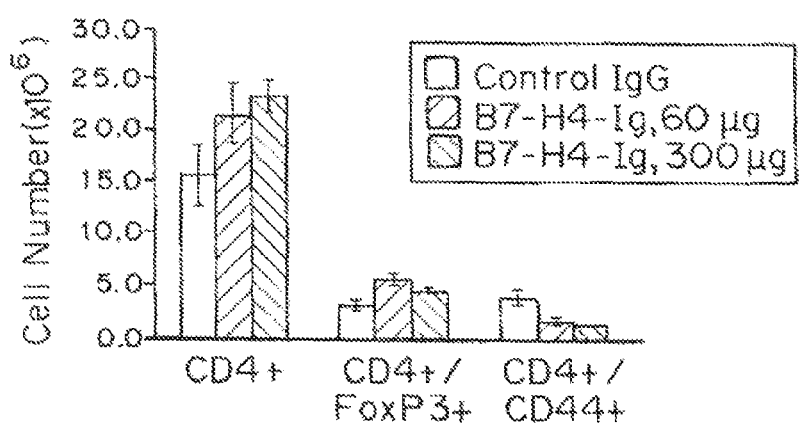
Figure 43C:
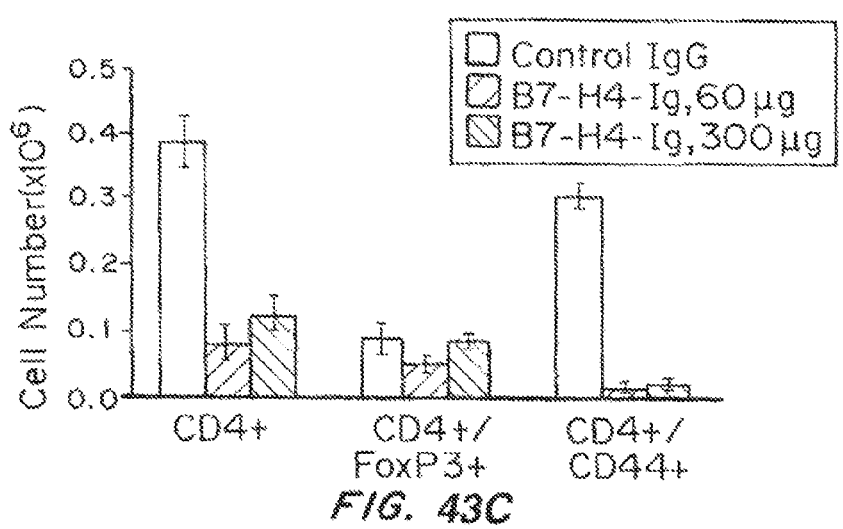
Figure 44:
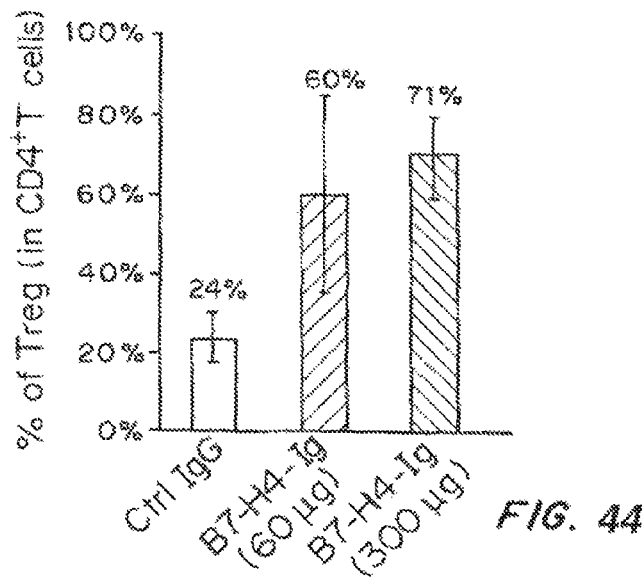
FIG. 44 is a bar graph showing the percentage of Treg in CD4+ T cells from FIG. 43C, for Control IgG, 60, or 300 μg B7-H4-Ig treatments.

Cells isolated from spleen, draining lymph node and also lumbar spinal cord were stained for CD4, CD44 and FoxP3 followed by FACS analysis to obtain the number of total $CD4^+$ T cells, Treg ($CD4^+/Foxp3^+$) and effector/memory $CD4^+$ T cells ($CD4^+/CD44^+$). The data is presented in FIGS. 43A, 43B, and 43C as the mean number of cells for each phenotype from individual mouse. When the number of Treg ($CD4^+/FoxP3^+$) cells was calculated, B7-H4-Ig treatment remarkably increased the number of Treg cells within the spleen (43A) and lymph node (43B), suggesting the increase in the $CD4^+$ T cell population was due in part to the increase of Treg cells. B7-H4-Ig treatment also decreased effector/memory T cells ($CD4^+/CD44^+$) within the CNS when compared to Control IgG treated mice (43C). Similar data was obtained after the full course of 12 treatments. FIGS. 43A, 43B, and 43C also reveals that while there were fewer $CD4^+$ T cells infiltrating into the CNS, the amount of Treg cells in the CNS appeared constant (43C), indicating that B7-H4-Ig altered the ratio of Treg cells to total $CD4^+$ T cells within the CNS. Indeed, as shown in FIG. 44, the percentage of Treg cells among $CD4^+$ T cells was significantly higher in the CNS from B7-H4-Ig treated mice compared with CNS from Control IgG injected mice.

The level of demyelination via anti-PLP staining in control IgG and B7-H4-Ig treated mice was also analyzed. The results indicate that there is not a significant, detectable difference in the level of PLP staining between groups, i.e., no significant difference in the level of demyelination. However, the T cell infiltrates into the CNS were also examined histologically, by staining and counting the total number of $CD4^+$ T cells, and $FoxP3^+$ cells in cross section samples taken from the lumbar spinal cord. Histological data correlates with the flow cytometric analysis with regard to the total number of $CD4^+$ T cells and the number of $FoxP3^+$ Treg cells present. The histology data is in line with the FACS data in demonstrating that B7-H4-Ig treatment increases the number of $FoxP3^+$ cells within the CNS. It also shows that the $FoxP3^+$ cells are co-localized with effector $CD4^+$ T cells within the CNS, allowing them to exert their suppressive effect on pathogenic T cells.

Overall the data clearly demonstrate that B7-H4-Ig treatment favorably alters the ratio of Treg cells to total $CD4^+$ T cells within the CNS, and is consistent with the proposed mechanism of action which suggests that B7-H4-Ig treatment both inhibits CD4+ T cell activation and increases Treg cell function and/or numbers. Similar findings were achieved after the full 12 doses (Day 50 post disease induction).

Figure 45A:
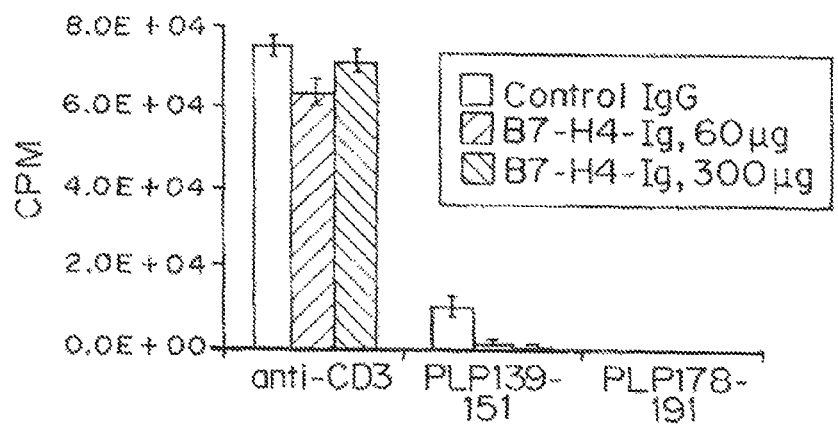
FIGS. 45A and 45B are bar graphs showing the proliferation (CPU (counts per minute)) of total splenocytes (A) and lymph node cells (B) isolated on day 35 from SJL mice immunized with 50 μg of PLP peptide emulsified in CFA, and activated in vitro in the presence of anti-CD3 (1μg/ml), PLP$_{139-151}$ or PLP$_{178-191}$ (20 μg/mL). Mice were treated with Control IgG or B7-H4-Ig during remission: 60 or 300 μg per dose, 3 doses/wk, for 2 weeks (6 doses).
Figure 45B:
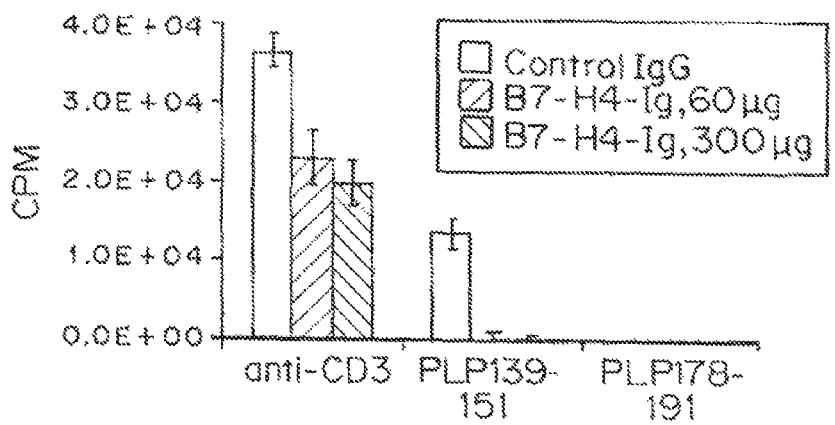
Figure 46:
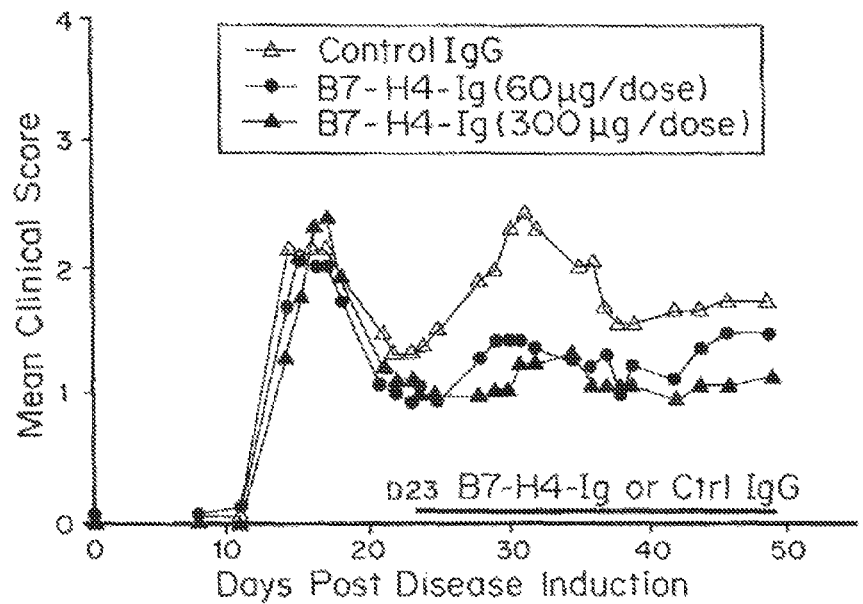
FIG. 46 is a line graph showing the mean clinical score of SJL mice over the 50 day time course (days) following disease induction. Mice were treated with 60 μg B7-H4-Ig (-●-), 300 μg B7-H4-Ig (-▲-), or Control IgG (-Δ-) three time a week beginning on day 23 post disease induction.

The impact of B7-H4-Ig treatment on epitope spreading was also examined. To do so, spleens and draining lymph nodes were collected from the same mice that were analyzed for the number and phenotype of $CD4^+$ T cells. SJL mouse were immunized with 50 µg of $PLP_{139-151}$ peptide emulsified in CFA. Mice were treated B7-H4-Ig during remission: 60 or 100 ug per dose, 3 doses/wk, for 2 weeks (6 doses). On Day 35 total splenocytes and lymph node cells ($5 \times 10^5$ cells per 200 ul culture) were activated in separate wells per mouse in the presence of anti-CD3 (1 µg/ml), $PLP_{139-151}$ or $PLP_{178-191}$ (20 µg/mL). At 24 hours following the initiation of culture, 1 µCi of $^3[H]$ tritiate thymidine was added to each well and wells were analyzed at 72 hours post the initiation of culture. This presented as the mean CPM. As shown in FIGS. 45A and 45B, treatment of mice with B7-H4-Ig decreased the proliferative response to both PLP$_{139-151}$ and PLP$_{178-191}$. Therefore, B7-H4-Ig treatment during remission of ongoing R-EAE in SJL mice appears to decrease epitope spreading via an increase in the number of Treg cells. The mean clinical score of this study presented in FIG. 46 show that B7-H4-Ig at both 3 mg/kg (60 μg/dose) and 15 mg/kg (300 μg/dose) doses significantly prevented the primary relapsing. The higher dose appears more efficacious to lower the disease score at later time points (beyond Day 42 post disease initiation).

Example 12: In Vivo Bioactivity of Human B7-H4-Ig in PLP Induced R-EAE Model

Figure 47:
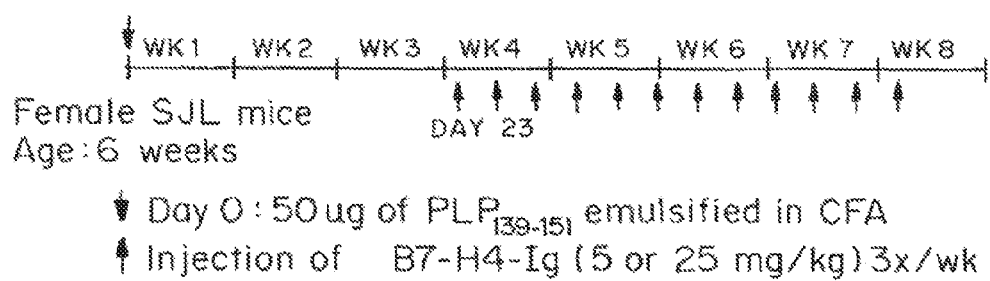
FIG. 47 is a schematic illustration of experimental auto-immune encephalomyelitis (EAE) induction and treatment regimen of human B7-H4-Ig in an in vivo study utilizing an auto-immune R-EAE murine model for Multiple Sclerosis (MS).

Human B7-H4-Ig was also tested for its therapeutic efficacy in the PLP$_{139-151}$-induced R-EAE mouse model. SJL mice were first immunized with PLP$_{139-151}$ peptide. Female SJL mice were first immunized with PLP$_{139-151}$ peptide emulsified in CFA and on Day 23 randomized into 3 groups. One group received control human IgG1 (Synagis), at 5 mg/kg (100 μg), 3 times a week for 4 weeks. The other 2 groups were given B7-H4-Ig at 5 or 25 mg/kg, 3 times a week for 4 weeks (FIG. 47). The disease course was followed for approximately 2 months to assess clinical disease following the grading system shown in Table 12 and long-term relapse rate as described above.

Figure 48A:
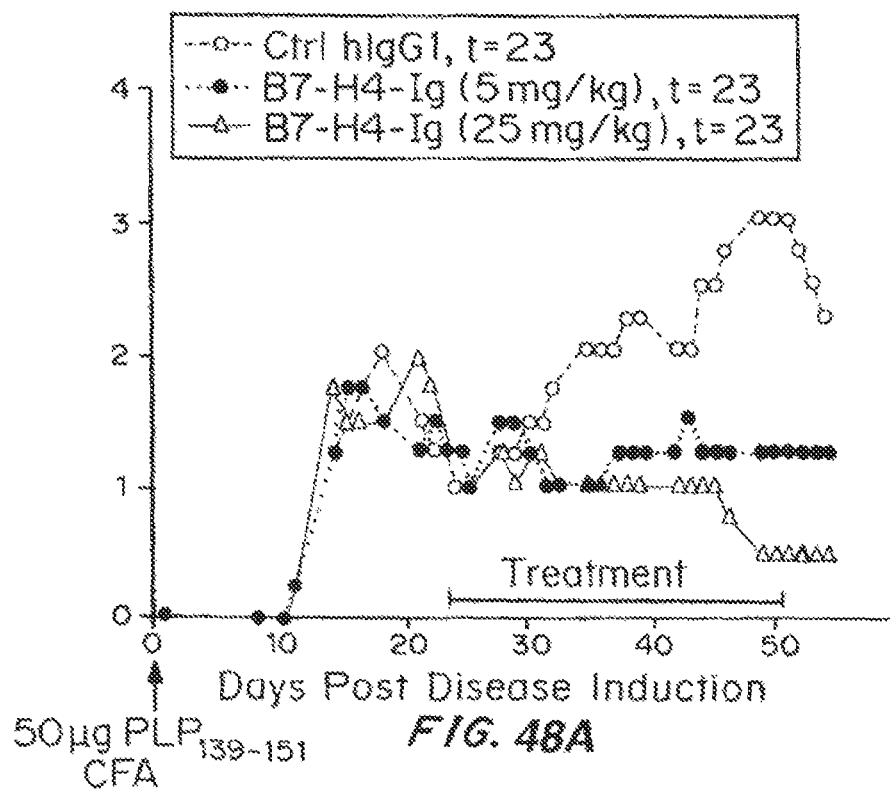
FIGS. 48A and 48B are line graphs showing the mean clinical score (A) and long term relapse rate (B) of SJL mice over the 55 day time course (days) following disease induction. Mice were treated with 100 μg human B7-H4-Ig (5 mg/kg), 500 μg human B7-H4-Ig (25 mg/kg), or 100 μg Control IgG, Synagis®, (5 mg/kg) three times a week for 4 weeks beginning on day 23 post disease induction.
Figure 48B:
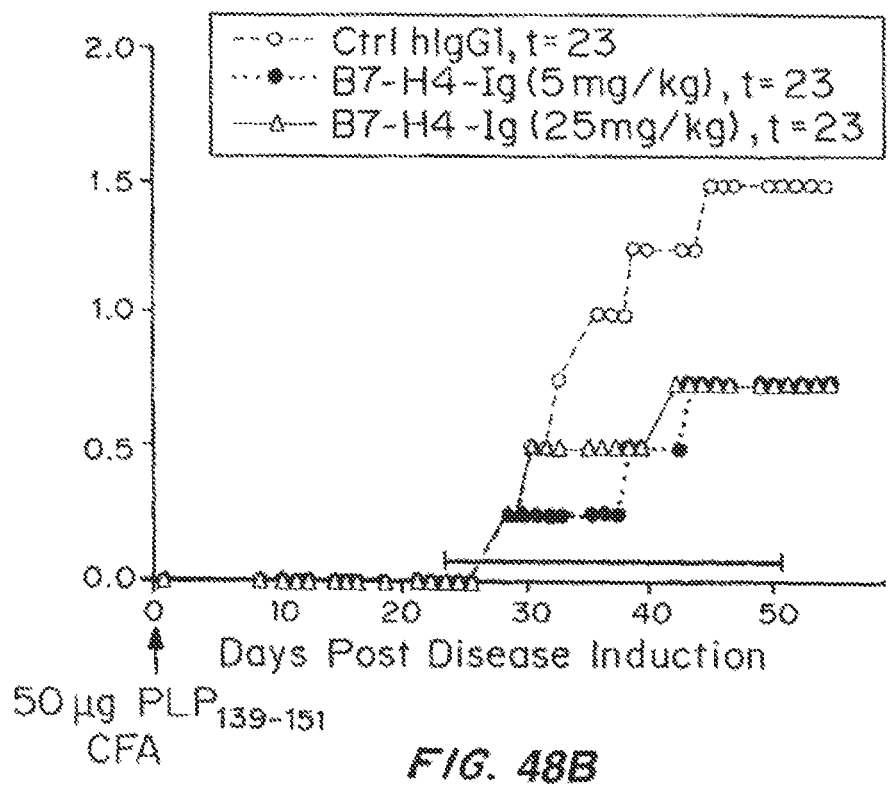

As shown in the FIGS. 48A and 48B, at two different dosing levels, 5 or 25 mg/kg, human B7-H4-Ig inhibited the primary disease relapse as determined by a reduction of mean clinical score (48A) and reduction in long-term relapse rate (48B). The higher dose (25 mg/kg) appears to result in a lower mean clinical score (48A); however, there was no difference in the relapse frequency between the low dose and high dose groups (48B); both doses were equally as effective in preventing relapsing episodes.

The data presented in Examples 5-12 show the highly effective and reproducible, therapeutic efficacy of B7-H4-Ig treatment in PLP$_{139-151}$-induced relapsing-remitting EAE (R-EAE). In addition, the bioactivity of B7-H4-Ig was determined both in vivo and in vitro. The data show that murine B7-H4-Ig inhibited proliferation and differentiation of naïve OVA$_{323-339}$-specific transgenic CD4$^+$ T cells stimulated in Th1 and Th17 lineage driving conditions in vitro. B7-H4-Ig also decreased the level of IFN-γ and IL-17 produced by Th1 cells and Th17 cells, respectively. The reduction of IL-17 skewing was less pronounced when CD4$^+$CD25$^+$ T regulatory cells were depleted from the AutoMax-purified CD4$^+$CD62L$^+$ naïve CD4$^+$ T cells, which in turn suggested that B7-H4-Ig also acts directly upon Tregs to inhibit Th17 effector differentiation and function. The effect of murine B7-H4-Ig on induction of inducible regulatory T cells (iTreg) in vitro using naïve CD4$^+$ T cells expanded in the presence of suboptimal concentrations of TGF-β and IL-2 for the induction of iTreg differentiation was also tested. The data showed that B7-H4-Ig enhances the differentiation of naïve CD4$^+$ T cells toward an iTreg phenotype in a dose-dependent manner as determined by FACS analysis of the FoxP3$^+$/CD25$^+$ cell population. Thus, B7-H4-Ig simultaneously targets multiple key pathogenic, inflammatory pathways involved in MS and other autoimmune diseases and further suppresses inflammation by inducing Tregs. This is the first direct evidence that B7-H4-Ig promotes iTreg induction. Coupled with its effects on Th1 and Th17 cell differentiation, this distinguishes B7-H4-Ig from all other drugs being developed for MS.

B7-H4-Ig was further tested for its ability to modulate the suppressive function of Tregs in an in vitro suppression assay. Natural Treg (nTreg) cells were purified from FoxP3-GFP transgenic mice using a MoFlo cell sorter to obtain CD4$^+$/FoxP3-GFP$^+$ nTreg cells. CD4$^+$/GFP$^-$ T responder cells were stimulated with an anti-CD3 antibody in the presence or absence of CD4$^+$/GFP$^+$ nTreg cells and murine B7-H4-Ig. In the absence of nTreg cells, B7-H4-Ig inhibited CD4$^+$ T cell activation and proliferation in a dose-dependent fashion, confirming previous findings. In the absence of murine B7-H4-Ig, nTreg cells prevented CD4$^+$ T cell activation and proliferation in a cell number dependent manner. However, a significant increase in the level of immune suppression of responder CD4$^+$/GFP$^-$ T cells was observed when both nTreg and B7-H4-Ig were present. The above in vitro analysis of B7-H4-Ig supports the model that B7-H4-Ig not only blocks naïve CD4$^+$ T cell activation and inhibits the differentiation of naïve helper T cells into pro-inflammatory Th1 and Th17 subsets, but also enhances naïve CD4$^+$ T cell differentiation into iTreg.

The ability of B7-H4-Ig to modulate the induction and progression of R-EAE in vivo was also tested. In the 1$^{st}$ in vivo study, the initiation of B7-H4-Ig treatment on the day of PLP$_{139-151}$/CFA peptide priming did not affect disease symptoms during the acute phase of R-EAE, but inhibited the primary disease relapse as determined by a significant reduction in mean clinical score and DTH responses to the spreading PLP$_{178-191}$ epitope. Likewise, initiation of B7-H4-Ig treatment during disease remission (Day 21 post disease induction) significantly reduced the severity of disease relapse concomitant with inhibition of T cell responses to the spreading PLP$_{178-191}$ epitope. In a repeat R-EAE study, in contrast to the first in vivo study, B7-H4-Ig treatment starting on the day of PLP$_{139-151}$/CFA peptide priming was shown to affect the disease symptoms during the acute phase of R-EAE. Subsequently, it was demonstrated that murine B7-H4-Ig increased Treg cell number in the periphery of treated mice. B7-H4-Ig blocked pathogenic CD4$^+$ T cell infiltration into the CNS and increased the percentage of protective Tregs in the CNS of R-EAE mice. This may explain the effect of B7-H4-Ig on both the primary and relapsing state of disease.

Human B7-H4-Ig was tested both in vitro and in vivo. Results from in vitro bioanalysis show that human B7-H4-Ig cross-reacted with murine naïve CD4$^+$ T cells and that it blocked murine Th1/Th17 proliferation and differentiation. Results from an in vivo R-EAE experiment revealed that human B7-H4-Ig inhibited disease as determined by a reduction in both the mean clinical score and the long-term relapse rate. Furthermore, identical in vitro and in vivo bioactivity was shown for B7-H4-Ig from different batches (lots) demonstrating consistency of the B7-H4-Ig production process. Taken together the present findings suggest that B7-H4-Ig induces an increase in the number and/or function of Tregs, and decreases Th1/Th17 responses.

Example 13: Diabetes Mouse Models

CTLA4KD/NOD Mice
Methods and Materials
Both female and male CTLA4KD/NOD mice (Chen et al., PNAS, 103(44):16400-16405 (2006)) at age of 2 weeks were randomly assigned into experimental groups: vehicle (11 mice), and B7-H4-Ig (12 mice). Mice were treated with B7-H4-Ig 3 times per week for 4 weeks (15 mg/kg, per i.p. injection), and monitored 3 times per week for glucose content in the urine first with Diastix. If Diastix showed positive, plasma was collected for blood glucose level. Diabetes was determined when blood glucose reached ≥600 mg/dL.

Results

Figure 49:
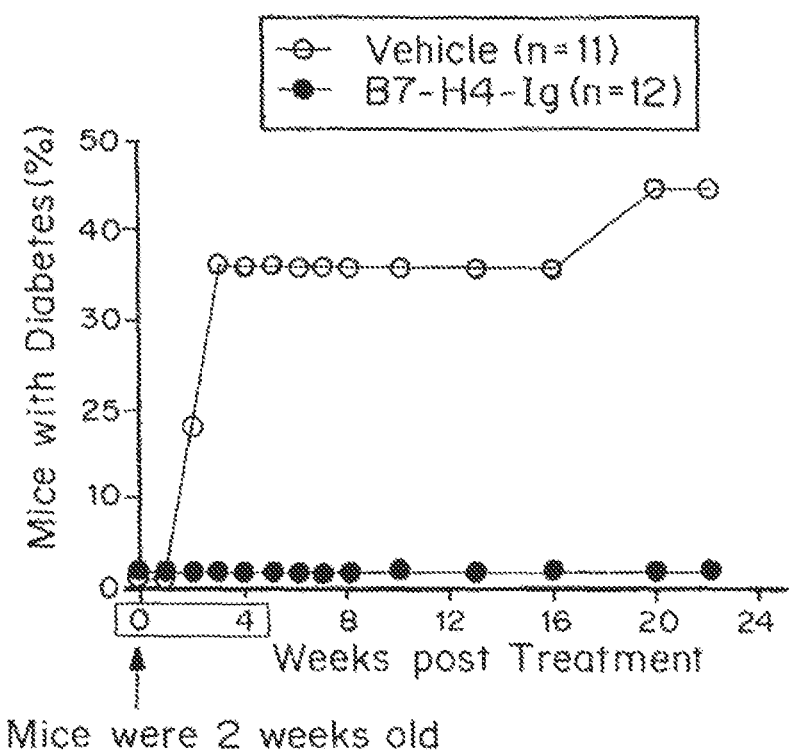
FIG. 49 is a line graph of % CTLA$_4$KD/NOD mice with diabetes versus weeks post treatment with B7-H4-Ig 3 times per week for 4 weeks (15 mg/kg, per i.p. injection). Mice were two weeks old.

FIG. 49 shows B7-H4-Ig prevents autoimmune diabetes development in CTLA$_4$KD/NOD mice. CTLA$_4$KD/NOD mice at age of 2 weeks were injected with either vehicle or B7-H4-Ig 3 times per week for 4 weeks (15 mg/kg, per i.p. injection). In line with published data (Chen et al., *PNAS, Modeling CTLA4-linked autoimmunity with RNA interference in mice,* 2006), 30-40% of the vehicle injected mice developed diabetes when the mice were 5 weeks old (3 weeks post vehicle injection). The B7-H4-Ig treated CTLA$_4$KD/NOD mice did not develop diabetes when the mice were 24 weeks old (22 weeks post B7-H4-Ig treatment).

CTLA$_4$KD/BDC2.5/NOD Mice

Methods and Materials

CTLA4KD/NOD mice (Chen, et al., *PNAS* (2006)) were bred with BDC2.5 TCR transgenic mice (Katz, et al., *Cell,* 74(6):1089-100 (1993)). Both female and male mice at age of 11 weeks were randomly assigned into experimental groups: vehicle (3 mice), and B7-H4-Ig (5 mice). Mice were treated with B7-H4-Ig 3 times per week for 4 weeks (15 mg/kg, per i.p. injection), and monitored 3 times per week for glucose content in the urine first with Diastix. If Diastix showed positive, plasma was collected for blood glucose level. Diabetes was determined when blood glucose reached ≥600 mg/dL.

Results

Figure 50:
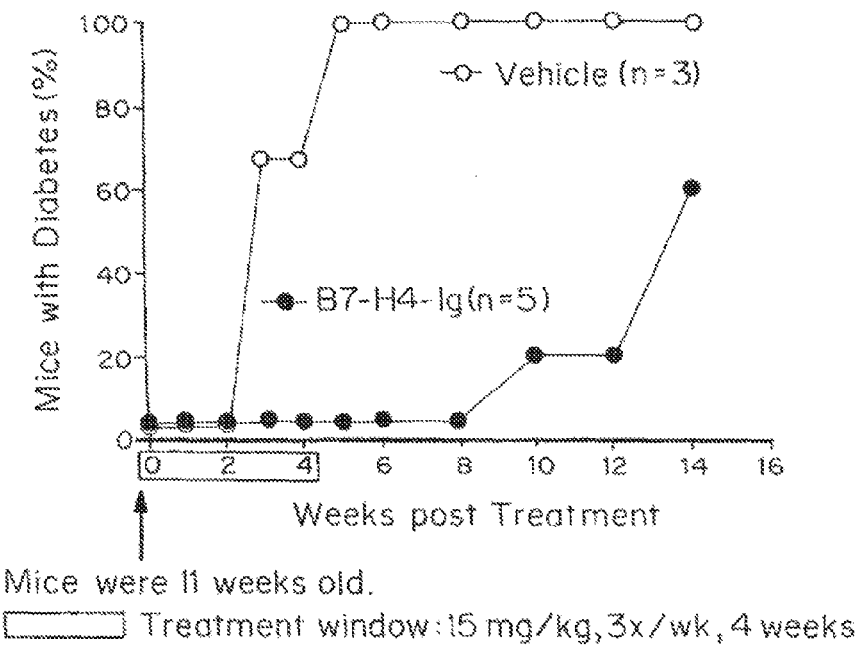
FIG. 50 is a line graph of % CTLA$_4$KD/BDC$_{2.5}$/NOD mice with diabetes versus weeks post treatment with B7-H4-Ig 3 times per week for 4 weeks (15 mg/kg, per i.p. injection). Mice were eleven weeks old.

FIG. 50 shows B7-H4-Ig delayed autoimmune diabetes in CTLA4KD/BDC2.5/NOD mice. CTLA4KD/BDC2.5/NOD mice at age of 11 weeks were injected with either vehicle or B7-H4-Ig 3 times per week for 4 weeks (15 mg/kg, per i.p. injection). In line with historical data (in communication with Dr. Chen), 100% of the vehicle injected mice developed diabetes when the mice were 16 weeks old (5 weeks post vehicle injection). The B7-H4-Ig treated CTLA4KD/BDC2.5/NOD mice did not develop diabetes until the mice reached 21 weeks old (10 weeks post B7-H4-Ig treatment).

Example 14: B7-H4-Ig Enhances Treg Activity

Methods and Materials

Preparation of Enteroantigen from Fecal Extracts

Extracts were prepared by removing the colon and cecum from mice and placing the content in PBS. This was sonicated 3 times for 30 seconds on ice, followed by centrifugation at 10,000 g for 10 min to remove insoluble material. The supernatant was collected, sterile filtered, and stored at −60° C. The protein concentration in the supernatants was typically 1 to 1.5 mg/mL as determined by the bicinchoninic acid (BCA) method.

B7-H4-Ig Treatment

Female wild-type Balb/c, 7 to 9 weeks of age, were injected with either 60 μg or 300 μg of B7-H4-Ig, intraperitoneally (IP), 3 times a week for 2 weeks. There were 5 mice in each group. B7-H4-Ig treated mice and also naïve control mice were euthanized for T cell isolation after 2 week treatment.

Preparation of CD4$^+$CD25$^-$ T Cells and CD4$^+$ CD25$^+$ T Cells

The CD4$^+$CD25$^-$ T cells were obtained as follows: CD4$^+$ T cells were positively selected from spleen single-cell suspensions using a mouse anti-CD4 monoclonal antibody-coated DYNABEAD® and the DETACHABEAD® system (Dynal AS, Oslo, Norway) according to the manufacturer's instructions. Then the CD4$^+$ T cells (<98% pure assessed by flow cytometry) were separated into CD25$^+$ and CD25$^-$ T cell populations by Miltenyi's magnetic bead technology (MACS®, Miltenyi Biotech, Belgisch Gladbach, Germany) using PE-labeled anti-CD25 monoclonal antibody, followed by the addition of anti-PE microbeads and depletion according to the manufacturer's instructions.

Preparation and Pulse of Antigen-Presenting Cells

Normal spleen cells from BALB/c mice were used as antigen-presenting cells (APC). The spleen cells were adjusted to 8×10$^6$ cells/mL, and 400 μg extract enteroantigen in a final volume of 2 mL was mixed in 24-well plates for antigen presentation. After incubation for 18 hours, the cells were washed 3 times in medium and irradiated (3000 rad) to eliminate APC proliferation.

Proliferation Assay

APCs were adjusted to 1.0×10$^6$ cells/mL, and 100 μL was added to each well of a 96-well round-bottom culture plate. CD4+CD25$^-$ T cells isolated from Balb/C mice were adjusted to 1×10$^6$ cells/mL, and 100 μL was added to the APCs. After 4 days of culture, proliferation was measured by adding 0.5 μCi of [$^3$H]-thymidine to each well, incubating for 18 hours, and harvesting the cells to count the incorporated thymidine.

Results

Figure 51:
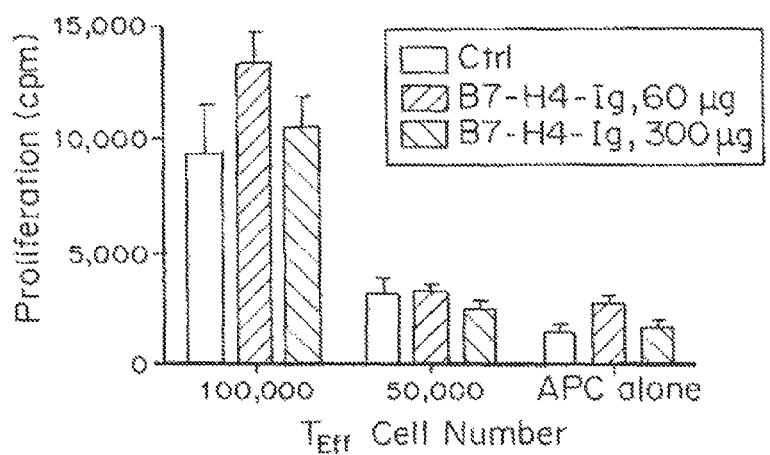
FIG. 51 is a bar graph of percent proliferation in Treg cells from control mice and mice treated with different doses of B7-H4-Ig. Treg cells were titrated into a 5 day enteroantigen specific CD4+CD25− proliferation assay. Each column represents mean cpm values of four replicate cultures expressed in percent of cultures not exposed to Treg and bars represent SD. Each group of three columns in the graph from left to right represents Tregs from mice treated with a control, B7-H4-Ig (60 µg) or B7-H4-Ig (300 µg).

In a standard in vitro, enteroantigen priming and proliferation assay, normal mouse CD4$^+$CD25$^-$ T cells were first added into 96-well plate and mixed with enteroantigen pulsed APC. CD4$^+$CD25$^+$ Treg cells were isolated from control or B7-H4-Ig treated mice and added in the above culture at 0, 6250, 12500 and 25000 Treg/well. FIG. 51 shows that Tregs from B7-H4-Ig treated mice were more potent in blocking enteroantigen priming and T cell proliferation when compared to Tregs from control mice. In addition, mice treated with a higher dose B7-H4-Ig (300 μg) gave rise to more effective Treg when compared to lower dose B7-H4-Ig (60 μg) treated ones, indicating a dose-dependent effect.

Figure 52:
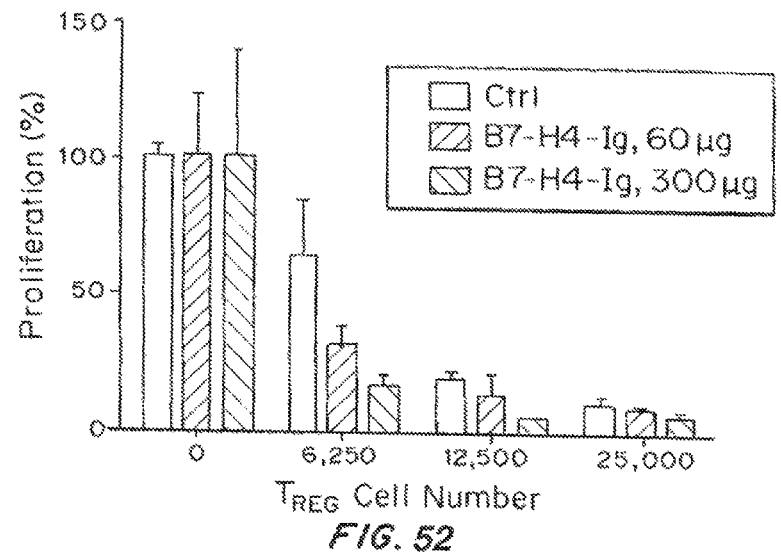
FIG. 52 is a bar graph of proliferation (cpm) in CD4+ CD25− cells recovered from control mice or mice treated with B7-H4-Ig and exposed to enteroantigen pulsed splenocyte APC for 5 days. Each column represents mean cpm values of four replicates cultures and bars represent SD. Each group of three columns in the graph from left to right represents Tregs from mice treated with a control, B7-H4-Ig (60 µg) or B7-H4-Ig (300 µg).

CD4$^+$CD25$^-$ T cells from B7-H4-Ig treated mice were also assessed for their responsiveness to enteroantigen priming and proliferation. FIG. 52 shows CD4$^+$CD25$^-$ T effector cells from B7-H4-Ig treated mice responded well to enteroantigen pulsed APC and that B7-H4-Ig treatment barely affected enteroantigen specific CD4$^+$CD25$^-$ T effector cell response.

The data suggest that Treg cells recovered from lymph nodes of B7-H4-Ig treated animals exhibit an increased activity compared with Treg cells obtained from control mice in blocking antigen priming and T cell proliferation. B7-H4-Ig treatment marginally affects enteroantigen specific CD4$^+$CD25$^-$ T effector cells.

Example 15: B7-H4-Ig Functions Early During the Activation of Naïve Cells and Differentiation into Th17 Cells to Inhibit IL-17A Production Methods and Materials CD4$^+$CD62L$^+$ naïve T cells were isolated from BALB/c mice as in the above examples, and activated by anti-CD3 and anti-CD28 bound beads in the presence of Th17 differentiation cocktail (TGF-β1 (10 ng/mL), IL-6 (50 ng/mL), IL-23 (4 ng/mL), anti-IL-4 (10 μg/mL), anti-IFN-γ (5 μg/mL) and anti-IL-2 (5 μg/mL)). Murine B7-H4-Ig (10 μg/mL) or retinoic acid (RA) (10 μM) was added to the cultures on day 0, day 1, or day 2 of the 4 day culture. IL-17A levels were measured by ELISA at the end of the 4 day culture.

Results

The Th17 assay is 4 days in duration. In order to determine when B7-H4-Ig is acting, the Th17 assay was performed with the addition of 10 μg/mL of murine B7-H4-Ig, 10 μg/mL of mouse IgG control, or 10 mM retinoic acid on Day 0, Day 1, or Day 2.

Figure 53:
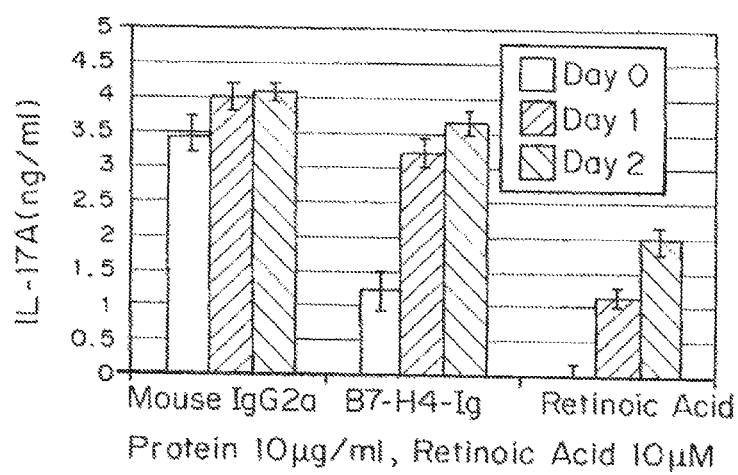
FIG. 53 is a bar graph showing the amount of IL-17A (ng/ml) secreted by Balb/C mouse naïve T cells activated by anti-CD3/CD28 in the presence of Th17 differentiation cocktail and either murine B7-H4-Ig, murine isotype IgG2a control, or retinoic acid (RA) added to the culture at day 9, day 1, or day 2 of the four day culture.

Both murine B7-H4-Ig and RA inhibited IL-17A most potently when added at the beginning of the assay (day 0), indicating that B7-H4-Ig functions early during the differentiation of naïve T cells to Th17 T cells to inhibit IL-17A production and/or secretion (FIG. 53).

Example 16: B7-H4-Ig Downregulates Expression of Genes Associated with Differentiation of Th17 Cells Methods and Materials CD4$^+$CD62L$^+$ naïve T cells were isolated from BALB/c mice as in the above examples, and activated by anti-CD3 and anti-CD28 bound beads in the presence of Th17 differentiation cocktail (TGF-β1 (10 ng/mL), IL-6 (50 ng/mL), IL-23 (4 ng/mL), anti-IL-4 (10 μg/mL), anti-IFN-γ (5 μg/mL) and anti-IL-2 (5 μg/mL)). Cells were incubated with either B7-H4-Ig (two different lots—#22 and #23—at 1 μg/mL) or isotype control. RNA was isolated from the cells and used for quantitative RT-PCR to test the expression levels of a large number of mRNAs associated with Th17 cells, Tregs, autoimmune disorders and inflammation (SA Biosciences mouse Th17 panel).

Human T cells were activated by anti-CD3 and anti-CD28 bound beads in the presence of Th17 differentiation cocktail (TGF-β1 (10 ng/mL), IL-6 (50 ng/mL), IL-23 (4 ng/mL), anti-IL-4 (10 μg/mL), anti-IFN-γ (5 μg/mL) and anti-IL-2 (5 μg/mL)). Cells were incubated with two different variants of B7-H4-Ig (1 μg/mL) identified as Q or L, or a humanized monoclonal IgG antibody directed against an epitope in the A antigenic site of the F protein of the Respiratory Syncytial Virus (Synagis), as an isotype control.

Results

Figure 54:
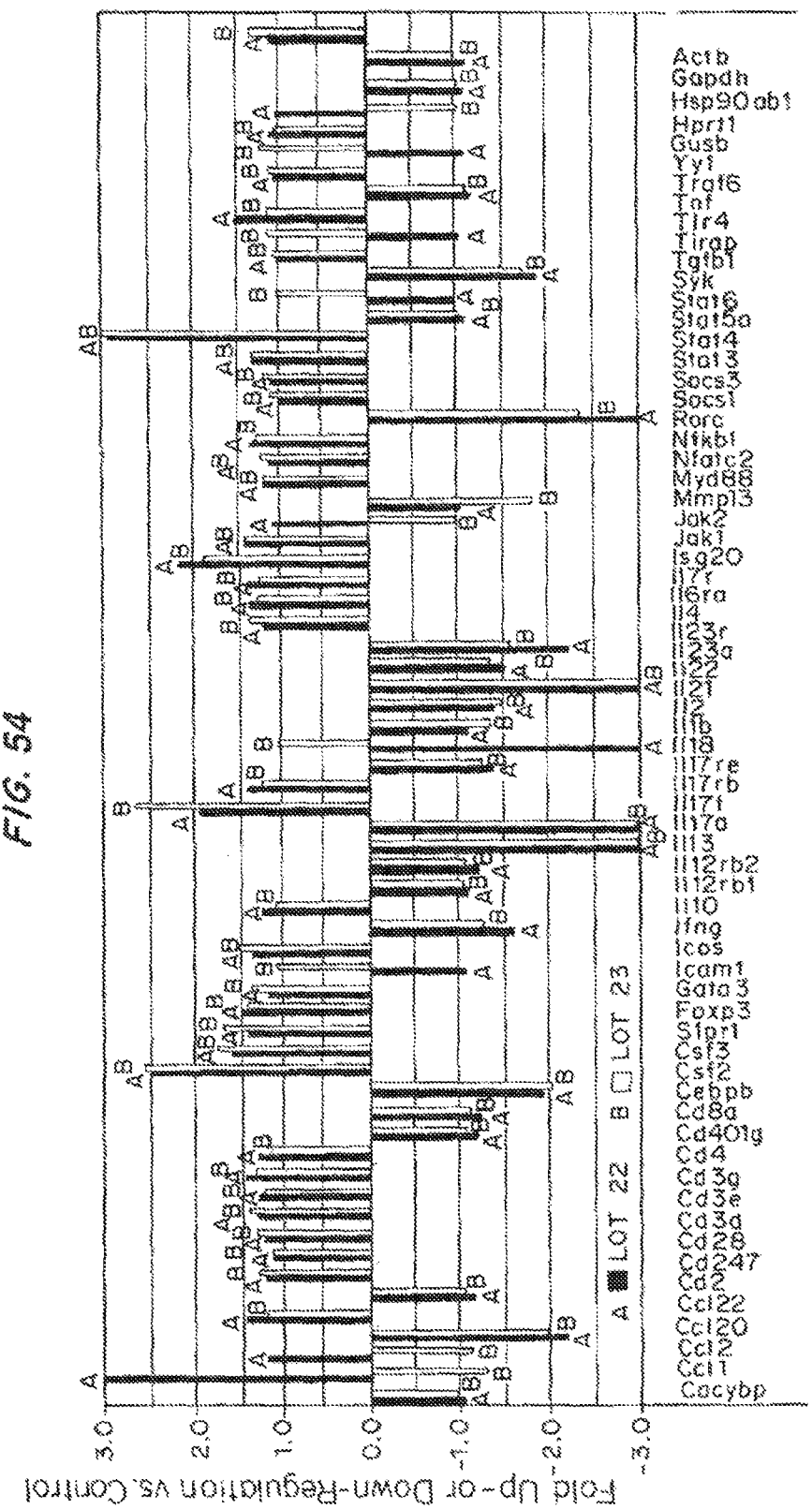
FIG. 54 is a bar graph showing the fold up- or down-regulation of mRNAs in mouse naïve T cells activated by anti-CD3/CD28 and murine B7-H4-Ig versus murine isotype control. All cells were cultured in the presence of Th17 differentiation cocktail. Expression of mRNAs involved in Th17 cells, Tregs, autoimmune disorders, and/or inflammation was tested by quantitative RT-PCR.
Figure 55:
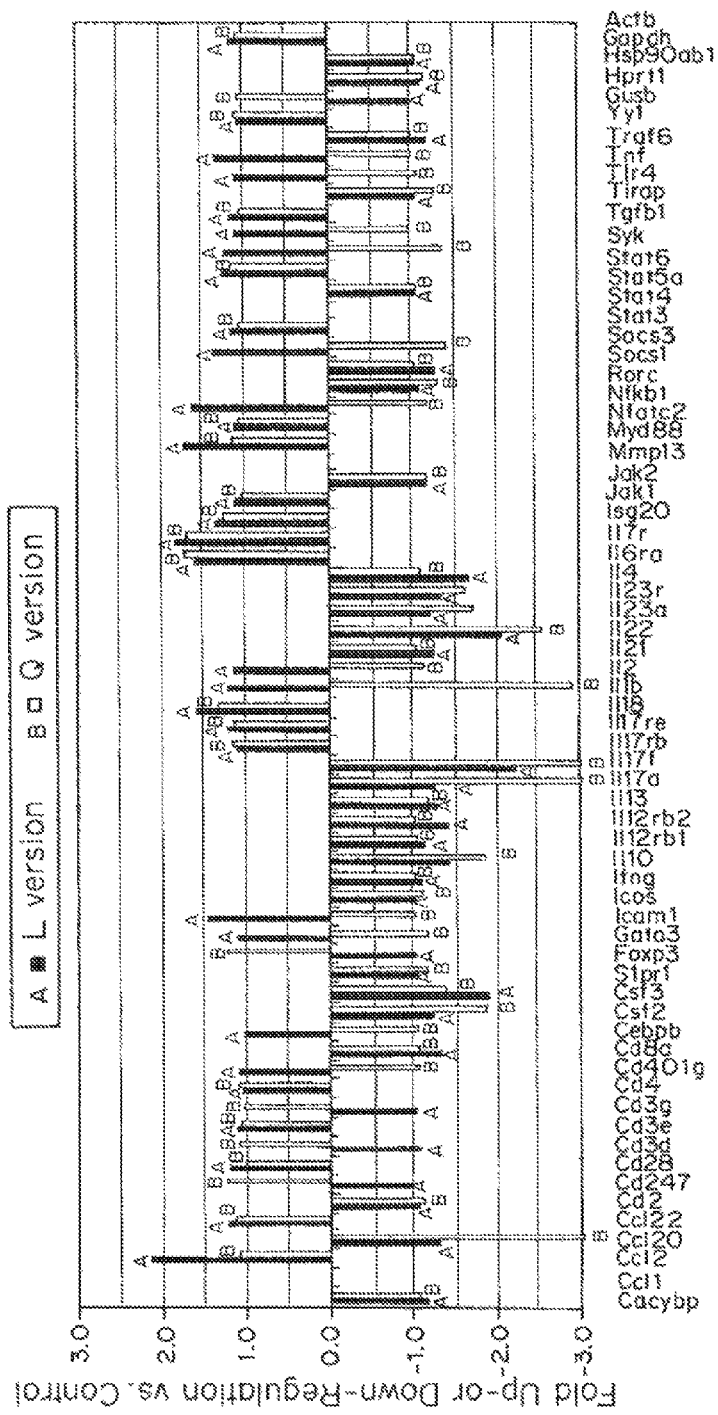
FIG. 55 is a bar graph showing the fold up- or down-regulation of mRNAs in human T cells activated by anti-CD3/CD28 and human B7-H4-Ig (1 µg/mL) with a Q or an L at position 46 of the fusion protein, or a humanized monoclonal IgG antibody directed against an epitope in the A antigenic site of the F protein of the Respiratory Syncytial Virus (Synagis), as an isotype control. All cells were cultured in the presence of Th17 differentiation cocktail. Expression of mRNAs involved in Th17 cells, Tregs, autoimmune disorders, and/or inflammation was tested by quantitative RT-PCR.

The quantitative RT-PCR results show that B7-H4-Ig downregulates the expression of mRNA involved in Th17 cell differentiation, such as the master Th17 transcription factor, RORc, and the Th17 effector molecules, IL-17A, IL-17F, IL-21, and IL-22 (Table 13 and FIGS. 54 and 55).

TABLE 13 mRNA upregulation or downregulation by B7-H4-Ig in activated Th17 cells

| Description | Symbol | Fold Up-or Down Regulation Test Sample/Control Sample | | | |
|---|---|---|---|---|---|
| | | Lot 22 | Lot 23 | L Version | Q Version |
| Calcyclin binding protein | Caybp | −1.02 | −1.00 | −1.20 | −1.05 |
| Chemokine (C-C motif) ligand 1 | Ccl1 | 3.75 | −1.33 | | |
| Chemokine (C-C motif) ligand 2 | Ccl2 | 1.18 | −1.11 | 2.07 | 1.03 |
| Chemokine (C-C motif) ligand 20 | Ccl20 | −2.22 | −2.00 | 1.38 | −3.04 |
| Chemokine (C-C motif) ligand 22 | Ccl22 | 1.36 | 1.15 | 1.17 | 1.10 |
| CD2 antigen | Cd2 | −1.19 | −1.06 | −1.06 | −1.14 |
| CD247 antigen | Cd247 | 1.23 | 1.26 | −1.00 | 1.23 |
| CD28 antigen | Cd28 | 1.10 | 1.10 | 1.20 | 1.01 |
| CD3 antigen, delta polypeptide | Cd3d | 1.23 | 1.26 | −1.04 | 1.03 |
| CD3 antigen, epsilon polypeptide | Cd3e | 1.27 | 1.37 | 1.08 | 1.04 |
| CD3 antigen, gamma polypeptide | Cd3g | 1.27 | 1.21 | −1.02 | 1.00 |
| CD4 antigen | Cd4 | 1.37 | 1.30 | 1.05 | 1.07 |
| CD40 ligand | Cd40lg | 1.26 | 1.15 | 1.05 | −1.10 |
| CD8 antigen, alpha chain | Cd8a | −1.19 | −1.08 | −1.35 | −1.13 |
| CCAAT/enhancer binding protein (C/EBP), beta | Cetpb | −1.27 | −1.11 | 1.01 | −1.09 |
| Colony stimulating factor 2 (granulocyte-macrophage) | Csf2 | −1.97 | −2.06 | −1.30 | −1.95 |
| Colony stimulating factor 3 (granulocyte) | Csf3 | 2.50 | 2.55 | −1.95 | −1.44 |
| Sphingosine-1-phosphate receptor 1 | S1pr1 | 1.57 | 1.72 | −1.05 | −1.18 |
| Forkhead box P3 | Foxp3 | 1.38 | 1.64 | −1.03 | 1.24 |
| GATA binding protein 3 | Gata3 | 1.47 | 1.41 | 1.06 | −1.17 |
| Intercellular adhesion molecule 1 | Icam1 | 1.14 | 1.32 | 1.42 | −1.04 |
| Inducible T-cell co-stimulator | Icos5 | −1.04 | 1.05 | −1.04 | −1.09 |
| Interferon gamma | Ifng | 1.36 | 1.54 | −1.08 | −1.02 |
| Interleukin 10 | Il10 | −1.63 | −1.26 | −1.48 | −1.87 |
| Interleukin 12 receptor, beta 1 | Il12rb1 | 1.24 | 1.06 | −1.12 | −1.05 |
| Interleukin 12 receptor, beta 2 | Il12rb2 | −1.09 | −1.05 | −1.47 | −1.02 |
| Interleukin 13 | Il13 | −1.24 | −1.07 | −1.27 | −1.22 |
| Interleukin 17A | Il17A | −5.29 | −6.88 | −1.29 | −3.31 |
| Interleukin 17F | Il17f | −5.15 | −3.79 | −2.26 | −3.31 |
| Interleukin 17 receptor B | Il17rb | 1.92 | 2.61 | 1.09 | 1.13 |
| Interleukin 17 receptor E | IL17re | 1.43 | 1.25 | 1.17 | 1.16 |
| Interleukin 18 | Il18 | −1.36 | −1.28 | 1.59 | 1.39 |
| Interleukin 1 beta | Il1b | −2.98 | 1.01 | 1.22 | −2.95 |
| Interleukin 2 | Il2 | −1.09 | −1.39 | 1.13 | −1.11 |
| Interleukin 21 | Il21 | −1.45 | −1.51 | −1.25 | −1.04 |
| Interleukin 22 | Il22 | −4.16 | −3.71 | −2.11 | −2.57 |
| Interleukin 23, alpha subunit p19 | Il23a | −1.49 | −1.36 | −1.23 | −1.76 |
| Interleukin 23 receptor | Il23r | −2.26 | −1.58 | −1.42 | −1.66 |
| Interleukin 4 | Il4 | 1.15 | 1.34 | −1.70 | −1.11 |
| Interleukin 6 receptor, alpha | Il6ra | 1.35 | 1.26 | 1.60 | 1.69 |
| Interleukin 7 receptor | Il7r | 1.33 | 1.26 | 1.78 | 1.69 |
| Interferon-stimulated protein | Isg20 | 2.16 | 1.88 | 1.30 | 1.25 |
| Janus kinase 1 | Jak1 | 1.40 | 1.39 | 1.08 | 1.02 |
| Janus kinase 2 | Jak2 | 1.09 | −1.00 | −1.18 | −1.18 |
| Matrix metallopeptidase 13 | Mmp13 | −1.02 | −1.89 | | |
| Myeloid differentiation primary response gene 88 | Myd88 | 1.19 | 1.17 | 1.72 | 1.14 |
| Nuclear factor of activated T-cells, cytoplasmic, calcineurin-dependent 1 | Nfatc2 | 1.15 | 1.23 | 1.09 | 1.06 |
| Nuclear factor of kappa light polypeptide gene enhancer in B-cells 2 | Ffkb1 | 1.33 | 1.29 | 1.54 | −1.21 |
| RAR-related orphan receptor gamma | Rorc | −3.93 | −2.40 | −1.10 | −1.37 |
| Suppressor of cytokine signaling 1 | Socs1 | 1.01 | 1.08 | −1.33 | −1.13 |
| Suppressor of cytokine signaling 3 | Socs3 | 1.12 | 1.16 | 1.34 | −1.47 |
| Signal transducer and activator of transcription 3 | Stat3 | 1.31 | 1.31 | 1.11 | 1.04 |
| Signal transducer and activator of transcription 4 | Stat4 | 2.89 | 4.29 | | |
| Signal transducer and activator of transcription 5A | Stat5a | −1.06 | −1.01 | −1.05 | −1.05 |
| Signal transducer and activator of transcription 6 | Stat6 | −1.00 | 1.02 | 1.20 | 1.12 |
| Spleen tyrosine kinase | Syk | −1.92 | −1.75 | 1.22 | −1.42 |
| Transforming growth factor, beta 1 | Tgfb1 | 1.03 | 1.05 | 1.10 | −1.02 |

TABLE 13-continued mRNA upregulation or downregulation
by B7-H4-Ig in activated Th17 cells

| | | Fold Up-or Down Regulation Test Sample/Control Sample | | | |
|---|---|---|---|---|---|
| Description | Symbol | Lot 22 | Lot 23 | L Version | Q Version |
| Toll-mterleukin 1 receptor (TIR) domain-containing adaptor protein | Tlrap | −1.02 | 1.10 | 1.15 | 1.02 |
| Toll-like receptor 4 | Tlr4 | 1.49 | 1.17 | −1.06 | −1.32 |
| Tumor necrosis factor | Tnf | −1.19 | −1.13 | 1.05 | −1.09 |
| Tnf receptor-associated factor 6 | Traf6 | 1.05 | 1.15 | 1.33 | −1.01 |
| YY1 transcription factor | Yy1 | −1.09 | 1.21 | −1.19 | −1.03 |
| Glucuronidase, beta | Gusb | 1.06 | 1.02 | 1.02 | 1.04 |
| Hypoxanthine guanine phosphoribosyl transferase 1 | Hprt1 | 1.03 | −1.02 | −1.01 | 1.03 |
| Heat shock protein 90 alpha (cytosolic), class B member 1 | Hsp90ab1 | −1.16 | −1.11 | −1.11 | −1.16 |
| Glyceraldehyde-3-phosphate dehydrogenase | Gapdh | −1.17 | −1.12 | −1.03 | −1.02 |
| Actin, beta | Actb | 1.24 | 1.26 | 1.13 | 1.10 |
| Low mRNA: less certain | | | | | |
| Chemokine (C-C motif) ligand 1 | Ccl1 | 3.75 | −1.33 | −2.47 | −2.33 |
| Chemokine (C-C motif) ligand 7 | Ccl7 | 1.24 | 1.31 | −3.32 | −3.17 |
| CD34 antigen | Cd34 | 1.08 | −1.65 | 1.27 | 1.66 |
| C-type lectin domain family 7, member a | Clec7a | −4.21 | 3.21 | −4.75 | −3.42 |
| Chemokine (C-X3-C motif) ligand 1 | Cx3cl1 | 7.42 | 8.71 | 1.09 | 2.66 |
| Chemokine (C-X-C motif) ligand 1 | Cxcl1 | 1.24 | 1.31 | 1.09 | 1.15 |
| Chemokine (C-X-C motif) ligand 12 | Cxcl12 | 2.13 | 1.31 | 1.09 | 1.15 |
| Chemokine (C-X-C motif) ligand 2 | Cxcl2 | −1.04 | 1.65 | 1.35 | −3.17 |
| Chemokine (C-X-C motif) ligand 5 | Cxcl5 | 1.67 | −1.80 | 2.88 | 1.15 |
| Interleukin 25 | Il25 | 3.67 | 1.31 | 1.09 | 1.15 |
| Interleukin 12B | Il12b | 1.24 | 1.31 | 1.09 | 1.15 |
| Interleukin 15 | Il15 | −2.31 | −2.56 | −1.16 | 1.12 |
| Interkeukin 17C | Il17c | 2.58 | 2.14 | −1.03 | 1.43 |
| Interleukin 17D | Il17d | 1.24 | 1.31 | 1.09 | 1.15 |
| Interleukin 17 receptor C | Il17rc | 2.32 | 2.12 | −1.70 | 1.07 |
| Interleukin 17 receptor D | Il17d | −1.16 | 1.59 | −1.79 | −1.67 |
| Interleukin 27 | Il27 | 1.65 | 1.59 | 1.99 | 2.87 |
| Interleukin 3 | Il3 | −1.41 | 2.27 | −1.74 | 1.38 |
| Interleukin 5 | Il5 | 2.59 | −1.21 | 1.09 | 1.68 |
| Interleukin 6 | Il6 | 1.14 | 1.21 | 1.13 | −1.15 |
| Matrix metallopeptidase 13 | Mmp13 | −1.02 | −1.89 | 5.00 | 1.75 |
| Matrix metallopeptidase 3 | Mmp3 | 1.24 | 1.31 | 1.09 | 1.15 |
| Matrix metallopeptidase 9 | Mmp9 | 1.78 | −1.24 | −2.87 | −1.53 |
| Signal transducer and activator of transcription 4 | Stat4 | 2.89 | 4.29 | −1.07 | −2.12 |
| T-box 21 | Tbx21 | −1.14 | 1.15 | −1.07 | −2.78 |

Example 17: Activity of Murine B7-H4-Ig in the Mouse TH17 Assay

Methods and Materials

Animals

BALB/c mice, female, 5-7 week old (Harlan) were used.

Isolation of Naïve CD4 Cells

Cell strainer

ACK lysis buffer

10× Hank's Balanced Salt Solution (Sigma H1641)

CD4 Negative selection kit (Miltenyi Biotec 130-090-860)

Anti-mouse CD25-Biotin (Miltenyi Biotec 130-092-569)

CD62L beads (Miltenyi Biotec 130-049-701)

96 Well Cell Culture Cluster (Costar 3595)

Culture Medium

Dynabeads® Mouse CD3/CD28 T cell Expander (Invitrogen 11452D)

HL-1 media (Lonza 344017)

1000× β-mercaptoethanol (2-Me, Invitrogen 21985-023)

Penicillin/streptomycin (P/S, Invitrogen 15070-063)

Non-essential Amino Acids (Invitrogen 11140-050)

L-Glutamine (Invitrogen 25030-081)

TH17 Differentiation Cocktail

Recombinant human TGF-β1 (R&D Systems 240-B-010)

Recombinant mouse IL-6 (eBioscience 4-8061)

Recombinant mouse IL-23 (eBioscience 14-8231)

Anti-mouse IL-2 (eBioscience 16-7021)

Anti-mouse IL-4 (eBioscience 16-7041)

Anti-mouse IFN-γ (eBioscience 16-7311)

B7-H4-Ig and Murine B7-H4-Ig

Murine B7-H4-Ig Lot 22

Murine B7-H4-Ig Lot 23

Human B7-H4-Ig (Q)

Human B7-H4-Ig (L)

Positive and Negative Controls

All trans-Retinoic Acid (ATRA, Sigma 82625)

ChromoPure Mouse IgG (Jackson ImmunoResearch 015-000-003)

Synagis® (MedImmune)

Analysis

Mouse IL-17A ELISA kit

Peripheral T cells were obtained from spleens and inguinal lymph nodes of 6-9 week old BALB/c mice by mechanical disruption through a cell strainer followed by red blood cell (RBC) lysis.

Naïve helper T cells (CD4$^+$CD62L$^+$) were obtained using the Miltenyi Biotec microbead system. CD4$^+$ cells are enriched by negative selection, and followed by a positive selection of CD62L$^+$. In some experiments CD25+ cells were also depleted.

After selection, cells are activated in vitro with anti-CD3/CD28 beads at a 1:1 cell:bead ratio in the presence of the T$_H$17 differentiation cocktail (TGF-β1 (10 ng/ml), IL-6 (50 ng/ml), IL-23 (4 ng/ml), anti-IL-2 (5 µg/ml), anti-IL-4 (10 µg/ml), and anti-IFN-γ (5 µg/ml)). Murine B7-H4-Ig is added at a final concentration of 1.25-20 µg/ml. Retinoic acid (RA) is used as positive control and mouse IgG is used as a negative control.

After 4 days of culture, cultures are spun down and supernatants are harvested and stored at <−65° C. until analyzed for IL-17A levels by ELISA.

Flow cytometry and intracellular staining (ICS) were used to assess the purity of the starting cell populations and the success of the differentiation protocol.

Results

Initial experiments were performed to demonstrate that murine B7-H4-Ig acts to reduce IL-17A expression by murine Th17 cells. CD4$^+$CD62L$^+$ T cells are stimulated and cultured for four days in Th17 promoting conditions in the presence of murine B7-H4-Ig, control mouse IgG, or retinoic acid (RA).

Figure 56:
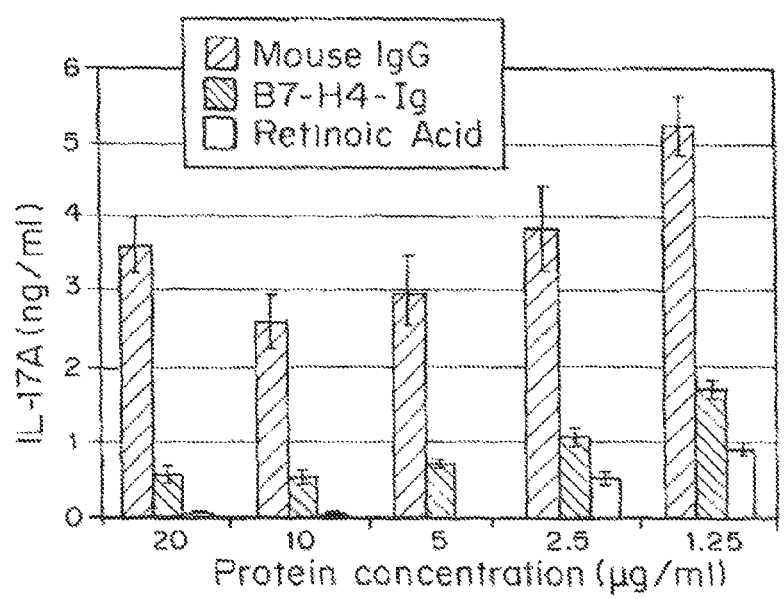
FIG. 56 is a bar graph of IL-17A (ng/ml) concentrations produced by TH17 cells treated with indicated concentrations of murine B7-H4-Ig, murine IgG control, or retinoic acid.

Supernatants were harvested on day 4 and analyzed by IL-17A ELISA. As shown in FIG. 56, both murine B7-H4-Ig and RA treatment lead to reduced IL-17A expression, relative to the control mouse IgG.

An experiment was preformed to see whether human B7-H4-Ig is active in the assay. Species cross-reactivity should be possible because the B7-H4 extracellular domain is 95% identical in human B7-H4 and its murine analog.

Protein concentrations of 20, 10, 5, 2.5, and 1.25 µg/mL were tested. Two variants of human B7-H4-Ig were compared with Synagis®, an irrelevant human IgG1 antibody therapeutic, and two lots of murine B7-H4-Ig were compared with mouse IgG control.

Figure 57:
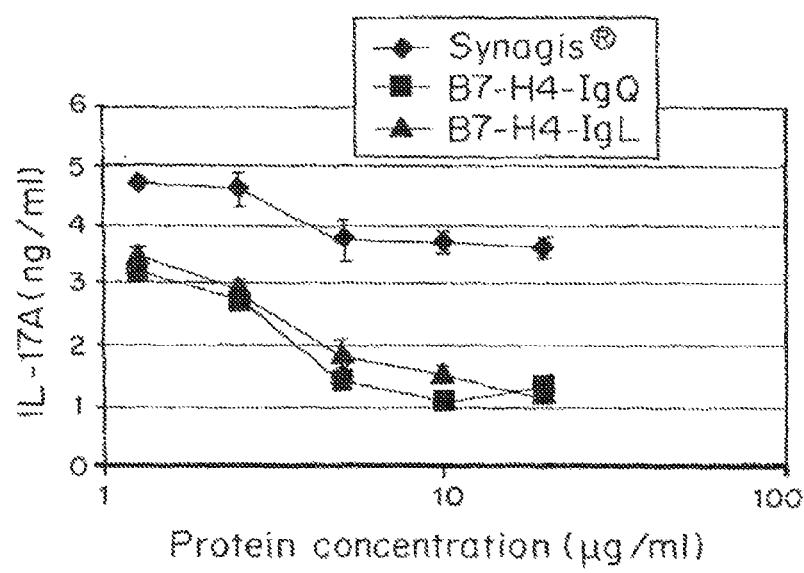
FIG. 57 is a line graph of IL-17A (ng/ml) versus protein concentration (µg/ml) showing activity of B7-H4-IgQ (■), B7-H4-IgL (▲) versus Synagis (◆) (an irrelevant human IgG$_1$ antibody) on mouse Th17 cells.
Figure 58:
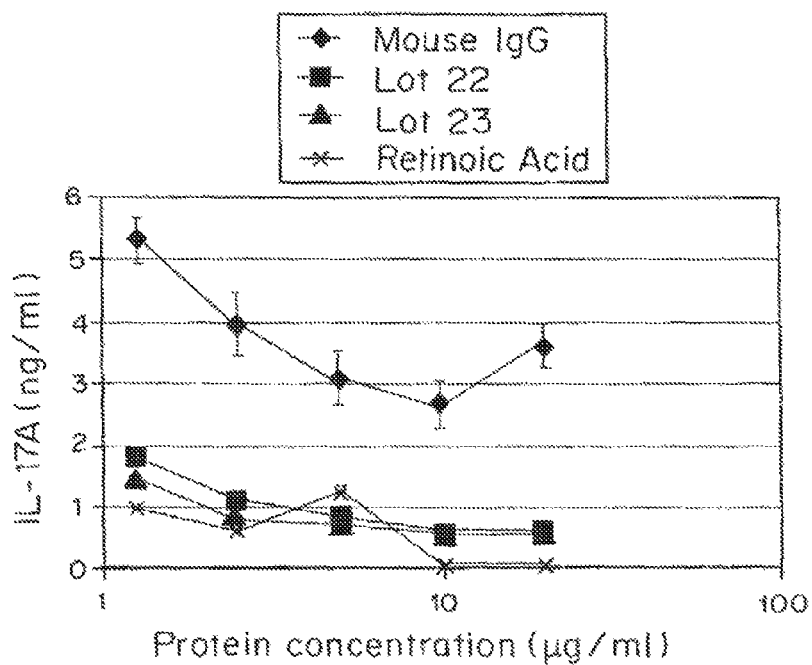
FIG. 58 a line graph of IL-17A (ng/ml) versus protein concentration (µg/ml) showing activity of murine B7-H4-Ig (lots 22 (■) and 23 (▲)) versus mouse IgG (◆) and retinoic acid controls (✶) on Th17 cells.

As shown in FIGS. 57 and 58, both human B7-H4-Ig and its murine analog are active on mouse cells in the Th17 assay.

Example 18: MRL/lpr Lupus Mouse Model

Materials and Methods
Treatment Regimen

Figure 59:
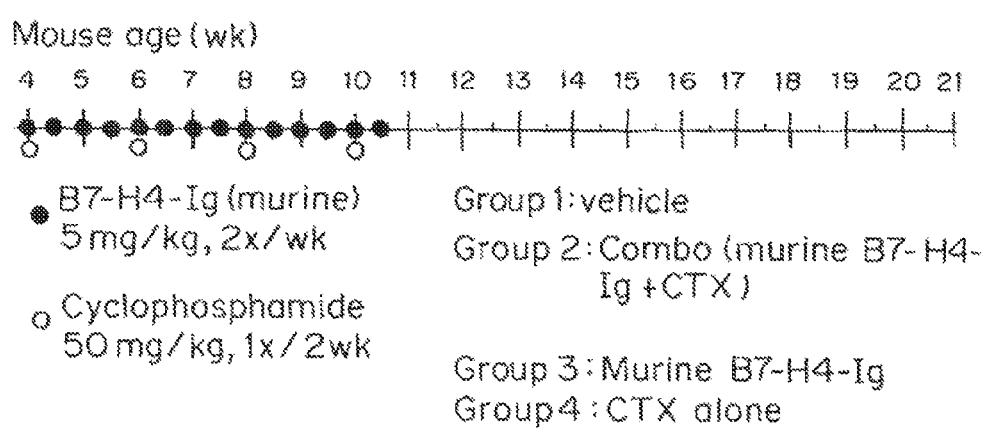
FIG. 59 is a schematic illustration of a treatment schedule for an in vivo study utilizing an MRL/lpr lupus mouse model.

MRL/lpr mice at 4 weeks of age were used in this experiment. Animals were tagged with metal tags on their right ears for identification. Cyclophosphamide (CTX) is the primary drug used for diffuse proliferative glomerulonephritis in patients with renal lupus, Daikh and Wofsy reported that combination treatment with CTX and CTLA4-Ig was more effective than either agent alone in reducing renal disease and prolonging survival of NZB/NZW F1 lupus mice with advanced nephritis (Daikh and Wofsy, *J Immunol.*, 166(5):2913-6 (2001)). In the proof-of-concept study, combination treatments with recombinant murine B7-H4-Ig and CTX were tested. Mice received single or combination treatment of murine B7-H4-Ig (Lot#DEV-110-5-006) at 5 mg/kg with or without CTX at 50 mg/kg via IP injection, once every 2 weeks (FIG. 59). Murine B7-H4-Ig dosing regimen at 5 mg/kg (100 µg/mouse/injection), twice a week, was chosen based on in vivo studies of monoclonal antibody and fusion proteins. Both single and combination treatments were diluted with PBS to generate a similar 500 µL injection sample which was administered using a 3 ml syringe with a gauge 27 needle. Blood samples (~200 µL) were taken from the submandibular vein (ARC SOP 8050.02.08) 3 days before the protein treatment and the every other week during and after treatments. Blood samples were collected in Microtainer® Blood Collection Tubes, and plasma was harvested from the supernatant of blood sample after centrifugation and stored at −80° C. freezer until use.

Anti-dsDNA Autoantibody Analysis

A positive anti-dsDNA autoantibody control was generated by pooling plasma from 5 aged MRL/lpr mice, approximately 8 months of age. The positive control plasma was aliquoted and stored at −80° C. freezer before use.

The dsDNA solution (10 mg/mL) was first generated by dissolving salmon testes DNA in PBS at 37° C. in a water bath followed by filtration through a 0.45 µm membrane filter. The dsDNA solution was aliquoted and stored at −80° C. before use.

On the day prior to the autoantibody ELISA, 100 µL of the dsDNA stock solution was first added to 10 mL of PBS resulting in a final concentration of 100 µg/ml. 100 µl of the diluted dsDNA was then added to each well of Immulon 2HB 96-well flat bottom microtiter plates. Plates were placed in a humidified incubator at 37° C. without lids for overnight coating. Plates were washed 4 times with 300 µL of PBS/T [0.1% (v/v) Tween-20 (polysorbate 20) in PBS] using a microtiter plate washer (hydroFLEX, TECAN. Software: HydroControl) and then blocked with 200 µL of blocking buffer (10% fetal bovine serum in PBS) at room temperature for at least 1 h followed by 4 washes with 300 µL of PBS/T. The negative control (normal Balb/C mouse plasma, 1:2000 dilution), positive controls (1:5000, 1:10000, 1:20000 dilutions), and samples (1:2000 dilution) were diluted with blocking buffer. Next, 100 µL of each diluted control and sample was added to corresponding wells (duplicate wells) and incubated at room temperature for 2 h or at 4° C. overnight followed by 4 washes with 300 µL of PBS/T. For detection, 100 µL of anti-mouse IgG-HRP (Sigma, A9309, diluted to 1:10000 in blocking buffer) was added to each well and the plate was incubated at room temperature for 1 h followed by 4 washes with 400 µL of PBS/T.

Later, 100 µL of room temperature, pre-warmed TMB Substrate Reagent was added to each well. When the color developed optimally (about 10 min), 100 µL of stop solution (1% sulfuric acid) was added. The plate was then read for absorbance at 450 nm ($OD_{450}$) using a microtiter plate reader (SPECTRAmax, Molecular Devices. Software: SoftMax Pro5.2).

All the blood samples were analyzed at the end of the study. The $OD_{450}$ value of test samples was normalized relatively to the internal positive control at the 1:10000 dilution. The relative value rather than the absolute Ab concentration was used for comparison.

Histology

To evaluate glomerulonephritis, mouse kidneys were harvested and fixed in 10% formalin (SAFEFIX II) and shipped to AML Laboratories (Rosedale, Md.). Sections of 7 nm were obtained and stained via standard H&E staining at AML Labs. Images were taken under the light microscope at low and high magnifications.

Proteinuria Analysis

Proteinuria was measured by testing fresh urine samples using urinalysis dipsticks (Germaine Laboratories, catalog #52100). A fresh urine drop was collected on the dip reagent pad. Approximately 1-2 minutes later, the color of the pad was compared with the color chart to determine the proteinuria level on a scale of 0 to 4+, where 0/trace=negative, 1+=30, 2+=100, 3+=300, and 4+=>2,000 mg/dl.

Results

Female MRL/lpr mice at age of 4 weeks were divided into 4 groups (FIG. 59): vehicle, CTX alone, murine B7-H4-Ig alone and CTX plus murine B7-H4-Ig combination treatment (Combo). CTX was given IP, 50 mg/kg, once every 2 weeks. Murine B7-H4-Ig was administrated IP, 100 µg (5 mg/kg), and twice every week. The Combo group received CTX injection every 2 weeks and murine B7-H4-Ig 2 times every week at 5 mg/kg. Mice were treated for 7 weeks.

TABLE 14

MRL/lpr mouse dsDNA autoantibody data table

| | Mouse # | Mouse Age (weeks) | | | | | | | |
|---|---|---|---|---|---|---|---|---|---|
| | | 4 | 7 | 8 | 9 | 10 | 11 | 15 | 19 |
| Control | 246 | 0.01 | 0.16 | 0.48 | 2.24 | 1.44 | 3.09 | 2.25 | 7.00 |
| | 247 | 0.20 | 0.20 | 0.19 | 1.23 | 1.16 | 3.05 | 3.79 | 5.97 |
| | 248 | 0.01 | 3.33 | 11.41 | 12.27 | 9.18 | 7.63 | 10.16 | 9.50 |
| | 249 | 0.11 | 2.53 | 4.07 | 2.68 | 1.66 | 2.75 | 3.98 | 4.54 |

TABLE 14-continued

MRL/lpr mouse dsDNA autoantibody data table

| | Mouse # | Mouse Age (weeks) | | | | | | | |
|---|---|---|---|---|---|---|---|---|---|
| | | 4 | 7 | 8 | 9 | 10 | 11 | 15 | 19 |
| CTX +<br>murine<br>B7-H4-<br>Ig | 250 | 0.21 | 0.12 | 0.40 | 1.16 | 0.86 | 0.96 | 6.05 | 6.10 |
| | 251 | 0.04 | 0.16 | 0.27 | 0.08 | 0.13 | 0.20 | 0.33 | 1.39 |
| | 252 | 0.09 | 0.11 | 0.62 | 0.94 | 0.71 | 0.60 | 2.37 | 0.85 |
| | 253 | 0.45 | 0.29 | 1.25 | 0.48 | 0.44 | 0.28 | 0.49 | 0.97 |
| | 254 | 0.17 | 0.36 | 0.19 | 0.58 | 0.74 | 0.55 | 0.59 | 0.91 |
| | 255 | 0.49 | 1.07 | 1.20 | 1.95 | 1.27 | 0.93 | 1.44 | * |
| Murine<br>B7-H4-<br>Ig | 256 | 0.12 | 0.14 | 1.63 | 1.33 | 1.36 | 2.19 | 3.35 | 4.52 |
| | 257 | 0.15 | 0.53 | 4.64 | 6.25 | 4.66 | 6.85 | 6.02 | 5.98 |
| | 258 | 0.22 | 0.73 | 0.76 | 0.92 | 0.54 | 0.71 | 1.24 | 1.57 |
| | 259 | 0.48 | 0.48 | 1.89 | 1.77 | 1.30 | 1.16 | 0.87 | 1.55 |
| | 260 | 0.13 | 0.33 | 1.09 | 0.82 | 0.60 | 0.56 | 2.27 | 3.16 |
| CTX | 261 | 0.15 | 0.55 | 2.50 | 3.46 | 1.50 | 2.97 | 2.93 | 2.61 |
| | 262 | 0.46 | 0.21 | 0.33 | 2.09 | 4.05 | 4.67 | 4.87 | 11.76 |
| | 263 | 0.05 | 1.07 | 2.03 | 2.26 | 2.95 | 3.75 | 2.62 | 3.05 |
| | 264 | 0.09 | 0.10 | 0.17 | 0.79 | 1.97 | 2.21 | 1.76 | 2.58 |
| | 265 | 0.01 | 0.10 | 0.06 | 0.26 | 0.39 | 0.55 | 1.11 | 1.26 |
| | | 0.01<br>(BW) | −0.02<br>(BW) | 0.00<br>(BW) | 0.02<br>(BW) | −0.02<br>(BW) | −0.01<br>(BW) | 0.00<br>(BW) | 0.01<br>(BW) |
| PC-1 (1:5k) | | 0.00<br>(BW) | 2.03<br>(PC) | 0.00<br>(BW) | 2.04<br>(PC) | 0.00<br>(BW) | 1.06<br>(PC) | 0.00<br>(BW) | 1.94<br>(PC) |
| PC-1 (1:10k) | | 0.00<br>(BW) | 1.00<br>(PC) | 0.00<br>(BW) | 1.00<br>(PC) | 0.00<br>(BW) | 1.00<br>(PC) | 0.00<br>(BW) | 1.00<br>(PC) |
| PC-1 (1:20k) | | 0.00<br>(BW) | 0.49<br>(PC) | 0.00<br>(BW) | 0.43<br>(PC) | 0.00<br>(BW) | 0.49<br>(PC) | 0.00<br>(BW) | 0.53<br>(PC) |

PC: autoantibody positive controls; diluted at 1:5000, 1:10000, 1:20000
BW: Blank wells
Control Group: Negative plasma (1:2000) from Balb/C mice
All MRL/lpr mouse plasma was diluted at 1:2000.
OD450 readings were normalized against the readings of positive control diluted at 1:10000 on the same ELISA plate.
* mouse accidently died at the previous blood collection time point.

Plasma was collected from MRL/lpr mice pre-treatment (4 wk) and periodically up to 21 weeks of age. Anti-ds-DNA auto antibody was assessed and normalized against an internal control, which was a pool of plasma collected from older MRL/lpr mice (Table 14).

Figure 60:
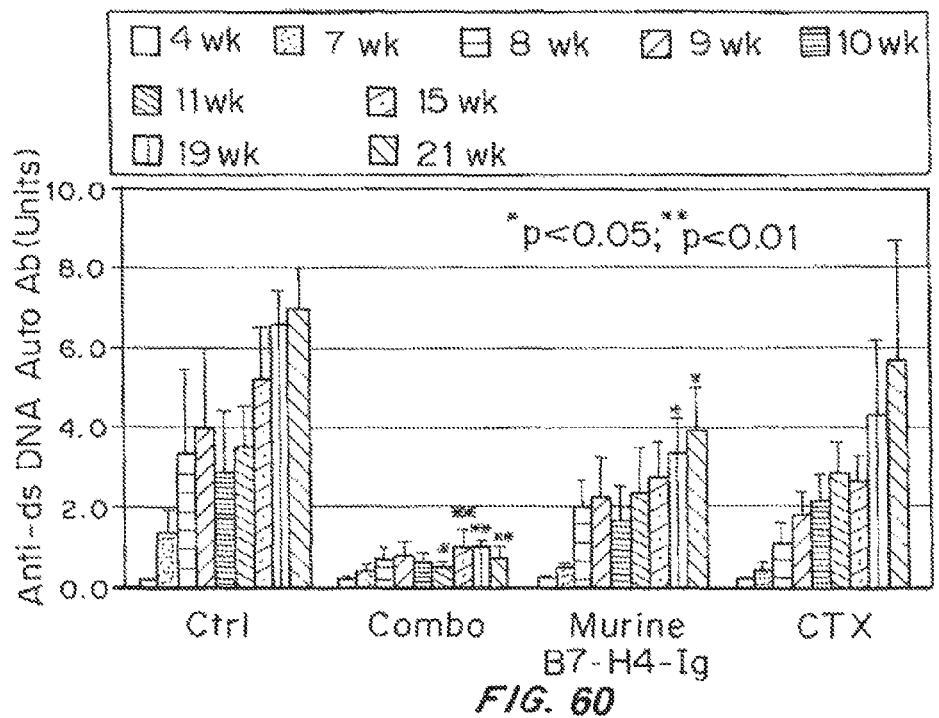
FIG. 60 is a bar graph showing anti-ds DNA auto antibodies (units) detected in plasma collected from MRL/lpr mice pre-treatment (4 week) and periodically up to 21 weeks of age in control, B7-H4-Ig and cyclophosphamide (CTX) combination treatment, B7-H4-Ig only treatment, and CTX only treatment groups. For each treatment group, bars from left to right show anti-ds DNA auto antibodies at 4, 7, 8, 9, 10, 11, 15, 19, and 21 weeks.

Combination of murine B7-H4-Ig and CTX significantly reduced anti-dsDNA auto antibody development in the MRL/lpr lupus mouse model. FIG. 60 shows the relative anti-dsDNA auto antibody measurements, demonstrating that combination treatment with murine B7-H4-Ig and CTX prevented auto antibody development in the treated MRL/lpr mice and that the combination treatment was more efficacious than CTX or murine B7-H4-Ig treatment alone. At later time points, weeks 19 and 21, murine B7-H4-Ig alone treatment also demonstrated significantly lower autoantibody level, suggesting murine B7-H4-Ig alone may be effective with an optimized dosing regimen.

Figure 61:
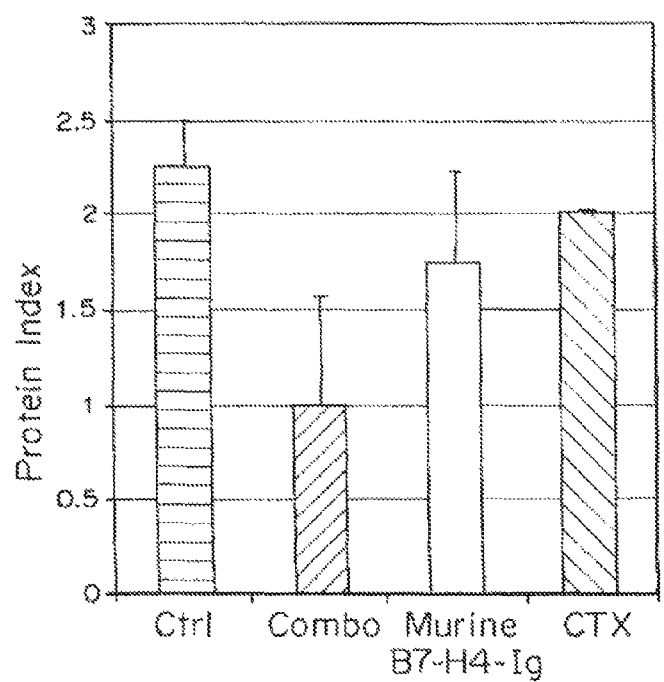
FIG. 61 is a bar graph showing the protein index (units) in control, B7-H4-Ig and cyclophosphamide (CTX) combination treatment, B7-H4-Ig only treatment, and CTX only treatment groups at 21 weeks.

This experiment was terminated when mice were 21 week old. Lymphoid organs were collected from control vehicle injected and treated mice. Combination of murine B7-H4-Ig and CTX significantly reduced lymphoproliferation in the MRL/lpr lupus mouse model. The combination treatment with murine B7-H4-Ig and CTX prevented enlargement of the spleen and lymph nodes. Proteinuria was analyzed using an AimStrip protein paper strip prior to euthanizing the animals. FIG. 61 reveals that proteinuria was significantly reduced in the mice with combination treatment of murine B7-H4-Ig and CTX compared with mice in the remaining groups.

Kidneys were harvested for histology. H&E staining of the kidney sections showed that the murine B7-H4-Ig and CTX combination treatment decreased vasculitis and prevented glomerular damage. In the vehicle injected mouse kidney, massive lymphocytic infiltration was observed around the blood vessels and red blood cells were seen inside the glomerulus.

In the MRL/lpr mice, combination treatment with recombinant murine B7-H4-Ig protein and CTX remarkably prevented lupus disease progression, demonstrated by lower anti-dsDNA autoantibody, no enlargement of lymphoid organs, lower proteinuria, less lymphocyte infiltration in the kidney and evidence of an intact glomerulus.

Example 19: Generation of Immature Dendritic Cells

Small Scale DC Generation from about 50 mL of Total Blood (n=3-5 Donors)
Fresh GM-CSF and IL-4 every 2 days+10% human AB serum
7 day culture
 Compare to serum free method
  Adding GM-CSF and IL-4 at the beginning of the differentiation
 5-6 day culture
Harvest imDC
 Marker analysis: CD3, 14, 80, 83, 86, 11C, HLA-DR
 APC-B7-H4-Ig binding, competition with anti-B7-H4
B7-H4-Ig in vitro assay
 Use LPS+10, 50, 250 µg/mL of B7-H4-Ig or control IgG1
 Collect supernatant for cytokine analysis—first TNFα and IL-6; save supernatant for other cytokine analysis in the future
 Harvest cells for DC maturation marker analysis: e.g. CD80, CD83, CCR7

Determining the role of B7-H4-Ig on DC maturation
Use DC maturation cocktail and study role of B7-H4 on DC maturation
  LPS alone; TNFα+PGE2; IL-1b+IL6+TNFa+PGE2 . . .
    2 day maturation versus 1 day maturation; regular dish or ultra-low adherent dish; minimize cell numbers for each well/assay
      Collect supernatant for cytokine analysis
      Harvest cells for DC maturation marker analysis: e.g. CD80, CD83, CCR7
Cells from 3-5 donors will be tested
Determine release criteria on imDC, e.g. cell markers and B7-H4-Ig binding
Determine maturation cocktail, timing and criteria on inhibition of cytokine and/or maturation markers
Reproducibility at a small scale
Process cells from 3 donors using the defined imDC parameters
Apply defined DC maturation cocktail and B7-H4-Ig
Analyze cytokine and mDC markers
Large scale generation of imDC
Start processing 2-3 leukopaks using the defined imDC conditions from small scale
1 leukopak generally result in $5 \times 10^8$ to $1 \times 10^9$ imDC
  Cryopreserve imDC
  Thaw cells for DC maturation & B7-H4-Ig function analysis
  Use maturation condition defined by small scale
  Try to minimize cell numbers/well
  Test robustness and reproducibility of the assay: cytokine and mDC markers
Provide imDC for receptor discovery—If small amount of cells are needed for the receptor discovery, imDC will be available from the small scale cell process after the confirmative studies Unless defined otherwise, all technical and scientific terms used herein have the same meanings as commonly understood by one of skill in the art to which the disclosed invention belongs.

Those skilled in the art will recognize, or be able to ascertain using no more than routine experimentation, many equivalents to the specific embodiments of the invention described herein. Such equivalents are intended to be encompassed by the following claims.

We claim:

1. A method for reducing inflammation in a human subject, the method comprising treating the subject according to a dosage regimen comprising intravenous administration of one or more doses of a fusion protein comprising a B7-H4 polypeptide comprising the IgV domain of SEQ ID NO: 63 or SEQ ID NO: 64 fused to a second polypeptide or fused to a linker peptide fused to a second polypeptide, wherein the dosage regimen is effective to achieve at least a 1.0 µg/ml concentration of the fusion protein in the subject post administration, and wherein the dosage regimen increases the ratio of regulatory T cells (Tregs) relative to total CD4+ cells and reduces inflammation in the subject for at least a week post administration.

2. The method of claim 1, wherein the dosage regimen comprises at least one dose of 3 mg/kg to 20 mg/kg of the fusion protein.

3. The method of claim 1, wherein the dosage regimen comprises intravenous administration of doses of the fusion protein to the subject at least two days apart and within two weeks.

4. The method of claim 1, wherein the dosage regimen comprises intravenous administration of doses of the fusion protein to the subject at least two days apart and within one week.

5. The method of claim 1, wherein the dosage regimen comprises intravenous administration of two or more doses of the fusion protein to the subject at least two days apart and within one week.

6. The method of claim 1, wherein the dosage regimen is effective to reduce inflammation in the subject for at least 10 days.

7. The method of claim 1, wherein the dosage regimen is effective to reduce inflammation in the subject for at least two weeks.

8. The method of claim 1, wherein the dosage regimen is effective to reduce inflammation in the subject for at least three weeks.

9. The method of claim 1, wherein the dosage regimen is effective to increase the ratio of Tregs relative to total CD4+ cells at a site of inflammation, in the draining lymph nodes, in the spleen, in the central nervous system, or combinations thereof.

10. The method of claim 1, wherein the dosage regimen is effective to reduce the ratio of effector or memory T cells relative to total CD4+ cells in the subject.

11. The method of claim 10, wherein the dosage regimen is effective to reduce the ratio of effector or memory T cells relative to total CD4+ cells at a site of inflammation in the subject.

12. The method of claim 1, wherein the second polypeptide comprises the hinge, CH2 and CH3 regions of an immunoglobulin.

13. The method of claim 12, wherein the immunoglobulin is a human IgG1.

14. The method of claim 1, wherein the subject has a disease selected from the group consisting of rheumatoid arthritis, systemic lupus erythematosus, alopecia areata, ankylosing spondylitis, antiphospholipid syndrome, autoimmune Addison's disease, autoimmune hemolytic anemia, autoimmune hepatitis, autoimmune inner ear disease, autoimmune lymphoproliferative syndrome (alps), autoimmune thrombocytopenic purpura (ATP), Behcet's disease, bullous pemphigoid, cardiomyopathy, celiac sprue-dermatitis, chronic fatigue syndrome immune deficiency syndrome (CFIDS), chronic inflammatory demyelinating polyneuropathy, cicatrical pemphigoid, cold agglutinin disease, Crest syndrome, Crohn's disease, Degos disease, dermatomyositis, dermatomyositis-juvenile, discoid lupus, essential mixed cryoglobulinemia, fibromyalgia-fibromyositis, Grave's disease, Guillain-Barre syndrome, Hashimoto's thyroiditis, idiopathic pulmonary fibrosis, idiopathic thrombocytopenia purpura (ITP), IgA nephropathy, insulin dependent diabetes (Type I), juvenile arthritis, Meniere's disease, mixed connective tissue disease, multiple sclerosis, myasthenia gravis, pemphigus vulgaris, pernicious anemia, polyarteritis nodosa, polychondritis, polyglandular syndromes, polymyalgia rheumatica, polymyositis and dermatomyositis, primary agammaglobulinemia, primary biliary cirrhosis, psoriasis, Raynaud's phenomenon, Reiter's syndrome, rheumatic fever, sarcoidosis, scleroderma, Sjogren's syndrome, stiff-man syndrome, Takayasu arteritis, temporal arteritis/giant cell arteritis, ulcerative colitis, uveitis, vasculitis, vitiligo, and Wegener's granulomatosis.

15. The method claim 14, wherein the disease is Sjogren's syndrome, multiple sclerosis, rheumatoid arthritis, Crohn's disease, or myasthenia gravis.

16. The method of claim 15, wherein the disease is rheumatoid arthritis.

17. A method for reducing inflammation in a human subject, the method comprising treating the subject according to a dosage regimen comprising intravenous administration of one or more doses of a fusion protein comprising the amino acid sequence of SEQ ID NO: 130, wherein the dosage regimen is effective to achieve at least a 1.0 µg/ml concentration of the fusion protein in the subject post administration, and wherein the dosage regimen increases the ratio of regulatory T cells (Tregs) relative to total CD4+ cells and reduces inflammation in the subject for at least a week post administration.

18. The method of claim 17, wherein the dosage regimen comprises at least one dose of 3 mg/kg to 20 mg/kg of the fusion protein.

19. The method of claim 17, wherein the dosage regimen comprises intravenous administration of doses of the fusion protein to the subject at least two days apart and within two weeks.

20. The method of claim 17, wherein the dosage regimen comprises intravenous administration of doses of the fusion protein to the subject at least two days apart and within one week.

21. The method of claim 17, wherein the dosage regimen comprises intravenous administration of two or more doses of the fusion protein to the subject at least two days apart and within one week.

22. The method of claim 17, wherein the dosage regimen is effective to reduce inflammation in the subject for at least 10 days.

23. The method of claim 17, wherein the dosage regimen is effective to reduce inflammation in the subject for at least two weeks.

24. The method of claim 17, wherein the dosage regimen is effective to reduce inflammation in the subject for at least three weeks.

25. The method of claim 17, wherein the dosage regimen is effective to increase the ratio of Tregs relative to total CD4+ cells at a site of inflammation, in the draining lymph nodes, in the spleen, in the central nervous system, or combinations thereof.

26. The method of claim 17, wherein the dosage regimen is effective to reduce the ratio of effector or memory T cells relative to total CD4+ cells in the subject.

27. The method of claim 26, wherein the dosage regimen is effective to reduce the ratio of effector or memory T cells relative to total CD4+ cells at a site of inflammation in the subject.

28. The method of claim 17, wherein the subject has a disease selected from the group consisting of rheumatoid arthritis, systemic lupus erythematosus, alopecia areata, ankylosing spondylitis, antiphospholipid syndrome, autoimmune Addison's disease, autoimmune hemolytic anemia, autoimmune hepatitis, autoimmune inner ear disease, autoimmune lymphoproliferative syndrome (alps), autoimmune thrombocytopenic purpura (ATP), Behcet's disease, bullous pemphigoid, cardiomyopathy, celiac sprue-dermatitis, chronic fatigue syndrome immune deficiency, syndrome (CFIDS), chronic inflammatory demyelinating polyneuropathy, cicatrical pemphigoid, cold agglutinin disease, Crest syndrome, Crohn's disease, Degos disease, dermatomyositis, dermatomyositis-juvenile, discoid lupus, essential mixed cryoglobulinemia, fibromyalgia-fibromyositis, Grave's disease, Guillain-Barre syndrome, Hashimoto's thyroiditis, idiopathic pulmonary fibrosis, idiopathic thrombocytopenia purpura (ITP), IgA nephropathy, insulin dependent diabetes (Type I), juvenile arthritis, Meniere's disease, mixed connective tissue disease, multiple sclerosis, myasthenia gravis, pemphigus vulgaris, pernicious anemia, polyarteritis nodosa, polychondritis, polyglandular syndromes, polymyalgia rheumatica, polymyositis and dermatomyositis, primary agammaglobulinemia, primary biliary cirrhosis, psoriasis, Raynaud's phenomenon, Reiter's syndrome, rheumatic fever, sarcoidosis, scleroderma, Sjogren's syndrome, stiff-man syndrome, Takayasu arteritis, temporal arteritis/giant cell arteritis, ulcerative colitis, uveitis, vasculitis, vitiligo, and Wegener's granulomatosis.

29. The method claim 28, wherein the disease is Sjogren's syndrome, multiple sclerosis, rheumatoid arthritis, Crohn's disease, or myasthenia gravis.

30. The method of claim 29, wherein the disease is rheumatoid arthritis.

31. A method for treating an autoimmune disorder in a human subject, the method comprising treating the subject according to a dosage regimen comprising intravenous administration of one or more doses of a fusion protein comprising a B7-H4 polypeptide comprising the IgV domain of SEQ ID NO: 63 or SEQ ID NO: 64 fused to a second polypeptide or fused to a linker peptide fused to a second polypeptide, wherein the dosage regimen is effective to achieve at least a 1.0 µg/ml concentration of the fusion protein in the subject post administration, and wherein the dosage regimen increases the ratio of regulatory T cells (Tregs) relative to total CD4+ cells and reduces inflammation in the subject for at least a week post administration.

32. The method of claim 31, wherein the dosage regimen comprises at least one dose of 3 mg/kg to 20 mg/kg of the fusion protein.

33. The method of claim 31, wherein the dosage regimen comprises intravenous administration of doses of the fusion protein to the subject at least two days apart and within two weeks.

34. The method of claim 31, wherein the dosage regimen comprises intravenous administration of doses of the fusion protein to the subject at least two days apart and within one week.

35. The method of claim 31, wherein the dosage regimen comprises intravenous administration of two or more doses of the fusion protein to the subject at least two days apart and within one week.

36. The method of claim 31, wherein the dosage regimen is effective to reduce inflammation in the subject for at least 10 days.

37. The method of claim 31, wherein the dosage regimen is effective to reduce inflammation in the subject for at least two weeks.

38. The method of claim 31, wherein the dosage regimen is effective to reduce inflammation in the subject for at least three weeks.

39. The method of claim 31, wherein the dosage regimen is effective to increase the ratio of Tregs relative to total CD4+ cells at a site of inflammation, in the draining lymph nodes, in the spleen, in the central nervous system, or combinations thereof.

40. The method of claim 31, wherein the dosage regimen is effective to reduce the ratio of effector or memory T cells relative to total CD4+ cells in the subject.

41. The method of claim 40, wherein the dosage regimen is effective to reduce the ratio of effector or memory T cells relative to total CD4+ cells at a site of inflammation in the subject.

42. The method of claim 31, wherein the second polypeptide comprises the hinge, CH2 and CH3 regions of an immunoglobulin.

43. The method of claim 42, wherein the immunoglobulin is a human IgG1.

44. A method for treating an autoimmune disorder in a human subject, the method comprising treating the subject according to a dosage regimen comprising intravenous administration of one or more doses of a fusion protein comprising the amino acid sequence of SEQ ID NO: 130, wherein the dosage regimen is effective to achieve at least a 1.0 µg/ml concentration of the fusion protein in the subject post administration, and wherein the dosage regimen increases the ratio of regulatory T cells (Tregs) relative to total CD4+ cells and reduces inflammation in the subject for at least a week post administration.

45. The method of claim 44, wherein the dosage regimen comprises at least one dose of 3 mg/kg to 20 mg/kg of the fusion protein.

46. The method of claim 44, wherein the dosage regimen comprises intravenous administration of doses of the fusion protein to the subject at least two days apart and within two weeks.

47. The method of claim 44, wherein the dosage regimen comprises intravenous administration of doses of the fusion protein to the subject at least two days apart and within one week.

48. The method of claim 44, wherein the dosage regimen comprises intravenous administration of two or more doses of the fusion protein to the subject at least two days apart and within one week.

49. The method of claim 44, wherein the dosage regimen is effective to reduce inflammation in the subject for at least 10 days.

50. The method of claim 44, wherein the dosage regimen is effective to reduce inflammation in the subject for at least two weeks.

51. The method of claim 44, wherein the dosage regimen is effective to reduce inflammation in the subject for at least three weeks.

52. The method of claim 44, wherein the dosage regimen is effective to increase the ratio of Tregs relative to total CD4+ cells at a site of inflammation, in the draining lymph nodes, in the spleen, in the central nervous system, or combinations thereof.

53. The method of claim 44, wherein the dosage regimen is effective to reduce the ratio of effector or memory T cells relative to total CD4+ cells in the subject.

54. The method of claim 53, wherein the dosage regimen is effective to reduce the ratio of effector or memory T cells relative to total CD4+ cells at a site of inflammation in the subject.

\* \* \* \* \*

SEQUENCE LISTING

```
<160> NUMBER OF SEQ ID NOS: 141

<210> SEQ ID NO 1
<211> LENGTH: 852
<212> TYPE: DNA
<213> ORGANISM: Mus musculus

<400> SEQUENCE: 1
atggcttcct tggggcagat catcttttgg agtattatta acatcatcat catcctggct      60
ggggccatcg cactcatcat tggctttggc atttcaggca agcacttcat cacggtcacg     120
accttcacct cagctggaaa cattggagag gacgggaccc tgagctgcac ttttgaacct     180
gacatcaaac tcaacggcat cgtcatccag tggctgaaag aaggcatcaa aggtttggtc     240
cacgagttca agaaggcaa agacgacctc tcacagcagc atgagatgtt cagaggccgc     300
acagcagtgt ttgctgatca ggtggtagtt ggcaatgctt ccctgagact gaaaaacgtg     360
cagctcacgg atgctggcac ctacacatgt tacatccgca cctcaaaagg caagggaat      420 gcaaaccttg agtataagac cggagccttc agtatgccag agataaatgt ggactataat     480
gccagttcag agagtttacg ctgcgaggct cctcggtggt tcccccagcc cacagtggcc     540
tgggcatctc aagtcgacca aggagccaat ttctcagaag tctccaacac cagctttgag     600
ttgaactctg agaatgtgac catgaaggtc gtatctgtgc tctacaatgt cacaatcaac     660
aacacatact cctgtatgat tgaaaacgac attgccaaag ccaccgggga catcaaagtg     720
acagattcag aggtcaaaag gcgaagtcag ctgcagttgc tgaactctgg gccttccccg     780
tgtgtttttt cttctgcctt tgtggctggc tgggcactcc tatctctctc ctgttgcctg     840
atgctaagat ga                                                         852

<210> SEQ ID NO 2
<211> LENGTH: 283
<212> TYPE: PRT
<213> ORGANISM: Mus musculus

<400> SEQUENCE: 2

Met Ala Ser Leu Gly Gln Ile Ile Phe Trp Ser Ile Ile Asn Ile Ile
  1               5                  10                  15
```

```
Ile Ile Leu Ala Gly Ala Ile Ala Leu Ile Ile Gly Phe Gly Ile Ser
             20                  25                  30

Gly Lys His Phe Ile Thr Val Thr Phe Thr Ser Ala Gly Asn Ile
         35                  40                  45

Gly Glu Asp Gly Thr Leu Ser Cys Thr Phe Glu Pro Asp Ile Lys Leu
 50                  55                  60

Asn Gly Ile Val Ile Gln Trp Leu Lys Glu Gly Ile Lys Gly Leu Val
 65                  70                  75                  80

His Glu Phe Lys Glu Gly Lys Asp Asp Leu Ser Gln Gln His Glu Met
                 85                  90                  95

Phe Arg Gly Arg Thr Ala Val Phe Ala Asp Gln Val Val Val Gly Asn
            100                 105                 110

Ala Ser Leu Arg Leu Lys Asn Val Gln Leu Thr Asp Ala Gly Thr Tyr
        115                 120                 125

Thr Cys Tyr Ile Arg Ser Ser Lys Gly Lys Gly Asn Ala Asn Leu Glu
130                 135                 140

Tyr Lys Thr Gly Ala Phe Ser Met Pro Glu Ile Asn Val Asp Tyr Asn
145                 150                 155                 160

Ala Ser Ser Glu Ser Leu Arg Cys Glu Ala Pro Arg Trp Phe Pro Gln
                165                 170                 175

Pro Thr Val Ala Trp Ala Ser Gln Val Asp Gln Gly Ala Asn Phe Ser
            180                 185                 190

Glu Val Ser Asn Thr Ser Phe Glu Leu Asn Ser Glu Asn Val Thr Met
        195                 200                 205

Lys Val Val Ser Val Leu Tyr Asn Val Thr Ile Asn Asn Thr Tyr Ser
210                 215                 220

Cys Met Ile Glu Asn Asp Ile Ala Lys Ala Thr Gly Asp Ile Lys Val
225                 230                 235                 240

Thr Asp Ser Glu Val Lys Arg Arg Ser Gln Leu Gln Leu Leu Asn Ser
                245                 250                 255

Gly Pro Ser Pro Cys Val Ser Ser Ala Phe Val Ala Gly Trp Ala
            260                 265                 270

Leu Leu Ser Leu Ser Cys Cys Leu Met Leu Arg
        275                 280

<210> SEQ ID NO 3
<211> LENGTH: 275
<212> TYPE: PRT
<213> ORGANISM: Mus musculus

<400> SEQUENCE: 3

Met Glu Trp Ser Trp Val Phe Leu Phe Phe Leu Ser Val Thr Thr Gly
1               5                   10                  15

Val His Ser Gly Phe Gly Ile Ser Gly Lys His Phe Ile Thr Val Thr
            20                  25                  30

Thr Phe Thr Ser Ala Gly Asn Ile Gly Glu Asp Gly Thr Leu Ser Cys
        35                  40                  45

Thr Phe Glu Pro Asp Ile Lys Leu Asn Gly Ile Val Ile Gln Trp Leu
 50                  55                  60

Lys Glu Gly Ile Lys Gly Leu Val His Glu Phe Lys Glu Gly Lys Asp
65                  70                  75                  80

Asp Leu Ser Gln Gln His Glu Met Phe Arg Gly Arg Thr Ala Val Phe
                85                  90                  95

Ala Asp Gln Val Val Val Gly Asn Ala Ser Leu Arg Leu Lys Asn Val
```

```
            100                 105                 110
Gln Leu Thr Asp Ala Gly Thr Tyr Thr Cys Tyr Ile Arg Ser Ser Lys
        115                 120                 125

Gly Lys Gly Asn Ala Asn Leu Glu Tyr Lys Thr Gly Ala Phe Ser Met
        130                 135                 140

Pro Glu Ile Asn Val Asp Tyr Asn Ala Ser Glu Ser Leu Arg Cys
145                 150                 155                 160

Glu Ala Pro Arg Trp Phe Pro Gln Pro Thr Val Ala Trp Ala Ser Gln
                165                 170                 175

Val Asp Gln Gly Ala Asn Phe Ser Glu Val Ser Asn Thr Ser Phe Glu
                180                 185                 190

Leu Asn Ser Glu Asn Val Thr Met Lys Val Val Ser Val Leu Tyr Asn
        195                 200                 205

Val Thr Ile Asn Asn Thr Tyr Ser Cys Met Ile Glu Asn Asp Ile Ala
        210                 215                 220

Lys Ala Thr Gly Asp Ile Lys Val Thr Asp Ser Glu Val Lys Arg Arg
225                 230                 235                 240

Ser Gln Leu Gln Leu Leu Asn Ser Gly Pro Ser Pro Cys Val Ser Ser
                245                 250                 255

Ser Ala Phe Val Ala Gly Trp Ala Leu Leu Ser Leu Ser Cys Cys Leu
                260                 265                 270

Met Leu Arg
        275

<210> SEQ ID NO 4
<211> LENGTH: 200
<212> TYPE: PRT
<213> ORGANISM: Mus musculus

<400> SEQUENCE: 4

Gly Phe Gly Ile Ser Gly Lys His Phe Ile Thr Val Thr Thr Phe Thr
1               5                   10                  15

Ser Ala Gly Asn Ile Gly Glu Asp Gly Thr Leu Ser Cys Thr Phe Glu
                20                  25                  30

Pro Asp Ile Lys Leu Asn Gly Ile Val Ile Gln Trp Leu Lys Glu Gly
            35                  40                  45

Ile Lys Gly Leu Val His Glu Phe Lys Glu Lys Asp Asp Leu Ser
        50                  55                  60

Gln Gln His Glu Met Phe Arg Gly Arg Thr Ala Val Phe Ala Asp Gln
65                  70                  75                  80

Val Val Val Gly Asn Ala Ser Leu Arg Leu Lys Asn Val Gln Leu Thr
                85                  90                  95

Asp Ala Gly Thr Tyr Thr Cys Tyr Ile Arg Ser Ser Lys Gly Lys Gly
            100                 105                 110

Asn Ala Asn Leu Glu Tyr Lys Thr Gly Ala Phe Ser Met Pro Glu Ile
        115                 120                 125

Asn Val Asp Tyr Asn Ala Ser Glu Ser Leu Arg Cys Glu Ala Pro
        130                 135                 140

Arg Trp Phe Pro Gln Pro Thr Val Ala Trp Ala Ser Gln Val Asp Gln
145                 150                 155                 160

Gly Ala Asn Phe Ser Glu Val Ser Asn Thr Ser Phe Glu Leu Asn Ser
                165                 170                 175

Glu Asn Val Thr Met Lys Val Val Ser Val Leu Tyr Asn Val Thr Ile
                180                 185                 190
```

-continued

Asn Asn Thr Tyr Ser Cys Met Ile
         195                 200

<210> SEQ ID NO 5
<211> LENGTH: 283
<212> TYPE: PRT
<213> ORGANISM: Mus musculus

<400> SEQUENCE: 5

Met Ala Ser Leu Gly Gln Ile Ile Phe Trp Ser Ile Ile Asn Ile Ile
1               5                   10                  15

Ile Ile Leu Ala Gly Ala Ile Ala Leu Ile Ile Gly Phe Gly Ile Ser
            20                  25                  30

Gly Lys His Phe Ile Thr Val Thr Phe Thr Ser Ala Gly Asn Ile
        35                  40                  45

Gly Glu Asp Gly Thr Leu Ser Cys Thr Phe Glu Pro Asp Ile Lys Leu
    50                  55                  60

Asn Gly Ile Val Ile Gln Trp Leu Lys Glu Gly Ile Lys Gly Leu Val
65                  70                  75                  80

His Glu Phe Lys Glu Gly Lys Asp Asp Leu Ser Gln Gln His Glu Met
                85                  90                  95

Phe Arg Gly Arg Thr Ala Val Phe Ala Asp Gln Val Val Gly Asn
            100                 105                 110

Ala Ser Leu Arg Leu Lys Asn Val Gln Leu Thr Asp Ala Gly Thr Tyr
        115                 120                 125

Thr Cys Tyr Ile Arg Thr Ser Lys Gly Lys Gly Asn Ala Asn Leu Glu
    130                 135                 140

Tyr Lys Thr Gly Ala Phe Ser Met Pro Glu Ile Asn Val Asp Tyr Asn
145                 150                 155                 160

Ala Ser Ser Glu Ser Leu Arg Cys Glu Ala Pro Arg Trp Phe Pro Gln
                165                 170                 175

Pro Thr Val Ala Trp Ala Ser Gln Val Asp Gln Gly Ala Asn Phe Ser
            180                 185                 190

Glu Val Ser Asn Thr Ser Phe Glu Leu Asn Ser Glu Asn Val Thr Met
        195                 200                 205

Lys Val Val Ser Val Leu Tyr Asn Val Thr Ile Asn Asn Thr Tyr Ser
    210                 215                 220

Cys Met Ile Glu Asn Asp Ile Ala Lys Ala Thr Gly Asp Ile Lys Val
225                 230                 235                 240

Thr Asp Ser Glu Val Lys Arg Arg Ser Gln Leu Gln Leu Leu Asn Ser
                245                 250                 255

Gly Pro Ser Pro Cys Val Phe Ser Ser Ala Phe Val Ala Gly Trp Ala
            260                 265                 270

Leu Leu Ser Leu Ser Cys Cys Leu Met Leu Arg
        275                 280

<210> SEQ ID NO 6
<211> LENGTH: 275
<212> TYPE: PRT
<213> ORGANISM: Mus musculus

<400> SEQUENCE: 6

Met Glu Trp Ser Trp Val Phe Leu Phe Phe Leu Ser Val Thr Thr Gly
1               5                   10                  15

Val His Ser Gly Phe Gly Ile Ser Gly Lys His Phe Ile Thr Val Thr
            20                  25                  30

```
Thr Phe Thr Ser Ala Gly Asn Ile Gly Glu Asp Gly Thr Leu Ser Cys
             35                  40                  45

Thr Phe Glu Pro Asp Ile Lys Leu Asn Gly Ile Val Ile Gln Trp Leu
 50                  55                  60

Lys Glu Gly Ile Lys Gly Leu Val His Glu Phe Lys Glu Gly Lys Asp
 65                  70                  75                  80

Asp Leu Ser Gln Gln His Glu Met Phe Arg Gly Arg Thr Ala Val Phe
                 85                  90                  95

Ala Asp Gln Val Val Gly Asn Ala Ser Leu Arg Leu Lys Asn Val
                100                 105                 110

Gln Leu Thr Asp Ala Gly Thr Tyr Thr Cys Tyr Ile Arg Thr Ser Lys
            115                 120                 125

Gly Lys Gly Asn Ala Asn Leu Glu Tyr Lys Thr Gly Ala Phe Ser Met
130                 135                 140

Pro Glu Ile Asn Val Asp Tyr Asn Ala Ser Ser Glu Ser Leu Arg Cys
145                 150                 155                 160

Glu Ala Pro Arg Trp Phe Pro Gln Pro Thr Val Ala Trp Ala Ser Gln
                165                 170                 175

Val Asp Gln Gly Ala Asn Phe Ser Glu Val Ser Asn Thr Ser Phe Glu
            180                 185                 190

Leu Asn Ser Glu Asn Val Thr Met Lys Val Ser Val Leu Tyr Asn
        195                 200                 205

Val Thr Ile Asn Asn Thr Tyr Ser Cys Met Ile Glu Asn Asp Ile Ala
    210                 215                 220

Lys Ala Thr Gly Asp Ile Lys Val Thr Asp Ser Glu Val Lys Arg Arg
225                 230                 235                 240

Ser Gln Leu Gln Leu Leu Asn Ser Gly Pro Ser Pro Cys Val Phe Ser
                245                 250                 255

Ser Ala Phe Val Ala Gly Trp Ala Leu Leu Ser Leu Ser Cys Cys Leu
            260                 265                 270

Met Leu Arg
        275

<210> SEQ ID NO 7
<211> LENGTH: 256
<212> TYPE: PRT
<213> ORGANISM: Mus musculus

<400> SEQUENCE: 7

Gly Phe Gly Ile Ser Gly Lys His Phe Ile Thr Val Thr Thr Phe Thr
 1               5                  10                  15

Ser Ala Gly Asn Ile Gly Glu Asp Gly Thr Leu Ser Cys Thr Phe Glu
                20                  25                  30

Pro Asp Ile Lys Leu Asn Gly Ile Val Ile Gln Trp Leu Lys Glu Gly
            35                  40                  45

Ile Lys Gly Leu Val His Glu Phe Lys Glu Gly Lys Asp Asp Leu Ser
        50                  55                  60

Gln Gln His Glu Met Phe Arg Gly Arg Thr Ala Val Phe Ala Asp Gln
 65                  70                  75                  80

Val Val Val Gly Asn Ala Ser Leu Arg Leu Lys Asn Val Gln Leu Thr
                 85                  90                  95

Asp Ala Gly Thr Tyr Thr Cys Tyr Ile Arg Thr Ser Lys Gly Lys Gly
            100                 105                 110

Asn Ala Asn Leu Glu Tyr Lys Thr Gly Ala Phe Ser Met Pro Glu Ile
        115                 120                 125
```

```
Asn Val Asp Tyr Asn Ala Ser Ser Glu Ser Leu Arg Cys Glu Ala Pro
        130                 135                 140

Arg Trp Phe Pro Gln Pro Thr Val Ala Trp Ala Ser Gln Val Asp Gln
145                 150                 155                 160

Gly Ala Asn Phe Ser Glu Val Ser Asn Thr Ser Phe Glu Leu Asn Ser
                165                 170                 175

Glu Asn Val Thr Met Lys Val Val Ser Val Leu Tyr Asn Val Thr Ile
            180                 185                 190

Asn Asn Thr Tyr Ser Cys Met Ile Glu Asn Asp Ile Ala Lys Ala Thr
            195                 200                 205

Gly Asp Ile Lys Val Thr Asp Ser Glu Val Lys Arg Arg Ser Gln Leu
        210                 215                 220

Gln Leu Leu Asn Ser Gly Pro Ser Pro Cys Val Phe Ser Ser Ala Phe
225                 230                 235                 240

Val Ala Gly Trp Ala Leu Leu Ser Leu Ser Cys Cys Leu Met Leu Arg
                245                 250                 255

<210> SEQ ID NO 8
<211> LENGTH: 849
<212> TYPE: DNA
<213> ORGANISM: Homo sapiens

<400> SEQUENCE: 8
atggcttccc tggggcagat cctcttctgg agcataatta gcatcatcat tattctggct      60
ggagcaattg cactcatcat tggctttggt atttcaggga cactccat cacagtcact       120 actgtcgcct cagctgggaa cattggggag gatggaatcc tgagctgcac ttttgaacct      180
gacatcaaac tttctgatat cgtgataaca tggctgaagg aaggtgtttt aggcttggtc      240
catgagttca agaaggcaa agatgagctg tcggagcagg atgaaatgtt cagaggccgg      300
acagcagtgt ttgctgatca agtgatagtt ggcaatgcct cttttgcggct gaaaaacgtg     360 caactcacag atgctggcac ctacaaatgt tatatcatca cttctaaagg caaggggaat      420
gctaaccttg agtataaaac tggagccttc agcatgccgg aagtgaatgt ggactataat      480
gccagctcag agaccttgcg tgtgaggct ccccgatggt tccccagcc acagtggtc         540 tgggcatccc aagttgacca gggagccaac ttctcggaag tctccaatac agctttgag      600 ctgaactctg agaatgtgac catgaaggtt gtgtctgtgc tctacaatgt tacgatcaac     660
aacacatact cctgtatgat tgaaaatgac attgccaaag caacagggga tatcaaagtg     720
acagaatcgg agatcaaaag gcggagtcac ctacagctgc taaactcaaa ggcttctctg     780
tgtgtctctt ctttctttgc catcagctgg gcacttctgc ctctcagccc ttacctgatg     840
ctaaaataa                                                             849

<210> SEQ ID NO 9
<211> LENGTH: 282
<212> TYPE: PRT
<213> ORGANISM: Homo sapiens

<400> SEQUENCE: 9

Met Ala Ser Leu Gly Gln Ile Leu Phe Trp Ser Ile Ile Ser Ile Ile
1               5                   10                  15

Ile Ile Leu Ala Gly Ala Ile Ala Leu Ile Ile Gly Phe Gly Ile Ser
            20                  25                  30

Gly Arg His Ser Ile Thr Val Thr Val Ala Ser Ala Gly Asn Ile
        35                  40                  45
```

Gly Glu Asp Gly Ile Leu Ser Cys Thr Phe Glu Pro Asp Ile Lys Leu
             50                  55                  60

Ser Asp Ile Val Ile Gln Trp Leu Lys Glu Gly Val Leu Gly Leu Val
 65                  70                  75                  80

His Glu Phe Lys Glu Gly Lys Asp Glu Leu Ser Glu Gln Asp Glu Met
                 85                  90                  95

Phe Arg Gly Arg Thr Ala Val Phe Ala Asp Gln Val Ile Val Gly Asn
            100                 105                 110

Ala Ser Leu Arg Leu Lys Asn Val Gln Leu Thr Asp Ala Gly Thr Tyr
            115                 120                 125

Lys Cys Tyr Ile Ile Thr Ser Lys Gly Lys Gly Asn Ala Asn Leu Glu
            130                 135                 140

Tyr Lys Thr Gly Ala Phe Ser Met Pro Glu Val Asn Val Asp Tyr Asn
145                 150                 155                 160

Ala Ser Ser Glu Thr Leu Arg Cys Glu Ala Pro Arg Trp Phe Pro Gln
                165                 170                 175

Pro Thr Val Val Trp Ala Ser Gln Val Asp Gln Gly Ala Asn Phe Ser
            180                 185                 190

Glu Val Ser Asn Thr Ser Phe Glu Leu Asn Ser Glu Asn Val Thr Met
            195                 200                 205

Lys Val Val Ser Val Leu Tyr Asn Val Thr Ile Asn Asn Thr Tyr Ser
            210                 215                 220

Cys Met Ile Glu Asn Asp Ile Ala Lys Ala Thr Gly Asp Ile Lys Val
225                 230                 235                 240

Thr Glu Ser Glu Ile Lys Arg Arg Ser His Leu Gln Leu Leu Asn Ser
                245                 250                 255

Lys Ala Ser Leu Cys Val Ser Ser Phe Phe Ala Ile Ser Trp Ala Leu
            260                 265                 270

Leu Pro Leu Ser Pro Tyr Leu Met Leu Lys
            275                 280

<210> SEQ ID NO 10
<211> LENGTH: 274
<212> TYPE: PRT
<213> ORGANISM: Homo sapiens

<400> SEQUENCE: 10

Met Glu Trp Ser Trp Val Phe Leu Phe Phe Leu Ser Val Thr Thr Gly
  1               5                  10                  15

Val His Ser Gly Phe Gly Ile Ser Gly Arg His Ser Ile Thr Val Thr
                 20                  25                  30

Thr Val Ala Ser Ala Gly Asn Ile Gly Glu Asp Gly Ile Leu Ser Cys
             35                  40                  45

Thr Phe Glu Pro Asp Ile Lys Leu Ser Asp Ile Val Ile Gln Trp Leu
 50                  55                  60

Lys Glu Gly Val Leu Gly Leu Val His Glu Phe Lys Glu Gly Lys Asp
 65                  70                  75                  80

Glu Leu Ser Glu Gln Asp Glu Met Phe Arg Gly Arg Thr Ala Val Phe
                 85                  90                  95

Ala Asp Gln Val Ile Val Gly Asn Ala Ser Leu Arg Leu Lys Asn Val
            100                 105                 110

Gln Leu Thr Asp Ala Gly Thr Tyr Lys Cys Tyr Ile Ile Thr Ser Lys
            115                 120                 125

Gly Lys Gly Asn Ala Asn Leu Glu Tyr Lys Thr Gly Ala Phe Ser Met

```
            130                 135                 140
Pro Glu Val Asn Val Asp Tyr Asn Ala Ser Ser Glu Thr Leu Arg Cys
145                 150                 155                 160

Glu Ala Pro Arg Trp Phe Pro Gln Pro Thr Val Val Trp Ala Ser Gln
                165                 170                 175

Val Asp Gln Gly Ala Asn Phe Ser Glu Val Ser Asn Thr Ser Phe Glu
            180                 185                 190

Leu Asn Ser Glu Asn Val Thr Met Lys Val Val Ser Val Leu Tyr Asn
        195                 200                 205

Val Thr Ile Asn Asn Thr Tyr Ser Cys Met Ile Glu Asn Asp Ile Ala
    210                 215                 220

Lys Ala Thr Gly Asp Ile Lys Val Thr Glu Ser Glu Ile Lys Arg Arg
225                 230                 235                 240

Ser His Leu Gln Leu Leu Asn Ser Lys Ala Ser Leu Cys Val Ser Ser
                245                 250                 255

Phe Phe Ala Ile Ser Trp Ala Leu Leu Pro Leu Ser Pro Tyr Leu Met
            260                 265                 270

Leu Lys

<210> SEQ ID NO 11
<211> LENGTH: 255
<212> TYPE: PRT
<213> ORGANISM: Homo sapiens

<400> SEQUENCE: 11

Gly Phe Gly Ile Ser Gly Arg His Ser Ile Thr Val Thr Thr Val Ala
1               5                   10                  15

Ser Ala Gly Asn Ile Gly Glu Asp Gly Ile Leu Ser Cys Thr Phe Glu
                20                  25                  30

Pro Asp Ile Lys Leu Ser Asp Ile Val Ile Gln Trp Leu Lys Glu Gly
            35                  40                  45

Val Leu Gly Leu Val His Glu Phe Lys Glu Gly Lys Asp Glu Leu Ser
        50                  55                  60

Glu Gln Asp Glu Met Phe Arg Gly Arg Thr Ala Val Phe Ala Asp Gln
65                  70                  75                  80

Val Ile Val Gly Asn Ala Ser Leu Arg Leu Lys Asn Val Gln Leu Thr
                85                  90                  95

Asp Ala Gly Thr Tyr Lys Cys Tyr Ile Ile Thr Ser Lys Gly Lys Gly
            100                 105                 110

Asn Ala Asn Leu Glu Tyr Lys Thr Gly Ala Phe Ser Met Pro Glu Val
        115                 120                 125

Asn Val Asp Tyr Asn Ala Ser Ser Glu Thr Leu Arg Cys Glu Ala Pro
    130                 135                 140

Arg Trp Phe Pro Gln Pro Thr Val Val Trp Ala Ser Gln Val Asp Gln
145                 150                 155                 160

Gly Ala Asn Phe Ser Glu Val Ser Asn Thr Ser Phe Glu Leu Asn Ser
                165                 170                 175

Glu Asn Val Thr Met Lys Val Val Ser Val Leu Tyr Asn Val Thr Ile
            180                 185                 190

Asn Asn Thr Tyr Ser Cys Met Ile Glu Asn Asp Ile Ala Lys Ala Thr
        195                 200                 205

Gly Asp Ile Lys Val Thr Glu Ser Glu Ile Lys Arg Arg Ser His Leu
    210                 215                 220

Gln Leu Leu Asn Ser Lys Ala Ser Leu Cys Val Ser Ser Phe Phe Ala
```

Ile Ser Trp Ala Leu Leu Pro Leu Ser Pro Tyr Leu Met Leu Lys
              245                 250                 255

<210> SEQ ID NO 12
<211> LENGTH: 282
<212> TYPE: PRT
<213> ORGANISM: Homo sapiens

<400> SEQUENCE: 12

Met Ala Ser Leu Gly Gln Ile Leu Phe Trp Ser Ile Ser Ile Ile
1               5                   10                  15

Ile Ile Leu Ala Gly Ala Ile Ala Leu Ile Ile Gly Phe Gly Ile Ser
                20                  25                  30

Gly Arg His Ser Ile Thr Val Thr Val Ala Ser Ala Gly Asn Ile
            35                  40                  45

Gly Glu Asp Gly Ile Gln Ser Cys Thr Phe Glu Pro Asp Ile Lys Leu
    50                  55                  60

Ser Asp Ile Val Ile Gln Trp Leu Lys Glu Gly Val Leu Gly Leu Val
65                  70                  75                  80

His Glu Phe Lys Glu Gly Lys Asp Glu Leu Ser Glu Gln Asp Glu Met
                85                  90                  95

Phe Arg Gly Arg Thr Ala Val Phe Ala Asp Gln Val Ile Val Gly Asn
            100                 105                 110

Ala Ser Leu Arg Leu Lys Asn Val Gln Leu Thr Asp Ala Gly Thr Tyr
        115                 120                 125

Lys Cys Tyr Ile Ile Thr Ser Lys Gly Lys Gly Asn Ala Asn Leu Glu
    130                 135                 140

Tyr Lys Thr Gly Ala Phe Ser Met Pro Glu Val Asn Val Asp Tyr Asn
145                 150                 155                 160

Ala Ser Ser Glu Thr Leu Arg Cys Glu Ala Pro Arg Trp Phe Pro Gln
                165                 170                 175

Pro Thr Val Val Trp Ala Ser Gln Val Asp Gln Gly Ala Asn Phe Ser
            180                 185                 190

Glu Val Ser Asn Thr Ser Phe Glu Leu Asn Ser Glu Asn Val Thr Met
        195                 200                 205

Lys Val Val Ser Val Leu Tyr Asn Val Thr Ile Asn Asn Thr Tyr Ser
    210                 215                 220

Cys Met Ile Glu Asn Asp Ile Ala Lys Ala Thr Gly Asp Ile Lys Val
225                 230                 235                 240

Thr Glu Ser Glu Ile Lys Arg Arg Ser His Leu Gln Leu Leu Asn Ser
                245                 250                 255

Lys Ala Ser Leu Cys Val Ser Ser Phe Phe Ala Ile Ser Trp Ala Leu
            260                 265                 270

Leu Pro Leu Ser Pro Tyr Leu Met Leu Lys
        275                 280

<210> SEQ ID NO 13
<211> LENGTH: 274
<212> TYPE: PRT
<213> ORGANISM: Homo sapiens

<400> SEQUENCE: 13

Met Glu Trp Ser Trp Val Phe Leu Phe Phe Leu Ser Val Thr Thr Gly
1               5                   10                  15

Val His Ser Gly Phe Gly Ile Ser Gly Arg His Ser Ile Thr Val Thr

```
            20                  25                  30
Thr Val Ala Ser Ala Gly Asn Ile Gly Glu Asp Gly Ile Gln Ser Cys
            35                  40                  45
Thr Phe Glu Pro Asp Ile Lys Leu Ser Asp Ile Val Ile Gln Trp Leu
 50                  55                  60
Lys Glu Gly Val Leu Gly Leu Val His Glu Phe Lys Glu Gly Lys Asp
 65                  70                  75                  80
Glu Leu Ser Glu Gln Asp Glu Met Phe Arg Gly Arg Thr Ala Val Phe
                85                  90                  95
Ala Asp Gln Val Ile Val Gly Asn Ala Ser Leu Arg Leu Lys Asn Val
            100                 105                 110
Gln Leu Thr Asp Ala Gly Thr Tyr Lys Cys Tyr Ile Ile Thr Ser Lys
        115                 120                 125
Gly Lys Gly Asn Ala Asn Leu Glu Tyr Lys Thr Gly Ala Phe Ser Met
    130                 135                 140
Pro Glu Val Asn Val Asp Tyr Asn Ala Ser Ser Glu Thr Leu Arg Cys
145                 150                 155                 160
Glu Ala Pro Arg Trp Phe Pro Gln Pro Thr Val Val Trp Ala Ser Gln
                165                 170                 175
Val Asp Gln Gly Ala Asn Phe Ser Glu Val Ser Asn Thr Ser Phe Glu
            180                 185                 190
Leu Asn Ser Glu Asn Val Thr Met Lys Val Val Ser Val Leu Tyr Asn
        195                 200                 205
Val Thr Ile Asn Asn Thr Tyr Ser Cys Met Ile Glu Asn Asp Ile Ala
    210                 215                 220
Lys Ala Thr Gly Asp Ile Lys Val Thr Glu Ser Glu Ile Lys Arg Arg
225                 230                 235                 240
Ser His Leu Gln Leu Leu Asn Ser Lys Ala Ser Leu Cys Val Ser Ser
                245                 250                 255
Phe Phe Ala Ile Ser Trp Ala Leu Leu Pro Leu Ser Pro Tyr Leu Met
            260                 265                 270
Leu Lys

<210> SEQ ID NO 14
<211> LENGTH: 255
<212> TYPE: PRT
<213> ORGANISM: Homo sapiens

<400> SEQUENCE: 14

Gly Phe Gly Ile Ser Gly Arg His Ser Ile Thr Val Thr Thr Val Ala
 1                   5                  10                  15
Ser Ala Gly Asn Ile Gly Glu Asp Gly Ile Gln Ser Cys Thr Phe Glu
            20                  25                  30
Pro Asp Ile Lys Leu Ser Asp Ile Val Ile Gln Trp Leu Lys Glu Gly
        35                  40                  45
Val Leu Gly Leu Val His Glu Phe Lys Glu Gly Lys Asp Glu Leu Ser
    50                  55                  60
Glu Gln Asp Glu Met Phe Arg Gly Arg Thr Ala Val Phe Ala Asp Gln
65                  70                  75                  80
Val Ile Val Gly Asn Ala Ser Leu Arg Leu Lys Asn Val Gln Leu Thr
                85                  90                  95
Asp Ala Gly Thr Tyr Lys Cys Tyr Ile Ile Thr Ser Lys Gly Lys Gly
            100                 105                 110
Asn Ala Asn Leu Glu Tyr Lys Thr Gly Ala Phe Ser Met Pro Glu Val
```

```
            115                 120                 125
Asn Val Asp Tyr Asn Ala Ser Ser Glu Thr Leu Arg Cys Glu Ala Pro
    130                 135                 140

Arg Trp Phe Pro Gln Pro Thr Val Val Trp Ala Ser Gln Val Asp Gln
145                 150                 155                 160

Gly Ala Asn Phe Ser Glu Val Ser Asn Thr Ser Phe Glu Leu Asn Ser
                165                 170                 175

Glu Asn Val Thr Met Lys Val Ser Val Leu Tyr Asn Val Thr Ile
            180                 185                 190

Asn Asn Thr Tyr Ser Cys Met Ile Glu Asn Asp Ile Ala Lys Ala Thr
        195                 200                 205

Gly Asp Ile Lys Val Thr Glu Ser Glu Ile Lys Arg Arg Ser His Leu
    210                 215                 220

Gln Leu Leu Asn Ser Lys Ala Ser Leu Cys Val Ser Ser Phe Phe Ala
225                 230                 235                 240

Ile Ser Trp Ala Leu Leu Pro Leu Ser Pro Tyr Leu Met Leu Lys
                245                 250                 255

<210> SEQ ID NO 15
<211> LENGTH: 278
<212> TYPE: PRT
<213> ORGANISM: Pan troglodytes

<400> SEQUENCE: 15

Met Lys Pro Leu Thr Ser Arg Ile Ile Ser Ile Ile Ile Leu Ala
1               5                   10                  15

Gly Ala Ile Ala Leu Ile Ile Gly Phe Gly Ile Ser Gly Arg His Ser
                20                  25                  30

Ile Thr Val Thr Thr Val Ala Ser Ala Gly Asn Ile Gly Glu Asp Gly
            35                  40                  45

Ile Leu Ser Cys Thr Phe Glu Pro Asp Ile Lys Leu Ser Asp Ile Val
    50                  55                  60

Ile Gln Trp Leu Lys Glu Gly Val Leu Gly Leu Val His Glu Phe Lys
65                  70                  75                  80

Glu Gly Lys Asp Glu Leu Ser Glu Gln Asp Glu Met Phe Arg Gly Arg
                85                  90                  95

Thr Ala Val Phe Ala Asp Gln Val Ile Val Gly Asn Ala Ser Leu Arg
            100                 105                 110

Leu Lys Asn Val Gln Leu Thr Asp Ala Gly Thr Tyr Lys Cys Tyr Ile
    115                 120                 125

Ile Thr Ser Lys Gly Lys Gly Asn Ala Asn Leu Glu Tyr Lys Thr Gly
130                 135                 140

Ala Phe Ser Met Pro Glu Val Asn Val Asp Tyr Asn Ala Ser Ser Glu
145                 150                 155                 160

Thr Leu Arg Cys Glu Ala Pro Arg Trp Phe Pro Gln Pro Thr Val Val
                165                 170                 175

Trp Ala Ser Gln Ile Asp Gln Gly Ala Asn Phe Ser Glu Val Ser Asn
            180                 185                 190

Thr Ser Phe Glu Leu Asn Ser Glu Asn Val Thr Met Lys Val Val Ser
    195                 200                 205

Val Leu Tyr Asn Ala Thr Ile Asn Asn Thr Tyr Ser Cys Met Ile Glu
210                 215                 220

Asn Asp Ile Ala Lys Ala Thr Gly Asp Ile Lys Val Thr Glu Ser Glu
225                 230                 235                 240
```

Ile Lys Arg Arg Ser His Leu Gln Leu Leu Asn Ser Lys Ala Ser Leu
            245                 250                 255

Cys Val Ser Ser Phe Phe Ala Ile Ser Trp Ala Leu Leu Pro Leu Ser
            260                 265                 270

Pro Tyr Leu Met Leu Lys
        275

<210> SEQ ID NO 16
<211> LENGTH: 255
<212> TYPE: PRT
<213> ORGANISM: Pan troglodytes

<400> SEQUENCE: 16

Gly Phe Gly Ile Ser Gly Arg His Ser Ile Thr Val Thr Thr Val Ala
1               5                   10                  15

Ser Ala Gly Asn Ile Gly Glu Asp Gly Ile Leu Ser Cys Thr Phe Glu
            20                  25                  30

Pro Asp Ile Lys Leu Ser Asp Ile Val Ile Gln Trp Leu Lys Glu Gly
        35                  40                  45

Val Leu Gly Leu Val His Glu Phe Lys Glu Gly Lys Asp Glu Leu Ser
    50                  55                  60

Glu Gln Asp Glu Met Phe Arg Gly Arg Thr Ala Val Phe Ala Asp Gln
65                  70                  75                  80

Val Ile Val Gly Asn Ala Ser Leu Arg Leu Lys Asn Val Gln Leu Thr
                85                  90                  95

Asp Ala Gly Thr Tyr Lys Cys Tyr Ile Ile Thr Ser Lys Gly Lys Gly
            100                 105                 110

Asn Ala Asn Leu Glu Tyr Lys Thr Gly Ala Phe Ser Met Pro Glu Val
        115                 120                 125

Asn Val Asp Tyr Asn Ala Ser Ser Glu Thr Leu Arg Cys Glu Ala Pro
    130                 135                 140

Arg Trp Phe Pro Gln Pro Thr Val Val Trp Ala Ser Gln Ile Asp Gln
145                 150                 155                 160

Gly Ala Asn Phe Ser Glu Val Ser Asn Thr Ser Phe Glu Leu Asn Ser
                165                 170                 175

Glu Asn Val Thr Met Lys Val Val Ser Val Leu Tyr Asn Ala Thr Ile
            180                 185                 190

Asn Asn Thr Tyr Ser Cys Met Ile Glu Asn Asp Ile Ala Lys Ala Thr
        195                 200                 205

Gly Asp Ile Lys Val Thr Glu Ser Glu Ile Lys Arg Arg Ser His Leu
    210                 215                 220

Gln Leu Leu Asn Ser Lys Ala Ser Leu Cys Val Ser Ser Phe Phe Ala
225                 230                 235                 240

Ile Ser Trp Ala Leu Leu Pro Leu Ser Pro Tyr Leu Met Leu Lys
                245                 250                 255

<210> SEQ ID NO 17
<211> LENGTH: 282
<212> TYPE: PRT
<213> ORGANISM: Macaca mulatta

<400> SEQUENCE: 17

Met Ala Ser Leu Gly Gln Ile Leu Phe Trp Ser Ile Ile Ser Ile Ile
1               5                   10                  15

Phe Ile Leu Ala Gly Ala Ile Ala Leu Ile Ile Gly Phe Gly Ile Ser
            20                  25                  30

Gly Arg His Ser Ile Thr Val Thr Val Ala Ser Gly Asn Ile
            35                  40                  45

Gly Glu Asp Gly Ile Leu Ser Cys Thr Phe Glu Pro Asp Ile Lys Leu
 50                  55                  60

Ser Asp Ile Val Ile Gln Trp Leu Lys Glu Gly Val Ile Gly Leu Val
65                  70                  75                  80

His Glu Phe Lys Glu Gly Lys Asp Glu Leu Ser Glu Gln Asp Glu Met
                85                  90                  95

Phe Arg Gly Arg Thr Ala Val Phe Ala Asp Gln Val Ile Val Gly Asn
            100                 105                 110

Ala Ser Leu Arg Leu Lys Asn Val Gln Leu Thr Asp Ala Gly Thr Tyr
        115                 120                 125

Lys Cys Tyr Ile Ile Thr Ser Lys Gly Lys Gly Asn Ala Asn Leu Glu
    130                 135                 140

Tyr Lys Thr Gly Ala Phe Ser Met Pro Glu Val Asn Val Asp Tyr Asn
145                 150                 155                 160

Ala Ser Ser Glu Thr Leu Arg Cys Glu Ala Pro Arg Trp Phe Pro Gln
                165                 170                 175

Pro Thr Val Val Trp Ala Ser Gln Val Asp Gln Gly Ala Asn Phe Ser
            180                 185                 190

Glu Val Ser Asn Thr Ser Phe Glu Leu Asn Ser Glu Asn Val Thr Met
        195                 200                 205

Lys Val Val Ser Val Leu Tyr Asn Val Thr Ile Asn Asn Thr Tyr Ser
    210                 215                 220

Cys Met Ile Glu Asn Asp Ile Ala Lys Ala Thr Gly Asp Ile Lys Val
225                 230                 235                 240

Thr Glu Ser Glu Ile Lys Arg Arg Ser His Leu Gln Leu Leu Asn Ser
                245                 250                 255

Lys Ala Ser Leu Cys Val Ser Ser Phe Leu Ala Ile Ser Trp Ala Leu
            260                 265                 270

Leu Pro Leu Ala Pro Tyr Leu Met Leu Lys
        275                 280

<210> SEQ ID NO 18
<211> LENGTH: 255
<212> TYPE: PRT
<213> ORGANISM: Macaca mulatta

<400> SEQUENCE: 18

Gly Phe Gly Ile Ser Gly Arg His Ser Ile Thr Val Thr Thr Val Ala
1               5                   10                  15

Ser Ala Gly Asn Ile Gly Glu Asp Gly Ile Leu Ser Cys Thr Phe Glu
            20                  25                  30

Pro Asp Ile Lys Leu Ser Asp Ile Val Ile Gln Trp Leu Lys Glu Gly
        35                  40                  45

Val Ile Gly Leu Val His Glu Phe Lys Glu Gly Lys Asp Glu Leu Ser
    50                  55                  60

Glu Gln Asp Glu Met Phe Arg Gly Arg Thr Ala Val Phe Ala Asp Gln
65                  70                  75                  80

Val Ile Val Gly Asn Ala Ser Leu Arg Leu Lys Asn Val Gln Leu Thr
                85                  90                  95

Asp Ala Gly Thr Tyr Lys Cys Tyr Ile Ile Thr Ser Lys Gly Lys Gly
            100                 105                 110

Asn Ala Asn Leu Glu Tyr Lys Thr Gly Ala Phe Ser Met Pro Glu Val
        115                 120                 125

```
Asn Val Asp Tyr Asn Ala Ser Ser Glu Thr Leu Arg Cys Glu Ala Pro
            130                 135                 140

Arg Trp Phe Pro Gln Pro Thr Val Val Trp Ala Ser Gln Val Asp Gln
145                 150                 155                 160

Gly Ala Asn Phe Ser Glu Val Ser Asn Thr Ser Phe Glu Leu Asn Ser
                165                 170                 175

Glu Asn Val Thr Met Lys Val Ser Val Leu Tyr Asn Val Thr Ile
            180                 185                 190

Asn Asn Thr Tyr Ser Cys Met Ile Glu Asn Asp Ile Ala Lys Ala Thr
            195                 200                 205

Gly Asp Ile Lys Val Thr Glu Ser Glu Ile Lys Arg Arg Ser His Leu
            210                 215                 220

Gln Leu Leu Asn Ser Lys Ala Ser Leu Cys Val Ser Ser Phe Leu Ala
225                 230                 235                 240

Ile Ser Trp Ala Leu Leu Pro Leu Ala Pro Tyr Leu Met Leu Lys
                245                 250                 255

<210> SEQ ID NO 19
<211> LENGTH: 282
<212> TYPE: PRT
<213> ORGANISM: Macaca fascicularis

<400> SEQUENCE: 19

Met Ala Ser Leu Gly Gln Ile Leu Phe Trp Ser Ile Ile Ser Ile Ile
1               5                   10                  15

Phe Ile Leu Ala Gly Ala Ile Ala Leu Ile Ile Gly Phe Gly Ile Ser
            20                  25                  30

Gly Arg His Ser Ile Thr Val Thr Thr Val Ala Ser Ala Gly Asn Ile
        35                  40                  45

Gly Glu Asp Gly Ile Leu Ser Cys Thr Phe Glu Pro Asp Ile Lys Leu
    50                  55                  60

Ser Asp Ile Val Ile Gln Trp Leu Lys Glu Gly Val Ile Gly Leu Val
65                  70                  75                  80

His Glu Phe Lys Glu Gly Lys Asp Glu Leu Ser Glu Gln Asp Glu Met
                85                  90                  95

Phe Arg Gly Arg Thr Ala Val Phe Ala Asp Gln Val Ile Val Gly Asn
            100                 105                 110

Ala Ser Leu Arg Leu Lys Asn Val Gln Leu Thr Asp Ala Gly Thr Tyr
        115                 120                 125

Lys Cys Tyr Ile Ile Thr Ser Lys Gly Lys Gly Asn Ala Asn Leu Glu
    130                 135                 140

Tyr Lys Thr Gly Ala Phe Ser Met Pro Glu Val Asn Val Asp Tyr Asn
145                 150                 155                 160

Ala Ser Ser Glu Thr Leu Arg Cys Glu Ala Pro Arg Trp Phe Pro Gln
                165                 170                 175

Pro Thr Val Val Trp Ala Ser Gln Val Asp Gln Gly Ala Asn Phe Ser
            180                 185                 190

Glu Val Ser Asn Thr Ser Phe Glu Leu Asn Ser Glu Asn Val Thr Met
        195                 200                 205

Lys Val Val Ser Val Leu Tyr Asn Val Thr Ile Asn Asn Thr Tyr Ser
    210                 215                 220

Cys Met Ile Glu Asn Asp Ile Ala Lys Ala Thr Gly Asp Ile Lys Val
225                 230                 235                 240

Thr Glu Ser Glu Ile Lys Arg Arg Ser His Leu Gln Leu Leu Asn Ser
```

```
                    245                 250                 255
Lys Ala Ser Leu Cys Val Ser Ser Phe Leu Ala Ile Ser Trp Ala Leu
                260                 265                 270

Pro Pro Leu Ala Pro Tyr Leu Met Leu Lys
                275                 280

<210> SEQ ID NO 20
<211> LENGTH: 255
<212> TYPE: PRT
<213> ORGANISM: Macaca fascicularis

<400> SEQUENCE: 20

Gly Phe Gly Ile Ser Gly Arg His Ser Ile Thr Val Thr Val Ala
1               5                   10                  15

Ser Ala Gly Asn Ile Gly Glu Asp Gly Ile Leu Ser Cys Thr Phe Glu
                20                  25                  30

Pro Asp Ile Lys Leu Ser Asp Ile Val Ile Gln Trp Leu Lys Glu Gly
                35                  40                  45

Val Ile Gly Leu Val His Glu Phe Lys Glu Gly Lys Asp Glu Leu Ser
            50                  55                  60

Glu Gln Asp Glu Met Phe Arg Gly Arg Thr Ala Val Phe Ala Asp Gln
65                  70                  75                  80

Val Ile Val Gly Asn Ala Ser Leu Arg Leu Lys Asn Val Gln Leu Thr
                85                  90                  95

Asp Ala Gly Thr Tyr Lys Cys Tyr Ile Ile Thr Ser Lys Gly Lys Gly
                100                 105                 110

Asn Ala Asn Leu Glu Tyr Lys Thr Gly Ala Phe Ser Met Pro Glu Val
                115                 120                 125

Asn Val Asp Tyr Asn Ala Ser Ser Glu Thr Leu Arg Cys Glu Ala Pro
                130                 135                 140

Arg Trp Phe Pro Gln Pro Thr Val Val Trp Ala Ser Gln Val Asp Gln
145                 150                 155                 160

Gly Ala Asn Phe Ser Glu Val Ser Asn Thr Ser Phe Glu Leu Asn Ser
                165                 170                 175

Glu Asn Val Thr Met Lys Val Val Ser Val Leu Tyr Asn Val Thr Ile
                180                 185                 190

Asn Asn Thr Tyr Ser Cys Met Ile Glu Asn Asp Ile Ala Lys Ala Thr
                195                 200                 205

Gly Asp Ile Lys Val Thr Glu Ser Glu Ile Lys Arg Arg Ser His Leu
            210                 215                 220

Gln Leu Leu Asn Ser Lys Ala Ser Leu Cys Val Ser Ser Phe Leu Ala
225                 230                 235                 240

Ile Ser Trp Ala Leu Pro Pro Leu Ala Pro Tyr Leu Met Leu Lys
                245                 250                 255

<210> SEQ ID NO 21
<211> LENGTH: 771
<212> TYPE: DNA
<213> ORGANISM: Mus musculus

<400> SEQUENCE: 21
atggcttcct tggggcagat catcttttgg agtattatta acatcatcat catcctggct      60
ggggccatcg cactcatcat tggctttggc atttcaggca agcacttcat cacggtcacg     120
accttcacct cagctggaaa cattggagag gacgggaccc tgagctgcac ttttgaacct     180
gacatcaaac tcaacggcat cgtcatccag tggctgaaag aaggcatcaa aggtttggtc     240
```

```
cacgagttca aagaaggcaa agacgacctc tcacagcagc atgagatgtt cagaggccgc      300
acagcagtgt ttgctgatca ggtggtagtt ggcaatgctt ccctgagact gaaaaacgtg      360
cagctcacgg atgctggcac ctacacatgt acatccgcag cctcaaaagg caagggaat       420 gcaaccttg agtataagac cggagccttc agtatgccag agataaatgt ggactataat       480
gccagttcag agagtttacg ctgcgaggct cctcggtggt tcccccagcc cacagtggcc      540
tgggcatctc aagtcgacca aggagccaat ttctcagaag tctccaacac cagctttgag      600
ttgaactctg agaatgtgac catgaaggtc gtatctgtgc tctacaatgt cacaatcaac      660
aacacatact cctgtatgat tgaaaacgac attgccaaag ccaccgggga catcaaagtg      720
acagattcag aggtcaaaag gcgaagtcag ctgcagttgc tgaactctgg g              771
```

<210> SEQ ID NO 22
<211> LENGTH: 747
<212> TYPE: DNA
<213> ORGANISM: Mus musculus

<400> SEQUENCE: 22

```
atggagtggt catgggtttt tctgttcttt cttagcgtga ctacaggcgt ccattcagga       60
ttcggcataa gcggcaagca cttcatcaca gttacaacgt ttacaagtgc ggggaacatt      120
ggggaagatg aacattgtc atgtacattt gagccagata tcaaactcaa tggaatagta       180
attcagtggc ttaaggaggg catcaagggc ctggtccacg aatttaagga ggggaaagac      240
gatctgtctc agcagcacga gatgttcagg ggcagaaccg ccgtcttcgc agaccaggtt      300
gtggtaggca acgccagttt gcggctgaaa aacgtgcagc tgactgacgc cggcacctac      360
acatgctata tccggtcctc taagggcaag gggaacgcta atctcgagta caaaacaggc      420
gccttttcta tgccagagat caacgtggac tataacgcaa gctctgaaag tctgagatgc      480
gaggcgccaa ggtggttccc tcagcccacc gtcgcgtggg cttcccaggt ggatcaaggc      540
gccaactttt ctgaggtttc taacaccagc ttcgaactga acagcgaaaa tgtgacaatg      600
aaggtagtca gcgttctgta taacgtgacc atcaacaata cttactcctg tatgatagaa      660
aatgatatag ccaaggctac aggagatatt aaagtgacgg attcagaagt gaaaaggagg      720
agtcaactgc aactcttgaa tagcggc                                          747
```

<210> SEQ ID NO 23
<211> LENGTH: 747
<212> TYPE: DNA
<213> ORGANISM: Mus musculus

<400> SEQUENCE: 23

```
atggagtggt catgggtttt tctgttcttt cttagcgtga ctacaggcgt ccattcagga       60
ttcggcataa gcggcaagca cttcatcaca gttacaacgt ttacaagtgc ggggaacatt      120
ggggaagatg aacattgtc atgtacattt gagccagata tcaaactcaa tggaatagta       180
attcagtggc ttaaggaggg catcaagggc ctggtccacg aatttaagga ggggaaagac      240
gatctgtctc agcagcacga gatgttcagg ggcagaaccg ccgtcttcgc agaccaggtt      300
gtggtaggca acgccagttt gcggctgaaa aacgtgcagc tgactgacgc cggcacctac      360
acatgctata tccggacctc taagggcaag gggaacgcta atctcgagta caaaacaggc      420
gccttttcta tgccagagat caacgtggac tataacgcaa gctctgaaag tctgagatgc      480
gaggcgccaa ggtggttccc tcagcccacc gtcgcgtggg cttcccaggt ggatcaaggc      540
```

```
gccaactttt ctgaggtttc taacaccagc ttcgaactga acagcgaaaa tgtgacaatg    600
aaggtagtca gcgttctgta taacgtgacc atcaacaata cttactcctg tatgatagaa    660
aatgatatag ccaaggctac aggagatatt aaagtgacgg attcagaagt gaaaaggagg    720
agtcaactgc aactcttgaa tagcggc                                        747
```

```
<210> SEQ ID NO 24
<211> LENGTH: 249
<212> TYPE: PRT
<213> ORGANISM: Mus musculus

<400> SEQUENCE: 24
```

Met Glu Trp Ser Trp Val Phe Leu Phe Phe Leu Ser Val Thr Thr Gly
1               5                   10                  15

Val His Ser Gly Phe Gly Ile Ser Gly Lys His Phe Ile Thr Val Thr
            20                  25                  30

Thr Phe Thr Ser Ala Gly Asn Ile Gly Glu Asp Gly Thr Leu Ser Cys
        35                  40                  45

Thr Phe Glu Pro Asp Ile Lys Leu Asn Gly Ile Val Ile Gln Trp Leu
    50                  55                  60

Lys Glu Gly Ile Lys Gly Leu Val His Glu Phe Lys Glu Gly Lys Asp
65                  70                  75                  80

Asp Leu Ser Gln Gln His Glu Met Phe Arg Gly Arg Thr Ala Val Phe
                85                  90                  95

Ala Asp Gln Val Val Val Gly Asn Ala Ser Leu Arg Leu Lys Asn Val
            100                 105                 110

Gln Leu Thr Asp Ala Gly Thr Tyr Thr Cys Tyr Ile Arg Ser Ser Lys
        115                 120                 125

Gly Lys Gly Asn Ala Asn Leu Glu Tyr Lys Thr Gly Ala Phe Ser Met
    130                 135                 140

Pro Glu Ile Asn Val Asp Tyr Asn Ala Ser Ser Glu Ser Leu Arg Cys
145                 150                 155                 160

Glu Ala Pro Arg Trp Phe Pro Gln Pro Thr Val Ala Trp Ala Ser Gln
                165                 170                 175

Val Asp Gln Gly Ala Asn Phe Ser Glu Val Ser Asn Thr Ser Phe Glu
            180                 185                 190

Leu Asn Ser Glu Asn Val Thr Met Lys Val Val Ser Val Leu Tyr Asn
        195                 200                 205

Val Thr Ile Asn Asn Thr Tyr Ser Cys Met Ile Glu Asn Asp Ile Ala
    210                 215                 220

Lys Ala Thr Gly Asp Ile Lys Val Thr Asp Ser Glu Val Lys Arg Arg
225                 230                 235                 240

Ser Gln Leu Gln Leu Leu Asn Ser Gly
                245

```
<210> SEQ ID NO 25
<211> LENGTH: 249
<212> TYPE: PRT
<213> ORGANISM: Mus musculus

<400> SEQUENCE: 25
```

Met Glu Trp Ser Trp Val Phe Leu Phe Phe Leu Ser Val Thr Thr Gly
1               5                   10                  15

Val His Ser Gly Phe Gly Ile Ser Gly Lys His Phe Ile Thr Val Thr
            20                  25                  30

Thr Phe Thr Ser Ala Gly Asn Ile Gly Glu Asp Gly Thr Leu Ser Cys

```
               35                  40                  45
Thr Phe Glu Pro Asp Ile Lys Leu Asn Gly Ile Val Ile Gln Trp Leu
 50                  55                  60

Lys Glu Gly Ile Lys Gly Leu Val His Glu Phe Lys Glu Gly Lys Asp
 65                  70                  75                  80

Asp Leu Ser Gln Gln His Glu Met Phe Arg Gly Arg Thr Ala Val Phe
                 85                  90                  95

Ala Asp Gln Val Val Gly Asn Ala Ser Leu Arg Leu Lys Asn Val
                100                 105                 110

Gln Leu Thr Asp Ala Gly Thr Tyr Thr Cys Tyr Ile Arg Thr Ser Lys
            115                 120                 125

Gly Lys Gly Asn Ala Asn Leu Glu Tyr Lys Thr Gly Ala Phe Ser Met
        130                 135                 140

Pro Glu Ile Asn Val Asp Tyr Asn Ala Ser Ser Glu Ser Leu Arg Cys
145                 150                 155                 160

Glu Ala Pro Arg Trp Phe Pro Gln Pro Thr Val Ala Trp Ala Ser Gln
                165                 170                 175

Val Asp Gln Gly Ala Asn Phe Ser Glu Val Ser Asn Thr Ser Phe Glu
            180                 185                 190

Leu Asn Ser Glu Asn Val Thr Met Lys Val Ser Val Leu Tyr Asn
        195                 200                 205

Val Thr Ile Asn Asn Thr Tyr Ser Cys Met Ile Glu Asn Asp Ile Ala
210                 215                 220

Lys Ala Thr Gly Asp Ile Lys Val Thr Asp Ser Glu Val Lys Arg Arg
225                 230                 235                 240

Ser Gln Leu Gln Leu Leu Asn Ser Gly
                245

<210> SEQ ID NO 26
<211> LENGTH: 257
<212> TYPE: PRT
<213> ORGANISM: Mus musculus

<400> SEQUENCE: 26

Met Ala Ser Leu Gly Gln Ile Ile Phe Trp Ser Ile Ile Asn Ile Ile
 1                   5                  10                  15

Ile Ile Leu Ala Gly Ala Ile Ala Leu Ile Ile Gly Phe Gly Ile Ser
                 20                  25                  30

Gly Lys His Phe Ile Thr Val Thr Phe Thr Ser Ala Gly Asn Ile
            35                  40                  45

Gly Glu Asp Gly Thr Leu Ser Cys Thr Phe Glu Pro Asp Ile Lys Leu
 50                  55                  60

Asn Gly Ile Val Ile Gln Trp Leu Lys Glu Gly Ile Lys Gly Leu Val
 65                  70                  75                  80

His Glu Phe Lys Glu Gly Lys Asp Asp Leu Ser Gln Gln His Glu Met
                 85                  90                  95

Phe Arg Gly Arg Thr Ala Val Phe Ala Asp Gln Val Val Gly Asn
                100                 105                 110

Ala Ser Leu Arg Leu Lys Asn Val Gln Leu Thr Asp Ala Gly Thr Tyr
            115                 120                 125

Thr Cys Tyr Ile Arg Ser Ser Lys Gly Lys Gly Asn Ala Asn Leu Glu
        130                 135                 140

Tyr Lys Thr Gly Ala Phe Ser Met Pro Glu Ile Asn Val Asp Tyr Asn
145                 150                 155                 160
```

```
Ala Ser Ser Glu Ser Leu Arg Cys Glu Ala Pro Arg Trp Phe Pro Gln
            165                 170                 175

Pro Thr Val Ala Trp Ala Ser Gln Val Asp Gln Gly Ala Asn Phe Ser
        180                 185                 190

Glu Val Ser Asn Thr Ser Phe Glu Leu Asn Ser Glu Asn Val Thr Met
            195                 200                 205

Lys Val Val Ser Val Leu Tyr Asn Val Thr Ile Asn Asn Thr Tyr Ser
        210                 215                 220

Cys Met Ile Glu Asn Asp Ile Ala Lys Ala Thr Gly Asp Ile Lys Val
225                 230                 235                 240

Thr Asp Ser Glu Val Lys Arg Arg Ser Gln Leu Gln Leu Leu Asn Ser
                245                 250                 255

Gly

<210> SEQ ID NO 27
<211> LENGTH: 257
<212> TYPE: PRT
<213> ORGANISM: Mus musculus

<400> SEQUENCE: 27

Met Ala Ser Leu Gly Gln Ile Ile Phe Trp Ser Ile Ile Asn Ile Ile
1               5                   10                  15

Ile Ile Leu Ala Gly Ala Ile Ala Leu Ile Ile Gly Phe Gly Ile Ser
            20                  25                  30

Gly Lys His Phe Ile Thr Val Thr Phe Thr Ser Ala Gly Asn Ile
        35                  40                  45

Gly Glu Asp Gly Thr Leu Ser Cys Thr Phe Glu Pro Asp Ile Lys Leu
50                  55                  60

Asn Gly Ile Val Ile Gln Trp Leu Lys Glu Gly Ile Lys Gly Leu Val
65                  70                  75                  80

His Glu Phe Lys Glu Gly Lys Asp Asp Leu Ser Gln Gln His Glu Met
                85                  90                  95

Phe Arg Gly Arg Thr Ala Val Phe Ala Asp Gln Val Val Val Gly Asn
            100                 105                 110

Ala Ser Leu Arg Leu Lys Asn Val Gln Leu Thr Asp Ala Gly Thr Tyr
        115                 120                 125

Thr Cys Tyr Ile Arg Thr Ser Lys Gly Lys Gly Asn Ala Asn Leu Glu
    130                 135                 140

Tyr Lys Thr Gly Ala Phe Ser Met Pro Glu Ile Asn Val Asp Tyr Asn
145                 150                 155                 160

Ala Ser Ser Glu Ser Leu Arg Cys Glu Ala Pro Arg Trp Phe Pro Gln
                165                 170                 175

Pro Thr Val Ala Trp Ala Ser Gln Val Asp Gln Gly Ala Asn Phe Ser
            180                 185                 190

Glu Val Ser Asn Thr Ser Phe Glu Leu Asn Ser Glu Asn Val Thr Met
        195                 200                 205

Lys Val Val Ser Val Leu Tyr Asn Val Thr Ile Asn Asn Thr Tyr Ser
    210                 215                 220

Cys Met Ile Glu Asn Asp Ile Ala Lys Ala Thr Gly Asp Ile Lys Val
225                 230                 235                 240

Thr Asp Ser Glu Val Lys Arg Arg Ser Gln Leu Gln Leu Leu Asn Ser
                245                 250                 255

Gly
```

<210> SEQ ID NO 28
<211> LENGTH: 230
<212> TYPE: PRT
<213> ORGANISM: Mus musculus

<400> SEQUENCE: 28

Gly Phe Gly Ile Ser Gly Lys His Phe Ile Thr Val Thr Thr Phe Thr
1               5                   10                  15

Ser Ala Gly Asn Ile Gly Glu Asp Gly Thr Leu Ser Cys Thr Phe Glu
            20                  25                  30

Pro Asp Ile Lys Leu Asn Gly Ile Val Ile Gln Trp Leu Lys Glu Gly
        35                  40                  45

Ile Lys Gly Leu Val His Glu Phe Lys Glu Gly Lys Asp Asp Leu Ser
    50                  55                  60

Gln Gln His Glu Met Phe Arg Gly Arg Thr Ala Val Phe Ala Asp Gln
65                  70                  75                  80

Val Val Val Gly Asn Ala Ser Leu Arg Leu Lys Asn Val Gln Leu Thr
                85                  90                  95

Asp Ala Gly Thr Tyr Thr Cys Tyr Ile Arg Ser Ser Lys Gly Lys Gly
            100                 105                 110

Asn Ala Asn Leu Glu Tyr Lys Thr Gly Ala Phe Ser Met Pro Glu Ile
        115                 120                 125

Asn Val Asp Tyr Asn Ala Ser Ser Glu Ser Leu Arg Cys Glu Ala Pro
    130                 135                 140

Arg Trp Phe Pro Gln Pro Thr Val Ala Trp Ala Ser Gln Val Asp Gln
145                 150                 155                 160

Gly Ala Asn Phe Ser Glu Val Ser Asn Thr Ser Phe Glu Leu Asn Ser
                165                 170                 175

Glu Asn Val Thr Met Lys Val Val Ser Val Leu Tyr Asn Val Thr Ile
            180                 185                 190

Asn Asn Thr Tyr Ser Cys Met Ile Glu Asn Asp Ile Ala Lys Ala Thr
        195                 200                 205

Gly Asp Ile Lys Val Thr Asp Ser Glu Val Lys Arg Arg Ser Gln Leu
    210                 215                 220

Gln Leu Leu Asn Ser Gly
225                 230

<210> SEQ ID NO 29
<211> LENGTH: 230
<212> TYPE: PRT
<213> ORGANISM: Mus musculus

<400> SEQUENCE: 29

Gly Phe Gly Ile Ser Gly Lys His Phe Ile Thr Val Thr Thr Phe Thr
1               5                   10                  15

Ser Ala Gly Asn Ile Gly Glu Asp Gly Thr Leu Ser Cys Thr Phe Glu
            20                  25                  30

Pro Asp Ile Lys Leu Asn Gly Ile Val Ile Gln Trp Leu Lys Glu Gly
        35                  40                  45

Ile Lys Gly Leu Val His Glu Phe Lys Glu Gly Lys Asp Asp Leu Ser
    50                  55                  60

Gln Gln His Glu Met Phe Arg Gly Arg Thr Ala Val Phe Ala Asp Gln
65                  70                  75                  80

Val Val Val Gly Asn Ala Ser Leu Arg Leu Lys Asn Val Gln Leu Thr
                85                  90                  95

Asp Ala Gly Thr Tyr Thr Cys Tyr Ile Arg Thr Ser Lys Gly Lys Gly

```
                100             105                 110
Asn Ala Asn Leu Glu Tyr Lys Thr Gly Ala Phe Ser Met Pro Glu Ile
            115                 120                 125

Asn Val Asp Tyr Asn Ala Ser Ser Glu Ser Leu Arg Cys Glu Ala Pro
            130                 135             140

Arg Trp Phe Pro Gln Pro Thr Val Ala Trp Ala Ser Gln Val Asp Gln
145                 150                 155                 160

Gly Ala Asn Phe Ser Glu Val Ser Asn Thr Ser Phe Glu Leu Asn Ser
                165                 170                 175

Glu Asn Val Thr Met Lys Val Val Ser Val Leu Tyr Asn Val Thr Ile
            180                 185                 190

Asn Asn Thr Tyr Ser Cys Met Ile Glu Asn Asp Ile Ala Lys Ala Thr
            195                 200                 205

Gly Asp Ile Lys Val Thr Asp Ser Glu Val Lys Arg Arg Ser Gln Leu
            210                 215                 220

Gln Leu Leu Asn Ser Gly
225                 230

<210> SEQ ID NO 30
<211> LENGTH: 387
<212> TYPE: DNA
<213> ORGANISM: Mus musculus

<400> SEQUENCE: 30
ggattcggca taagcggcaa gcacttcatc acagttacaa cgtttacaag tgcggggaac      60
attggggaag atggaacatt gtcatgtaca tttgagccag atatcaaact caatggaata     120
gtaattcagt ggcttaagga gggcatcaag ggcctggtcc acgaatttaa ggaggggaaa     180
gacgatctgt ctcagcagca cgagatgttc agggcagaa ccgccgtctt cgcagaccag      240
gttgtggtag gcaacgccag tttgcggctg aaaaacgtgc agctgactga cgccggcacc     300
tacacatgct atatccggtc tctaagggc aaggggaacg ctaatctcga gtacaaaaca      360
ggcgcctttt ctatgccaga gatcaac                                         387

<210> SEQ ID NO 31
<211> LENGTH: 387
<212> TYPE: DNA
<213> ORGANISM: Mus musculus

<400> SEQUENCE: 31
ggattcggca taagcggcaa gcacttcatc acagttacaa cgtttacaag tgcggggaac      60
attggggaag atggaacatt gtcatgtaca tttgagccag atatcaaact caatggaata     120
gtaattcagt ggcttaagga gggcatcaag ggcctggtcc acgaatttaa ggaggggaaa     180
gacgatctgt ctcagcagca cgagatgttc agggcagaa ccgccgtctt cgcagaccag      240
gttgtggtag gcaacgccag tttgcggctg aaaaacgtgc agctgactga cgccggcacc     300
tacacatgct atatccggac tctaagggc aaggggaacg ctaatctcga gtacaaaaca      360
ggcgcctttt ctatgccaga gatcaac                                         387

<210> SEQ ID NO 32
<211> LENGTH: 129
<212> TYPE: PRT
<213> ORGANISM: Mus musculus

<400> SEQUENCE: 32

Gly Phe Gly Ile Ser Gly Lys His Phe Ile Thr Val Thr Thr Phe Thr
```

```
           1               5                  10                 15
        Ser Ala Gly Asn Ile Gly Glu Asp Gly Thr Leu Ser Cys Thr Phe Glu
                        20                  25                 30

Pro Asp Ile Lys Leu Asn Gly Ile Val Ile Gln Trp Leu Lys Glu Gly
                        35                  40              45

Ile Lys Gly Leu Val His Glu Phe Lys Glu Gly Lys Asp Asp Leu Ser
                50                      55                 60

Gln Gln His Glu Met Phe Arg Gly Arg Thr Ala Val Phe Ala Asp Gln
         65                      70                  75                  80

Val Val Val Gly Asn Ala Ser Leu Arg Leu Lys Asn Val Gln Leu Thr
                            85                  90                 95

Asp Ala Gly Thr Tyr Thr Cys Tyr Ile Arg Ser Ser Lys Gly Lys Gly
                        100                 105                110

Asn Ala Asn Leu Glu Tyr Lys Thr Gly Ala Phe Ser Met Pro Glu Ile
                        115                 120                125

Asn
```

<210> SEQ ID NO 33
<211> LENGTH: 129
<212> TYPE: PRT
<213> ORGANISM: Mus musculus

<400> SEQUENCE: 33

```
        Gly Phe Gly Ile Ser Gly Lys His Phe Ile Thr Val Thr Thr Phe Thr
         1               5                  10                 15

Ser Ala Gly Asn Ile Gly Glu Asp Gly Thr Leu Ser Cys Thr Phe Glu
                        20                  25                 30

Pro Asp Ile Lys Leu Asn Gly Ile Val Ile Gln Trp Leu Lys Glu Gly
                        35                  40              45

Ile Lys Gly Leu Val His Glu Phe Lys Glu Gly Lys Asp Asp Leu Ser
                50                      55                 60

Gln Gln His Glu Met Phe Arg Gly Arg Thr Ala Val Phe Ala Asp Gln
         65                      70                  75                  80

Val Val Val Gly Asn Ala Ser Leu Arg Leu Lys Asn Val Gln Leu Thr
                            85                  90                 95

Asp Ala Gly Thr Tyr Thr Cys Tyr Ile Arg Thr Ser Lys Gly Lys Gly
                        100                 105                110

Asn Ala Asn Leu Glu Tyr Lys Thr Gly Ala Phe Ser Met Pro Glu Ile
                        115                 120                125

Asn
```

<210> SEQ ID NO 34
<211> LENGTH: 747
<212> TYPE: DNA
<213> ORGANISM: Homo sapiens

<400> SEQUENCE: 34

| | | |
|---|---|---|
| atggcttccc tggggcagat cctcttctgg agcataatta gcatcatcat tattctggct | | 60 |
| ggagcaattg cactcatcat tggctttggt atttcaggga cactccat cacagtcact | | 120 |
| actgtcgcct cagctgggaa cattggggag gatggaatcc tgagctgcac ttttgaacct | | 180 |
| gacatcaaac tttctgatat cgtgatacaa tggctgaagg aaggtgtttt aggcttggtc | | 240 |
| catgagttca agaaggcaa agatgagctg tcggagcagg atgaaatgtt cagaggccgg | | 300 |
| acagcagtgt ttgctgatca agtgatagtt ggcaatgcct ctttgcggct gaaaacgtg | | 360 |

| | |
|---|---|
| caactcacag atgctggcac ctacaaatgt tatatcatca cttctaaagg caaggggaat | 420 |
| gctaaccttg agtataaaac tggagccttc agcatgccgg aagtgaatgt ggactataat | 480 |
| gccagctcag agaccttgcg gtgtgaggct ccccgatggt tcccccagcc cacagtggtc | 540 |
| tgggcatccc aagttgacca gggagccaac ttctcggaag tctccaatac cagctttgag | 600 |
| ctgaactctg agaatgtgac catgaaggtt gtgtctgtgc tctacaatgt tacgatcaac | 660 |
| aacacatact cctgtatgat tgaaaatgac attgccaaag caacaggga tatcaaagtg | 720 |
| acagaatcgg agatcaaaag gcggagt | 747 |

<210> SEQ ID NO 35
<211> LENGTH: 735
<212> TYPE: DNA
<213> ORGANISM: Homo sapiens

<400> SEQUENCE: 35

| | |
|---|---|
| atggcttccc tggggcagat cctcttctgg agcataatta gcatcatcat tattctggct | 60 |
| ggagcaattg cactcatcat tggctttggt atttcaggga cactccat cacagtcact | 120 |
| actgtcgcct cagctgggaa cattggggag gatggaatcc tgagctgcac ttttgaacct | 180 |
| gacatcaaac tttctgatat cgtgatacaa tggctgaagg aaggtgtttt aggcttggtc | 240 |
| catgagttca agaaggcaa agatgagctg tcggagcagg atgaaatgtt cagaggccgg | 300 |
| acagcagtgt ttgctgatca agtgatagtt ggcaatgcct ctttgcggct gaaaaacgtg | 360 |
| caactcacag atgctggcac ctacaaatgt tatatcatca cttctaaagg caaggggaat | 420 |
| gctaaccttg agtataaaac tggagccttc agcatgccgg aagtgaatgt ggactataat | 480 |
| gccagctcag agaccttgcg gtgtgaggct ccccgatggt tcccccagcc cacagtggtc | 540 |
| tgggcatccc aagttgacca gggagccaac ttctcggaag tctccaatac cagctttgag | 600 |
| ctgaactctg agaatgtgac catgaaggtt gtgtctgtgc tctacaatgt tacgatcaac | 660 |
| aacacatact cctgtatgat tgaaaatgac attgccaaag caacaggga tatcaaagtg | 720 |
| acagaatcgg agatc | 735 |

<210> SEQ ID NO 36
<211> LENGTH: 777
<212> TYPE: DNA
<213> ORGANISM: Homo sapiens

<400> SEQUENCE: 36

| | |
|---|---|
| atggcttccc tggggcagat cctcttctgg agcataatta gcatcatcat tattctggct | 60 |
| ggagcaattg cactcatcat tggctttggt atttcaggga cactccat cacagtcact | 120 |
| actgtcgcct cagctgggaa cattggggag gatggaatcc tgagctgcac ttttgaacct | 180 |
| gacatcaaac tttctgatat cgtgatacaa tggctgaagg aaggtgtttt aggcttggtc | 240 |
| catgagttca agaaggcaa agatgagctg tcggagcagg atgaaatgtt cagaggccgg | 300 |
| acagcagtgt ttgctgatca agtgatagtt ggcaatgcct ctttgcggct gaaaaacgtg | 360 |
| caactcacag atgctggcac ctacaaatgt tatatcatca cttctaaagg caaggggaat | 420 |
| gctaaccttg agtataaaac tggagccttc agcatgccgg aagtgaatgt ggactataat | 480 |
| gccagctcag agaccttgcg gtgtgaggct ccccgatggt tcccccagcc cacagtggtc | 540 |
| tgggcatccc aagttgacca gggagccaac ttctcggaag tctccaatac cagctttgag | 600 |
| ctgaactctg agaatgtgac catgaaggtt gtgtctgtgc tctacaatgt tacgatcaac | 660 |
| aacacatact cctgtatgat tgaaaatgac attgccaaag caacaggga tatcaaagtg | 720 |

```
acagaatcgg agatcaaaag gcggagtcac ctacagctgc taaactcaaa ggcttct      777
```

<210> SEQ ID NO 37
<211> LENGTH: 723
<212> TYPE: DNA
<213> ORGANISM: Homo sapiens

<400> SEQUENCE: 37

```
atggaatgga gctgggtatt tctgttttc ctgtcagtaa cgactggcgt ccattcaggc    60
ttcggcatca gtggacggca cagtatcaca gtgaccaccg tcgcctccgc tggcaatata  120
ggtgaggatg gcatccagtc ctgtaccttt gagccggaca tcaaactgtc tgacatagtg  180
atacaatggc tgaaggaggg ggtgctcggt ctggtacatg agtttaagga agggaaggat  240
gaactgtccg agcaggatga gatgttccgg gggaggaccg ctgtgttcgc cgatcaggta  300
atcgtcggaa atgcaagtct cagattgaaa aatgtgcaac tgactgatgc tggcacgtat  360
aaatgctaca ttatcacaag taagggcaaa ggaaatgcta accttgagta taaaacaggc  420
gcattctcaa tgcccgaggt caatgtcgac tataatgcca gcagtgaaaac attgcgctgt  480
gaagctcccc gctggttccc ccagccaacc gtggtctggg cctctcaggt tgatcagggg  540
gctaactttt ccgaggtgag caacaccagc ttcgaactca actctgagaa tgtgaccatg  600
aaagttgtgt ctgtcctgta taatgtaaca atcaacaaca cttattcatg catgattgaa  660
aacgacatcg ccaaggcaac aggtgatatt aaggtaactg aatccgagat caaacggcgg  720
tct                                                                723
```

<210> SEQ ID NO 38
<211> LENGTH: 711
<212> TYPE: DNA
<213> ORGANISM: Homo sapiens

<400> SEQUENCE: 38

```
atggaatgga gctgggtatt tctgttttc ctgtcagtaa cgactggcgt ccattcaggc    60
ttcggcatca gtggacggca cagtatcaca gtgaccaccg tcgcctccgc tggcaatata  120
ggtgaggatg gcatccagtc ctgtaccttt gagccggaca tcaaactgtc tgacatagtg  180
atacaatggc tgaaggaggg ggtgctcggt ctggtacatg agtttaagga agggaaggat  240
gaactgtccg agcaggatga gatgttccgg gggaggaccg ctgtgttcgc cgatcaggta  300
atcgtcggaa atgcaagtct cagattgaaa aatgtgcaac tgactgatgc tggcacgtat  360
aaatgctaca ttatcacaag taagggcaaa ggaaatgcta accttgagta taaaacaggc  420
gcattctcaa tgcccgaggt caatgtcgac tataatgcca gcagtgaaaac attgcgctgt  480
gaagctcccc gctggttccc ccagccaacc gtggtctggg cctctcaggt tgatcagggg  540
gctaactttt ccgaggtgag caacaccagc ttcgaactca actctgagaa tgtgaccatg  600
aaagttgtgt ctgtcctgta taatgtaaca atcaacaaca cttattcatg catgattgaa  660
aacgacatcg ccaaggcaac aggtgatatt aaggtaactg aatccgagat c            711
```

<210> SEQ ID NO 39
<211> LENGTH: 753
<212> TYPE: DNA
<213> ORGANISM: Homo sapiens

<400> SEQUENCE: 39

```
atggaatgga gctgggtatt tctgttttc ctgtcagtaa cgactggcgt ccattcaggc    60
```

```
ttcggcatca gtggacggca cagtatcaca gtgaccaccg tcgcctccgc tggcaatata    120
ggtgaggatg gcatccagtc ctgtacccttt gagccggaca tcaaactgtc tgacatagtg   180
atacaatggc tgaaggaggg ggtgctcggt ctggtacatg agtttaagga agggaaggat    240
gaactgtccg agcaggatga gatgttccgg gggaggaccg ctgtgttcgc cgatcaggta    300
atcgtcggaa atgcaagtct cagattgaaa aatgtgcaac tgactgatgc tggcacgtat    360
aaatgctaca ttatcacaag taagggcaaa ggaaatgcta accttgagta taaaacaggc    420
gcattctcaa tgcccgaggt caatgtcgac tataatgcca gcagtgaaaac attgcgctgt    480 gaagctcccc gctggttccc ccagccaacc gtggtctggg cctctcaggt tgatcagggg    540
gctaactttt ccgaggtgag caacaccagc ttcgaactca actctgagaa tgtgaccatg    600
aaagttgtgt ctgtcctgta taatgtaaca atcaacaaca cttattcatg catgattgaa    660
aacgacatcg ccaaggcaac aggtgatatt aaggtaactg aatccgagat caaacggcgg    720
tctcacctac agctgctaaa ctcaaaggct tct                                  753
```

<210> SEQ ID NO 40
<211> LENGTH: 723
<212> TYPE: DNA
<213> ORGANISM: Homo sapiens

<400> SEQUENCE: 40

```
atggaatgga gctgggtatt tctgtttttc ctgtcagtaa cgactggcgt ccattcaggc     60
ttcggcatca gtggacggca cagtatcaca gtgaccaccg tcgcctccgc tggcaatata    120
ggtgaggatg gcatcctgtc ctgtaccttt gagccggaca tcaaactgtc tgacatagtg    180
atacaatggc tgaaggaggg ggtgctcggt ctggtacatg agtttaagga agggaaggat    240
gaactgtccg agcaggatga gatgttccgg gggaggaccg ctgtgttcgc cgatcaggta    300
atcgtcggaa atgcaagtct cagattgaaa aatgtgcaac tgactgatgc tggcacgtat    360
aaatgctaca ttatcacaag taagggcaaa ggaaatgcta accttgagta taaaacaggc    420
gcattctcaa tgcccgaggt caatgtcgac tataatgcca gcagtgaaaac attgcgctgt    480 gaagctcccc gctggttccc ccagccaacc gtggtctggg cctctcaggt tgatcagggg    540
gctaactttt ccgaggtgag caacaccagc ttcgaactca actctgagaa tgtgaccatg    600
aaagttgtgt ctgtcctgta taatgtaaca atcaacaaca cttattcatg catgattgaa    660
aacgacatcg ccaaggcaac aggtgatatt aaggtaactg aatccgagat caaacggcgg    720
tct                                                                   723
```

<210> SEQ ID NO 41
<211> LENGTH: 711
<212> TYPE: DNA
<213> ORGANISM: Homo sapiens

<400> SEQUENCE: 41

```
atggaatgga gctgggtatt tctgtttttc ctgtcagtaa cgactggcgt ccattcaggc     60
ttcggcatca gtggacggca cagtatcaca gtgaccaccg tcgcctccgc tggcaatata    120
ggtgaggatg gcatcctgtc ctgtaccttt gagccggaca tcaaactgtc tgacatagtg    180
atacaatggc tgaaggaggg ggtgctcggt ctggtacatg agtttaagga agggaaggat    240
gaactgtccg agcaggatga gatgttccgg gggaggaccg ctgtgttcgc cgatcaggta    300
atcgtcggaa atgcaagtct cagattgaaa aatgtgcaac tgactgatgc tggcacgtat    360
aaatgctaca ttatcacaag taagggcaaa ggaaatgcta accttgagta taaaacaggc    420
```

```
gcattctcaa tgcccgaggt caatgtcgac tataatgcca gcagtgaaac attgcgctgt    480
gaagctcccc gctggttccc ccagccaacc gtggtctggg cctctcaggt tgatcagggg    540
gctaactttt ccgaggtgag caacaccagc ttcgaactca actctgagaa tgtgaccatg    600
aaagttgtgt ctgtcctgta taatgtaaca atcaacaaca cttattcatg catgattgaa    660
aacgacatcg ccaaggcaac aggtgatatt aaggtaactg aatccgagat c             711
```

<210> SEQ ID NO 42
<211> LENGTH: 753
<212> TYPE: DNA
<213> ORGANISM: Homo sapiens

<400> SEQUENCE: 42

```
atggaatgga gctgggtatt tctgtttttc ctgtcagtaa cgactggcgt ccattcaggc     60
ttcggcatca gtggacggca cagtatcaca gtgaccaccg tcgcctccgc tggcaatata    120
ggtgaggatg gcatcctgtc ctgtacccttt gagccggaca tcaaactgtc tgacatagtg   180
atacaatggc tgaaggaggg ggtgctcggt ctggtacatg agtttaagga agggaaggat    240
gaactgtccg agcaggatga gatgttccgg gggaggaccg ctgtgttcgc cgatcaggta    300
atcgtcggaa atgcaagtct cagattgaaa atgtgcaac tgactgatgc tggcacgtat    360
aaatgctaca ttatcacaag taagggcaaa ggaaatgcta accttgagta taaaacaggc    420
gcattctcaa tgcccgaggt caatgtcgac tataatgcca gcagtgaaac attgcgctgt    480
gaagctcccc gctggttccc ccagccaacc gtggtctggg cctctcaggt tgatcagggg    540
gctaactttt ccgaggtgag caacaccagc ttcgaactca actctgagaa tgtgaccatg    600
aaagttgtgt ctgtcctgta taatgtaaca atcaacaaca cttattcatg catgattgaa    660
aacgacatcg ccaaggcaac aggtgatatt aaggtaactg aatccgagat caaacggcgg    720
tctcacctac agctgctaaa ctcaaaggct tct                                 753
```

<210> SEQ ID NO 43
<211> LENGTH: 241
<212> TYPE: PRT
<213> ORGANISM: Homo sapiens

<400> SEQUENCE: 43

```
Met Glu Trp Ser Trp Val Phe Leu Phe Phe Leu Ser Val Thr Thr Gly
1               5                   10                  15

Val His Ser Gly Phe Gly Ile Ser Gly Arg His Ser Ile Thr Val Thr
            20                  25                  30

Thr Val Ala Ser Ala Gly Asn Ile Gly Glu Asp Gly Ile Gln Ser Cys
        35                  40                  45

Thr Phe Glu Pro Asp Ile Lys Leu Ser Asp Ile Val Ile Gln Trp Leu
    50                  55                  60

Lys Glu Gly Val Leu Gly Leu Val His Glu Phe Lys Glu Gly Lys Asp
65                  70                  75                  80

Glu Leu Ser Glu Gln Asp Glu Met Phe Arg Gly Arg Thr Ala Val Phe
                85                  90                  95

Ala Asp Gln Val Ile Val Gly Asn Ala Ser Leu Arg Leu Lys Asn Val
            100                 105                 110

Gln Leu Thr Asp Ala Gly Thr Tyr Lys Cys Tyr Ile Ile Thr Ser Lys
        115                 120                 125

Gly Lys Gly Asn Ala Asn Leu Glu Tyr Lys Thr Gly Ala Phe Ser Met
    130                 135                 140
```

Pro Glu Val Asn Val Asp Tyr Asn Ala Ser Ser Glu Thr Leu Arg Cys
145                 150                 155                 160

Glu Ala Pro Arg Trp Phe Pro Gln Pro Thr Val Val Trp Ala Ser Gln
            165                 170                 175

Val Asp Gln Gly Ala Asn Phe Ser Glu Val Ser Asn Thr Ser Phe Glu
                180                 185                 190

Leu Asn Ser Glu Asn Val Thr Met Lys Val Val Ser Val Leu Tyr Asn
            195                 200                 205

Val Thr Ile Asn Asn Thr Tyr Ser Cys Met Ile Glu Asn Asp Ile Ala
        210                 215                 220

Lys Ala Thr Gly Asp Ile Lys Val Thr Glu Ser Glu Ile Lys Arg Arg
225                 230                 235                 240

Ser

<210> SEQ ID NO 44
<211> LENGTH: 237
<212> TYPE: PRT
<213> ORGANISM: Homo sapiens

<400> SEQUENCE: 44

Met Glu Trp Ser Trp Val Phe Leu Phe Phe Leu Ser Val Thr Thr Gly
1               5                   10                  15

Val His Ser Gly Phe Gly Ile Ser Gly Arg His Ser Ile Thr Val Thr
            20                  25                  30

Thr Val Ala Ser Ala Gly Asn Ile Gly Glu Asp Gly Ile Gln Ser Cys
        35                  40                  45

Thr Phe Glu Pro Asp Ile Lys Leu Ser Asp Ile Val Ile Gln Trp Leu
    50                  55                  60

Lys Glu Gly Val Leu Gly Leu Val His Glu Phe Lys Glu Gly Lys Asp
65                  70                  75                  80

Glu Leu Ser Glu Gln Asp Glu Met Phe Arg Gly Arg Thr Ala Val Phe
            85                  90                  95

Ala Asp Gln Val Ile Val Gly Asn Ala Ser Leu Arg Leu Lys Asn Val
        100                 105                 110

Gln Leu Thr Asp Ala Gly Thr Tyr Lys Cys Tyr Ile Ile Thr Ser Lys
    115                 120                 125

Gly Lys Gly Asn Ala Asn Leu Glu Tyr Lys Thr Gly Ala Phe Ser Met
130                 135                 140

Pro Glu Val Asn Val Asp Tyr Asn Ala Ser Ser Glu Thr Leu Arg Cys
145                 150                 155                 160

Glu Ala Pro Arg Trp Phe Pro Gln Pro Thr Val Val Trp Ala Ser Gln
            165                 170                 175

Val Asp Gln Gly Ala Asn Phe Ser Glu Val Ser Asn Thr Ser Phe Glu
                180                 185                 190

Leu Asn Ser Glu Asn Val Thr Met Lys Val Val Ser Val Leu Tyr Asn
            195                 200                 205

Val Thr Ile Asn Asn Thr Tyr Ser Cys Met Ile Glu Asn Asp Ile Ala
        210                 215                 220

Lys Ala Thr Gly Asp Ile Lys Val Thr Glu Ser Glu Ile
225                 230                 235

<210> SEQ ID NO 45
<211> LENGTH: 251
<212> TYPE: PRT
<213> ORGANISM: Homo sapiens

<400> SEQUENCE: 45

```
Met Glu Trp Ser Trp Val Phe Leu Phe Phe Leu Ser Val Thr Thr Gly
1               5                   10                  15

Val His Ser Gly Phe Gly Ile Ser Gly Arg His Ser Ile Thr Val Thr
            20                  25                  30

Thr Val Ala Ser Ala Gly Asn Ile Gly Glu Asp Gly Ile Gln Ser Cys
        35                  40                  45

Thr Phe Glu Pro Asp Ile Lys Leu Ser Asp Ile Val Ile Gln Trp Leu
    50                  55                  60

Lys Glu Gly Val Leu Gly Leu Val His Glu Phe Lys Glu Gly Lys Asp
65                  70                  75                  80

Glu Leu Ser Glu Gln Asp Glu Met Phe Arg Gly Arg Thr Ala Val Phe
                85                  90                  95

Ala Asp Gln Val Ile Val Gly Asn Ala Ser Leu Arg Leu Lys Asn Val
            100                 105                 110

Gln Leu Thr Asp Ala Gly Thr Tyr Lys Cys Tyr Ile Ile Thr Ser Lys
        115                 120                 125

Gly Lys Gly Asn Ala Asn Leu Glu Tyr Lys Thr Gly Ala Phe Ser Met
130                 135                 140

Pro Glu Val Asn Val Asp Tyr Asn Ala Ser Ser Glu Thr Leu Arg Cys
145                 150                 155                 160

Glu Ala Pro Arg Trp Phe Pro Gln Pro Thr Val Val Trp Ala Ser Gln
                165                 170                 175

Val Asp Gln Gly Ala Asn Phe Ser Glu Val Ser Asn Thr Ser Phe Glu
            180                 185                 190

Leu Asn Ser Glu Asn Val Thr Met Lys Val Val Ser Val Leu Tyr Asn
        195                 200                 205

Val Thr Ile Asn Asn Thr Tyr Ser Cys Met Ile Glu Asn Asp Ile Ala
210                 215                 220

Lys Ala Thr Gly Asp Ile Lys Val Thr Glu Ser Glu Ile Lys Arg Arg
225                 230                 235                 240

Ser His Leu Gln Leu Leu Asn Ser Lys Ala Ser
                245                 250
```

<210> SEQ ID NO 46
<211> LENGTH: 241
<212> TYPE: PRT
<213> ORGANISM: Homo sapiens

<400> SEQUENCE: 46

```
Met Glu Trp Ser Trp Val Phe Leu Phe Phe Leu Ser Val Thr Thr Gly
1               5                   10                  15

Val His Ser Gly Phe Gly Ile Ser Gly Arg His Ser Ile Thr Val Thr
            20                  25                  30

Thr Val Ala Ser Ala Gly Asn Ile Gly Glu Asp Gly Ile Leu Ser Cys
        35                  40                  45

Thr Phe Glu Pro Asp Ile Lys Leu Ser Asp Ile Val Ile Gln Trp Leu
    50                  55                  60

Lys Glu Gly Val Leu Gly Leu Val His Glu Phe Lys Glu Gly Lys Asp
65                  70                  75                  80

Glu Leu Ser Glu Gln Asp Glu Met Phe Arg Gly Arg Thr Ala Val Phe
                85                  90                  95

Ala Asp Gln Val Ile Val Gly Asn Ala Ser Leu Arg Leu Lys Asn Val
            100                 105                 110
```

Gln Leu Thr Asp Ala Gly Thr Tyr Lys Cys Tyr Ile Ile Thr Ser Lys
            115                 120                 125

Gly Lys Gly Asn Ala Asn Leu Glu Tyr Lys Thr Gly Ala Phe Ser Met
        130                 135                 140

Pro Glu Val Asn Val Asp Tyr Asn Ala Ser Ser Glu Thr Leu Arg Cys
145                 150                 155                 160

Glu Ala Pro Arg Trp Phe Pro Gln Pro Thr Val Val Trp Ala Ser Gln
                165                 170                 175

Val Asp Gln Gly Ala Asn Phe Ser Glu Val Ser Asn Thr Ser Phe Glu
            180                 185                 190

Leu Asn Ser Glu Asn Val Thr Met Lys Val Val Ser Val Leu Tyr Asn
        195                 200                 205

Val Thr Ile Asn Asn Thr Tyr Ser Cys Met Ile Glu Asn Asp Ile Ala
    210                 215                 220

Lys Ala Thr Gly Asp Ile Lys Val Thr Glu Ser Glu Ile Lys Arg Arg
225                 230                 235                 240

Ser

<210> SEQ ID NO 47
<211> LENGTH: 237
<212> TYPE: PRT
<213> ORGANISM: Homo sapiens

<400> SEQUENCE: 47

Met Glu Trp Ser Trp Val Phe Leu Phe Phe Leu Ser Val Thr Thr Gly
1               5                   10                  15

Val His Ser Gly Phe Gly Ile Ser Gly Arg His Ser Ile Thr Val Thr
            20                  25                  30

Thr Val Ala Ser Ala Gly Asn Ile Gly Glu Asp Gly Ile Leu Ser Cys
        35                  40                  45

Thr Phe Glu Pro Asp Ile Lys Leu Ser Asp Ile Val Ile Gln Trp Leu
    50                  55                  60

Lys Glu Gly Val Leu Gly Leu Val His Glu Phe Lys Glu Gly Lys Asp
65                  70                  75                  80

Glu Leu Ser Glu Gln Asp Glu Met Phe Arg Gly Arg Thr Ala Val Phe
                85                  90                  95

Ala Asp Gln Val Ile Val Gly Asn Ala Ser Leu Arg Leu Lys Asn Val
            100                 105                 110

Gln Leu Thr Asp Ala Gly Thr Tyr Lys Cys Tyr Ile Ile Thr Ser Lys
        115                 120                 125

Gly Lys Gly Asn Ala Asn Leu Glu Tyr Lys Thr Gly Ala Phe Ser Met
    130                 135                 140

Pro Glu Val Asn Val Asp Tyr Asn Ala Ser Ser Glu Thr Leu Arg Cys
145                 150                 155                 160

Glu Ala Pro Arg Trp Phe Pro Gln Pro Thr Val Val Trp Ala Ser Gln
                165                 170                 175

Val Asp Gln Gly Ala Asn Phe Ser Glu Val Ser Asn Thr Ser Phe Glu
            180                 185                 190

Leu Asn Ser Glu Asn Val Thr Met Lys Val Val Ser Val Leu Tyr Asn
        195                 200                 205

Val Thr Ile Asn Asn Thr Tyr Ser Cys Met Ile Glu Asn Asp Ile Ala
    210                 215                 220

Lys Ala Thr Gly Asp Ile Lys Val Thr Glu Ser Glu Ile
225                 230                 235

<210> SEQ ID NO 48
<211> LENGTH: 251
<212> TYPE: PRT
<213> ORGANISM: Homo sapiens

<400> SEQUENCE: 48

Met Glu Trp Ser Trp Val Phe Leu Phe Phe Leu Ser Val Thr Thr Gly
1               5                   10                  15

Val His Ser Gly Phe Gly Ile Ser Gly Arg His Ser Ile Thr Val Thr
            20                  25                  30

Thr Val Ala Ser Ala Gly Asn Ile Gly Glu Asp Gly Ile Leu Ser Cys
        35                  40                  45

Thr Phe Glu Pro Asp Ile Lys Leu Ser Asp Ile Val Ile Gln Trp Leu
    50                  55                  60

Lys Glu Gly Val Leu Gly Leu Val His Glu Phe Lys Glu Gly Lys Asp
65                  70                  75                  80

Glu Leu Ser Glu Gln Asp Glu Met Phe Arg Gly Arg Thr Ala Val Phe
                85                  90                  95

Ala Asp Gln Val Ile Val Gly Asn Ala Ser Leu Arg Leu Lys Asn Val
            100                 105                 110

Gln Leu Thr Asp Ala Gly Thr Tyr Lys Cys Tyr Ile Ile Thr Ser Lys
        115                 120                 125

Gly Lys Gly Asn Ala Asn Leu Glu Tyr Lys Thr Gly Ala Phe Ser Met
    130                 135                 140

Pro Glu Val Asn Val Asp Tyr Asn Ala Ser Ser Glu Thr Leu Arg Cys
145                 150                 155                 160

Glu Ala Pro Arg Trp Phe Pro Gln Pro Thr Val Val Trp Ala Ser Gln
                165                 170                 175

Val Asp Gln Gly Ala Asn Phe Ser Glu Val Ser Asn Thr Ser Phe Glu
            180                 185                 190

Leu Asn Ser Glu Asn Val Thr Met Lys Val Val Ser Val Leu Tyr Asn
        195                 200                 205

Val Thr Ile Asn Asn Thr Tyr Ser Cys Met Ile Glu Asn Asp Ile Ala
    210                 215                 220

Lys Ala Thr Gly Asp Ile Lys Val Thr Glu Ser Glu Ile Lys Arg Arg
225                 230                 235                 240

Ser His Leu Gln Leu Leu Asn Ser Lys Ala Ser
                245                 250

<210> SEQ ID NO 49
<211> LENGTH: 249
<212> TYPE: PRT
<213> ORGANISM: Homo sapiens

<400> SEQUENCE: 49

Met Ala Ser Leu Gly Gln Ile Leu Phe Trp Ser Ile Ile Ser Ile Ile
1               5                   10                  15

Ile Ile Leu Ala Gly Ala Ile Ala Leu Ile Ile Gly Phe Gly Ile Ser
            20                  25                  30

Gly Arg His Ser Ile Thr Val Thr Val Ala Ser Ala Gly Asn Ile
        35                  40                  45

Gly Glu Asp Gly Ile Gln Ser Cys Thr Phe Glu Pro Asp Ile Lys Leu
    50                  55                  60

Ser Asp Ile Val Ile Gln Trp Leu Lys Glu Gly Val Leu Gly Leu Val
65                  70                  75                  80

-continued

```
His Glu Phe Lys Glu Gly Lys Asp Glu Leu Ser Glu Gln Asp Glu Met
                 85                  90                  95

Phe Arg Gly Arg Thr Ala Val Phe Ala Asp Gln Val Ile Val Gly Asn
            100                 105                 110

Ala Ser Leu Arg Leu Lys Asn Val Gln Leu Thr Asp Ala Gly Thr Tyr
        115                 120                 125

Lys Cys Tyr Ile Ile Thr Ser Lys Gly Lys Gly Asn Ala Asn Leu Glu
    130                 135                 140

Tyr Lys Thr Gly Ala Phe Ser Met Pro Glu Val Asn Val Asp Tyr Asn
145                 150                 155                 160

Ala Ser Ser Glu Thr Leu Arg Cys Glu Ala Pro Arg Trp Phe Pro Gln
                165                 170                 175

Pro Thr Val Val Trp Ala Ser Gln Val Asp Gln Gly Ala Asn Phe Ser
            180                 185                 190

Glu Val Ser Asn Thr Ser Phe Glu Leu Asn Ser Glu Asn Val Thr Met
        195                 200                 205

Lys Val Val Ser Val Leu Tyr Asn Val Thr Ile Asn Asn Thr Tyr Ser
    210                 215                 220

Cys Met Ile Glu Asn Asp Ile Ala Lys Ala Thr Gly Asp Ile Lys Val
225                 230                 235                 240

Thr Glu Ser Glu Ile Lys Arg Arg Ser
                245

<210> SEQ ID NO 50
<211> LENGTH: 245
<212> TYPE: PRT
<213> ORGANISM: Homo sapiens

<400> SEQUENCE: 50

Met Ala Ser Leu Gly Gln Ile Leu Phe Trp Ser Ile Ile Ser Ile Ile
1               5                   10                  15

Ile Ile Leu Ala Gly Ala Ile Ala Leu Ile Ile Gly Phe Gly Ile Ser
            20                  25                  30

Gly Arg His Ser Ile Thr Val Thr Thr Val Ala Ser Ala Gly Asn Ile
        35                  40                  45

Gly Glu Asp Gly Ile Gln Ser Cys Thr Phe Glu Pro Asp Ile Lys Leu
    50                  55                  60

Ser Asp Ile Val Ile Gln Trp Leu Lys Glu Gly Val Leu Gly Leu Val
65                  70                  75                  80

His Glu Phe Lys Glu Gly Lys Asp Glu Leu Ser Glu Gln Asp Glu Met
                85                  90                  95

Phe Arg Gly Arg Thr Ala Val Phe Ala Asp Gln Val Ile Val Gly Asn
            100                 105                 110

Ala Ser Leu Arg Leu Lys Asn Val Gln Leu Thr Asp Ala Gly Thr Tyr
        115                 120                 125

Lys Cys Tyr Ile Ile Thr Ser Lys Gly Lys Gly Asn Ala Asn Leu Glu
    130                 135                 140

Tyr Lys Thr Gly Ala Phe Ser Met Pro Glu Val Asn Val Asp Tyr Asn
145                 150                 155                 160

Ala Ser Ser Glu Thr Leu Arg Cys Glu Ala Pro Arg Trp Phe Pro Gln
                165                 170                 175

Pro Thr Val Val Trp Ala Ser Gln Val Asp Gln Gly Ala Asn Phe Ser
            180                 185                 190

Glu Val Ser Asn Thr Ser Phe Glu Leu Asn Ser Glu Asn Val Thr Met
```

195                 200                 205
Lys Val Val Ser Val Leu Tyr Asn Val Thr Ile Asn Asn Thr Tyr Ser
    210                 215                 220

Cys Met Ile Glu Asn Asp Ile Ala Lys Ala Thr Gly Asp Ile Lys Val
225                 230                 235                 240

Thr Glu Ser Glu Ile
            245

<210> SEQ ID NO 51
<211> LENGTH: 259
<212> TYPE: PRT
<213> ORGANISM: Homo sapiens

<400> SEQUENCE: 51

Met Ala Ser Leu Gly Gln Ile Leu Phe Trp Ser Ile Ile Ser Ile Ile
1               5                   10                  15

Ile Ile Leu Ala Gly Ala Ile Ala Leu Ile Ile Gly Phe Gly Ile Ser
            20                  25                  30

Gly Arg His Ser Ile Thr Val Thr Val Ala Ser Ala Gly Asn Ile
        35                  40                  45

Gly Glu Asp Gly Ile Gln Ser Cys Thr Phe Glu Pro Asp Ile Lys Leu
    50                  55                  60

Ser Asp Ile Val Ile Gln Trp Leu Lys Glu Gly Val Leu Gly Leu Val
65                  70                  75                  80

His Glu Phe Lys Glu Gly Lys Asp Glu Leu Ser Glu Gln Asp Glu Met
                85                  90                  95

Phe Arg Gly Arg Thr Ala Val Phe Ala Asp Gln Val Ile Val Gly Asn
            100                 105                 110

Ala Ser Leu Arg Leu Lys Asn Val Gln Leu Thr Asp Ala Gly Thr Tyr
        115                 120                 125

Lys Cys Tyr Ile Ile Thr Ser Lys Gly Lys Gly Asn Ala Asn Leu Glu
130                 135                 140

Tyr Lys Thr Gly Ala Phe Ser Met Pro Glu Val Asn Val Asp Tyr Asn
145                 150                 155                 160

Ala Ser Ser Glu Thr Leu Arg Cys Glu Ala Pro Arg Trp Phe Pro Gln
            165                 170                 175

Pro Thr Val Val Trp Ala Ser Gln Val Asp Gln Gly Ala Asn Phe Ser
        180                 185                 190

Glu Val Ser Asn Thr Ser Phe Glu Leu Asn Ser Glu Asn Val Thr Met
    195                 200                 205

Lys Val Val Ser Val Leu Tyr Asn Val Thr Ile Asn Asn Thr Tyr Ser
    210                 215                 220

Cys Met Ile Glu Asn Asp Ile Ala Lys Ala Thr Gly Asp Ile Lys Val
225                 230                 235                 240

Thr Glu Ser Glu Ile Lys Arg Arg Ser His Leu Gln Leu Leu Asn Ser
            245                 250                 255

Lys Ala Ser

<210> SEQ ID NO 52
<211> LENGTH: 249
<212> TYPE: PRT
<213> ORGANISM: Homo sapiens

<400> SEQUENCE: 52

Met Ala Ser Leu Gly Gln Ile Leu Phe Trp Ser Ile Ile Ser Ile Ile
1               5                   10                  15

Ile Ile Leu Ala Gly Ala Ile Ala Leu Ile Ile Gly Phe Gly Ile Ser
            20                  25                  30

Gly Arg His Ser Ile Thr Val Thr Val Ala Ser Ala Gly Asn Ile
        35                  40                  45

Gly Glu Asp Gly Ile Leu Ser Cys Thr Phe Glu Pro Asp Ile Lys Leu
 50                  55                  60

Ser Asp Ile Val Ile Gln Trp Leu Lys Glu Gly Val Leu Gly Leu Val
 65                  70                  75                  80

His Glu Phe Lys Glu Gly Lys Asp Glu Leu Ser Glu Gln Asp Glu Met
            85                  90                  95

Phe Arg Gly Arg Thr Ala Val Phe Ala Asp Gln Val Ile Val Gly Asn
            100                 105                 110

Ala Ser Leu Arg Leu Lys Asn Val Gln Leu Thr Asp Ala Gly Thr Tyr
            115                 120                 125

Lys Cys Tyr Ile Ile Thr Ser Lys Gly Lys Gly Asn Ala Asn Leu Glu
130                 135                 140

Tyr Lys Thr Gly Ala Phe Ser Met Pro Glu Val Asn Val Asp Tyr Asn
145                 150                 155                 160

Ala Ser Ser Glu Thr Leu Arg Cys Glu Ala Pro Arg Trp Phe Pro Gln
            165                 170                 175

Pro Thr Val Val Trp Ala Ser Gln Val Asp Gln Gly Ala Asn Phe Ser
            180                 185                 190

Glu Val Ser Asn Thr Ser Phe Glu Leu Asn Ser Glu Asn Val Thr Met
            195                 200                 205

Lys Val Val Ser Val Leu Tyr Asn Val Thr Ile Asn Asn Thr Tyr Ser
            210                 215                 220

Cys Met Ile Glu Asn Asp Ile Ala Lys Ala Thr Gly Asp Ile Lys Val
225                 230                 235                 240

Thr Glu Ser Glu Ile Lys Arg Arg Ser
                245

<210> SEQ ID NO 53
<211> LENGTH: 245
<212> TYPE: PRT
<213> ORGANISM: Homo sapiens

<400> SEQUENCE: 53

Met Ala Ser Leu Gly Gln Ile Leu Phe Trp Ser Ile Ile Ser Ile Ile
 1                5                  10                  15

Ile Ile Leu Ala Gly Ala Ile Ala Leu Ile Ile Gly Phe Gly Ile Ser
            20                  25                  30

Gly Arg His Ser Ile Thr Val Thr Val Ala Ser Ala Gly Asn Ile
        35                  40                  45

Gly Glu Asp Gly Ile Leu Ser Cys Thr Phe Glu Pro Asp Ile Lys Leu
 50                  55                  60

Ser Asp Ile Val Ile Gln Trp Leu Lys Glu Gly Val Leu Gly Leu Val
 65                  70                  75                  80

His Glu Phe Lys Glu Gly Lys Asp Glu Leu Ser Glu Gln Asp Glu Met
            85                  90                  95

Phe Arg Gly Arg Thr Ala Val Phe Ala Asp Gln Val Ile Val Gly Asn
            100                 105                 110

Ala Ser Leu Arg Leu Lys Asn Val Gln Leu Thr Asp Ala Gly Thr Tyr
            115                 120                 125

Lys Cys Tyr Ile Ile Thr Ser Lys Gly Lys Gly Asn Ala Asn Leu Glu

```
                130                 135                 140
Tyr Lys Thr Gly Ala Phe Ser Met Pro Glu Val Asn Val Asp Tyr Asn
145                 150                 155                 160

Ala Ser Ser Glu Thr Leu Arg Cys Glu Ala Pro Arg Trp Phe Pro Gln
                165                 170                 175

Pro Thr Val Val Trp Ala Ser Gln Val Asp Gln Gly Ala Asn Phe Ser
                180                 185                 190

Glu Val Ser Asn Thr Ser Phe Glu Leu Asn Ser Glu Asn Val Thr Met
                195                 200                 205

Lys Val Val Ser Val Leu Tyr Asn Val Thr Ile Asn Asn Thr Tyr Ser
                210                 215                 220

Cys Met Ile Glu Asn Asp Ile Ala Lys Ala Thr Gly Asp Ile Lys Val
225                 230                 235                 240

Thr Glu Ser Glu Ile
                245

<210> SEQ ID NO 54
<211> LENGTH: 259
<212> TYPE: PRT
<213> ORGANISM: Homo sapiens

<400> SEQUENCE: 54

Met Ala Ser Leu Gly Gln Ile Leu Phe Trp Ser Ile Ile Ser Ile Ile
1               5                   10                  15

Ile Ile Leu Ala Gly Ala Ile Ala Leu Ile Ile Gly Phe Gly Ile Ser
                20                  25                  30

Gly Arg His Ser Ile Thr Val Thr Val Ala Ser Ala Gly Asn Ile
                35                  40                  45

Gly Glu Asp Gly Ile Leu Ser Cys Thr Phe Glu Pro Asp Ile Lys Leu
                50                  55                  60

Ser Asp Ile Val Ile Gln Trp Leu Lys Glu Gly Val Leu Gly Leu Val
65                  70                  75                  80

His Glu Phe Lys Glu Gly Lys Asp Glu Leu Ser Glu Gln Asp Glu Met
                85                  90                  95

Phe Arg Gly Arg Thr Ala Val Phe Ala Asp Gln Val Ile Val Gly Asn
                100                 105                 110

Ala Ser Leu Arg Leu Lys Asn Val Gln Leu Thr Asp Ala Gly Thr Tyr
                115                 120                 125

Lys Cys Tyr Ile Ile Thr Ser Lys Gly Lys Gly Asn Ala Asn Leu Glu
                130                 135                 140

Tyr Lys Thr Gly Ala Phe Ser Met Pro Glu Val Asn Val Asp Tyr Asn
145                 150                 155                 160

Ala Ser Ser Glu Thr Leu Arg Cys Glu Ala Pro Arg Trp Phe Pro Gln
                165                 170                 175

Pro Thr Val Val Trp Ala Ser Gln Val Asp Gln Gly Ala Asn Phe Ser
                180                 185                 190

Glu Val Ser Asn Thr Ser Phe Glu Leu Asn Ser Glu Asn Val Thr Met
                195                 200                 205

Lys Val Val Ser Val Leu Tyr Asn Val Thr Ile Asn Asn Thr Tyr Ser
                210                 215                 220

Cys Met Ile Glu Asn Asp Ile Ala Lys Ala Thr Gly Asp Ile Lys Val
225                 230                 235                 240

Thr Glu Ser Glu Ile Lys Arg Arg Ser His Leu Gln Leu Leu Asn Ser
                245                 250                 255
```

Lys Ala Ser

<210> SEQ ID NO 55
<211> LENGTH: 222
<212> TYPE: PRT
<213> ORGANISM: Homo sapiens

<400> SEQUENCE: 55

Gly Phe Gly Ile Ser Gly Arg His Ser Ile Thr Val Thr Thr Val Ala
1               5                   10                  15

Ser Ala Gly Asn Ile Gly Glu Asp Gly Ile Gln Ser Cys Thr Phe Glu
            20                  25                  30

Pro Asp Ile Lys Leu Ser Asp Ile Val Ile Gln Trp Leu Lys Glu Gly
        35                  40                  45

Val Leu Gly Leu Val His Glu Phe Lys Glu Gly Lys Asp Glu Leu Ser
    50                  55                  60

Glu Gln Asp Glu Met Phe Arg Gly Arg Thr Ala Val Phe Ala Asp Gln
65                  70                  75                  80

Val Ile Val Gly Asn Ala Ser Leu Arg Leu Lys Asn Val Gln Leu Thr
                85                  90                  95

Asp Ala Gly Thr Tyr Lys Cys Tyr Ile Ile Thr Ser Lys Gly Lys Gly
            100                 105                 110

Asn Ala Asn Leu Glu Tyr Lys Thr Gly Ala Phe Ser Met Pro Glu Val
        115                 120                 125

Asn Val Asp Tyr Asn Ala Ser Ser Glu Thr Leu Arg Cys Glu Ala Pro
    130                 135                 140

Arg Trp Phe Pro Gln Pro Thr Val Val Trp Ala Ser Gln Val Asp Gln
145                 150                 155                 160

Gly Ala Asn Phe Ser Glu Val Ser Asn Thr Ser Phe Glu Leu Asn Ser
                165                 170                 175

Glu Asn Val Thr Met Lys Val Val Ser Val Leu Tyr Asn Val Thr Ile
            180                 185                 190

Asn Asn Thr Tyr Ser Cys Met Ile Glu Asn Asp Ile Ala Lys Ala Thr
        195                 200                 205

Gly Asp Ile Lys Val Thr Glu Ser Glu Ile Lys Arg Arg Ser
    210                 215                 220

<210> SEQ ID NO 56
<211> LENGTH: 222
<212> TYPE: PRT
<213> ORGANISM: Homo sapiens

<400> SEQUENCE: 56

Gly Phe Gly Ile Ser Gly Arg His Ser Ile Thr Val Thr Thr Val Ala
1               5                   10                  15

Ser Ala Gly Asn Ile Gly Glu Asp Gly Ile Leu Ser Cys Thr Phe Glu
            20                  25                  30

Pro Asp Ile Lys Leu Ser Asp Ile Val Ile Gln Trp Leu Lys Glu Gly
        35                  40                  45

Val Leu Gly Leu Val His Glu Phe Lys Glu Gly Lys Asp Glu Leu Ser
    50                  55                  60

Glu Gln Asp Glu Met Phe Arg Gly Arg Thr Ala Val Phe Ala Asp Gln
65                  70                  75                  80

Val Ile Val Gly Asn Ala Ser Leu Arg Leu Lys Asn Val Gln Leu Thr
                85                  90                  95

Asp Ala Gly Thr Tyr Lys Cys Tyr Ile Ile Thr Ser Lys Gly Lys Gly

```
                100                 105                 110
Asn Ala Asn Leu Glu Tyr Lys Thr Gly Ala Phe Ser Met Pro Glu Val
            115                 120                 125

Asn Val Asp Tyr Asn Ala Ser Ser Glu Thr Leu Arg Cys Glu Ala Pro
        130                 135                 140

Arg Trp Phe Pro Gln Pro Thr Val Val Trp Ala Ser Gln Val Asp Gln
145                 150                 155                 160

Gly Ala Asn Phe Ser Glu Val Ser Asn Thr Ser Phe Glu Leu Asn Ser
                165                 170                 175

Glu Asn Val Thr Met Lys Val Val Ser Val Leu Tyr Asn Val Thr Ile
            180                 185                 190

Asn Asn Thr Tyr Ser Cys Met Ile Glu Asn Asp Ile Ala Lys Ala Thr
        195                 200                 205

Gly Asp Ile Lys Val Thr Glu Ser Glu Ile Lys Arg Arg Ser
210                 215                 220
```

<210> SEQ ID NO 57
<211> LENGTH: 218
<212> TYPE: PRT
<213> ORGANISM: Homo sapiens

<400> SEQUENCE: 57

```
Gly Phe Gly Ile Ser Gly Arg His Ser Ile Thr Val Thr Val Ala
1               5                   10                  15

Ser Ala Gly Asn Ile Gly Glu Asp Gly Ile Gln Ser Cys Thr Phe Glu
            20                  25                  30

Pro Asp Ile Lys Leu Ser Asp Ile Val Ile Gln Trp Leu Lys Glu Gly
        35                  40                  45

Val Leu Gly Leu Val His Glu Phe Lys Glu Gly Lys Asp Glu Leu Ser
    50                  55                  60

Glu Gln Asp Glu Met Phe Arg Gly Arg Thr Ala Val Phe Ala Asp Gln
65                  70                  75                  80

Val Ile Val Gly Asn Ala Ser Leu Arg Leu Lys Asn Val Gln Leu Thr
                85                  90                  95

Asp Ala Gly Thr Tyr Lys Cys Tyr Ile Ile Thr Ser Lys Gly Lys Gly
            100                 105                 110

Asn Ala Asn Leu Glu Tyr Lys Thr Gly Ala Phe Ser Met Pro Glu Val
        115                 120                 125

Asn Val Asp Tyr Asn Ala Ser Ser Glu Thr Leu Arg Cys Glu Ala Pro
    130                 135                 140

Arg Trp Phe Pro Gln Pro Thr Val Val Trp Ala Ser Gln Val Asp Gln
145                 150                 155                 160

Gly Ala Asn Phe Ser Glu Val Ser Asn Thr Ser Phe Glu Leu Asn Ser
                165                 170                 175

Glu Asn Val Thr Met Lys Val Val Ser Val Leu Tyr Asn Val Thr Ile
            180                 185                 190

Asn Asn Thr Tyr Ser Cys Met Ile Glu Asn Asp Ile Ala Lys Ala Thr
        195                 200                 205

Gly Asp Ile Lys Val Thr Glu Ser Glu Ile
    210                 215
```

<210> SEQ ID NO 58
<211> LENGTH: 218
<212> TYPE: PRT
<213> ORGANISM: Homo sapiens

```
<400> SEQUENCE: 58

Gly Phe Gly Ile Ser Gly Arg His Ser Ile Thr Val Thr Thr Val Ala
1               5                   10                  15

Ser Ala Gly Asn Ile Gly Glu Asp Gly Ile Leu Ser Cys Thr Phe Glu
            20                  25                  30

Pro Asp Ile Lys Leu Ser Asp Ile Val Ile Gln Trp Leu Lys Glu Gly
        35                  40                  45

Val Leu Gly Leu Val His Glu Phe Lys Glu Gly Lys Asp Glu Leu Ser
    50                  55                  60

Glu Gln Asp Glu Met Phe Arg Gly Arg Thr Ala Val Phe Ala Asp Gln
65                  70                  75                  80

Val Ile Val Gly Asn Ala Ser Leu Arg Leu Lys Asn Val Gln Leu Thr
                85                  90                  95

Asp Ala Gly Thr Tyr Lys Cys Tyr Ile Ile Thr Ser Lys Gly Lys Gly
            100                 105                 110

Asn Ala Asn Leu Glu Tyr Lys Thr Gly Ala Phe Ser Met Pro Glu Val
        115                 120                 125

Asn Val Asp Tyr Asn Ala Ser Ser Glu Thr Leu Arg Cys Glu Ala Pro
    130                 135                 140

Arg Trp Phe Pro Gln Pro Thr Val Val Trp Ala Ser Gln Val Asp Gln
145                 150                 155                 160

Gly Ala Asn Phe Ser Glu Val Ser Asn Thr Ser Phe Glu Leu Asn Ser
                165                 170                 175

Glu Asn Val Thr Met Lys Val Val Ser Val Leu Tyr Asn Val Thr Ile
            180                 185                 190

Asn Asn Thr Tyr Ser Cys Met Ile Glu Asn Asp Ile Ala Lys Ala Thr
        195                 200                 205

Gly Asp Ile Lys Val Thr Glu Ser Glu Ile
    210                 215

<210> SEQ ID NO 59
<211> LENGTH: 232
<212> TYPE: PRT
<213> ORGANISM: Homo sapiens

<400> SEQUENCE: 59

Gly Phe Gly Ile Ser Gly Arg His Ser Ile Thr Val Thr Thr Val Ala
1               5                   10                  15

Ser Ala Gly Asn Ile Gly Glu Asp Gly Ile Gln Ser Cys Thr Phe Glu
            20                  25                  30

Pro Asp Ile Lys Leu Ser Asp Ile Val Ile Gln Trp Leu Lys Glu Gly
        35                  40                  45

Val Leu Gly Leu Val His Glu Phe Lys Glu Gly Lys Asp Glu Leu Ser
    50                  55                  60

Glu Gln Asp Glu Met Phe Arg Gly Arg Thr Ala Val Phe Ala Asp Gln
65                  70                  75                  80

Val Ile Val Gly Asn Ala Ser Leu Arg Leu Lys Asn Val Gln Leu Thr
                85                  90                  95

Asp Ala Gly Thr Tyr Lys Cys Tyr Ile Ile Thr Ser Lys Gly Lys Gly
            100                 105                 110

Asn Ala Asn Leu Glu Tyr Lys Thr Gly Ala Phe Ser Met Pro Glu Val
        115                 120                 125

Asn Val Asp Tyr Asn Ala Ser Ser Glu Thr Leu Arg Cys Glu Ala Pro
    130                 135                 140
```

```
Arg Trp Phe Pro Gln Pro Thr Val Val Trp Ala Ser Gln Val Asp Gln
145                 150                 155                 160

Gly Ala Asn Phe Ser Glu Val Ser Asn Thr Ser Phe Glu Leu Asn Ser
                165                 170                 175

Glu Asn Val Thr Met Lys Val Val Ser Val Leu Tyr Asn Val Thr Ile
            180                 185                 190

Asn Asn Thr Tyr Ser Cys Met Ile Glu Asn Asp Ile Ala Lys Ala Thr
        195                 200                 205

Gly Asp Ile Lys Val Thr Glu Ser Glu Ile Lys Arg Arg Ser His Leu
    210                 215                 220

Gln Leu Leu Asn Ser Lys Ala Ser
225                 230
```

<210> SEQ ID NO 60
<211> LENGTH: 232
<212> TYPE: PRT
<213> ORGANISM: Homo sapiens

<400> SEQUENCE: 60

```
Gly Phe Gly Ile Ser Gly Arg His Ser Ile Thr Val Thr Val Ala
1               5                   10                  15

Ser Ala Gly Asn Ile Gly Glu Asp Gly Ile Leu Ser Cys Thr Phe Glu
                20                  25                  30

Pro Asp Ile Lys Leu Ser Asp Ile Val Ile Gln Trp Leu Lys Glu Gly
            35                  40                  45

Val Leu Gly Leu Val His Glu Phe Lys Glu Gly Lys Asp Glu Leu Ser
        50                  55                  60

Glu Gln Asp Glu Met Phe Arg Gly Arg Thr Ala Val Phe Ala Asp Gln
65                  70                  75                  80

Val Ile Val Gly Asn Ala Ser Leu Arg Leu Lys Asn Val Gln Leu Thr
                85                  90                  95

Asp Ala Gly Thr Tyr Lys Cys Tyr Ile Ile Thr Ser Lys Gly Lys Gly
            100                 105                 110

Asn Ala Asn Leu Glu Tyr Lys Thr Gly Ala Phe Ser Met Pro Glu Val
        115                 120                 125

Asn Val Asp Tyr Asn Ala Ser Ser Glu Thr Leu Arg Cys Glu Ala Pro
130                 135                 140

Arg Trp Phe Pro Gln Pro Thr Val Val Trp Ala Ser Gln Val Asp Gln
145                 150                 155                 160

Gly Ala Asn Phe Ser Glu Val Ser Asn Thr Ser Phe Glu Leu Asn Ser
                165                 170                 175

Glu Asn Val Thr Met Lys Val Val Ser Val Leu Tyr Asn Val Thr Ile
            180                 185                 190

Asn Asn Thr Tyr Ser Cys Met Ile Glu Asn Asp Ile Ala Lys Ala Thr
        195                 200                 205

Gly Asp Ile Lys Val Thr Glu Ser Glu Ile Lys Arg Arg Ser His Leu
    210                 215                 220

Gln Leu Leu Asn Ser Lys Ala Ser
225                 230
```

<210> SEQ ID NO 61
<211> LENGTH: 387
<212> TYPE: DNA
<213> ORGANISM: Homo sapiens

<400> SEQUENCE: 61

```
ggcttcggca tcagtggacg gcacagtatc acagtgacca ccgtcgcctc cgctggcaat    60
ataggtgagg atggcatcca gtcctgtacc tttgagccgg acatcaaact gtctgacata   120
gtgatacaat ggctgaagga gggggtgctc ggtctggtac atgagtttaa ggaagggaag   180
gatgaactgt ccgagcagga tgagatgttc cggggagga ccgctgtgtt cgccgatcag    240
gtaatcgtcg gaaatgcaag tctcagattg aaaaatgtgc aactgactga tgctggcacg   300
tataaatgct acattatcac aagtaagggc aaaggaaatg ctaaccttga gtataaaaca   360
ggcgcattct caatgcccga ggtcaat                                       387
```

<210> SEQ ID NO 62
<211> LENGTH: 387
<212> TYPE: DNA
<213> ORGANISM: Homo sapiens

<400> SEQUENCE: 62

```
ggcttcggca tcagtggacg gcacagtatc acagtgacca ccgtcgcctc cgctggcaat    60
ataggtgagg atggcatcct gtcctgtacc tttgagccgg acatcaaact gtctgacata   120
gtgatacaat ggctgaagga gggggtgctc ggtctggtac atgagtttaa ggaagggaag   180
gatgaactgt ccgagcagga tgagatgttc cggggagga ccgctgtgtt cgccgatcag    240
gtaatcgtcg gaaatgcaag tctcagattg aaaaatgtgc aactgactga tgctggcacg   300
tataaatgct acattatcac aagtaagggc aaaggaaatg ctaaccttga gtataaaaca   360
ggcgcattct caatgcccga ggtcaat                                       387
```

<210> SEQ ID NO 63
<211> LENGTH: 129
<212> TYPE: PRT
<213> ORGANISM: Homo sapiens

<400> SEQUENCE: 63

| Gly | Phe | Gly | Ile | Ser | Gly | Arg | His | Ser | Ile | Thr | Val | Thr | Thr | Val | Ala |
|---|---|---|---|---|---|---|---|---|---|---|---|---|---|---|---|
| 1 | | | | 5 | | | | | 10 | | | | | 15 | |

| Ser | Ala | Gly | Asn | Ile | Gly | Glu | Asp | Gly | Ile | Gln | Ser | Cys | Thr | Phe | Glu |
|---|---|---|---|---|---|---|---|---|---|---|---|---|---|---|---|
| | | | 20 | | | | | 25 | | | | | 30 | | |

| Pro | Asp | Ile | Lys | Leu | Ser | Asp | Ile | Val | Ile | Gln | Trp | Leu | Lys | Glu | Gly |
|---|---|---|---|---|---|---|---|---|---|---|---|---|---|---|---|
| | | 35 | | | | | 40 | | | | | 45 | | | |

| Val | Leu | Gly | Leu | Val | His | Glu | Phe | Lys | Glu | Gly | Lys | Asp | Glu | Leu | Ser |
|---|---|---|---|---|---|---|---|---|---|---|---|---|---|---|---|
| | 50 | | | | | 55 | | | | | 60 | | | | |

| Glu | Gln | Asp | Glu | Met | Phe | Arg | Gly | Arg | Thr | Ala | Val | Phe | Ala | Asp | Gln |
|---|---|---|---|---|---|---|---|---|---|---|---|---|---|---|---|
| 65 | | | | | 70 | | | | | 75 | | | | | 80 |

| Val | Ile | Val | Gly | Asn | Ala | Ser | Leu | Arg | Leu | Lys | Asn | Val | Gln | Leu | Thr |
|---|---|---|---|---|---|---|---|---|---|---|---|---|---|---|---|
| | | | | 85 | | | | | 90 | | | | | 95 | |

| Asp | Ala | Gly | Thr | Tyr | Lys | Cys | Tyr | Ile | Ile | Thr | Ser | Lys | Gly | Lys | Gly |
|---|---|---|---|---|---|---|---|---|---|---|---|---|---|---|---|
| | | | 100 | | | | | 105 | | | | | 110 | | |

| Asn | Ala | Asn | Leu | Glu | Tyr | Lys | Thr | Gly | Ala | Phe | Ser | Met | Pro | Glu | Val |
|---|---|---|---|---|---|---|---|---|---|---|---|---|---|---|---|
| | | | 115 | | | | | 120 | | | | | 125 | | |

Asn

<210> SEQ ID NO 64
<211> LENGTH: 129
<212> TYPE: PRT
<213> ORGANISM: Homo sapiens

<400> SEQUENCE: 64

Gly Phe Gly Ile Ser Gly Arg His Ser Ile Thr Val Thr Thr Val Ala

```
1               5                   10                  15
Ser Ala Gly Asn Ile Gly Glu Asp Gly Ile Leu Ser Cys Thr Phe Glu
            20                  25                  30
Pro Asp Ile Lys Leu Ser Asp Ile Val Ile Gln Trp Leu Lys Glu Gly
            35                  40                  45
Val Leu Gly Leu Val His Glu Phe Lys Glu Gly Lys Asp Glu Leu Ser
        50                  55                  60
Glu Gln Asp Glu Met Phe Arg Gly Arg Thr Ala Val Phe Ala Asp Gln
65                  70                  75                  80
Val Ile Val Gly Asn Ala Ser Leu Arg Leu Lys Asn Val Gln Leu Thr
                85                  90                  95
Asp Ala Gly Thr Tyr Lys Cys Tyr Ile Ile Thr Ser Lys Gly Lys Gly
            100                 105                 110
Asn Ala Asn Leu Glu Tyr Lys Thr Gly Ala Phe Ser Met Pro Glu Val
            115                 120                 125
Asn
```

<210> SEQ ID NO 65
<211> LENGTH: 245
<212> TYPE: PRT
<213> ORGANISM: Pan troglodytes

<400> SEQUENCE: 65

```
Met Lys Pro Leu Thr Ser Arg Ile Ile Ser Ile Ile Ile Ile Leu Ala
1               5                   10                  15
Gly Ala Ile Ala Leu Ile Ile Gly Phe Gly Ile Ser Gly Arg His Ser
            20                  25                  30
Ile Thr Val Thr Thr Val Ala Ser Ala Gly Asn Ile Gly Glu Asp Gly
            35                  40                  45
Ile Leu Ser Cys Thr Phe Glu Pro Asp Ile Lys Leu Ser Asp Ile Val
        50                  55                  60
Ile Gln Trp Leu Lys Glu Gly Val Leu Gly Leu Val His Glu Phe Lys
65                  70                  75                  80
Glu Gly Lys Asp Glu Leu Ser Glu Gln Asp Glu Met Phe Arg Gly Arg
                85                  90                  95
Thr Ala Val Phe Ala Asp Gln Val Ile Val Gly Asn Ala Ser Leu Arg
            100                 105                 110
Leu Lys Asn Val Gln Leu Thr Asp Ala Gly Thr Tyr Lys Cys Tyr Ile
            115                 120                 125
Ile Thr Ser Lys Gly Lys Gly Asn Ala Asn Leu Glu Tyr Lys Thr Gly
        130                 135                 140
Ala Phe Ser Met Pro Glu Val Asn Val Asp Tyr Asn Ala Ser Ser Glu
145                 150                 155                 160
Thr Leu Arg Cys Glu Ala Pro Arg Trp Phe Pro Gln Pro Thr Val Val
                165                 170                 175
Trp Ala Ser Gln Ile Asp Gln Gly Ala Asn Phe Ser Glu Val Ser Asn
            180                 185                 190
Thr Ser Phe Glu Leu Asn Ser Glu Asn Val Thr Met Lys Val Val Ser
            195                 200                 205
Val Leu Tyr Asn Ala Thr Ile Asn Asn Thr Tyr Ser Cys Met Ile Glu
        210                 215                 220
Asn Asp Ile Ala Lys Ala Thr Gly Asp Ile Lys Val Thr Glu Ser Glu
225                 230                 235                 240
Ile Lys Arg Arg Ser
```

245

<210> SEQ ID NO 66
<211> LENGTH: 241
<212> TYPE: PRT
<213> ORGANISM: Pan troglodytes

<400> SEQUENCE: 66

Met Lys Pro Leu Thr Ser Arg Ile Ile Ser Ile Ile Ile Leu Ala
1               5                   10                  15

Gly Ala Ile Ala Leu Ile Ile Gly Phe Gly Ile Ser Gly Arg His Ser
            20                  25                  30

Ile Thr Val Thr Thr Val Ala Ser Ala Gly Asn Ile Gly Glu Asp Gly
        35                  40                  45

Ile Leu Ser Cys Thr Phe Glu Pro Asp Ile Lys Leu Ser Asp Ile Val
    50                  55                  60

Ile Gln Trp Leu Lys Glu Gly Val Leu Gly Leu Val His Glu Phe Lys
65                  70                  75                  80

Glu Gly Lys Asp Glu Leu Ser Glu Gln Asp Glu Met Phe Arg Gly Arg
                85                  90                  95

Thr Ala Val Phe Ala Asp Gln Val Ile Val Gly Asn Ala Ser Leu Arg
            100                 105                 110

Leu Lys Asn Val Gln Leu Thr Asp Ala Gly Thr Tyr Lys Cys Tyr Ile
        115                 120                 125

Ile Thr Ser Lys Gly Lys Gly Asn Ala Asn Leu Glu Tyr Lys Thr Gly
    130                 135                 140

Ala Phe Ser Met Pro Glu Val Asn Val Asp Tyr Asn Ala Ser Ser Glu
145                 150                 155                 160

Thr Leu Arg Cys Glu Ala Pro Arg Trp Phe Pro Gln Pro Thr Val Val
                165                 170                 175

Trp Ala Ser Gln Ile Asp Gln Gly Ala Asn Phe Ser Glu Val Ser Asn
            180                 185                 190

Thr Ser Phe Glu Leu Asn Ser Glu Asn Val Thr Met Lys Val Val Ser
        195                 200                 205

Val Leu Tyr Asn Ala Thr Ile Asn Asn Thr Tyr Ser Cys Met Ile Glu
    210                 215                 220

Asn Asp Ile Ala Lys Ala Thr Gly Asp Ile Lys Val Thr Glu Ser Glu
225                 230                 235                 240

Ile

<210> SEQ ID NO 67
<211> LENGTH: 255
<212> TYPE: PRT
<213> ORGANISM: Pan troglodytes

<400> SEQUENCE: 67

Met Lys Pro Leu Thr Ser Arg Ile Ile Ser Ile Ile Ile Leu Ala
1               5                   10                  15

Gly Ala Ile Ala Leu Ile Ile Gly Phe Gly Ile Ser Gly Arg His Ser
            20                  25                  30

Ile Thr Val Thr Thr Val Ala Ser Ala Gly Asn Ile Gly Glu Asp Gly
        35                  40                  45

Ile Leu Ser Cys Thr Phe Glu Pro Asp Ile Lys Leu Ser Asp Ile Val
    50                  55                  60

Ile Gln Trp Leu Lys Glu Gly Val Leu Gly Leu Val His Glu Phe Lys
65                  70                  75                  80

```
Glu Gly Lys Asp Glu Leu Ser Glu Gln Asp Glu Met Phe Arg Gly Arg
                85                  90                  95
Thr Ala Val Phe Ala Asp Gln Val Ile Val Gly Asn Ala Ser Leu Arg
                100                 105                 110
Leu Lys Asn Val Gln Leu Thr Asp Ala Gly Thr Tyr Lys Cys Tyr Ile
                115                 120                 125
Ile Thr Ser Lys Gly Lys Gly Asn Ala Asn Leu Glu Tyr Lys Thr Gly
            130                 135                 140
Ala Phe Ser Met Pro Glu Val Asn Val Asp Tyr Asn Ala Ser Ser Glu
145                 150                 155                 160
Thr Leu Arg Cys Glu Ala Pro Arg Trp Phe Pro Gln Pro Thr Val Val
                165                 170                 175
Trp Ala Ser Gln Ile Asp Gln Gly Ala Asn Phe Ser Glu Val Ser Asn
                180                 185                 190
Thr Ser Phe Glu Leu Asn Ser Glu Asn Val Thr Met Lys Val Val Ser
                195                 200                 205
Val Leu Tyr Asn Ala Thr Ile Asn Asn Thr Tyr Ser Cys Met Ile Glu
                210                 215                 220
Asn Asp Ile Ala Lys Ala Thr Gly Asp Ile Lys Val Thr Glu Ser Glu
225                 230                 235                 240
Ile Lys Arg Arg Ser His Leu Gln Leu Leu Asn Ser Lys Ala Ser
                245                 250                 255

<210> SEQ ID NO 68
<211> LENGTH: 222
<212> TYPE: PRT
<213> ORGANISM: Pan troglodytes

<400> SEQUENCE: 68

Gly Phe Gly Ile Ser Gly Arg His Ser Ile Thr Val Thr Thr Val Ala
1               5                   10                  15
Ser Ala Gly Asn Ile Gly Glu Asp Gly Ile Leu Ser Cys Thr Phe Glu
                20                  25                  30
Pro Asp Ile Lys Leu Ser Asp Ile Val Ile Gln Trp Leu Lys Glu Gly
                35                  40                  45
Val Leu Gly Leu Val His Glu Phe Lys Glu Gly Lys Asp Glu Leu Ser
            50                  55                  60
Glu Gln Asp Glu Met Phe Arg Gly Arg Thr Ala Val Phe Ala Asp Gln
65                  70                  75                  80
Val Ile Val Gly Asn Ala Ser Leu Arg Leu Lys Asn Val Gln Leu Thr
                85                  90                  95
Asp Ala Gly Thr Tyr Lys Cys Tyr Ile Ile Thr Ser Lys Gly Lys Gly
                100                 105                 110
Asn Ala Asn Leu Glu Tyr Lys Thr Gly Ala Phe Ser Met Pro Glu Val
                115                 120                 125
Asn Val Asp Tyr Asn Ala Ser Ser Glu Thr Leu Arg Cys Glu Ala Pro
            130                 135                 140
Arg Trp Phe Pro Gln Pro Thr Val Val Trp Ala Ser Gln Ile Asp Gln
145                 150                 155                 160
Gly Ala Asn Phe Ser Glu Val Ser Asn Thr Ser Phe Glu Leu Asn Ser
                165                 170                 175
Glu Asn Val Thr Met Lys Val Val Ser Val Leu Tyr Asn Ala Thr Ile
                180                 185                 190
Asn Asn Thr Tyr Ser Cys Met Ile Glu Asn Asp Ile Ala Lys Ala Thr
```

```
                    195                 200                 205

Gly Asp Ile Lys Val Thr Glu Ser Glu Ile Lys Arg Arg Ser
    210                 215                 220

<210> SEQ ID NO 69
<211> LENGTH: 218
<212> TYPE: PRT
<213> ORGANISM: Pan troglodytes

<400> SEQUENCE: 69

Gly Phe Gly Ile Ser Gly Arg His Ser Ile Thr Val Thr Thr Val Ala
1               5                   10                  15

Ser Ala Gly Asn Ile Gly Glu Asp Gly Ile Leu Ser Cys Thr Phe Glu
            20                  25                  30

Pro Asp Ile Lys Leu Ser Asp Ile Val Ile Gln Trp Leu Lys Glu Gly
        35                  40                  45

Val Leu Gly Leu Val His Glu Phe Lys Glu Gly Lys Asp Glu Leu Ser
    50                  55                  60

Glu Gln Asp Glu Met Phe Arg Gly Arg Thr Ala Val Phe Ala Asp Gln
65                  70                  75                  80

Val Ile Val Gly Asn Ala Ser Leu Arg Leu Lys Asn Val Gln Leu Thr
                85                  90                  95

Asp Ala Gly Thr Tyr Lys Cys Tyr Ile Ile Thr Ser Lys Gly Lys Gly
            100                 105                 110

Asn Ala Asn Leu Glu Tyr Lys Thr Gly Ala Phe Ser Met Pro Glu Val
        115                 120                 125

Asn Val Asp Tyr Asn Ala Ser Ser Glu Thr Leu Arg Cys Glu Ala Pro
    130                 135                 140

Arg Trp Phe Pro Gln Pro Thr Val Val Trp Ala Ser Gln Ile Asp Gln
145                 150                 155                 160

Gly Ala Asn Phe Ser Glu Val Ser Asn Thr Ser Phe Glu Leu Asn Ser
                165                 170                 175

Glu Asn Val Thr Met Lys Val Val Ser Val Leu Tyr Asn Ala Thr Ile
            180                 185                 190

Asn Asn Thr Tyr Ser Cys Met Ile Glu Asn Asp Ile Ala Lys Ala Thr
        195                 200                 205

Gly Asp Ile Lys Val Thr Glu Ser Glu Ile
    210                 215

<210> SEQ ID NO 70
<211> LENGTH: 232
<212> TYPE: PRT
<213> ORGANISM: Macaca mulatta

<400> SEQUENCE: 70

Gly Phe Gly Ile Ser Gly Arg His Ser Ile Thr Val Thr Thr Val Ala
1               5                   10                  15

Ser Ala Gly Asn Ile Gly Glu Asp Gly Ile Leu Ser Cys Thr Phe Glu
            20                  25                  30

Pro Asp Ile Lys Leu Ser Asp Ile Val Ile Gln Trp Leu Lys Glu Gly
        35                  40                  45

Val Leu Gly Leu Val His Glu Phe Lys Glu Gly Lys Asp Glu Leu Ser
    50                  55                  60

Glu Gln Asp Glu Met Phe Arg Gly Arg Thr Ala Val Phe Ala Asp Gln
65                  70                  75                  80

Val Ile Val Gly Asn Ala Ser Leu Arg Leu Lys Asn Val Gln Leu Thr
```

```
            85                  90                  95
Asp Ala Gly Thr Tyr Lys Cys Tyr Ile Ile Thr Ser Lys Gly Lys Gly
            100                 105                 110

Asn Ala Asn Leu Glu Tyr Lys Thr Gly Ala Phe Ser Met Pro Glu Val
            115                 120                 125

Asn Val Asp Tyr Asn Ala Ser Ser Glu Thr Leu Arg Cys Glu Ala Pro
        130                 135                 140

Arg Trp Phe Pro Gln Pro Thr Val Val Trp Ala Ser Gln Ile Asp Gln
145                 150                 155                 160

Gly Ala Asn Phe Ser Glu Val Ser Asn Thr Ser Phe Glu Leu Asn Ser
                165                 170                 175

Glu Asn Val Thr Met Lys Val Val Ser Val Leu Tyr Asn Ala Thr Ile
            180                 185                 190

Asn Asn Thr Tyr Ser Cys Met Ile Glu Asn Asp Ile Ala Lys Ala Thr
        195                 200                 205

Gly Asp Ile Lys Val Thr Glu Ser Glu Ile Lys Arg Arg Ser His Leu
    210                 215                 220

Gln Leu Leu Asn Ser Lys Ala Ser
225                 230

<210> SEQ ID NO 71
<211> LENGTH: 249
<212> TYPE: PRT
<213> ORGANISM: Macaca mulatta

<400> SEQUENCE: 71

Met Ala Ser Leu Gly Gln Ile Leu Phe Trp Ser Ile Ile Ser Ile Ile
1               5                   10                  15

Phe Ile Leu Ala Gly Ala Ile Ala Leu Ile Ile Gly Phe Gly Ile Ser
            20                  25                  30

Gly Arg His Ser Ile Thr Val Thr Val Ala Ser Ala Gly Asn Ile
        35                  40                  45

Gly Glu Asp Gly Ile Leu Ser Cys Thr Phe Glu Pro Asp Ile Lys Leu
    50                  55                  60

Ser Asp Ile Val Ile Gln Trp Leu Lys Glu Gly Val Ile Gly Leu Val
65                  70                  75                  80

His Glu Phe Lys Glu Gly Lys Asp Glu Leu Ser Glu Gln Asp Glu Met
                85                  90                  95

Phe Arg Gly Arg Thr Ala Val Phe Ala Asp Gln Val Ile Val Gly Asn
            100                 105                 110

Ala Ser Leu Arg Leu Lys Asn Val Gln Leu Thr Asp Ala Gly Thr Tyr
        115                 120                 125

Lys Cys Tyr Ile Ile Thr Ser Lys Gly Lys Gly Asn Ala Asn Leu Glu
    130                 135                 140

Tyr Lys Thr Gly Ala Phe Ser Met Pro Glu Val Asn Val Asp Tyr Asn
145                 150                 155                 160

Ala Ser Ser Glu Thr Leu Arg Cys Glu Ala Pro Arg Trp Phe Pro Gln
                165                 170                 175

Pro Thr Val Val Trp Ala Ser Gln Val Asp Gln Gly Ala Asn Phe Ser
            180                 185                 190

Glu Val Ser Asn Thr Ser Phe Glu Leu Asn Ser Glu Asn Val Thr Met
        195                 200                 205

Lys Val Val Ser Val Leu Tyr Asn Val Thr Ile Asn Asn Thr Tyr Ser
    210                 215                 220
```

```
Cys Met Ile Glu Asn Asp Ile Ala Lys Ala Thr Gly Asp Ile Lys Val
225                 230                 235                 240

Thr Glu Ser Glu Ile Lys Arg Arg Ser
            245
```

<210> SEQ ID NO 72
<211> LENGTH: 245
<212> TYPE: PRT
<213> ORGANISM: Macaca mulatta

<400> SEQUENCE: 72

```
Met Ala Ser Leu Gly Gln Ile Leu Phe Trp Ser Ile Ile Ser Ile Ile
1               5                   10                  15

Phe Ile Leu Ala Gly Ala Ile Ala Leu Ile Ile Gly Phe Gly Ile Ser
                20                  25                  30

Gly Arg His Ser Ile Thr Val Thr Val Ala Ser Ala Gly Asn Ile
            35                  40                  45

Gly Glu Asp Gly Ile Leu Ser Cys Thr Phe Glu Pro Asp Ile Lys Leu
    50                  55                  60

Ser Asp Ile Val Ile Gln Trp Leu Lys Glu Gly Val Ile Gly Leu Val
65                  70                  75                  80

His Glu Phe Lys Glu Gly Lys Asp Glu Leu Ser Glu Gln Asp Glu Met
                85                  90                  95

Phe Arg Gly Arg Thr Ala Val Phe Ala Asp Gln Val Ile Val Gly Asn
            100                 105                 110

Ala Ser Leu Arg Leu Lys Asn Val Gln Leu Thr Asp Ala Gly Thr Tyr
        115                 120                 125

Lys Cys Tyr Ile Ile Thr Ser Lys Gly Lys Gly Asn Ala Asn Leu Glu
130                 135                 140

Tyr Lys Thr Gly Ala Phe Ser Met Pro Glu Val Asn Val Asp Tyr Asn
145                 150                 155                 160

Ala Ser Ser Glu Thr Leu Arg Cys Glu Ala Pro Arg Trp Phe Pro Gln
                165                 170                 175

Pro Thr Val Val Trp Ala Ser Gln Val Asp Gln Gly Ala Asn Phe Ser
            180                 185                 190

Glu Val Ser Asn Thr Ser Phe Glu Leu Asn Ser Glu Asn Val Thr Met
        195                 200                 205

Lys Val Val Ser Val Leu Tyr Asn Val Thr Ile Asn Asn Thr Tyr Ser
    210                 215                 220

Cys Met Ile Glu Asn Asp Ile Ala Lys Ala Thr Gly Asp Ile Lys Val
225                 230                 235                 240

Thr Glu Ser Glu Ile
            245
```

<210> SEQ ID NO 73
<211> LENGTH: 259
<212> TYPE: PRT
<213> ORGANISM: Macaca mulatta

<400> SEQUENCE: 73

```
Met Ala Ser Leu Gly Gln Ile Leu Phe Trp Ser Ile Ile Ser Ile Ile
1               5                   10                  15

Phe Ile Leu Ala Gly Ala Ile Ala Leu Ile Ile Gly Phe Gly Ile Ser
                20                  25                  30

Gly Arg His Ser Ile Thr Val Thr Val Ala Ser Ala Gly Asn Ile
            35                  40                  45
```

Gly Glu Asp Gly Ile Leu Ser Cys Thr Phe Glu Pro Asp Ile Lys Leu
            50                  55                  60

Ser Asp Ile Val Ile Gln Trp Leu Lys Glu Gly Val Ile Gly Leu Val
 65                  70                  75                  80

His Glu Phe Lys Glu Gly Lys Asp Glu Leu Ser Glu Gln Asp Glu Met
                 85                  90                  95

Phe Arg Gly Arg Thr Ala Val Phe Ala Asp Gln Val Ile Val Gly Asn
            100                 105                 110

Ala Ser Leu Arg Leu Lys Asn Val Gln Leu Thr Asp Ala Gly Thr Tyr
            115                 120                 125

Lys Cys Tyr Ile Ile Thr Ser Lys Gly Lys Gly Asn Ala Asn Leu Glu
130                 135                 140

Tyr Lys Thr Gly Ala Phe Ser Met Pro Glu Val Asn Val Asp Tyr Asn
145                 150                 155                 160

Ala Ser Ser Glu Thr Leu Arg Cys Glu Ala Pro Arg Trp Phe Pro Gln
                165                 170                 175

Pro Thr Val Val Trp Ala Ser Gln Val Asp Gln Gly Ala Asn Phe Ser
            180                 185                 190

Glu Val Ser Asn Thr Ser Phe Glu Leu Asn Ser Glu Asn Val Thr Met
            195                 200                 205

Lys Val Val Ser Val Leu Tyr Asn Val Thr Ile Asn Asn Thr Tyr Ser
            210                 215                 220

Cys Met Ile Glu Asn Asp Ile Ala Lys Ala Thr Gly Asp Ile Lys Val
225                 230                 235                 240

Thr Glu Ser Glu Ile Lys Arg Arg Ser His Leu Gln Leu Leu Asn Ser
                245                 250                 255

Lys Ala Ser

<210> SEQ ID NO 74
<211> LENGTH: 222
<212> TYPE: PRT
<213> ORGANISM: Macaca mulatta

<400> SEQUENCE: 74

Gly Phe Gly Ile Ser Gly Arg His Ser Ile Thr Val Thr Thr Val Ala
 1               5                  10                  15

Ser Ala Gly Asn Ile Gly Glu Asp Gly Ile Leu Ser Cys Thr Phe Glu
                 20                  25                  30

Pro Asp Ile Lys Leu Ser Asp Ile Val Ile Gln Trp Leu Lys Glu Gly
             35                  40                  45

Val Ile Gly Leu Val His Glu Phe Lys Glu Gly Lys Asp Glu Leu Ser
 50                  55                  60

Glu Gln Asp Glu Met Phe Arg Gly Arg Thr Ala Val Phe Ala Asp Gln
 65                  70                  75                  80

Val Ile Val Gly Asn Ala Ser Leu Arg Leu Lys Asn Val Gln Leu Thr
                 85                  90                  95

Asp Ala Gly Thr Tyr Lys Cys Tyr Ile Ile Thr Ser Lys Gly Lys Gly
            100                 105                 110

Asn Ala Asn Leu Glu Tyr Lys Thr Gly Ala Phe Ser Met Pro Glu Val
            115                 120                 125

Asn Val Asp Tyr Asn Ala Ser Ser Glu Thr Leu Arg Cys Glu Ala Pro
            130                 135                 140

Arg Trp Phe Pro Gln Pro Thr Val Val Trp Ala Ser Gln Val Asp Gln
145                 150                 155                 160

```
Gly Ala Asn Phe Ser Glu Val Ser Asn Thr Ser Phe Glu Leu Asn Ser
                165                 170                 175

Glu Asn Val Thr Met Lys Val Val Ser Val Leu Tyr Asn Val Thr Ile
            180                 185                 190

Asn Asn Thr Tyr Ser Cys Met Ile Glu Asn Asp Ile Ala Lys Ala Thr
        195                 200                 205

Gly Asp Ile Lys Val Thr Glu Ser Glu Ile Lys Arg Arg Ser
210                 215                 220
```

<210> SEQ ID NO 75
<211> LENGTH: 218
<212> TYPE: PRT
<213> ORGANISM: Macaca mulatta

<400> SEQUENCE: 75

```
Gly Phe Gly Ile Ser Gly Arg His Ser Ile Thr Val Thr Thr Val Ala
1               5                   10                  15

Ser Ala Gly Asn Ile Gly Glu Asp Gly Ile Leu Ser Cys Thr Phe Glu
            20                  25                  30

Pro Asp Ile Lys Leu Ser Asp Ile Val Ile Gln Trp Leu Lys Glu Gly
        35                  40                  45

Val Ile Gly Leu Val His Glu Phe Lys Glu Gly Lys Asp Glu Leu Ser
50                  55                  60

Glu Gln Asp Glu Met Phe Arg Gly Arg Thr Ala Val Phe Ala Asp Gln
65                  70                  75                  80

Val Ile Val Gly Asn Ala Ser Leu Arg Leu Lys Asn Val Gln Leu Thr
                85                  90                  95

Asp Ala Gly Thr Tyr Lys Cys Tyr Ile Ile Thr Ser Lys Gly Lys Gly
            100                 105                 110

Asn Ala Asn Leu Glu Tyr Lys Thr Gly Ala Phe Ser Met Pro Glu Val
        115                 120                 125

Asn Val Asp Tyr Asn Ala Ser Ser Glu Thr Leu Arg Cys Glu Ala Pro
    130                 135                 140

Arg Trp Phe Pro Gln Pro Thr Val Val Trp Ala Ser Gln Val Asp Gln
145                 150                 155                 160

Gly Ala Asn Phe Ser Glu Val Ser Asn Thr Ser Phe Glu Leu Asn Ser
                165                 170                 175

Glu Asn Val Thr Met Lys Val Val Ser Val Leu Tyr Asn Val Thr Ile
            180                 185                 190

Asn Asn Thr Tyr Ser Cys Met Ile Glu Asn Asp Ile Ala Lys Ala Thr
        195                 200                 205

Gly Asp Ile Lys Val Thr Glu Ser Glu Ile
210                 215
```

<210> SEQ ID NO 76
<211> LENGTH: 232
<212> TYPE: PRT
<213> ORGANISM: Macaca fascicularis

<400> SEQUENCE: 76

```
Gly Phe Gly Ile Ser Gly Arg His Ser Ile Thr Val Thr Thr Val Ala
1               5                   10                  15

Ser Ala Gly Asn Ile Gly Glu Asp Gly Ile Leu Ser Cys Thr Phe Glu
            20                  25                  30

Pro Asp Ile Lys Leu Ser Asp Ile Val Ile Gln Trp Leu Lys Glu Gly
        35                  40                  45
```

-continued

```
Val Ile Gly Leu Val His Glu Phe Lys Glu Gly Lys Asp Glu Leu Ser
 50                  55                  60

Glu Gln Asp Glu Met Phe Arg Gly Arg Thr Ala Val Phe Ala Asp Gln
 65                  70                  75                  80

Val Ile Val Gly Asn Ala Ser Leu Arg Leu Lys Asn Val Gln Leu Thr
                 85                  90                  95

Asp Ala Gly Thr Tyr Lys Cys Tyr Ile Ile Thr Ser Lys Gly Lys Gly
            100                 105                 110

Asn Ala Asn Leu Glu Tyr Lys Thr Gly Ala Phe Ser Met Pro Glu Val
        115                 120                 125

Asn Val Asp Tyr Asn Ala Ser Ser Glu Thr Leu Arg Cys Glu Ala Pro
130                 135                 140

Arg Trp Phe Pro Gln Pro Thr Val Val Trp Ala Ser Gln Val Asp Gln
145                 150                 155                 160

Gly Ala Asn Phe Ser Glu Val Ser Asn Thr Ser Phe Glu Leu Asn Ser
                165                 170                 175

Glu Asn Val Thr Met Lys Val Val Ser Val Leu Tyr Asn Val Thr Ile
            180                 185                 190

Asn Asn Thr Tyr Ser Cys Met Ile Glu Asn Asp Ile Ala Lys Ala Thr
        195                 200                 205

Gly Asp Ile Lys Val Thr Glu Ser Glu Ile Lys Arg Arg Ser His Leu
210                 215                 220

Gln Leu Leu Asn Ser Lys Ala Ser
225                 230

<210> SEQ ID NO 77
<211> LENGTH: 249
<212> TYPE: PRT
<213> ORGANISM: Macaca fascicularis

<400> SEQUENCE: 77

Met Ala Ser Leu Gly Gln Ile Leu Phe Trp Ser Ile Ile Ser Ile Ile
 1               5                  10                  15

Phe Ile Leu Ala Gly Ala Ile Ala Leu Ile Ile Gly Phe Gly Ile Ser
                20                  25                  30

Gly Arg His Ser Ile Thr Val Thr Val Ala Ser Ala Gly Asn Ile
         35                  40                  45

Gly Glu Asp Gly Ile Leu Ser Cys Thr Phe Glu Pro Asp Ile Lys Leu
 50                  55                  60

Ser Asp Ile Val Ile Gln Trp Leu Lys Glu Gly Val Ile Gly Leu Val
 65                  70                  75                  80

His Glu Phe Lys Glu Gly Lys Asp Glu Leu Ser Glu Gln Asp Glu Met
                 85                  90                  95

Phe Arg Gly Arg Thr Ala Val Phe Ala Asp Gln Val Ile Val Gly Asn
            100                 105                 110

Ala Ser Leu Arg Leu Lys Asn Val Gln Leu Thr Asp Ala Gly Thr Tyr
        115                 120                 125

Lys Cys Tyr Ile Ile Thr Ser Lys Gly Lys Gly Asn Ala Asn Leu Glu
130                 135                 140

Tyr Lys Thr Gly Ala Phe Ser Met Pro Glu Val Asn Val Asp Tyr Asn
145                 150                 155                 160

Ala Ser Ser Glu Thr Leu Arg Cys Glu Ala Pro Arg Trp Phe Pro Gln
                165                 170                 175

Pro Thr Val Val Trp Ala Ser Gln Val Asp Gln Gly Ala Asn Phe Ser
            180                 185                 190
```

```
Glu Val Ser Asn Thr Ser Phe Glu Leu Asn Ser Glu Asn Val Thr Met
            195                 200                 205

Lys Val Val Ser Val Leu Tyr Asn Val Thr Ile Asn Asn Thr Tyr Ser
            210                 215                 220

Cys Met Ile Glu Asn Asp Ile Ala Lys Ala Thr Gly Asp Ile Lys Val
225                 230                 235                 240

Thr Glu Ser Glu Ile Lys Arg Arg Ser
                245

<210> SEQ ID NO 78
<211> LENGTH: 245
<212> TYPE: PRT
<213> ORGANISM: Macaca fascicularis

<400> SEQUENCE: 78

Met Ala Ser Leu Gly Gln Ile Leu Phe Trp Ser Ile Ile Ser Ile Ile
1               5                   10                  15

Phe Ile Leu Ala Gly Ala Ile Ala Leu Ile Ile Gly Phe Gly Ile Ser
            20                  25                  30

Gly Arg His Ser Ile Thr Val Thr Thr Val Ala Ser Ala Gly Asn Ile
            35                  40                  45

Gly Glu Asp Gly Ile Leu Ser Cys Thr Phe Glu Pro Asp Ile Lys Leu
        50                  55                  60

Ser Asp Ile Val Ile Gln Trp Leu Lys Glu Gly Val Ile Gly Leu Val
65                  70                  75                  80

His Glu Phe Lys Glu Gly Lys Asp Glu Leu Ser Glu Gln Asp Glu Met
                85                  90                  95

Phe Arg Gly Arg Thr Ala Val Phe Ala Asp Gln Val Ile Val Gly Asn
            100                 105                 110

Ala Ser Leu Arg Leu Lys Asn Val Gln Leu Thr Asp Ala Gly Thr Tyr
            115                 120                 125

Lys Cys Tyr Ile Ile Thr Ser Lys Gly Lys Gly Asn Ala Asn Leu Glu
        130                 135                 140

Tyr Lys Thr Gly Ala Phe Ser Met Pro Glu Val Asn Val Asp Tyr Asn
145                 150                 155                 160

Ala Ser Ser Glu Thr Leu Arg Cys Glu Ala Pro Arg Trp Phe Pro Gln
                165                 170                 175

Pro Thr Val Val Trp Ala Ser Gln Val Asp Gln Gly Ala Asn Phe Ser
            180                 185                 190

Glu Val Ser Asn Thr Ser Phe Glu Leu Asn Ser Glu Asn Val Thr Met
            195                 200                 205

Lys Val Val Ser Val Leu Tyr Asn Val Thr Ile Asn Asn Thr Tyr Ser
            210                 215                 220

Cys Met Ile Glu Asn Asp Ile Ala Lys Ala Thr Gly Asp Ile Lys Val
225                 230                 235                 240

Thr Glu Ser Glu Ile
                245

<210> SEQ ID NO 79
<211> LENGTH: 259
<212> TYPE: PRT
<213> ORGANISM: Macaca fascicularis

<400> SEQUENCE: 79

Met Ala Ser Leu Gly Gln Ile Leu Phe Trp Ser Ile Ile Ser Ile Ile
1               5                   10                  15
```

```
Phe Ile Leu Ala Gly Ala Ile Ala Leu Ile Ile Gly Phe Gly Ile Ser
             20                  25                  30

Gly Arg His Ser Ile Thr Val Thr Val Ala Ser Ala Gly Asn Ile
         35                  40                  45

Gly Glu Asp Gly Ile Leu Ser Cys Thr Phe Glu Pro Asp Ile Lys Leu
 50                  55                  60

Ser Asp Ile Val Ile Gln Trp Leu Lys Glu Gly Val Ile Gly Leu Val
 65                  70                  75                  80

His Glu Phe Lys Glu Gly Lys Asp Glu Leu Ser Glu Gln Asp Glu Met
             85                  90                  95

Phe Arg Gly Arg Thr Ala Val Phe Ala Asp Gln Val Ile Val Gly Asn
            100                 105                 110

Ala Ser Leu Arg Leu Lys Asn Val Gln Leu Thr Asp Ala Gly Thr Tyr
            115                 120                 125

Lys Cys Tyr Ile Ile Thr Ser Lys Gly Lys Gly Asn Ala Asn Leu Glu
130                 135                 140

Tyr Lys Thr Gly Ala Phe Ser Met Pro Glu Val Asn Val Asp Tyr Asn
145                 150                 155                 160

Ala Ser Ser Glu Thr Leu Arg Cys Glu Ala Pro Arg Trp Phe Pro Gln
            165                 170                 175

Pro Thr Val Val Trp Ala Ser Gln Val Asp Gln Gly Ala Asn Phe Ser
            180                 185                 190

Glu Val Ser Asn Thr Ser Phe Glu Leu Asn Ser Glu Asn Val Thr Met
            195                 200                 205

Lys Val Val Ser Val Leu Tyr Asn Val Thr Ile Asn Asn Thr Tyr Ser
            210                 215                 220

Cys Met Ile Glu Asn Asp Ile Ala Lys Ala Thr Gly Asp Ile Lys Val
225                 230                 235                 240

Thr Glu Ser Glu Ile Lys Arg Arg Ser His Leu Gln Leu Leu Asn Ser
            245                 250                 255

Lys Ala Ser

<210> SEQ ID NO 80
<211> LENGTH: 222
<212> TYPE: PRT
<213> ORGANISM: Macaca fascicularis

<400> SEQUENCE: 80

Gly Phe Gly Ile Ser Gly Arg His Ser Ile Thr Val Thr Val Ala
 1               5                  10                  15

Ser Ala Gly Asn Ile Gly Glu Asp Gly Ile Leu Ser Cys Thr Phe Glu
             20                  25                  30

Pro Asp Ile Lys Leu Ser Asp Ile Val Ile Gln Trp Leu Lys Glu Gly
             35                  40                  45

Val Ile Gly Leu Val His Glu Phe Lys Glu Gly Lys Asp Glu Leu Ser
 50                  55                  60

Glu Gln Asp Glu Met Phe Arg Gly Arg Thr Ala Val Phe Ala Asp Gln
 65                  70                  75                  80

Val Ile Val Gly Asn Ala Ser Leu Arg Leu Lys Asn Val Gln Leu Thr
             85                  90                  95

Asp Ala Gly Thr Tyr Lys Cys Tyr Ile Ile Thr Ser Lys Gly Lys Gly
            100                 105                 110

Asn Ala Asn Leu Glu Tyr Lys Thr Gly Ala Phe Ser Met Pro Glu Val
            115                 120                 125
```

```
Asn Val Asp Tyr Asn Ala Ser Ser Glu Thr Leu Arg Cys Glu Ala Pro
            130                 135                 140

Arg Trp Phe Pro Gln Pro Thr Val Val Trp Ala Ser Gln Val Asp Gln
145                 150                 155                 160

Gly Ala Asn Phe Ser Glu Val Ser Asn Thr Ser Phe Glu Leu Asn Ser
                165                 170                 175

Glu Asn Val Thr Met Lys Val Val Ser Val Leu Tyr Asn Val Thr Ile
            180                 185                 190

Asn Asn Thr Tyr Ser Cys Met Ile Glu Asn Asp Ile Ala Lys Ala Thr
        195                 200                 205

Gly Asp Ile Lys Val Thr Glu Ser Glu Ile Lys Arg Arg Ser
    210                 215                 220
```

<210> SEQ ID NO 81
<211> LENGTH: 218
<212> TYPE: PRT
<213> ORGANISM: Macaca fascicularis

<400> SEQUENCE: 81

```
Gly Phe Gly Ile Ser Gly Arg His Ser Ile Thr Val Thr Thr Val Ala
1               5                   10                  15

Ser Ala Gly Asn Ile Gly Glu Asp Gly Ile Leu Ser Cys Thr Phe Glu
            20                  25                  30

Pro Asp Ile Lys Leu Ser Asp Ile Val Ile Gln Trp Leu Lys Glu Gly
        35                  40                  45

Val Ile Gly Leu Val His Glu Phe Lys Glu Gly Lys Asp Glu Leu Ser
    50                  55                  60

Glu Gln Asp Glu Met Phe Arg Gly Arg Thr Ala Val Phe Ala Asp Gln
65                  70                  75                  80

Val Ile Val Gly Asn Ala Ser Leu Arg Leu Lys Asn Val Gln Leu Thr
                85                  90                  95

Asp Ala Gly Thr Tyr Lys Cys Tyr Ile Ile Thr Ser Lys Gly Lys Gly
            100                 105                 110

Asn Ala Asn Leu Glu Tyr Lys Thr Gly Ala Phe Ser Met Pro Glu Val
        115                 120                 125

Asn Val Asp Tyr Asn Ala Ser Ser Glu Thr Leu Arg Cys Glu Ala Pro
    130                 135                 140

Arg Trp Phe Pro Gln Pro Thr Val Val Trp Ala Ser Gln Val Asp Gln
145                 150                 155                 160

Gly Ala Asn Phe Ser Glu Val Ser Asn Thr Ser Phe Glu Leu Asn Ser
                165                 170                 175

Glu Asn Val Thr Met Lys Val Val Ser Val Leu Tyr Asn Val Thr Ile
            180                 185                 190

Asn Asn Thr Tyr Ser Cys Met Ile Glu Asn Asp Ile Ala Lys Ala Thr
        195                 200                 205

Gly Asp Ile Lys Val Thr Glu Ser Glu Ile
    210                 215
```

<210> SEQ ID NO 82
<211> LENGTH: 232
<212> TYPE: PRT
<213> ORGANISM: Macaca fascicularis

<400> SEQUENCE: 82

```
Gly Phe Gly Ile Ser Gly Arg His Ser Ile Thr Val Thr Thr Val Ala
1               5                   10                  15
```

```
Ser Ala Gly Asn Ile Gly Glu Asp Gly Ile Leu Ser Cys Thr Phe Glu
            20                  25                  30

Pro Asp Ile Lys Leu Ser Asp Ile Val Ile Gln Trp Leu Lys Glu Gly
        35                  40                  45

Val Ile Gly Leu Val His Glu Phe Lys Glu Gly Lys Asp Glu Leu Ser
50                  55                  60

Glu Gln Asp Glu Met Phe Arg Gly Arg Thr Ala Val Phe Ala Asp Gln
65                  70                  75                  80

Val Ile Val Gly Asn Ala Ser Leu Arg Leu Lys Asn Val Gln Leu Thr
                85                  90                  95

Asp Ala Gly Thr Tyr Lys Cys Tyr Ile Ile Thr Ser Lys Gly Lys Gly
            100                 105                 110

Asn Ala Asn Leu Glu Tyr Lys Thr Gly Ala Phe Ser Met Pro Glu Val
        115                 120                 125

Asn Val Asp Tyr Asn Ala Ser Ser Glu Thr Leu Arg Cys Glu Ala Pro
130                 135                 140

Arg Trp Phe Pro Gln Pro Thr Val Val Trp Ala Ser Gln Val Asp Gln
145                 150                 155                 160

Gly Ala Asn Phe Ser Glu Val Ser Asn Thr Ser Phe Glu Leu Asn Ser
                165                 170                 175

Glu Asn Val Thr Met Lys Val Val Ser Val Leu Tyr Asn Val Thr Ile
            180                 185                 190

Asn Asn Thr Tyr Ser Cys Met Ile Glu Asn Asp Ile Ala Lys Ala Thr
        195                 200                 205

Gly Asp Ile Lys Val Thr Glu Ser Glu Ile Lys Arg Arg Ser His Leu
210                 215                 220

Gln Leu Leu Asn Ser Lys Ala Ser
225                 230

<210> SEQ ID NO 83
<211> LENGTH: 129
<212> TYPE: PRT
<213> ORGANISM: Pan troglodytes

<400> SEQUENCE: 83

Gly Phe Gly Ile Ser Gly Arg His Ser Ile Thr Val Thr Thr Val Ala
1               5                   10                  15

Ser Ala Gly Asn Ile Gly Glu Asp Gly Ile Leu Ser Cys Thr Phe Glu
            20                  25                  30

Pro Asp Ile Lys Leu Ser Asp Ile Val Ile Gln Trp Leu Lys Glu Gly
        35                  40                  45

Val Leu Gly Leu Val His Glu Phe Lys Glu Gly Lys Asp Glu Leu Ser
50                  55                  60

Glu Gln Asp Glu Met Phe Arg Gly Arg Thr Ala Val Phe Ala Asp Gln
65                  70                  75                  80

Val Ile Val Gly Asn Ala Ser Leu Arg Leu Lys Asn Val Gln Leu Thr
                85                  90                  95

Asp Ala Gly Thr Tyr Lys Cys Tyr Ile Ile Thr Ser Lys Gly Lys Gly
            100                 105                 110

Asn Ala Asn Leu Glu Tyr Lys Thr Gly Ala Phe Ser Met Pro Glu Val
        115                 120                 125

Asn

<210> SEQ ID NO 84
```

```
<211> LENGTH: 129
<212> TYPE: PRT
<213> ORGANISM: Macaca mulatta

<400> SEQUENCE: 84
```

| | | | | | | | | | | | | | | |
|---|---|---|---|---|---|---|---|---|---|---|---|---|---|---|
| Gly | Phe | Gly | Ile | Ser | Gly | Arg | His | Ser | Ile | Thr | Val | Thr | Thr | Val | Ala |
| 1 | | | | 5 | | | | | 10 | | | | | 15 | |
| Ser | Ala | Gly | Asn | Ile | Gly | Glu | Asp | Gly | Ile | Leu | Ser | Cys | Thr | Phe | Glu |
| | | | 20 | | | | | 25 | | | | | 30 | | |
| Pro | Asp | Ile | Lys | Leu | Ser | Asp | Ile | Val | Ile | Gln | Trp | Leu | Lys | Glu | Gly |
| | | | | 35 | | | | | 40 | | | | | 45 | |
| Val | Ile | Gly | Leu | Val | His | Glu | Phe | Lys | Glu | Gly | Lys | Asp | Glu | Leu | Ser |
| | 50 | | | | | 55 | | | | | 60 | | | | |
| Glu | Gln | Asp | Glu | Met | Phe | Arg | Gly | Arg | Thr | Ala | Val | Phe | Ala | Asp | Gln |
| 65 | | | | | 70 | | | | | 75 | | | | | 80 |
| Val | Ile | Val | Gly | Asn | Ala | Ser | Leu | Arg | Leu | Lys | Asn | Val | Gln | Leu | Thr |
| | | | | 85 | | | | | 90 | | | | | 95 | |
| Asp | Ala | Gly | Thr | Tyr | Lys | Cys | Tyr | Ile | Ile | Thr | Ser | Lys | Gly | Lys | Gly |
| | | | | 100 | | | | | 105 | | | | | 110 | |
| Asn | Ala | Asn | Leu | Glu | Tyr | Lys | Thr | Gly | Ala | Phe | Ser | Met | Pro | Glu | Val |
| | | | 115 | | | | | 120 | | | | | 125 | | |
| Asn | | | | | | | | | | | | | | | |

```
<210> SEQ ID NO 85
<211> LENGTH: 129
<212> TYPE: PRT
<213> ORGANISM: Macaca fascicularis

<400> SEQUENCE: 85
```

| | | | | | | | | | | | | | | | |
|---|---|---|---|---|---|---|---|---|---|---|---|---|---|---|---|
| Gly | Phe | Gly | Ile | Ser | Gly | Arg | His | Ser | Ile | Thr | Val | Thr | Thr | Val | Ala |
| 1 | | | | 5 | | | | | 10 | | | | | 15 | |
| Ser | Ala | Gly | Asn | Ile | Gly | Glu | Asp | Gly | Ile | Leu | Ser | Cys | Thr | Phe | Glu |
| | | | 20 | | | | | 25 | | | | | 30 | | |
| Pro | Asp | Ile | Lys | Leu | Ser | Asp | Ile | Val | Ile | Gln | Trp | Leu | Lys | Glu | Gly |
| | | | | 35 | | | | | 40 | | | | | 45 | |
| Val | Ile | Gly | Leu | Val | His | Glu | Phe | Lys | Glu | Gly | Lys | Asp | Glu | Leu | Ser |
| | 50 | | | | | 55 | | | | | 60 | | | | |
| Glu | Gln | Asp | Glu | Met | Phe | Arg | Gly | Arg | Thr | Ala | Val | Phe | Ala | Asp | Gln |
| 65 | | | | | 70 | | | | | 75 | | | | | 80 |
| Val | Ile | Val | Gly | Asn | Ala | Ser | Leu | Arg | Leu | Lys | Asn | Val | Gln | Leu | Thr |
| | | | | 85 | | | | | 90 | | | | | 95 | |
| Asp | Ala | Gly | Thr | Tyr | Lys | Cys | Tyr | Ile | Ile | Thr | Ser | Lys | Gly | Lys | Gly |
| | | | | 100 | | | | | 105 | | | | | 110 | |
| Asn | Ala | Asn | Leu | Glu | Tyr | Lys | Thr | Gly | Ala | Phe | Ser | Met | Pro | Glu | Val |
| | | | 115 | | | | | 120 | | | | | 125 | | |
| Asn | | | | | | | | | | | | | | | |

```
<210> SEQ ID NO 86
<211> LENGTH: 696
<212> TYPE: DNA
<213> ORGANISM: Homo sapiens

<400> SEQUENCE: 86
gagcctaagt catgtgacaa gacccatacg tgcccaccct gtcccgctcc agaactgctg      60
gggggaccta gcgttttctt gttccccccca aagcccaagg acaccctcat gatctcacgg     120
actcccgaag taacatgcgt agtagtcgac gtgagccacg aggatcctga agtgaagttt     180
```

-continued

```
aattggtacg tggacggagt cgaggtgcat aatgccaaaa ctaaacctcg ggaggagcag      240
tataacagta cctaccgcgt ggtatccgtc ttgacagtgc tccaccagga ctggctgaat      300
ggtaaggagt ataaatgcaa ggtcagcaac aaagctcttc ccgccccaat tgaaaagact      360
atcagcaagg ccaagggaca accccgcgag ccccaggttt acacccttcc accttcacga      420
gacgagctga ccaagaacca ggtgtctctg acttgtctgg tcaaaggttt ctatccttcc      480
gacatcgcag tggagtggga gtcaaacggg cagcctgaga taactacaa gaccacaccc       540 ccagtgcttg atagcgatgg gagcttttc ctctacagta agctgactgt ggacaaatcc       600
cgctggcagc agggaaacgt tttctcttgt agcgtcatgc atgaggccct ccacaaccat      660
tatactcaga aaagcctgag tctgagtccc ggcaaa                                696
```

<210> SEQ ID NO 87
<211> LENGTH: 681
<212> TYPE: DNA
<213> ORGANISM: Homo sapiens

<400> SEQUENCE: 87

```
gacaagaccc atacgtgccc accctgtccc gctccagaac tgctgggggg acctagcgtt       60
ttcttgttcc ccccaaagcc caaggacacc ctcatgatct cacggactcc cgaagtaaca      120
tgcgtagtag tcgacgtgag ccacgaggat cctgaagtga agtttaattg gtacgtggac      180
ggagtcgagg tgcataatgc caaaactaaa cctcgggagg agcagtataa cagtacctac      240
cgcgtggtat ccgtcttgac agtgctccac caggactggc tgaatggtaa ggagtataaa      300
tgcaaggtca gcaacaaagc tcttcccgcc ccaattgaaa agactatcag caaggccaag      360
ggacaacccc gcgagcccca ggtttacacc cttccaccct cacgagacga gctgaccaag      420
aaccaggtgt ctctgacttg tctggtcaaa ggtttctatc cttccgacat cgcagtggag      480
tgggagtcaa acgggcagcc tgagaataac tacaagacca ccccccagt gcttgatagc      540 gatgggagct ttttcctcta cagtaagctg actgtggaca atcccgctg gcagcaggga      600 aacgttttct cttgtagcgt catgcatgag gccctccaca accattatac tcagaaaagc      660
ctgagtctga gtcccggcaa a                                                681
```

<210> SEQ ID NO 88
<211> LENGTH: 232
<212> TYPE: PRT
<213> ORGANISM: Homo sapiens

<400> SEQUENCE: 88

```
Glu Pro Lys Ser Cys Asp Lys Thr His Thr Cys Pro Pro Cys Pro Ala
1               5                   10                  15

Pro Glu Leu Leu Gly Gly Pro Ser Val Phe Leu Phe Pro Pro Lys Pro
            20                  25                  30

Lys Asp Thr Leu Met Ile Ser Arg Thr Pro Glu Val Thr Cys Val Val
        35                  40                  45

Val Asp Val Ser His Glu Asp Pro Glu Val Lys Phe Asn Trp Tyr Val
    50                  55                  60

Asp Gly Val Glu Val His Asn Ala Lys Thr Lys Pro Arg Glu Glu Gln
65                  70                  75                  80

Tyr Asn Ser Thr Tyr Arg Val Val Ser Val Leu Thr Val Leu His Gln
                85                  90                  95

Asp Trp Leu Asn Gly Lys Glu Tyr Lys Cys Lys Val Ser Asn Lys Ala
            100                 105                 110
```

Leu Pro Ala Pro Ile Glu Lys Thr Ile Ser Lys Ala Lys Gly Gln Pro
            115                 120                 125

Arg Glu Pro Gln Val Tyr Thr Leu Pro Pro Ser Arg Asp Glu Leu Thr
        130                 135                 140

Lys Asn Gln Val Ser Leu Thr Cys Leu Val Lys Gly Phe Tyr Pro Ser
145                 150                 155                 160

Asp Ile Ala Val Glu Trp Glu Ser Asn Gly Gln Pro Glu Asn Asn Tyr
                165                 170                 175

Lys Thr Thr Pro Pro Val Leu Asp Ser Asp Gly Ser Phe Phe Leu Tyr
            180                 185                 190

Ser Lys Leu Thr Val Asp Lys Ser Arg Trp Gln Gln Gly Asn Val Phe
        195                 200                 205

Ser Cys Ser Val Met His Glu Ala Leu His Asn His Tyr Thr Gln Lys
210                 215                 220

Ser Leu Ser Leu Ser Pro Gly Lys
225                 230

<210> SEQ ID NO 89
<211> LENGTH: 227
<212> TYPE: PRT
<213> ORGANISM: Homo sapiens

<400> SEQUENCE: 89

Asp Lys Thr His Thr Cys Pro Pro Cys Pro Ala Pro Glu Leu Leu Gly
1               5                   10                  15

Gly Pro Ser Val Phe Leu Phe Pro Pro Lys Pro Lys Asp Thr Leu Met
            20                  25                  30

Ile Ser Arg Thr Pro Glu Val Thr Cys Val Val Val Asp Val Ser His
        35                  40                  45

Glu Asp Pro Glu Val Lys Phe Asn Trp Tyr Val Asp Gly Val Glu Val
    50                  55                  60

His Asn Ala Lys Thr Lys Pro Arg Glu Glu Gln Tyr Asn Ser Thr Tyr
65                  70                  75                  80

Arg Val Val Ser Val Leu Thr Val Leu His Gln Asp Trp Leu Asn Gly
                85                  90                  95

Lys Glu Tyr Lys Cys Lys Val Ser Asn Lys Ala Leu Pro Ala Pro Ile
            100                 105                 110

Glu Lys Thr Ile Ser Lys Ala Lys Gly Gln Pro Arg Glu Pro Gln Val
        115                 120                 125

Tyr Thr Leu Pro Pro Ser Arg Asp Glu Leu Thr Lys Asn Gln Val Ser
    130                 135                 140

Leu Thr Cys Leu Val Lys Gly Phe Tyr Pro Ser Asp Ile Ala Val Glu
145                 150                 155                 160

Trp Glu Ser Asn Gly Gln Pro Glu Asn Asn Tyr Lys Thr Thr Pro Pro
                165                 170                 175

Val Leu Asp Ser Asp Gly Ser Phe Phe Leu Tyr Ser Lys Leu Thr Val
            180                 185                 190

Asp Lys Ser Arg Trp Gln Gln Gly Asn Val Phe Ser Cys Ser Val Met
        195                 200                 205

His Glu Ala Leu His Asn His Tyr Thr Gln Lys Ser Leu Ser Leu Ser
    210                 215                 220

Pro Gly Lys
225

-continued

<210> SEQ ID NO 90
<211> LENGTH: 699
<212> TYPE: DNA
<213> ORGANISM: Mus musculus

<400> SEQUENCE: 90

| | | | | | |
|---|---|---|---|---|---|
| gagccaagag | gtcctacgat | caagccctgc | ccgccttgta | aatgcccagc | tccaaatttg | 60 |
| ctgggtggac | cgtcagtctt | tatcttcccg | ccaaagataa | aggacgtctt | gatgattagt | 120 |
| ctgagcccca | tcgtgacatg | cgttgtggtg | gatgtttcag | aggatgaccc | cgacgtgcaa | 180 |
| atcagttggt | tcgttaacaa | cgtggaggtg | cataccgctc | aaacccagac | ccacagagag | 240 |
| gattataaca | gcaccctgcg | ggtagtgtcc | gccctgccga | tccagcatca | ggattggatg | 300 |
| agcgggaaag | agttcaagtg | taaggtaaac | aacaaagatc | tgccagcgcc | gattgaacga | 360 |
| accattagca | agccgaaagg | gagcgtgcgc | gcacctcagg | tttacgtcct | tcctccacca | 420 |
| gaagaggaga | tgacgaaaaa | gcaggtgacc | ctgacatgca | tggtaactga | ctttatgcca | 480 |
| gaagatattt | acgtggaatg | gactaataac | ggaaagacag | agctcaatta | caagaacact | 540 |
| gagcctgttc | tggattctga | tggcagctac | tttatgtact | ccaaattgag | ggtcgagaag | 600 |
| aagaattggg | tcgagagaaa | cagttatagt | tgctcagtgg | tgcatgaggg | cctccataat | 660 |
| catcacacca | caaagtcctt | cagccgaacg | cccgggaaa | | | 699 |

<210> SEQ ID NO 91
<211> LENGTH: 233
<212> TYPE: PRT
<213> ORGANISM: Artificial Sequence
<220> FEATURE:
<223> OTHER INFORMATION: Synthetic fusion protein

<400> SEQUENCE: 91

Glu Pro Arg Gly Pro Thr Ile Lys Pro Cys Pro Pro Cys Lys Cys Pro
1               5                   10                  15

Ala Pro Asn Leu Leu Gly Gly Pro Ser Val Phe Ile Phe Pro Pro Lys
                20                  25                  30

Ile Lys Asp Val Leu Met Ile Ser Leu Ser Pro Ile Val Thr Cys Val
            35                  40                  45

Val Val Asp Val Ser Glu Asp Asp Pro Asp Val Gln Ile Ser Trp Phe
        50                  55                  60

Val Asn Asn Val Glu Val His Thr Ala Gln Thr Gln Thr His Arg Glu
65                  70                  75                  80

Asp Tyr Asn Ser Thr Leu Arg Val Val Ser Ala Leu Pro Ile Gln His
                85                  90                  95

Gln Asp Trp Met Ser Gly Lys Glu Phe Lys Cys Lys Val Asn Asn Lys
            100                 105                 110

Asp Leu Pro Ala Pro Ile Glu Arg Thr Ile Ser Lys Pro Lys Gly Ser
        115                 120                 125

Val Arg Ala Pro Gln Val Tyr Val Leu Pro Pro Glu Glu Glu Met
    130                 135                 140

Thr Lys Lys Gln Val Thr Leu Thr Cys Met Val Thr Asp Phe Met Pro
145                 150                 155                 160

Glu Asp Ile Tyr Val Glu Trp Thr Asn Asn Gly Lys Thr Glu Leu Asn
                165                 170                 175

Tyr Lys Asn Thr Glu Pro Val Leu Asp Ser Asp Gly Ser Tyr Phe Met
            180                 185                 190

Tyr Ser Lys Leu Arg Val Glu Lys Lys Asn Trp Val Glu Arg Asn Ser
        195                 200                 205

Tyr Ser Cys Ser Val His Glu Gly Leu His Asn His His Thr Thr
    210                 215                 220

Lys Ser Phe Ser Arg Thr Pro Gly Lys
225                 230

<210> SEQ ID NO 92
<211> LENGTH: 4
<212> TYPE: PRT
<213> ORGANISM: Artificial Sequence
<220> FEATURE:
<223> OTHER INFORMATION: Synthetic linker sequence

<400> SEQUENCE: 92

Asp Ser Gly Ser
1

<210> SEQ ID NO 93
<211> LENGTH: 4
<212> TYPE: PRT
<213> ORGANISM: Artificial Sequence
<220> FEATURE:
<223> OTHER INFORMATION: Synthetic linker peptide

<400> SEQUENCE: 93

Gly Gly Gly Ser
1

<210> SEQ ID NO 94
<211> LENGTH: 15
<212> TYPE: PRT
<213> ORGANISM: Artificial Sequence
<220> FEATURE:
<223> OTHER INFORMATION: Synthetic linker peptide

<400> SEQUENCE: 94

Gly Gly Gly Gly Ser Gly Gly Gly Ser Gly Gly Gly Gly Ser
1                 5                  10                  15

<210> SEQ ID NO 95
<211> LENGTH: 20
<212> TYPE: PRT
<213> ORGANISM: Artificial Sequence
<220> FEATURE:
<223> OTHER INFORMATION: Synthetic linker peptide

<400> SEQUENCE: 95

Gly Gly Gly Gly Ser Gly Gly Gly Gly Ser Gly Gly Gly Gly Ser Gly
1                 5                  10                  15

Gly Gly Gly Ser
            20

<210> SEQ ID NO 96
<211> LENGTH: 1470
<212> TYPE: DNA
<213> ORGANISM: Artificial Sequence
<220> FEATURE:
<223> OTHER INFORMATION: Synthetic fusion nucleotide

<400> SEQUENCE: 96
atggcttcct tggggcagat catcttttgg agtattatta acatcatcat catcctggct      60
ggggccatcg cactcatcat tggctttggc atttcaggca agcacttcat cacggtcacg     120
accttcacct cagctggaaa cattggagag gacgggaccc tgagctgcac ttttgaacct     180
gacatcaaac tcaacggcat cgtcatccag tggctgaaag aaggcatcaa aggtttggtc     240

```
cacgagttca aagaaggcaa agacgacctc tcacagcagc atgagatgtt cagaggccgc    300
acagcagtgt ttgctgatca ggtggtagtt ggcaatgctt ccctgagact gaaaaacgtg    360
cagctcacgg atgctggcac ctacacatgt tacatccgca cctcaaaagg caagggaat    420 gcaaaccttg agtataagac cggagccttc agtatgccag agataaatgt ggactataat    480
gccagttcag agagtttacg ctgcgaggct cctcggtggt tcccccagcc cacagtggcc    540
tgggcatctc aagtcgacca aggagccaat ttctcagaag tctccaacac cagctttgag    600
ttgaactctg agaatgtgac catgaaggtc gtatctgtgc tctacaatgt cacaatcaac    660
aacacatact cctgtatgat tgaaaacgac attgccaaag ccaccgggga catcaaagtg    720
acagattcag aggtcaaaag gcgaagtcag ctgcagttgc tgaactctgg ggagccaaga    780
ggtcctacga tcaagccctg cccgccttgt aaatgcccag ctccaaattt gctgggtgga    840
ccgtcagtct ttatcttccc gccaaagata aggacgtct tgatgattag tctgagcccc    900
atcgtgacat gcgttgtggt ggatgtttca gaggatgacc ccgacgtgca aatcagttgg    960
ttcgttaaca acgtggaggt gcataccgct caaacccaga cccacagaga ggattataac    1020
agcaccctgc gggtagtgtc cgccctgccg atccagcatc aggattggat gagcgggaaa    1080
gagttcaagt gtaaggtaaa caacaaagat ctgccagcgc cgattgaacg aaccattagc    1140
aagccgaaag ggagcgtgcg cgcacctcag gtttacgtcc ttcctccacc agaagaggag    1200
atgacgaaaa agcaggtgac cctgacatgc atggtaactg actttatgcc agaagatatt    1260
tacgtggaat ggactaataa cggaaagaca gagctcaatt acaagaacac tgagcctgtt    1320
ctggattctg atggcagcta ctttatgtac tccaaattga gggtcgagaa gaagaattgg    1380
gtcgagagaa acagttatag ttgctcagtg gtgcatgagg gcctccataa tcatcacacc    1440
acaaagtcct tcagccgaac gcccgggaaa                                    1470

<210> SEQ ID NO 97
<211> LENGTH: 1446
<212> TYPE: DNA
<213> ORGANISM: Artificial Sequence
<220> FEATURE:
<223> OTHER INFORMATION: Synthetic fusion nucleotide

<400> SEQUENCE: 97
atggagtggt catgggtttt tctgttcttt cttagcgtga ctacaggcgt ccattcagga     60
ttcggcataa gcggcaagca cttcatcaca gttacaacgt ttacaagtgc ggggaacatt    120
ggggaagatg gaacattgtc atgtacattt gagccagata tcaaactcaa tggaatagta    180
attcagtggc ttaaggaggg catcaagggc ctggtccacg aatttaagga ggggaaagac    240
gatctgtctc agcagcacga gatgttcagg gcagaaccg ccgtcttcgc agaccaggtt    300
gtggtaggca acgccagttt gcggctgaaa aacgtgcagc tgactgacgc cggcacctac    360
acatgctata tccggtcctc taagggcaag gggaacgcta atctcgagta caaacaggc    420 gcctttttcta tgccagagat caacgtggac tataacgcaa gctctgaaag tctgagatgc    480
gaggcgccaa ggtggttccc tcagcccacc gtcgcgtggg cttcccaggt ggatcaaggc    540
gccaactttt ctgaggtttc taacaccagc ttcgaactga cagcgaaaaa tgtgacaatg    600
aaggtagtca gcgttctgta aacgtgacc atcaacaata cttactcctg tatgatagaa    660
aatgatatag ccaaggctac aggagatatt aaagtgacgg attcagaagt gaaaaggagg    720
agtcaactgc aactcttgaa tagcggcgag ccaagaggtc ctacgatcaa gccctgcccg    780
```

| | |
|---|---|
| ccttgtaaat gcccagctcc aaatttgctg gtggaccgt cagtctttat cttcccgcca | 840 |
| aagataaagg acgtcttgat gattagtctg agccccatcg tgacatgcgt tgtggtggat | 900 |
| gtttcagagg atgaccccga cgtgcaaatc agttggttcg ttaacaacgt ggaggtgcat | 960 |
| accgctcaaa cccagaccca cagagaggat tataacagca ccctgcgggt agtgtccgcc | 1020 |
| ctgccgatcc agcatcagga ttggatgagc gggaagagt tcaagtgtaa ggtaaacaac | 1080 |
| aaagatctgc cagcgccgat tgaacgaacc attagcaagc cgaagggag cgtgcgcgca | 1140 |
| cctcaggttt acgtccttcc tccaccagaa gaggagatga cgaaaaagca ggtgaccctg | 1200 |
| acatgcatgg taactgactt tatgccagaa gatatttacg tggaatggac taataacgga | 1260 |
| aagacagagc tcaattacaa gaacactgag cctgttctgg attctgatgg cagctacttt | 1320 |
| atgtactcca aattgagggt cgagaagaag aattgggtcg agagaaacag ttatagttgc | 1380 |
| tcagtggtgc atgagggcct ccataatcat cacaccacaa agtccttcag ccgaacgccc | 1440 |
| gggaaa | 1446 |

<210> SEQ ID NO 98
<211> LENGTH: 1446
<212> TYPE: DNA
<213> ORGANISM: Artificial Sequence
<220> FEATURE:
<223> OTHER INFORMATION: Synthetic fusion nucleotide

<400> SEQUENCE: 98

| | |
|---|---|
| atggagtggt catgggtttt tctgttctt cttagcgtga ctacaggcgt ccattcagga | 60 |
| ttcggcataa gcgcaagca cttcatcaca gttacaacgt ttacaagtgc ggggaacatt | 120 |
| ggggaagatg gaacattgtc atgtacattt gagccagata tcaaactcaa tggaatagta | 180 |
| attcagtggc ttaaggaggg catcaagggc ctggtccacg aatttaagga ggggaaagac | 240 |
| gatctgtctc agcagcacga tgttcagg gcagaaccg ccgtcttcgc agaccaggtt | 300 |
| gtggtaggca acgccagttt gcggctgaaa aacgtgcagc tgactgacgc cggcacctac | 360 |
| acatgctata tccggaccct taagggcaag gggaacgcta atctcgagta caaaacaggc | 420 |
| gccttttcta tgccagagat caacgtggac tataacgcaa gctctgaaag tctgagatgc | 480 |
| gaggcgccaa ggtggttccc tcagcccacc gtcgcgtggg cttcccaggt ggatcaaggc | 540 |
| gccaactttt ctgaggtttc taacaccagc ttcgaactga acagcgaaaa tgtgacaatg | 600 |
| aaggtagtca gcgttctgta aacgtgacc atcaacaata cttactcctg tatgatagaa | 660 |
| aatgatatag ccaaggctac aggagatatt aaagtgacgg attcagaagt gaaaaggagg | 720 |
| agtcaactgc aactcttgaa tagcggcgag ccaagaggtc ctacgatcaa gccctgcccg | 780 |
| ccttgtaaat gcccagctcc aaatttgctg gtggaccgt cagtctttat cttcccgcca | 840 |
| aagataaagg acgtcttgat gattagtctg agccccatcg tgacatgcgt tgtggtggat | 900 |
| gtttcagagg atgaccccga cgtgcaaatc agttggttcg ttaacaacgt ggaggtgcat | 960 |
| accgctcaaa cccagaccca cagagaggat tataacagca ccctgcgggt agtgtccgcc | 1020 |
| ctgccgatcc agcatcagga ttggatgagc gggaagagt tcaagtgtaa ggtaaacaac | 1080 |
| aaagatctgc cagcgccgat tgaacgaacc attagcaagc cgaagggag cgtgcgcgca | 1140 |
| cctcaggttt acgtccttcc tccaccagaa gaggagatga cgaaaaagca ggtgaccctg | 1200 |
| acatgcatgg taactgactt tatgccagaa gatatttacg tggaatggac taataacgga | 1260 |
| aagacagagc tcaattacaa gaacactgag cctgttctgg attctgatgg cagctacttt | 1320 |
| atgtactcca aattgagggt cgagaagaag aattgggtcg agagaaacag ttatagttgc | 1380 |

```
tcagtggtgc atgagggcct ccataatcat cacaccacaa agtccttcag ccgaacgccc   1440
gggaaa                                                              1446
```

<210> SEQ ID NO 99
<211> LENGTH: 490
<212> TYPE: PRT
<213> ORGANISM: Artificial Sequence
<220> FEATURE:
<223> OTHER INFORMATION: Synthetic fusion protein

<400> SEQUENCE: 99

```
Met Ala Ser Leu Gly Gln Ile Ile Phe Trp Ser Ile Ile Asn Ile Ile
1               5                   10                  15

Ile Ile Leu Ala Gly Ala Ile Ala Leu Ile Ile Gly Phe Gly Ile Ser
            20                  25                  30

Gly Lys His Phe Ile Thr Val Thr Phe Thr Ser Ala Gly Asn Ile
        35                  40                  45

Gly Glu Asp Gly Thr Leu Ser Cys Thr Phe Glu Pro Asp Ile Lys Leu
    50                  55                  60

Asn Gly Ile Val Ile Gln Trp Leu Lys Glu Gly Ile Lys Gly Leu Val
65                  70                  75                  80

His Glu Phe Lys Glu Gly Lys Asp Asp Leu Ser Gln Gln His Glu Met
                85                  90                  95

Phe Arg Gly Arg Thr Ala Val Phe Ala Asp Gln Val Val Gly Asn
            100                 105                 110

Ala Ser Leu Arg Leu Lys Asn Val Gln Leu Thr Asp Ala Gly Thr Tyr
        115                 120                 125

Thr Cys Tyr Ile Arg Ser Ser Lys Gly Lys Gly Asn Ala Asn Leu Glu
    130                 135                 140

Tyr Lys Thr Gly Ala Phe Ser Met Pro Glu Ile Asn Val Asp Tyr Asn
145                 150                 155                 160

Ala Ser Ser Glu Ser Leu Arg Cys Glu Ala Pro Arg Trp Phe Pro Gln
                165                 170                 175

Pro Thr Val Ala Trp Ala Ser Gln Val Asp Gln Gly Ala Asn Phe Ser
            180                 185                 190

Glu Val Ser Asn Thr Ser Phe Glu Leu Asn Ser Glu Asn Val Thr Met
        195                 200                 205

Lys Val Val Ser Val Leu Tyr Asn Val Thr Ile Asn Asn Thr Tyr Ser
    210                 215                 220

Cys Met Ile Glu Asn Asp Ile Ala Lys Ala Thr Gly Asp Ile Lys Val
225                 230                 235                 240

Thr Asp Ser Glu Val Lys Arg Arg Ser Gln Leu Gln Leu Leu Asn Ser
                245                 250                 255

Gly Glu Pro Arg Gly Pro Thr Ile Lys Pro Cys Pro Pro Cys Lys Cys
            260                 265                 270

Pro Ala Pro Asn Leu Leu Gly Gly Pro Ser Val Phe Ile Phe Pro Pro
        275                 280                 285

Lys Ile Lys Asp Val Leu Met Ile Ser Leu Ser Pro Ile Val Thr Cys
    290                 295                 300

Val Val Val Asp Val Ser Glu Asp Asp Pro Asp Val Gln Ile Ser Trp
305                 310                 315                 320

Phe Val Asn Asn Val Glu Val His Thr Ala Gln Thr Gln Thr His Arg
                325                 330                 335

Glu Asp Tyr Asn Ser Thr Leu Arg Val Val Ser Ala Leu Pro Ile Gln
```

```
                340                 345                 350
His Gln Asp Trp Met Ser Gly Lys Glu Phe Lys Cys Lys Val Asn Asn
            355                 360                 365

Lys Asp Leu Pro Ala Pro Ile Glu Arg Thr Ile Ser Lys Pro Lys Gly
        370                 375                 380

Ser Val Arg Ala Pro Gln Val Tyr Val Leu Pro Pro Glu Glu Glu
385                 390                 395                 400

Met Thr Lys Lys Gln Val Thr Leu Thr Cys Met Val Thr Asp Phe Met
                405                 410                 415

Pro Glu Asp Ile Tyr Val Glu Trp Thr Asn Asn Gly Lys Thr Glu Leu
            420                 425                 430

Asn Tyr Lys Asn Thr Glu Pro Val Leu Asp Ser Asp Gly Ser Tyr Phe
        435                 440                 445

Met Tyr Ser Lys Leu Arg Val Glu Lys Lys Asn Trp Val Glu Arg Asn
    450                 455                 460

Ser Tyr Ser Cys Ser Val Val His Glu Gly Leu His Asn His His Thr
465                 470                 475                 480

Thr Lys Ser Phe Ser Arg Thr Pro Gly Lys
                485                 490

<210> SEQ ID NO 100
<211> LENGTH: 490
<212> TYPE: PRT
<213> ORGANISM: Artificial Sequence
<220> FEATURE:
<223> OTHER INFORMATION: Synthetic fusion protein

<400> SEQUENCE: 100

Met Ala Ser Leu Gly Gln Ile Ile Phe Trp Ser Ile Ile Asn Ile Ile
1               5                   10                  15

Ile Ile Leu Ala Gly Ala Ile Ala Leu Ile Ile Gly Phe Gly Ile Ser
            20                  25                  30

Gly Lys His Phe Ile Thr Val Thr Thr Phe Thr Ser Ala Gly Asn Ile
        35                  40                  45

Gly Glu Asp Gly Thr Leu Ser Cys Thr Phe Glu Pro Asp Ile Lys Leu
    50                  55                  60

Asn Gly Ile Val Ile Gln Trp Leu Lys Glu Gly Ile Lys Gly Leu Val
65                  70                  75                  80

His Glu Phe Lys Glu Gly Lys Asp Asp Leu Ser Gln Gln His Glu Met
                85                  90                  95

Phe Arg Gly Arg Thr Ala Val Phe Ala Asp Gln Val Val Val Gly Asn
            100                 105                 110

Ala Ser Leu Arg Leu Lys Asn Val Gln Leu Thr Asp Ala Gly Thr Tyr
        115                 120                 125

Thr Cys Tyr Ile Arg Thr Ser Lys Gly Lys Gly Asn Ala Asn Leu Glu
    130                 135                 140

Tyr Lys Thr Gly Ala Phe Ser Met Pro Glu Ile Asn Val Asp Tyr Asn
145                 150                 155                 160

Ala Ser Ser Glu Ser Leu Arg Cys Glu Ala Pro Arg Trp Phe Pro Gln
                165                 170                 175

Pro Thr Val Ala Trp Ala Ser Gln Val Asp Gln Gly Ala Asn Phe Ser
            180                 185                 190

Glu Val Ser Asn Thr Ser Phe Glu Leu Asn Ser Glu Asn Val Thr Met
        195                 200                 205

Lys Val Val Ser Val Leu Tyr Asn Val Thr Ile Asn Asn Thr Tyr Ser
```

```
            210                 215                 220
Cys Met Ile Glu Asn Asp Ile Ala Lys Ala Thr Gly Asp Ile Lys Val
225                 230                 235                 240

Thr Asp Ser Glu Val Lys Arg Arg Ser Gln Leu Gln Leu Leu Asn Ser
                245                 250                 255

Gly Glu Pro Arg Gly Pro Thr Ile Lys Pro Cys Pro Pro Cys Lys Cys
                260                 265                 270

Pro Ala Pro Asn Leu Leu Gly Gly Pro Ser Val Phe Ile Phe Pro Pro
                275                 280                 285

Lys Ile Lys Asp Val Leu Met Ile Ser Leu Ser Pro Ile Val Thr Cys
                290                 295                 300

Val Val Val Asp Val Ser Glu Asp Asp Pro Asp Val Gln Ile Ser Trp
305                 310                 315                 320

Phe Val Asn Asn Val Glu Val His Thr Ala Gln Thr Gln Thr His Arg
                325                 330                 335

Glu Asp Tyr Asn Ser Thr Leu Arg Val Val Ser Ala Leu Pro Ile Gln
                340                 345                 350

His Gln Asp Trp Met Ser Gly Lys Glu Phe Lys Cys Lys Val Asn Asn
                355                 360                 365

Lys Asp Leu Pro Ala Pro Ile Glu Arg Thr Ile Ser Lys Pro Lys Gly
                370                 375                 380

Ser Val Arg Ala Pro Gln Val Tyr Val Leu Pro Pro Pro Glu Glu Glu
385                 390                 395                 400

Met Thr Lys Lys Gln Val Thr Leu Thr Cys Met Val Thr Asp Phe Met
                405                 410                 415

Pro Glu Asp Ile Tyr Val Glu Trp Thr Asn Asn Gly Lys Thr Glu Leu
                420                 425                 430

Asn Tyr Lys Asn Thr Glu Pro Val Leu Asp Ser Asp Gly Ser Tyr Phe
                435                 440                 445

Met Tyr Ser Lys Leu Arg Val Glu Lys Lys Asn Trp Val Glu Arg Asn
                450                 455                 460

Ser Tyr Ser Cys Ser Val Val His Glu Gly Leu His Asn His His Thr
465                 470                 475                 480

Thr Lys Ser Phe Ser Arg Thr Pro Gly Lys
                485                 490

<210> SEQ ID NO 101
<211> LENGTH: 482
<212> TYPE: PRT
<213> ORGANISM: Artificial Sequence
<220> FEATURE:
<223> OTHER INFORMATION: Synthetic fusion protein

<400> SEQUENCE: 101

Met Glu Trp Ser Trp Val Phe Leu Phe Phe Leu Ser Val Thr Thr Gly
1               5                   10                  15

Val His Ser Gly Phe Gly Ile Ser Gly Lys His Phe Ile Thr Val Thr
                20                  25                  30

Thr Phe Thr Ser Ala Gly Asn Ile Gly Glu Asp Gly Thr Leu Ser Cys
                35                  40                  45

Thr Phe Glu Pro Asp Ile Lys Leu Asn Gly Ile Val Ile Gln Trp Leu
                50                  55                  60

Lys Glu Gly Ile Lys Gly Leu Val His Glu Phe Lys Glu Gly Lys Asp
65                  70                  75                  80

Asp Leu Ser Gln Gln His Glu Met Phe Arg Gly Arg Thr Ala Val Phe
```

```
                85                  90                  95
Ala Asp Gln Val Val Gly Asn Ala Ser Leu Arg Leu Lys Asn Val
            100                 105                 110
Gln Leu Thr Asp Ala Gly Thr Tyr Thr Cys Tyr Ile Arg Ser Ser Lys
            115                 120                 125
Gly Lys Gly Asn Ala Asn Leu Glu Tyr Lys Thr Gly Ala Phe Ser Met
            130                 135                 140
Pro Glu Ile Asn Val Asp Tyr Asn Ala Ser Ser Glu Ser Leu Arg Cys
145                 150                 155                 160
Glu Ala Pro Arg Trp Phe Pro Gln Pro Thr Val Ala Trp Ala Ser Gln
                165                 170                 175
Val Asp Gln Gly Ala Asn Phe Ser Glu Val Ser Asn Thr Ser Phe Glu
                180                 185                 190
Leu Asn Ser Glu Asn Val Thr Met Lys Val Val Ser Val Leu Tyr Asn
                195                 200                 205
Val Thr Ile Asn Asn Thr Tyr Ser Cys Met Ile Glu Asn Asp Ile Ala
                210                 215                 220
Lys Ala Thr Gly Asp Ile Lys Val Thr Asp Ser Glu Val Lys Arg Arg
225                 230                 235                 240
Ser Gln Leu Gln Leu Leu Asn Ser Gly Glu Pro Arg Gly Pro Thr Ile
                245                 250                 255
Lys Pro Cys Pro Pro Cys Lys Cys Pro Ala Pro Asn Leu Leu Gly Gly
                260                 265                 270
Pro Ser Val Phe Ile Phe Pro Pro Lys Ile Lys Asp Val Leu Met Ile
                275                 280                 285
Ser Leu Ser Pro Ile Val Thr Cys Val Val Val Asp Val Ser Glu Asp
                290                 295                 300
Asp Pro Asp Val Gln Ile Ser Trp Phe Val Asn Asn Val Glu Val His
305                 310                 315                 320
Thr Ala Gln Thr Gln Thr His Arg Glu Asp Tyr Asn Ser Thr Leu Arg
                325                 330                 335
Val Val Ser Ala Leu Pro Ile Gln His Gln Asp Trp Met Ser Gly Lys
                340                 345                 350
Glu Phe Lys Cys Lys Val Asn Asn Lys Asp Leu Pro Ala Pro Ile Glu
                355                 360                 365
Arg Thr Ile Ser Lys Pro Lys Gly Ser Val Arg Ala Pro Gln Val Tyr
                370                 375                 380
Val Leu Pro Pro Pro Glu Glu Glu Met Thr Lys Lys Gln Val Thr Leu
385                 390                 395                 400
Thr Cys Met Val Thr Asp Phe Met Pro Glu Asp Ile Tyr Val Glu Trp
                405                 410                 415
Thr Asn Asn Gly Lys Thr Glu Leu Asn Tyr Lys Asn Thr Glu Pro Val
                420                 425                 430
Leu Asp Ser Asp Gly Ser Tyr Phe Met Tyr Ser Lys Leu Arg Val Glu
                435                 440                 445
Lys Lys Asn Trp Val Glu Arg Asn Ser Tyr Ser Cys Ser Val Val His
                450                 455                 460
Glu Gly Leu His Asn His His Thr Thr Lys Ser Phe Ser Arg Thr Pro
465                 470                 475                 480
Gly Lys

<210> SEQ ID NO 102
<211> LENGTH: 482
```

<212> TYPE: PRT
<213> ORGANISM: Artificial Sequence
<220> FEATURE:
<223> OTHER INFORMATION: Synthetic fusion protein

<400> SEQUENCE: 102

```
Met Glu Trp Ser Trp Val Phe Leu Phe Phe Leu Ser Val Thr Thr Gly
1               5                   10                  15

Val His Ser Gly Phe Gly Ile Ser Gly Lys His Phe Ile Thr Val Thr
            20                  25                  30

Thr Phe Thr Ser Ala Gly Asn Ile Gly Glu Asp Gly Thr Leu Ser Cys
        35                  40                  45

Thr Phe Glu Pro Asp Ile Lys Leu Asn Gly Ile Val Ile Gln Trp Leu
    50                  55                  60

Lys Glu Gly Ile Lys Gly Leu Val His Glu Phe Lys Glu Gly Lys Asp
65                  70                  75                  80

Asp Leu Ser Gln Gln His Glu Met Phe Arg Gly Arg Thr Ala Val Phe
                85                  90                  95

Ala Asp Gln Val Val Gly Asn Ala Ser Leu Arg Leu Lys Asn Val
            100                 105                 110

Gln Leu Thr Asp Ala Gly Thr Tyr Thr Cys Tyr Ile Arg Thr Ser Lys
            115                 120                 125

Gly Lys Gly Asn Ala Asn Leu Glu Tyr Lys Thr Gly Ala Phe Ser Met
        130                 135                 140

Pro Glu Ile Asn Val Asp Tyr Asn Ala Ser Ser Glu Ser Leu Arg Cys
145                 150                 155                 160

Glu Ala Pro Arg Trp Phe Pro Gln Pro Thr Val Ala Trp Ala Ser Gln
                165                 170                 175

Val Asp Gln Gly Ala Asn Phe Ser Glu Val Ser Asn Thr Ser Phe Glu
            180                 185                 190

Leu Asn Ser Glu Asn Val Thr Met Lys Val Val Ser Val Leu Tyr Asn
        195                 200                 205

Val Thr Ile Asn Asn Thr Tyr Ser Cys Met Ile Glu Asn Asp Ile Ala
210                 215                 220

Lys Ala Thr Gly Asp Ile Lys Val Thr Asp Ser Glu Val Lys Arg Arg
225                 230                 235                 240

Ser Gln Leu Gln Leu Leu Asn Ser Gly Glu Pro Arg Gly Pro Thr Ile
                245                 250                 255

Lys Pro Cys Pro Pro Cys Lys Cys Pro Ala Pro Asn Leu Leu Gly Gly
            260                 265                 270

Pro Ser Val Phe Ile Phe Pro Pro Lys Ile Lys Asp Val Leu Met Ile
        275                 280                 285

Ser Leu Ser Pro Ile Val Thr Cys Val Val Asp Val Ser Glu Asp
        290                 295                 300

Asp Pro Asp Val Gln Ile Ser Trp Phe Val Asn Asn Val Glu Val His
305                 310                 315                 320

Thr Ala Gln Thr Gln Thr His Arg Glu Asp Tyr Asn Ser Thr Leu Arg
                325                 330                 335

Val Val Ser Ala Leu Pro Ile Gln His Gln Asp Trp Met Ser Gly Lys
            340                 345                 350

Glu Phe Lys Cys Lys Val Asn Asn Lys Asp Leu Pro Ala Pro Ile Glu
        355                 360                 365

Arg Thr Ile Ser Lys Pro Lys Gly Ser Val Arg Ala Pro Gln Val Tyr
    370                 375                 380
```

```
Val Leu Pro Pro Pro Glu Glu Glu Met Thr Lys Lys Gln Val Thr Leu
385                 390                 395                 400

Thr Cys Met Val Thr Asp Phe Met Pro Glu Asp Ile Tyr Val Glu Trp
                405                 410                 415

Thr Asn Asn Gly Lys Thr Glu Leu Asn Tyr Lys Asn Thr Glu Pro Val
            420                 425                 430

Leu Asp Ser Asp Gly Ser Tyr Phe Met Tyr Ser Lys Leu Arg Val Glu
        435                 440                 445

Lys Lys Asn Trp Val Glu Arg Asn Ser Tyr Ser Cys Ser Val Val His
    450                 455                 460

Glu Gly Leu His Asn His His Thr Thr Lys Ser Phe Ser Arg Thr Pro
465                 470                 475                 480

Gly Lys

<210> SEQ ID NO 103
<211> LENGTH: 463
<212> TYPE: PRT
<213> ORGANISM: Artificial Sequence
<220> FEATURE:
<223> OTHER INFORMATION: Synthetic fusion protein

<400> SEQUENCE: 103

Gly Phe Gly Ile Ser Gly Lys His Phe Ile Thr Val Thr Thr Phe Thr
1               5                   10                  15

Ser Ala Gly Asn Ile Gly Glu Asp Gly Thr Leu Ser Cys Thr Phe Glu
                20                  25                  30

Pro Asp Ile Lys Leu Asn Gly Ile Val Ile Gln Trp Leu Lys Glu Gly
            35                  40                  45

Ile Lys Gly Leu Val His Glu Phe Lys Glu Gly Lys Asp Asp Leu Ser
    50                  55                  60

Gln Gln His Glu Met Phe Arg Gly Arg Thr Ala Val Phe Ala Asp Gln
65                  70                  75                  80

Val Val Val Gly Asn Ala Ser Leu Arg Leu Lys Asn Val Gln Leu Thr
                85                  90                  95

Asp Ala Gly Thr Tyr Thr Cys Tyr Ile Arg Ser Ser Lys Gly Lys Gly
            100                 105                 110

Asn Ala Asn Leu Glu Tyr Lys Thr Gly Ala Phe Ser Met Pro Glu Ile
        115                 120                 125

Asn Val Asp Tyr Asn Ala Ser Ser Glu Ser Leu Arg Cys Glu Ala Pro
130                 135                 140

Arg Trp Phe Pro Gln Pro Thr Val Ala Trp Ala Ser Gln Val Asp Gln
145                 150                 155                 160

Gly Ala Asn Phe Ser Glu Val Ser Asn Thr Ser Phe Glu Leu Asn Ser
                165                 170                 175

Glu Asn Val Thr Met Lys Val Val Ser Val Leu Tyr Asn Val Thr Ile
            180                 185                 190

Asn Asn Thr Tyr Ser Cys Met Ile Glu Asn Asp Ile Ala Lys Ala Thr
        195                 200                 205

Gly Asp Ile Lys Val Thr Asp Ser Glu Val Lys Arg Arg Ser Gln Leu
    210                 215                 220

Gln Leu Leu Asn Ser Gly Glu Pro Arg Gly Pro Thr Ile Lys Pro Cys
225                 230                 235                 240

Pro Pro Cys Lys Cys Pro Ala Pro Asn Leu Leu Gly Gly Pro Ser Val
                245                 250                 255

Phe Ile Phe Pro Pro Lys Ile Lys Asp Val Leu Met Ile Ser Leu Ser
```

```
                  260                 265                 270
Pro Ile Val Thr Cys Val Val Asp Val Ser Glu Asp Pro Asp
            275                 280                 285

Val Gln Ile Ser Trp Phe Val Asn Asn Val Glu Val His Thr Ala Gln
        290                 295                 300

Thr Gln Thr His Arg Glu Asp Tyr Asn Ser Thr Leu Arg Val Val Ser
305                 310                 315                 320

Ala Leu Pro Ile Gln His Gln Asp Trp Met Ser Gly Lys Glu Phe Lys
                325                 330                 335

Cys Lys Val Asn Asn Lys Asp Leu Pro Ala Pro Ile Glu Arg Thr Ile
            340                 345                 350

Ser Lys Pro Lys Gly Ser Val Arg Ala Pro Gln Val Tyr Val Leu Pro
        355                 360                 365

Pro Pro Glu Glu Glu Met Thr Lys Lys Gln Val Thr Leu Thr Cys Met
    370                 375                 380

Val Thr Asp Phe Met Pro Glu Asp Ile Tyr Val Glu Trp Thr Asn Asn
385                 390                 395                 400

Gly Lys Thr Glu Leu Asn Tyr Lys Asn Thr Glu Pro Val Leu Asp Ser
                405                 410                 415

Asp Gly Ser Tyr Phe Met Tyr Ser Lys Leu Arg Val Glu Lys Lys Asn
            420                 425                 430

Trp Val Glu Arg Asn Ser Tyr Ser Cys Ser Val Val His Glu Gly Leu
        435                 440                 445

His Asn His His Thr Thr Lys Ser Phe Ser Arg Thr Pro Gly Lys
    450                 455                 460

<210> SEQ ID NO 104
<211> LENGTH: 463
<212> TYPE: PRT
<213> ORGANISM: Artificial Sequence
<220> FEATURE:
<223> OTHER INFORMATION: Synthetic fusion protein

<400> SEQUENCE: 104

Gly Phe Gly Ile Ser Gly Lys His Phe Ile Thr Val Thr Thr Phe Thr
1               5                   10                  15

Ser Ala Gly Asn Ile Gly Glu Asp Gly Thr Leu Ser Cys Thr Phe Glu
            20                  25                  30

Pro Asp Ile Lys Leu Asn Gly Ile Val Ile Gln Trp Leu Lys Glu Gly
        35                  40                  45

Ile Lys Gly Leu Val His Glu Phe Lys Glu Gly Lys Asp Asp Leu Ser
    50                  55                  60

Gln Gln His Glu Met Phe Arg Gly Arg Thr Ala Val Phe Ala Asp Gln
65                  70                  75                  80

Val Val Val Gly Asn Ala Ser Leu Arg Leu Lys Asn Val Gln Leu Thr
                85                  90                  95

Asp Ala Gly Thr Tyr Thr Cys Tyr Ile Arg Thr Ser Lys Gly Lys Gly
            100                 105                 110

Asn Ala Asn Leu Glu Tyr Lys Thr Gly Ala Phe Ser Met Pro Glu Ile
        115                 120                 125

Asn Val Asp Tyr Asn Ala Ser Ser Glu Ser Leu Arg Cys Glu Ala Pro
    130                 135                 140

Arg Trp Phe Pro Gln Pro Thr Val Ala Trp Ala Ser Gln Val Asp Gln
145                 150                 155                 160

Gly Ala Asn Phe Ser Glu Val Ser Asn Thr Ser Phe Glu Leu Asn Ser
```

165                 170                 175
Glu Asn Val Thr Met Lys Val Ser Val Leu Tyr Asn Val Thr Ile
            180                 185                 190

Asn Asn Thr Tyr Ser Cys Met Ile Glu Asn Asp Ile Ala Lys Ala Thr
        195                 200                 205

Gly Asp Ile Lys Val Thr Asp Ser Glu Val Lys Arg Arg Ser Gln Leu
    210                 215                 220

Gln Leu Leu Asn Ser Gly Glu Pro Arg Gly Pro Thr Ile Lys Pro Cys
225                 230                 235                 240

Pro Pro Cys Lys Cys Pro Ala Pro Asn Leu Leu Gly Gly Pro Ser Val
                245                 250                 255

Phe Ile Phe Pro Pro Lys Ile Lys Asp Val Leu Met Ile Ser Leu Ser
            260                 265                 270

Pro Ile Val Thr Cys Val Val Asp Val Ser Glu Asp Asp Pro Asp
        275                 280                 285

Val Gln Ile Ser Trp Phe Val Asn Asn Val Glu Val His Thr Ala Gln
    290                 295                 300

Thr Gln Thr His Arg Glu Asp Tyr Asn Ser Thr Leu Arg Val Val Ser
305                 310                 315                 320

Ala Leu Pro Ile Gln His Gln Asp Trp Met Ser Gly Lys Glu Phe Lys
                325                 330                 335

Cys Lys Val Asn Asn Lys Asp Leu Pro Ala Pro Ile Glu Arg Thr Ile
            340                 345                 350

Ser Lys Pro Lys Gly Ser Val Arg Ala Pro Gln Val Tyr Val Leu Pro
        355                 360                 365

Pro Pro Glu Glu Glu Met Thr Lys Lys Gln Val Thr Leu Thr Cys Met
    370                 375                 380

Val Thr Asp Phe Met Pro Glu Asp Ile Tyr Val Glu Trp Thr Asn Asn
385                 390                 395                 400

Gly Lys Thr Glu Leu Asn Tyr Lys Asn Thr Glu Pro Val Leu Asp Ser
                405                 410                 415

Asp Gly Ser Tyr Phe Met Tyr Ser Lys Leu Arg Val Glu Lys Lys Asn
            420                 425                 430

Trp Val Glu Arg Asn Ser Tyr Ser Cys Ser Val Val His Glu Gly Leu
        435                 440                 445

His Asn His His Thr Thr Lys Ser Phe Ser Arg Thr Pro Gly Lys
    450                 455                 460

<210> SEQ ID NO 105
<211> LENGTH: 1443
<212> TYPE: PRT
<213> ORGANISM: Artificial Sequence
<220> FEATURE:
<223> OTHER INFORMATION: Synthetic fusion protein

<400> SEQUENCE: 105

Ala Thr Gly Gly Cys Thr Thr Cys Cys Cys Thr Gly Gly Gly Cys
1               5                   10                  15

Ala Gly Ala Thr Cys Cys Thr Cys Thr Thr Cys Thr Gly Gly Ala Gly
                20                  25                  30

Cys Ala Thr Ala Ala Thr Thr Ala Gly Cys Ala Thr Cys Ala Thr Cys
            35                  40                  45

Ala Thr Thr Ala Thr Thr Cys Thr Gly Gly Cys Thr Gly Gly Ala Gly
        50                  55                  60

Cys Ala Ala Thr Thr Gly Cys Ala Cys Thr Cys Ala Thr Cys Ala Thr

-continued

```
            65                  70                  75                  80
Thr Gly Gly Cys Thr Thr Thr Gly Gly Thr Ala Thr Thr Thr Cys Ala
                    85                  90                  95
Gly Gly Gly Ala Gly Ala Cys Ala Cys Thr Cys Cys Ala Thr Cys Ala
                    100                 105                 110
Cys Ala Gly Thr Cys Ala Cys Thr Ala Cys Thr Gly Thr Cys Gly Cys
                    115                 120                 125
Cys Thr Cys Ala Gly Cys Thr Gly Gly Ala Ala Cys Ala Thr Thr
            130                 135                 140
Gly Gly Gly Gly Ala Gly Ala Thr Gly Ala Ala Thr Cys Cys
145                 150                 155                 160
Thr Gly Ala Gly Cys Thr Gly Cys Ala Cys Thr Thr Thr Gly Ala
                    165                 170                 175
Ala Cys Cys Thr Gly Ala Cys Ala Thr Cys Ala Ala Ala Cys Thr Thr
                    180                 185                 190
Thr Cys Thr Gly Ala Thr Ala Thr Cys Gly Thr Gly Ala Thr Ala Cys
                    195                 200                 205
Ala Ala Thr Gly Gly Cys Thr Gly Ala Ala Gly Gly Ala Ala Gly Gly
            210                 215                 220
Thr Gly Thr Thr Thr Thr Ala Gly Gly Cys Thr Thr Gly Gly Thr Cys
225                 230                 235                 240
Cys Ala Thr Gly Ala Gly Thr Thr Cys Ala Ala Ala Gly Ala Ala Gly
                    245                 250                 255
Gly Cys Ala Ala Ala Gly Ala Thr Gly Ala Gly Cys Thr Gly Thr Cys
                    260                 265                 270
Gly Gly Ala Gly Cys Ala Gly Gly Ala Thr Gly Ala Ala Ala Thr Gly
                    275                 280                 285
Thr Thr Cys Ala Gly Ala Gly Gly Cys Cys Gly Gly Ala Cys Ala Gly
                    290                 295                 300
Cys Ala Gly Thr Gly Thr Thr Thr Gly Cys Thr Gly Ala Thr Cys Ala
305                 310                 315                 320
Ala Gly Thr Gly Ala Thr Ala Gly Thr Thr Gly Gly Cys Ala Ala Thr
                    325                 330                 335
Gly Cys Cys Thr Cys Thr Thr Thr Gly Cys Gly Gly Cys Thr Gly Ala
                    340                 345                 350
Ala Ala Ala Ala Cys Gly Thr Gly Cys Ala Ala Cys Thr Cys Ala Cys
                    355                 360                 365
Ala Gly Ala Thr Gly Cys Thr Gly Gly Cys Ala Cys Cys Thr Ala Cys
                    370                 375                 380
Ala Ala Ala Thr Gly Thr Thr Ala Thr Ala Thr Cys Ala Thr Cys Ala
385                 390                 395                 400
Cys Thr Thr Cys Thr Ala Ala Ala Gly Gly Cys Ala Ala Gly Gly Gly
                    405                 410                 415
Gly Ala Ala Thr Gly Cys Thr Ala Ala Cys Cys Thr Thr Gly Ala Gly
                    420                 425                 430
Thr Ala Thr Ala Ala Ala Ala Cys Thr Gly Gly Ala Gly Cys Cys Thr
                    435                 440                 445
Thr Cys Ala Gly Cys Ala Thr Gly Cys Cys Gly Gly Ala Ala Gly Thr
                    450                 455                 460
Gly Ala Ala Thr Gly Thr Gly Gly Ala Cys Thr Ala Thr Ala Ala Thr
465                 470                 475                 480
Gly Cys Cys Ala Gly Cys Thr Cys Ala Gly Ala Gly Ala Cys Cys Thr
                    485                 490                 495
```

```
Thr Gly Cys Gly Gly Thr Gly Thr Gly Ala Gly Gly Cys Thr Cys Cys
            500                 505                 510

Cys Cys Gly Ala Thr Gly Gly Thr Thr Cys Cys Cys Cys Cys Ala Gly
        515                 520                 525

Cys Cys Cys Ala Cys Ala Gly Thr Gly Gly Thr Cys Thr Gly Gly Gly
        530                 535                 540

Cys Ala Thr Cys Cys Cys Ala Ala Gly Thr Thr Gly Ala Cys Cys Ala
545                 550                 555                 560

Gly Gly Gly Ala Gly Cys Cys Ala Ala Cys Thr Thr Cys Thr Cys Gly
                565                 570                 575

Gly Ala Ala Gly Thr Cys Thr Cys Cys Ala Ala Thr Ala Cys Cys Ala
            580                 585                 590

Gly Cys Thr Thr Thr Gly Ala Gly Cys Thr Gly Ala Ala Cys Thr Cys
        595                 600                 605

Thr Gly Ala Gly Ala Ala Thr Gly Thr Gly Ala Cys Cys Ala Thr Gly
            610                 615                 620

Ala Ala Gly Gly Thr Thr Gly Thr Gly Thr Cys Thr Gly Thr Gly Cys
625                 630                 635                 640

Thr Cys Thr Ala Cys Ala Ala Thr Gly Thr Thr Ala Cys Gly Ala Thr
                645                 650                 655

Cys Ala Ala Cys Ala Ala Cys Ala Cys Ala Thr Ala Cys Thr Cys Cys
            660                 665                 670

Thr Gly Thr Ala Thr Gly Ala Thr Thr Gly Ala Ala Ala Ala Thr Gly
        675                 680                 685

Ala Cys Ala Thr Thr Gly Cys Cys Ala Ala Ala Gly Cys Ala Ala Cys
        690                 695                 700

Ala Gly Gly Gly Ala Thr Ala Thr Cys Ala Ala Ala Gly Ala Thr Gly
705                 710                 715                 720

Ala Cys Ala Gly Ala Ala Thr Cys Gly Gly Ala Gly Ala Thr Cys Ala
            725                 730                 735

Ala Ala Ala Gly Gly Cys Gly Gly Ala Gly Thr Gly Ala Gly Cys Cys
                740                 745                 750

Thr Ala Ala Gly Thr Cys Ala Thr Gly Thr Gly Ala Cys Ala Ala Gly
        755                 760                 765

Ala Cys Cys Cys Ala Thr Ala Cys Gly Thr Gly Cys Cys Cys Ala Cys
        770                 775                 780

Cys Cys Thr Gly Thr Cys Cys Gly Cys Thr Cys Ala Gly Ala
785                 790                 795                 800

Ala Cys Thr Gly Cys Thr Gly Gly Gly Gly Gly Ala Cys Cys Thr
            805                 810                 815

Ala Gly Cys Gly Thr Thr Thr Cys Thr Gly Thr Thr Cys Cys
        820                 825                 830

Cys Cys Cys Cys Ala Ala Ala Gly Cys Cys Ala Ala Gly Gly Ala
        835                 840                 845

Cys Ala Cys Cys Cys Thr Cys Ala Thr Gly Ala Thr Cys Thr Cys Ala
850                 855                 860

Cys Gly Gly Ala Cys Thr Cys Cys Cys Gly Ala Ala Gly Thr Ala Ala
865                 870                 875                 880

Cys Ala Thr Gly Cys Gly Thr Gly Ala Gly Thr Gly Thr Gly Ala
            885                 890                 895

Cys Gly Thr Gly Ala Gly Cys Cys Ala Cys Gly Ala Gly Gly Ala Thr
        900                 905                 910
```

```
Cys Cys Thr Gly Ala Ala Gly Thr Gly Ala Ala Gly Thr Thr Ala
            915                 920                 925
Ala Thr Thr Gly Gly Thr Ala Cys Gly Thr Gly Ala Cys Gly Gly
    930                 935                 940
Ala Gly Thr Cys Gly Ala Gly Gly Thr Gly Cys Ala Thr Ala Thr
945                 950                 955                 960
Gly Cys Cys Ala Ala Ala Cys Thr Ala Ala Cys Cys Thr Cys
                965                 970                 975
Gly Gly Gly Ala Gly Gly Ala Gly Cys Ala Gly Thr Ala Ala Ala
            980                 985                 990
Cys Ala Gly Thr Ala Cys Cys Thr Ala Cys Cys Gly Cys Gly Thr Gly
        995                 1000                1005
Gly Thr Ala Thr Cys Cys Gly Thr Cys Thr Thr Gly Ala Cys Ala
    1010                1015                1020
Gly Thr Gly Cys Thr Cys Cys Ala Cys Cys Ala Gly Gly Ala Cys
    1025                1030                1035
Thr Gly Gly Cys Thr Gly Ala Ala Thr Gly Gly Thr Ala Ala Gly
    1040                1045                1050
Gly Ala Gly Thr Ala Thr Ala Ala Ala Thr Gly Cys Ala Ala Gly
    1055                1060                1065
Gly Thr Cys Ala Gly Cys Ala Ala Cys Ala Ala Ala Gly Cys Thr
    1070                1075                1080
Cys Thr Thr Cys Cys Cys Gly Cys Cys Cys Cys Ala Ala Thr Thr
    1085                1090                1095
Gly Ala Ala Ala Ala Gly Ala Cys Thr Ala Thr Cys Ala Gly Cys
    1100                1105                1110
Ala Ala Gly Gly Cys Cys Ala Ala Gly Gly Gly Ala Cys Ala Ala
    1115                1120                1125
Cys Cys Cys Cys Gly Cys Gly Ala Gly Cys Cys Cys Cys Ala Gly
    1130                1135                1140
Gly Thr Thr Thr Ala Cys Ala Cys Cys Cys Thr Cys Cys Cys Ala
    1145                1150                1155
Cys Cys Thr Thr Cys Ala Cys Gly Ala Gly Ala Cys Gly Ala Gly
    1160                1165                1170
Cys Thr Gly Ala Cys Cys Ala Ala Gly Ala Ala Cys Cys Ala Gly
    1175                1180                1185
Gly Thr Gly Thr Cys Thr Cys Thr Gly Ala Cys Thr Thr Gly Thr
    1190                1195                1200
Cys Thr Gly Gly Thr Cys Ala Ala Ala Gly Gly Thr Thr Thr Cys
    1205                1210                1215
Thr Ala Thr Cys Cys Thr Cys Cys Gly Ala Cys Ala Thr Cys
    1220                1225                1230
Gly Cys Ala Gly Thr Gly Gly Ala Gly Thr Gly Gly Ala Gly
    1235                1240                1245
Thr Cys Ala Ala Ala Cys Gly Gly Gly Cys Ala Gly Cys Cys Thr
    1250                1255                1260
Gly Ala Gly Ala Ala Thr Ala Cys Thr Ala Cys Ala Ala Gly
    1265                1270                1275
Ala Cys Cys Ala Cys Ala Cys Cys Cys Cys Cys Ala Gly Thr Gly
    1280                1285                1290
Cys Thr Thr Gly Ala Thr Ala Gly Cys Gly Ala Thr Gly Gly Gly
    1295                1300                1305
Ala Gly Cys Thr Thr Thr Thr Thr Cys Cys Thr Cys Thr Ala Cys
    1310                1315                1320
```

| | | | | | | | | | | |
|---|---|---|---|---|---|---|---|---|---|---|
| | | 1310 | | | 1315 | | | 1320 | | |
| Ala | Gly | Thr | Ala | Ala | Gly | Cys | Thr | Gly | Ala | Cys | Thr | Gly | Thr | Gly |
| | | 1325 | | | 1330 | | | 1335 | | |
| Gly | Ala | Cys | Ala | Ala | Ala | Thr | Cys | Cys | Gly | Cys | Thr | Gly | Gly |
| | | 1340 | | | 1345 | | | 1350 | | |
| Cys | Ala | Gly | Cys | Ala | Gly | Gly | Gly | Ala | Ala | Cys | Gly | Thr | Thr |
| | | 1355 | | | 1360 | | | 1365 | | |
| Thr | Thr | Cys | Thr | Cys | Thr | Thr | Gly | Thr | Ala | Gly | Cys | Gly | Thr | Cys |
| | | 1370 | | | 1375 | | | 1380 | | |
| Ala | Thr | Gly | Cys | Ala | Thr | Gly | Ala | Gly | Gly | Cys | Cys | Thr | Cys |
| | | 1385 | | | 1390 | | | 1395 | | |
| Cys | Ala | Cys | Ala | Ala | Cys | Cys | Ala | Thr | Thr | Ala | Thr | Ala | Cys | Thr |
| | | 1400 | | | 1405 | | | 1410 | | |
| Cys | Ala | Gly | Ala | Ala | Ala | Ala | Gly | Cys | Cys | Thr | Gly | Ala | Gly | Thr |
| | | 1415 | | | 1420 | | | 1425 | | |
| Cys | Thr | Gly | Ala | Gly | Thr | Cys | Cys | Cys | Gly | Gly | Cys | Ala | Ala | Ala |
| | | 1430 | | | 1435 | | | 1440 | | |

<210> SEQ ID NO 106
<211> LENGTH: 1419
<212> TYPE: DNA
<213> ORGANISM: Artificial Sequence
<220> FEATURE:
<223> OTHER INFORMATION: Synthetic fusion nucleotide

<400> SEQUENCE: 106

```
atggaatgga gctgggtatt tctgttttc ctgtcagtaa cgactggcgt ccattcaggc      60
ttcggcatca gtggacggca cagtatcaca gtgaccaccg tcgcctccgc tggcaatata    120
ggtgaggatg gcatccagtc ctgtacccttt gagccggaca tcaaactgtc tgacatagtg    180
atacaatggc tgaaggaggg ggtgctcggt ctggtacatg agtttaagga agggaaggat    240
gaactgtccg agcaggatga aatgttccgg ggaggaccg ctgtgttcgc cgatcaggta    300
atcgtcggaa atgcaagtct cagattgaaa atgtgcaac tgactgatgc tggcacgtat    360
aaatgctaca ttatcacaag taagggcaaa ggaaatgcta accttgagta taaaacaggc    420
gcattctcaa tgcccgaggt caatgtcgac tataatgcca gcagtgaaac attgcgctgt    480
gaagctcccc gctggttccc ccagccaacc gtggtctggg cctctcaggt tgatcagggg    540
gctaactttt ccgaggtgag caacaccagc ttcgaactca actctgagaa tgtgaccatg    600
aaagttgtgt ctgtcctgta atgtaaca atcaacaaca cttattcatg catgattgaa    660
aacgacatcg ccaaggcaac aggtgatatt aaggtaactg aatccgagat caaacggcgg    720
tctgagccta agtcatgtga caagacccat acgtgcccac cctgtcccgc tccagaactg    780
ctgggggac ctagcgtttt cttgttcccc ccaaagccca aggacaccct catgatctca    840
cggactcccg aagtaacatg cgtagtagtc gacgtgagcc acgaggatcc tgaagtgaag    900
tttaattggt acgtggacgg agtcgaggtg cataatgcca aaactaaacc tcgggaggag    960
cagtataaca gtacctaccg cgtggtatcc gtcttgacag tgctccacca ggactggctg   1020
aatggtaagg agtataaaatg caaggtcagc aacaaagctc ttcccgcccc aattgaaaag   1080
actatcagca aggccaaggg acaaccccgc gagcccagg tttacaccct tccaccttca   1140
cgagacgagc tgaccaagaa ccaggtgtct ctgacttgtc tggtcaaagg tttctatcct   1200
tccgacatcg cagtggagtg ggagtcaaac gggcagcctg agaataacta caagaccaca   1260
cccccagtgc ttgatagcga tgggagcttt ttcctctaca gtaagctgac tgtggacaaa   1320
```

-continued

| tcccgctggc agcagggaaa cgttttctct tgtagcgtca tgcatgaggc cctccacaac | 1380 |
| cattatactc agaaaagcct gagtctgagt cccggcaaa | 1419 |

<210> SEQ ID NO 107
<211> LENGTH: 1404
<212> TYPE: DNA
<213> ORGANISM: Artificial Sequence
<220> FEATURE:
<223> OTHER INFORMATION: Synthetic fusion nucleotide

<400> SEQUENCE: 107

| atggaatgga gctgggtatt tctgttttc ctgtcagtaa cgactggcgt ccattcaggc | 60 |
| ttcggcatca gtggacggca cagtatcaca gtgaccaccg tcgcctccgc tggcaatata | 120 |
| ggtgaggatg gcatccagtc ctgtaccttt gagccggaca tcaaactgtc tgacatagtg | 180 |
| atacaatggc tgaaggaggg ggtgctcggt ctggtacatg agtttaagga agggaaggat | 240 |
| gaactgtccg agcaggatga gatgttccgg ggaggaccg ctgtgttcgc cgatcaggta | 300 |
| atcgtcggaa atgcaagtct cagattgaaa atgtgcaac tgactgatgc tggcacgtat | 360 |
| aaatgctaca ttatcacaag taagggcaaa ggaaatgcta accttgagta taaaacaggc | 420 |
| gcattctcaa tgcccgaggt caatgtcgac tataatgcca gcagtgaaac attgcgctgt | 480 |
| gaagctcccc gctggttccc ccagccaacc gtggtctggg cctctcaggt tgatcagggg | 540 |
| gctaacttt ccgaggtgag caacaccagc ttcgaactca actctgagaa tgtgaccatg | 600 |
| aaagttgtgt ctgtcctgta taatgtaaca atcaacaaca cttattcatg catgattgaa | 660 |
| aacgacatcg ccaaggcaac aggtgatatt aaggtaactg aatccgagat caaacggcgg | 720 |
| tctgacaaga cccatacgtg cccaccctgt cccgctccag aactgctggg gggacctagc | 780 |
| gtttctcttgt tccccccaaa gcccaaggac accctcatga tctcacggac tcccgaagta | 840 |
| acatgcgtag tagtcgacgt gagccacgag gatcctgaag tgaagtttaa ttggtacgtg | 900 |
| gacggagtcg aggtgcataa tgccaaaact aaacctcggg aggagcagta taacagtacc | 960 |
| taccgcgtgg tatccgtctt gacagtgctc caccaggact ggctgaatgg taaggagtat | 1020 |
| aaatgcaagg tcagcaacaa agctcttccc gccccaattg aaaagactat cagcaaggcc | 1080 |
| aagggacaac cccgcgagcc ccaggtttac acccttccac cttcacgaga cgagctgacc | 1140 |
| aagaaccagg tgtctctgac ttgtctggtc aaaggttct atccttccga catcgcagtg | 1200 |
| gagtgggagt caaacgggca gcctgagaat aactacaaga ccacacccc agtgcttgat | 1260 |
| agcgatggga gcttttcct ctacagtaag ctgactgtgg acaaatcccg ctggcagcag | 1320 |
| ggaaacgttt tctcttgtag cgtcatgcat gaggccctcc acaaccatta tactcagaaa | 1380 |
| agcctgagtc tgagtcccgg caaa | 1404 |

<210> SEQ ID NO 108
<211> LENGTH: 1392
<212> TYPE: DNA
<213> ORGANISM: Artificial Sequence
<220> FEATURE:
<223> OTHER INFORMATION: Synthetic fusion nucleotide

<400> SEQUENCE: 108

| atggaatgga gctgggtatt tctgttttc ctgtcagtaa cgactggcgt ccattcaggc | 60 |
| ttcggcatca gtggacggca cagtatcaca gtgaccaccg tcgcctccgc tggcaatata | 120 |
| ggtgaggatg gcatccagtc ctgtaccttt gagccggaca tcaaactgtc tgacatagtg | 180 |

| | |
|---|---|
| atacaatggc tgaaggaggg ggtgctcggt ctggtacatg agtttaagga agggaaggat | 240 |
| gaactgtccg agcaggatga gatgttccgg gggaggaccg ctgtgttcgc cgatcaggta | 300 |
| atcgtcggaa atgcaagtct cagattgaaa aatgtgcaac tgactgatgc tggcacgtat | 360 |
| aaatgctaca ttatcacaag taagggcaaa ggaaatgcta accttgagta taaaacaggc | 420 |
| gcattctcaa tgcccgaggt caatgtcgac tataatgcca gcagtgaaac attgcgctgt | 480 |
| gaagctcccc gctggttccc ccagccaacc gtggtctggg cctctcaggt tgatcagggg | 540 |
| gctaactttt ccgaggtgag caacaccagc ttcgaactca actctgagaa tgtgaccatg | 600 |
| aaagttgtgt ctgtcctgta taatgtaaca atcaacaaca cttattcatg catgattgaa | 660 |
| aacgacatcg ccaaggcaac aggtgatatt aaggtaactg aatccgagat cgacaagacc | 720 |
| catacgtgcc caccctgtcc cgctccagaa ctgctggggg gacctagcgt tttcttgttc | 780 |
| cccccaaagc ccaaggacac cctcatgatc tcacggactc ccgaagtaac atgcgtagta | 840 |
| gtcgacgtga gccacgagga tcctgaagtg aagtttaatt ggtacgtgga cggagtcgag | 900 |
| gtgcataatg ccaaaactaa acctcgggag gagcagtata acagtaccta ccgcgtggta | 960 |
| tccgtcttga cagtgctcca ccaggactgg ctgaatggta aggagtataa atgcaaggtc | 1020 |
| agcaacaaag ctcttcccgc cccaattgaa aagactatca gcaaggccaa gggacaaccc | 1080 |
| cgcgagcccc aggtttacac ccttccacct tcacgagacg agctgaccaa gaaccaggtg | 1140 |
| tctctgactt gtctggtcaa aggttttctat ccttccgaca tcgcagtgga gtgggagtca | 1200 |
| aacgggcagc ctgagaataa ctacaagacc acaccccag tgcttgatag cgatgggagc | 1260 |
| ttttcctct acagtaagct gactgtggac aaatcccgct ggcagcaggg aaacgttttc | 1320 |
| tcttgtagcg tcatgcatga ggccctccac aaccattata ctcagaaaag cctgagtctg | 1380 |
| agtcccggca aa | 1392 |

<210> SEQ ID NO 109
<211> LENGTH: 1428
<212> TYPE: DNA
<213> ORGANISM: Artificial Sequence
<220> FEATURE:
<223> OTHER INFORMATION: Synthetic fusion nucleotide

<400> SEQUENCE: 109

| | |
|---|---|
| atggaatgga gctgggtatt tctgttttc ctgtcagtaa cgactggcgt ccattcaggc | 60 |
| ttcggcatca gtggacggca cagtatcaca gtgaccaccg tcgcctccgc tggcaatata | 120 |
| ggtgaggatg gcatccagtc ctgtacccttt gagcccgaca tcaaactgtc tgacatagtg | 180 |
| atacaatggc tgaaggaggg ggtgctcggt ctggtacatg agtttaagga agggaaggat | 240 |
| gaactgtccg agcaggatga gatgttccgg gggaggaccg ctgtgttcgc cgatcaggta | 300 |
| atcgtcggaa atgcaagtct cagattgaaa aatgtgcaac tgactgatgc tggcacgtat | 360 |
| aaatgctaca ttatcacaag taagggcaaa ggaaatgcta accttgagta taaaacaggc | 420 |
| gcattctcaa tgcccgaggt caatgtcgac tataatgcca gcagtgaaac attgcgctgt | 480 |
| gaagctcccc gctggttccc ccagccaacc gtggtctggg cctctcaggt tgatcagggg | 540 |
| gctaactttt ccgaggtgag caacaccagc ttcgaactca actctgagaa tgtgaccatg | 600 |
| aaagttgtgt ctgtcctgta taatgtaaca atcaacaaca cttattcatg catgattgaa | 660 |
| aacgacatcg ccaaggcaac aggtgatatt aaggtaactg aatccgagat caaacgcgg | 720 |
| tctcacctgc agctgctgaa ctccaaggac aagacccata cgtgcccacc ctgtcccgct | 780 |
| ccagaactgc tggggggacc tagcgttttc ttgttccccc caaagcccaa ggacaccctc | 840 |

```
atgatctcac ggactcccga agtaacatgc gtagtagtcg acgtgagcca cgaggatcct    900
gaagtgaagt ttaattggta cgtggacgga gtcgaggtgc ataatgccaa aactaaacct    960
cgggaggagc agtataacag tacctaccgc gtggtatccg tcttgacagt gctccaccag   1020
gactggctga atggtaagga gtataaatgc aaggtcagca acaaagctct tcccgcccca   1080
attgaaaaga ctatcagcaa ggccaaggga caaccccgcg agccccaggt ttacacccCtt  1140
ccaccttcac gagacgagct gaccaagaac caggtgtctc tgacttgtct ggtcaaaggt   1200
ttctatcctt ccgacatcgc agtggagtgg gagtcaaacg ggcagcctga gaataactac   1260
aagaccacac ccccagtgct tgatagcgat gggagctttt tcctctacag taagctgact   1320
gtggacaaat cccgctggca gcagggaaac gttttctctt gtagcgtcat gcatgaggcc   1380
ctccacaacc attatactca gaaaagcctg agtctgagtc ccggcaaa                1428
```

<210> SEQ ID NO 110
<211> LENGTH: 1419
<212> TYPE: DNA
<213> ORGANISM: Artificial Sequence
<220> FEATURE:
<223> OTHER INFORMATION: Synthetic fusion nucleotide

<400> SEQUENCE: 110

```
atggaatgga gctgggtatt tctgttttttc ctgtcagtaa cgactggcgt ccattcaggc     60
ttcggcatca gtgacggca cagtatcaca gtgaccaccg tcgcctccgc tggcaatata    120
ggtgaggatg gcatcctgtc ctgtacctttt gagccggaca tcaaactgtc tgacatagtg   180
atacaatggc tgaaggaggg ggtgctcggt ctggtacatg agtttaagga agggaaggat   240
gaactgtccg agcaggatga gatgttccgg gggaggaccg ctgtgttcgc cgatcaggta   300
atcgtcggaa atgcaagtct cagattgaaa aatgtgcaac tgactgatgc tggcacgtat   360
aaatgctaca ttatcacaag taagggcaaa ggaaatgcta accttgagta taaaacaggc   420
gcattctcaa tgcccgaggt caatgtcgac tataatgcca gcagtgaaac attgcgctgt   480
gaagctcccc gctggttccc ccagccaacc gtggtctggg cctctcaggt tgatcagggg   540
gctaactttt ccgaggtgag caacaccagc ttcgaactca actctgagaa tgtgaccatg   600
aaagttgtgt ctgtcctgta taatgtaaca atcaacaaca cttattcatg catgattgaa   660
aacgacatcg ccaaggcaac aggtgatatt aaggtaactg aatccgagat caaacggcgg   720
tctgagccta agtcatgtga caagacccat acgtgcccac cctgtccgc tccagaactg   780
ctgggggga ctagcgtttt cttgttcccc ccaaagccca aggacaccct catgatctca   840
cggactcccg aagtaacatg cgtagtagtc gacgtgagcc acgaggatcc tgaagtgaag   900
tttaattggt acgtggacgg agtcgaggtg cataatgcca aaactaaacc tcgggaggag   960
cagtataaca gtacctaccg cgtggtatcc gtcttgacag tgctccacca ggactggctg  1020
aatggtaagg agtataaatg caaggtcagc aacaaagctc ttcccgcccc aattgaaaag  1080
actatcagca aggccaaggg acaaccccgc gagccccagg tttacaccct tccaccttca  1140
cgagacgagc tgaccaagaa ccaggtgtct ctgacttgtc tggtcaaagg tttctatcct  1200
tccgacatcg cagtggagtg ggagtcaaac ggcagcctga gaataacta caagaccaca  1260
ccccagtgc ttgatagcga tgggagcttt ttcctctaca gtaagctgac tgtggacaaa  1320
tcccgctggc agcagggaaa cgttttctct gtagcgtca tgcatgaggc ctccacaac  1380
cattatactc agaaaagcct gagtctgagt cccggcaaa                         1419
```

<210> SEQ ID NO 111
<211> LENGTH: 1404
<212> TYPE: DNA
<213> ORGANISM: Artificial Sequence
<220> FEATURE:
<223> OTHER INFORMATION: Synthetic fusion nucleotide

<400> SEQUENCE: 111

```
atggaatgga gctgggtatt tctgtttttc ctgtcagtaa cgactggcgt ccattcaggc      60
ttcggcatca gtggacggca cagtatcaca gtgaccaccg tcgcctccgc tggcaatata     120
ggtgaggatg gcatcctgtc ctgtacccttt gagccggaca tcaaactgtc tgacatagtg    180
atacaatggc tgaaggaggg ggtgctcggt ctggtacatg agtttaagga agggaaggat     240
gaactgtccg agcaggatga gatgttccgg ggggaggaccg ctgtgttcgc cgatcaggta    300
atcgtcggaa atgcaagtct cagattgaaa aatgtgcaac tgactgatgc tggcacgtat    360
aaatgctaca ttatcacaag taagggcaaa ggaaatgcta accttgagta taaaacaggc    420
gcattctcaa tgcccgaggt caatgtcgac tataatgcca gcagtgaaac attgcgctgt    480
gaagctcccc gctggttccc ccagccaacc gtggtctggg cctctcaggt tgatcagggg    540
gctaactttt ccgaggtgag caacaccagc ttcgaactca actctgagaa tgtgaccatg    600
aaagttgtgt ctgtcctgta taatgtaaca atcaacaaca cttattcatg catgattgaa    660
aacgacatcg ccaaggcaac aggtgatatt aaggtaactg aatccgagat caaacggcgg    720
tctgacaaga cccatacgtg cccaccctgt cccgctccag aactgctggg gggacctagc    780
gttttcttgt tcccccaaa gcccaaggac accctcatga tctcacggac tcccgaagta    840
acatgcgtag tagtcgacgt gagccacgag gatcctgaag tgaagtttaa ttggtacgtg    900
gacggagtcg aggtgcataa tgccaaaact aaacctcggg aggagcagta taacagtacc    960
taccgcgtgg tatccgtctt gacagtgctc caccaggact ggctgaatgg taaggagtat   1020
aaatgcaagg tcagcaacaa agctcttccc gccccaattg aaaagactat cagcaaggcc   1080
aagggacaac cccgcgagcc ccaggtttac accctttcac cttcacgaga cgagctgacc   1140
aagaaccagg tgtctctgac ttgtctggtc aaaggtttct atccttccga catcgcagtg   1200
gagtgggagt caaacgggca gcctgagaat aactacaaga ccacacccc agtgcttgat    1260
agcgatggga gcttttttcct ctacagtaag ctgactgtgg acaaatcccg ctggcagcag   1320
ggaaacgttt tctcttgtag cgtcatgcat gaggccctcc acaaccatta tactcagaaa   1380
agcctgagtc tgagtcccgg caaa                                          1404
```

<210> SEQ ID NO 112
<211> LENGTH: 1392
<212> TYPE: DNA
<213> ORGANISM: Artificial Sequence
<220> FEATURE:
<223> OTHER INFORMATION: Synthetic fusion nucleotide

<400> SEQUENCE: 112

```
atggaatgga gctgggtatt tctgtttttc ctgtcagtaa cgactggcgt ccattcaggc      60
ttcggcatca gtggacggca cagtatcaca gtgaccaccg tcgcctccgc tggcaatata     120
ggtgaggatg gcatcctgtc ctgtaccttt gagccggaca tcaaactgtc tgacatagtg    180
atacaatggc tgaaggaggg ggtgctcggt ctggtacatg agtttaagga agggaaggat    240
gaactgtccg agcaggatga gatgttccgg ggggaggaccg ctgtgttcgc cgatcaggta   300
atcgtcggaa atgcaagtct cagattgaaa aatgtgcaac tgactgatgc tggcacgtat    360
```

```
aaatgctaca ttatcacaag taagggcaaa ggaaatgcta accttgagta taaaacaggc    420
gcattctcaa tgcccgaggt caatgtcgac tataatgcca gcagtgaaac attgcgctgt    480
gaagctcccc gctggttccc ccagccaacc gtggtctggg cctctcaggt tgatcagggg    540
gctaactttt ccgaggtgag caacaccagc ttcgaactca actctgagaa tgtgaccatg    600
aaagttgtgt ctgtcctgta taatgtaaca atcaacaaca cttattcatg catgattgaa    660
aacgacatcg ccaaggcaac aggtgatatt aaggtaactg aatccgagat cgacaagacc    720
catacgtgcc caccctgtcc cgctccagaa ctgctggggg gacctagcgt tttcttgttc    780
cccccaaagc ccaaggacac cctcatgatc tcacggactc ccgaagtaac atgcgtagta    840
gtcgacgtga gccacgagga tcctgaagtg aagtttaatt ggtacgtgga cggagtcgag    900
gtgcataatg ccaaaactaa acctcgggag gagcagtata acagtaccta ccgcgtggta    960
tccgtcttga cagtgctcca ccaggactgg ctgaatggta aggagtataa atgcaaggtc   1020
agcaacaaag ctcttcccgc cccaattgaa aagactatca gcaaggccaa gggacaaccc   1080
cgcgagcccc aggtttacac ccttccacct tcacgagacg agctgaccaa gaaccaggtg   1140
tctctgactt gtctggtcaa aggtttctat ccttccgaca tcgcagtgga gtgggagtca   1200
aacgggcagc ctgagaataa ctacaagacc acacccccag tgcttgatag cgatgggagc   1260
ttttccctct acagtaagct gactgtggac aaatcccgct ggcagcaggg aaacgttttc   1320
tcttgtagcg tcatgcatga ggccctccac aaccattata ctcagaaaag cctgagtctg   1380
agtcccggca aa                                                       1392
```

<210> SEQ ID NO 113
<211> LENGTH: 1428
<212> TYPE: DNA
<213> ORGANISM: Artificial Sequence
<220> FEATURE:
<223> OTHER INFORMATION: Synthetic fusion nucleotide

<400> SEQUENCE: 113

```
atggaatgga gctgggtatt tctgttttc ctgtcagtaa cgactggcgt ccattcaggc    60
ttcggcatca gtgacggca cagtatcaca gtgaccaccg tcgcctccgc tggcaatata   120
ggtgaggatg gcatcctgtc ctgtacccttt gagccggaca tcaaactgtc tgacatagtg   180
atacaatggc tgaaggaggg ggtgctcggt ctggtacatg agtttaagga agggaaggat   240
gaactgtccg agcaggatga gatgttccgg gggaggaccg ctgtgttcgc gatcaggta   300 atcgtcggaa atgcaagtct cagattgaaa aatgtgcaac tgactgatgc tggcacgtat   360
aaatgctaca ttatcacaag taagggcaaa ggaaatgcta accttgagta taaaacaggc   420
gcattctcaa tgcccgaggt caatgtcgac tataatgcca gcagtgaaac attgcgctgt   480
gaagctcccc gctggttccc ccagccaacc gtggtctggg cctctcaggt tgatcagggg   540
gctaactttt ccgaggtgag caacaccagc ttcgaactca actctgagaa tgtgaccatg   600
aaagttgtgt ctgtcctgta taatgtaaca atcaacaaca cttattcatg catgattgaa   660
aacgacatcg ccaaggcaac aggtgatatt aaggtaactg aatccgagat caaacggcgg   720
tctcacctgc agctgctgaa ctccaaggac aagacccata cgtgcccacc ctgtcccgct   780
ccagaactgc tggggggacc tagcgttttc ttgttccccc caaagcccaa ggacaccctc   840
atgatctcac ggactcccga agtaacatgc gtagtagtcg acgtgagcca cgaggatcct   900
gaagtgaagt ttaattggta cgtggacgga gtcgaggtgc ataatgccaa aactaaacct   960
```

-continued

```
cgggaggagc agtataacag tacctaccgc gtggtatccg tcttgacagt gctccaccag  1020
gactggctga atggtaagga gtataaatgc aaggtcagca acaaagctct tcccgcccca  1080
attgaaaaga ctatcagcaa ggccaaggga caaccccgcg agccccaggt ttacacccTt  1140
ccaccttcac gagacgagct gaccaagaac caggtgtctc tgacttgtct ggtcaaaggt  1200
ttctatcctt ccgacatcgc agtggagtgg gagtcaaacg gcagcctga gaataactac  1260 aagaccacac ccccagtgct tgatagcgat gggagctttt tcctctacag taagctgact  1320
gtggacaaat cccgctggca gcagggaaac gtttTctctt gtagcgtcat gcatgaggcc  1380
ctccacaacc attatactca gaaaagcctg agtctgagtc cggcaaa            1428
```

<210> SEQ ID NO 114
<211> LENGTH: 481
<212> TYPE: PRT
<213> ORGANISM: Artificial Sequence
<220> FEATURE:
<223> OTHER INFORMATION: Synthetis fusion protein

<400> SEQUENCE: 114

```
Met Ala Ser Leu Gly Gln Ile Leu Phe Trp Ser Ile Ile Ser Ile Ile
1               5                   10                  15

Ile Ile Leu Ala Gly Ala Ile Ala Leu Ile Ile Gly Phe Gly Ile Ser
                20                  25                  30

Gly Arg His Ser Ile Thr Val Thr Val Ala Ser Ala Gly Asn Ile
            35                  40                  45

Gly Glu Asp Gly Ile Gln Ser Cys Thr Phe Glu Pro Asp Ile Lys Leu
        50                  55                  60

Ser Asp Ile Val Ile Gln Trp Leu Lys Glu Gly Val Leu Gly Leu Val
65                  70                  75                  80

His Glu Phe Lys Glu Gly Lys Asp Glu Leu Ser Glu Gln Asp Glu Met
                85                  90                  95

Phe Arg Gly Arg Thr Ala Val Phe Ala Asp Gln Val Ile Val Gly Asn
            100                 105                 110

Ala Ser Leu Arg Leu Lys Asn Val Gln Leu Thr Asp Ala Gly Thr Tyr
        115                 120                 125

Lys Cys Tyr Ile Ile Thr Ser Lys Gly Lys Gly Asn Ala Asn Leu Glu
    130                 135                 140

Tyr Lys Thr Gly Ala Phe Ser Met Pro Glu Val Asn Val Asp Tyr Asn
145                 150                 155                 160

Ala Ser Ser Glu Thr Leu Arg Cys Glu Ala Pro Arg Trp Phe Pro Gln
                165                 170                 175

Pro Thr Val Val Trp Ala Ser Gln Val Asp Gln Gly Ala Asn Phe Ser
            180                 185                 190

Glu Val Ser Asn Thr Ser Phe Glu Leu Asn Ser Glu Asn Val Thr Met
        195                 200                 205

Lys Val Val Ser Val Leu Tyr Asn Val Thr Ile Asn Asn Thr Tyr Ser
    210                 215                 220

Cys Met Ile Glu Asn Asp Ile Ala Lys Ala Thr Gly Asp Ile Lys Val
225                 230                 235                 240

Thr Glu Ser Glu Ile Lys Arg Arg Ser Glu Pro Lys Ser Cys Asp Lys
                245                 250                 255

Thr His Thr Cys Pro Pro Cys Pro Ala Pro Glu Leu Leu Gly Gly Pro
            260                 265                 270

Ser Val Phe Leu Phe Pro Pro Lys Pro Lys Asp Thr Leu Met Ile Ser
        275                 280                 285
```

```
Arg Thr Pro Glu Val Thr Cys Val Val Asp Val Ser His Glu Asp
            290                 295                 300

Pro Glu Val Lys Phe Asn Trp Tyr Val Asp Gly Val Glu Val His Asn
305                 310                 315                 320

Ala Lys Thr Lys Pro Arg Glu Glu Gln Tyr Asn Ser Thr Tyr Arg Val
                325                 330                 335

Val Ser Val Leu Thr Val Leu His Gln Asp Trp Leu Asn Gly Lys Glu
            340                 345                 350

Tyr Lys Cys Lys Val Ser Asn Lys Ala Leu Pro Ala Pro Ile Glu Lys
        355                 360                 365

Thr Ile Ser Lys Ala Lys Gly Gln Pro Arg Glu Pro Gln Val Tyr Thr
    370                 375                 380

Leu Pro Pro Ser Arg Asp Glu Leu Thr Lys Asn Gln Val Ser Leu Thr
385                 390                 395                 400

Cys Leu Val Lys Gly Phe Tyr Pro Ser Asp Ile Ala Val Glu Trp Glu
                405                 410                 415

Ser Asn Gly Gln Pro Glu Asn Asn Tyr Lys Thr Thr Pro Pro Val Leu
            420                 425                 430

Asp Ser Asp Gly Ser Phe Phe Leu Tyr Ser Lys Leu Thr Val Asp Lys
        435                 440                 445

Ser Arg Trp Gln Gln Gly Asn Val Phe Ser Cys Ser Val Met His Glu
450                 455                 460

Ala Leu His Asn His Tyr Thr Gln Lys Ser Leu Ser Leu Ser Pro Gly
465                 470                 475                 480

Lys

<210> SEQ ID NO 115
<211> LENGTH: 536
<212> TYPE: PRT
<213> ORGANISM: Artificial Sequence
<220> FEATURE:
<223> OTHER INFORMATION: Synthetic fusion protein

<400> SEQUENCE: 115

Met Ala Ser Leu Gly Gln Ile Leu Phe Trp Ser Ile Ile Ser Ile Ile
1               5                   10                  15

Ile Ile Leu Ala Gly Ala Ile Ala Leu Ile Ile Gly Phe Gly Ile Ser
            20                  25                  30

Gly Arg His Ser Ile Thr Val Thr Thr Val Ala Ser Ala Gly Asn Ile
        35                  40                  45

Gly Glu Asp Gly Ile Gln Ser Cys Thr Phe Glu Pro Met Ala Ser Leu
    50                  55                  60

Gly Gln Ile Leu Phe Trp Ser Ile Ile Ser Ile Ile Ile Ile Leu Ala
65                  70                  75                  80

Gly Ala Ile Ala Leu Ile Ile Gly Phe Gly Ile Ser Gly Arg His Ser
                85                  90                  95

Ile Thr Val Thr Thr Val Ala Ser Ala Gly Asn Ile Gly Glu Asp Gly
            100                 105                 110

Ile Gln Ser Cys Thr Phe Glu Pro Asp Ile Lys Leu Ser Asp Ile Val
        115                 120                 125

Ile Gln Trp Leu Lys Glu Gly Val Leu Gly Leu Val His Glu Phe Lys
    130                 135                 140

Glu Gly Lys Asp Glu Leu Ser Glu Gln Asp Glu Met Phe Arg Gly Arg
145                 150                 155                 160
```

```
Thr Ala Val Phe Ala Asp Gln Val Ile Val Gly Asn Ala Ser Leu Arg
                165                 170                 175
Leu Lys Asn Val Gln Leu Thr Asp Ala Gly Thr Tyr Lys Cys Tyr Ile
            180                 185                 190
Ile Thr Ser Lys Gly Lys Gly Asn Ala Asn Leu Glu Tyr Lys Thr Gly
        195                 200                 205
Ala Phe Ser Met Pro Glu Val Asn Val Asp Tyr Asn Ala Ser Ser Glu
    210                 215                 220
Thr Leu Arg Cys Glu Ala Pro Arg Trp Phe Pro Gln Pro Thr Val Val
225                 230                 235                 240
Trp Ala Ser Gln Val Asp Gln Gly Ala Asn Phe Ser Glu Val Ser Asn
                245                 250                 255
Thr Ser Phe Glu Leu Asn Ser Glu Asn Val Thr Met Lys Val Val Ser
            260                 265                 270
Val Leu Tyr Asn Val Thr Ile Asn Asn Thr Tyr Ser Cys Met Ile Glu
        275                 280                 285
Asn Asp Ile Ala Lys Ala Thr Gly Asp Ile Lys Val Thr Glu Ser Glu
    290                 295                 300
Ile Lys Arg Arg Ser Asp Lys Thr His Thr Cys Pro Pro Cys Pro Ala
305                 310                 315                 320
Pro Glu Leu Leu Gly Gly Pro Ser Val Phe Leu Phe Pro Pro Lys Pro
                325                 330                 335
Lys Asp Thr Leu Met Ile Ser Arg Thr Pro Glu Val Thr Cys Val Val
            340                 345                 350
Val Asp Val Ser His Glu Asp Pro Glu Val Lys Phe Asn Trp Tyr Val
        355                 360                 365
Asp Gly Val Glu Val His Asn Ala Lys Thr Lys Pro Arg Glu Glu Gln
    370                 375                 380
Tyr Asn Ser Thr Tyr Arg Val Val Ser Val Leu Thr Val Leu His Gln
385                 390                 395                 400
Asp Trp Leu Asn Gly Lys Glu Tyr Lys Cys Lys Val Ser Asn Lys Ala
                405                 410                 415
Leu Pro Ala Pro Ile Glu Lys Thr Ile Ser Lys Ala Lys Gly Gln Pro
            420                 425                 430
Arg Glu Pro Gln Val Tyr Thr Leu Pro Pro Ser Arg Asp Glu Leu Thr
        435                 440                 445
Lys Asn Gln Val Ser Leu Thr Cys Leu Val Lys Gly Phe Tyr Pro Ser
    450                 455                 460
Asp Ile Ala Val Glu Trp Glu Ser Asn Gly Gln Pro Glu Asn Asn Tyr
465                 470                 475                 480
Lys Thr Thr Pro Pro Val Leu Asp Ser Asp Gly Ser Phe Phe Leu Tyr
                485                 490                 495
Ser Lys Leu Thr Val Asp Lys Ser Arg Trp Gln Gln Gly Asn Val Phe
            500                 505                 510
Ser Cys Ser Val Met His Glu Ala Leu His Asn His Tyr Thr Gln Lys
        515                 520                 525
Ser Leu Ser Leu Ser Pro Gly Lys
    530                 535

<210> SEQ ID NO 116
<211> LENGTH: 472
<212> TYPE: PRT
<213> ORGANISM: Artificial Sequence
<220> FEATURE:
<223> OTHER INFORMATION: Synthetic fusion protein
```

<400> SEQUENCE: 116

```
Met Ala Ser Leu Gly Gln Ile Leu Phe Trp Ser Ile Ile Ser Ile Ile
1               5                   10                  15

Ile Ile Leu Ala Gly Ala Ile Ala Leu Ile Ile Gly Phe Gly Ile Ser
            20                  25                  30

Gly Arg His Ser Ile Thr Val Thr Val Ala Ser Ala Gly Asn Ile
        35                  40                  45

Gly Glu Asp Gly Ile Gln Ser Cys Thr Phe Glu Pro Asp Ile Lys Leu
50                  55                  60

Ser Asp Ile Val Ile Gln Trp Leu Lys Glu Gly Val Leu Gly Leu Val
65                  70                  75                  80

His Glu Phe Lys Glu Gly Lys Asp Glu Leu Ser Glu Gln Asp Glu Met
                85                  90                  95

Phe Arg Gly Arg Thr Ala Val Phe Ala Asp Gln Val Ile Val Gly Asn
            100                 105                 110

Ala Ser Leu Arg Leu Lys Asn Val Gln Leu Thr Asp Ala Gly Thr Tyr
        115                 120                 125

Lys Cys Tyr Ile Ile Thr Ser Lys Gly Lys Gly Asn Ala Asn Leu Glu
130                 135                 140

Tyr Lys Thr Gly Ala Phe Ser Met Pro Glu Val Asn Val Asp Tyr Asn
145                 150                 155                 160

Ala Ser Ser Glu Thr Leu Arg Cys Glu Ala Pro Arg Trp Phe Pro Gln
                165                 170                 175

Pro Thr Val Val Trp Ala Ser Gln Val Asp Gln Gly Ala Asn Phe Ser
            180                 185                 190

Glu Val Ser Asn Thr Ser Phe Glu Leu Asn Ser Glu Asn Val Thr Met
        195                 200                 205

Lys Val Val Ser Val Leu Tyr Asn Val Thr Ile Asn Asn Thr Tyr Ser
210                 215                 220

Cys Met Ile Glu Asn Asp Ile Ala Lys Ala Thr Gly Asp Ile Lys Val
225                 230                 235                 240

Thr Glu Ser Glu Ile Asp Lys Thr His Thr Cys Pro Pro Cys Pro Ala
                245                 250                 255

Pro Glu Leu Leu Gly Gly Pro Ser Val Phe Leu Phe Pro Pro Lys Pro
            260                 265                 270

Lys Asp Thr Leu Met Ile Ser Arg Thr Pro Glu Val Thr Cys Val Val
        275                 280                 285

Val Asp Val Ser His Glu Asp Pro Glu Val Lys Phe Asn Trp Tyr Val
290                 295                 300

Asp Gly Val Glu Val His Asn Ala Lys Thr Lys Pro Arg Glu Glu Gln
305                 310                 315                 320

Tyr Asn Ser Thr Tyr Arg Val Val Ser Val Leu Thr Val Leu His Gln
                325                 330                 335

Asp Trp Leu Asn Gly Lys Glu Tyr Lys Cys Lys Val Ser Asn Lys Ala
            340                 345                 350

Leu Pro Ala Pro Ile Glu Lys Thr Ile Ser Lys Ala Lys Gly Gln Pro
        355                 360                 365

Arg Glu Pro Gln Val Tyr Thr Leu Pro Pro Ser Arg Asp Glu Leu Thr
370                 375                 380

Lys Asn Gln Val Ser Leu Thr Cys Leu Val Lys Gly Phe Tyr Pro Ser
385                 390                 395                 400

Asp Ile Ala Val Glu Trp Glu Ser Asn Gly Gln Pro Glu Asn Asn Tyr
```

405              410              415
Lys Thr Thr Pro Pro Val Leu Asp Ser Asp Gly Ser Phe Phe Leu Tyr
            420              425              430

Ser Lys Leu Thr Val Asp Lys Ser Arg Trp Gln Gln Gly Asn Val Phe
            435              440              445

Ser Cys Ser Val Met His Glu Ala Leu His Asn His Tyr Thr Gln Lys
            450              455              460

Ser Leu Ser Leu Ser Pro Gly Lys
465              470

<210> SEQ ID NO 117
<211> LENGTH: 484
<212> TYPE: PRT
<213> ORGANISM: Artificial Sequence
<220> FEATURE:
<223> OTHER INFORMATION: Synthetic fusion protein

<400> SEQUENCE: 117

Met Ala Ser Leu Gly Gln Ile Leu Phe Trp Ser Ile Ile Ser Ile Ile
1               5                10               15

Ile Ile Leu Ala Gly Ala Ile Ala Leu Ile Ile Gly Phe Gly Ile Ser
            20               25               30

Gly Arg His Ser Ile Thr Val Thr Thr Val Ala Ser Ala Gly Asn Ile
        35               40               45

Gly Glu Asp Gly Ile Gln Ser Cys Thr Phe Glu Pro Asp Ile Lys Leu
    50               55               60

Ser Asp Ile Val Ile Gln Trp Leu Lys Glu Gly Val Leu Gly Leu Val
65               70               75               80

His Glu Phe Lys Glu Gly Lys Asp Glu Leu Ser Glu Gln Asp Glu Met
            85               90               95

Phe Arg Gly Arg Thr Ala Val Phe Ala Asp Gln Val Ile Val Gly Asn
            100              105              110

Ala Ser Leu Arg Leu Lys Asn Val Gln Leu Thr Asp Ala Gly Thr Tyr
            115              120              125

Lys Cys Tyr Ile Ile Thr Ser Lys Gly Lys Gly Asn Ala Asn Leu Glu
        130              135              140

Tyr Lys Thr Gly Ala Phe Ser Met Pro Glu Val Asn Val Asp Tyr Asn
145              150              155              160

Ala Ser Ser Glu Thr Leu Arg Cys Glu Ala Pro Arg Trp Phe Pro Gln
            165              170              175

Pro Thr Val Val Trp Ala Ser Gln Val Asp Gln Gly Ala Asn Phe Ser
            180              185              190

Glu Val Ser Asn Thr Ser Phe Glu Leu Asn Ser Glu Asn Val Thr Met
            195              200              205

Lys Val Val Ser Val Leu Tyr Asn Val Thr Ile Asn Asn Thr Tyr Ser
        210              215              220

Cys Met Ile Glu Asn Asp Ile Ala Lys Ala Thr Gly Asp Ile Lys Val
225              230              235              240

Thr Glu Ser Glu Ile Lys Arg Arg Ser His Leu Gln Leu Leu Asn Ser
            245              250              255

Lys Asp Lys Thr His Thr Cys Pro Pro Cys Pro Ala Pro Glu Leu Leu
            260              265              270

Gly Gly Pro Ser Val Phe Leu Phe Pro Pro Lys Pro Lys Asp Thr Leu
        275              280              285

Met Ile Ser Arg Thr Pro Glu Val Thr Cys Val Val Val Asp Val Ser

```
               290                 295                 300

His Glu Asp Pro Glu Val Lys Phe Asn Trp Tyr Val Asp Gly Val Glu
305                 310                 315                 320

Val His Asn Ala Lys Thr Lys Pro Arg Glu Glu Gln Tyr Asn Ser Thr
                325                 330                 335

Tyr Arg Val Val Ser Val Leu Thr Val Leu His Gln Asp Trp Leu Asn
                340                 345                 350

Gly Lys Glu Tyr Lys Cys Lys Val Ser Asn Lys Ala Leu Pro Ala Pro
            355                 360                 365

Ile Glu Lys Thr Ile Ser Lys Ala Lys Gly Gln Pro Arg Glu Pro Gln
        370                 375                 380

Val Tyr Thr Leu Pro Pro Ser Arg Asp Glu Leu Thr Lys Asn Gln Val
385                 390                 395                 400

Ser Leu Thr Cys Leu Val Lys Gly Phe Tyr Pro Ser Asp Ile Ala Val
                405                 410                 415

Glu Trp Glu Ser Asn Gly Gln Pro Glu Asn Asn Tyr Lys Thr Thr Pro
                420                 425                 430

Pro Val Leu Asp Ser Asp Gly Ser Phe Phe Leu Tyr Ser Lys Leu Thr
            435                 440                 445

Val Asp Lys Ser Arg Trp Gln Gln Gly Asn Val Phe Ser Cys Ser Val
        450                 455                 460

Met His Glu Ala Leu His Asn His Tyr Thr Gln Lys Ser Leu Ser Leu
465                 470                 475                 480

Ser Pro Gly Lys

<210> SEQ ID NO 118
<211> LENGTH: 481
<212> TYPE: PRT
<213> ORGANISM: Artificial Sequence
<220> FEATURE:
<223> OTHER INFORMATION: Synthetic fusion protein

<400> SEQUENCE: 118

Met Ala Ser Leu Gly Gln Ile Leu Phe Trp Ser Ile Ile Ser Ile Ile
1               5                   10                  15

Ile Ile Leu Ala Gly Ala Ile Ala Leu Ile Ile Gly Phe Gly Ile Ser
                20                  25                  30

Gly Arg His Ser Ile Thr Val Thr Val Ala Ser Ala Gly Asn Ile
            35                  40                  45

Gly Glu Asp Gly Ile Leu Ser Cys Thr Phe Glu Pro Asp Ile Lys Leu
        50                  55                  60

Ser Asp Ile Val Ile Gln Trp Leu Lys Glu Gly Val Leu Gly Leu Val
65                  70                  75                  80

His Glu Phe Lys Glu Gly Lys Asp Glu Leu Ser Glu Gln Asp Glu Met
                85                  90                  95

Phe Arg Gly Arg Thr Ala Val Phe Ala Asp Gln Val Ile Val Gly Asn
                100                 105                 110

Ala Ser Leu Arg Leu Lys Asn Val Gln Leu Thr Asp Ala Gly Thr Tyr
            115                 120                 125

Lys Cys Tyr Ile Ile Thr Ser Lys Gly Lys Gly Asn Ala Asn Leu Glu
        130                 135                 140

Tyr Lys Thr Gly Ala Phe Ser Met Pro Glu Val Asn Val Asp Tyr Asn
145                 150                 155                 160

Ala Ser Ser Glu Thr Leu Arg Cys Glu Ala Pro Arg Trp Phe Pro Gln
                165                 170                 175
```

```
Pro Thr Val Val Trp Ala Ser Gln Val Asp Gln Gly Ala Asn Phe Ser
            180                 185                 190

Glu Val Ser Asn Thr Ser Phe Glu Leu Asn Ser Glu Asn Val Thr Met
            195                 200                 205

Lys Val Val Ser Val Leu Tyr Asn Val Thr Ile Asn Asn Thr Tyr Ser
            210                 215                 220

Cys Met Ile Glu Asn Asp Ile Ala Lys Ala Thr Gly Asp Ile Lys Val
225                 230                 235                 240

Thr Glu Ser Glu Ile Lys Arg Arg Ser Glu Pro Lys Ser Cys Asp Lys
                245                 250                 255

Thr His Thr Cys Pro Pro Cys Pro Ala Pro Glu Leu Leu Gly Gly Pro
            260                 265                 270

Ser Val Phe Leu Phe Pro Pro Lys Pro Lys Asp Thr Leu Met Ile Ser
            275                 280                 285

Arg Thr Pro Glu Val Thr Cys Val Val Val Asp Val Ser His Glu Asp
            290                 295                 300

Pro Glu Val Lys Phe Asn Trp Tyr Val Asp Gly Val Glu Val His Asn
305                 310                 315                 320

Ala Lys Thr Lys Pro Arg Glu Glu Gln Tyr Asn Ser Thr Tyr Arg Val
                325                 330                 335

Val Ser Val Leu Thr Val Leu His Gln Asp Trp Leu Asn Gly Lys Glu
            340                 345                 350

Tyr Lys Cys Lys Val Ser Asn Lys Ala Leu Pro Ala Pro Ile Glu Lys
            355                 360                 365

Thr Ile Ser Lys Ala Lys Gly Gln Pro Arg Glu Pro Gln Val Tyr Thr
            370                 375                 380

Leu Pro Pro Ser Arg Asp Glu Leu Thr Lys Asn Gln Val Ser Leu Thr
385                 390                 395                 400

Cys Leu Val Lys Gly Phe Tyr Pro Ser Asp Ile Ala Val Glu Trp Glu
                405                 410                 415

Ser Asn Gly Gln Pro Glu Asn Asn Tyr Lys Thr Thr Pro Pro Val Leu
            420                 425                 430

Asp Ser Asp Gly Ser Phe Phe Leu Tyr Ser Lys Leu Thr Val Asp Lys
            435                 440                 445

Ser Arg Trp Gln Gln Gly Asn Val Phe Ser Cys Ser Val Met His Glu
450                 455                 460

Ala Leu His Asn His Tyr Thr Gln Lys Ser Leu Ser Leu Ser Pro Gly
465                 470                 475                 480

Lys

<210> SEQ ID NO 119
<211> LENGTH: 476
<212> TYPE: PRT
<213> ORGANISM: Artificial Sequence
<220> FEATURE:
<223> OTHER INFORMATION: Synthetic fusion protein

<400> SEQUENCE: 119

Met Ala Ser Leu Gly Gln Ile Leu Phe Trp Ser Ile Ile Ser Ile Ile
1               5                   10                  15

Ile Ile Leu Ala Gly Ala Ile Ala Leu Ile Ile Gly Phe Gly Ile Ser
            20                  25                  30

Gly Arg His Ser Ile Thr Val Thr Val Ala Ser Ala Gly Asn Ile
        35                  40                  45
```

Gly Glu Asp Gly Ile Leu Ser Cys Thr Phe Glu Pro Asp Ile Lys Leu
 50                  55                  60

Ser Asp Ile Val Ile Gln Trp Leu Lys Glu Gly Val Leu Gly Leu Val
 65                  70                  75                  80

His Glu Phe Lys Glu Gly Lys Asp Glu Leu Ser Glu Gln Asp Glu Met
                 85                  90                  95

Phe Arg Gly Arg Thr Ala Val Phe Ala Asp Gln Val Ile Val Gly Asn
            100                 105                 110

Ala Ser Leu Arg Leu Lys Asn Val Gln Leu Thr Asp Ala Gly Thr Tyr
        115                 120                 125

Lys Cys Tyr Ile Ile Thr Ser Lys Gly Lys Gly Asn Ala Asn Leu Glu
130                 135                 140

Tyr Lys Thr Gly Ala Phe Ser Met Pro Glu Val Asn Val Asp Tyr Asn
145                 150                 155                 160

Ala Ser Ser Glu Thr Leu Arg Cys Glu Ala Pro Arg Trp Phe Pro Gln
                165                 170                 175

Pro Thr Val Val Trp Ala Ser Gln Val Asp Gln Gly Ala Asn Phe Ser
            180                 185                 190

Glu Val Ser Asn Thr Ser Phe Glu Leu Asn Ser Glu Asn Val Thr Met
        195                 200                 205

Lys Val Val Ser Val Leu Tyr Asn Val Thr Ile Asn Asn Thr Tyr Ser
210                 215                 220

Cys Met Ile Glu Asn Asp Ile Ala Lys Ala Thr Gly Asp Ile Lys Val
225                 230                 235                 240

Thr Glu Ser Glu Ile Lys Arg Arg Ser Asp Lys Thr His Thr Cys Pro
                245                 250                 255

Pro Cys Pro Ala Pro Glu Leu Leu Gly Gly Pro Ser Val Phe Leu Phe
            260                 265                 270

Pro Pro Lys Pro Lys Asp Thr Leu Met Ile Ser Arg Thr Pro Glu Val
        275                 280                 285

Thr Cys Val Val Val Asp Val Ser His Glu Asp Pro Glu Val Lys Phe
290                 295                 300

Asn Trp Tyr Val Asp Gly Val Glu Val His Asn Ala Lys Thr Lys Pro
305                 310                 315                 320

Arg Glu Glu Gln Tyr Asn Ser Thr Tyr Arg Val Val Ser Val Leu Thr
                325                 330                 335

Val Leu His Gln Asp Trp Leu Asn Gly Lys Glu Tyr Lys Cys Lys Val
            340                 345                 350

Ser Asn Lys Ala Leu Pro Ala Pro Ile Glu Lys Thr Ile Ser Lys Ala
        355                 360                 365

Lys Gly Gln Pro Arg Glu Pro Gln Val Tyr Thr Leu Pro Pro Ser Arg
370                 375                 380

Asp Glu Leu Thr Lys Asn Gln Val Ser Leu Thr Cys Leu Val Lys Gly
385                 390                 395                 400

Phe Tyr Pro Ser Asp Ile Ala Val Glu Trp Glu Ser Asn Gly Gln Pro
                405                 410                 415

Glu Asn Asn Tyr Lys Thr Thr Pro Pro Val Leu Asp Ser Asp Gly Ser
            420                 425                 430

Phe Phe Leu Tyr Ser Lys Leu Thr Val Asp Lys Ser Arg Trp Gln Gln
        435                 440                 445

Gly Asn Val Phe Ser Cys Ser Val Met His Glu Ala Leu His Asn His
450                 455                 460

Tyr Thr Gln Lys Ser Leu Ser Leu Ser Pro Gly Lys 465            470            475

<210> SEQ ID NO 120
<211> LENGTH: 472
<212> TYPE: PRT
<213> ORGANISM: Artificial Sequence
<220> FEATURE:
<223> OTHER INFORMATION: Synthetic fusion protein

<400> SEQUENCE: 120

Met Ala Ser Leu Gly Gln Ile Leu Phe Trp Ser Ile Ile Ser Ile Ile
1               5                   10                  15

Ile Ile Leu Ala Gly Ala Ile Ala Leu Ile Ile Gly Phe Gly Ile Ser
            20                  25                  30

Gly Arg His Ser Ile Thr Val Thr Val Ala Ser Ala Gly Asn Ile
        35                  40                  45

Gly Glu Asp Gly Ile Leu Ser Cys Thr Phe Glu Pro Asp Ile Lys Leu
    50                  55                  60

Ser Asp Ile Val Ile Gln Trp Leu Lys Glu Gly Val Leu Gly Leu Val
65                  70                  75                  80

His Glu Phe Lys Glu Gly Lys Asp Glu Leu Ser Glu Gln Asp Glu Met
                85                  90                  95

Phe Arg Gly Arg Thr Ala Val Phe Ala Asp Gln Val Ile Val Gly Asn
            100                 105                 110

Ala Ser Leu Arg Leu Lys Asn Val Gln Leu Thr Asp Ala Gly Thr Tyr
        115                 120                 125

Lys Cys Tyr Ile Ile Thr Ser Lys Gly Lys Gly Asn Ala Asn Leu Glu
130                 135                 140

Tyr Lys Thr Gly Ala Phe Ser Met Pro Glu Val Asn Val Asp Tyr Asn
145                 150                 155                 160

Ala Ser Ser Glu Thr Leu Arg Cys Glu Ala Pro Arg Trp Phe Pro Gln
                165                 170                 175

Pro Thr Val Val Trp Ala Ser Gln Val Asp Gln Gly Ala Asn Phe Ser
            180                 185                 190

Glu Val Ser Asn Thr Ser Phe Glu Leu Asn Ser Glu Asn Val Thr Met
        195                 200                 205

Lys Val Val Ser Val Leu Tyr Asn Val Thr Ile Asn Asn Thr Tyr Ser
    210                 215                 220

Cys Met Ile Glu Asn Asp Ile Ala Lys Ala Thr Gly Asp Ile Lys Val
225                 230                 235                 240

Thr Glu Ser Glu Ile Asp Lys Thr His Thr Cys Pro Pro Cys Pro Ala
                245                 250                 255

Pro Glu Leu Leu Gly Gly Pro Ser Val Phe Leu Phe Pro Pro Lys Pro
            260                 265                 270

Lys Asp Thr Leu Met Ile Ser Arg Thr Pro Glu Val Thr Cys Val Val
        275                 280                 285

Val Asp Val Ser His Glu Asp Pro Glu Val Lys Phe Asn Trp Tyr Val
    290                 295                 300

Asp Gly Val Glu Val His Asn Ala Lys Thr Lys Pro Arg Glu Glu Gln
305                 310                 315                 320

Tyr Asn Ser Thr Tyr Arg Val Val Ser Val Leu Thr Val Leu His Gln
                325                 330                 335

Asp Trp Leu Asn Gly Lys Glu Tyr Lys Cys Lys Val Ser Asn Lys Ala
            340                 345                 350

Leu Pro Ala Pro Ile Glu Lys Thr Ile Ser Lys Ala Lys Gly Gln Pro

```
                355                 360                 365
Arg Glu Pro Gln Val Tyr Thr Leu Pro Pro Ser Arg Asp Glu Leu Thr
370                 375                 380
Lys Asn Gln Val Ser Leu Thr Cys Leu Val Lys Gly Phe Tyr Pro Ser
385                 390                 395                 400
Asp Ile Ala Val Glu Trp Glu Ser Asn Gly Gln Pro Glu Asn Asn Tyr
                405                 410                 415
Lys Thr Thr Pro Pro Val Leu Asp Ser Asp Gly Ser Phe Phe Leu Tyr
                420                 425                 430
Ser Lys Leu Thr Val Asp Lys Ser Arg Trp Gln Gln Gly Asn Val Phe
                435                 440                 445
Ser Cys Ser Val Met His Glu Ala Leu His Asn His Tyr Thr Gln Lys
                450                 455                 460
Ser Leu Ser Leu Ser Pro Gly Lys
465                 470

<210> SEQ ID NO 121
<211> LENGTH: 484
<212> TYPE: PRT
<213> ORGANISM: Artificial Sequence
<220> FEATURE:
<223> OTHER INFORMATION: Synthetic fusion protein

<400> SEQUENCE: 121

Met Ala Ser Leu Gly Gln Ile Leu Phe Trp Ser Ile Ser Ile Ile
1               5                   10                  15

Ile Ile Leu Ala Gly Ala Ile Ala Leu Ile Ile Gly Phe Gly Ile Ser
                20                  25                  30

Gly Arg His Ser Ile Thr Val Thr Thr Val Ala Ser Ala Gly Asn Ile
            35                  40                  45

Gly Glu Asp Gly Ile Leu Ser Cys Thr Phe Glu Pro Asp Ile Lys Leu
        50                  55                  60

Ser Asp Ile Val Ile Gln Trp Leu Lys Glu Gly Val Leu Gly Leu Val
65                  70                  75                  80

His Glu Phe Lys Glu Gly Lys Asp Glu Leu Ser Glu Gln Asp Glu Met
                85                  90                  95

Phe Arg Gly Arg Thr Ala Val Phe Ala Asp Gln Val Ile Val Gly Asn
            100                 105                 110

Ala Ser Leu Arg Leu Lys Asn Val Gln Leu Thr Asp Ala Gly Thr Tyr
        115                 120                 125

Lys Cys Tyr Ile Ile Thr Ser Lys Gly Lys Gly Asn Ala Asn Leu Glu
130                 135                 140

Tyr Lys Thr Gly Ala Phe Ser Met Pro Glu Val Asn Val Asp Tyr Asn
145                 150                 155                 160

Ala Ser Ser Glu Thr Leu Arg Cys Glu Ala Pro Arg Trp Phe Pro Gln
                165                 170                 175

Pro Thr Val Val Trp Ala Ser Gln Val Asp Gln Gly Ala Asn Phe Ser
            180                 185                 190

Glu Val Ser Asn Thr Ser Phe Glu Leu Asn Ser Glu Asn Val Thr Met
        195                 200                 205

Lys Val Val Ser Val Leu Tyr Asn Val Thr Ile Asn Asn Thr Tyr Ser
        210                 215                 220

Cys Met Ile Glu Asn Asp Ile Ala Lys Ala Thr Gly Asp Ile Lys Val
225                 230                 235                 240

Thr Glu Ser Glu Ile Lys Arg Arg Ser His Leu Gln Leu Leu Asn Ser
```

```
                245                 250                 255
Lys Asp Lys Thr His Thr Cys Pro Pro Cys Pro Ala Pro Glu Leu Leu
            260                 265                 270

Gly Gly Pro Ser Val Phe Leu Phe Pro Pro Lys Pro Lys Asp Thr Leu
        275                 280                 285

Met Ile Ser Arg Thr Pro Glu Val Thr Cys Val Val Val Asp Val Ser
    290                 295                 300

His Glu Asp Pro Glu Val Lys Phe Asn Trp Tyr Val Asp Gly Val Glu
305                 310                 315                 320

Val His Asn Ala Lys Thr Lys Pro Arg Glu Glu Gln Tyr Asn Ser Thr
                325                 330                 335

Tyr Arg Val Val Ser Val Leu Thr Val Leu His Gln Asp Trp Leu Asn
            340                 345                 350

Gly Lys Glu Tyr Lys Cys Lys Val Ser Asn Lys Ala Leu Pro Ala Pro
        355                 360                 365

Ile Glu Lys Thr Ile Ser Lys Ala Lys Gly Gln Pro Arg Glu Pro Gln
    370                 375                 380

Val Tyr Thr Leu Pro Pro Ser Arg Asp Glu Leu Thr Lys Asn Gln Val
385                 390                 395                 400

Ser Leu Thr Cys Leu Val Lys Gly Phe Tyr Pro Ser Asp Ile Ala Val
                405                 410                 415

Glu Trp Glu Ser Asn Gly Gln Pro Glu Asn Asn Tyr Lys Thr Thr Pro
            420                 425                 430

Pro Val Leu Asp Ser Asp Gly Ser Phe Phe Leu Tyr Ser Lys Leu Thr
        435                 440                 445

Val Asp Lys Ser Arg Trp Gln Gln Gly Asn Val Phe Ser Cys Ser Val
    450                 455                 460

Met His Glu Ala Leu His Asn His Tyr Thr Gln Lys Ser Leu Ser Leu
465                 470                 475                 480

Ser Pro Gly Lys

<210> SEQ ID NO 122
<211> LENGTH: 473
<212> TYPE: PRT
<213> ORGANISM: Artificial Sequence
<220> FEATURE:
<223> OTHER INFORMATION: Synthetic fusion protein

<400> SEQUENCE: 122

Met Glu Trp Ser Trp Val Phe Leu Phe Phe Leu Ser Val Thr Thr Gly
1               5                   10                  15

Val His Ser Gly Phe Gly Ile Ser Gly Arg His Ser Ile Thr Val Thr
            20                  25                  30

Thr Val Ala Ser Ala Gly Asn Ile Gly Glu Asp Gly Ile Gln Ser Cys
        35                  40                  45

Thr Phe Glu Pro Asp Ile Lys Leu Ser Asp Ile Val Ile Gln Trp Leu
    50                  55                  60

Lys Glu Gly Val Leu Gly Leu Val His Glu Phe Lys Glu Gly Lys Asp
65                  70                  75                  80

Glu Leu Ser Glu Gln Asp Glu Met Phe Arg Gly Arg Thr Ala Val Phe
                85                  90                  95

Ala Asp Gln Val Ile Val Gly Asn Ala Ser Leu Arg Leu Lys Asn Val
            100                 105                 110

Gln Leu Thr Asp Ala Gly Thr Tyr Lys Cys Tyr Ile Ile Thr Ser Lys
        115                 120                 125
```

Gly Lys Gly Asn Ala Asn Leu Glu Tyr Lys Thr Gly Ala Phe Ser Met
            130                 135                 140

Pro Glu Val Asn Val Asp Tyr Asn Ala Ser Ser Glu Thr Leu Arg Cys
145                 150                 155                 160

Glu Ala Pro Arg Trp Phe Pro Gln Pro Thr Val Val Trp Ala Ser Gln
                165                 170                 175

Val Asp Gln Gly Ala Asn Phe Ser Glu Val Ser Asn Thr Ser Phe Glu
            180                 185                 190

Leu Asn Ser Glu Asn Val Thr Met Lys Val Val Ser Val Leu Tyr Asn
        195                 200                 205

Val Thr Ile Asn Asn Thr Tyr Ser Cys Met Ile Glu Asn Asp Ile Ala
    210                 215                 220

Lys Ala Thr Gly Asp Ile Lys Val Thr Glu Ser Glu Ile Lys Arg Arg
225                 230                 235                 240

Ser Glu Pro Lys Ser Cys Asp Lys Thr His Thr Cys Pro Pro Cys Pro
                245                 250                 255

Ala Pro Glu Leu Leu Gly Gly Pro Ser Val Phe Leu Phe Pro Pro Lys
            260                 265                 270

Pro Lys Asp Thr Leu Met Ile Ser Arg Thr Pro Glu Val Thr Cys Val
        275                 280                 285

Val Val Asp Val Ser His Glu Asp Pro Glu Val Lys Phe Asn Trp Tyr
    290                 295                 300

Val Asp Gly Val Glu Val His Asn Ala Lys Thr Lys Pro Arg Glu Glu
305                 310                 315                 320

Gln Tyr Asn Ser Thr Tyr Arg Val Val Ser Val Leu Thr Val Leu His
                325                 330                 335

Gln Asp Trp Leu Asn Gly Lys Glu Tyr Lys Cys Lys Val Ser Asn Lys
            340                 345                 350

Ala Leu Pro Ala Pro Ile Glu Lys Thr Ile Ser Lys Ala Lys Gly Gln
        355                 360                 365

Pro Arg Glu Pro Gln Val Tyr Thr Leu Pro Pro Ser Arg Asp Glu Leu
    370                 375                 380

Thr Lys Asn Gln Val Ser Leu Thr Cys Leu Val Lys Gly Phe Tyr Pro
385                 390                 395                 400

Ser Asp Ile Ala Val Glu Trp Glu Ser Asn Gly Gln Pro Glu Asn Asn
                405                 410                 415

Tyr Lys Thr Thr Pro Pro Val Leu Asp Ser Asp Gly Ser Phe Phe Leu
            420                 425                 430

Tyr Ser Lys Leu Thr Val Asp Lys Ser Arg Trp Gln Gln Gly Asn Val
        435                 440                 445

Phe Ser Cys Ser Val Met His Glu Ala Leu His Asn His Tyr Thr Gln
    450                 455                 460

Lys Ser Leu Ser Leu Ser Pro Gly Lys
465                 470

<210> SEQ ID NO 123
<211> LENGTH: 468
<212> TYPE: PRT
<213> ORGANISM: Artificial Sequence
<220> FEATURE:
<223> OTHER INFORMATION: Synthetic fusion protein

<400> SEQUENCE: 123

Met Glu Trp Ser Trp Val Phe Leu Phe Phe Leu Ser Val Thr Thr Gly
1               5                   10                  15

```
Val His Ser Gly Phe Gly Ile Ser Gly Arg His Ser Ile Thr Val Thr
         20                  25                  30

Thr Val Ala Ser Ala Gly Asn Ile Gly Glu Asp Gly Ile Gln Ser Cys
         35                  40                  45

Thr Phe Glu Pro Asp Ile Lys Leu Ser Asp Ile Val Ile Gln Trp Leu
 50                  55                  60

Lys Glu Gly Val Leu Gly Leu Val His Glu Phe Lys Glu Gly Lys Asp
 65                  70                  75                  80

Glu Leu Ser Glu Gln Asp Glu Met Phe Arg Gly Arg Thr Ala Val Phe
             85                  90                  95

Ala Asp Gln Val Ile Val Gly Asn Ala Ser Leu Arg Leu Lys Asn Val
            100                 105                 110

Gln Leu Thr Asp Ala Gly Thr Tyr Lys Cys Tyr Ile Ile Thr Ser Lys
            115                 120                 125

Gly Lys Gly Asn Ala Asn Leu Glu Tyr Lys Thr Gly Ala Phe Ser Met
130                 135                 140

Pro Glu Val Asn Val Asp Tyr Asn Ala Ser Ser Glu Thr Leu Arg Cys
145                 150                 155                 160

Glu Ala Pro Arg Trp Phe Pro Gln Pro Thr Val Val Trp Ala Ser Gln
                165                 170                 175

Val Asp Gln Gly Ala Asn Phe Ser Glu Val Ser Asn Thr Ser Phe Glu
                180                 185                 190

Leu Asn Ser Glu Asn Val Thr Met Lys Val Val Ser Val Leu Tyr Asn
            195                 200                 205

Val Thr Ile Asn Asn Thr Tyr Ser Cys Met Ile Glu Asn Asp Ile Ala
            210                 215                 220

Lys Ala Thr Gly Asp Ile Lys Val Thr Glu Ser Glu Ile Lys Arg Arg
225                 230                 235                 240

Ser Asp Lys Thr His Thr Cys Pro Pro Cys Pro Ala Pro Glu Leu Leu
                245                 250                 255

Gly Gly Pro Ser Val Phe Leu Phe Pro Pro Lys Pro Lys Asp Thr Leu
            260                 265                 270

Met Ile Ser Arg Thr Pro Glu Val Thr Cys Val Val Val Asp Val Ser
            275                 280                 285

His Glu Asp Pro Glu Val Lys Phe Asn Trp Tyr Val Asp Gly Val Glu
290                 295                 300

Val His Asn Ala Lys Thr Lys Pro Arg Glu Glu Gln Tyr Asn Ser Thr
305                 310                 315                 320

Tyr Arg Val Val Ser Val Leu Thr Val Leu His Gln Asp Trp Leu Asn
                325                 330                 335

Gly Lys Glu Tyr Lys Cys Lys Val Ser Asn Lys Ala Leu Pro Ala Pro
            340                 345                 350

Ile Glu Lys Thr Ile Ser Lys Ala Lys Gly Gln Pro Arg Glu Pro Gln
            355                 360                 365

Val Tyr Thr Leu Pro Pro Ser Arg Asp Glu Leu Thr Lys Asn Gln Val
            370                 375                 380

Ser Leu Thr Cys Leu Val Lys Gly Phe Tyr Pro Ser Asp Ile Ala Val
385                 390                 395                 400

Glu Trp Glu Ser Asn Gly Gln Pro Glu Asn Asn Tyr Lys Thr Thr Pro
                405                 410                 415

Pro Val Leu Asp Ser Asp Gly Ser Phe Phe Leu Tyr Ser Lys Leu Thr
            420                 425                 430
```

Val Asp Lys Ser Arg Trp Gln Gln Gly Asn Val Phe Ser Cys Ser Val
            435                 440                 445
Met His Glu Ala Leu His Asn His Tyr Thr Gln Lys Ser Leu Ser Leu
    450                 455                 460
Ser Pro Gly Lys
465

<210> SEQ ID NO 124
<211> LENGTH: 464
<212> TYPE: PRT
<213> ORGANISM: Artificial Sequence
<220> FEATURE:
<223> OTHER INFORMATION: Synthetic fusion protein

<400> SEQUENCE: 124

Met Glu Trp Ser Trp Val Phe Leu Phe Phe Leu Ser Val Thr Thr Gly
1               5                   10                  15
Val His Ser Gly Phe Gly Ile Ser Gly Arg His Ser Ile Thr Val Thr
                20                  25                  30
Thr Val Ala Ser Ala Gly Asn Ile Gly Glu Asp Gly Ile Gln Ser Cys
            35                  40                  45
Thr Phe Glu Pro Asp Ile Lys Leu Ser Asp Ile Val Ile Gln Trp Leu
        50                  55                  60
Lys Glu Gly Val Leu Gly Leu Val His Glu Phe Lys Glu Gly Lys Asp
65                  70                  75                  80
Glu Leu Ser Glu Gln Asp Glu Met Phe Arg Gly Arg Thr Ala Val Phe
                85                  90                  95
Ala Asp Gln Val Ile Val Gly Asn Ala Ser Leu Arg Leu Lys Asn Val
            100                 105                 110
Gln Leu Thr Asp Ala Gly Thr Tyr Lys Cys Tyr Ile Ile Thr Ser Lys
        115                 120                 125
Gly Lys Gly Asn Ala Asn Leu Glu Tyr Lys Thr Gly Ala Phe Ser Met
130                 135                 140
Pro Glu Val Asn Val Asp Tyr Asn Ala Ser Ser Glu Thr Leu Arg Cys
145                 150                 155                 160
Glu Ala Pro Arg Trp Phe Pro Gln Pro Thr Val Val Trp Ala Ser Gln
                165                 170                 175
Val Asp Gln Gly Ala Asn Phe Ser Glu Val Ser Asn Thr Ser Phe Glu
            180                 185                 190
Leu Asn Ser Glu Asn Val Thr Met Lys Val Val Ser Val Leu Tyr Asn
        195                 200                 205
Val Thr Ile Asn Asn Thr Tyr Ser Cys Met Ile Glu Asn Asp Ile Ala
    210                 215                 220
Lys Ala Thr Gly Asp Ile Lys Val Thr Glu Ser Glu Ile Asp Lys Thr
225                 230                 235                 240
His Thr Cys Pro Pro Cys Pro Ala Pro Glu Leu Leu Gly Gly Pro Ser
                245                 250                 255
Val Phe Leu Phe Pro Pro Lys Pro Lys Asp Thr Leu Met Ile Ser Arg
            260                 265                 270
Thr Pro Glu Val Thr Cys Val Val Val Asp Val Ser His Glu Asp Pro
        275                 280                 285
Glu Val Lys Phe Asn Trp Tyr Val Asp Gly Val Glu Val His Asn Ala
    290                 295                 300
Lys Thr Lys Pro Arg Glu Glu Gln Tyr Asn Ser Thr Tyr Arg Val Val
305                 310                 315                 320

```
Ser Val Leu Thr Val Leu His Gln Asp Trp Leu Asn Gly Lys Glu Tyr
                325                 330                 335
Lys Cys Lys Val Ser Asn Lys Ala Leu Pro Ala Pro Ile Glu Lys Thr
            340                 345                 350
Ile Ser Lys Ala Lys Gly Gln Pro Arg Glu Pro Gln Val Tyr Thr Leu
            355                 360                 365
Pro Pro Ser Arg Asp Glu Leu Thr Lys Asn Gln Val Ser Leu Thr Cys
370                 375                 380
Leu Val Lys Gly Phe Tyr Pro Ser Asp Ile Ala Val Glu Trp Glu Ser
385                 390                 395                 400
Asn Gly Gln Pro Glu Asn Asn Tyr Lys Thr Thr Pro Pro Val Leu Asp
                405                 410                 415
Ser Asp Gly Ser Phe Phe Leu Tyr Ser Lys Leu Thr Val Asp Lys Ser
            420                 425                 430
Arg Trp Gln Gln Gly Asn Val Phe Ser Cys Ser Val Met His Glu Ala
            435                 440                 445
Leu His Asn His Tyr Thr Gln Lys Ser Leu Ser Leu Ser Pro Gly Lys
            450                 455                 460
```

<210> SEQ ID NO 125
<211> LENGTH: 476
<212> TYPE: PRT
<213> ORGANISM: Artificial Sequence
<220> FEATURE:
<223> OTHER INFORMATION: Synthetic fusion protein

<400> SEQUENCE: 125

```
Met Glu Trp Ser Trp Val Phe Leu Phe Phe Leu Ser Val Thr Thr Gly
1               5                   10                  15
Val His Ser Gly Phe Gly Ile Ser Gly Arg His Ser Ile Thr Val Thr
            20                  25                  30
Thr Val Ala Ser Ala Gly Asn Ile Gly Glu Asp Gly Ile Gln Ser Cys
        35                  40                  45
Thr Phe Glu Pro Asp Ile Lys Leu Ser Asp Ile Val Ile Gln Trp Leu
    50                  55                  60
Lys Glu Gly Val Leu Gly Leu Val His Glu Phe Lys Glu Gly Lys Asp
65                  70                  75                  80
Glu Leu Ser Glu Gln Asp Glu Met Phe Arg Gly Arg Thr Ala Val Phe
                85                  90                  95
Ala Asp Gln Val Ile Val Gly Asn Ala Ser Leu Arg Leu Lys Asn Val
            100                 105                 110
Gln Leu Thr Asp Ala Gly Thr Tyr Lys Cys Tyr Ile Ile Thr Ser Lys
        115                 120                 125
Gly Lys Gly Asn Ala Asn Leu Glu Tyr Lys Thr Gly Ala Phe Ser Met
    130                 135                 140
Pro Glu Val Asn Val Asp Tyr Asn Ala Ser Ser Glu Thr Leu Arg Cys
145                 150                 155                 160
Glu Ala Pro Arg Trp Phe Pro Gln Pro Thr Val Val Trp Ala Ser Gln
                165                 170                 175
Val Asp Gln Gly Ala Asn Phe Ser Glu Val Ser Asn Thr Ser Phe Glu
            180                 185                 190
Leu Asn Ser Glu Asn Val Thr Met Lys Val Val Ser Val Leu Tyr Asn
        195                 200                 205
Val Thr Ile Asn Asn Thr Tyr Ser Cys Met Ile Glu Asn Asp Ile Ala
    210                 215                 220
```

```
Lys Ala Thr Gly Asp Ile Lys Val Thr Glu Ser Glu Ile Lys Arg Arg
225                 230                 235                 240

Ser His Leu Gln Leu Leu Asn Ser Lys Asp Lys Thr His Thr Cys Pro
            245                 250                 255

Pro Cys Pro Ala Pro Glu Leu Leu Gly Gly Pro Ser Val Phe Leu Phe
            260                 265                 270

Pro Pro Lys Pro Lys Asp Thr Leu Met Ile Ser Arg Thr Pro Glu Val
            275                 280                 285

Thr Cys Val Val Val Asp Val Ser His Glu Asp Pro Glu Val Lys Phe
            290                 295                 300

Asn Trp Tyr Val Asp Gly Val Glu Val His Asn Ala Lys Thr Lys Pro
305                 310                 315                 320

Arg Glu Glu Gln Tyr Asn Ser Thr Tyr Arg Val Val Ser Val Leu Thr
            325                 330                 335

Val Leu His Gln Asp Trp Leu Asn Gly Lys Glu Tyr Lys Cys Lys Val
            340                 345                 350

Ser Asn Lys Ala Leu Pro Ala Pro Ile Glu Lys Thr Ile Ser Lys Ala
            355                 360                 365

Lys Gly Gln Pro Arg Glu Pro Gln Val Tyr Thr Leu Pro Pro Ser Arg
370                 375                 380

Asp Glu Leu Thr Lys Asn Gln Val Ser Leu Thr Cys Leu Val Lys Gly
385                 390                 395                 400

Phe Tyr Pro Ser Asp Ile Ala Val Glu Trp Glu Ser Asn Gly Gln Pro
            405                 410                 415

Glu Asn Asn Tyr Lys Thr Thr Pro Pro Val Leu Asp Ser Asp Gly Ser
            420                 425                 430

Phe Phe Leu Tyr Ser Lys Leu Thr Val Asp Lys Ser Arg Trp Gln Gln
            435                 440                 445

Gly Asn Val Phe Ser Cys Ser Val Met His Glu Ala Leu His Asn His
    450                 455                 460

Tyr Thr Gln Lys Ser Leu Ser Leu Ser Pro Gly Lys
465                 470                 475

<210> SEQ ID NO 126
<211> LENGTH: 473
<212> TYPE: PRT
<213> ORGANISM: Artificial Sequence
<220> FEATURE:
<223> OTHER INFORMATION: Synthetic fusion protein

<400> SEQUENCE: 126

Met Glu Trp Ser Trp Val Phe Leu Phe Phe Leu Ser Val Thr Thr Gly
1               5                   10                  15

Val His Ser Gly Phe Gly Ile Ser Gly Arg His Ser Ile Thr Val Thr
            20                  25                  30

Thr Val Ala Ser Ala Gly Asn Ile Gly Glu Asp Gly Ile Leu Ser Cys
        35                  40                  45

Thr Phe Glu Pro Asp Ile Lys Leu Ser Asp Ile Val Ile Gln Trp Leu
    50                  55                  60

Lys Glu Gly Val Leu Gly Leu Val His Glu Phe Lys Glu Gly Lys Asp
65                  70                  75                  80

Glu Leu Ser Glu Gln Asp Glu Met Phe Arg Gly Arg Thr Ala Val Phe
            85                  90                  95

Ala Asp Gln Val Ile Val Gly Asn Ala Ser Leu Arg Leu Lys Asn Val
            100                 105                 110
```

Gln Leu Thr Asp Ala Gly Thr Tyr Lys Cys Tyr Ile Ile Thr Ser Lys
115                 120                 125

Gly Lys Gly Asn Ala Asn Leu Glu Tyr Lys Thr Gly Ala Phe Ser Met
130                 135                 140

Pro Glu Val Asn Val Asp Tyr Asn Ala Ser Ser Glu Thr Leu Arg Cys
145                 150                 155                 160

Glu Ala Pro Arg Trp Phe Pro Gln Pro Thr Val Val Trp Ala Ser Gln
                165                 170                 175

Val Asp Gln Gly Ala Asn Phe Ser Glu Val Ser Asn Thr Ser Phe Glu
                180                 185                 190

Leu Asn Ser Glu Asn Val Thr Met Lys Val Val Ser Val Leu Tyr Asn
                195                 200                 205

Val Thr Ile Asn Asn Thr Tyr Ser Cys Met Ile Glu Asn Asp Ile Ala
210                 215                 220

Lys Ala Thr Gly Asp Ile Lys Val Thr Glu Ser Glu Ile Lys Arg Arg
225                 230                 235                 240

Ser Glu Pro Lys Ser Cys Asp Lys Thr His Thr Cys Pro Pro Cys Pro
                245                 250                 255

Ala Pro Glu Leu Leu Gly Gly Pro Ser Val Phe Leu Phe Pro Pro Lys
                260                 265                 270

Pro Lys Asp Thr Leu Met Ile Ser Arg Thr Pro Glu Val Thr Cys Val
                275                 280                 285

Val Val Asp Val Ser His Glu Asp Pro Glu Val Lys Phe Asn Trp Tyr
                290                 295                 300

Val Asp Gly Val Glu Val His Asn Ala Lys Thr Lys Pro Arg Glu Glu
305                 310                 315                 320

Gln Tyr Asn Ser Thr Tyr Arg Val Val Ser Val Leu Thr Val Leu His
                325                 330                 335

Gln Asp Trp Leu Asn Gly Lys Glu Tyr Lys Cys Lys Val Ser Asn Lys
                340                 345                 350

Ala Leu Pro Ala Pro Ile Glu Lys Thr Ile Ser Lys Ala Lys Gly Gln
                355                 360                 365

Pro Arg Glu Pro Gln Val Tyr Thr Leu Pro Pro Ser Arg Asp Glu Leu
370                 375                 380

Thr Lys Asn Gln Val Ser Leu Thr Cys Leu Val Lys Gly Phe Tyr Pro
385                 390                 395                 400

Ser Asp Ile Ala Val Glu Trp Glu Ser Asn Gly Gln Pro Glu Asn Asn
                405                 410                 415

Tyr Lys Thr Thr Pro Pro Val Leu Asp Ser Asp Gly Ser Phe Phe Leu
                420                 425                 430

Tyr Ser Lys Leu Thr Val Asp Lys Ser Arg Trp Gln Gln Gly Asn Val
                435                 440                 445

Phe Ser Cys Ser Val Met His Glu Ala Leu His Asn His Tyr Thr Gln
450                 455                 460

Lys Ser Leu Ser Leu Ser Pro Gly Lys
465                 470

<210> SEQ ID NO 127
<211> LENGTH: 468
<212> TYPE: PRT
<213> ORGANISM: Artificial Sequence
<220> FEATURE:
<223> OTHER INFORMATION: Synthetic fusion protein

<400> SEQUENCE: 127

```
Met Glu Trp Ser Trp Val Phe Leu Phe Phe Leu Ser Val Thr Thr Gly
1               5                   10                  15

Val His Ser Gly Phe Gly Ile Ser Gly Arg His Ser Ile Thr Val Thr
            20                  25                  30

Thr Val Ala Ser Ala Gly Asn Ile Gly Glu Asp Gly Ile Leu Ser Cys
        35                  40                  45

Thr Phe Glu Pro Asp Ile Lys Leu Ser Asp Ile Val Ile Gln Trp Leu
    50                  55                  60

Lys Glu Gly Val Leu Gly Leu Val His Glu Phe Lys Glu Gly Lys Asp
65              70                  75                  80

Glu Leu Ser Glu Gln Asp Glu Met Phe Arg Gly Arg Thr Ala Val Phe
                85                  90                  95

Ala Asp Gln Val Ile Val Gly Asn Ala Ser Leu Arg Leu Lys Asn Val
            100                 105                 110

Gln Leu Thr Asp Ala Gly Thr Tyr Lys Cys Tyr Ile Ile Thr Ser Lys
        115                 120                 125

Gly Lys Gly Asn Ala Asn Leu Glu Tyr Lys Thr Gly Ala Phe Ser Met
130                 135                 140

Pro Glu Val Asn Val Asp Tyr Asn Ala Ser Ser Glu Thr Leu Arg Cys
145                 150                 155                 160

Glu Ala Pro Arg Trp Phe Pro Gln Pro Thr Val Val Trp Ala Ser Gln
                165                 170                 175

Val Asp Gln Gly Ala Asn Phe Ser Glu Val Ser Asn Thr Ser Phe Glu
            180                 185                 190

Leu Asn Ser Glu Asn Val Thr Met Lys Val Val Ser Val Leu Tyr Asn
        195                 200                 205

Val Thr Ile Asn Asn Thr Tyr Ser Cys Met Ile Glu Asn Asp Ile Ala
    210                 215                 220

Lys Ala Thr Gly Asp Ile Lys Val Thr Glu Ser Glu Ile Lys Arg Arg
225                 230                 235                 240

Ser Asp Lys Thr His Thr Cys Pro Pro Cys Pro Ala Pro Glu Leu Leu
                245                 250                 255

Gly Gly Pro Ser Val Phe Leu Phe Pro Pro Lys Pro Lys Asp Thr Leu
            260                 265                 270

Met Ile Ser Arg Thr Pro Glu Val Thr Cys Val Val Val Asp Val Ser
        275                 280                 285

His Glu Asp Pro Glu Val Lys Phe Asn Trp Tyr Val Asp Gly Val Glu
290                 295                 300

Val His Asn Ala Lys Thr Lys Pro Arg Glu Glu Gln Tyr Asn Ser Thr
305                 310                 315                 320

Tyr Arg Val Val Ser Val Leu Thr Val Leu His Gln Asp Trp Leu Asn
                325                 330                 335

Gly Lys Glu Tyr Lys Cys Lys Val Ser Asn Lys Ala Leu Pro Ala Pro
            340                 345                 350

Ile Glu Lys Thr Ile Ser Lys Ala Lys Gly Gln Pro Arg Glu Pro Gln
        355                 360                 365

Val Tyr Thr Leu Pro Pro Ser Arg Asp Glu Leu Thr Lys Asn Gln Val
370                 375                 380

Ser Leu Thr Cys Leu Val Lys Gly Phe Tyr Pro Ser Asp Ile Ala Val
385                 390                 395                 400

Glu Trp Glu Ser Asn Gly Gln Pro Glu Asn Asn Tyr Lys Thr Thr Pro
                405                 410                 415

Pro Val Leu Asp Ser Asp Gly Ser Phe Phe Leu Tyr Ser Lys Leu Thr
```

```
                420             425             430
Val Asp Lys Ser Arg Trp Gln Gln Gly Asn Val Phe Ser Cys Ser Val
            435             440             445

Met His Glu Ala Leu His Asn His Tyr Thr Gln Lys Ser Leu Ser Leu
        450             455             460

Ser Pro Gly Lys
465

<210> SEQ ID NO 128
<211> LENGTH: 464
<212> TYPE: PRT
<213> ORGANISM: Artificial Sequence
<220> FEATURE:
<223> OTHER INFORMATION: Synthetic fusion protein

<400> SEQUENCE: 128

Met Glu Trp Ser Trp Val Phe Leu Phe Phe Leu Ser Val Thr Thr Gly
1               5                   10                  15

Val His Ser Gly Phe Gly Ile Ser Gly Arg His Ser Ile Thr Val Thr
            20                  25                  30

Thr Val Ala Ser Ala Gly Asn Ile Gly Glu Asp Gly Ile Leu Ser Cys
        35                  40                  45

Thr Phe Glu Pro Asp Ile Lys Leu Ser Asp Ile Val Ile Gln Trp Leu
    50                  55                  60

Lys Glu Gly Val Leu Gly Leu Val His Glu Phe Lys Glu Gly Lys Asp
65                  70                  75                  80

Glu Leu Ser Glu Gln Asp Glu Met Phe Arg Gly Arg Thr Ala Val Phe
                85                  90                  95

Ala Asp Gln Val Ile Val Gly Asn Ala Ser Leu Arg Leu Lys Asn Val
            100                 105                 110

Gln Leu Thr Asp Ala Gly Thr Tyr Lys Cys Tyr Ile Ile Thr Ser Lys
        115                 120                 125

Gly Lys Gly Asn Ala Asn Leu Glu Tyr Lys Thr Gly Ala Phe Ser Met
    130                 135                 140

Pro Glu Val Asn Val Asp Tyr Asn Ala Ser Ser Glu Thr Leu Arg Cys
145                 150                 155                 160

Glu Ala Pro Arg Trp Phe Pro Gln Pro Thr Val Val Trp Ala Ser Gln
                165                 170                 175

Val Asp Gln Gly Ala Asn Phe Ser Glu Val Ser Asn Thr Ser Phe Glu
            180                 185                 190

Leu Asn Ser Glu Asn Val Thr Met Lys Val Val Ser Val Leu Tyr Asn
        195                 200                 205

Val Thr Ile Asn Asn Thr Tyr Ser Cys Met Ile Glu Asn Asp Ile Ala
    210                 215                 220

Lys Ala Thr Gly Asp Ile Lys Val Thr Glu Ser Glu Ile Asp Lys Thr
225                 230                 235                 240

His Thr Cys Pro Pro Cys Pro Ala Pro Glu Leu Leu Gly Gly Pro Ser
                245                 250                 255

Val Phe Leu Phe Pro Pro Lys Pro Lys Asp Thr Leu Met Ile Ser Arg
            260                 265                 270

Thr Pro Glu Val Thr Cys Val Val Asp Val Ser His Glu Asp Pro
        275                 280                 285

Glu Val Lys Phe Asn Trp Tyr Val Asp Gly Val Glu Val His Asn Ala
    290                 295                 300

Lys Thr Lys Pro Arg Glu Glu Gln Tyr Asn Ser Thr Tyr Arg Val Val
```

```
                305                 310                 315                 320
Ser Val Leu Thr Val Leu His Gln Asp Trp Leu Asn Gly Lys Glu Tyr
                    325                 330                 335

Lys Cys Lys Val Ser Asn Lys Ala Leu Pro Ala Pro Ile Glu Lys Thr
                    340                 345                 350

Ile Ser Lys Ala Lys Gly Gln Pro Arg Glu Pro Gln Val Tyr Thr Leu
                    355                 360                 365

Pro Pro Ser Arg Asp Glu Leu Thr Lys Asn Gln Val Ser Leu Thr Cys
                    370                 375                 380

Leu Val Lys Gly Phe Tyr Pro Ser Asp Ile Ala Val Glu Trp Glu Ser
385                 390                 395                 400

Asn Gly Gln Pro Glu Asn Asn Tyr Lys Thr Thr Pro Pro Val Leu Asp
                    405                 410                 415

Ser Asp Gly Ser Phe Phe Leu Tyr Ser Lys Leu Thr Val Asp Lys Ser
                    420                 425                 430

Arg Trp Gln Gln Gly Asn Val Phe Ser Cys Ser Val Met His Glu Ala
                    435                 440                 445

Leu His Asn His Tyr Thr Gln Lys Ser Leu Ser Leu Ser Pro Gly Lys
                    450                 455                 460

<210> SEQ ID NO 129
<211> LENGTH: 476
<212> TYPE: PRT
<213> ORGANISM: Artificial Sequence
<220> FEATURE:
<223> OTHER INFORMATION: Synthetic fusion protein

<400> SEQUENCE: 129

Met Glu Trp Ser Trp Val Phe Leu Phe Phe Leu Ser Val Thr Thr Gly
1               5                   10                  15

Val His Ser Gly Phe Gly Ile Ser Gly Arg His Ser Ile Thr Val Thr
                20                  25                  30

Thr Val Ala Ser Ala Gly Asn Ile Gly Glu Asp Gly Ile Leu Ser Cys
                35                  40                  45

Thr Phe Glu Pro Asp Ile Lys Leu Ser Asp Ile Val Ile Gln Trp Leu
50                  55                  60

Lys Glu Gly Val Leu Gly Leu Val His Glu Phe Lys Glu Gly Lys Asp
65                  70                  75                  80

Glu Leu Ser Glu Gln Asp Glu Met Phe Arg Gly Arg Thr Ala Val Phe
                85                  90                  95

Ala Asp Gln Val Ile Val Gly Asn Ala Ser Leu Arg Leu Lys Asn Val
                100                 105                 110

Gln Leu Thr Asp Ala Gly Thr Tyr Lys Cys Tyr Ile Ile Thr Ser Lys
                115                 120                 125

Gly Lys Gly Asn Ala Asn Leu Glu Tyr Lys Thr Gly Ala Phe Ser Met
                130                 135                 140

Pro Glu Val Asn Val Asp Tyr Asn Ala Ser Ser Glu Thr Leu Arg Cys
145                 150                 155                 160

Glu Ala Pro Arg Trp Phe Pro Gln Pro Thr Val Val Trp Ala Ser Gln
                165                 170                 175

Val Asp Gln Gly Ala Asn Phe Ser Glu Val Ser Asn Thr Ser Phe Glu
                180                 185                 190

Leu Asn Ser Glu Asn Val Thr Met Lys Val Val Ser Val Leu Tyr Asn
                195                 200                 205

Val Thr Ile Asn Asn Thr Tyr Ser Cys Met Ile Glu Asn Asp Ile Ala
```

```
            210                 215                 220
Lys Ala Thr Gly Asp Ile Lys Val Thr Glu Ser Glu Ile Lys Arg Arg
225                 230                 235                 240

Ser His Leu Gln Leu Leu Asn Ser Lys Asp Lys Thr His Thr Cys Pro
            245                 250                 255

Pro Cys Pro Ala Pro Glu Leu Leu Gly Gly Pro Ser Val Phe Leu Phe
            260                 265                 270

Pro Pro Lys Pro Lys Asp Thr Leu Met Ile Ser Arg Thr Pro Glu Val
            275                 280                 285

Thr Cys Val Val Val Asp Val Ser His Glu Asp Pro Glu Val Lys Phe
            290                 295                 300

Asn Trp Tyr Val Asp Gly Val Glu Val His Asn Ala Lys Thr Lys Pro
305                 310                 315                 320

Arg Glu Glu Gln Tyr Asn Ser Thr Tyr Arg Val Val Ser Val Leu Thr
            325                 330                 335

Val Leu His Gln Asp Trp Leu Asn Gly Lys Glu Tyr Lys Cys Lys Val
            340                 345                 350

Ser Asn Lys Ala Leu Pro Ala Pro Ile Glu Lys Thr Ile Ser Lys Ala
            355                 360                 365

Lys Gly Gln Pro Arg Glu Pro Gln Val Tyr Thr Leu Pro Pro Ser Arg
370                 375                 380

Asp Glu Leu Thr Lys Asn Gln Val Ser Leu Thr Cys Leu Val Lys Gly
385                 390                 395                 400

Phe Tyr Pro Ser Asp Ile Ala Val Glu Trp Glu Ser Asn Gly Gln Pro
            405                 410                 415

Glu Asn Asn Tyr Lys Thr Thr Pro Pro Val Leu Asp Ser Asp Gly Ser
            420                 425                 430

Phe Phe Leu Tyr Ser Lys Leu Thr Val Asp Lys Ser Arg Trp Gln Gln
            435                 440                 445

Gly Asn Val Phe Ser Cys Ser Val Met His Glu Ala Leu His Asn His
            450                 455                 460

Tyr Thr Gln Lys Ser Leu Ser Leu Ser Pro Gly Lys
465                 470                 475

<210> SEQ ID NO 130
<211> LENGTH: 454
<212> TYPE: PRT
<213> ORGANISM: Artificial Sequence
<220> FEATURE:
<223> OTHER INFORMATION: Synthetic fusion protein

<400> SEQUENCE: 130

Gly Phe Gly Ile Ser Gly Arg His Ser Ile Thr Val Thr Thr Val Ala
1               5                   10                  15

Ser Ala Gly Asn Ile Gly Glu Asp Gly Ile Gln Ser Cys Thr Phe Glu
            20                  25                  30

Pro Asp Ile Lys Leu Ser Asp Ile Val Ile Gln Trp Leu Lys Glu Gly
        35                  40                  45

Val Leu Gly Leu Val His Glu Phe Lys Glu Gly Lys Asp Glu Leu Ser
    50                  55                  60

Glu Gln Asp Glu Met Phe Arg Gly Arg Thr Ala Val Phe Ala Asp Gln
65                  70                  75                  80

Val Ile Val Gly Asn Ala Ser Leu Arg Leu Lys Asn Val Gln Leu Thr
                85                  90                  95

Asp Ala Gly Thr Tyr Lys Cys Tyr Ile Ile Thr Ser Lys Gly Lys Gly
```

```
                100                 105                 110
Asn Ala Asn Leu Glu Tyr Lys Thr Gly Ala Phe Ser Met Pro Glu Val
            115                 120                 125
Asn Val Asp Tyr Asn Ala Ser Ser Glu Thr Leu Arg Cys Glu Ala Pro
        130                 135                 140
Arg Trp Phe Pro Gln Pro Thr Val Val Trp Ala Ser Gln Val Asp Gln
145                 150                 155                 160
Gly Ala Asn Phe Ser Glu Val Ser Asn Thr Ser Phe Glu Leu Asn Ser
                165                 170                 175
Glu Asn Val Thr Met Lys Val Val Ser Val Leu Tyr Asn Val Thr Ile
            180                 185                 190
Asn Asn Thr Tyr Ser Cys Met Ile Glu Asn Asp Ile Ala Lys Ala Thr
        195                 200                 205
Gly Asp Ile Lys Val Thr Glu Ser Glu Ile Lys Arg Arg Ser Glu Pro
210                 215                 220
Lys Ser Cys Asp Lys Thr His Thr Cys Pro Pro Cys Pro Ala Pro Glu
225                 230                 235                 240
Leu Leu Gly Gly Pro Ser Val Phe Leu Phe Pro Pro Lys Pro Lys Asp
                245                 250                 255
Thr Leu Met Ile Ser Arg Thr Pro Glu Val Thr Cys Val Val Val Asp
            260                 265                 270
Val Ser His Glu Asp Pro Glu Val Lys Phe Asn Trp Tyr Val Asp Gly
        275                 280                 285
Val Glu Val His Asn Ala Lys Thr Lys Pro Arg Glu Glu Gln Tyr Asn
290                 295                 300
Ser Thr Tyr Arg Val Val Ser Val Leu Thr Val Leu His Gln Asp Trp
305                 310                 315                 320
Leu Asn Gly Lys Glu Tyr Lys Cys Lys Val Ser Asn Lys Ala Leu Pro
                325                 330                 335
Ala Pro Ile Glu Lys Thr Ile Ser Lys Ala Lys Gly Gln Pro Arg Glu
            340                 345                 350
Pro Gln Val Tyr Thr Leu Pro Pro Ser Arg Asp Glu Leu Thr Lys Asn
        355                 360                 365
Gln Val Ser Leu Thr Cys Leu Val Lys Gly Phe Tyr Pro Ser Asp Ile
    370                 375                 380
Ala Val Glu Trp Glu Ser Asn Gly Gln Pro Glu Asn Asn Tyr Lys Thr
385                 390                 395                 400
Thr Pro Pro Val Leu Asp Ser Asp Gly Ser Phe Phe Leu Tyr Ser Lys
                405                 410                 415
Leu Thr Val Asp Lys Ser Arg Trp Gln Gln Gly Asn Val Phe Ser Cys
            420                 425                 430
Ser Val Met His Glu Ala Leu His Asn His Tyr Thr Gln Lys Ser Leu
        435                 440                 445
Ser Leu Ser Pro Gly Lys
    450

<210> SEQ ID NO 131
<211> LENGTH: 449
<212> TYPE: PRT
<213> ORGANISM: Artificial Sequence
<220> FEATURE:
<223> OTHER INFORMATION: Synthetic fusion protein

<400> SEQUENCE: 131

Gly Phe Gly Ile Ser Gly Arg His Ser Ile Thr Val Thr Thr Val Ala
```

-continued

```
1               5                   10                  15
Ser Ala Gly Asn Ile Gly Glu Asp Gly Ile Gln Ser Cys Thr Phe Glu
            20                  25                  30

Pro Asp Ile Lys Leu Ser Asp Ile Val Ile Gln Trp Leu Lys Glu Gly
            35                  40                  45

Val Leu Gly Leu Val His Glu Phe Lys Glu Gly Lys Asp Glu Leu Ser
            50                  55                  60

Glu Gln Asp Glu Met Phe Arg Gly Arg Thr Ala Val Phe Ala Asp Gln
65                  70                  75                  80

Val Ile Val Gly Asn Ala Ser Leu Arg Leu Lys Asn Val Gln Leu Thr
                85                  90                  95

Asp Ala Gly Thr Tyr Lys Cys Tyr Ile Ile Thr Ser Lys Gly Lys Gly
            100                 105                 110

Asn Ala Asn Leu Glu Tyr Lys Thr Gly Ala Phe Ser Met Pro Glu Val
            115                 120                 125

Asn Val Asp Tyr Asn Ala Ser Ser Glu Thr Leu Arg Cys Glu Ala Pro
            130                 135                 140

Arg Trp Phe Pro Gln Pro Thr Val Val Trp Ala Ser Gln Val Asp Gln
145                 150                 155                 160

Gly Ala Asn Phe Ser Glu Val Ser Asn Thr Ser Phe Glu Leu Asn Ser
                165                 170                 175

Glu Asn Val Thr Met Lys Val Val Ser Val Leu Tyr Asn Val Thr Ile
            180                 185                 190

Asn Asn Thr Tyr Ser Cys Met Ile Glu Asn Asp Ile Ala Lys Ala Thr
            195                 200                 205

Gly Asp Ile Lys Val Thr Glu Ser Glu Ile Lys Arg Arg Ser Asp Lys
            210                 215                 220

Thr His Thr Cys Pro Pro Cys Pro Ala Pro Glu Leu Leu Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
            260                 265                 270

Pro Glu Val Lys Phe Asn Trp Tyr Val Asp Gly Val Glu Val His Asn
            275                 280                 285

Ala Lys Thr Lys Pro Arg Glu Glu Gln Tyr Asn Ser Thr Tyr Arg Val
            290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
                325                 330                 335

Thr Ile Ser Lys Ala Lys Gly Gln Pro Arg Glu Pro Gln Val Tyr Thr
            340                 345                 350

Leu Pro Pro Ser Arg Asp Glu Leu Thr Lys Asn Gln Val Ser Leu Thr
            355                 360                 365

Cys Leu Val Lys Gly Phe Tyr Pro Ser Asp Ile Ala Val Glu Trp Glu
            370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
                405                 410                 415

Ser Arg Trp Gln Gln Gly Asn Val Phe Ser Cys Ser Val Met His Glu
            420                 425                 430
```

Ala Leu His Asn His Tyr Thr Gln Lys Ser Leu Ser Leu Ser Pro Gly
            435                 440                 445

Lys

<210> SEQ ID NO 132
<211> LENGTH: 445
<212> TYPE: PRT
<213> ORGANISM: Artificial Sequence
<220> FEATURE:
<223> OTHER INFORMATION: Synthetic fusion protein

<400> SEQUENCE: 132

Gly Phe Gly Ile Ser Gly Arg His Ser Ile Thr Val Thr Thr Val Ala
1               5                   10                  15

Ser Ala Gly Asn Ile Gly Glu Asp Gly Ile Gln Ser Cys Thr Phe Glu
            20                  25                  30

Pro Asp Ile Lys Leu Ser Asp Ile Val Ile Gln Trp Leu Lys Glu Gly
        35                  40                  45

Val Leu Gly Leu Val His Glu Phe Lys Glu Gly Lys Asp Glu Leu Ser
50                  55                  60

Glu Gln Asp Glu Met Phe Arg Gly Arg Thr Ala Val Phe Ala Asp Gln
65                  70                  75                  80

Val Ile Val Gly Asn Ala Ser Leu Arg Leu Lys Asn Val Gln Leu Thr
                85                  90                  95

Asp Ala Gly Thr Tyr Lys Cys Tyr Ile Ile Thr Ser Lys Gly Lys Gly
            100                 105                 110

Asn Ala Asn Leu Glu Tyr Lys Thr Gly Ala Phe Ser Met Pro Glu Val
        115                 120                 125

Asn Val Asp Tyr Asn Ala Ser Ser Glu Thr Leu Arg Cys Glu Ala Pro
130                 135                 140

Arg Trp Phe Pro Gln Pro Thr Val Val Trp Ala Ser Gln Val Asp Gln
145                 150                 155                 160

Gly Ala Asn Phe Ser Glu Val Ser Asn Thr Ser Phe Glu Leu Asn Ser
                165                 170                 175

Glu Asn Val Thr Met Lys Val Val Ser Val Leu Tyr Asn Val Thr Ile
            180                 185                 190

Asn Asn Thr Tyr Ser Cys Met Ile Glu Asn Asp Ile Ala Lys Ala Thr
        195                 200                 205

Gly Asp Ile Lys Val Thr Glu Ser Glu Ile Lys Thr His Thr Cys
210                 215                 220

Pro Pro Cys Pro Ala Pro Glu Leu Leu Gly Gly Pro Ser Val Phe Leu
225                 230                 235                 240

Phe Pro Pro Lys Pro Lys Asp Thr Leu Met Ile Ser Arg Thr Pro Glu
                245                 250                 255

Val Thr Cys Val Val Val Asp Val Ser His Glu Asp Pro Glu Val Lys
            260                 265                 270

Phe Asn Trp Tyr Val Asp Gly Val Glu Val His Asn Ala Lys Thr Lys
        275                 280                 285

Pro Arg Glu Glu Gln Tyr Asn Ser Thr Tyr Arg Val Val Ser Val Leu
290                 295                 300

Thr Val Leu His Gln Asp Trp Leu Asn Gly Lys Glu Tyr Lys Cys Lys
305                 310                 315                 320

Val Ser Asn Lys Ala Leu Pro Ala Pro Ile Glu Lys Thr Ile Ser Lys
                325                 330                 335

```
Ala Lys Gly Gln Pro Arg Glu Pro Gln Val Tyr Thr Leu Pro Pro Ser
            340                 345                 350

Arg Asp Glu Leu Thr Lys Asn Gln Val Ser Leu Thr Cys Leu Val Lys
            355                 360                 365

Gly Phe Tyr Pro Ser Asp Ile Ala Val Glu Trp Glu Ser Asn Gly Gln
        370                 375                 380

Pro Glu Asn Asn Tyr Lys Thr Thr Pro Pro Val Leu Asp Ser Asp Gly
385                 390                 395                 400

Ser Phe Phe Leu Tyr Ser Lys Leu Thr Val Asp Lys Ser Arg Trp Gln
                405                 410                 415

Gln Gly Asn Val Phe Ser Cys Ser Val Met His Glu Ala Leu His Asn
            420                 425                 430

His Tyr Thr Gln Lys Ser Leu Ser Leu Ser Pro Gly Lys
        435                 440                 445

<210> SEQ ID NO 133
<211> LENGTH: 457
<212> TYPE: PRT
<213> ORGANISM: Artificial Sequence
<220> FEATURE:
<223> OTHER INFORMATION: Synthetic fusion protein

<400> SEQUENCE: 133

Gly Phe Gly Ile Ser Gly Arg His Ser Ile Thr Val Thr Val Ala
1               5                   10                  15

Ser Ala Gly Asn Ile Gly Glu Asp Gly Ile Gln Ser Cys Thr Phe Glu
                20                  25                  30

Pro Asp Ile Lys Leu Ser Asp Ile Val Ile Gln Trp Leu Lys Glu Gly
            35                  40                  45

Val Leu Gly Leu Val His Glu Phe Lys Glu Gly Lys Asp Glu Leu Ser
        50                  55                  60

Glu Gln Asp Glu Met Phe Arg Gly Arg Thr Ala Val Phe Ala Asp Gln
65                  70                  75                  80

Val Ile Val Gly Asn Ala Ser Leu Arg Leu Lys Asn Val Gln Leu Thr
                85                  90                  95

Asp Ala Gly Thr Tyr Lys Cys Tyr Ile Ile Thr Ser Lys Gly Lys Gly
            100                 105                 110

Asn Ala Asn Leu Glu Tyr Lys Thr Gly Ala Phe Ser Met Pro Glu Val
        115                 120                 125

Asn Val Asp Tyr Asn Ala Ser Ser Glu Thr Leu Arg Cys Glu Ala Pro
130                 135                 140

Arg Trp Phe Pro Gln Pro Thr Val Val Trp Ala Ser Gln Val Asp Gln
145                 150                 155                 160

Gly Ala Asn Phe Ser Glu Val Ser Asn Thr Ser Phe Glu Leu Asn Ser
                165                 170                 175

Glu Asn Val Thr Met Lys Val Val Ser Val Leu Tyr Asn Val Thr Ile
            180                 185                 190

Asn Asn Thr Tyr Ser Cys Met Ile Glu Asn Asp Ile Ala Lys Ala Thr
        195                 200                 205

Gly Asp Ile Lys Val Thr Glu Ser Glu Ile Lys Arg Arg Ser His Leu
210                 215                 220

Gln Leu Leu Asn Ser Lys Asp Lys Thr His Thr Cys Pro Pro Cys Pro
225                 230                 235                 240

Ala Pro Glu Leu Leu Gly Gly Pro Ser Val Phe Leu Phe Pro Pro Lys
                245                 250                 255
```

Pro Lys Asp Thr Leu Met Ile Ser Arg Thr Pro Glu Val Thr Cys Val
           260                 265                 270

Val Val Asp Val Ser His Glu Asp Pro Glu Val Lys Phe Asn Trp Tyr
       275                 280                 285

Val Asp Gly Val Glu Val His Asn Ala Lys Thr Lys Pro Arg Glu Glu
   290                 295                 300

Gln Tyr Asn Ser Thr Tyr Arg Val Val Ser Val Leu Thr Val Leu His
305                 310                 315                 320

Gln Asp Trp Leu Asn Gly Lys Glu Tyr Lys Cys Lys Val Ser Asn Lys
               325                 330                 335

Ala Leu Pro Ala Pro Ile Glu Lys Thr Ile Ser Lys Ala Lys Gly Gln
           340                 345                 350

Pro Arg Glu Pro Gln Val Tyr Thr Leu Pro Pro Ser Arg Asp Glu Leu
       355                 360                 365

Thr Lys Asn Gln Val Ser Leu Thr Cys Leu Val Lys Gly Phe Tyr Pro
   370                 375                 380

Ser Asp Ile Ala Val Glu Trp Glu Ser Asn Gly Gln Pro Glu Asn Asn
385                 390                 395                 400

Tyr Lys Thr Thr Pro Pro Val Leu Asp Ser Asp Gly Ser Phe Phe Leu
               405                 410                 415

Tyr Ser Lys Leu Thr Val Asp Lys Ser Arg Trp Gln Gln Gly Asn Val
           420                 425                 430

Phe Ser Cys Ser Val Met His Glu Ala Leu His Asn His Tyr Thr Gln
       435                 440                 445

Lys Ser Leu Ser Leu Ser Pro Gly Lys
   450                 455

<210> SEQ ID NO 134
<211> LENGTH: 454
<212> TYPE: PRT
<213> ORGANISM: Artificial Sequence
<220> FEATURE:
<223> OTHER INFORMATION: Synthetic fusion protein

<400> SEQUENCE: 134

Gly Phe Gly Ile Ser Gly Arg His Ser Ile Thr Val Thr Thr Val Ala
1               5                   10                  15

Ser Ala Gly Asn Ile Gly Glu Asp Gly Ile Leu Ser Cys Thr Phe Glu
           20                  25                  30

Pro Asp Ile Lys Leu Ser Asp Ile Val Ile Gln Trp Leu Lys Glu Gly
       35                  40                  45

Val Leu Gly Leu Val His Glu Phe Lys Glu Gly Lys Asp Glu Leu Ser
   50                  55                  60

Glu Gln Asp Glu Met Phe Arg Gly Arg Thr Ala Val Phe Ala Asp Gln
65                  70                  75                  80

Val Ile Val Gly Asn Ala Ser Leu Arg Leu Lys Asn Val Gln Leu Thr
               85                  90                  95

Asp Ala Gly Thr Tyr Lys Cys Tyr Ile Ile Thr Ser Lys Gly Lys Gly
           100                 105                 110

Asn Ala Asn Leu Glu Tyr Lys Thr Gly Ala Phe Ser Met Pro Glu Val
       115                 120                 125

Asn Val Asp Tyr Asn Ala Ser Ser Glu Thr Leu Arg Cys Glu Ala Pro
   130                 135                 140

Arg Trp Phe Pro Gln Pro Thr Val Val Trp Ala Ser Gln Val Asp Gln
145                 150                 155                 160

Gly Ala Asn Phe Ser Glu Val Ser Asn Thr Ser Phe Glu Leu Asn Ser
                165                 170                 175

Glu Asn Val Thr Met Lys Val Ser Val Leu Tyr Asn Val Thr Ile
            180                 185                 190

Asn Asn Thr Tyr Ser Cys Met Ile Glu Asn Asp Ile Ala Lys Ala Thr
            195                 200                 205

Gly Asp Ile Lys Val Thr Glu Ser Glu Ile Lys Arg Arg Ser Glu Pro
            210                 215                 220

Lys Ser Cys Asp Lys Thr His Thr Cys Pro Pro Cys Pro Ala Pro Glu
225                 230                 235                 240

Leu Leu Gly Gly Pro Ser Val Phe Leu Phe Pro Pro Lys Pro Lys Asp
                245                 250                 255

Thr Leu Met Ile Ser Arg Thr Pro Glu Val Thr Cys Val Val Val Asp
            260                 265                 270

Val Ser His Glu Asp Pro Glu Val Lys Phe Asn Trp Tyr Val Asp Gly
            275                 280                 285

Val Glu Val His Asn Ala Lys Thr Lys Pro Arg Glu Glu Gln Tyr Asn
            290                 295                 300

Ser Thr Tyr Arg Val Val Ser Val Leu Thr Val Leu His Gln Asp Trp
305                 310                 315                 320

Leu Asn Gly Lys Glu Tyr Lys Cys Lys Val Ser Asn Lys Ala Leu Pro
                325                 330                 335

Ala Pro Ile Glu Lys Thr Ile Ser Lys Ala Lys Gly Gln Pro Arg Glu
            340                 345                 350

Pro Gln Val Tyr Thr Leu Pro Pro Ser Arg Asp Glu Leu Thr Lys Asn
            355                 360                 365

Gln Val Ser Leu Thr Cys Leu Val Lys Gly Phe Tyr Pro Ser Asp Ile
370                 375                 380

Ala Val Glu Trp Glu Ser Asn Gly Gln Pro Glu Asn Asn Tyr Lys Thr
385                 390                 395                 400

Thr Pro Pro Val Leu Asp Ser Asp Gly Ser Phe Phe Leu Tyr Ser Lys
                405                 410                 415

Leu Thr Val Asp Lys Ser Arg Trp Gln Gln Gly Asn Val Phe Ser Cys
            420                 425                 430

Ser Val Met His Glu Ala Leu His Asn His Tyr Thr Gln Lys Ser Leu
            435                 440                 445

Ser Leu Ser Pro Gly Lys
    450

<210> SEQ ID NO 135
<211> LENGTH: 449
<212> TYPE: PRT
<213> ORGANISM: Artificial Sequence
<220> FEATURE:
<223> OTHER INFORMATION: Synthetic fusion protein

<400> SEQUENCE: 135

Gly Phe Gly Ile Ser Gly Arg His Ser Ile Thr Val Thr Thr Val Ala
1               5                   10                  15

Ser Ala Gly Asn Ile Gly Glu Asp Gly Ile Leu Ser Cys Thr Phe Glu
                20                  25                  30

Pro Asp Ile Lys Leu Ser Asp Ile Val Ile Gln Trp Leu Lys Glu Gly
            35                  40                  45

Val Leu Gly Leu Val His Glu Phe Lys Glu Gly Lys Asp Glu Leu Ser
        50                  55                  60

Glu Gln Asp Glu Met Phe Arg Gly Arg Thr Ala Val Phe Ala Asp Gln
65                  70                  75                  80

Val Ile Val Gly Asn Ala Ser Leu Arg Leu Lys Asn Val Gln Leu Thr
            85                  90                  95

Asp Ala Gly Thr Tyr Lys Cys Tyr Ile Ile Thr Ser Lys Gly Lys Gly
            100                 105                 110

Asn Ala Asn Leu Glu Tyr Lys Thr Gly Ala Phe Ser Met Pro Glu Val
            115                 120                 125

Asn Val Asp Tyr Asn Ala Ser Ser Glu Thr Leu Arg Cys Glu Ala Pro
            130                 135                 140

Arg Trp Phe Pro Gln Pro Thr Val Val Trp Ala Ser Gln Val Asp Gln
145                 150                 155                 160

Gly Ala Asn Phe Ser Glu Val Ser Asn Thr Ser Phe Glu Leu Asn Ser
            165                 170                 175

Glu Asn Val Thr Met Lys Val Val Ser Val Leu Tyr Asn Val Thr Ile
            180                 185                 190

Asn Asn Thr Tyr Ser Cys Met Ile Glu Asn Asp Ile Ala Lys Ala Thr
            195                 200                 205

Gly Asp Ile Lys Val Thr Glu Ser Glu Ile Lys Arg Arg Ser Asp Lys
210                 215                 220

Thr His Thr Cys Pro Pro Cys Pro Ala Pro Glu Leu Leu Gly Gly Pro
225                 230                 235                 240

Ser Val Phe Leu Phe Pro Pro Lys Pro Lys Asp Thr Leu Met Ile Ser
            245                 250                 255

Arg Thr Pro Glu Val Thr Cys Val Val Val Asp Val Ser His Glu Asp
            260                 265                 270

Pro Glu Val Lys Phe Asn Trp Tyr Val Asp Gly Val Glu Val His Asn
            275                 280                 285

Ala Lys Thr Lys Pro Arg Glu Glu Gln Tyr Asn Ser Thr Tyr Arg Val
            290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
            325                 330                 335

Thr Ile Ser Lys Ala Lys Gly Gln Pro Arg Glu Pro Gln Val Tyr Thr
            340                 345                 350

Leu Pro Pro Ser Arg Asp Glu Leu Thr Lys Asn Gln Val Ser Leu Thr
            355                 360                 365

Cys Leu Val Lys Gly Phe Tyr Pro Ser Asp Ile Ala Val Glu Trp Glu
370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
            405                 410                 415

Ser Arg Trp Gln Gln Gly Asn Val Phe Ser Cys Ser Val Met His Glu
            420                 425                 430

Ala Leu His Asn His Tyr Thr Gln Lys Ser Leu Ser Leu Ser Pro Gly
            435                 440                 445

Lys

<210> SEQ ID NO 136
<211> LENGTH: 445
<212> TYPE: PRT
<213> ORGANISM: Artificial Sequence
<220> FEATURE:
<223> OTHER INFORMATION: Synthetic fusion protein

<400> SEQUENCE: 136

```
Gly Phe Gly Ile Ser Gly Arg His Ser Ile Thr Val Thr Thr Val Ala
1               5                   10                  15

Ser Ala Gly Asn Ile Gly Glu Asp Gly Ile Leu Ser Cys Thr Phe Glu
            20                  25                  30

Pro Asp Ile Lys Leu Ser Asp Ile Val Ile Gln Trp Leu Lys Glu Gly
        35                  40                  45

Val Leu Gly Leu Val His Glu Phe Lys Glu Gly Lys Asp Glu Leu Ser
    50                  55                  60

Glu Gln Asp Glu Met Phe Arg Gly Arg Thr Ala Val Phe Ala Asp Gln
65                  70                  75                  80

Val Ile Val Gly Asn Ala Ser Leu Arg Leu Lys Asn Val Gln Leu Thr
                85                  90                  95

Asp Ala Gly Thr Tyr Lys Cys Tyr Ile Ile Thr Ser Lys Gly Lys Gly
            100                 105                 110

Asn Ala Asn Leu Glu Tyr Lys Thr Gly Ala Phe Ser Met Pro Glu Val
        115                 120                 125

Asn Val Asp Tyr Asn Ala Ser Ser Glu Thr Leu Arg Cys Glu Ala Pro
130                 135                 140

Arg Trp Phe Pro Gln Pro Thr Val Val Trp Ala Ser Gln Val Asp Gln
145                 150                 155                 160

Gly Ala Asn Phe Ser Glu Val Ser Asn Thr Ser Phe Glu Leu Asn Ser
                165                 170                 175

Glu Asn Val Thr Met Lys Val Val Ser Val Leu Tyr Asn Val Thr Ile
            180                 185                 190

Asn Asn Thr Tyr Ser Cys Met Ile Glu Asn Asp Ile Ala Lys Ala Thr
        195                 200                 205

Gly Asp Ile Lys Val Thr Glu Ser Glu Ile Asp Lys Thr His Thr Cys
210                 215                 220

Pro Pro Cys Pro Ala Pro Glu Leu Leu Gly Gly Pro Ser Val Phe Leu
225                 230                 235                 240

Phe Pro Pro Lys Pro Lys Asp Thr Leu Met Ile Ser Arg Thr Pro Glu
                245                 250                 255

Val Thr Cys Val Val Val Asp Val Ser His Glu Asp Pro Glu Val Lys
            260                 265                 270

Phe Asn Trp Tyr Val Asp Gly Val Glu Val His Asn Ala Lys Thr Lys
        275                 280                 285

Pro Arg Glu Glu Gln Tyr Asn Ser Thr Tyr Arg Val Val Ser Val Leu
290                 295                 300

Thr Val Leu His Gln Asp Trp Leu Asn Gly Lys Glu Tyr Lys Cys Lys
305                 310                 315                 320

Val Ser Asn Lys Ala Leu Pro Ala Pro Ile Glu Lys Thr Ile Ser Lys
                325                 330                 335

Ala Lys Gly Gln Pro Arg Glu Pro Gln Val Tyr Thr Leu Pro Pro Ser
            340                 345                 350

Arg Asp Glu Leu Thr Lys Asn Gln Val Ser Leu Thr Cys Leu Val Lys
        355                 360                 365

Gly Phe Tyr Pro Ser Asp Ile Ala Val Glu Trp Glu Ser Asn Gly Gln
370                 375                 380

Pro Glu Asn Asn Tyr Lys Thr Thr Pro Pro Val Leu Asp Ser Asp Gly
385                 390                 395                 400
```

```
Ser Phe Phe Leu Tyr Ser Lys Leu Thr Val Asp Lys Ser Arg Trp Gln
            405                 410                 415

Gln Gly Asn Val Phe Ser Cys Ser Val Met His Glu Ala Leu His Asn
            420                 425                 430

His Tyr Thr Gln Lys Ser Leu Ser Leu Ser Pro Gly Lys
            435                 440                 445

<210> SEQ ID NO 137
<211> LENGTH: 457
<212> TYPE: PRT
<213> ORGANISM: Artificial Sequence
<220> FEATURE:
<223> OTHER INFORMATION: Synthetic fusion protein

<400> SEQUENCE: 137

Gly Phe Gly Ile Ser Gly Arg His Ser Ile Thr Val Thr Thr Val Ala
1               5                   10                  15

Ser Ala Gly Asn Ile Gly Glu Asp Gly Ile Leu Ser Cys Thr Phe Glu
            20                  25                  30

Pro Asp Ile Lys Leu Ser Asp Ile Val Ile Gln Trp Leu Lys Glu Gly
            35                  40                  45

Val Leu Gly Leu Val His Glu Phe Lys Glu Gly Lys Asp Glu Leu Ser
50                  55                  60

Glu Gln Asp Glu Met Phe Arg Gly Arg Thr Ala Val Phe Ala Asp Gln
65                  70                  75                  80

Val Ile Val Gly Asn Ala Ser Leu Arg Leu Lys Asn Val Gln Leu Thr
            85                  90                  95

Asp Ala Gly Thr Tyr Lys Cys Tyr Ile Ile Thr Ser Lys Gly Lys Gly
            100                 105                 110

Asn Ala Asn Leu Glu Tyr Lys Thr Gly Ala Phe Ser Met Pro Glu Val
            115                 120                 125

Asn Val Asp Tyr Asn Ala Ser Ser Glu Thr Leu Arg Cys Glu Ala Pro
            130                 135                 140

Arg Trp Phe Pro Gln Pro Thr Val Val Trp Ala Ser Gln Val Asp Gln
145                 150                 155                 160

Gly Ala Asn Phe Ser Glu Val Ser Asn Thr Ser Phe Glu Leu Asn Ser
            165                 170                 175

Glu Asn Val Thr Met Lys Val Val Ser Val Leu Tyr Asn Val Thr Ile
            180                 185                 190

Asn Asn Thr Tyr Ser Cys Met Ile Glu Asn Asp Ile Ala Lys Ala Thr
            195                 200                 205

Gly Asp Ile Lys Val Thr Glu Ser Glu Ile Lys Arg Arg Ser His Leu
            210                 215                 220

Gln Leu Leu Asn Ser Lys Asp Lys Thr His Thr Cys Pro Pro Cys Pro
225                 230                 235                 240

Ala Pro Glu Leu Leu Gly Gly Pro Ser Val Phe Leu Phe Pro Pro Lys
            245                 250                 255

Pro Lys Asp Thr Leu Met Ile Ser Arg Thr Pro Glu Val Thr Cys Val
            260                 265                 270

Val Val Asp Val Ser His Glu Asp Pro Glu Val Lys Phe Asn Trp Tyr
            275                 280                 285

Val Asp Gly Val Glu Val His Asn Ala Lys Thr Lys Pro Arg Glu Glu
            290                 295                 300

Gln Tyr Asn Ser Thr Tyr Arg Val Val Ser Val Leu Thr Val Leu His
305                 310                 315                 320
```

-continued

```
Gln Asp Trp Leu Asn Gly Lys Glu Tyr Lys Cys Lys Val Ser Asn Lys
            325                 330                 335

Ala Leu Pro Ala Pro Ile Glu Lys Thr Ile Ser Lys Ala Lys Gly Gln
        340                 345                 350

Pro Arg Glu Pro Gln Val Tyr Thr Leu Pro Pro Ser Arg Asp Glu Leu
    355                 360                 365

Thr Lys Asn Gln Val Ser Leu Thr Cys Leu Val Lys Gly Phe Tyr Pro
370                 375                 380

Ser Asp Ile Ala Val Glu Trp Glu Ser Asn Gly Gln Pro Glu Asn Asn
385                 390                 395                 400

Tyr Lys Thr Thr Pro Pro Val Leu Asp Ser Asp Gly Ser Phe Phe Leu
                405                 410                 415

Tyr Ser Lys Leu Thr Val Asp Lys Ser Arg Trp Gln Gln Gly Asn Val
            420                 425                 430

Phe Ser Cys Ser Val Met His Glu Ala Leu His Asn His Tyr Thr Gln
        435                 440                 445

Lys Ser Leu Ser Leu Ser Pro Gly Lys
    450                 455

<210> SEQ ID NO 138
<211> LENGTH: 17
<212> TYPE: PRT
<213> ORGANISM: Artificial Sequence
<220> FEATURE:
<223> OTHER INFORMATION: OVA323-339 Peptide

<400> SEQUENCE: 138

Ile Ser Gln Ala Val His Ala Ala His Ala Glu Ile Asn Glu Ala Gly
1               5                   10                  15

Arg

<210> SEQ ID NO 139
<211> LENGTH: 13
<212> TYPE: PRT
<213> ORGANISM: Artificial Sequence
<220> FEATURE:
<223> OTHER INFORMATION: PLP130-151 Peptide

<400> SEQUENCE: 139

His Ser Leu Gly Lys Trp Leu Gly His Pro Asp Lys Phe
1               5                   10

<210> SEQ ID NO 140
<211> LENGTH: 14
<212> TYPE: PRT
<213> ORGANISM: Artificial Sequence
<220> FEATURE:
<223> OTHER INFORMATION: PLP130-151 Peptide

<400> SEQUENCE: 140

Asn Thr Trp Thr Thr Cys Gln Ser Ile Ala Phe Pro Ser Lys
1               5                   10

<210> SEQ ID NO 141
<211> LENGTH: 21
<212> TYPE: PRT
<213> ORGANISM: Artificial Sequence
<220> FEATURE:
<223> OTHER INFORMATION: MOG35-55 Peptide

<400> SEQUENCE: 141
```

-continued

```
Met Glu Val Gly Trp Tyr Arg Ser Pro Phe Ser Arg Val Val His Leu
1               5                   10                  15

Tyr Arg Asn Gly Lys
            20
```